United States Patent
Bookser et al.

(10) Patent No.: US 11,434,247 B1
(45) Date of Patent: Sep. 6, 2022

(54) SUBSTITUTED FURANOPYRIMIDINE COMPOUNDS AS PDE1 INHIBITORS

(71) Applicant: Dart NeuroScience, LLC, Dallas, TX (US)

(72) Inventors: Brett Bookser, San Diego, CA (US); Iriny Botrous, San Diego, CA (US); Aaron Burns, San Diego, CA (US); DeMichael Chung, San Diego, CA (US); Brian Dyck, San Diego, CA (US); Andrew Kleinke, San Diego, CA (US); Dange Vijay Kumar, San Diego, CA (US); Margaret McCarrick, San Diego, CA (US); Nicholas Raffaele, San Diego, CA (US); Joe Tran, San Marcos, CA (US); Michael Weinhouse, Lanai City, HI (US)

(73) Assignee: Dart Neuroscience LLC, Dallas, TX (US)

( * ) Notice: Subject to any disclaimer, the term of this patent is extended or adjusted under 35 U.S.C. 154(b) by 0 days.

(21) Appl. No.: 16/766,258

(22) PCT Filed: Nov. 26, 2018

(86) PCT No.: PCT/US2018/062493
§ 371 (c)(1),
(2) Date: May 21, 2020

(87) PCT Pub. No.: WO2019/104285
PCT Pub. Date: May 31, 2019

Related U.S. Application Data

(60) Provisional application No. 62/591,105, filed on Nov. 27, 2017.

(51) Int. Cl.
*C07D 491/048* (2006.01)
*C07D 519/00* (2006.01)

(52) U.S. Cl.
CPC ....... *C07D 491/048* (2013.01); *C07D 519/00* (2013.01)

(58) Field of Classification Search
CPC .............. C07D 491/048; C07D 519/00; A61K 31/519; A61P 25/16
See application file for complete search history.

(56) References Cited

U.S. PATENT DOCUMENTS

| | | | |
|---|---|---|---|
| 4,938,949 A | 7/1990 | Borch et al. | |
| 5,294,612 A | 3/1994 | Bacon et al. | |
| 5,824,683 A | 10/1998 | Kittrick et al. | |
| 6,174,884 B1 | 1/2001 | Haning et al. | |
| 6,235,742 B1 | 5/2001 | Bell et al. | |
| 7,022,709 B2 | 4/2006 | Böss et al. | |
| 7,268,128 B2 | 9/2007 | Inoue et al. | |
| 7,868,015 B2 | 1/2011 | Tully et al. | |
| 7,947,731 B2 | 5/2011 | Tully et al. | |
| 8,697,710 B2 | 4/2014 | Li et al. | |
| 8,846,693 B2 | 9/2014 | Li et al. | |
| 8,859,564 B2 | 10/2014 | Li et al. | |
| 8,927,556 B2 | 1/2015 | Li et al. | |
| 9,023,849 B2 | 5/2015 | Follmann et al. | |

(Continued)

FOREIGN PATENT DOCUMENTS

| | | |
|---|---|---|
| EP | 0063381 | 10/1982 |
| EP | 0636626 | 2/1995 |

(Continued)

OTHER PUBLICATIONS

Jordan, V.C., Tamoxifen: A most unlikely pioneering medicine, Nature Reviews: Drug Discovery, vol. 2, 2003, pp. 205-213.*
Damasio, Alzheimer's Disease and related dementias, Cecil Textbook of Medicine, 20th Edition, vol. 2, pp. 1992-1996, 1996.*
Layzer, Degenerative diseases of the nervous system, Cecil Textbook of Medicine, 20th Edition, vol. 2, pp. 2050-2057, 1996.*
Abel et al., 1997, Genetic demonstration of a role for PKA in the late phase of LTP and in hippocampus-based long-term memory. Cell. 88(5):615-626.
Ahn et al., 1997, Potent tetracyclic guanine inhibitors of PDE1 and PDE5 cyclic guanosine monophosphate phosphodiesterases with oral antihypertensive activity. J Med Chem., 40(14):2196-2210.

(Continued)

*Primary Examiner* — Deepak R Rao
(74) *Attorney, Agent, or Firm* — Knobbe, Martens, Olson & Bear LLP

(57) ABSTRACT

Substituted furanopyrimidine chemical entities of Formula (I): wherein $R^a$ has any of the values described herein, and compositions comprising such chemical entities; methods of making them; and their use in a wide range of methods, including metabolic and reaction kinetic studies; detection and imaging techniques; radioactive therapies; modulating and treating disorders mediated by PDE1 activity or dopaminergic signaling; treating neurological disorders, CNS disorders, dementia, neurodegenerative diseases, and trauma-dependent losses of function; treating stroke, including cognitive and motor deficits during stroke rehabilitation; facilitating neuroprotection and neurorecovery; enhancing the efficiency of cognitive and motor training, including animal skill training protocols; and treating peripheral disorders, including cardiovascular, renal, hematological, gastroenterological, liver, cancer, fertility, and metabolic disorders.

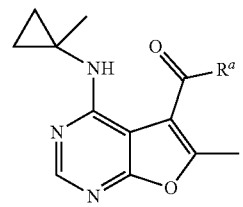

24 Claims, No Drawings

(56) References Cited

U.S. PATENT DOCUMENTS

| | | | |
|---|---|---|---|
| 9,290,511 | B2 | 3/2016 | Madge et al. |
| 2005/0004142 | A1 | 1/2005 | Adams et al. |
| 2007/0275984 | A1 | 11/2007 | Imogai et al. |
| 2008/0188525 | A1 | 8/2008 | Hallam et al. |
| 2009/0053140 | A1 | 2/2009 | Scott et al. |
| 2009/0137549 | A1 | 5/2009 | Edward et al. |
| 2010/0063047 | A1 | 3/2010 | Borchardt et al. |
| 2010/0173878 | A1 | 7/2010 | Li et al. |
| 2010/0273754 | A1 | 10/2010 | Li |
| 2012/0065200 | A1 | 3/2012 | Barbosa et al. |
| 2013/0338124 | A1 | 12/2013 | Li et al. |
| 2013/0338139 | A1 | 12/2013 | Allan et al. |
| 2014/0018361 | A1 | 1/2014 | Harriman et al. |
| 2015/0175584 | A1 | 6/2015 | Kehler et al. |
| 2015/0191463 | A1 | 7/2015 | Nagai et al. |
| 2016/0039829 | A1 | 2/2016 | Li et al. |
| 2016/0083391 | A1 | 3/2016 | Burdi et al. |
| 2016/0311831 | A1 | 10/2016 | Kehler et al. |
| 2016/0347759 | A1 | 12/2016 | Kehler et al. |
| 2017/0022186 | A1 | 1/2017 | Kehler et al. |
| 2017/0273985 | A1 | 9/2017 | Burdi et al. |
| 2017/0298072 | A1 | 10/2017 | Kehler et al. |
| 2018/0044343 | A1 | 2/2018 | Fujii et al. |
| 2019/0177327 | A1 | 6/2019 | Bookser et al. |
| 2020/0148685 | A1 | 5/2020 | Gomez et al. |

FOREIGN PATENT DOCUMENTS

| | | |
|---|---|---|
| EP | 0729758 | 9/1996 |
| EP | 0995751 | 4/2000 |
| EP | 1460077 | 9/2004 |
| EP | 2644590 | 10/2013 |
| JP | H08253484 | 10/1996 |
| WO | WO 1991/19717 | 12/1991 |
| WO | WO 1993/07149 | 4/1993 |
| WO | WO 1994/19351 | 9/1994 |
| WO | WO 1996/16657 | 6/1996 |
| WO | WO 1996/28429 | 9/1996 |
| WO | WO 1996/28448 | 9/1996 |
| WO | WO 1997/19947 | 6/1997 |
| WO | WO 2000/011002 | 3/2000 |
| WO | WO 2002/009713 | 2/2002 |
| WO | WO 2004/024082 | 3/2004 |
| WO | WO 2004/096811 | 11/2004 |
| WO | WO 2004/111054 | 12/2004 |
| WO | WO 2003/053975 | 4/2005 |
| WO | WO 2006/133261 | 12/2006 |
| WO | WO 2007/079862 | 7/2007 |
| WO | WO 2008/055959 | 5/2008 |
| WO | WO 2008/057402 | 5/2008 |
| WO | WO 2008/070095 | 6/2008 |
| WO | WO 2008/139293 | 11/2008 |
| WO | WO 2009/067166 | 5/2009 |
| WO | WO 2010/084438 | 7/2010 |
| WO | WO 2013/104598 | 7/2013 |
| WO | WO 2014/026328 | 2/2014 |
| WO | WO 2014/131855 | 9/2014 |
| WO | WO 2016/020307 | 2/2016 |
| WO | WO 2014/017643 | 7/2016 |
| WO | WO 2016/174188 | 11/2016 |
| WO | WO 2016/191935 | 12/2016 |
| WO | WO 2016/192083 | 12/2016 |
| WO | WO 2016/196071 | 12/2016 |
| WO | WO 2016/196417 | 12/2016 |
| WO | WO 2016/209749 | 12/2016 |
| WO | WO 2017/000276 | 1/2017 |
| WO | WO 2017/000277 | 1/2017 |
| WO | WO 2017/003894 | 1/2017 |
| WO | WO 2017/003895 | 1/2017 |
| WO | WO 2017/139186 | 8/2017 |
| WO | WO 2017/146116 | 8/2017 |
| WO | WO 2017/178350 | 10/2017 |

OTHER PUBLICATIONS

Alberini C.M., 2009, Transcription Factors in Long-Term Memory and Synaptic Plasticity. Physiol. Rev. 89(1) in 46 pages.

Allen et al., 2012, Exercise and Motor Training in People with Parkinson's Disease: A Systematic Review of Participant Characteristics, Intervention Delivery, Retention Rates, Adherence, and Adverse Events in Clinical Trials. Parkinsons Dis. Article ID 854328 in 15 pages.

Banerjee et al., 2012, Isothiazole and isoxazole fused pyrimidones as PDE7 inhibitors: SAR and pharmacokinetic evaluation. Bioorg Med Chem Lett. 22:3223-3228.

Banerjee et al., 2012, Imidazopyridazinones as novel PDE7 inhibitors: SAR and in vivo studies in Parkinson's disease model. Bioorg Med Chem Lett. 22(19):6286-6291.

Barnes et al., 2001, Synthesis and Structure—Activity Relationships of Guanine Analogues as Phosphodiesterase 7 (PDE7) Inhibitors. Bioorg Med Chem Lett. 11:1081-1083.

Belleville et al., 2006, Improvement of episodic memory in persons with mild cognitive impairment and healthy older adults: evidence from a cognitive intervention program. Dement Geriatr Cogn Disord. 22(5-6):486-499.

Bender et al., 2006, Cyclic nucleotide phosphodiesterases: molecular regulation to clinical use. Pharmacol Rev. 58(3):488-520.

Berge et al., 1977, Pharmaceutical salts. J Pharm Sci. 66(1):1-19.

Bevins et al., 2006, Object recognition in rats and mice: a one-trial non-matching-to-sample learning task to study 'recognition memory'. Nat Protoc. 1(3):1306-1311.

Bourtchouladze et al., 1998, Different training procedures recruit either one or two critical periods for contextual memory consolidation, each of which requires protein synthesis and PKA. Learn Mem. 5(4-5):365-374.

Bourtchouladze et al., 2003, A mouse model of Rubinstein-Taybi syndrome: Defective long-term memory is ameliorated by inhibitors of phosphodiesterase 4. PNAS USA. 100(18):10518-10522.

CAS Database Registry No. 1031631-67-0; Furo [2,3-d]pyrimidine-5-carboxylic acid, Entered STN: Jun. 29, 2008, 1 page.

Chein et al., 2010, Expanding the mind's workspace: training and transfer effects with a complex working memory span task. Psychon Bull Rev. 17(2):193-199.

Chen et al., 1996, Hippocampal lesions impair contextual fear conditioning in two strains of mice. Behav Neurosci. 110(5):1177-1180. [Best available copy].

Cheng et al., 2007, Cyclic nucleotide phosphodiesterase (PDE) inhibitors: novel therapeutic agents for progressive renal disease. Exp Biol Med (Maywood) 232(1):38-51.

Dean et al., 2000, Task-related circuit training improves performance of locomotor tasks in chronic stroke: a randomized, controlled pilot trial. Arch Phys Med Rehabil. 81(4):409-417.

De Tejada et al., 2001, The phosphodiesterase inhibitory selectivity and the in vitro and in vivo potency of the new PDE5 inhibitor vardenafil. Int J Impot Res. 13(5):282-290.

Dousa T.P., 1999, Cyclic-3',5'-nucleotide phosphodiesterase isozymes in cell biology and pathophysiology of the kidney. Kidney Int. 55(1):29-62.

Dumas et al., 2013, A review of cognition in Huntington's disease. Front Biosci (Schol Ed). Chapter 2; 29 pages.

Dyck et al., 2017, Discovery of Selective Phosphodiesterase 1 Inhibitors with Memory Enhancing Properties. J Med Chem. 60(8):3472-3483.

Endo et al., 2015, Discovery and SAR study of 2-(4-pyridylamino)thieno[3,2-d] pyrimidin-4(3H)-ones as soluble and highly potent PDE7 inhibitors. Bioorg Med Chem Lett. 25:649-653.

Fanselow M.S., 1984, Opiate modulation of the active and inactive components of the postshock reaction: parallels between naloxone pretreatment and shock intensity. Behav Neurosci. 98(2):269-277.

Fischer et al., 2007, Hand rehabilitation following stroke: a pilot study of assisted finger extension training in a virtual environment. Top Stroke Rehabil. 14(1):1-12.

(56) References Cited

OTHER PUBLICATIONS

Frankland et al., 1998, The dorsal hippocampus is essential for context discrimination but not for contextual conditioning. Behav Neurosci. 112(4):863-874.
Frazzitta et al., 2009, Rehabilitation treatment of gait in patients with Parkinson's disease with freezing: a comparison between two physical therapy protocols using visual and auditory cues with or without treadmill training. Mov Disord. 24(8):1139-1143.
Garcia et al., 2014, Modulation of cAMP-specific PDE without emetogenic activity: new sulfide-like PDE7 inhibitors. J Med Chem. 57(2):8590-8607.
Gewald et al., 2011, Synthesis and structure-activity relationship studies of dihydronaphthyridinediones as a novel structural class of potent and selective PDE7 inhibitors. Bioorg Med Chem Lett. 21(22):6652-6656.
Giese et al., 1998, Autophosphorylation at Thr286 of the alpha calcium-calmodulin kinase II in LTP and learning. Science. 279(5352):870-873.
Go et al., 2013, Heart Disease and Stroke Statistics; A Report From the American Heart Association. Circulation. 129:e28-e92.
Goldman et al., 2011, Mild Cognitive Impairment in Parkinson's Disease. Minerva Med. 102(6):441-459.
Goraya et al., 2005, Ca2+-calmodulin-dependent phosphodiesterase (PDE1): current perspectives. Cell Signal 17(7):789-797.
Gordon et al., 2004, Physical activity and exercise recommendations for stroke survivors: an American Heart Association scientific statement from the Council on Clinical Cardiology, Subcommittee on Exercise, Cardiac Rehabilitation, and Prevention; the Council on Cardiovascular Nursing; the Council on Nutrition, Physical Activity, and Metabolism; and the Stroke Council. Stroke. 35(5):1230-1240.
Hill et al., 2015, Increasing Adult Hippocampal Neurogenesis is Sufficient to Reduce Anxiety and Depression-Like Behaviors. Neuropsychopharmacology. 40(10):2368-2378.
Hummelsheim et al., 1999, Repetitive sensorimotor training for arm and hand in a patient with locked-in syndrome. Scand J Rehabil Med. 31(4):250-256.
Humphrey et al., 2014, Small-molecule phosphodiesterase probes: discovery of potent and selective CNS-penetrable quinazoline inhibitors of PDE1. Med Chem Comm. 5:1290-1298.
Jaeggi et al., 2008, Improving fluid intelligence with training on working memory. Pnas U S A. 105(19):6829-6833.
Jaeggi et al., 2011, Short- and long-term benefits of cognitive training. PNAS U S A. 108(25):10081-10086.
Jakovljevic et al., 2006, The effects of nimodipine and L-NAME on coronary flow and oxidative stress parameters in isolated rat heart. Acta Physiol Hung. 93(4):251-261.
Jankowska et al., 2017, PDE7-Selective and Dual Inhibitors: Advances in Chemical and Biological Research. Curr Med Chem. 24:673-700.
Jonsdottir et al., 2007, Concepts of motor learning applied to a rehabilitation protocol using biofeedback to improve gait in a chronic stroke patient: an A-B system study with multiple gait analyses. Neurorehabil Neural Repair 21(2):191-194.
Kakiuchi et al., 1970, Calcium dependent phosphodiesterase activity and its activating factor (PAF) from brain studies on cyclic 3',5'-nucleotide phosphodiesterase (3). Biochem Biophys Res Commun., 41(5):1104-1110.
Keefe et al., 2012, Cognitive impairment in schizophrenia. Handb Exp Pharmacol. 213:11-37.
Kempson et al., 2005, Fused pyrimidine based inhibitors of phosphodiesterase 7 (PDE7): synthesis and initial structure-activity relationships. Bioorg Med Chem Ltts. 15:1829-1833.
Keravis et al., 2012, Cyclic nucleotide phosphodiesterase (PDE) isozymes as targets of the intracellular signalling network: benefits of PDE inhibitors in various diseases and perspectives for future therapeutic developments. Br J Pharmacol. 165(5):1288-1305.
Kheirbek et al., 2012, Neurogenesis and generalization: a new approach to stratify and treat anxiety disorders. Nat Neurosci. 15(12):1613-1620.

Kim et al., 1993, Effects of amygdala, hippocampus, and periaqueductal gray lesions on short- and long-term contextual fear. Behav Neurosci. 107(6):1093-1098.
Kim et al., 2014, Effect of Dual-task Rehabilitative Training on Cognitive and Motor Function of Stroke Patients. J Phys Ther Sci. 26(1):1-6.
Klingberg et al., 2005, Computerized training of working memory in children with ADHD—a randomized, controlled trial. J Am Acad Child Adolesc Psychiatry 44(2):177-186.
Klingberg, 2010, Training and plasticity of working memory. Trends Cogn Sci. 14(7):317-324.
Kogan et al., 1996, Spaced training induces normal long-term memory in CREB mutant mice. Curr Biol. 7(1):1-11.
Krakauer J.W., 2006, Motor learning: its relevance to stroke recovery and neurorehabilitation. Curr Opin Neurol. 19:84-90.
Kwakkel et al., 1996, Predicting disability in stroke—a critical review of the literature. Age Ageing 25(6):479-489.
Laursen et al., 2017, Novel selective PDE type 1 inhibitors cause vasodilatation and lower blood pressure in rats. Br J Pharmacol. 174(15):2563-2575.
Li et al., 2016, Discovery of Potent and Selective Inhibitors of Phosphodiesterase 1 for the Treatment of Cognitive Impairment Associated with Neurodegenerative and Neuropsychiatric Diseases. J Med Chem. 59(3):1149-1164.
Litvan et al., 2012, Diagnostic Criteria for Mild Cognitive Impairment in Parkinson's Disease: Movement Disorder Society Task Force Guidelines. Mov Disord. 27(3):349-356.
Lorthiois et al., 2004, Spiroquinazolinones as novel, potent, and selective PDE7 inhibitors. Part 1. Bioorg Med Chem Lett. 14:4623-4626.
Lustig et al., 2009, Aging, training, and the brain: A review and future directions. Neuropsychol Rev. 19(4):504-522.
Maren et al., 1997, Neurotoxic lesions of the dorsal hippocampus and Pavlovian fear conditioning in rats. Behav Brain Res. 88(2):261-274.
Maren et al., 1997, Electrolytic lesions of the fimbria/fornix, dorsal hippocampus, or entorhinal cortex produce anterograde deficits in contextual fear conditioning in rats. Neurobiol Learn Mem. 67(2):142-149.
Maurice et al., 2003, Cyclic nucleotide phosphodiesterase activity, expression, and targeting in cells of the cardiovascular system. Mol Pharm. 64(3):533-546.
Medina A.E., 2011, Therapeutic Utility of Phosphodiesterase Type I Inhibitors in Neurological Conditions. Front Neurosci. 5:21 in 5 pages.
Merzenich et al., 1996, Temporal processing deficits of language-learning impaired children ameliorated by training. Science 271(5245):77-81.
Miller et al., 2009, Role of Ca2+/calmodulin-stimulated cyclic nucleotide phosphodiesterase 1 in mediating cardiomyocyte hypertrophy. Circ Res. 105(10):956-964.
Miller et al., 2011, Cyclic nucleotide phosphodiesterase 1A: a key regulator of cardiac fibroblast activation and extracellular matrix remodeling in the heart. Basic Res Cardiol. 106(6):1023-1039.
Ming et al., 2011, Adult Neurogenesis in the Mammalian Brain: Significant Answers and Significant Questions. Neuron 70(4):687-702.
Morales-Garcia et al., 2014, Silencing phosphodiesterase 7B gene by lentiviral-shRNA interference attenuates neurodegeneration and motor deficits in hemiparkinsonian mice. Neurobiol Aging. 36:1160-1173.
Morales-Garcia et al., 2016, Phosphodiesterase7 Inhibition Activates Adult Neurogenesis in Hippocampus and Subventricular Zone In Vitro and In Vivo. Stem Cells. 35(2):458-472.
Mumby D.G., 2001, Perspectives on object-recognition memory following hippocampal damage: lessons from studies in rats. Behav Brain Res. 127(1-2):159-181.
Murray et al., 2007, Expression and activity of cAMP phosphodiesterase isoforms in pulmonary artery smooth muscle cells from patients with pulmonary hypertension: role for PDE1. Am J Physiol Lung Cell Mol Physiol., 292(1):L294-L303.

(56) References Cited

OTHER PUBLICATIONS

Nakayama et al., 1994, Recovery of upper extremity function in stroke patients: the Copenhagen Stroke Study. Arch Phys Med Rehabil. 75(4):394-398.

Ngyyen et al., 2000, Strain-dependent Differences in LTP and Hippocampus-dependent Memory in Inbred Mice. Learn Mem. 7(3):170-179.

Nishi et al., 2010, Advanced research on dopamine signaling to develop drugs for the treatment of mental disorders: biochemical and behavioral profiles of phosphodiesterase inhibition in dopaminergic neurotransmission. J Pharmacol Sci.114:6-16.

Oujamaa et al., 2009, Rehabilitation of arm function after stroke. Literature review. Ann Phys Rehabil Med. 52(3):269-293.

Owen et al., 2010, Putting brain training to the test. Nature 465:775-778.

Park et al., 2009, The Adaptive Brain: Aging and Neurocognitive Scaffolding.Ann Rev Psych. 60:173-196.

Phillips et al., 1992, Differential contribution of amygdala and hippocampus to cued and contextual fear conditioning. Behav Neurosci. 106(2):274-285.

Pitts et al., 2004, Identification of purine inhibitors of phosphodiesterase 7 (PDE7). Bioorg Med Chern Lett. 14:2955-2958.

Ramirez et al., 2014, Regulation of dopamine signaling in the striatum by phosphodiesterase inhibitors: novel therapeutics to treat neurological and psychiatric disorders. Cent Nerv Syst Agents Med Chem 14(2):72-82.

Reed et al., 2002, Phosphodiesterase 1B knock-out mice exhibit exaggerated locomotor hyperactivity and DARPP-32 phosphorylation in response to dopamine agonists and display impaired spatial learning. J Neurosci. 22(12):5188-5197.

Rider et al., 1991, Effects of massed versus distributed practice on gross and fine motor proficiency of educable mentally handicapped adolescents. Percept Mot Skills. 73(1):219-224.

Robinson et al., 1996, Discovery of the hemifumarate and (alpha-L-alanyloxy)methyl ether as prodrugs of an antirheumatic oxindole: prodrugs for the enolic OH group. J Med Chem. 39(1):10-18.

Sanberg et al., 1998, The catalepsy test: its ups and downs. Behav Neurosci. 102(5):748-759.

Sancesario et al., 2004, Down-regulation of nitrergic transmission in the rat striatum after chronic nigrostriatal deafferentation. Eur J Neurosci. 20(4):989-1000.

Sasaki et al., 2004, Transcriptional activation of phosphodiesterase 7B1 by dopamine D1 receptor stimulation through the cyclic AMP/cyclic AMP-dependent protein kinase/cyclic AMP-response element binding protein pathway in primary striatal neurons. J Neurochem. 89(2):474-483.

Schermuly et al., 2007, Phosphodiesterase 1 upregulation in pulmonary arterial hypertension: target for reverse-remodeling therapy. Circulation. 115(17):2331-2339.

Schmidt C.J., 2010, Phosphodiesterase Inhibitors as Potential Cognition Enhancing Agents. Curr Top Med Chem. 10(2):222-230.

Sharma et al., 2006, Regulation of calmodulin-stimulated cyclic nucleotide phosphodiesterase (PDE1): review. Int J Mol Med. 18(1):95-105.

Shors et al., 2001, Neurogenesis in the adult is involved in the formation of tracememories. Nature 410(6826):372-376.

Shors et al., 2004, Memory traces of trace memories: neurogenesis, synaptogenesis and awareness. Trends Neurosci. 27(5):250-256.

Silva et al., 1996, Impaired learning in mice with abnormal short-lived plasticity. Curr Biol. 6(11):1509-1518.

Silver et al., 1994, Cyclic GMP potentiation by WIN 58237, a novel cyclic nucleotide phosphodiesterase inhibitor. J Pharmacol Exp Ther., 271(3):1143-1149.

Teng et al., 2000, Contrasting effects on discrimination learning after hippocampal lesions and conjoint hippocampal-caudate lesions in monkeys. J Neurosci. 20(10):3853-3863.

Terrett et al., 1996, Sildenafil (VIAGRATM), a potent and selective inhibitor of type 5 cGMP phosphodiesterase with utility for the treatment of male erectile dysfunction. Bioorg. Med. Chem. Lett., 6(15):1819-1824.

Tsao et al., 2010, Motor training of the lumbar paraspinal muscles induces immediate changes in motor coordination in patients with recurrent low back pain. J Pain 11(11):1120-1128.

Vergne et al., 2004, Discovery of thiadiazoles as a novel structural class of potent and selective PDE7 inhibitors. Part 1: design, synthesis and structure-activity relationship studies. Bioorg Med Chem Lett. 14(18):4607-4613.

Vergne et al., 2004, Discovery of thiadiazoles as a novel structural class of potent and selective PDE7 inhibitors. Part 2: metabolism-directed optimization studies towards orally bioavailable derivatives. Bioorg Med Chem Lett. 14, 4615-4621.

Vitolo et al., 2002, Amyloid B-peptide inhibition of the PKA/CREB pathway and long-term potentiation: Reversibility by drugs that enhance cAMP signaling. PNAS U.S.A. 99(20):13217-13221.

Volpe et al., 2008, Intensive sensorimotor arm training mediated by therapist or robot improves hemiparesis in patients with chronic stroke. Neurorehabil Neural Repair. 22(3):305-310.

Wang et al., 2010, Cyclic Nucleotide Signaling in Polycystic Kidney Disease. Kidney Int. 77(2):129-140.

Wang et al., 2015, Phosphodiesterase: an interface connecting cognitive deficits to neuropsychiatric and neurodegenerative diseases. Curr Pharm Des. 21(3):303-316.

Wang et al., 2017, Generation and phenotypic characterization of Pde1a mutant mice. PLoS One 12(7):e0181087 in 19 pages.

Whitall et al., 2000, Repetitive bilateral arm training with rhythmic auditory cueing improves motor function in chronic hemiparetic stroke. Stroke 31(1):2390-2395.

International Search Report and Written Opinion dated Feb. 26, 2019 for Application No. PCT/US2018/062493, filed Nov. 26, 2018.

He et al., 2017, The Selection of a Pharmaceutical Salt—the Effect of the Acidity of the Counterion on Its Solubility and Potential Biopharmaceutical Performance; J Pharma Sciences (2018) 107: 419-425; avail. Online Oct. 28, 2017.

Nakayamada et al., Chemical JAK inhibitors for the treatment of rheumatoid arthritis. Exp Opin Pharmacother. (2016) 17(16):2215-25.

\* cited by examiner

SUBSTITUTED FURANOPYRIMIDINE COMPOUNDS AS PDE1 INHIBITORS

CROSS REFERENCE TO RELATED APPLICATIONS

This application is U.S. National Phase under 35 U.S.C. § 371 of International Application No. PCT/US2018/062493, filed Nov. 26, 2018, designating the U.S. and published in English as International Pub. No. WO 2019/104285, which claims the benefit of U.S. Provisional Application No. 62/591,105, filed Nov. 27, 2017, each of which is incorporated herein by reference in its entirety.

BACKGROUND

Field

The present invention relates to certain substituted furanopyrimidine compounds and related chemical entities; compositions containing them; processes for making them; and their use in various methods and therapies, including the enhancement of neuroplasticity, and the treatment of neurological, cognitive, cardiovascular, gastrointestinal, renal disorders, and other conditions and diseases involving PDE1, dopaminergic, or cyclic nucleotide signaling.

Description of the Related Technology

The cyclic nucleotides, adenosine and guanosine 3',5'-cyclic monophosphate (cAMP and cGMP) are second messengers in cellular signaling cascades activated by diverse transduction pathways, such as those triggered by neurotransmitters and hormones. See, e.g., Kelly and Brandon, 2009, *Prog. Brain Res.* 179, 67-73; Schmidt, 2010, *Curr. Top. Med. Chem.* 10, 222-230. Once generated, cAMP and cGMP transmit their signals through various tertiary effectors, such as cAMP dependent protein kinase (PKA), cGMP dependent protein kinase (PKG), and other proteins. In turn, these effectors modulate additional targets in downstream cascades, such as enzymes and transcription factors, ultimately resulting in cellular changes that impact numerous physiological processes, including neuronal plasticity and survival, muscle contraction, sensory transduction, cell division, stress response, and inflammation.

Cyclic nucleotide levels are subject to tight regulatory controls, including the action of phosphodiesterases (PDEs), a superfamily of intracellular enzymes that hydrolyze cAMP and cGMP to their inactive non-cyclic forms, 5'-AMP and 5'-GMP. See, e.g., Bender and Beavo, 2006, *Pharmacol. Rev.* 58, 488-520. Mammalian PDEs can be divided into 11 families, PDE1-11, based on structural, biochemical, and pharmacological properties. Some are cAMP-selective hydrolases (PDE4, 7, and 8), some are cGMP-selective hydrolases (PDE5, 6, and 9), and some hydrolyze both cAMP and cGMP (PDE1, 2, 3, 10, and 11). By regulating cAMP and cGMP levels, PDEs play a key role in modulating cyclic nucleotide cascades, and they have become desirable targets for treating various diseases and disorders due to their different tissue distribution and functional properties. See, e.g., Keravis and Lugnier, 2001, *Br. J. Pharmacol.* 165, 1288-1305. Alterations in cyclic nucleotide concentrations, for example, can impact biochemical and physiological process linked to cognitive function (Kelly and Brandon, 2009, *Prog. Brain Res.* 179, 67-73; Schmidt, 2010, *Curr. Top. Med. Chem.* 10, 222-230; Perez-Gonzalez et al., 2013, *Neurobiol. Aging.* 34, 2133-2145; Lipina et al., 2013, *Neuropharmacology* 64, 295-214; Morales-Garcia et al., 2016, *Stem Cells.* 35, 458-472).

The PDE1 family, which hydrolyzes both cAMP and cGMP, is distinguished from other PDEs by requiring calcium ($Ca^{2+}$) and calmodulin (CaM) for full activation (Goraya and Cooper, 2005, *Cell. Signal.* 17, 789-797). The binding of $Ca^{2+}$-CaM complexes at sites near the N-terminus of PDE1 stimulates hydrolysis of cyclic nucleotides. In intact cells, PDE1 is almost exclusively activated by $Ca^{2+}$ entering the cell from the extracellular space. PDE1 is therefore a point of convergence and integration for multiple signaling pathways that regulate numerous downstream targets and cellular events. For review, see Bender and Beavo, 2006, *Pharmacol. Rev.* 58, 488-520; Sharma et al., 2006, *Int. J. Mol. Med.* 18, 95-105.

The PDE1 family comprises three members, encoded by separate genes (pde1a, pde1b, and pde1c) that give rise to multiple isoforms via alternative splicing and differential transcription. All PDE1 enzymes appear to hydrolyze both cAMP and cGMP, although they can differ in their relative affinities for each, as well as their relative affinities for calcium and CaM. For review, see Bender and Beavo, 2006, *Pharmacol. Rev.* 58, 488-520. PDE1 isoforms show distinct but overlapping patterns of expression throughout the body. In the brain, PDE1 is expressed in numerous regions, including the striatum, cerebral cortex, frontal lobe, hippocampus, cerebellum, and amygdala. Brain expression patterns of PDE1B correlate closely with that of dopamine receptors, implicating PDE1 in the modulation of dopamine signaling, a role supported by experiments in PDE1B knockout mice (Reed et al., 2002, *J. Neurosci.* 22, 5188-5197). Outside the brain, PDE1 is expressed in numerous areas, including muscle, heart, kidney, pancreas, lungs, stomach, and liver. In the cardiovascular system, PDE1 appears to play a central role in organizing cAMP microdomains and mediating hormonal specificity in cardiac cells. See Maurice et al., 2003, *Mol. Pharm.* 64, 533-546.

Such properties implicate PDE1 in numerous physiological and pathological processes. Alterations in cyclic nucleotide signaling pathways, including those involving PDE1, are implicated in various disorders of the brain, such as depression, schizophrenia and cognitive disorders. See, e.g., Keravis and Lugnier, 2012, *Br. J. Pharmacol.* 165, 1288-1305. Inhibiting PDE1 activity in the nervous system, for example, can increase cAMP or cGMP levels and consequently induce expression of neuronal plasticity-related genes, neurotrophic factors, and neuroprotective molecules. Similarly, PDE1 enzymes and cyclic nucleotides have been implicated in the etiology of vascular disorders, such as hypertension, myocardial infarction, and heart failure, as well as the development and progression of renal disease. See, e.g., Miller et al., 2011, *Basic Res. Cardiol.* 106, 1023-1039; Miller et al, 2009, *Circ. Res.* 105, 956-964; Wang et al., 2010, *Kidney Int.* 77. 129-140; Cheng et al., 2007, *Soc. Exp. Biol. Med.* 232, 38-51; Dousa, 1999, *Kidney Int.* 55, 29-62.

These and other studies highlight the interest in PDE1 as a target for treating numerous disorders and modulating physiological processes, such as cognition. There is a substantial need for PDE1 inhibitors with desirable pharmacological and therapeutic properties, such as effective potency, exposure, selectivity, and safety. The present invention addresses these and other needs in the art by disclosing substituted furanopyrimidine chemical entities as potent, selective, and well-tolerated PDE1 inhibitors.

SUMMARY

The present disclosure relates to substituted furanopyrimidine chemical entities; compositions including such entities; processes for making them; and their use in various methods, including the treatment of neurological and peripheral disorders associated with PDE1, as disclosed herein.

Some embodiments provide a chemical entity of Formula (I), and more specifically, a compound, or pharmaceutically acceptable salt of a compound of Formula (I):

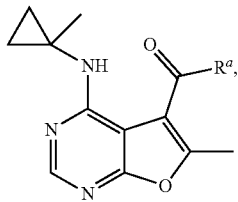
(I)

wherein $R^a$ has any of the values described herein.

In some embodiments, a chemical entity of Formula (I) is a chemical entity of Formula (Ia), or more specifically, a compound or a pharmaceutically acceptable salt of a compound of Formula (Ia):

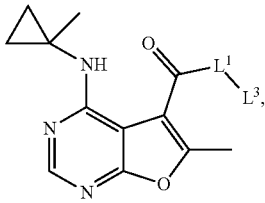
(Ia)

wherein $L^1$ and $L^3$ have any of the values described herein

In some embodiments, a chemical entity of Formula (I) is a chemical entity of Formula (Tb), or more specifically, a compound or a pharmaceutically acceptable salt of a compound of Formula (Tb):

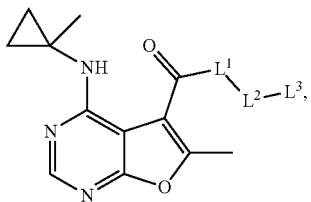
(Ib)

wherein $L^1$, $L^2$, and $L^3$ have any of the values described herein.

In some embodiments, a chemical entity of Formula (I) is a chemical entity of Formula (Iba), or more specifically, a compound or a pharmaceutically acceptable salt of a compound of Formula (Iba):

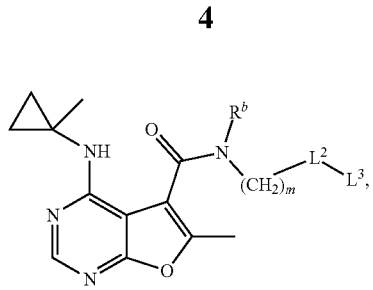
(Iba)

wherein $L^2$, $L^3$, m and $R^b$ have any of the values described herein.

In some embodiments, a chemical entity of Formula (I) is a chemical entity of Formula (Ibb), or more specifically, a compound or a pharmaceutically acceptable salt of a compound of Formula (Ibb):

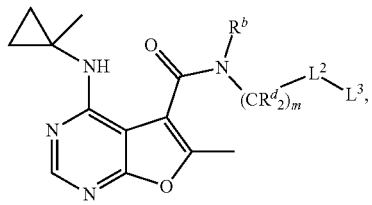
(Ibb)

wherein $L^2$, $L^3$, m, $R^d$ and $R^b$ have any of the values described herein.

In some embodiments, a chemical entity of Formula (I) is a chemical entity of Formula (Ic), or more specifically, a compound or a pharmaceutically acceptable salt of a compound of Formula (Ic):

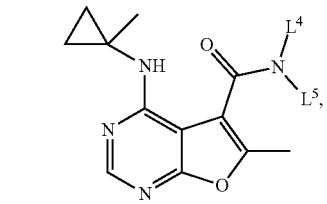
(Ic)

wherein $L^4$ and $L^5$ have any of the values described herein.

In some embodiments, a chemical entity of Formula (I) is a chemical entity of Formula (Icaa) or (Icab), or more specifically, a compound or a pharmaceutically acceptable salt of a compound of Formula (Icaa) or (Icab):

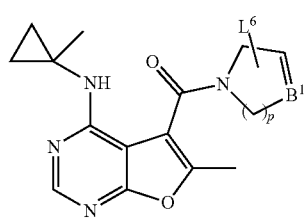
(Icaa)

or

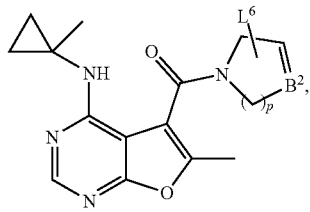
(Icab)

wherein $L^6$, $B^1$, $B^2$, and p have any of the values described herein.

In some embodiments, a chemical entity of Formula (I) is a chemical entity of Formula (Icb), or more specifically, a compound or a pharmaceutically acceptable salt of a compound of Formula (Icb):

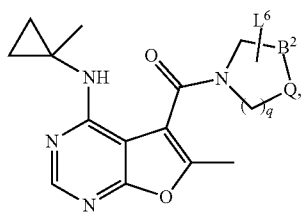
(Icb)

wherein $L^6$, $B^2$, Q, and q have any of the values described herein.

In some embodiments, a chemical entity of Formula (I) is a chemical entity of Formula (Icc), or more specifically, a compound or a pharmaceutically acceptable salt of a compound of Formula (Icc):

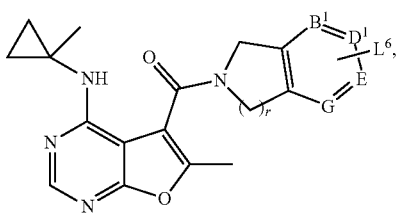
(Icc)

wherein $L^6$, $B^1$, $D^1$, E, G, and r have any of the values described herein.

In some embodiments, the chemical entity is selected from any of the species described or exemplified herein, and more particularly, is a compound, or pharmaceutically acceptable salt thereof.

In some embodiments, the chemical entities, and compositions including such entities, are used in a wide range of methods, as described herein. In some embodiments, the methods include metabolic and reaction kinetic studies, detection and imaging techniques, and radioactive treatments. In some embodiments, the methods include inhibiting PDE1, treating disorders that are mediated by PDE1, treating disorders characterized by alterations in dopamine signaling, enhancing neuronal plasticity, conferring neuroprotection, and promoting neurogenesis. In some embodiments, the methods include treating neurological disorders, particularly CNS disorders, and more particularly, mental and psychiatric disorders, cognitive disorders, movement disorders, and neurodegenerative disorders. In some embodiments, the methods are directed to treating peripheral disorders, including cardiovascular, renal, hematological, gastrointestinal, liver, fertility, cancer, and metabolic disorders.

In some embodiments, the chemical entities, and compositions including such entities, are useful as augmenting agents to increase the efficiency of cognitive and motor training, including training during post-stroke rehabilitation or post-traumatic brain injury (TBI) rehabilitation; and to increase the efficiency of non-human animal training protocols.

The disclosure is further directed to the general and specific embodiments defined, respectively, and by the independent and dependent claims appended hereto, which are incorporated by reference herein. Additional embodiments, features, and advantages of the disclosure will be apparent from the following detailed description and through practice of the exemplary embodiments.

DETAILED DESCRIPTION

The invention may be more fully appreciated by reference to the following description, including the examples. Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described herein. In addition, the materials, methods, and examples are illustrative only and not intended to be limiting.

For the sake of brevity, all publications, including patent applications, patents, and other citations mentioned herein, are incorporated by reference in their entirety. Citation of any such publication, however, shall not be construed as an admission that it is prior art to the present invention.

Terms and Definitions

The use of headings and subheadings provided in the sections of this specification is solely for convenience of reference and does not limit the various embodiments herein, which are to be construed by reference to the specification as a whole.

General

As used herein, the term "about" or "approximately" means within an acceptable range for a particular value as determined by one skilled in the art, and may depend in part on how the value is measured or determined, e.g., the limitations of the measurement system or technique. For example, "about" can mean a range of up to 20%, up to 10%, up to 5%, or up to 1% or less on either side of a given value. To provide a more concise description, some of the quantitative expressions given herein are not qualified with the term "about." It is understood that, whether the term "about" is used explicitly or not, every quantity given herein is meant to refer to both the actual given value and the approximation of such given value that would reasonably be inferred based on the ordinary skill in the art, including equivalents and approximations due to the experimental and/or measurement conditions for such given value. Accordingly, for any embodiment of the invention in which a numerical value is prefaced by "about" or "approximately", the disclosure includes an embodiment in which the exact value is recited. Conversely, for any embodiment of the invention in which a numerical value is not prefaced by "about" or "approximately", the disclosure includes an embodiment in which the value is prefaced by "about" or "approximately".

As used herein, the terms "a," "an," and "the" are to be understood as meaning both singular and plural, unless explicitly stated otherwise. Thus, "a," "an," and "the" (and grammatical variations thereof where appropriate) refer to one or more.

Furthermore, although items, elements or components of the embodiments may be described or claimed in the singular, the plural is contemplated to be within the scope thereof, unless limitation to the singular is explicitly stated.

The terms "comprising" and "including" are used herein in their open, non-limiting sense. Other terms and phrases used in this document, and variations thereof, unless otherwise expressly stated, should be construed as open ended, as opposed to limiting. As examples of the foregoing: the term "example" is used to provide exemplary instances of the item in discussion, not an exhaustive or limiting list thereof; adjectives such as "conventional," "normal," "known" and terms of similar meaning should not be construed as limiting the item described to a given time period or to an item available as of a given time, but instead should be read to encompass conventional, or normal technologies that may be available or known now or at any time in the future. Likewise, where this document refers to technologies that would be apparent or known to one of ordinary skill in the art, such technologies encompass those apparent or known to the skilled artisan now or at any time in the future.

As will become apparent to one of ordinary skill in the art after reading this document, the illustrated embodiments and their various alternatives may be implemented without confinement to the illustrated examples.

Chemical Terms

The term "alkyl" refers to a fully saturated aliphatic hydrocarbon group (i.e., contains no double or triple bonds). The alkyl moiety may be a straight- or branched-chain alkyl group having from 1 to 12 carbon atoms in the chain, and more particularly, has 1, 2, 3, 4, 5, 6, 7, 8, 9, 10, 11, or 12 carbons in the chain. Preferably, the alkyl moiety is —$C_{1-6}$alkyl, and more preferably is $C_{1-4}$alkyl. Examples of alkyl groups include, but are not limited to, methyl (Me, which also may be structurally depicted by the symbol, "—"), ethyl (Et), n-propyl, isopropyl, butyl, isobutyl, sec-butyl, tert-butyl (tBu), pentyl, isopentyl, tert-pentyl, hexyl, and isohexyl. Alkyl groups may be optionally substituted with one or more substituents including, but not limited to, hydroxyl, alkoxy, thioalkoxy, amino, aminoalkyl, and cyano.

The term "alkenyl" refers to unsaturated acyclic aliphatic moieties having at least one carbon-carbon double bond. The term alkenyl includes all possible geometric isomers including E and Z isomers of said alkenyl moiety unless specifically indicated. Examples of alkenyl radicals include ethenyl, propenyl, butenyl, 1,4-butadienyl, and the like.

The term "alkynyl" refers to optionally substituted unsaturated acyclic aliphatic moieties having at least one carbon-carbon triple bond. Examples of alkynyl radicals include ethynyl, propynyl, butynyl and the like.

The term "haloalkyl" refers to a straight- or branched-chain alkyl group having from 1 to 12 carbon atoms in the chain substituting one or more hydrogens with halogens. Examples of haloalkyl groups include, but are not limited to, —$CF_3$, —$CHF_2$, —$CH_2F$, —$CH_2CF_3$, —$CH_2CHF_2$, —$CH_2CH_2F$, —$CH_2CH_2Cl$, and —$CH_2CF_2CF_3$.

The term "alkoxy" includes a straight chain or branched alkyl group with an oxygen atom linking the alkyl group to the rest of the molecule. Examples of alkoxy groups include, but are not limited to, methoxy, ethoxy, propoxy, iso-propoxy, butoxy, t-butoxy, and pentoxy. "Aminoalkyl," "thioalkyl," and "sulfonylalkyl" are analogous to alkoxy, replacing the terminal oxygen atom of alkoxy with, respectively, NH (or NR), S, and $SO_2$ where R is selected from hydrogen, $C_{1-6}$alkyl, $C_{2-6}$alkenyl, $C_{2-6}$alkynyl, $C_{3-7}$cycloalkyl, phenyl, 5-, 6-, 9-, or 10-membered heteroaryl, and 5-10 membered heterocycloalkyl, as defined herein.

The term "haloalkoxy" refers to alkoxy groups substituting one or more hydrogens with halogens. Examples of haloalkoxy groups include, but are not limited to, —$OCF_3$, —$OCHF_2$, —$OCH_2F$, —$OCH_2CF_3$, —$OCH_2CHF_2$, —$OCH_2CH_2Cl$, —$OCH_2CF_2CF_3$, and —$OCH(CH_3)CHF_2$.

The term "amino group" refers to an —$NH_2$ group.

The term "cyano" refers to the group —CN.

The term "aryl" refers to a monocyclic, or fused or spiro polycyclic, aromatic carbocycle (ring structure having ring atoms that are all carbon), having from 3 to 15 ring atoms per ring (carbon atoms in aryl groups are $sp^2$ hybridized). Illustrative examples of aryl groups include the following moieties:

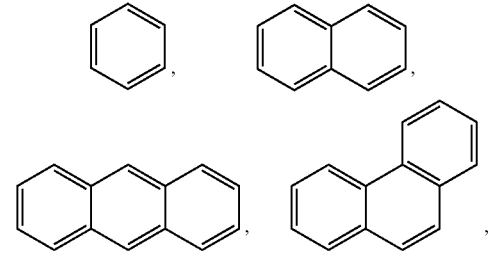

and the like.

The term "phenyl" represents the following moiety:

The term "aryloxy" refers to a group having the formula, —O—R, wherein R is an aryl group.

The term "cycloalkyl" refers to a fully saturated or partially saturated carbocycle, such as monocyclic, fused polycyclic, bridged monocyclic, bridged polycyclic, spirocyclic, or spiro polycyclic carbocycle having from 3 to 15 ring atoms per carbocycle. Where the term cycloalkyl is qualified by a specific characterization, such as monocyclic, fused polycyclic, bridged polycyclic, spirocyclic, and spiro polycyclic, then such term cycloalkyl refers only to the carbocycle so characterized. Illustrative examples of cycloalkyl groups include the following entities, in the form of properly bonded moieties:

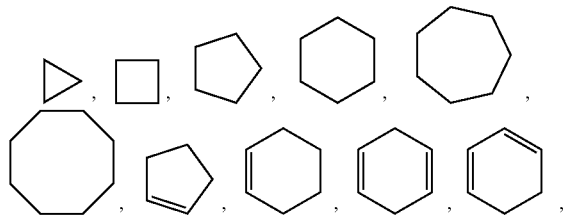

-continued

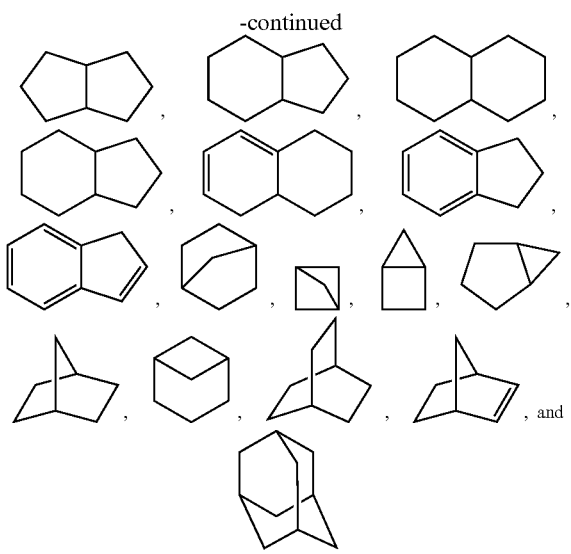

A "heterocycloalkyl" refers to a monocyclic, or fused, bridged, or spiro polycyclic ring structure that is fully saturated or partially saturated and includes at least one heteroatom selected from nitrogen, oxygen, and sulfur in the ring backbone. A heterocycloalkyl may have any degree of saturation provided that at least one ring in a polycyclic ring structure is not aromatic. The heteroatom(s) may be present in either a non-aromatic or aromatic ring in the polycyclic structure. The heterocycloalkyl group may have 3 to 20 ring members (i.e., the number of atoms making up the ring backbone, including carbon atoms and heteroatoms), although the present definition also covers the occurrence of the term "heterocycloalkyl" where no numerical range is designated. The heterocycloalkyl group may be designated as "3-15-membered heterocycloalkyl," "4-10-membered heterocycloalkyl," "3-15-membered $C_{2-14}$heterocycloalkyl," "5-9-membered $C_{4-8}$heterocycloalkyl," "5-10-membered $C_{4-9}$heterocycloalkyl," "5-membered $C_{3-4}$heterocycloalkyl," "6-membered $C_{4-5}$heterocycloalkyl," "7-membered $C_{5-6}$heterocycloalkyl," "bicyclic or tricyclic 9-15-membered $C_{8-14}$heterocycloalkyl," "monocyclic or bicyclic 3-10-membered $C_{2-9}$heterocycloalkyl," "bicyclic 8-10-membered $C_{4-9}$heterocycloalkyl," "bicyclic 8-10-membered $C_{5-9}$heterocycloalkyl," "monocyclic 4-7-membered $C_{3-6}$ heterocycloalkyl," "monocyclic 5-6-membered $C_{3-5}$ heterocycloalkyl," or similar designations. The heterocycloalkyl may be a 5-10 membered ring or ring system comprising one to four heteroatoms each independently selected from nitrogen, oxygen, and sulfur. The heterocycloalkyl may be a monocyclic five-membered ring comprising one to three heteroatoms each independently selected from nitrogen, oxygen, and sulfur. The heterocycloalkyl may be a monocyclic six-membered ring comprising one to three heteroatoms each independently selected from nitrogen, oxygen, and sulfur. The heterocycloalkyl may be a bicyclic nine-membered ring comprising one to three heteroatoms each independently selected from nitrogen, oxygen, and sulfur. The heterocycloalkyl may be a bicyclic ten-membered ring comprising one to three heteroatoms each independently selected from nitrogen, oxygen, and sulfur. The heterocycloalkyl may be optionally substituted. Illustrative unsubstituted heterocycloalkyl entities, in the form of properly bonded moieties, include:

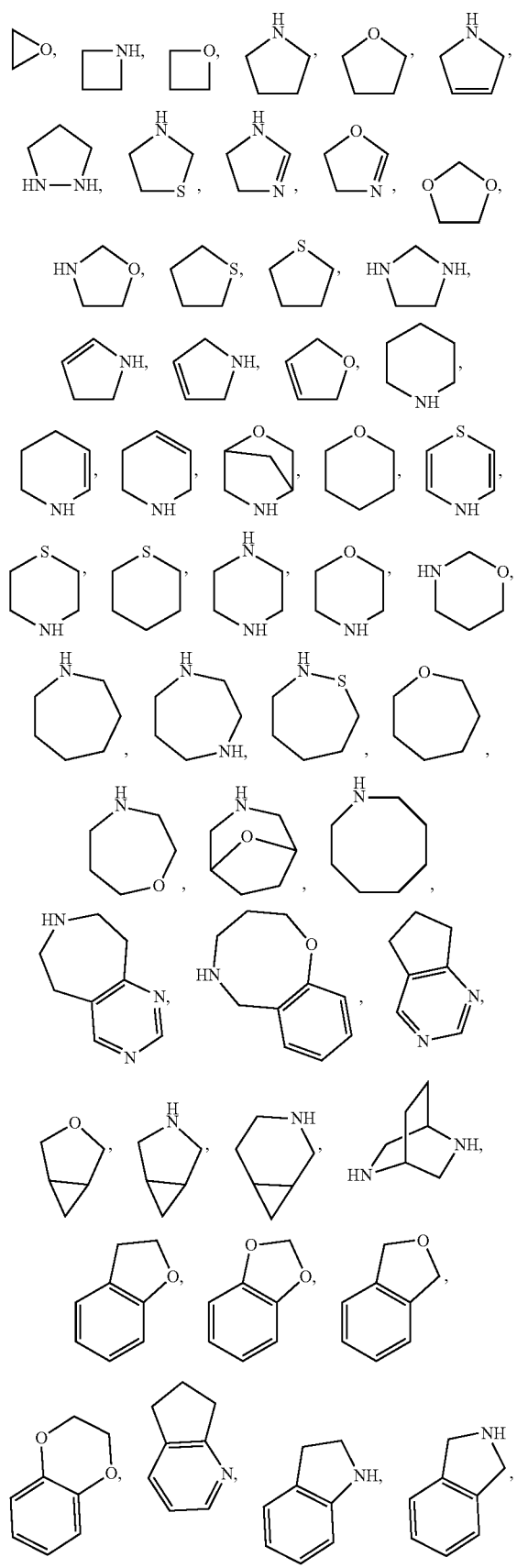

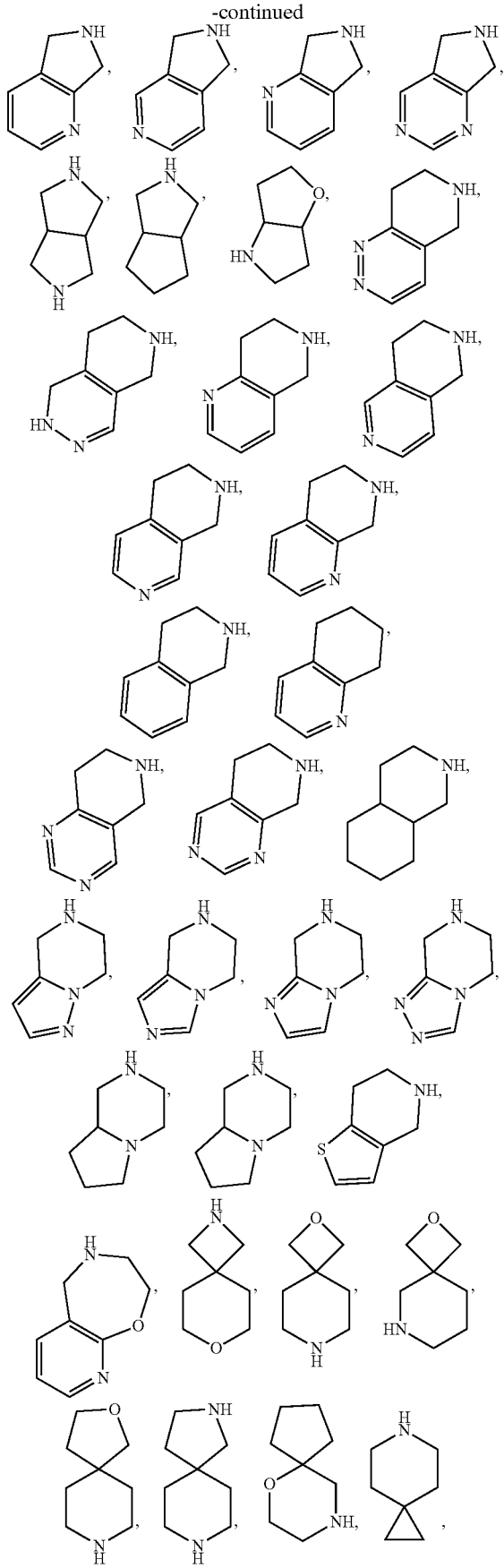
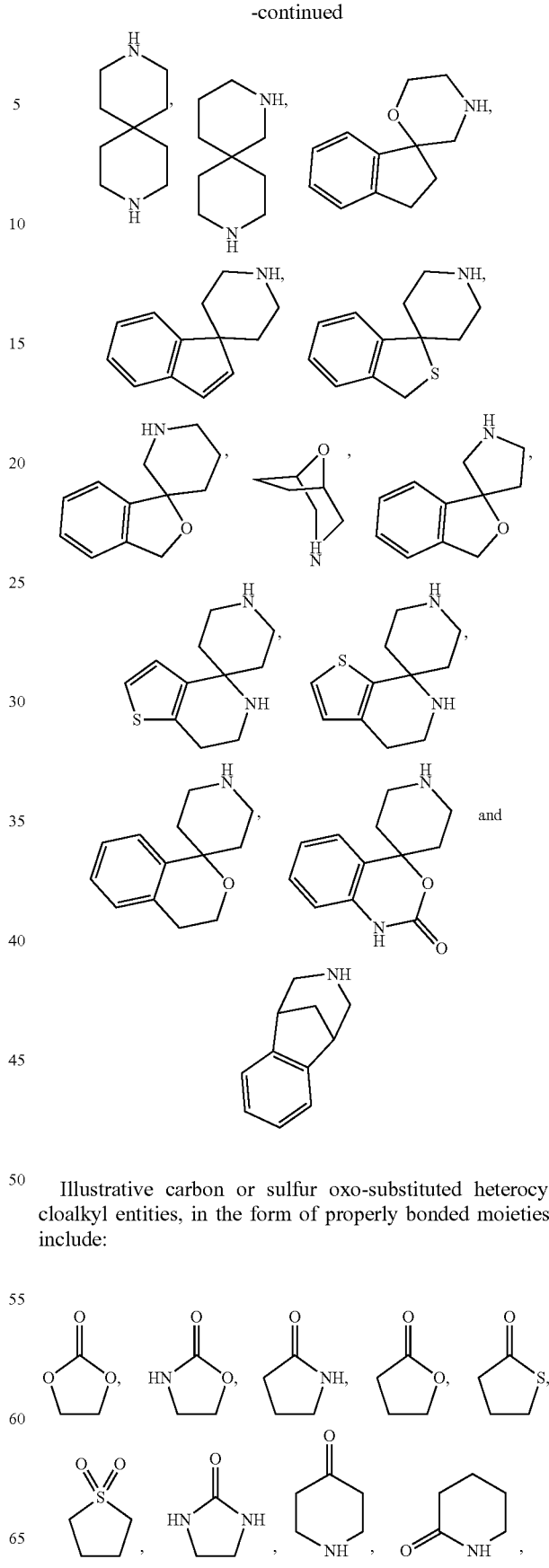
Illustrative carbon or sulfur oxo-substituted heterocycloalkyl entities, in the form of properly bonded moieties, include:

10 ring members or 5 to 7 ring members. The heteroaryl group may be designated as "5-9-membered heteroaryl," "5-10-membered heteroaryl," "5-9-membered $C_{4-8}$heteroaryl," "5-10-membered $C_{4-9}$heteroaryl," "5-6-membered $C_{3-5}$heteroaryl," "6-membered $C_{4-5}$heteroaryl," "5-membered $C_{3-4}$heteroaryl," or similar designations. The heteroaryl may be a 5-10 membered ring or ring system comprising one to four heteroatoms each independently selected from nitrogen, oxygen, and sulfur. The heteroaryl may be a monocyclic five-membered ring comprising one to four heteroatoms each independently selected from nitrogen, oxygen, and sulfur. The heteroaryl may be a monocyclic six-membered ring comprising one to four heteroatoms each independently selected from nitrogen, oxygen, and sulfur. The heteroaryl may be a bicyclic nine-membered ring comprising one to four heteroatoms each independently selected from nitrogen, oxygen, and sulfur. The heteroaryl may be a bicyclic ten-membered ring comprising one to four heteroatoms each independently selected from nitrogen, oxygen, and sulfur. In some embodiments, the heteroaryl may be a tautomer of a heterocycloalkyl where the heteroaryl is the predominate form under equilibrium conditions. Illustrative examples of heteroaryl groups include the following entities, in the form of properly bonded moieties:

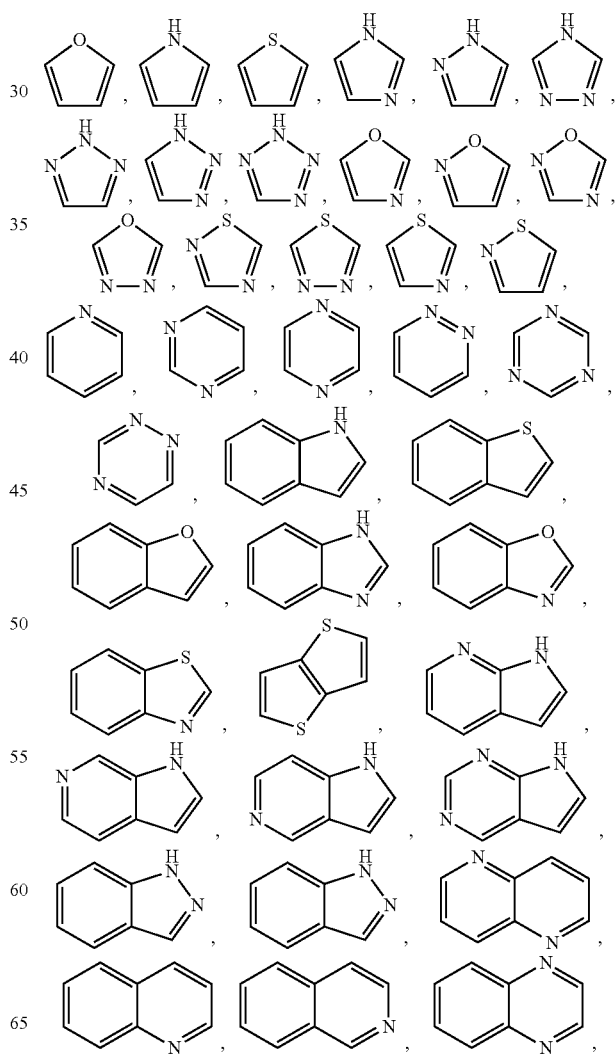

The term "heteroaryl" refers to an aromatic monocyclic, fused bicyclic, or fused polycyclic ring or ring system having one or more heteroatoms selected from nitrogen, oxygen, and sulfur in the ring backbone. When the heteroaryl is a ring system each ring in the ring system is fully unsaturated. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to

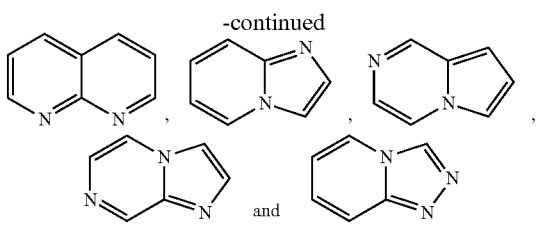

A "cycloalkoxy" refers to a monocyclic, or fused, bridged, or spiro polycyclic ring structure that is fully saturated or partially saturated having at least two carbons and at least one oxygen in the ring backbone. A cycloalkoxy may have any degree of saturation provided that at least one ring in a polycyclic ring structure is not aromatic. The oxygen may be present in the non-aromatic or aromatic ring in the polycyclic structure. The cycloalkoxy group may have 3 to 20 ring members (i.e., the number of atoms making up the ring backbone, including carbon atoms and heteroatoms), although the present definition also covers the occurrence of the term "cycloalkoxy" where no numerical range is designated. The cycloalkoxy group may be designated as "3-15 membered cycloalkoxy," "4-10 membered cycloalkoxy," "3-15 membered $C_{2-14}$cycloalkoxy," "5-9 membered $C_{4-8}$cycloalkoxy," "5-10 membered $C_{4-9}$cycloalkoxy," "5-membered $C_{3-4}$cycloalkoxy," "6-membered $C_{4-5}$cycloalkoxy," "7-membered $C_{5-6}$cycloalkoxy," or similar designations. The cycloalkoxy may be a 5-10 membered ring or ring system comprising one oxygen and the remainder carbon in the ring backbone. The cycloalkoxy may be optionally substituted. Illustrative unsubstituted cycloalkoxy entities, in the form of properly bonded moieties, include:

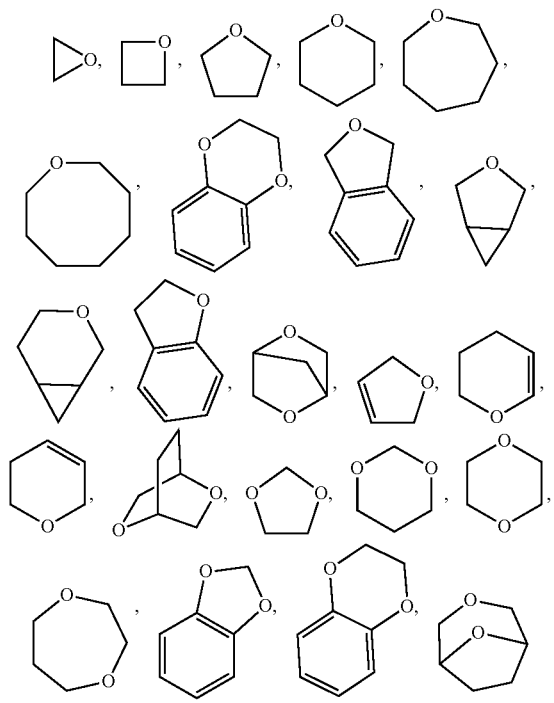

Those skilled in the art will recognize that the species of aryl, cycloalkyl, heterocycloalkyl, and heteroaryl groups listed or illustrated above are not exhaustive, and that additional species within the scope of these defined terms may also be selected.

The term "halogen" represents chlorine, fluorine, bromine or iodine. The term "halo" represents chloro, fluoro, bromo or iodo.

The term "heteroatom" used herein refers to, for example, O (oxygen), S (sulfur), or N (nitrogen).

By "optional" or "optionally" is meant that the subsequently described event or circumstance may or may not occur, and that the description includes instances where the event or circumstance occurs and instances or circumstances where it does not. For example, "optionally substituted alkyl" encompasses both "unsubstituted alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

The term "substituted" means that the specified group or moiety bears one or more substituents. A substituted group is derived from the unsubstituted parent group in which there has been an exchange of one or more hydrogen atoms for another atom or group or derived from the unsubstituted parent group in which there has been an addition of one or more atoms or group to a carbon, nitrogen or sulfur. Where the term "substituted" is used to describe a structural system, unless specified otherwise, the substitution is meant to occur at any valency-allowed position on the system. The term "unsubstituted" means that the specified group bears no substituents.

For simplicity, groups described herein that are capable of more than one point of attachment (i.e., divalent, trivalent, polyvalent) may be referred to with a common term. For example, the term "$C_{3-10}$cycloalkyl" can be used to describe a three to ten membered cycloalkyl group ($L^3$) that is monovalent, as in -$L^1$-$L^3$, wherein $L^3$ has one point of attachment, and that can also be divalent ($L^2$), as in -$L^1$-$L^2$-$L^3$, wherein $L^2$ has two points of attachment.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_2$-$C_6$ alkenyl, $C_2$-$C_6$ alkynyl, $C_3$-$C_7$ cycloalkyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-cycloalkyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocycloalkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocycloalkyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$) alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$ cycloalkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocycloalkyl-oxy (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl-oxy (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-cycloalkyl-$C_1$-$C_6$-alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocycloalkyl-$C_1$-$C_6$-alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$)alkoxy (optionally substituted with halo, $C_1$-$C_6$ alkyl, $C_1$-$C_6$ alkoxy, $C_1$-$C_6$ haloalkyl, and $C_1$-$C_6$ haloalkoxy), sulfhydryl (mercapto), halo($C_1$-$C_6$)alkyl (e.g., —$CF_3$), halo($C_1$-$C_6$)alkoxy (e.g., —$OCF_3$), $C_1$-$C_6$ alkylthio, arylthio (optionally substituted with halo, $C_1$-$C_6$ alkyl, $C_1$-$C_6$ alkoxy, $C_1$-$C_6$ haloalkyl, and $C_1$-$C_6$ haloalkoxy), amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents unless the optional substituents are otherwise specifically identified.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers.

As used herein, "tautomer" refers to the migration of protons between adjacent single and double bonds. The tautomerization process is reversible. Compounds described herein can undergo any possible tautomerization that is within the physical characteristics of the compound. The following is an example tautomerization that can occur in compounds described herein:

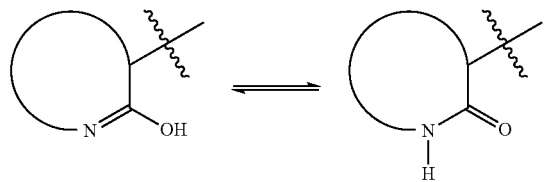

The symbols ▬▬ and ◥▬ are used as meaning the same spatial arrangement in chemical structures shown herein. Analogously, the symbols ׀׀׀׀׀׀ and ׀׀׀׀׀ are used as meaning the same spatial arrangement in chemical structures shown herein.

Where compounds described herein exist in various tautomeric forms, the term "compound" is intended to include all tautomeric forms (tautomers) of the compound.

The term "chiral" refers to molecules, which have the property of non-superimposability of the mirror image partner.

"Stereoisomers" are compounds, which have identical chemical constitution, but differ with regard to the arrangement of the atoms or groups in space.

A "diastereomer" is a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis, crystallization in the presence of a resolving agent, or chromatography, using, for example a chiral HPLC column.

"Enantiomers" refer to two stereoisomers of a compound, which are non-superimposable mirror images of one another. A 50:50 mixture of enantiomers is referred to as a racemic mixture or a racemate, which may occur where there has been no stereoselection or stereospecificity in a chemical reaction or process.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., Stereochemistry of Organic Compounds (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory.

A "racemic mixture" or "racemate" is an equimolar (or 50:50) mixture of two enantiomeric species, devoid of optical activity. A racemic mixture may occur where there has been no stereoselection or stereospecificity in a chemical reaction or process.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

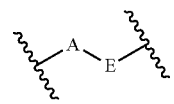

includes the substituent being oriented such that the A is attached at the leftmost attachment point of the molecule as well as the case in which A is attached at the rightmost attachment point of the molecule.

Chemical Entities

As used herein, the term "chemical entity" collectively refers to a compound, along with all pharmaceutically acceptable forms thereof, including pharmaceutically acceptable salts, chelates, solvates, conformers, crystalline forms/polymorphs, tautomers, prodrugs, metabolites, and mixtures thereof. In some embodiments, the chemical entity is selected from the group consisting of a compound and pharmaceutically acceptable salts thereof.

Chelates

The term "chelate" refers to the chemical entity formed by the coordination of a compound to a metal ion at two (or more) points.

Solvates

Additionally, any formula given herein is intended to refer also to solvates, including hydrates, of compounds herein, and mixtures thereof, even if such forms are not listed explicitly. Some embodiments provide a solvate of a compound of Formula (I), and the use of such solvates in methods described herein. Certain compounds of Formula (I) or pharmaceutically acceptable salts of compounds of Formula (I) may be obtained as solvates. In some embodiments, the solvent is water and the solvates are hydrates.

More particularly, solvates include those formed from the interaction or complexes of compounds of the invention with one or more solvents, either in solution or as a solid or crystalline form. Such solvent molecules are those commonly used in the pharmaceutical art, which are known to be innocuous to the recipient, e.g., water, ethanol, ethylene glycol, and the like. Other solvents may be used as intermediate solvates in the preparation of more desirable solvates, such as methanol, methyl t-butyl ether, ethyl acetate, methyl acetate, (S)-propylene glycol, (R)-propylene glycol, 1,4-butyne-diol, and the like. Hydrates include a molecule of a compound associated with water molecules.

Conformers and Crystalline Forms/Polymorphs

Some embodiments provide conformer and crystalline forms of a compound of Formula (I), and their use in methods of the present disclosure. A conformer is a structure that is a conformational isomer.

Conformational isomerism is the phenomenon of molecules with the same structural formula but different conformations (conformers) of atoms about a rotating bond.

Polymorphs refer to a solid material that can exist in more than one form or crystal structure, where each form or crystal structure is different from the other form(s) or crystal structure(s). Therefore, a single compound may give rise to a variety of polymorphic forms having different and distinct physical properties, such as solubility profiles, melting point temperatures, hygroscopicity, particle shape, density, flowability, compactibility and x-ray diffraction peaks. In certain embodiments, compounds of Formula (I) are obtained in crystalline form. In addition, certain crystalline forms of compounds of Formula (I) or pharmaceutically acceptable salts of compounds of Formula (I) may be obtained as co-crystals. In still other embodiments, compounds of Formula (I) may be obtained in one of several polymorphic forms, as a mixture of crystalline forms, as a polymorphic form, or as an amorphous form.

Compounds

As used herein, a "compound" refers to any one of: (a) the actually recited form of such compound; and (b) any of the forms of such compound in the medium in which the compound is being considered when named. For example, reference herein to a compound such as R—OH encompasses reference to any one of, for example, R—OH(s), R—OH(sol), and R—O—(sol). In this example, R—OH(s) refers to the solid compound, as it could be for example in a tablet or some other solid pharmaceutical composition or preparation; R—OH(sol) refers to the undissociated form of the compound in a solvent; and R—O-(sol) refers to the dissociated form of the compound in a solvent, such as the dissociated form of the compound in an aqueous environment, whether such dissociated form derives from R—OH, from a salt thereof, or from any other entity that yields R—O— upon dissociation in the medium being considered.

In another example, an expression such as "modulate activity of PDE1 or an associated signaling pathway" refers to the exposure of PDE1 to the form, or forms, of the compound R—OH that exists, or exist, in the medium in which such exposure takes place. In this regard, if such compound is, for example, in an aqueous environment, it is understood that the compound R—OH is in the same such medium, and therefore PDE1 is being exposed to the compound as it exists in the medium such as R—OH (aq) and/or R—O—(aq), where the subscript "(aq)" stands for "aqueous" according to its conventional meaning in chemistry and biochemistry. A hydroxyl functional group has been chosen in these nomenclature examples; this choice is not intended, however, as a limitation but is merely an illustration. It is understood that analogous examples can be provided in terms of other functional groups, including, but not limited to, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation and deprotonation. No further examples in this regard are provided herein because these interactions and transformations in a given medium are known by any one of ordinary skill in the art.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of species for the same variable elsewhere in the formula, unless otherwise stated.

Salts

Embodiments include pharmaceutically acceptable salts of the compounds represented by Formula (I), and methods using such salts.

A "pharmaceutically acceptable salt" is intended to mean a salt of a free acid or base of a compound represented by Formula (I) that is non-toxic, biologically tolerable, or otherwise biologically suitable for administration to the subject. See, generally, G. S. Paulekuhn et al., 2007, *J. Med. Chem.* 50, 6665-6672; Berge et al., 1977, *J. Pharm. Sci.* 66, 1-19; Stahl and Wermuth (eds), Pharmaceutical Salts: Properties, Selection, and Use: 2nd Revised Edition (2011) Wiley-VCS, Zurich, Switzerland. Examples of pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form pharmaceutically acceptable salt bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, borate, nitrate, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, y-hydroxybutyrates, glycolates, tartrates, methanesulfonates, propanesulfonates, naphthalene-1-sulfonates, naphthalene-2-sulfonates, besylate, mesylate and mandelates.

When the compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

When the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-O-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

Prodrugs

Some embodiments provide prodrugs of the compounds of Formula (I), and the use of such pharmaceutically acceptable prodrugs in methods of the present disclosure, particularly therapeutic methods.

The term "prodrug" means a precursor of a designated compound that is initially inactive or partially inactive, and that following administration to a subject, yields the compound in vivo via a chemical or physiological process such as solvolysis or enzymatic cleavage, or under physiological conditions (e.g., a prodrug on being brought to physiological pH is converted to an active pharmacological compound of Formula (I)).

A "pharmaceutically acceptable prodrug" is a prodrug that is preferably non-toxic, biologically tolerable, and otherwise biologically suitable for administration to the subject. Prodrugs are often useful because, in some situations, they can be easier to administer than the parent drug. They can, for instance, be bioavailable by oral administration whereas the parent is not. The prodrug can also have improved solubility in pharmaceutical compositions over the parent drug.

Prodrugs may be determined using routine techniques known or available in the art Prodrugs may be produced, for instance, by derivatizing free carboxyl groups, free hydroxy groups, or free amino groups. See, e.g., Bundgaard (ed.), 1985, Design of prodrugs, Elsevier; Krogsgaard-Larsen et al., (eds.), 1991, Design and Application of Prodrugs, Harwood Academic Publishers; Fleisher et al., *Adv. Drug Delivery Rev.* 1996, 19, 115-130; Robinson et al., 1996, *J. Med. Chem.* 39, 10-18.

Tautomers

Some embodiments provide tautomers of compounds of Formula (I), as defined further herein, which may also be used in the methods of the disclosure.

Metabolites

Some embodiments provide pharmaceutically active metabolites of the compounds of Formula (I), which may also be used in the methods of the disclosure. A "pharmaceutically active metabolite" means a pharmacologically active product of metabolism in the body of a compound of Formula (I) or salt thereof. Preferably, the metabolite is in an isolated form outside the body.

Active metabolites of a compound may be determined using routine techniques known or available in the art. For example, isolated metabolites can be enzymatically and synthetically produced (e.g., Bertolini et al., 1997, *J. Med. Chem.* 40, 2011-2016; Shan et al., 1997, *J. Pharm. Sci.* 86, 765-767; Bagshawe, 1995, *Drug Dev. Res.* 34, 220-230; and Bodor, 1984, *Adv. Drug Res.* 13, 224-231).

Isotopes

Isotopes may be present in the compounds described. Each chemical element present in a compound either specifically or generically described herein may include any isotope of the element. Any formula given herein is also intended to represent unlabeled forms as well as isotopically-labeled forms of the compounds. Isotopically-labeled compounds have structures depicted by the formulas given herein except that one or more atoms are replaced by an atom having a selected atomic mass or mass number. Examples of isotopes that can be incorporated into compounds of the embodiments include isotopes of hydrogen, carbon, nitrogen, oxygen, phosphorus, sulfur, fluorine, chlorine, and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively.

Compositions

The term "composition," as in pharmaceutical composition, is intended to encompass a product comprising the active ingredient(s) (e.g., one or more of the presently disclosed chemical entities), and the inert ingredient(s) (pharmaceutically acceptable excipients) that make up the carrier, as well as any product which results, directly or indirectly, from combination, complexation, or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a chemical entity of Formula (I) and a pharmaceutically acceptable excipient.

The term "pharmaceutically acceptable," as used in connection with compositions of the invention, refers to molecular entities and other ingredients of such compositions that are physiologically tolerable and do not typically produce untoward reactions when administered to an animal (e.g., human). The term "pharmaceutically acceptable" can also mean approved by a regulatory agency of the Federal or a state government or listed in the U.S. Pharmacopeia or other generally recognized pharmacopeia for use in animals (e.g. mammals), and more particularly in humans.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluents to facilitate administration of an agent and that is compatible therewith. Examples of excipients include calcium carbonate, calcium phosphate, various sugars and types of starch, cellulose derivatives, gelatin, vegetable oils, and polyethylene glycols. Suitable pharmaceutical carriers include those described in Remington: The Science and Practice of Pharmacy, $21^{st}$ Ed., Lippincott Williams & Wilkins (2005).

A "pharmaceutically acceptable salt" is intended to mean a salt of a free acid or base of a compound represented by Formula (I), as previously defined herein. The term "carrier" refers to an adjuvant, vehicle, or excipients, with which the compound is administered. In preferred embodiments of this invention, the carrier is a solid carrier. Suitable pharmaceutical carriers include those described in Remington: The Science and Practice of Pharmacy, $21^{st}$ Ed., Lippincott Williams & Wilkins (2005).

The term "dosage form," as used herein, is the form in which the dose is to be administered to the subject or patient. The drug is generally administered as part of a formulation that includes nonmedical agents. The dosage form has unique physical and pharmaceutical characteristics. Dosage forms, for example, may be solid, liquid or gaseous. "Dosage forms" may include for example, a capsule, tablet, caplet, gel caplet (gelcap), syrup, a liquid composition, a powder, a concentrated powder, a concentrated powder admixed with a liquid, a chewable form, a swallowable form, a dissolvable form, an effervescent, a granulated form, and an oral liquid solution. In a specific embodiment, the dosage form is a solid dosage form, and more specifically, comprises a tablet or capsule.

As used herein, the term "inert" refer to any inactive ingredient of a described composition. The definition of "inactive ingredient" as used herein follows that of the U.S. Food and Drug Administration, as defined in 21 C.F.R. 201.3(b)(8), which is any component of a drug product other than the active ingredient.

As used herein, "suitable for oral administration" refers to a sterile, pharmaceutical product produced under good manufacturing practices (GMP) that is prepared and presented in a manner such that the composition is not likely to cause any untoward or deleterious effects when orally administered to a subject. Unless specified otherwise, all of the compositions disclosed herein are suitable for oral administration.

Methods and Uses

As used herein, the term "disorder" is used interchangeably with "disease" or "condition". For example, a CNS disorder also means a CNS disease or a CNS condition.

As used herein, the term "cognitive impairment" is used interchangeably with "cognitive dysfunction" or "cognitive deficit," all of which are deemed to cover the same therapeutic indications.

The terms "treating," "treatment," and "treat" cover therapeutic methods directed to a disease-state in a subject and include: (i) preventing the disease-state from occurring, in particular, when the subject is predisposed to the disease-state but has not yet been diagnosed as having it; (ii) inhibiting the disease-state, e.g., arresting its development (progression) or delaying its onset; and (iii) relieving the disease-state, e.g., causing regression of the disease state until a desired endpoint is reached. Treating also includes ameliorating a symptom of a disease (e.g., reducing the pain, discomfort, or deficit), wherein such amelioration may be directly affecting the disease (e.g., affecting the disease's cause, transmission, or expression) or not directly affecting the disease. Particularly with respect to progressive disease-states or conditions, maintaining the status quo, or arresting the progression of symptoms, is understood to be an amelioration of such symptoms.

As used in the present disclosure, the term "effective amount" is interchangeable with "therapeutically effective amount" and means an amount or dose of a compound or composition effective in treating the particular disease, condition, or disorder disclosed herein, and thus "treating" includes producing a desired preventative, inhibitory, relieving, or ameliorative effect. In methods of treatment according to the invention, "an effective amount" of at least one compound according to the invention is administered to a subject (e.g., a mammal). An "effective amount" also means an amount or dose of a compound or composition effective to modulate activity of PDE1 or an associated signaling pathway. The "effective amount" will vary, depending on the compound, the disease, the type of treatment desired, and its severity, and age, weight, etc.

As used herein, the term "PDE1" refers to all translation products coded by transcripts of any or all three genes, PDE1A, PDE1B, and PDE1C. The amino acid and nucleotide sequences that encode PDE1 of various species are known to those skilled in the art and can be found, for example, in GenBank under accession numbers AJ401610.1, AJ401609.1, and Fiddock et al., 2002, *Cell. Signal.* 14, 53-60.

The term "animal" is interchangeable with "subject" and may be a vertebrate, in particular, a mammal, and more particularly, a human, and includes a laboratory animal in the context of a clinical trial or screening or activity experiment. Thus, as can be readily understood by one of ordinary skill in the art, the compositions and methods of the present invention are particularly suited to administration to any vertebrate, particularly a mammal, and more particularly, a human.

As used herein, a "control animal" or a "normal animal" is an animal that is of the same species as, and otherwise comparable to (e.g., similar age, sex), the animal that is trained under conditions sufficient to induce transcription-dependent memory formation in that animal.

By "enhance," "enhancing" or "enhancement" is meant the ability to potentiate, increase, improve or make greater or better, relative to normal, a biochemical or physiological action or effect. For example, enhancing long term memory formation refers to the ability to potentiate or increase long term memory formation in an animal relative to (or "compared to") the normal long term memory formation of the animal or controls. As a result, long term memory acquisition is faster or better retained. Enhancing performance of a cognitive task refers to the ability to potentiate or improve performance of a specified cognitive task by an animal relative to the normal performance of the cognitive task by the animal or controls.

As used herein, the term "training protocol," or "training," refers to either "cognitive training" or "motor training."

Reference will now be made to embodiments of the present invention, examples of which are illustrated by and described in conjunction with the accompanying examples.

While certain embodiments are described herein, it is understood that the described embodiments are not intended to limit the scope of the invention. On the contrary, the present disclosure is intended to cover alternatives, modifications, and equivalents that can be included within the invention as defined by the appended claims.

Chemical Entities

Some embodiments provide certain substituted furanopyrimidine chemical entities which are useful, for example, as inhibitors of PDE1 enzymatic activity.

In some embodiments, the chemical entities include the compounds disclosed herein and pharmaceutically acceptable salts, chelates, solvates, conformers, crystalline forms/polymorphs, tautomers, prodrugs, metabolites, and mixtures thereof. In some embodiments, the chemical entities include the compounds disclosed herein and pharmaceutically acceptable salts thereof.

Some embodiments provide a chemical entity of Formula (I):

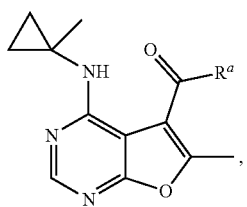

wherein, $R^a$ has any of the values described herein.

In some embodiments of a chemical entity of Formula (I), $R^a$ is -$L^1$-$L^3$, -$L^1$-$L^2$-$L^3$, or —N($L^4$)-$L^5$;

$L^1$ is selected from the group consisting of: —N($R^b$)—, —N($R^b$)—(C($R^b$)$_2$)$_m$—, —N($R^b$)(CH$_2$)$_m$O—, —NHNH—, 3-15-membered heterocycloalkyl, and 5-10-membered heteroaryl, said 3-15-membered heterocycloalkyl or 5-10-membered heteroaryl optionally substituted with one to four $R^{1A}$, where each $R^{1A}$ is independently selected from the group consisting of: halo, —OH, =O, —NH$_2$, —NHC$_{1-4}$alkyl, —N(C$_{1-4}$ alkyl)$_2$, —NO$_2$, —SO$_2$CH$_3$, —CN, —C$_{1-6}$alkyl, —C$_{1-6}$ haloalkyl, —C$_{1-6}$alkyl-OH, —C$_{1-6}$alkoxy, —C$_{1-6}$haloalkoxy, —C$_{1-6}$alkyl-O—C$_{1-4}$alkyl, —C(O)C$_{1-6}$alkyl, —COOC$_{1-6}$alkyl, —C(O)NH$_2$, and —C$_{3-7}$cycloalkyl;

each m is independently 0, 1, 2, or 3;

each $R^b$ is independently —H, —OH, —C$_{1-6}$alkyl, —C$_{1-6}$haloalkyl, —C$_{1-6}$alkyl-OH, —C$_{1-6}$alkyl-O—C$_{1-4}$alkyl, —C(O)C$_{1-6}$alkyl, —C$_{3-7}$cycloalkyl, —C$_{2-6}$ alkenyl, or —C$_{2-6}$alkynyl;

$L^2$ is selected from the group consisting of: —N($R^c$)—, —N($R^c$)(CH$_2$)$_m$—, —O—, —S—, —C$_{1-6}$alkyl, —C$_{1-6}$haloalkyl, —C$_{1-6}$alkoxy, —C$_{1-6}$haloalkoxy, —C$_{2-6}$alkenyl, —C$_{2-6}$alkynyl, —C(O)C$_{1-6}$alkyl, —CHR$^c$—, —(CH$_2$)$_m$NH—, —(CH$_2$)$_m$O—, —(CH$_2$)$_m$S—, —C$_{3-10}$cycloalkyl, 3-15-membered heterocycloalkyl, phenyl, benzyl, and 5-10-membered heteroaryl, said —C$_{1-6}$alkyl, —C$_{3-10}$cycloalkyl, 3-15-membered heterocycloalkyl, phenyl, benzyl, and 5-10-membered heteroaryl optionally substituted with one to four $R^{1B}$, where each $R^{1B}$ is independently selected from the group consisting of: halo, —OH, =O, —NH$_2$, —NHC$_{1-4}$alkyl, —N(C$_{1-4}$ alkyl)$_2$, —NO$_2$, —SO$_2$CH$_3$, —CN, —C$_{1-6}$ alkyl, —C$_{1-6}$haloalkyl, —C$_{1-6}$alkyl-OH, —C$_{1-6}$alkoxy, —C$_{1-6}$haloalkoxy, —C$_{1-6}$alkyl-O—C$_{1-4}$alkyl, —C(O) C$_{1-6}$alkyl, —COOC$_{1-6}$alkyl, —C(O)NH$_2$, —C$_{3-7}$cycloalkyl, 3-15-membered heterocycloalkyl, phenyl, benzyl, and 5-10-membered heteroaryl;

each $R^c$ is independently —H, —C$_{1-6}$alkyl, —C$_{1-6}$haloalkyl, —C$_{1-6}$alkyl-OH, —C$_{1-6}$alkyl-O—C$_{1-4}$alkyl, —C(O)C$_{1-6}$alkyl, —C$_{3-7}$cycloalkyl, —C$_{2-6}$alkenyl, or —C$_{2-6}$alkynyl;

$L^3$ is selected from the group consisting of: —H, —OH, —CN, —NH$_2$, —NHC$_{1-4}$alkyl, —N(C$_{1-4}$alkyl)$_2$, —N($R^{1DD}$)$_2$, —N=S(=O)(CH$_3$)$_2$, —NO$_2$, —SO$_2$CH$_3$, halo, —C$_{1-6}$alkyl, —C$_{1-6}$haloalkyl, —C$_{1-6}$ alkoxy, —C$_{1-6}$haloalkoxy, —C$_{2-6}$alkenyl, —C$_{2-6}$alkynyl, —C(O) C$_{1-6}$alkyl, —C(O)NH$_2$, —C$_{1-6}$alkyl-O—C$_{1-4}$alkyl, —C$_{3-10}$cycloalkyl, 3-15-membered heterocycloalkyl, phenyl, benzyl, and 5-10-membered heteroaryl, said —C$_{1-6}$alkyl, —C$_{3-10}$cycloalkyl, 3-15-membered heterocycloalkyl, phenyl, benzyl, and 5-10-membered heteroaryl optionally substituted with one to four $R^{1C}$, where each $R^{1C}$ is independently selected from the group consisting of: halo, —OH, =O, —NH$_2$, —NHC$_{1-4}$alkyl, —N(C$_{1-4}$alkyl)$_2$, —NO$_2$, —SO$_2$CH$_3$, —CN, —C$_{1-6}$alkyl, —C$_{1-6}$haloalkyl, —C$_{1-6}$alkyl-OH, —C$_{1-6}$alkoxy, —C$_{1-6}$ haloalkoxy, —C$_{1-6}$alkyl-O—C$_{1-4}$alkyl, —C(O) C$_{1-6}$alkyl, —COOC$_{1-6}$alkyl, —C(O)NH$_2$, —C$_{3-7}$cycloalkyl, 3-15-membered heterocycloalkyl, phenyl and 5-10-membered heteroaryl;

each $R^{1DD}$ is independently selected from the group consisting of: —H, —C$_{1-6}$alkyl, —C$_{1-6}$haloalkyl, —C$_{1-6}$alkyl-OH, —C$_{1-6}$alkyl-O—C$_{1-4}$alkyl, —C(O) C$_{1-6}$alkyl, —COOC$_{1-6}$alkyl, —C$_{3-7}$cycloalkyl, 3-15-membered heterocycloalkyl, phenyl and 5-10-membered heteroaryl;

$L^4$ and $L^5$ taken together with the nitrogen to which they are attached to form a 3-15-membered heterocycloalkyl or 5-10-membered heteroaryl ring, optionally substituted with one to four $R^{1D}$, where each $R^{1D}$ is independently selected from the group consisting of: $L^6$, =O, —C$_{1-6}$alkyl-OH, —C$_{1-6}$alkyl-O—C$_{1-4}$alkyl, and —COOC$_{1-6}$alkyl; and $L^6$ is selected from the group consisting of: —H, —OH, —CN, —NH$_2$, —NHC$_{1-4}$alkyl, —N(C$_{1-4}$alkyl)$_2$, —N=S(=O)(CH$_3$)$_2$, —NO$_2$, —SO$_2$CH$_3$, halo, —C$_{1-6}$ alkyl, —C$_{1-6}$haloalkyl, —C$_{1-6}$alkoxy, —C$_{1-6}$haloalkoxy, —C$_{2-6}$alkenyl, —C$_{2-6}$alkynyl, —C(O)C$_{1-6}$alkyl, —C(O)NH$_2$, —C$_{3-10}$cycloalkyl, —C$_{1-6}$alkyl-O—C$_{1-4}$alkyl, 3-15-membered heterocycloalkyl, phenyl, benzyl, and 5-10-membered heteroaryl, said —C$_{1-6}$alkyl, —C$_{3-10}$cycloalkyl, 3-15-membered heterocycloalkyl, phenyl, benzyl, and 5-10-membered heteroaryl optionally substituted with one to four $R^{1E}$ where each $R^{1E}$ is independently selected from the group consisting of: halo, —OH, =O, —NH$_2$, —NHC$_{1-4}$alkyl, —N(C$_{1-4}$alkyl)$_2$, —NO$_2$, —SO$_2$CH$_3$, —CN, —C$_{1-6}$alkyl, —C$_{1-6}$haloalkyl, —C$_{1-6}$alkyl-OH, —C$_{1-6}$alkoxy, —C$_{1-6}$ haloalkoxy, —C$_{1-6}$alkyl-O—C$_{1-4}$alkyl, —C(O) C$_{1-6}$alkyl, —COOC$_{1-6}$alkyl, —C(O)NH$_2$, —C$_{3-7}$cycloalkyl, 3-15-membered heterocycloalkyl, phenyl and 5-10-membered heteroaryl.

In certain embodiments, a chemical entity of Formula (I) is a chemical entity of Formula (Ia), and more particularly, is a compound of Formula (Ia), or a pharmaceutically acceptable salt of a compound of Formula (Ia):

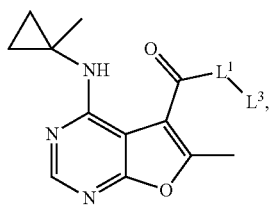

(Ia)

wherein $L^1$ and $L^3$ have any of the values described herein.

In certain embodiments of a chemical entity of Formula (Ia), $L^1$ is selected from the group consisting of: —N($R^b$)—, —N($R^b$)—(C$R^{b2}$)$_m$—, —N($R^b$)(CH$_2$)$_m$O—, —NHNH—, 3-15-membered heterocycloalkyl, and 5-10-membered heteroaryl, said 3-15-membered heterocycloalkyl or 5-10-membered heteroaryl optionally substituted with one to four $R^{1A}$, where each $R^{1A}$ is independently selected from the group consisting of: halo, —OH, =O, —NH$_2$, —NHC$_{1-4}$alkyl, —N(C$_{1-4}$alkyl)$_2$, —NO$_2$, —SO$_2$CH$_3$, —CN, —C$_{1-6}$alkyl, —C$_{1-6}$haloalkyl, —C$_{1-6}$alkyl-OH, —C$_{1-6}$alkoxy, —C$_{1-6}$haloalkoxy, —C$_{1-6}$alkyl-O—C$_{1-4}$alkyl, —C(O)C$_{1-6}$alkyl, —COOC$_{1-6}$alkyl, —C(O)NH$_2$, and —C$_{3-7}$cycloalkyl;

each m is independently 0, 1, 2, or 3;

each $R^b$ is independently —H, —OH, —C$_{1-6}$alkyl, —C$_{1-6}$haloalkyl, —C$_{1-6}$alkyl-OH, —C$_{1-6}$alkyl-O—C$_{1-4}$alkyl, —C(O)C$_{1-6}$alkyl, —C$_{3-7}$cycloalkyl, —C$_{2-6}$alkenyl, or —C$_{2-6}$alkynyl.

$L^3$ is selected from the group consisting of: —H, —OH, —CN, —NH$_2$, —NHC$_{1-4}$alkyl, —N(C$_{1-4}$alkyl)$_2$, —N($R^{1DD}$)$_2$, —N=S(=O)(CH$_3$)$_2$, —NO$_2$, —SO$_2$CH$_3$, halo, —C$_{1-6}$alkyl, —C$_{1-6}$haloalkyl, —C$_{1-6}$alkoxy, —C$_{1-6}$haloalkoxy, —C$_{2-6}$alkenyl, —C$_{2-6}$alkynyl, —C$_{1-6}$alkyl-O—C$_{1-4}$alkyl, —C(O)C$_{1-6}$alkyl, —C(O)NH$_2$, —C$_{3-10}$cycloalkyl, 3-15-membered heterocycloalkyl, phenyl, benzyl, and 5-10-membered heteroaryl, said —C$_{1-6}$alkyl, —C$_{3-10}$cycloalkyl, —C$_{3-7}$cycloalkoxy, 3-15-membered heterocycloalkyl, phenyl, benzyl, and 5-10-membered heteroaryl optionally substituted with one to four $R^{1C}$, where each $R^{1C}$ is independently selected from the group consisting of: halo, —OH, =O, —NH$_2$, —NHC$_{1-4}$alkyl, —N(C$_{1-4}$alkyl)$_2$, —NO$_2$, —SO$_2$CH$_3$, —CN, —C$_{1-6}$alkyl, —C$_{1-6}$haloalkyl, —C$_{1-6}$alkyl-OH, —C$_{1-6}$alkoxy, —C$_{1-6}$haloalkoxy, —C$_{1-6}$alkyl-O—C$_{1-4}$alkyl, —C(O)C$_{1-6}$alkyl, —COOC$_{1-6}$alkyl, —C(O)NH$_2$, —C$_{3-7}$cycloalkyl, 3-15-membered heterocycloalkyl, phenyl and 5-10-membered heteroaryl; and each $R^{1DD}$ is independently selected from the group consisting of: —H, —C$_{1-6}$alkyl, —C$_{1-6}$haloalkyl, —C$_{1-6}$alkyl-OH, —C$_{1-6}$alkyl-O—C$_{1-4}$alkyl, —C(O)C$_{1-6}$alkyl, —COOC$_{1-6}$alkyl, —C$_{3-7}$cycloalkyl, 3-15-membered heterocycloalkyl, phenyl and 5-10-membered heteroaryl.

In certain embodiments, a chemical entity of Formula (I) is a chemical entity of Formula (Ib), and more particularly, is a compound of Formula (Ib), or a pharmaceutically acceptable salt of a compound of Formula (Ib):

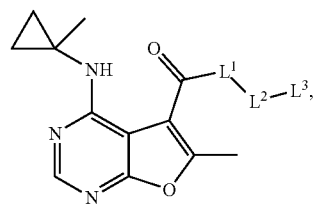

(Ib)

wherein $L^1$, $L^2$, and $L^3$ have any of the values described herein.

In certain embodiments of a chemical entity of Formula (Ib), $L^1$ is selected from the group consisting of: —N($R^b$)—, —N($R^b$)—(C$R^{b2}$)$_m$—, —N($R^b$)(CH$_2$)$_m$O—, —NHNH—, 3-15-membered heterocycloalkyl, and 5-10-membered heteroaryl, said 3-15-membered heterocycloalkyl or 5-10-membered heteroaryl optionally substituted with one to four $R^{1A}$, where each $R^{1A}$ is independently selected from the group consisting of: halo, —OH, =O, —NH$_2$, —NHC$_{1-4}$alkyl, —N(C$_{1-4}$alkyl)$_2$, —NO$_2$, —SO$_2$CH$_3$, —CN, —C$_{1-6}$alkyl, —C$_{1-6}$haloalkyl, —C$_{1-6}$alkyl-OH, —C$_{1-6}$alkoxy, —C$_{1-6}$haloalkoxy, —C$_{1-6}$alkyl-O—C$_{1-4}$alkyl, —C(O)C$_{1-6}$alkyl, —COOC$_{1-6}$alkyl, —C(O)NH$_2$, and —C$_{3-7}$cycloalkyl;

each m is independently 0, 1, 2, or 3;

each $R^b$ is independently —H, —OH, —C$_{1-6}$alkyl, —C$_{1-6}$haloalkyl, —C$_{1-6}$alkyl-OH, —C$_{1-6}$alkyl-O—C$_{1-4}$alkyl, —C(O)C$_{1-6}$alkyl, —C$_{3-7}$cycloalkyl, —C$_{2-6}$alkenyl, or —C$_{2-6}$alkynyl;

$L^2$ is selected from the group consisting of: —N($R^c$)—, —N($R^c$)(CH$_2$)$_m$—, —O—, —S—, —C$_{1-6}$alkyl, —C$_{1-6}$haloalkyl, —C$_{1-6}$alkoxy, —C$_{1-6}$haloalkoxy, —C$_{2-6}$alkenyl, —C$_{2-6}$alkynyl, —C(O)C$_{1-6}$alkyl, —CH$R^c$—, —(CH$_2$)$_m$NH—, —(CH$_2$)$_m$O—, —(CH$_2$)$_m$S—, —C$_{3-10}$cycloalkyl, 3-15-membered heterocycloalkyl, phenyl, benzyl, and 5-10-membered heteroaryl, said —C$_{1-6}$alkyl, —C$_{3-10}$cycloalkyl, 3-15-membered heterocycloalkyl, phenyl, and 5-10-membered heteroaryl optionally substituted with one to four $R^{1B}$, where each $R^{1B}$ is independently selected from the group consisting of: halo, —OH, =O, —NH$_2$, —NHC$_{1-4}$alkyl, N(C$_{1-4}$alkyl)$_2$, —NO$_2$, —SO$_2$CH$_3$, —CN, —C$_{1-6}$alkyl, —C$_{1-6}$haloalkyl, —C$_{1-6}$alkyl-OH, —C$_{1-6}$alkoxy, —C$_{1-6}$haloalkoxy, —C$_{1-6}$alkyl-O—C$_{1-4}$alkyl, —C(O)C$_{1-6}$alkyl, —COOC$_{1-6}$alkyl, —C(O)NH$_2$, —C$_{3-7}$ cycloalkyl, 3-15-membered heterocycloalkyl, phenyl, benzyl, and 5-10-membered heteroaryl;

each $R^c$ is independently —H, —C$_{1-6}$alkyl, —C$_{1-6}$haloalkyl, —C$_{1-6}$alkyl-OH, —C$_{1-6}$alkyl-O—C$_{1-4}$alkyl, —C(O)C$_{1-6}$alkyl, —C$_{3-7}$cycloalkyl, —C$_{2-6}$alkenyl, or —C$_{2-6}$alkynyl;

$L^3$ is selected from the group consisting of: —H, —OH, —CN, —NH$_2$, —NHC$_{1-4}$alkyl, —N(C$_{1-4}$alkyl)$_2$, —N($R^{1DD}$)$_2$, —N=S(=O)(CH$_3$)$_2$, —NO$_2$, —SO$_2$CH$_3$, halo, —C$_{1-6}$alkyl, —C$_{1-6}$haloalkyl, —C$_{1-6}$alkoxy, —C$_{1-6}$haloalkoxy, —C$_{2-6}$alkenyl, —C$_{2-6}$alkynyl, —C$_{1-6}$alkyl-O—C$_{1-4}$alkyl, —C(O)C$_{1-6}$alkyl, —C(O)NH$_2$, —C$_{3-10}$cycloalkyl, 3-15-membered heterocycloalkyl, phenyl, benzyl, and 5-10-membered heteroaryl, said —C$_{1-6}$alkyl, —C$_{3-10}$cycloalkyl, —C$_{3-7}$cycloalkoxy, 3-15-membered heterocycloalkyl, phenyl, benzyl, and 5-10-membered heteroaryl optionally substituted with one to four $R^{1C}$, where each $R^{1C}$ is independently selected from the group consisting of: halo, —OH, =O, —NH$_2$, —NHC$_{1-4}$alkyl, —N(C$_{1-4}$alkyl)$_2$, —NO$_2$, —SO$_2$CH$_3$, —CN, —C$_{1-6}$alkyl, —C$_{1-6}$haloalkyl, —C$_{1-6}$alkyl-OH, —C$_{1-6}$alkoxy, —C$_{1-6}$haloalkoxy, —C$_{1-6}$alkyl-O—C$_{1-4}$alkyl, —C(O)C$_{1-6}$alkyl, —COOC$_{1-6}$alkyl, —C(O)NH$_2$, —C$_{3-7}$cycloalkyl, 3-15-membered heterocycloalkyl, phenyl and 5-10-membered heteroaryl; and each R$^{1DD}$ is independently selected from the group consisting of: —H, —C$_{1-6}$alkyl, —C$_{1-6}$haloalkyl, —C$_{1-6}$alkyl-OH, —C$_{1-6}$alkyl-O—C$_{1-4}$alkyl, —C(O)C$_{1-6}$alkyl, —COOC$_{1-6}$alkyl, —C$_{3-7}$cycloalkyl, 3-15-membered heterocycloalkyl, phenyl and 5-10-membered heteroaryl.

In some embodiments of a chemical entity of Formula (I), (Ia), or (Ib) disclosed herein:
L$^1$ is selected from a group consisting of: —N(R$^b$)—, —N(R$^b$)—(CR$^{b2}$)$_m$, —N(R$^b$)(CH$_2$)$_m$O—, and —NHNH—; each m is independently 0, 1, 2, or 3; and each R$^b$ is independently —H, —C$_{1-6}$alkyl, —C$_{1-6}$haloalkyl, —C$_{1-6}$alkyl-OH, —C$_{1-6}$alkyl-O—C$_{1-4}$alkyl, —C(O)C$_{1-6}$alkyl, —C$_{3-7}$cycloalkyl, —C$_{2-6}$alkenyl, or —C$_{2-6}$alkynyl.

In some embodiments of a chemical entity of Formula (I), (Ia), or (Ib) disclosed herein:
L$^1$ is —N(R$^b$)— or —N(R$^b$)—(CR$^b_2$)$_m$—; each m is independently 0, 1, 2, or 3; and each R$^b$ is independently —H, —C$_{1-6}$alkyl, —C$_{1-6}$haloalkyl, or —C$_{3-7}$cycloalkyl.

In some embodiments of a chemical entity of Formula (I), (Ia), or (Ib) disclosed herein:
L$^1$ is —NH— or —NHCH$_2$—.

In some embodiments of a chemical entity of Formula (I), (Ia), or (Ib) disclosed herein:
L$^1$ is a 3-15-membered heterocycloalkyl or 5-10-membered heteroaryl, said 3-15-membered heterocycloalkyl or 5-10-membered heteroaryl optionally substituted with one to four R$^{1A}$.

In some embodiments of a chemical entity of Formula (I), (Ia), or (Tb) disclosed herein:
L$^1$ is selected from the group consisting of: azetidine, pyrrolidine, 2,5-dihydro-1H-pyrrole, 2,3-dihydro-1H-pyrrole, imidazolidine, piperidine, 1,2,3,6-tetrahydropyridine, 1,2,3,4-tetrahydropyridine, piperazine, morpholine, 3-azabicyclo[3.1.0]hexane, octahydrocyclopenta[c]pyrrole, octahydrocyclopenta[b]pyrrole, 6,7-dihydro-5H-pyrrolo[3,4-d]pyrimidine, 6,7-dihydro-5H-pyrrolo[3,2-d]pyrimidine, 5,6,7,8-tetrahydropyrido[4,3-c]pyridazine, 5,6,7,8-tetrahydropyrido[3,4-c]pyridazine, 5,6,7,8-tetrahydropyrido[3,2-c]pyridazine, 5,6,7,8-tetrahydropyrido[4,3-d]pyrimidine, 5,6,7,8-tetrahydropyrido[3,4-d]pyrimidine, 5,6,7,8-tetrahydro-1,6-naphthyridine, 5,6,7,8-tetrahydro-1,7-naphthyridine, 1,2,3,4-tetrahydro-2,6-naphthyridine, 1,2,3,4-tetrahydro-2,7-naphthyridine, 1,2,3,4-tetrahydroisoquinoline, 1,2,3,4-tetrahydroquinoline, 6,7-dihydro-5H-pyrrolo[3,4-b]pyridine, 2,3-dihydro-1H-pyrrolo[3,4-c]pyridine, isoindoline, 5,6,7,8-tetrahydroimidazo[1,2-a]pyrazine, 5,6,7,8-tetrahydroimidazo[1,5-a]pyrazine, 4,5,6,7-tetrahydropyrazolo[1,5-a]pyrazine, 5,6,7,8-tetrahydro-2,6-naphthyridin-1(2H)-one, 5,6,7,8-tetrahydropyrido[3,4-d]pyrimidin-4(3H)-one, 4,5,6,7-tetrahydrothieno[3,2-c]pyridine, octahydropyrrolo[1,2-a]pyrazine, octahydropyrrolo[1,2-c]pyrimidine, hexahydro-2H-furo[3,2-b]pyrrole, hexahydro-2H-furo[2,3-c]pyrrole, hexahydro-1H-furo[3,4-c]pyrrole, hexahydro-1H-furo[3,4-b]pyrrole, decahydroisoquinoline, decahydroquinoline, azepane, diazepane, 8-oxa-3-azabicyclo[3.2.1]octane, 6,7,8,9-tetrahydro-5H-pyrimido[4,5-d]azepine, 3,4,5,6-tetrahydro-2H-benzo[b][1,5]oxazocine, spiro[indoline-3,3'-piperidin]-2-one, spiro[indoline-3,3'-pyrrolidin]-2-one, 2,3-dihydrospiro[indene-1,2'-morpholine], 3H-spiro[isobenzofuran-1,3'-piperidine], 3H-spiro[isobenzofuran-1,3'-pyrrolidine], spiro[benzo[d][1,3]oxazine-4,4'-piperidin]-2(1H)-one, spiro[indene-1,4'-piperidine], 3H-spiro[benzo[c]thiophene-1,4'-piperidine], and 2,3,4,5-tetrahydro-1H-1,5-methanobenzo[d]azepine, said 3-15-membered heterocycloalkyl optionally substituted with one to four R$^{1A}$.

In some embodiments of a chemical entity of Formula (I), (Ia), or (Ib) disclosed herein:
L$^1$ is selected from the group consisting of: azetidine, pyrrolidine, piperidine, azepane, 1,2,3,6-tetrahydropyridine, 1,2,3,4-tetrahydropyridine, and 2,3-dihydro-1H-pyrrole.

In some embodiments of a chemical entity of Formula (I), (Ia), or (Tb) disclosed herein:
L$^1$ is selected from the group consisting of: imidazolidine, piperazine, diazepane and morpholine.

In some embodiments of a chemical entity of Formula (I), (Ia), or (Tb) disclosed herein:
L$^1$ is selected from the group consisting of: 6,7-dihydro-5H-pyrrolo[3,4-d]pyrimidine, 6,7-dihydro-5H-pyrrolo[3,2-d]pyrimidine, 5,6,7,8-tetrahydropyrido[4,3-c]pyridazine, 5,6,7,8-tetrahydropyrido[3,4-c]pyridazine, 5,6,7,8-tetrahydropyrido[3,2-c]pyridazine, 5,6,7,8-tetrahydropyrido[4,3-d]pyrimidine, 5,6,7,8-tetrahydropyrido[3,4-d]pyrimidine, 5,6,7,8-tetrahydro-1,6-naphthyridine, 5,6,7,8-tetrahydro-1,7-naphthyridine, 1,2,3,4-tetrahydro-2,6-naphthyridine, 1,2,3,4-tetrahydro-2,7-naphthyridine, 1,2,3,4-tetrahydroisoquinoline, 1,2,3,4-tetrahydroquinoline, 6,7-dihydro-5H-pyrrolo[3,4-b]pyridine, 2,3-dihydro-1H-pyrrolo[3,4-c]pyridine, and isoindoline.

In some embodiments of a chemical entity of Formula (I), (Ia), or (Tb) disclosed herein:
L$^1$ is selected from the group consisting of: 5,6,7,8-tetrahydroimidazo[1,2-a]pyrazine, 5,6,7,8-tetrahydroimidazo[1,5-a]pyrazine, 4,5,6,7-tetrahydropyrazolo[1,5-a]pyrazine, octahydropyrrolo[1,2-a]pyrazine, and octahydropyrrolo[1,2-c]pyrimidine.

In some embodiments of a chemical entity of Formula (I), (Ia), or (Tb) disclosed herein:
L$^1$ is selected from the group consisting of: 3-azabicyclo[3.1.0]hexane, octahydrocyclopenta[b]pyrrole, octahydrocyclopenta[c]pyrrole, 4,5,6,7-tetrahydrothieno[3,2-c]pyridine, hexahydro-2H-furo[3,2-b]pyrrole, hexahydro-2H-furo[2,3-c]pyrrole, hexahydro-1H-furo[3,4-c]pyrrole, hexahydro-1H-furo[3,4-b]pyrrole, decahydroisoquinoline, decahydroquinoline, 8-oxa-3-azabicyclo[3.2.1]octane, 6,7,8,9-tetrahydro-5H-pyrimido[4,5-d]azepine, 3,4,5,6-tetrahydro-2H-benzo[b][1,5]oxazocine, spiro[indoline-3,3'-piperidin]-2-one, spiro[indoline-3,3'-pyrrolidin]-2-one, 2,3-dihydrospiro[indene-1,2'-morpholine], 3H-spiro[isobenzofuran-1,3'-piperidine], 3H-spiro[isobenzofuran-1,3'-pyrrolidine], spiro[benzo[d][1,3]oxazine-4,4'-piperidin]-2(1H)-one, spiro[indene-1,4'-piperidine], 3H-spiro[benzo[c]thiophene-1,4'-piperidine], and 2,3,4,5-tetrahydro-JH-1,5-methanobenzo[d]azepine.

In some embodiments of a chemical entity of Formula (I), (Ia), or (Ib) disclosed herein:
L$^1$ is a 5-10-membered heteroaryl selected from the group consisting of: pyrazole, imidazole, pyrrole, oxazole, thiazole, indole, and indazole, said 5-10-membered heteroaryl optionally substituted with one to four R$^{1A}$.

In some embodiments of a chemical entity of Formula (I), (Ia), or (Tb) disclosed herein:
L$^1$ is pyrazole, optionally substituted with one to four R$^{1A}$.

In some embodiments of a chemical entity of Formula (I), (Ia), or (Tb) disclosed herein: R$^a$ is -L$^1$-L$^3$ or -L$^1$-L$^2$-L$^3$, and R$^{1A}$ is independently selected from the group consisting of: halo, —OH, =O, —NH$_2$, —NHC$_{1-4}$alkyl, —N(C$_{1-4}$alkyl)$_2$, —NO$_2$, —SO$_2$CH$_3$, —CN, —C$_{1-6}$alkyl, —C$_{1-6}$haloalkyl, —C$_{1-6}$alkyl-OH, —C$_{1-6}$alkoxy, —C$_{1-6}$haloalkoxy, —C$_{1-6}$ alkyl-O—C$_{1-4}$alkyl, —C(O)C$_{1-6}$alkyl, —COOC$_{1-6}$alkyl, —C(O)NH$_2$, and —C$_{3-7}$cycloalkyl.

In certain embodiments, a chemical entity of Formula (I) is a chemical entity of Formula (Iba), and more particularly, is a compound of Formula (Iba), or a pharmaceutically acceptable salt of a compound of Formula (Iba):

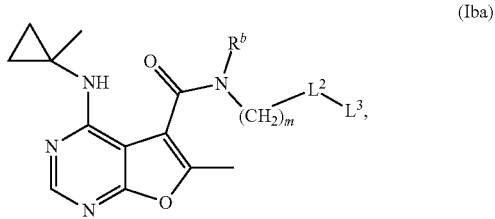

(Iba)

wherein R$^b$, L$^2$, m, and L$^3$ have any of the values described herein.

In certain embodiments of a chemical entity of Formula (Iba),
L$^2$ is —C$_{3-10}$cycloalkyl, 3-15-membered heterocycloalkyl, phenyl, or 5-10-membered heteroaryl, said —C$_{3-10}$cycloalkyl, 3-15-membered heterocycloalkyl, phenyl, and 5-10-membered heteroaryl optionally substituted with one to four R$^{1B}$, where each R$^{1B}$ is independently selected from the group consisting of: halo, —OH, =O, —NH$_2$, —NHC$_{1-4}$alkyl, —N(C$_{1-4}$alkyl)$_2$, —NO$_2$, —CN, —C$_{1-6}$alkyl, —C$_{1-6}$haloalkyl, —C$_{1-6}$alkyl-OH, —C$_{1-6}$alkoxy, —C$_{1-6}$haloalkoxy, and —C$_{1-6}$alkyl-O—C$_{1-4}$alkyl;
R$^b$ is —H, —C$_{1-6}$alkyl, —C$_{1-6}$haloalkyl, —C$_{1-6}$alkyl-OH, —C$_{3-6}$cycloalkyl, —C$_{2-6}$alkenyl, or —C$_{2-6}$alkynyl;
L$^3$ is —H, —OH, —CN, —NH$_2$, —NHC$_{1-4}$alkyl, —N(C$_{1-4}$alkyl)$_2$, —NO$_2$, halo, —C$_{1-6}$alkyl, —C$_{1-6}$haloalkyl, —C$_{1-6}$alkoxy, —C$_{1-6}$haloalkoxy, —C$_{2-6}$alkenyl, —C$_{2-6}$alkynyl, —C$_{1-6}$alkyl-O—C$_{1-4}$alkyl, —C$_{3-10}$cycloalkyl, 3-15-membered heterocycloalkyl, phenyl, benzyl, or 5-10-membered heteroaryl, said —C$_{1-6}$alkyl, —C$_{3-10}$cycloalkyl, 3-15-membered heterocycloalkyl, phenyl, benzyl, and 5-10-membered heteroaryl optionally substituted with one to four R$^{1C}$, where each R$^{1C}$ is independently selected from the group consisting of: halo, —OH, =O, —NH$_2$, —NHC$_{1-4}$alkyl, —N(C$_{1-4}$alkyl)$_2$, —NO$_2$, —CN, —C$_{1-6}$alkyl, —C$_{1-6}$haloalkyl, —C$_{1-6}$alkyl-OH, —C$_{1-6}$alkoxy, —C$_{1-6}$haloalkoxy, and —C$_{1-6}$alkyl-O—C$_{1-4}$alkyl; and
m is 0, 1 or 2.

In certain embodiments, a chemical entity of Formula (I) is a chemical entity of Formula (Ibb), and more particularly, is a compound of Formula (Ibb), or a pharmaceutically acceptable salt of a compound of Formula (Ibb):

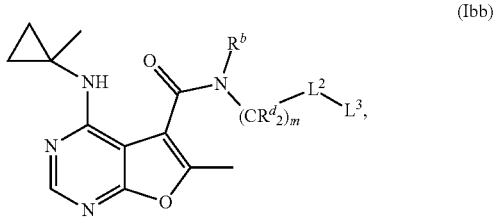

(Ibb)

wherein R$^b$, R$^d$, m, L$^2$, and L$^3$ have any of the values described herein.

In certain embodiments of a chemical entity of Formula (Ibb),

L$^2$ is —C$_{3-10}$cycloalkyl, 3-15-membered heterocycloalkyl, phenyl, or 5-10-membered heteroaryl, said —C$_{3-10}$cycloalkyl, 3-15-membered heterocycloalkyl, phenyl, and 5-10-membered heteroaryl optionally substituted with one to four R$^{1B}$, where each R$^{1B}$ is independently selected from the group consisting of: halo, —OH, =O, —NH$_2$, —NHC$_{1-4}$alkyl, —N(C$_{1-4}$alkyl)$_2$, —NO$_2$, —CN, —C$_{1-6}$alkyl, —C$_{1-6}$haloalkyl, —C$_{1-6}$alkyl-OH, —C$_{1-6}$alkoxy, —C$_{1-6}$haloalkoxy, and —C$_{1-6}$alkyl-O—C$_{1-4}$alkyl; L$^3$ is —H, —OH, —CN, —NH$_2$, —NHC$_{1-4}$alkyl, —N(C$_{1-4}$alkyl)$_2$, —NO$_2$, halo, —C$_{1-6}$alkyl, —C$_{1-6}$haloalkyl, —C$_{1-6}$alkoxy, —C$_{1-6}$haloalkoxy, —C$_{2-6}$alkenyl, —C$_{2-6}$alkynyl, —C$_{1-6}$alkyl-O—C$_{1-4}$alkyl, —C$_{3-10}$cycloalkyl, 3-15-membered heterocycloalkyl, phenyl, benzyl, or 5-10-membered heteroaryl, said —C$_{1-6}$alkyl, —C$_{3-10}$cycloalkyl, 3-15-membered heterocycloalkyl, phenyl, benzyl, and 5-10-membered heteroaryl optionally substituted with one to four R$^{1C}$, where each R$^{1C}$ is independently selected from the group consisting of: halo, —OH, =O, —NH$_2$, —NHC$_{1-4}$alkyl, —N(C$_{1-4}$alkyl)$_2$, —NO$_2$, —CN, —C$_{1-6}$alkyl, —C$_{1-6}$haloalkyl, —C$_{1-6}$alkyl-OH, —C$_{1-6}$alkoxy, —C$_{1-6}$haloalkoxy, and —C$_{1-6}$alkyl-O—C$_{1-4}$alkyl;
R$^b$ is —H, —C$_{1-6}$alkyl, —C$_{1-6}$haloalkyl, —C$_{1-6}$alkyl-OH, —C$_{3-6}$cycloalkyl, —C$_{2-6}$alkenyl, or —C$_{2-6}$alkynyl;
each R$^d$ is independently selected from the group consisting of: —H, —C$_{1-6}$alkyl, —C$_{1-6}$haloalkyl, —C$_{1-6}$alkyl-OH, —C$_{3-6}$cycloalkyl; and
m is 0, 1 or 2.

In certain embodiments, a chemical entity of Formula (I) is a chemical entity of Formula (Ic), and more particularly, is a compound of Formula (Ic), or a pharmaceutically acceptable salt of a compound of Formula (Ic):

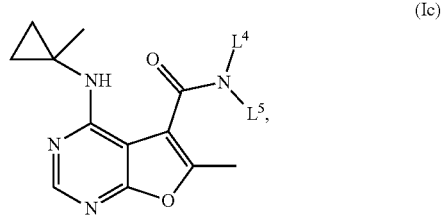

(Ic)

wherein L$^4$ and L$^5$ have any of the values described herein.

In certain embodiments of a chemical entity of Formula (Ic), L$^4$ and L$^5$ are taken together with the nitrogen to which they are attached to form a 3-15-membered heterocycloalkyl or 5-10-membered heteroaryl ring, optionally substituted with one to four R$^{1D}$, where each R$^{1D}$ is independently selected from the group consisting of: L$^6$, =O, —C$_{1-6}$alkyl-OH, —C$_{1-6}$alkyl-O—C$_{1-4}$alkyl, and —COOC$_{1-6}$alkyl; and L$^6$ is selected from the group consisting of: —H, —OH, —CN, —NH$_2$, —NHC$_{1-4}$alkyl, —N(C$_{1-4}$alkyl)$_2$, —N=S(=O)(CH$_3$)$_2$, —NO$_2$, —SO$_2$CH$_3$, halo, —C$_{1-6}$alkyl, —C$_{1-6}$haloalkyl, —C$_{1-6}$alkoxy, —C$_{1-6}$haloalkoxy, —C$_{2-6}$alkenyl, —C$_{2-6}$alkynyl, —C(O)C$_{1-6}$alkyl, —C(O)NH$_2$, —C$_{3-10}$cycloalkyl, —C$_{1-6}$alkyl-O—C$_{1-4}$alkyl, 3-15-membered heterocycloalkyl, phenyl, benzyl, and 5-10-membered heteroaryl, said —C$_{1-6}$alkyl, —C$_{3-10}$cycloalkyl, —C$_{3-7}$cycloalkoxy, 3-15-membered heterocycloalkyl, phenyl, benzyl, and 5-10-membered heteroaryl optionally substituted with one or more R$^{1E}$, where each R$^{1E}$ is independently selected from the group consisting of: halo, —OH, =O, —NH$_2$, —NHC$_{1-4}$ alkyl, —N(C$_{1-4}$alkyl)$_2$, —NO$_2$, —SO$_2$CH$_3$, —CN, —C$_{1-6}$alkyl, —C$_{1-6}$haloalkyl, —C$_{1-6}$alkyl-OH, —C$_{1-6}$alkoxy, —C$_{1-6}$haloalkoxy, —C$_{1-6}$alkyl-O—

$C_{1-4}$alkyl, —C(O)$C_{1-6}$alkyl, —COO$C_{1-6}$alkyl, —C(O)NH$_2$, —$C_{3-7}$cycloalkyl, 3-15-membered heterocycloalkyl, phenyl and 5-10-membered heteroaryl.

In certain embodiments, a chemical entity of Formula (I) is a chemical entity of Formula (Icaa) or (Icab), and more particularly, is a compound of Formula (Icaa) or (Icab), or a pharmaceutically acceptable salt of a compound of Formula (Icaa) or (Icab):

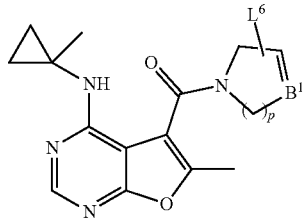

(Icaa)

or

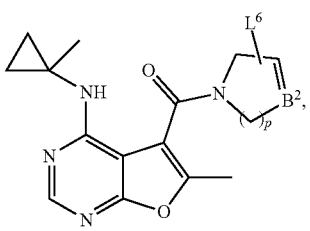

(Icab)

wherein $L^6$, $B^1$, $B^2$ and p have any of the values described herein.

In certain embodiments of a chemical entity of Formula (Icaa) or (Icab), $L^6$ is selected from the group consisting of: —H, —OH, —CN, —NH$_2$, —NH$C_{1-4}$alkyl, —N($C_{1-4}$alkyl)$_2$, —NO$_2$, —SO$_2$CH$_3$, halo, —$C_{1-6}$alkyl, —$C_{1-6}$haloalkyl, —$C_{1-6}$alkoxy, —$C_{1-6}$haloalkoxy, —$C_{2-6}$alkenyl, —$C_{2-6}$alkynyl, —C(O)$C_{1-6}$alkyl, —C(O)NH$_2$, —$C_{3-10}$cycloalkyl, —$C_{1-6}$alkyl-O—$C_{1-4}$alkyl, -3-15-membered heterocycloalkyl, phenyl, benzyl, and 5-10-membered heteroaryl, said —$C_{1-6}$alkyl, —$C_{3-10}$cycloalkyl, 3-15-membered heterocycloalkyl, phenyl, benzyl, and 5-10-membered heteroaryl optionally substituted with one to four $R^{1E}$, where each $R^{1E}$ is independently selected from the group consisting of: halo, —OH, =O, —NH$_2$, —NH$C_{1-4}$alkyl, —N($C_{1-4}$alkyl)$_2$, —NO$_2$, —SO$_2$CH$_3$, —CN, —$C_{1-6}$alkyl, —$C_{1-6}$haloalkyl, —$C_{1-6}$alkyl-OH, —$C_{1-6}$alkoxy, —$C_{1-6}$haloalkoxy, —$C_{1-6}$alkyl-O—$C_{1-4}$alkyl, —C(O)$C_{1-6}$alkyl, —COO$C_{1-6}$alkyl, —C(O)NH$_2$, and —$C_{3-7}$cycloalkyl;

$B^1$ is CH or C($R^{1D}$);
$B^2$ is CH$_2$ or CH($R^{1D}$);
$R^{1D}$ is $L^6$, =O, —$C_{1-6}$alkyl-OH, or —$C_{1-6}$alkyl-O—$C_{1-4}$alkyl; and
p is 0, 1, 2 or 3.

In certain embodiments, a chemical entity of Formula (I) is a chemical entity of Formula (Icb), and more particularly, is a compound of Formula (Icb), or a pharmaceutically acceptable salt of a compound of Formula (Icb):

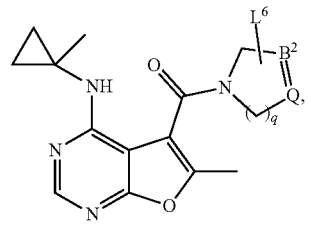

(Icb)

wherein $L^6$, $B^2$, Q, and q have any of the values described herein.

In certain embodiments of a chemical entity of Formula (Icb), $L^6$ is selected from the group consisting of: —H, —OH, —CN, —NH$_2$, —NH$C_{1-4}$alkyl, —N($C_{1-4}$alkyl)$_2$, —NO$_2$, —SO$_2$CH$_3$, halo, —$C_{1-6}$alkyl, —$C_{1-6}$haloalkyl, —$C_{1-6}$alkoxy, —$C_{1-6}$haloalkoxy, —$C_{2-6}$alkenyl, —$C_{2-6}$alkynyl, —C(O)$C_{1-6}$alkyl, —C(O)NH$_2$, —$C_{3-10}$cycloalkyl, —$C_{1-6}$alkyl-O—$C_{1-4}$alkyl, 3-15-membered heterocycloalkyl, phenyl, benzyl, and 5-10-membered heteroaryl, said —$C_{1-6}$alkyl, —$C_{3-10}$cycloalkyl, 3-15-membered heterocycloalkyl, phenyl, benzyl, and 5-10-membered heteroaryl optionally substituted with one to four $R^{1E}$, where each $R^{1E}$ is independently selected from the group consisting of: halo, —OH, =O, —NH$_2$, —NH$C_{1-4}$alkyl, —N($C_{1-4}$alkyl)$_2$, —NO$_2$, —SO$_2$CH$_3$, —CN, —$C_{1-6}$alkyl, —$C_{1-6}$haloalkyl, —$C_{1-6}$alkyl-OH, —$C_{1-6}$alkoxy, —$C_{1-6}$haloalkoxy, —$C_{1-6}$alkyl-O—$C_{1-4}$alkyl, —C(O)$C_{1-6}$alkyl, —COO$C_{1-6}$alkyl, —C(O)NH$_2$, and —$C_{3-7}$cycloalkyl;

$B^2$ is CH$_2$ or CH($R^{1D}$);
$R^{1D}$ is $L^6$, =O, —$C_{1-6}$alkyl-OH, or —$C_{1-6}$alkyl-O—$C_{1-4}$alkyl;
Q is NH, N($R^{1D}$), or O; and
each q is 1, 2, or 3.

In certain embodiments, a chemical entity of Formula (I) is a chemical entity of Formula (Icc), and more particularly, is a compound of Formula (Icc), or a pharmaceutically acceptable salt of a compound of Formula (Icc):

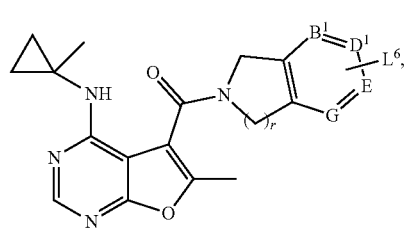

(Icc)

wherein $L^6$, $B^1$, $D^1$, E, G, and r have any of the values described herein.

In certain embodiments of a chemical entity of Formula (Icc), $L^6$ is selected from the group consisting of: —H, —OH, —CN, —NH$_2$, —NH$C_{1-4}$alkyl, —N($C_{1-4}$alkyl)$_2$, —N=S (=O)(CH$_3$)$_2$, —NO$_2$, —SO$_2$CH$_3$, halo, —$C_{1-6}$alkyl, —$C_{1-6}$haloalkyl, —$C_{1-6}$alkoxy, —$C_{1-6}$haloalkoxy, —$C_{2-6}$alkenyl, —$C_{2-6}$alkynyl, —C(O)$C_{1-6}$alkyl, —C(O)NH$_2$, —$C_{3-10}$cycloalkyl, —$C_{1-6}$alkyl-O—$C_{1-4}$alkyl, 3-15-membered heterocycloalkyl, phenyl, benzyl, and 5-10-membered heteroaryl, said —$C_{1-6}$alkyl, —$C_{3-10}$cycloalkyl, 3-15-membered heterocycloalkyl, phenyl, benzyl, and 5-10-membered heteroaryl optionally substituted with one to four $R^{1E}$, where each $R^{1E}$ is independently selected from the group consisting of: halo, —OH, =O, —NH$_2$, —NHC$_{1-4}$alkyl, —N(C$_{1-4}$alkyl)$_2$, —NO$_2$, —SO$_2$CH$_3$, —CN, —C$_{1-6}$alkyl, —C$_{1-6}$haloalkyl, —C$_{1-6}$alkyl-OH, —C$_{1-6}$alkoxy, —C$_{1-6}$haloalkoxy, —C$_{1-6}$alkyl-O—C$_{1-4}$alkyl, —C(O)C$_{1-6}$alkyl, —COOC$_{1-6}$alkyl, —C(O)NH$_2$, and —C$_{3-7}$cycloalkyl;

each B$^1$, D$^1$, E, and G is either CH, C(R$^{1D}$), or N, provided that no more than two of B$^1$, D$^1$, E, and G are simultaneously N;

each R$^{1D}$ is independently selected from the group consisting of: L$^6$, =O, —C$_{1-6}$alkyl-OH, and —C$_{1-6}$alkyl-O—C$_{1-4}$alkyl; and r is 1 or 2.

In some embodiments of a chemical entity of Formula (Icc) disclosed herein:
L$^6$ is selected from the group consisting of: —H, halo, —C$_{1-6}$alkyl, —C$_{1-6}$haloalkyl, —C$_{1-6}$alkoxy, and —C$_{1-6}$haloalkoxy;
B$^1$ and E are N;
D$^1$ and G are independently CH or C(R$^{1D}$);
and r is 2.

In some embodiments of a chemical entity of Formula (I), (Ia), (Ib), (Iba), or (Ibb) disclosed herein:
L$^6$ is selected from the group consisting of: —H, halo, —C$_{1-6}$alkyl, —C$_{1-6}$haloalkyl, —C$_{1-6}$alkoxy, and —C$_{1-6}$haloalkoxy;
D$^1$ and G are N;
B$^1$ and E are independently CH or C(R$^{1D}$);
and r is 2.

In some embodiments of a chemical entity of Formula (I), (Ia), (Ib), (Iba), or (Ibb) disclosed herein:
L$^2$ is —N(R$^c$)—, —NR$^c$(CH$_2$)$_m$—, —O—, —S—, —C$_{1-4}$alkyl, —C$_{1-4}$haloalkyl, —C$_{1-4}$alkoxy, —C$_{1-4}$haloalkoxy, —C$_{2-5}$alkenyl, —C$_{2-5}$alkynyl, —C(O)C$_{1-4}$alkyl, —CHR$^c$—, —(CH$_2$)$_m$NH—, —(CH$_2$)$_m$O—, or —(CH$_2$)$_m$S—, said —C$_{1-4}$alkyl optionally substituted with one to three R$^{1B}$, where each R$^{1B}$ is independently selected from the group consisting of: —F, —Cl, —Br, —I, —OH, =O, —NH$_2$, —NHC$_{1-4}$alkyl, —N(C$_{1-4}$alkyl)$_2$, —NO$_2$, —SO$_2$CH$_3$, —CN, —C$_{1-4}$alkyl, —C$_{1-4}$haloalkyl, —C$_{1-4}$alkyl-OH, —C$_{1-4}$alkoxy, —C$_{1-4}$haloalkoxy, —C$_{1-4}$alkyl-O—C$_{1-4}$alkyl, —C(O)C$_{1-4}$alkyl, —COOC$_{1-4}$alkyl, —C(O)NH$_2$, and —C$_{3-6}$cycloalkyl.

In some embodiments of a chemical entity of Formula (I), (Ia), (Tb), (Iba), or (Ibb) disclosed herein:
L$^2$ is selected from the group consisting of: —C$_{3-10}$cycloalkyl, 3-10-membered heterocycloalkyl, phenyl, and 5-10-membered heteroaryl, said —C$_{3-10}$cycloalkyl, 3-10-membered heterocycloalkyl, phenyl, and 5-10-membered heteroaryl optionally substituted with one to three R$^{1B}$.

In some embodiments of a chemical entity of Formula (I), (Ia), (Tb), (Iba), or (Ibb) disclosed herein:
L$^2$ is cyclopropyl, cyclobutyl, cyclopentyl, cyclohexyl, cycloheptyl, bicyclo[1.1.1]pentan-1-yl, adamantanyl, or 2,3-dihydro-1H-inden-5-yl, each optionally substituted with one to three R$^{1B}$.

In some embodiments of a chemical entity of Formula (I), (Ia), (Tb), (Iba), or (Ibb) disclosed herein:
L$^2$ is selected from the group consisting of: azetidine, pyrrolidine, piperidine, azepane, dihydropyrrole, tetrahydropyridine, imidazoline, piperazine, diazepane, morpholine, oxetane, tetrahydrofuran, tetrahydropyran, benzo[d][1,3]dioxole, 2,3-dihydrobenzo[b][1,4]dioxine, tetrahydroquinoline, tetrahydroisoquinoline, quinolin-2(1H)-one, decahydroisoquinoline, decahydroquinoline, 6,7-dihydro-5H-cyclopenta[b]pyridine, 6,7-dihydro-5H-cyclopenta[d]pyrimidine, 2,3-dihydrobenzo[b][1,4]dioxine, pyrimidinone, 3-oxabicyclo[3.1.0]hexane, 3-azabicyclo[3.1.0]hexane, 8-oxa-3-azabicyclo[3.2.1]octane, pyrimidin-4(3H)-one, octahydrocyclopentapyrrole, 6,7-dihydro-5H-pyrrolo[3,4-d]pyrimidine, 6,7-dihydro-5H-pyrrolo[3,2-d]pyrimidine, 5,6,7,8-tetrahydropyrido[4,3-c]pyridazine, 5,6,7,8-tetrahydropyrido[3,4-c]pyridazine, 5,6,7,8-tetrahydropyrido[3,2-c]pyridazine, 5,6,7,8-tetrahydropyrido[4,3-d]pyrimidine, 5,6,7,8-tetrahydropyrido[3,4-d]pyrimidine, tetrahydronaphthyridine, 6,7-dihydro-5H-pyrrolo[3,4-b]pyridine, 2,3-dihydro-1H-pyrrolo[3,4-c]pyridine, and isoindoline, each optionally substituted with one to four R$^{1B}$, where each R$^{1B}$ is independently selected from the group consisting of: —F, —Cl, —Br, —I, —OH, =O, —NH$_2$, —NHC$_{1-4}$alkyl, —N(C$_{1-4}$alkyl)$_2$, —NO$_2$, —SO$_2$CH$_3$, —CN, —C$_{1-4}$alkyl, —C$_{1-4}$haloalkyl, —C$_{1-4}$alkyl-OH, —C$_{1-4}$alkoxy, —C$_{1-4}$haloalkoxy, —C$_{1-4}$alkyl-O—C$_{1-4}$alkyl, —C(O)C$_{1-4}$alkyl, —COOC$_{1-4}$alkyl, —C(O)NH$_2$, and —C$_{3-6}$cycloalkyl.

In some embodiments of a chemical entity of Formula (I), (Ia), (Ib), (Iba), or (Ibb) disclosed herein:
L$^2$ is selected from the group consisting of: azetidine, pyrrolidine, piperidine, azepane, imidazoline, piperazine, diazepane, morpholine, oxetane, tetrahydrofuran, tetrahydropyran, benzo[d][1,3]dioxole, 2,3-dihydrobenzo[b][1,4]dioxine, tetrahydroquinoline, tetrahydroisoquinoline, quinolin-2(1H)-one, decahydroisoquinoline, decahydroquinoline, 6,7-dihydro-5H-cyclopenta[b]pyridine, 6,7-dihydro-5H-cyclopenta[d]pyrimidine, 2,3-dihydrobenzo[b][1,4]dioxine, pyrimidinone, 3-oxabicyclo[3.1.0]hexane, 3-azabicyclo[3.1.0]hexane, 8-oxa-3-azabicyclo[3.2.1]octane, and pyrimidin-4(3H)-one, each optionally substituted with one to three R$^{1B}$, where each R$^{1B}$ is independently selected from the group consisting of: halo, —OH, =O, —NH$_2$, —NHC$_{1-4}$ alkyl, —N(C$_{1-4}$alkyl)$_2$, —CN, —C$_{1-4}$alkyl, —C$_{1-4}$haloalkyl, —C$_{1-4}$alkyl-OH, —C$_{1-4}$alkoxy, —C$_{1-4}$haloalkoxy, —C$_{1-4}$alkyl-O—C$_{1-4}$alkyl, —C(O)C$_{1-4}$alkyl, —COOC$_{1-4}$alkyl, —C(O)NH$_2$, and —C$_{3-6}$cycloalkyl.

In some embodiments of a chemical entity of Formula (I), (Ia), (Ib), (Iba), or (Ibb) disclosed herein:
L$^2$ is phenyl, optionally substituted with one to three R$^{1B}$.

In some embodiments of a chemical entity of Formula (I), (Ia), (Ib), (Iba), or (Ibb) disclosed herein:
L$^2$ is a 5-10-membered heteroaryl selected from the group consisting of: pyridine, pyridazine, pyrazine, pyrimidine, pyrrole, furan, thiophene, pyrazole, imidazole, thiazole, isothiazole, oxazole, isoxazole, triazole, oxadiazole, thiadiazole, tetrazole, indole, indazole, benzimidazole, benzoxazole, benzothiazole, [1,2,4]triazolo[4,3-a]pyridine, and imidazo[1,2-a]pyrazine, each optionally substituted with one to three R$^{1B}$, where each R$^{1B}$ is independently selected from the group consisting of: halo, —OH, =O, —NH$_2$, —NHC$_{1-4}$alkyl, —N(C$_{1-4}$alkyl)$_2$, —NO$_2$, —SO$_2$CH$_3$, —CN, —C$_{1-4}$alkyl, —C$_{1-4}$haloalkyl, —C$_{1-4}$alkyl-OH, —C$_{1-4}$alkoxy, —C$_{1-4}$haloalkoxy, —C$_{1-4}$alkyl-O—C$_{1-4}$alkyl, —C(O)C$_{1-4}$alkyl, —COOC$_{1-4}$alkyl, —C(O)NH$_2$, and —C$_{3-6}$cycloalkyl.

In some embodiments of a chemical entity of Formula (I), (Ia), (Tb), (Iba), or (Ibb) disclosed herein:
L$^2$ is pyridine, pyridazine, pyrazine, pyrimidine, pyrrole, pyrazole, imidazole, thiazole, oxazole, and isoxazole, each optionally substituted with one to three R$^{1B}$, where each R$^{1B}$ is independently selected from the group consisting of: —F, —Cl, —Br, —I, —OH, =O, —NH$_2$, —NHC$_{1-4}$alkyl, —N(C$_{1-4}$alkyl)$_2$, —NO$_2$, —SO$_2$CH$_3$, —CN, —C$_{1-4}$alkyl, —C$_{1-4}$haloalkyl, —C$_{1-4}$alkyl-OH, —C$_{1-4}$alkoxy, —C$_{1-4}$haloalkoxy, —C$_{1-4}$alkyl-O—C$_{1-4}$alkyl, —C(O)C$_{1-4}$alkyl, —COOC$_{1-4}$alkyl, —C(O)NH$_2$, and —C$_{3-6}$cycloalkyl.

In some embodiments of a chemical entity of Formula (I), (Ia), (Tb), (Iba), or (Ibb) disclosed herein:
$L^3$ is selected from the group consisting of: —H, —OH, —CN, —NH$_2$, —NHC$_{1-4}$alkyl, —N(C$_{1-4}$alkyl)$_2$, —N=S(=O)(CH$_3$)$_2$, —NO$_2$, —SO$_2$CH$_3$, —F, —Cl, —Br, —I, —C$_{1-4}$alkyl, —C$_{1-4}$haloalkyl, —C$_{1-4}$alkoxy, —C$_{1-4}$haloalkoxy, —C$_{2-5}$alkenyl, —C$_{2-5}$alkynyl, —C$_{1-6}$alkyl-O—C$_{1-4}$alkyl, —C(O)C$_{1-6}$alkyl, and —C(O)NH$_2$, said —C$_{1-4}$alkyl, optionally substituted with one to three R$^{1C}$.

In some embodiments of a chemical entity of Formula (I), (Ia), (Tb), (Iba), or (Ibb) disclosed herein:
$L^3$ is selected from the group consisting of: —H, —OH, —CN, —NH$_2$, —NHC$_{1-4}$alkyl, —N(C$_{1-4}$alkyl)$_2$, —F, —Cl, —Br, —I, —C$_{1-4}$alkyl, —C$_{1-4}$haloalkyl, —C$_{1-4}$alkoxy, —C$_{1-4}$haloalkoxy, said —C$_{1-4}$alkyl, optionally substituted with one to three R$^{1C}$.

In some embodiments of a chemical entity of Formula (I), (Ia), (Tb), (Iba), or (Ibb) disclosed herein:
$L^3$ is selected from the group consisting of: —C$_{3-10}$cycloalkyl, 3-10-membered heterocycloalkyl, phenyl, and 5-10-membered heteroaryl, said —C$_{3-10}$cycloalkyl, 3-10-membered heterocycloalkyl, phenyl, and 5-10-membered heteroaryl optionally substituted with one to three R$^{1C}$.

In some embodiments of a chemical entity of Formula (I), (Ia), (Ib), (Iba), or (Ibb) disclosed herein:
$L^3$ is cyclopropyl, cyclobutyl, cyclopentyl, cyclohexyl cycloheptyl, bicyclo[1.1.1]pentan-1-yl, adamantanyl, or 2,3-dihydro-1H-inden-5-yl, each optionally substituted with one to three R$^{1C}$.

In some embodiments of a chemical entity of Formula (I), (Ia), (Ib), (Iba), or (Ibb) disclosed herein:
$L^3$ is selected from the group consisting of: azetidine, pyrrolidine, piperidine, azepane, dihydropyrrole, tetrahydropyridine, imidazoline, piperazine, diazepane, morpholine, oxetane, tetrahydrofuran, tetrahydropyran, benzo[d][1,3]dioxole, 2,3-dihydrobenzo[b][1,4]dioxine, tetrahydroquinoline, tetrahydroisoquinoline, quinolin-2(1H)-one, decahydroisoquinoline, decahydroquinoline, 6,7-dihydro-5H-cyclopenta[b]pyridine, 6,7-dihydro-5H-cyclopenta[d]pyrimidine, 2,3-dihydrobenzo[b][1,4]dioxine, pyrimidinone, 3-oxabicyclo[3.1.0]hexane, 3-azabicyclo[3.1.0]hexane, 8-oxa-3-azabicyclo[3.2.1]octane, pyrimidin-4(3H)-one, octahydrocyclopentapyrrole, 6,7-dihydro-5H-pyrrolo[3,4-d]pyrimidine, 6,7-dihydro-5H-pyrrolo[3,2-d]pyrimidine, 5,6,7,8-tetrahydropyrido[4,3-c]pyridazine, 5,6,7,8-tetrahydropyrido[3,4-c]pyridazine, 5,6,7,8-tetrahydropyrido[3,2-c]pyridazine, 5,6,7,8-tetrahydropyrido[4,3-d]pyrimidine, 5,6,7,8-tetrahydropyrido[3,4-d]pyrimidine, tetrahydronaphthyridine, 6,7-dihydro-5H-pyrrolo[3,4-b]pyridine, 2,3-dihydro-1H-pyrrolo[3,4-c]pyridine, and isoindoline, each optionally substituted with one to three R$^{1C}$ is independently selected from the group consisting of: halo, —OH, =O, —NH$_2$, —NHC$_{1-4}$alkyl, —N(C$_{1-4}$alkyl)$_2$, —NO$_2$, —SO$_2$CH$_3$, —CN, —C$_{1-6}$alkyl, —C$_{1-6}$haloalkyl, —C$_{1-6}$alkyl-OH, —C$_{1-6}$alkoxy, —C$_{1-6}$haloalkoxy, —C$_{1-6}$alkyl-O—C$_{1-4}$alkyl, —C(O)C$_{1-6}$alkyl, —COOC$_{1-6}$alkyl, —C(O)NH$_2$, and —C$_{3-7}$cycloalkyl.

In some embodiments of a chemical entity of Formula (I), (Ia), (Ib), (Iba), or (Ibb) disclosed herein:
$L^3$ is selected from the group consisting of: azetidine, pyrrolidine, piperidine, azepane, imidazoline, piperazine, diazepane, morpholine, oxetane, tetrahydrofuran, tetrahydropyran, benzo[d][1,3]dioxole, 2,3-dihydrobenzo[b][1,4]dioxine, tetrahydroquinoline, tetrahydroisoquinoline, quinolin-2(1H)-one, decahydroisoquinoline, decahydroquinoline, 6,7-dihydro-5H-cyclopenta[b]pyridine, 6,7-dihydro-5H-cyclopenta[d]pyrimidine, 2,3-dihydrobenzo[b][1,4]dioxine, pyrimidinone, 3-oxabicyclo[3.1.0]hexane, 3-azabicyclo[3.1.0]hexane, 8-oxa-3-azabicyclo[3.2.1]octane, and pyrimidin-4(3H)-one, each optionally substituted with one to three R$^{1C}$, where each R$^{1C}$ is independently selected from the group consisting of: —F, —Cl, —Br, —I, —OH, =O, —NH$_2$, —NHC$_{1-4}$alkyl, —N(C$_{1-4}$alkyl)$_2$, —CN, —C$_{1-4}$alkyl, —C$_{1-4}$haloalkyl, —C$_{1-4}$alkyl-OH, —C$_{1-4}$alkoxy, —C$_{1-4}$haloalkoxy, —C$_{1-4}$alkyl-O—C$_{1-4}$alkyl, and —C$_{3-6}$cycloalkyl.

In some embodiments of a chemical entity of Formula (I), (Ia), (Tb), (Iba), or (Ibb) disclosed herein:
$L^3$ is phenyl, optionally substituted with one to three R$^{1C}$.

In some embodiments of a chemical entity of Formula (I), (Ia), (Tb), (Iba), or (Ibb) disclosed herein:
$L^3$ is selected from the group consisting of: pyridine, pyridazine, pyrazine, pyrimidine, pyrrole, furan, thiophene, pyrazole, imidazole, thiazole, isothiazole, oxazole, isoxazole, triazole, oxadiazole, thiadiazole, tetrazole, indole, indazole, benzimidazole, benzoxazole, benzothiazole, [1,2,4]triazolo[4,3-a]pyridine, and imidazo[1,2-a]pyrazine, each optionally substituted with one to four R$^{1C}$, where each R$^{1C}$ is independently selected from the group consisting of: —F, —Cl, —Br, —I, —OH, =O, —NH$_2$, —NHC$_{1-4}$alkyl, —N(C$_{1-4}$alkyl)$_2$, —CN, —C$_{1-6}$alkyl, —C$_{1-6}$haloalkyl, —C$_{1-6}$alkyl-OH, —C$_{1-6}$alkoxy, —C$_{1-6}$haloalkoxy, —C$_{1-6}$alkyl-O—C$_{1-4}$alkyl, —C(O)C$_{1-6}$alkyl, —COOC$_{1-6}$alkyl, —C(O)NH$_2$, and —C$_{3-7}$cycloalkyl.

In some embodiments of a chemical entity of Formula (I), (Ia), (Tb), (Iba), or (Ibb) disclosed herein:
$L^3$ is selected from the group consisting of: pyridine, pyridazine, pyrazine, pyrimidine, pyrrole, pyrazole, imidazole, thiazole, oxazole, and isoxazole, each optionally substituted with one to three R$^{1C}$, where each R$^{1C}$ is independently selected from the group consisting of: —F, —Cl, —Br, —I, —OH, =O, —NH$_2$, —NHC$_{1-4}$alkyl, —N(C$_{1-4}$alkyl)$_2$, —CN, —C$_{1-4}$alkyl, —C$_{1-4}$haloalkyl, —C$_{1-4}$alkyl-OH, —C$_{1-4}$alkoxy, —C$_{1-4}$haloalkoxy and —C$_{3-6}$cycloalkyl.

In some embodiments of a chemical entity of Formula (I), (Ia), (Tb), (Iba), or (Ibb) disclosed herein:
$L^3$ is selected from the group consisting of: pyrrole, pyrazole, imidazole, thiazole, oxazole, and isoxazole, each optionally substituted with one to three R$^{1C}$, where each R$^{1C}$ is independently selected from the group consisting of: —F, —Cl, —Br, —I, —OH, =O, —NH$_2$, —NHC$_{1-4}$alkyl, —N(C$_{1-4}$alkyl)$_2$, —CN, —C$_{1-4}$alkyl, —C$_{1-4}$haloalkyl, —C$_{1-4}$alkyl-OH, —C$_{1-4}$alkoxy, —C$_{1-4}$haloalkoxy, and —C$_{3-6}$cycloalkyl.

In some embodiments of a chemical entity of Formula (I) or (Ic) disclosed herein:
$L^4$ and $L^5$ are taken together with the nitrogen to which they are attached to form a azetidine, pyrrolidine, 2,5-dihydro-1H-pyrrole, 2,3-dihydro-1H-pyrrole, imidazolidine, piperidine, 1,2,3,6-tetrahydropyridine, 1,2,3,4-tetrahydropyridine, piperazine, morpholine, 3-azabicyclo[3.1.0]hexane, octahydrocyclopenta[c]pyrrole, octahydrocyclopenta[b]pyrrole, 6,7-dihydro-5H-pyrrolo[3,4-d]pyrimidine, 6,7-dihydro-5H-pyrrolo[3,2-d]pyrimidine, 5,6,7,8-tetrahydropyrido[4,3-c]pyridazine, 5,6,7,8-tetrahydropyrido[3,4-c]pyridazine, 5,6,7,8-tetrahydropyrido[3,2-c]pyridazine, 5,6,7,8-tetrahydropyrido[4,3-d]pyrimidine, 5,6,7,8-tetrahydropyrido[3,4-d]pyrimidine, 5,6,7,8-tetrahydro-1,6-naphthyridine, 5,6,7,8-tetrahydro-1,7-naphthyridine, 1,2,3,4-tetrahydro-2,6-naphthyridine, 1,2,3,4-tetrahydro-2,7-naphthyridine, 1,2,3,4-tetrahydroisoquinoline, 1,2,3,4-tetrahydroquinoline, 6,7-dihydro-5H-pyrrolo[3,4-b]pyridine, 2,3-dihydro-1H-pyrrolo[3,4-c]pyridine, isoindoline, 5,6,7,8-tetrahydroimidazo[1,2-a]pyrazine, 5,6,7,8-tetrahydroimidazo[1,5-a]pyrazine, 4,5,6,7-tetrahydropyrazolo[1,5-a]pyrazine, 5,6,7,8-tetrahydro-2,6-naphthyridin-1(2H)-one, 5,6,7,8-tetrahydropyrido[3,4-d]pyrimidin-4(3H)-one, 4,5,6,7-tetrahydrothieno[3,2-c]pyridine, octahydropyrrolo[1,2-a]pyrazine, octahydropyrrolo[1,2-c]pyrimidine, hexahydro-2H-furo[3,2-b]pyrrole, hexahydro-2H-furo[2,3-c]pyrrole, hexahydro-1H-furo[3,4-c]pyrrole, hexahydro-1H-furo[3,4-b]pyrrole, decahydroisoquinoline, decahydroquinoline, azepane, diazepane, 8-oxa-3-azabicyclo[3.2.1]octane, 6,7,8,9-tetrahydro-5H-pyrimido[4,5-d]azepine, 3,4,5,6-tetrahydro-2H-benzo[b][1,5]oxazocine, spiro[indoline-3,3'-piperidin]-2-one, spiro[indoline-3,3'-pyrrolidin]-2-one, 2,3-dihydrospiro[indene-1,2'-morpholine], 3H-spiro[isobenzofuran-1,3'-piperidine], 3H-spiro[isobenzofuran-1,3'-pyrrolidine], spiro[benzo[d][1,3]oxazine-4,4'-piperidin]-2(1H)-one, spiro[indene-1,4'-piperidine], 3H-spiro[benzo[c]thiophene-1,4'-piperidine], or 2,3,4,5-tetrahydro-1H-1,5-methanobenzo[d]azepine, each optionally substituted with one to three $R^{1D}$ In some embodiments of a chemical entity of Formula (I) or (Ic) disclosed herein:

$L^4$ and $L^5$ are taken together with the nitrogen to which they are attached to form a azetidine, pyrrolidine, piperidine, azepane, 1,2,3,6-tetrahydropyridine, 1,2,3,4-tetrahydropyridine, or 2,3-dihydro-1H-pyrrole, each optionally substituted with one to three $R^{1D}$ In some embodiments of a chemical entity of Formula (I) or (Ic) disclosed herein:

$L^4$ and $L^5$ are taken together with the nitrogen to which they are attached to form a imidazolidine, piperazine, diazepane, or morpholine, each optionally substituted with one to three $R^{1D}$.

In some embodiments of a chemical entity of Formula (I) or (Ic) disclosed herein:

$L^4$ and $L^5$ are taken together with the nitrogen to which they are attached to form a 6,7-dihydro-5H-pyrrolo[3,4-d]pyrimidine, 6,7-dihydro-5H-pyrrolo[3,2-d]pyrimidine, 5,6,7,8-tetrahydropyrido[4,3-c]pyridazine, 5,6,7,8-tetrahydropyrido[3,4-c]pyridazine, 5,6,7,8-tetrahydropyrido[3,2-c]pyridazine, 5,6,7,8-tetrahydropyrido[4,3-d]pyrimidine, 5,6,7,8-tetrahydropyrido[3,4-d]pyrimidine, 5,6,7,8-tetrahydro-1,6-naphthyridine, 5,6,7,8-tetrahydro-1,7-naphthyridine, 1,2,3,4-tetrahydro-2,6-naphthyridine, 1,2,3,4-tetrahydro-2,7-naphthyridine, 1,2,3,4-tetrahydroisoquinoline, 1,2,3,4-tetrahydroquinoline, 6,7-dihydro-5H-pyrrolo[3,4-b]pyridine, 2,3-dihydro-1H-pyrrolo[3,4-c]pyridine, or isoindoline, each optionally substituted with one to three $R^{1D}$ In some embodiments of a chemical entity of Formula (I) or (Ic) disclosed herein:

$L^4$ and $L^5$ are taken together with the nitrogen to which they are attached to form a 5,6,7,8-tetrahydroimidazo[1,2-a]pyrazine, 5,6,7,8-tetrahydroimidazo[1,5-a]pyrazine, 4,5,6,7-tetrahydropyrazolo[1,5-a]pyrazine, octahydropyrrolo[1,2-a]pyrazine, or octahydropyrrolo[1,2-c]pyrimidine, each optionally substituted with one to three $R^{1D}$ In some embodiments of a chemical entity of Formula (I) or (Ic) disclosed herein:

$L^4$ and $L^5$ are taken together with the nitrogen to which they are attached to form a: 3-azabicyclo[3.1.0]hexane, octahydrocyclopenta[b]pyrrole, octahydrocyclopenta[c]pyrrole, 4,5,6,7-tetrahydrothieno[3,2-c]pyridine, hexahydro-2H-furo[3,2-b]pyrrole, hexahydro-2H-furo[2,3-c]pyrrole, hexahydro-1H-furo[3,4-c]pyrrole, hexahydro-1H-furo[3,4-b]pyrrole, decahydroisoquinoline, decahydroquinoline, 8-oxa-3-azabicyclo[3.2.1]octane, 6,7,8,9-tetrahydro-5H-pyrimido[4,5-d]azepine, 3,4,5,6-tetrahydro-2H-benzo[b][1,5] oxazocine, spiro[indoline-3,3'-piperidin]-2-one, spiro[indoline-3,3'-pyrrolidin]-2-one, 2,3-dihydrospiro[indene-1,2'-morpholine], 3H-spiro[isobenzofuran-1,3'-piperidine], 3H-spiro[isobenzofuran-1,3'-pyrrolidine], spiro[benzo[d][1,3]oxazine-4,4'-piperidin]-2(1H)-one, spiro[indene-1,4'-piperidine], 3H-spiro[benzo[c]thiophene-1,4'-piperidine], or 2,3,4,5-tetrahydro-1H-1,5-methanobenzo[d]azepine, each optionally substituted with one to three $R^{1D}$.

In some embodiments of a chemical entity of Formula (I) or (Ic) disclosed herein:

$L^4$ and $L^5$ are taken together with the nitrogen to which they are attached to form a pyrazole, imidazole, pyrrole, oxazole, thiazole, indole, or indazole, each optionally substituted with one to three $R^{1D}$.

In some embodiments of a chemical entity of Formula (I) or (Ic) disclosed herein:

$L^4$ and $L^5$ are taken together with the nitrogen to which they are attached to form a pyrazole, optionally substituted with one to three $R^{1D}$.

In some embodiments of a chemical entity of Formula (I), (Ia), (Ib), (Iba), or (Ibb) disclosed herein:

each Re is independently —H, —$C_{1-3}$alkyl, —$C_{1-3}$haloalkyl, —$C_{1-3}$alkyl-OH, —$C_{1-3}$alkyl-O—$C_{1-3}$alkyl, or —$C_{3-5}$cycloalkyl.

In some embodiments of a chemical entity of Formula (I), (Ic), (Icaa), (Icab), (Icb), or (Icc) disclosed herein:

$L^6$ is selected from the group consisting of: —H, —OH, —CN, —NH$_2$, —NHC$_{1-4}$alkyl, —N(C$_{1-4}$alkyl)$_2$, —F, —Cl, —Br, —I, —C$_{1-4}$alkyl, —C$_{1-4}$haloalkyl, —C$_{1-4}$alkoxy, —C$_{1-4}$haloalkoxy, —C(O)C$_{1-4}$alkyl, —C(O)NH$_2$, —C$_{3-10}$cycloalkyl, —C$_{1-4}$alkyl-O—C$_{1-4}$alkyl, 3-10-membered heterocycloalkyl, phenyl, benzyl, and 5-10-membered heteroaryl, said —C$_{1-4}$alkyl, —C$_{3-10}$cycloalkyl, —C$_{3-7}$cycloalkoxy, 3-10-membered heterocycloalkyl, phenyl, benzyl, and 5-10-membered heteroaryl optionally substituted with one or more $R^{1E}$, where each $R^{1E}$ is independently selected from the group consisting of: halo, —OH, =O, —NH$_2$, —NHC$_{1-4}$ alkyl, —N(C$_{1-4}$alkyl)$_2$, —NO$_2$, —CN, —C$_{1-4}$alkyl, —C$_{1-4}$haloalkyl, —C$_{1-4}$alkyl-OH, —C$_{1-4}$alkoxy, —C$_{1-4}$haloalkoxy, —C$_{1-4}$alkyl-O—C$_{1-4}$alkyl, and —C$_{3-6}$cycloalkyl.

In some embodiments of a chemical entity of Formula (I), (Ia), (Ib), (Iba), or (Ibb) disclosed herein:

$R^c$ is —H, —C$_{1-4}$alkyl, or —C$_{1-4}$haloalkyl.

In some embodiments of a chemical entity of Formula (Ibb) disclosed herein:

each $R^d$ is independently —H or —C$_{1-4}$alkyl.

In some embodiments of a chemical entity of Formula (I), (Ia), (Ib), (Iba), or (Ibb) disclosed herein:

$R^{1B}$ is independently selected from the group consisting of: —F, —Cl, —OH, —C$_{1-4}$alkyl, —C$_{1-4}$haloalkyl, —C$_{1-4}$alkyl-OH, —C$_{1-4}$alkoxy, and —C$_{1-4}$haloalkoxy.

In some embodiments of a chemical entity of Formula (I), (Ia), (Ib), (Iba), or (Ibb) disclosed herein:

each $R^{1C}$ is independently selected from the group consisting of: —F, —Cl, —OH, —C$_{1-4}$alkyl, —C$_{1-4}$haloalkyl, —C$_{1-4}$alkyl-OH, —C$_{1-4}$alkoxy, and —C$_{1-4}$haloalkoxy.

In some embodiments of a chemical entity of Formula (I) or (Ic) disclosed herein:

each $R^{1D}$ is independently selected from the group consisting of: $L^6$ or =O.

In some embodiments of a chemical entity of Formula (I), (Ic), (Ica), (Icb), or (Icc) disclosed herein:

each $R^{1E}$ is independently selected from the group consisting of: —F, —Cl, —OH, —C$_{1-4}$alkyl, —C$_{1-4}$haloalkyl, —C$_{1-4}$alkyl-OH, —C$_{1-4}$alkoxy, and —C$_{1-4}$haloalkoxy.

In some embodiments of a chemical entity of Formula (Iba) or (Ibb) disclosed herein:
each $R^b$ is independently —H, —$C_{1-6}$alkyl, or —$C_{1-6}$haloalkyl.

In some embodiments of a chemical entity of Formula (Iba) or (Ibb) disclosed herein:
m is 0.

In some embodiments of a chemical entity of Formula (Iba) or (Ibb) disclosed herein:
m is 1.

In some embodiments of a chemical entity of Formula (Iba) or (Ibb) disclosed herein:
m is 2.

In some embodiments of a chemical entity of Formula (Iba) or (Ibb) disclosed herein:
$L^2$ is —$C_{3-7}$cycloalkyl, 3-10-membered heterocycloalkyl, phenyl, or 5-10-membered heteroaryl, said —$C_{3-7}$cycloalkyl, 3-10-membered heterocycloalkyl, phenyl, and 5-10-membered heteroaryl optionally substituted with one to three $R^{1B}$, where each $R^{1B}$ is independently selected from the group consisting of: —F, —Cl, —Br, —CN, —$C_{1-4}$alkyl, —$C_{1-4}$haloalkyl, —$C_{1-4}$alkyl-OH, —$C_{1-4}$alkoxy, and —$C_{1-4}$haloalkoxy;
$L^3$ is —H, halo, —$C_{1-6}$alkyl, or —$C_{1-4}$alkoxy;
$R^b$ is —H, —$C_{1-3}$alkyl, or —$C_{1-3}$haloalkyl; and
m is 0 or 1.

In some embodiments of a chemical entity of Formula (Iba) or (Ibb) disclosed herein:
$L^2$ is —$C_{3-7}$cycloalkyl, 3-10-membered heterocycloalkyl, phenyl, or 5-10-membered heteroaryl, said —$C_{3-7}$cycloalkyl, 3-10-membered heterocycloalkyl, phenyl, and 5-10-membered heteroaryl optionally substituted with one to three $R^{1B}$, where each $R^{1B}$ is independently selected from the group consisting of: —F, —Cl, —Br, —CN, —$C_{1-4}$alkyl, —$C_{1-4}$haloalkyl, —$C_{1-4}$alkyl-OH, —$C_{1-4}$alkoxy, and —$C_{1-4}$haloalkoxy;
$L^3$ is —$C_{3-7}$cycloalkyl, 3-10-membered heterocycloalkyl, phenyl, benzyl, or 5-10-membered heteroaryl, said —$C_{3-7}$cycloalkyl, 3-10-membered heterocycloalkyl, phenyl, benzyl, and 5-10-membered heteroaryl optionally substituted with one to three $R^{1C}$, where each $R^{1C}$ is independently selected from the group consisting of: —F, —Cl, —Br, —CN, —$C_{1-4}$alkyl, —$C_{1-4}$haloalkyl, —$C_{1-4}$alkyl-OH, —$C_{1-4}$alkoxy, and —$C_{1-4}$haloalkoxy;
$R^b$ is —H, —$C_{1-3}$alkyl, or —$C_{1-3}$haloalkyl; and
m is 0 or 1.

In some embodiments of a chemical entity of Formula (Iba) or (Ibb) disclosed herein:
$L^2$ is —$C_{3-7}$cycloalkyl said —$C_{3-7}$cycloalkyl optionally substituted with one to three $R^{1B}$, where each $R^{1B}$ is independently selected from the group consisting of: —F, —Cl, —Br, —CN, —$C_{1-4}$alkyl, and —$C_{1-4}$haloalkyl;
$L^3$ is —H, halo, or —$C_{1-4}$alkyl;
$R^b$ is —H, —$C_{1-3}$alkyl, or —$C_{1-3}$haloalkyl; and
m is 0 or 1.

In some embodiments of a chemical entity of Formula (Iba) or (Ibb) disclosed herein:
$L^2$ is phenyl or 5-10-membered heteroaryl, said phenyl or 5-10-membered heteroaryl optionally substituted with one to three $R^{1B}$, where each $R^{1B}$ is independently selected from the group consisting of: —F, —Cl, —Br, —CN, —$C_{1-4}$alkyl, —$C_{1-4}$haloalkyl, —$C_{1-4}$alkyl-OH, —$C_{1-4}$alkoxy, and —$C_{1-4}$haloalkoxy;
$L^3$ is —$C_{3-7}$cycloalkyl, 3-10-membered heterocycloalkyl, phenyl, or 5-10-membered heteroaryl, said —$C_{3-7}$cycloalkyl, 3-10-membered heterocycloalkyl, phenyl, and 5-10-membered heteroaryl optionally substituted with one to three $R^{1C}$, where each $R^{1C}$ is independently selected from the group consisting of: —F, —Cl, —Br, —CN, —$C_{1-4}$alkyl, —$C_{1-4}$haloalkyl, —$C_{1-4}$alkyl-OH, —$C_{1-4}$alkoxy, and —$C_{1-4}$haloalkoxy;
$R^b$ is —H, —$C_{1-3}$alkyl, or —$C_{1-3}$haloalkyl; and
m is 0 or 1.

In some embodiments of a chemical entity of Formula (Iba) or (Ibb) disclosed herein:
$L^2$ is phenyl or 5-10-membered heteroaryl, said phenyl or 5-10-membered heteroaryl optionally substituted with one to three $R^{1B}$, where each $R^{1B}$ is independently selected from the group consisting of: —F, —Cl, —Br, —CN, —$C_{1-4}$alkyl, —$C_{1-4}$haloalkyl, —$C_{1-4}$alkyl-OH, —$C_{1-4}$alkoxy, and —$C_{1-4}$haloalkoxy;
$L^3$ is —H, halo, —$C_{1-6}$alkyl, or —$C_{1-4}$alkoxy;
$R^b$ is —H, —$C_{1-3}$alkyl, or —$C_{1-3}$haloalkyl; and
m is 1 or 2.

In some embodiments of a chemical entity of Formula (Iba) or (Ibb) disclosed herein:
$L^2$ is phenyl or 5-6-membered heteroaryl, said phenyl and 5-6-membered heteroaryl optionally substituted with one to three $R^{1B}$, where each $R^{1B}$ is independently selected from the group consisting of: —F, —Cl, —Br, —$C_{1-3}$alkyl, —$C_{1-3}$haloalkyl, —$C_{1-3}$alkoxy, and —$C_{1-3}$haloalkoxy; $L^3$ is —H, -halo, —$C_{1-6}$alkyl, or —$C_{1-4}$alkoxy;
$R^b$ is —H or —$CH_3$; and
m is 1 or 2.

In some embodiments of a chemical entity of Formula (Iba) or (Ibb) disclosed herein:
$L^2$ is pyridine, pyridazine, pyrazine, or pyrimidine, each optionally substituted with one to three $R^{1B}$, where each $R^{1B}$ is independently selected from the group consisting of: —F, —Cl, —Br, —CN, —$C_{1-4}$alkyl, —$C_{1-4}$haloalkyl, —$C_{1-4}$alkyl-OH, —$C_{1-4}$alkoxy, and —$C_{1-4}$haloalkoxy; $L^3$ is —H, halo, —$C_{1-6}$alkyl, or —$C_{1-4}$alkoxy;
$R^b$ is —H, —$C_{1-3}$alkyl, or —$C_{1-3}$haloalkyl; and
m is 1.

In some embodiments of a chemical entity of Formula (Iba) or (Ibb) disclosed herein:
$L^2$ is pyrrole, pyrazole, imidazole, thiazole, oxazole or isoxazole, each optionally substituted with one to three $R^{1B}$, where each $R^{1B}$ is independently selected from the group consisting of: —F, —Cl, —Br, —CN, —$C_{1-4}$alkyl, —$C_{1-4}$haloalkyl, —$C_{1-4}$alkyl-OH, —$C_{1-4}$alkoxy, and —$C_{1-4}$haloalkoxy;
$L^3$ is —H, halo, —$C_{1-6}$alkyl, or —$C_{1-4}$alkoxy;
$R^b$ is —H, —$C_{1-3}$alkyl, or —$C_{1-3}$haloalkyl; and
m is 1.

In some embodiments of a chemical entity of Formula (Icaa), (Icab), (Icb), or (Icc) disclosed herein:
$L^6$ is selected from the group consisting of: —H, —OH, —CN, —$NO_2$, halo, —$C_{1-6}$alkyl, —$C_{1-6}$haloalkyl, —$C_{1-6}$alkoxy, —$C_{1-6}$haloalkoxy, and —$C_{3-7}$cycloalkyl.

In some embodiments of a chemical entity of Formula (Icaa), (Icab), (Icb), or (Icc) disclosed herein:
$L^6$ is phenyl or 5-6-membered heteroaryl, said phenyl and 5-6-membered heteroaryl optionally substituted with one or more $R^{1E}$, where each $R^{1E}$ is independently selected from the group consisting of: halo, —OH, =O, —$NH_2$, —$NHC_{1-4}$alkyl, —N($C_{1-4}$alkyl)$_2$, —$NO_2$, —CN, —$C_{1-6}$alkyl, —$C_{1-6}$haloalkyl, —$C_{1-6}$alkyl-OH, —$C_{1-6}$-alkoxy, —$C_{1-6}$haloalkoxy, and —$C_{1-6}$alkyl-O—$C_{1-4}$alkyl.

In some embodiments of a chemical entity of Formula (Icc) disclosed herein:
r is 2, $B^1$ is N, E is N, and $D^1$ and G are independently CH or C($R^{1D}$).

In some embodiments of a chemical entity of Formula (Icc) disclosed herein:
r is 2, $D^1$ is N, G is N, and $B^1$ and E are independently CH or $C(R^{1D})$ In some embodiments of a chemical entity of Formula (I), (Ia), or (Ib) disclosed herein:
$L^1$ is monocyclic or bicyclic 5-10-membered $C_{4-9}$heteroaryl, comprising one to three heteroatoms, each independently selected from nitrogen, oxygen, and sulfur.

In some embodiments of a chemical entity of Formula (I), (Ia), or (Ib) disclosed herein:
$L^1$ is monocyclic or bicyclic 5-9-membered $C_{4-8}$heteroaryl, comprising one to three heteroatoms, each independently selected from nitrogen, oxygen, and sulfur.

In some embodiments of a chemical entity of Formula (I), (Ia), or (Ib) disclosed herein:
$L^1$ is a monocyclic 5-6-membered $C_{3-5}$heteroaryl, comprising one to three heteroatoms, each independently selected from nitrogen, oxygen, and sulfur.

In some embodiments of a chemical entity of Formula (I), (Ia), or (Ib) disclosed herein:
$L^1$ is a monocyclic 6-membered $C_{4-5}$heteroaryl, comprising one to two heteroatoms, each independently selected from nitrogen, oxygen, and sulfur.

In some embodiments of a chemical entity of Formula (I), (Ia), or (Ib) disclosed herein:
$L^1$ is a monocyclic 5-membered $C_{3-4}$heteroaryl, comprising one to two heteroatoms, each independently selected from nitrogen, oxygen, and sulfur.

In some embodiments of a chemical entity of Formula (I), (Ia), or (Ib) disclosed herein:
$L^1$ is a bicyclic or tricyclic 9-15-membered $C_{8-14}$heterocycloalkyl, comprising one to three heteroatoms, each independently selected from nitrogen, oxygen, and sulfur.

In some embodiments of a chemical entity of Formula (I), (Ia), or (Ib) disclosed herein:
$L^1$ is a monocyclic or bicyclic 3-10-membered $C_{2-9}$heterocycloalkyl, comprising one to four heteroatoms, each independently selected from nitrogen, oxygen, and sulfur.

In some embodiments of a chemical entity of Formula (I), (Ia), or (Tb) disclosed herein:
$L^1$ is a bicyclic 8-10-membered $C_{4-9}$heterocycloalkyl, comprising one to four heteroatoms, each independently selected from nitrogen, oxygen, and sulfur.

In some embodiments of a chemical entity of Formula (I), (Ia), or (Tb) disclosed herein:
$L^1$ is a bicyclic 8-10-membered $C_{5-9}$heterocycloalkyl, comprising one to three nitrogen atoms.

In some embodiments of a chemical entity of Formula (I), (Ia), or (Tb) disclosed herein:
$L^1$ is a monocyclic 4-7-membered $C_{3-6}$ heterocycloalkyl, comprising one to two heteroatoms, each independently selected from nitrogen, oxygen, and sulfur.

In some embodiments of a chemical entity of Formula (I), (Ia), or (Tb) disclosed herein:
$L^1$ is a monocyclic 5-6-membered $C_{3-5}$ heterocycloalkyl, comprising one to two heteroatoms, each independently selected from nitrogen, oxygen, and sulfur.

In some embodiments of a chemical entity of Formula (I), (Ia), or (Tb) disclosed herein:
$L^1$ is a monocyclic 4-7-membered $C_{3-6}$ heterocycloalkyl, comprising one to two nitrogen atoms.

In some embodiments of a chemical entity of Formula (I), (Ia), or (Tb) disclosed herein:
$L^1$ is a monocyclic 5-6-membered $C_{3-5}$ heterocycloalkyl, comprising one to two nitrogen atoms.

In some embodiments of a chemical entity of Formula (I), (Ib), (Iba), or (Ibb) disclosed herein:
$L^2$ is monocyclic or bicyclic 5-10-membered $C_{4-9}$heteroaryl, comprising one to three heteroatoms, each independently selected from nitrogen, oxygen, and sulfur.

In some embodiments of a chemical entity of Formula (I), (Ib), (Iba), or (Ibb) disclosed herein:
$L^2$ is monocyclic or bicyclic 5-9-membered $C_{4-8}$heteroaryl, comprising one to three heteroatoms, each independently selected from nitrogen, oxygen, and sulfur.

In some embodiments of a chemical entity of Formula (I), (Ib), (Iba), or (Ibb) disclosed herein:
$L^2$ is a monocyclic 5-6-membered $C_{3-5}$heteroaryl, comprising one to three heteroatoms, each independently selected from nitrogen, oxygen, and sulfur.

In some embodiments of a chemical entity of Formula (I), (Ib), (Iba), or (Ibb) disclosed herein:
$L^2$ is a monocyclic 6-membered $C_{4-5}$heteroaryl, comprising one to two heteroatoms, each independently selected from nitrogen, oxygen, and sulfur.

In some embodiments of a chemical entity of Formula (I), (Ib), (Iba), or (Ibb) disclosed herein:
$L^2$ is a monocyclic 5-membered $C_{3-4}$heteroaryl, comprising one to two heteroatoms, each independently selected from nitrogen, oxygen, and sulfur.

In some embodiments of a chemical entity of Formula (I), (Ib), (Iba), or (Ibb) disclosed herein:
$L^2$ is a monocyclic or bicyclic 3-15-membered $C_{2-14}$heterocycloalkyl In some embodiments of a chemical entity of Formula (I), (Ib), (Iba), or (Ibb) disclosed herein:
$L^2$ is a monocyclic or bicyclic 3-10-membered $C_{2-9}$heterocycloalkyl, comprising one to four heteroatoms, each independently selected from nitrogen, oxygen, and sulfur.

In some embodiments of a chemical entity of Formula (I), (Ib), (Iba), or (Ibb) disclosed herein:
$L^2$ is a bicyclic 8-10-membered $C_{4-9}$heterocycloalkyl, comprising one to four heteroatoms, each independently selected from nitrogen, oxygen, and sulfur.

In some embodiments of a chemical entity of Formula (I), (Ib), (Iba), or (Ibb) disclosed herein:
$L^2$ is a monocyclic 4-7-membered $C_{3-6}$ heterocycloalkyl, comprising one to two heteroatoms, each independently selected from nitrogen, oxygen, and sulfur.

In some embodiments of a chemical entity of Formula (I), (Ib), (Iba), or (Ibb) disclosed herein:
$L^2$ is a monocyclic 5-6-membered $C_{3-5}$ heterocycloalkyl, comprising one to two heteroatoms, each independently selected from nitrogen, oxygen, and sulfur.

In some embodiments of a chemical entity of Formula (I), (Ib), (Iba), or (Ibb) disclosed herein:
$L^2$ is a monocyclic 4-7-membered $C_{3-6}$ heterocycloalkyl, comprising one to two nitrogen atoms.

In some embodiments of a chemical entity of Formula (I), (Ib), (Iba), or (Ibb) disclosed herein:
$L^2$ is a monocyclic 5-6-membered $C_{3-5}$ heterocycloalkyl, comprising one to two nitrogen atoms.

In some embodiments of a chemical entity of Formula (I), (Ia), (Tb), (Iba), or (Ibb) disclosed herein:
$L^3$ is monocyclic or bicyclic 5-10-membered $C_{4-9}$heteroaryl, comprising one to three heteroatoms, each independently selected from nitrogen, oxygen, and sulfur.

In some embodiments of a chemical entity of Formula (I), (Ia), (Tb), (Iba), or (Ibb) disclosed herein:
$L^3$ is monocyclic or bicyclic 5-9-membered $C_{4-8}$heteroaryl, comprising one to three heteroatoms, each independently selected from nitrogen, oxygen, and sulfur.

In some embodiments of a chemical entity of Formula (I), (Ia), (Tb), (Iba), or (Ibb) disclosed herein:
$L^3$ is a monocyclic 5-6-membered $C_{3-5}$heteroaryl, comprising one to three heteroatoms, each independently selected from nitrogen, oxygen, and sulfur.

In some embodiments of a chemical entity of Formula (I), (Ia), (Tb), (Iba), or (Ibb) disclosed herein:
$L^3$ is a monocyclic 6-membered $C_{4-5}$heteroaryl, comprising one to two heteroatoms, each independently selected from nitrogen, oxygen, and sulfur.

In some embodiments of a chemical entity of Formula (I), (Ia), (Tb), (Iba), or (Ibb) disclosed herein:
$L^3$ is a monocyclic 5-membered $C_{2-4}$heteroaryl, comprising one to three heteroatoms, each independently selected from nitrogen, oxygen, and sulfur.

In some embodiments of a chemical entity of Formula (I), (Ia), (Tb), (Iba), or (Ibb) disclosed herein:
$L^3$ is a monocyclic or bicyclic 3-15-membered $C_{2-14}$heterocycloalkyl In some embodiments of a chemical entity of Formula (I), (Ia), (Tb), (Iba), or (Ibb) disclosed herein:
$L^3$ is a bicyclic 8-10-membered $C_{4-9}$heterocycloalkyl, comprising one to four heteroatoms, each independently selected from nitrogen, oxygen, and sulfur.

In some embodiments of a chemical entity of Formula (I), (Ia), (Tb), (Iba), or (Ibb) disclosed herein:
$L^3$ is a monocyclic 4-7-membered $C_{3-6}$ heterocycloalkyl, comprising one to two heteroatoms, each independently selected from nitrogen, oxygen, and sulfur.

In some embodiments of a chemical entity of Formula (I), (Ia), (Tb), (Iba), or (Ibb) disclosed herein:
$L^3$ is a monocyclic 5-6-membered $C_{3-5}$ heterocycloalkyl, comprising one to two heteroatoms, each independently selected from nitrogen, oxygen, and sulfur.

In some embodiments of a chemical entity of Formula (I), (Ia), (Tb), (Iba), or (Ibb) disclosed herein:
$L^3$ is a monocyclic 4-7-membered $C_{3-6}$ heterocycloalkyl, comprising one to two nitrogen atoms.

In some embodiments of a chemical entity of Formula (I), (Ia), (Tb), (Iba), or (Ibb) disclosed herein:
$L^3$ is a monocyclic 5-6-membered $C_{3-5}$ heterocycloalkyl, comprising one to two nitrogen atoms.

In some embodiments of a chemical entity of Formula (I) or (Ic) disclosed herein:
$L^4$ and $L^5$ come together with the nitrogen to which they attached to form a monocyclic 5-membered $C_{3-4}$heteroaryl, comprising one to two heteroatoms, each independently selected from nitrogen, oxygen, and sulfur.

In some embodiments of a chemical entity of Formula (I) or (Ic) disclosed herein:
$L^4$ and $L^5$ come together with the nitrogen to which they attached to form a bicyclic or tricyclic 9-15-membered $C_{8-14}$heterocycloalkyl, comprising one to three heteroatoms, each independently selected from nitrogen, oxygen, and sulfur.

In some embodiments of a chemical entity of Formula (I) or (Ic) disclosed herein:
$L^4$ and $L^5$ come together with the nitrogen to which they attached to form a monocyclic or bicyclic 3-10-membered $C_{2-9}$heterocycloalkyl, comprising one to four heteroatoms, each independently selected from nitrogen, oxygen, and sulfur.

In some embodiments of a chemical entity of Formula (I) or (Ic) disclosed herein:
$L^4$ and $L^5$ come together with the nitrogen to which they attached to form a bicyclic 8-10-membered $C_{4-9}$heterocycloalkyl, comprising one to four heteroatoms, each independently selected from nitrogen, oxygen, and sulfur.

In some embodiments of a chemical entity of Formula (I) or (Ic) disclosed herein:
$L^4$ and $L^5$ come together with the nitrogen to which they attached to form a bicyclic 8-10-membered $C_{5-9}$heterocycloalkyl, comprising one to three nitrogen atoms.

In some embodiments of a chemical entity of Formula (I) or (Ic) disclosed herein:
$L^4$ and $L^5$ come together with the nitrogen to which they attached to form a monocyclic 4-7-membered $C_{3-6}$ heterocycloalkyl, comprising one to two heteroatoms, each independently selected from nitrogen, oxygen, and sulfur.

In some embodiments of a chemical entity of Formula (I) or (Ic) disclosed herein:
$L^4$ and $L^5$ come together with the nitrogen to which they attached to form a monocyclic 5-6-membered $C_{3-5}$ heterocycloalkyl, comprising one to two heteroatoms, each independently selected from nitrogen, oxygen, and sulfur.

In some embodiments of a chemical entity of Formula (I) or (Ic) disclosed herein:
$L^4$ and $L^5$ come together with the nitrogen to which they attached to form a monocyclic 4-7-membered $C_{3-6}$ heterocycloalkyl, comprising one to two nitrogen atoms.

In some embodiments of a chemical entity of Formula (I) or (Ic) disclosed herein:
$L^4$ and $L^5$ come together with the nitrogen to which they attached to form a monocyclic 5-6-membered $C_{3-5}$ heterocycloalkyl, comprising one to two nitrogen atoms.

In some embodiments of a chemical entity of Formula (I), (Ic), (Icaa), (Icab), (Icb) or (Icc) disclosed herein:
$L^6$ is a monocyclic 5-6-membered $C_{3-5}$heteroaryl, comprising one to three heteroatoms, each independently selected from nitrogen, oxygen, and sulfur.

In some embodiments of a chemical entity of Formula (I), (Ic), (Icaa), (Icab), (Icb) or (Icc) disclosed herein:
$L^6$ is a monocyclic 6-membered $C_{4-5}$heteroaryl, comprising one to two heteroatoms, each independently selected from nitrogen, oxygen, and sulfur.

In some embodiments of a chemical entity of Formula (I), (Ic), (Icaa), (Icab), (Icb) or (Icc) disclosed herein:
$L^6$ is a monocyclic 5-membered $C_{3-4}$heteroaryl, comprising one to two heteroatoms, each independently selected from nitrogen, oxygen, and sulfur.

In some embodiments of a chemical entity of Formula (I), (Ic), (Icaa), (Icab), (Icb) or (Icc) disclosed herein:
$L^6$ is a monocyclic 5-6-membered $C_{3-5}$ heterocycloalkyl, comprising one to two heteroatoms, each independently selected from nitrogen, oxygen, and sulfur.

In some embodiments of a chemical entity of Formula (I), (Ic), (Icaa), (Icab), (Icb) or (Icc) disclosed herein:
$L^6$ is a monocyclic 5-6-membered $C_{3-5}$ heterocycloalkyl, comprising one to two nitrogen atoms.

In some embodiments, a chemical entity is selected from compounds of Examples 1-814, and all pharmaceutically acceptable forms thereof, including pharmaceutically acceptable chelates, solvates, conformers, crystalline forms/polymorphs, salts, prodrugs, and pharmaceutically active metabolites. In other embodiments, a chemical entity is selected from compounds of Examples 1-814 and pharmaceutically acceptable salts thereof. In still other embodiments, a chemical entity is a compound selected from Examples 1-814.

Further embodiments are provided by pharmaceutically acceptable salts of compounds of Formula (I), tautomers of compounds of Formula (I), pharmaceutically acceptable prodrugs of compounds of Formula (I), and pharmaceutically active metabolites of compounds of Formula (I).

Isotopically-Labeled Compounds

Compounds of Formula (I) may include any isotope where one or more atoms are replaced by an atom having an atomic mass or mass number different from the atomic mass or mass number usually found in nature. For example, the isotopes may be isotopes of carbon, chlorine, fluorine, hydrogen, iodine, nitrogen, oxygen, phosphorous, sulfur, and technetium, including $^{11}C$, $^{13}C$, $^{14}C$, $^{36}Cl$, $^{18}F$, $^{2}H$, $^{3}H$, $^{123}I$, $^{125}I$, $^{13}N$ $^{15}N$, $^{15}O$, $^{17}O$, $^{18}O$, $^{31}P$, $^{32}P$, $^{35}S$, and $^{99m}Tc$.

Compounds of the present invention (and all forms of such compounds, such as pharmaceutically acceptable salts) that contain the aforementioned isotopes or other isotopes of other atoms are within the scope of the invention. Isotopically-labeled compounds of the present embodiments are useful in binding affinity studies, as well as drug and substrate tissue distribution and target occupancy assays. For example, isotopically labeled compounds are particularly useful in SPECT (single photon emission computed tomography) and in PET (positron emission tomography), as discussed further herein. In addition, isotopically labelled compounds are useful for improving the absorption, distribution, metabolism and/or excretion (ADME) properties of drugs. For instance, replacement of one or more hydrogen atoms with deuterium ($^{2}H$) can modify the metabolism of a drug and improve the metabolic profile by decreasing the metabolic clearance in vivo, extending the half-life, reducing $C_{max}$ or reducing levels of potentially toxic metabolites.

Compositions

In some embodiments, the chemical entities disclosed herein, and more particularly, compounds and pharmaceutically acceptable salts thereof, are used, alone or in combination with one or more additional active ingredients, to formulate pharmaceutical compositions.

In some embodiments, a pharmaceutical composition can comprise: (a) an effective amount of at least one chemical entity of the present disclosure; and (b) a pharmaceutically acceptable carrier.

In some embodiments, a pharmaceutical composition comprises a compound, or pharmaceutically acceptable salt thereof, of any of the embodiments and examples disclosed herein; and a pharmaceutically acceptable carrier. In specific embodiments, a pharmaceutical composition comprises a compound of any one of Examples 1-814; and a pharmaceutically acceptable carrier.

Formulations and Administration

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Osol, ed.), 1980, 1553-1593.

Any suitable route of administration may be employed for providing an animal, especially a human, with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent, or excipient used will depend upon the means and purpose for which the compound of the present invention is being applied. Solvents are generally selected based on solvents recognized by persons skilled in the art as safe (GRAS) to be administered to an animal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., a compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable and appropriate dosage of the drug.

The pharmaceutical composition (or formulation) for application may be packaged in a variety of ways, depending upon the method used to administer the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Dosage Forms

The chemical entities, and more particularly, compounds and pharmaceutically acceptable salts thereof, may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be in a range from 1% to 65% or 2 to 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are typically prepared by incorporating the active compound in the required amount in the appropriate solvent with a variety of the other ingredients enumerated above, as required, followed by filter sterilization. In the case of sterile powders for the preparation of sterile injectable solutions, common methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid. These compositions and formulations can be prepared according to ordinary skill in the art.

Useful solid carriers include finely divided solids such as talc, clay, microcrystalline cellulose, silica, alumina, and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Dosages

Useful dosages of the chemical entities and compounds (active agents) of the present disclosure can be determined by comparing their in vitro activity and in vivo activity in animal models. Methods for the extrapolation of effective dosages in mice, and other animals, to humans are known to the art. Useful dosages of the compounds of formula I can be determined by comparing their in vitro activity, and in vivo activity in animal models. Methods for the extrapolation of effective dosages in mice, and other animals, to humans are known to the art (e.g., U.S. Pat. No. 4,938,949).

Effective amounts or doses of the active agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, concomitant medications, and the judgment of the treating physician. An exemplary dose can be in the range from 0.0001 to 200 mg of active agent per day, from 0.001 to 200 mg per day, from 0.05 to 100 mg per day, from 0.1 to 10 mg/day, from 1 to 200 mg/day, or from 5 to 50 mg/day.

In some embodiments, the desired dose may be presented in a unit dosage form; for example, a composition containing from 0.01 to 1000 mg, from 0.1 to 200 mg, from 0.5 to 100 mg, or from 1 to 50 mg, of active ingredient per unit dosage form.

In other embodiments, the desired dose may be presented in divided doses administered at appropriate intervals, for example, as two, three, four, or more sub-doses per day. (e.g., BID, TID, QID). The sub-dose itself may be further divided, e.g., into a number of temporally-distinct administrations used according to the compositions and methods of the present invention.

Methods and Uses

Uses of Isotopically-Labeled Compounds

In some embodiments, the present disclosure provides methods of using isotopically labeled compounds of the present invention in: (i) metabolic studies (with, for example, $^{14}C$), and reaction kinetic studies (with, for example $^2H$ or $^3H$); (ii) detection or imaging techniques [such as positron emission tomography (PET) or single-photon emission computed tomography (SPECT)] including drug or substrate tissue distribution assays; or (iii) radioactive treatment of patients.

Isotopically labeled compounds and related chemical entities of Formula (I) can generally be prepared by carrying out the procedures disclosed in the schemes or in the examples and preparations described below by substituting a readily available isotopically labeled reagent for a non-isotopically labeled reagent. Compounds labeled with $^{18}F$ or $^{11}C$ may be particularly preferred for PET, and an $^{123}I$-labeled compound may be particularly preferred for SPECT studies. Further substitution of compounds of Formula (I) with heavier isotopes such as deuterium (i.e., $^2H$) may afford certain therapeutic advantages resulting from greater metabolic stability, for example increased in vivo half-life or reduced dosage requirements.

Therapeutic Methods

Generally

Chemical entities and compositions of the present disclosure are useful in various therapeutic methods (or in the manufacture of a medicament for use in such methods), comprising administering to a subject in need thereof a chemical entity or composition herein. In a specific aspect, the chemical entity is a compound of Formula (I) or a pharmaceutically acceptable salt thereof. More particularly, the chemical entity is a compound of Formula (Ia), (Ib), (Ic), (Iba), (Ibb), (Icaa), (Icab), (Icb), or (Icc), or a pharmaceutically acceptable salt thereof.

Such therapeutic methods can be directed to a wide range of indications, as described further herein, including cognitive or motor deficits associated with neurological disorders, neurodegenerative disorders, immunological and inflammatory disorders, and numerous peripheral disorders.

In some embodiments, chemical entities and compositions herein are useful in methods of inhibiting PDE1 activity, comprising exposing PDE1 to an effective amount of a chemical entity or composition of any one of the embodiments disclosed herein. In some embodiments, the PDE1 is in an animal, and more particularly, is in a human subject.

In some embodiments, chemical entities and compositions herein are useful in methods of treating a subject suffering from or diagnosed with a disorder mediated by PDE1 activity, comprising administering to a subject in need thereof an effective amount of a chemical entity or composition of any one of the embodiments herein. In one aspect, the subject is diagnosed with a disorder mediated by PDE1 activity. In another aspect, the subject is suffering from a disorder mediated by PDE1 activity.

In some embodiments, chemical entities and compositions herein are useful in methods of enhancing neuronal plasticity, an essential property of the brain that can be impaired in numerous CNS disorders and augmented in healthy animals. Without being limited by mechanism, such chemical entities can enhance cyclic adenosine monophosphate (cAMP) response element binding protein (CREB) pathway function in cells, modulating transcription of multiple genes involved in synaptic plasticity (See, e.g., Tully et al., 2003, Nat. Rev. Drug Discov. 2, 267-277; Alberini, 2009, Physiol. Rev. 89, 121-145; Medina, 2011, Front. Neurosci. 5, 21). Accordingly, in some embodiments, the present disclosure provides methods of enhancing neuronal plasticity, comprising administering to a subject in need thereof an effective amount of a chemical entity or composition of any one of the embodiments herein. In specific embodiments, chemical entities of the present disclosure are useful in methods of enhancing cognitive or motor function, comprising administering to a subject in need thereof an effective amount of a chemical entity or composition of any one of the embodiments disclosed herein.

In some embodiments, chemical entities and compositions herein are used as neuroprotective agents, for example, by enhancing neuronal growth and survival. Accordingly, the present disclosure provides methods of conferring neuroprotection, comprising administering to a subject in need thereof an effective amount of a chemical entity or composition described herein.

In some embodiments, chemical entities and compositions herein are used as agents to promote neurogenesis, which may be applicable to treating neurological disorders, as described further herein. PDE1B is highly expressed in the dentate gyrus and olfactory bulb, the two areas where neurogenesis occurs in the adult nervous system. Neurogenesis in the hippocampus has been implicated in memory formation in depression, and in cognitive deficits underlying neuropsychiatric disease, including, but not limited to, PTSD and other anxiety disorders. See, e.g., Shors et al., 2001, Nature 410, 372-376; Shors et al., 2004, Trends Neurosci. 27, 250-256; Ming and Song, 2011, Neuron 70, 687-702; Hill et al., 2015, Neuropsychopharmacology 40, 2368-2378; Kheirbek et al., 2012, Nat. Neurosci. 15, 1613-1620.

In some embodiments, chemical entities and compositions herein are used as treating disorders that include aberrant or dysregulated signaling pathways mediated by PDE1. Such PDE1-related signaling pathways include, but are not limited to, those involving nitric oxide, natriuretic peptides (e.g., ANP, BNP, CNP), dopamine, noradrenalin, neurotensin, cholecystokinin (CCK), vasoactive intestinal peptide (VIP), serotonin, glutamate (e.g., NMDA receptor, AMPA receptor), GABA, acetylcholine, adenosine (e.g., A2A receptor), cannabinoids, natriuretic peptides (e.g., ANP, BNP, CNP), and endorphins.

In a specific aspect, they are useful in modulating dopaminergic signaling or treating disorders characterized by alterations in dopamine signaling, particularly dopaminergic signaling mediated by the dopamine receptor D1, which in humans is encoded by the DRD1 gene. See, e.g., Nishi and Snyder, 2010, J. Pharmacol. Sci. 114, 6-16.

In some embodiments, chemical entities and compositions are used as "agents" (or "augmenting agents") to increase the efficiency of training protocols that facilitate functional reorganization in targeted "domains" (or "functions") in the brain.

In some embodiments, chemical entities and compositions are used in combination with other therapies or with other active agents, as described further herein.

Neurological Disorders

In some embodiments the present disclosure provides methods of treating neurological disorders, comprising administering to a subject in need thereof a chemical entity or composition described herein. In a specific aspect, the chemical entity is a compound of Formula (I) or a pharmaceutically acceptable salt thereof. More particularly, the chemical entity is a compound of Formula (Ia), (Ib), (Ic), (Iba), (Ibb), (Icaa), (Icab), (Icb), or (Icc), or a pharmaceutically acceptable salt thereof.

In some embodiments, the method is directed to a neurological impairment ("neurological deficit") associated with the neurological disorder, including a cognitive impairment ("cognitive deficit") or a motor impairment ("motor deficit") associated with the pathology of the neurological disorder.

A cognitive impairment can manifest, for example, as a deficit in: attention (e.g., sustained attention, divided attention, selective attention, processing speed); executive function (e.g., planning, decision, and working memory); memory (e.g., immediate memory; recent memory, including free recall, cued recall, and recognition memory; and long-term memory, which can be divided into explicit memory (e.g., declarative memory), such as episodic, semantic, and autobiographical memory, and into implicit memory (e.g., procedural memory)); expressive language, including naming, word recall, fluency, grammar, and syntax; understanding speech or writing (e.g., aphasia); perceptual-motor functions (e.g., abilities encompassed under visual perception, visual-constructional, perceptual-motor praxis, and gnosis); and social cognition (e.g., recognition of emotions, theory of mind). In certain embodiments, the cognitive deficit is a deficit in memory and more particularly, a deficit in long-term memory.

A motor impairment can manifest, for example, as weakness or paralysis, deficits in upper and lower extremity function, problems with balance or coordination, impairments of gross motor skills, and deficits in fine motor skills.

A neurological disorder (or condition or disease) is any disorder of the body's nervous system. Neurological disorders can be categorized according to the primary location affected, the primary type of dysfunction involved, and the primary type of cause. The broadest division is between disorders of the central nervous system (CNS), which comprises the nerves in the brain and spinal cord, and disorders of the peripheral nervous system (PNS), which comprises the nerves outside the brain and spinal cord.

Many CNS disorders are amenable for treatment with chemical entities and compositions, including those discussed herein. As used herein, the terms "Neurodevelopment disorders," "Schizophrenia spectrum and other psychotic disorders," "Bipolar and related disorders," "Depressive disorders," "Anxiety disorders," "Obsessive-compulsive and related disorders," "Dissociative disorders," "Disruptive, impulse-control, and conduct disorders," "Trauma- and stressor-related disorders," "Feeding and eating disorders," "Sleep disorders," "Sexual disorders," "Substance-related and addictive disorders," "Personality disorders," "Somatic symptom disorders," "Neurodegenerative disorders," "Neurocognitive disorders," "Delirium," "Dementias," and "Age-associated cognitive deficits, include the diagnosis and classification of these CNS conditions and disorders (and related CNS conditions and disorders) as described in the Diagnostic and Statistical Manual of Mental Disorders (DSM-5; $5^{th}$ ed., 2013, American Psychiatric Association). The skilled artisan will recognize that there are alternative nomenclature and classification systems for these CNS disorders, and that these systems evolve with medical and scientific progress. Thus, these terms in this paragraph are intended to include like disorders that are described in other diagnostic sources.

Mental and Psychiatric Disorders:

In certain embodiments, chemical entities and compositions herein are useful in treating mental or psychiatric disorders, and more particularly, a cognitive impairment associated with the pathology of such disorders. In a specific aspect, the chemical entity is a compound of Formula (I), or pharmaceutically acceptable salt thereof. More particularly, the chemical entity is a compound of Formula (Ia), (Ib), (Ic), (Iba), (Ibb), (Icaa), (Icab), (Icb), or (Icc), or a pharmaceutically acceptable salt thereof.

Mental and psychiatric disorders are well known in the art, and include, but are not limited to, one or more of the following:

Neurodevelopmental (or "developmental" disorders), such as intellectual disability disorders (e.g., Rubinstein-Taybi syndrome, Down syndrome and Fragile X syndrome); communication disorders; autism-spectrum disorders; attention-deficit/hyperactivity disorders; specific learning, language, or reading (e.g., dyslexia) disorders; motor disorders; fetal alcohol spectrum disorders (FASD); and other neurodevelopmental disorders;

Schizophrenia spectrum and other psychotic disorders, such as schizophrenia, schizotypal (personality) disorder, delusional disorder, brief psychotic disorder, schizoaffective disorder, substance/medication-induced psychotic disorder, psychotic disorder due to another medical condition, catatonia, catatonia associated with another mental disorder (catatonia specifier), catatonic disorder due to another medical condition, unspecified catatonia, schizophreniform disorder, and other schizophrenia spectrum and psychotic disorders;

Bipolar and related disorders, such as Bipolar I and II disorders, cyclothymic disorders, and other bipolar and related disorders;

Depressive disorders, such as major depressive disorder, persistent depressive disorder (dysthymia), a major depressive episode of the mild, moderate, or severe type, a depressive episode with melancholic features, a depressive episode with catatonic features, seasonal depression (seasonal affective disorder), disruptive mood dysregulation disorder, premenstrual dysphoric disorder, substance/medication-induced depressive disorder, depressive disorder due to another medical condition, mood disorders due to a general medical conditions, and other depressive disorder;

Anxiety disorders, such as specific phobia, agoraphobia, social anxiety disorder (social phobia), panic attack, panic disorder, acute stress disorder, generalized anxiety disorder, posttraumatic stress disorder (PTSD), and other anxiety disorders;

Obsessive-compulsive and related disorders, such as obsessive-compulsive disorder (OCD), body dysmorphic disorder, hoarding disorder, trichotillomania (hair-pulling disorder), excoriation (skin-picking) disorder, substance/medication-induced obsessive-compulsive and related disorder, obsessive-compulsive and related disorder due to another medical condition, and other specified obsessive-compulsive and related disorder and unspecified obsessive-compulsive and related disorder (e.g., body-focused repetitive behavior disorder, obsessional jealousy), and other obsessive-compulsive and related disorders;

Dissociative disorders, such as dissociative identity disorder, dissociative amnesia, depersonalization/derealization disorder, dissociative subtypes (in conjunction with other disorders), and other dissociative disorders;

Disruptive, impulse-control, and conduct disorders, such as conduct disorder, antisocial personality disorder, pyromania, kleptomania, and other disruptive, impulse-control, and conduct disorders;

Trauma- and stressor-related disorders, such as reactive attachment disorder, disinhibited social engagement disorder, posttraumatic stress disorder, acute stress disorder, adjustment disorders, and other trauma- and stressor-related disorders;

Feeding and eating disorders, such as pica, rumination disorder, avoidant/restrictive food intake disorder, anorexia, bulimia, binge-eating disorder, and other feeding and eating disorders;

Sleep disorders, such as sleep-wake disorders, insomnia disorder, hypersomnolence disorder, narcolepsy, breathing-related sleep disorders, sleep apnea, circadian rhythm sleep-wake disorders, non-rapid eye movement (NREM) sleep arousal disorders, nightmare disorder, rapid eye movement (REM) sleep behavior disorder, restless legs syndrome, and substance/medication-induced sleep disorder, parasomnias, and other sleep-wake disorders;

Sexual disorders, such as arousal disorders, desire disorders, dysfunctions, substance- and medication-induced dysfunctions, impotence and other sexual disorders;

Substance-related and addictive disorders, such as those involving alcohol, drugs, stimulants, opioids, tobacco, and non-substance-related addictive disorders; and other substance-related and addictive disorders;

Personality disorders, such as antisocial personality disorder, borderline personality disorder, histrionic personality disorder, narcissistic personality disorder, avoidant personality disorder, dependent personality disorder, obsessive-compulsive personality disorder, paranoid personality disorder, schizoid personality disorder, schizotypal personality disorder, personality change due to another medical condition, and other personality disorders; and Somatic symptom and related disorders, such as somatic symptom disorder, illness anxiety disorder (hypochondriasis), factitious disorder, factitious disorder imposed on another, pain disorders, conversion disorder, and other somatic symptom and related disorders.

Schizophrenia:

In specific embodiments, the mental or psychiatric disorder is a schizophrenia spectrum or psychotic disorder, and, in particular, is schizophrenia. Schizophrenia is a devastating neurological disorder, characterized by a combination of symptoms, which may include negative, positive, or cognitive symptoms. Negative symptoms can include flat affect (lack or decline in emotional response), alogia (lack or decline in speech), avolition (lack or decline in motivation), anhedonia (the inability to experience pleasure from activities usually found enjoyable), and asociality (lack of motivation to engage in social interaction, or a preference for solitary activities). Positive symptoms include paranoia, hallucinations, and delusions. Cognitive symptoms can include impairments in such functions as attention, memory, reasoning, and processing speed. See, e.g., Keefe and Harvey, 2012, *Handb. Exp. Pharmacol.* 213, 11-23. Intracellular signaling of dopamine D1 and various serotonin receptors, which signal through cyclic nucleotides, is known to be defective in schizophrenia, as well as depression and other cognitive disorders. More generally, PDEs, include PDE1, have been implicated at the interface between cognitive deficits and neuropsychiatric disorders. See, e.g., Wang et al., 2015, *Curr. Pharm. Des.* 21, 303-316.

Accordingly, the present disclosure provides a method of treating schizophrenia, comprising administering to a subject in need thereof an effective amount of a chemical entity or composition herein. In a specific aspect, the chemical entity is a compound of Formula (I), or pharmaceutically acceptable salt thereof. More particularly, the chemical entity is a compound of Formula (Ia), (Ib), (Ic), (Iba), (Ibb), (Icaa), (Icab), (Icb), or (Icc), or a pharmaceutically acceptable salt thereof. In some embodiments, the treatment is directed to a positive symptom of schizophrenia. In some embodiments, treatment is directed to a negative symptom of schizophrenia. In some embodiments, treatment is directed to cognitive impairment associated with schizophrenia (CIAS). In some embodiments, the treatment also include a cognitive training protocol.

Addictive Disorders:

In specific embodiments, the mental or psychiatric disorder is an addictive disorder. In one aspect, the subject is addicted to an addictive agent selected from the group consisting of alcohol, nicotine, marijuana, a marijuana derivative, an opioid agonist (such as morphine, methadone, fentanyl, sufentanil, or heroin), a benzodiazepine, a barbiturate, and a psychostimulant, such as cocaine or amphetamine. In another aspect, the addiction is associated with an obsessive-compulsive disorder. In another aspect, the disorder is associated with a primary impulse-control disorder, such as binge eating, pathological gambling, addiction to pornography, sex addiction, compulsive spending, anorexia, bulimia, kleptomania, pyromania, trichotillomania, compulsive over-exercising, or compulsive overworking.

Accordingly, the present disclosure provides a method of treating an addictive disorder, comprising administering to a subject in need thereof an effective amount of a chemical entity or composition herein. In a specific embodiment, the chemical entity is a compound of Formula (I), or pharmaceutically acceptable salt thereof. More particularly, the chemical entity is a compound of Formula (Ia), (Ib), (Ic), (Iba), (Ibb), (Icaa), (Icab), (Icb), or (Icc), or a pharmaceutically acceptable salt thereof.

Cognitive Disorders:

In specific embodiments, the present disclosure provides a method of treating a cognitive disorder, and more particularly, a neurological impairment associated with the disorder, comprising administering to a subject in need thereof an effective amount of a chemical entity or composition described herein. In a specific aspect, the chemical entity is a compound of Formula (I), or pharmaceutically acceptable salt thereof. More particularly, the chemical entity is a compound of Formula (Ia), (Tb), (Ic), (Iba), (Ibb), (Icaa), (Icab), (Icb), or (Icc), or a pharmaceutically acceptable salt thereof.

A "cognitive disorder" (or "neurocognitive disorder") is one in which the primary clinical feature is impaired cognition, i.e., a disorder in which the primary cognitive deficit has not been present since birth or very early life and therefore represents a decline from a previously attained level of functioning. Such disorders, include one or more of the following:

Delirium, such as substance-intoxication (or withdrawal) delirium, medication-induced delirium, and other forms of delirium;

Dementias and other cognitive impairments due to acquired diseases, such as HIV infection, or transmissible encephalopathies; or due to neurodegenerative or progressive nervous system diseases, such as Alzheimer's disease, Parkinson's disease (in particular Parkinson's Disease Dementia (PDD)), Huntington's disease, Lewy body disease, Pick's disease, a prion disease (e.g., Creutzfeldt-Jakob disease), Amyotrophic lateral sclerosis (ALS), multiple sclerosis (MS), frontotemporal lobar degeneration (FTLD), and corticobasal degeneration; dementia due to a vascular disease ("vascular disease"); autoimmune disorders; and other dementias and neurodegenerative diseases.

Age-associated cognitive decline, including age-associated memory impairment (AAMI), also referred to as age-related memory impairment (AMI) (See, e.g., Crook et al., 1986, *Devel. Neuropsychol.* 2, 261-276); and cognitive decline affecting patients in early stages of cognitive decline, as in Mild Cognitive Impairment (MCI) (See, e.g., Arnáiz and Almkvist, 2003, *Acta Neurol. Scand. Suppl.* 179, 34-41);

Trauma-dependent losses of function, including vascular diseases, such as stroke (e.g., ischemic or hemorrhagic stroke) or ischemia; infarction, including cerebral and myocardial; microvascular or macrovascular disease arising from diabetes or arthrosclerosis; traumatic brain injury (TBI), such as brain trauma including subdural hematoma and brain tumor; head trauma (closed and penetrating); head injury; tumors, such as nervous system cancers, including cerebral tumors affecting the thalamic or temporal lobe; hypoxia, and viral, fungal, or bacterial infection (e.g., encephalitis, or meningitis); excitotoxicity; and seizures; and Cognitive impairments due to chemotherapy, such as post-chemotherapy cognitive impairments (PCCI); chemotherapy-induced cognitive dysfunction or impairments; chemo brain; or chemo fog.

Such cognitive disorders can include neurological impairments other than cognitive impairments. For example, trauma-dependent losses of function, such as stroke, traumatic brain injury, head trauma, and head injury, can include impairments in multiple neurological functions, such as impairments in motor functions.

Age Associated Cognitive Decline:

In specific embodiments, the cognitive disorder is age-associated cognitive decline.

In one aspect, the age-related cognitive decline is age-associated memory impairment (AAMI). AAMI is a decline in various cognitive abilities, in particular memory abilities, associated with normal aging. For example, AAMI subjects show a decline in the ability to encode new memories of events or facts, as well as in working memory (Hedden and Gabrieli, 2004, *Nat. Rev. Neurosci.* 5, 87-96). In addition, AAMI subjects, when compared with age-matched controls, appeared to be impaired in tests of executive functions associated with frontal lobe function. These and other studies suggest an important role for frontal lobe dysfunction in the memory loss of elderly people (Nilsson, 2003, *Acta Scand. Suppl.* 179, 7-13). In general, an AAMI diagnosis identifies persons with subjectively and objectively evidenced memory loss without cognitive decline impaired enough to warrant the diagnosis of dementia. For example, the NIH working group has established multiple criteria for a diagnosis of AAMI in a person aged 50 or older, including the presence of subjective memory decline, objective evidence of memory loss, evidence of adequate intellectual function, and the absence of dementia (or other memory-affecting disease) (Crook et al., 1986, *Devel. Neuropsychol.* 2, 261-276). Individuals with AAMI have been shown to have a three-fold greater risk for development of dementia than individuals who do not meet AAMI criteria (Goldman and Morris, 2002, *Alzheimer Dis. Assoc. Disord.* 75, 72-79).

In another aspect, the age-associated cognitive decline is Mild Cognitive Impairment, which may be diagnosed when an individual's memory declines below the level considered normal for that age group. In other words, MCI is a condition in which people face memory problems more often than that of the average person their age. Symptoms often include misplacing items, forgetting events or appointments, and having trouble thinking of desired words (e.g., Arnáiz and Almkvist, 2003, *Acta Neurol. Scand. Suppl.* 179, 34-41). MCI can represent a transitional state between cognitive changes of normal aging and Alzheimer's disease (AD). Many people who experience mild cognitive impairment are at a high risk of developing Alzheimer's disease. About 12% of people aged 65 or older diagnosed with MCI go on to develop Alzheimer's disease within a year, and about 40% develop Alzheimer's within three years. This is a much higher rate than in the general population, in which only about 1% of people aged 65 or older develop Alzheimer's each year. Thus, people with MCI are considered at heightened risk to develop Alzheimer's disease. Some patients with MCI, however, never progress to AD.

Accordingly, the disclosure includes methods of treating age-associated cognitive decline, and more particularly, age-related memory impairment or mild cognitive impairment, comprising administering to a subject in need thereof an effective amount of a chemical entity or composition disclosed herein. In a specific aspect, the chemical entity is a compound of Formula (I), or pharmaceutically acceptable salt thereof. More particularly, the chemical entity is a compound of Formula (Ia), (Ib), (Ic), (Iba), (Ibb), (Icaa), (Icab), (Icb), or (Icc), or a pharmaceutically acceptable salt thereof.

Trauma-Dependent Loss of Function:

In specific embodiments, the cognitive disorder is a trauma-dependent loss of function, and more particularly, stroke or TBI. Accordingly, the disclosure includes methods of treating a trauma-dependent loss of function, and more particularly, stroke or TBI, comprising administering to a subject in need thereof an effective amount of a chemical entity or composition disclosed herein.

Movement Disorders:

In certain embodiments, the present disclosure provides methods of treating movement and motor disorders, and more particularly, a movement or motor impairment associated with the pathology of such disorders, comprising administering to a subject in need thereof an effective amount of a chemical entity or composition described herein. In a specific aspect, the chemical entity is a compound of Formula (I), or pharmaceutically acceptable salt thereof. More particularly, the chemical entity is a compound of Formula (Ia), (Tb), (Ic), (Iba), (Ibb), (Icaa), (Icab), (Icb), or (Icc), or a pharmaceutically acceptable salt thereof.

Loss of dopaminergic neurotransmission in striatum is a central cause of neurodegenerative diseases leading to movement disorders, such as Parkinson's disease and Huntington's disease. See, e.g., Sasaki et al., 2004, *J. Neurochem.* 89, 474-483; Morales-Garcia et al., 2014, *Neurobiol. Aging.* 36, 1160-1173; Banerjee et al., 2012, *Bioorg. Med. Chem. Lett.* 22, 6286-6291. PDE1 is highly expressed in the striatum, and growing amount of evidence suggest that phosphodiesterases play a critical role in modulating dopamine signaling in the brain (Ramirez and Smith, 2014, *Cent. Nerv. Syst. Agents Med. Chem.* 14, 72-82).

Movement disorders include, but are not limited to, basal ganglia disorders, Parkinson's disease, Post-Encephalitic Parkinsonism, Dopamine-Responsive Dystonia, Hallervorden-Spatz Syndrome (HSS), Restless Leg Syndromes, Wilson's Disease, Shy-Drager Syndrome, Periodic Limb Movement Disorder (PLMD), Periodic Limb Movements in Sleep (PLMS), Tourette's Syndrome, Restless Leg(s) Syndrome (RLS); chorea, such as that in Huntington's disease; myoclonus (including generalized myoclonus and focal myoclonus); tics (including simple tics, complex tics and symptomatic tics); and hyperkinetic, hypokinetic, and dyskinetic disorders; movement disorders induced by drugs, diseases associated with striatal hypofunction; and other movement and motor disorders.

In specific embodiments, the dyskinetic disorder is a drug-induced dyskinesia. More particularly, the dyskinetic disorder is levodopa induced dyskinesia (LID) or tardive dyskinesia (TD), which represent the most common forms of drug-induced dyskinesias. For example, uncontrolled stimulation of supersensitized dopamine D1 receptors in the direct striatonigral pathway are thought to mediate LIDs. In addition, long-term blockade of dopamine D2 receptors in the basal ganglia by dopamine D2 antagonists (e.g., neuroleptics) may produce compensatory supersensitivity of dopamine receptors and TD. Accordingly, in specific embodiments, then present disclosure provides methods of treating LID (or TD), comprising administering to a subject in need therefor an effective amount of a chemical entity of any of the embodiments disclosed herein.

In certain embodiments, the movement disorder is a basal ganglia disorder.

In other embodiments, the movement disorder includes kinesias and akinetic-rigid syndromes, such as Parkinson's disease or corticobasal degeneration; Tourette's syndrome, epilepsy, muscular spasms, and disorders associated with muscular spasticity or weakness; dyskinesias, including tremors, such as rest tremor, postural tremor and intention tremor.

In specific embodiments, the movement disorder is Parkinson's disease or Huntington's disease, as discussed further herein.

In some embodiments, the methods are directed to a specific movement abnormality associated with the pathology of a movement or motor disorder. Movement abnormalities include, but are not limited to, tremors, resting tremors, rigidity, bradykinesia, and deficient postural reflexes.

Neurodegenerative Disorders:

In specific embodiments, the disclosure provides methods of treating a neurodegenerative disorder, and more particularly treating a neurological impairment associated with the pathology of a neurodegenerative disorder, comprising administering to a subject in need thereof an effective amount of a chemical entity or composition described herein.

Neurodegenerative disorders can result from a primary nervous system disease or a primary nervous system injury. Chronic neuroinflammation is a hallmark of neurodegenerative disorders, and in animal and cellular models, PDE1 inhibition shows neuroprotective and anti-inflammatory effects that are expected to be beneficial in treating neuroinflammation and other hallmarks of such disorders.

Accordingly, in some embodiments, the therapeutic methods are directed to neurodegenerative disorders resulting from a primary nervous system disease. Such diseases include, but are not limited to, Parkinson's disease, Alzheimer's disease, Huntington's disease, Lewy body disease, Pick's disease, a prion disease (e.g., Creutzfeldt-Jakob disease), Amyotrophic lateral sclerosis (ALS), multiple sclerosis (MS), frontotemporal lobar degeneration (FTLD), and corticobasal degeneration.

In other embodiments, the therapeutic methods are directed to a neurodegenerative disorder resulting from a primary nervous system injury. Such primary injuries can include, but are not limited to, stroke, including hemorrhagic stroke and ischemic stroke; a traumatic brain injury (TBI), which can include closed head injuries and blunt trauma, including those caused by participation in sports, and penetrating trauma, such as gunshot wounds; spinal cord injuries; glaucoma, cerebral ischemia, or damages caused by surgery such as tumor excision.

Parkinson's Disease:

In specific embodiments, the present disclosure provides methods of treating Parkinson's disease, comprising administering to a subject in need thereof an effective amount of a chemical entity or composition described herein. Parkinson's disease (PD), also known as Parkinson's, idiopathic Parkinsonism, or primary Parkinsonism, is a degenerative disorder of the CNS estimated to afflict more than 5 million people worldwide. It is a slowly progressive neurological condition, characterized by tremors, stiffness, slowness of movement (bradykinesia) and impaired balance. Altered cAMP/cGMP levels are associated with Parkinson's disease, and PDE1B activity is increased in models of Parkinson' disease (Sancesario et al., 2004, *Eur. J. Neurosci.* 20, 989-1000).

While Parkinson's disease has been defined by its motor hallmarks, non-motor features such as cognitive impairment and dementia have been increasingly recognized. For example, MCI is common in a significant fraction (with estimates ranging from 20%-50%) of non-demented PD patients. See, e.g., Broeders et al., 2013, *Neurology* 81, 346-352. While diagnostic criteria are not completely uniform, PD patients with MCI (PD-MCI patients) typically exhibit non-amnestic deficits in cognitive domains such as executive function, attention, and visuospatial function (Litvan et al., 2012, *Mov. Disord.* 27, 349-356). The cognitive phenotype of PD-MCI is heterogeneous, however, with some patients demonstrating amnestic deficits. Certain PD-MCI patients may be at high risk for developing dementia. (e.g., Goldman and Litvan, 2011, *Minerva Med.* 102, 441-459).

Thus, in specific embodiments, chemical entities and compositions herein can be used to treat motor deficits associated with PD, and in other embodiments to treat cognitive impairments associated with PD, including in PD-MCI subjects. In a specific aspect, the chemical entity is a compound of Formula (I), or pharmaceutically acceptable salt thereof. More particularly, the chemical entity is a compound of Formula (Ia), (Ib), (Ic), (Iba), (Ibb), (Icaa), (Icab), (Icb), or (Icc), or a pharmaceutically acceptable salt thereof.

Alzheimer's Disease:

In specific embodiments, the present disclosure provides methods of treating Alzheimer's disease (AD), comprising administering to an animal in need thereof an effective amount of a chemical entity or composition disclosed herein. In a specific aspect, the chemical entity is a compound of Formula (I), or pharmaceutically acceptable salt thereof. More particularly, the chemical entity is a compound of Formula (Ia), (Ib), (Ic), (Iba), (Ibb), (Icaa), (Icab), (Icb), or (Icc), or a pharmaceutically acceptable salt thereof.

Alzheimer's disease is a neurodegenerative disorder that involves the progressive loss of memory and other cognitive functions. Although the pathogenesis of AD is not well known, its etiology is associated with the presence of β-amyloid (or senile) plaques; deficiencies in neurotransmission; loss of neurons, especially in the cortex and hippocampus; neurofibrillary tangles; and the hyperphosphorylation and intraneuronal deposition of the microtubule-associated protein tau in the form of filaments; intraneuronal deposition of aggregated tau filaments. In Alzheimer's accumulation of the amyloid-β protein may lead to a reduction on CREB phosphorylation, which may be related to the cognitive deficits seen in this condition, and more generally, increasing cAMP or cGMP levels by PDE4 inhibition can restore neuronal plasticity in Alzheimer models (Vitolo et al., 2002, *Proc. Natl. Acad. Sci. U.S.A.* 99, 13217-13221; Medina, 2011, *Front. Neurosci.* 5, 21).

Huntington's Disease:

In specific embodiments, the disclosure provides a method of treating Huntington's disease (or "Huntington's chorea"), comprising administering to a subject in need thereof an effective amount of a chemical entity or chemical entity disclosed herein. In a specific aspect, the chemical entity is a compound of Formula (I), or pharmaceutically acceptable salt thereof. More particularly, the chemical entity is a compound of Formula (Ia), (Ib), (Ic), (Iba), (Ibb), (Icaa), (Icab), (Icb), or (Icc), or a pharmaceutically acceptable salt thereof.

There are two forms of Huntington's disease: adult-onset Huntington's disease, which is the most common form and usually begins in subjects aged in the mid 30's and 40's, and early-onset Huntington's disease, which accounts for a small number of cases and begins in childhood or adolescence. Symptoms of Huntington's disease include behavioral changes, abnormal and unusual movements, and worsening dementia (e.g., Dumas et al., 2013, *Front. Biosci.* (Schol. Ed) 5, 1-18). Huntington's disease (HD, or Huntington chorea) is a genetic disorder, whose pathology includes degeneration of striatal neurons in the basal ganglia responsible for movement and coordination. PDE1 is highly expressed in the striatum, and PDE1 inhibition has been shown to confer protection against behavioral and biochemical toxicities in an experimental models of Huntington's disease (Gupta and Sharma, 2014, *Eur. J. Pharmacol.* 732, 111-122). A detailed set of criteria for the diagnosis of Huntington's disease is set forth in the Diagnostic and Statistical Manual of Mental Disorders (DSM-5; $5^{th}$ ed., 2013, American Psychiatric Association).

Augmented Training

In some embodiments, chemical entities, and compositions thereof, of the present disclosure are used as augmenting agents in methods to increase the efficiency of training protocols for enhancing a neurological function or treating a neurological impairment associated with a neurological disorder. Such methods are known as "augmented training," and more particularly, in the case of cognitive impairments, "augmented cognitive training," and in the case of motor impairments, "augmented motor training." Augmenting agents can act by shortening the time that methods of rehabilitating (or enhancing) a cognitive or motor function result in improved performance or a functional gain. Such augmented training therefore comprises a specific training protocol for a particular brain function, such as that underlying declarative memory, performance of a fine motor skill, a specific locomotor function, language acquisition, executive function, etc.; and a general administration of an augmenting agent of the present disclosure.

Training (or a "training protocol") generally requires many sessions to attain the desired benefits, for example, to rehabilitate a motor deficit or language deficit following stroke. This can be costly and time-consuming, deterring subject compliance and the realization of real world benefits that endure over time. The efficiency of such training protocols can be improved by administering certain agents (known as augmenting agents) in conjunction with the training protocol (See, e.g., U.S. Pat. Nos. 7,868,015; 7,947, 731; U.S. 2008-0188525). When administered in combination with training protocols (or "training"), augmenting agents enhance functional reorganization in targeted domains (or "functions") in the brain.

Cognitive domains (or "functions") that can be targeted by training protocols include, but are not limited to, the following: attention (e.g., sustained attention, divided attention, selective attention, processing speed); executive function (e.g., planning, decision, and working memory); learning and memory (e.g., immediate memory; recent memory, including free recall, cued recall, and recognition memory; and long-term memory, which can be divided into explicit memory (e.g., declarative memory) memory, such as episodic, semantic, and autobiographical memory, and into implicit memory (e.g., procedural memory)); language (e.g., expressive language, including naming, word recall, fluency, grammar, and syntax; and receptive language); perceptual-motor functions (e.g., abilities encompassed under visual perception, visuo-constructional, perceptual-motor praxis, and gnosis); and social cognition (e.g., recognition of emotions, theory of mind). In specific embodiments, the cognitive function is learning and memory, and more particularly, long term memory.

Motor domains (or functions) that can be targeted by training protocols include, but are not limited to, those involved in gross body control, coordination, posture, and balance; bilateral coordination; upper and lower limb coordination; muscle strength and agility; locomotion and movement; motor planning and integration; manual coordination and dexterity; gross and fine motor skills; and eye-hand coordination.

Training Protocols:

Training protocols (or "modules") include cognitive training and motor training protocols. Training protocols are well-known in the art and typically comprise a set of distinct exercises that can be process-specific or skill-based. See, e.g., Kim et al., 2014, *J. Phys. Ther. Sci.* 26, 1-6; Allen et al., 2012, *Parkinson's Dis.* 1-15; Jaeggi et al., 2011, *Proc. Natl. Acad. Sci. USA* 108, 10081-10086; Chein et al., 2010, *Psychon. Bull. Rev.* 17, 193-199; Klingberg, 2010, *Trends Cogn. Sci.* 14, 317-324; Owen et al., 2010, *Nature* 465, 775-778; Tsao et al., 2010, *J. Pain* 11, 1120-1128; Lustig et al., 2009, *Neuropsychol. Rev.* 19, 504-522; Park and Reuter-Lorenz, 2009, *Ann. Rev. Psych.* 60, 173-196; Oujamaa et al., 2009, *Ann. Phys. Rehabil. Med.* 52, 269-293; Frazzitta et al., 2009, *Mov. Disord.* 8, 1139-1143; Jaeggi et al., 2008, *Proc. Natl. Acad. Sci. USA* 105, 6829-6833; Volpe et al., 2008, *Neurorehabil. Neural Repair* 22, 305-310; Fischer et al., 2007, *Top. Stroke Rehab.* 14, 1-12; Jonsdottir et al., 2007, *Neurorehabil. Neural Repair* 21, 191-194; Stewart et al., 2006, *J. Neurol. Sci.* 244, 89-95; Krakauer, 2006, *Curr. Opin. Neurol.* 19, 84-90; Belleville et al., 2006, *Dement. Geriatr. Cogn. Disord.* 22, 486-499; Klingberg et al., 2005, *J. Am. Acad. Child. Adolesc. Psychiatry* 44, 177-186; Dean et al., 2000, *Arch. Phys. Med. Rehabil.* 81, 409-417; Whitall et al., 2000, *Stroke* 31, 2390-2395; Hummelsheim and Eickhof, 1999, *Scand. J. Rehabil. Med.* 31, 250-256; Merzenich et al., 1996, *Science* 271, 77-81; Merzenich et al., 1996, *Cold Spring Harb. Symp. Quant. Biol.* 61, 1-8; Rider and Abdulahad, 1991, *Percept. Mot. Skills* 73, 219-224.

Process-specific training focuses on improving a particular domain such as attention, memory, language, executive function, or motor function. Here the goal of training is to obtain a general improvement that transfers from the trained activities to untrained activities based on the same cognitive or motor function or domain.

Skill-based training is aimed at improving performance of a particular activity or ability, such as learning a new language, performing a musical instrument, improving memory, or learning a fine motor skill. The different exercises within such a protocol will focus on core components within one or more domains underlying the skill. Modules for increasing memory, for example, may include tasks directed to specific domains involved in memory processing, e.g., the recognition and use of facts, and the acquisition and comprehension of explicit knowledge rules.

In some embodiments, the battery of exercises is administered as part of a single training session. In one aspect, the training protocol comprises multiple training sessions, each separated by a discrete interval. In another aspect, the number of training sessions sufficient to improve performance is reduced compared to that produced by training alone.

In a further aspect, the augmenting agent is a PDE1 inhibitor, and more particularly, is a chemical entity of the present disclosure, and is administered in conjunction with training. The phrase "in conjunction with" means that the augmenting agent enhances CREB pathway function during training. In some embodiments, the deficit is a motor deficit. In other embodiments, the deficit is a cognitive deficit. In still other embodiments, the deficit may include both a cognitive and motor deficit. In other aspects, the compound is administered before and during each training session. In one aspect, the subject is a human. In some embodiments, the subject is a non-human, and more particularly, is a primate or a canine.

In one aspect, a chemical entity or composition of the present disclosure can be used as an augmenting agent in conjunction with any psychotherapeutic approach intended to modulate cognitive function in the brain, thereby enhancing the efficacy of such therapy by reducing the amount of training, e.g., the number of sessions, necessary to attain benefits. In a specific aspect, the chemical entity is a compound of Formula (I), or pharmaceutically acceptable salt thereof. More particularly, the chemical entity is a compound of Formula (Ia), (Ib), (Ic), (Iba), (Ibb), (Icaa), (Icab), (Icb), or (Icc), or a pharmaceutically acceptable salt thereof.

Accordingly, in some embodiments, the disclosure provides the use of a chemical entity or composition herein in a method of augmented training to treat a neurological disorder, the method comprising: (a) providing training to an animal in need of treatment of a neurological impairment associated with the neurological disorder under conditions sufficient to produce an improvement in performance by said animal of a neurological function whose deficit is associated with said neurological impairment; (b) administering the chemical entity or composition to the animal in conjunction with said training; (c) repeating said providing and administering steps one or more times; and (d) reducing the amount of training sufficient to produce the improvement in performance, relative to the improvement in performance produced by training alone. In specific embodiments, the animal is a human subject. In some aspects, the augmented training is augmented cognitive training. In some aspects, the neurological impairment is a cognitive impairment. In some aspects, the neurological impairment is a motor impairment. In a specific aspect, the neurological disorder is stroke or traumatic brain injury. In some aspects, the augmented training is provided to a stroke patient during post-stroke rehabilitation, as described further herein. In a specific aspect, the chemical entity is a compound of Formula (I), or pharmaceutically acceptable salt thereof. In some embodiments, training comprises spaced training sessions. In other embodiments, training comprises massed training sessions.

Animal Skill Protocols:

In some embodiments, chemical entities of the present invention are used to enhance the efficiency of training protocols directed to cognitive and motor skills in an animal. Such augmented training (augmenting agent and training) reduces the time necessary to acquire a cognitive or motor skill, and/or enhance function or cognitive ability beyond what would be possible by training alone in the non-human animal.

In particular embodiments, the animal is a non-human animal, and more particularly, is a service animal, a category that includes, but is not limited to, dogs, miniature horses, and capuchin monkeys. Service animals may be involved in public service or private service, and the training protocols will be appropriately matched to these objections. For example, training protocols directed to public service include public order maintenance, search and rescue, and contraband detection, and training protocols directed to private service include private security, handicap assistance, health care, psychiatric assistance, and pest control.

The training protocol may be directed to a single skill, such as the detection of a specific contraband category by a service animal. In other embodiments, the training protocol may be directed to a complex set of skills, such as those underlying search and rescue training of a service animal; for a complex set of skills, training will therefore comprise more than one tasks.

Accordingly, in some embodiments, the present invention provides a method of teaching a non-human animal one or more skills, comprising (a) administering to a non-human animal in need thereof a PDE1 inhibitor; (b) providing training to the animal under conditions sufficient to improve performance of the one or more skills; and (c) repeating steps (a) and (b) one or more times, whereby the amount of training sufficient to improve the performance is reduced compared to that produced by training alone.

Stroke:

In certain embodiments, chemical entities and compositions of the present disclosure are useful in methods of treating a trauma-dependent loss of function, and more particularly, stroke. Stroke is a leading cause of serious long-term disability in adults and is the second leading cause of death worldwide (e.g., Go et al., 2014, *Circulation* 129, e28-e92). Stroke is comprises two main types: 1) ischemic stroke which occurs when blood vessels supplying the brain are blocked by clot formation (85% of all strokes) and 2) hemorrhagic stroke which occurs when blood vessels rupture within the brain (13-15% of all strokes). Stroke care is a temporal continuum that includes medical intervention during the acute phase of stroke and subsequent rehabilitative therapy directed to restoring function during the post-stroke phase of stroke.

Acute Treatments:

Treatments following the onset of stroke directly target the initial damage triggered by ischemic or hemorrhagic stroke. Acute treatment options for ischemic stroke include pharmacotherapy with intravenous recombinant tissue plasminogen activator (r-tPA) to thrombolyze the clot, or the use of endovascular procedures or mechanical thrombectomy to physically remove the clot. Acute treatment options for hemorrhagic stroke typically involve endovascular or surgical procedures to physically repair the rupture.

Post-Stroke Rehabilitation:

Following the acute phase of stroke—and typically after the patient has been medically stabilized—the focus of stroke treatment shifts to restoring function by rehabilitation. Depending on the severity and location of the stroke as well as the timing and effectiveness of acute interventions, post-stroke symptoms may persist and can include motor deficits (e.g., hemiparesis, apraxia), speech impairment (e.g., aphasia), visual impairments (e.g., visual field loss), emotional and behavioral changes (e.g., depression, anxiety), and mental and cognitive changes (e.g., confusion, apathy, cognitive impairment) (Winstein et al., 2016, *Stroke* 47, e98-e169). Rehabilitation (also referred to as "stroke rehabilitation" or "post-stroke rehabilitation") is directed to post-stroke deficits, such as cognitive and motor deficits that persist after the initial stroke injury. The goal is to restore and recover neurological functions, e.g., physical, intellectual, psychological, and social functions, as much as possible to compensate for the permanent tissue loss (e.g., 1995 Clinical Guideline by the Department of Health and Human Services on Post-Stroke Rehabilitation).

Stroke rehabilitation is typically a comprehensive program coordinated by a team of medical professionals, which may include occupational, speech, and physical therapists. A physical therapist on the team, for example, may focus on maintaining and restoring range of motion and strength in affected limbs, maximizing mobility in walking, improving manual dexterity, and rehabilitating other motor and sensorimotor functions. A mental health professional may be involved in the treatment of loss of cognitive skills. Rehabilitation services can occur in multiple environments, such as a rehabilitation hospital, long-term care facility, outpatient clinic, or at home.

Neurological functions impacted by stroke (and which can be targeted during rehabilitation) include impairments in cognitive and motor functions. Cognitive function impairments, for example, can manifest as deficits in understanding speech or writing (aphasia); knowing the right words but having trouble saying them clearly (dysarthria); as well as deficits in other cognitive functions, such as attention, reasoning, planning, execution, and learning and memory. Motor function impairments, for example, can manifest as weakness (hemiparesis) or paralysis (hemiplegia) on one side of the body that may affect the whole side or just the arm or leg; as problems with balance or coordination; as deficits in gross motor skills such as gait and walking speed; as deficits in fine motor skills or manual dexterity; and as deficits in upper and lower extremity function.

In the United States, more than 700,000 people suffer a stroke each year, two-thirds of these survive and require rehabilitation. Unfortunately, recovery is generally only partial and considerable deficits persist in many patients (e.g., Gordon et al., 2004, *Stroke* 35, 1230-1240). For example, after standard rehabilitation, approximately 30% to 60% of patients are left without functional use of their paretic/plegic arm (Gowland, 1982, *Physiother. Can.* 34, 77-84; Kwakkel et al., 1996, *Age Ageing* 25, 479-489), and despite intensive rehabilitation efforts, only approximately 5% to 20% reach complete functional recovery of their arm (Nakayama et al., 1994, *Arch. Phys. Med. Rehabil.* 75, 394-398).

As discussed herein, chemical entities, and compositions thereof, of the present disclosure are used as augmenting agents to increase the efficiency of training protocols for treating a neurological impairment, which encompasses impairments due to traumatic events such as stroke. Accordingly, in some embodiments, the present disclosure provides methods of treating a neurological deficit during post-stroke rehabilitation comprising: (a) administering to a subject in need thereof a PDE1 inhibitor disclosed herein during recovery of the subject from stroke; (b) providing training to the subject under conditions sufficient to improve performance of a neurological function whose impairment is due to the deficit; and (c) repeating steps (a) and (b) one or more times, whereby the amount of training sufficient to improve the performance is reduced compared to that produced by training alone.

In some embodiments, administration can begin during the acute stage. In other embodiments, the PDE1 inhibitor is administered only after the acute stage, i.e., during post-stroke rehabilitation, which may include sub-acute and chronic stages. In some embodiments, administration occurs during the acute stage and post-stroke stage. In some embodiments, the PDE1 inhibitor is administered chronically, meaning that it is indicated for long-term use after the acute stage of the stroke has ended and the patient has been medically stabilized.

In other embodiments, the subject is a post-stroke patient, and PDE1 inhibitors are administered during stroke rehabilitation to treat stroke deficits (or "post-stroke deficits") resulting from impaired neurological functions. In some embodiments, the deficit is a motor deficit, including upper or lower extremity motor deficit. In other embodiments, the deficit is a cognitive deficit, such as such as aphasia, apraxia, and mental and cognitive changes, particularly, a deficit in memory formation, and more specifically, a deficit in long-term memory formation. In still other embodiments, the deficit may include a cognitive and motor deficit. In another aspect, training comprises a battery of tasks directed to the neurological function. In a specific aspect, the reduction in the amount of training is a reduction in the number of training sessions.

In a further embodiment, the administering step (a) is in conjunction with the training step (b). In one aspect, the subject is a human. In another aspect, the subject has undergone neuronal stem cell manipulation. In other aspects, the compound is administered before and during each training session.

Traumatic Brain Injury

In some embodiments, chemical entities and compositions are useful in methods of treating traumatic brain injury (TBI), and in more specific embodiments, treating motor or cognitive impairments during rehabilitation of TBI after the initial trauma.

TBI, also known as intracranial injury, occurs when an external force injures the brain. TBI can be classified based on severity, mechanism (closed or penetrating head injury), or other features (e.g., occurring in a specific location or over a widespread area). TBI can result in physical, cognitive, social, emotional, and behavioral symptoms. Causes include falls, vehicle collisions, gunshot injuries, and explosives. Outcomes can range from complete recovery to permanent disability or death.

Like stroke care, TBI case is a temporal continuum that includes acute (or sub-acute) treatments directed to the injury itself and subsequent rehabilitative therapy directed to restoring function.

Accordingly, in some embodiments, the chemical entities and compositions of the present disclosure are useful during the acute (or sub-acute) stage of TBI, during which their administration can treat neuroinflammatory and neurodegenerative events following the primary injury.

Some embodiments provide the use of a PDE1 inhibitor disclosed during TBI rehabilitation to treat TBI deficits (or "post-TBI deficits") resulting from impaired neurological functions. Some embodiments provide methods of treating a neurological deficit during post-TBI rehabilitation comprising: (a) administering to a subject in need thereof a PDE1 inhibitor during recovery of the subject from TBI; (b)

providing training to the subject under conditions sufficient to improve performance of a neurological function whose impairment is due to the deficit; and (c) repeating steps (a) and (b) one or more times, whereby the amount of training sufficient to improve the performance is reduced compared to that produced by training alone.

In one aspect, the PDE1 inhibitor is a chemical entity of the present disclosure, and more specifically, is a compound, or pharmaceutically acceptable salt thereof, of Formula (I). More particularly, the chemical entity is a compound of Formula (Ia), (Ib), (Ic), (Iba), (Ibb), (Icaa), (Icab), (Icb), or (Icc), or a pharmaceutically acceptable salt thereof. In some embodiments, the deficit is a motor deficit. In other embodiments, the deficit is a cognitive deficit, particularly, a deficit in memory formation, and more specifically, a deficit in long-term memory formation. In still other embodiments, the deficit may include a cognitive and motor deficit. In another aspect, training comprises a battery of tasks directed to the neurological function. In a specific aspect, the reduction in the amount of training is a reduction in the number of training sessions.

In a further embodiment, the administering step (a) is in conjunction with the training step (b). In one aspect, the subject is a human. In another aspect, the subject has undergone neuronal stem cell manipulation. In other aspects, the compound is administered before and during each training session.

Peripheral Disorders

In some embodiments, the present disclosure provides methods of treating a peripheral disorder (i.e., a disorder other than a primary neurological disorder), comprising administering to a subject in need thereof an effective amount of a chemical entity or composition disclosed herein. In one embodiment of these methods, the chemical entity is a compound, or pharmaceutically acceptable salt thereof, of Formula (I). More particularly, the chemical entity is a compound of Formula (Ia), (Ib), (Ic), (Iba), (Ibb), (Icaa), (Icab), (Icb), or (Icc), or a pharmaceutically acceptable salt thereof.

Peripheral disorders involving PDE1 include a wide variety of diseases, based on numerous biological studies and the expression of PDE1subtypes in peripheral tissues, such as the heart, lungs, veins and arteries, smooth muscle, skeletal muscle, skin, adrenal gland, thyroid, pancreas, esophagus, stomach, small intestine, colon, liver, leukocytes, testis, ovary, bladder, and kidney. See, e.g., Bender and Beavo, 2006, *Pharmacol. Rev.* 58, 488-520. Accordingly, peripheral disorders that can be treated by compounds and compositions of the present invention include, but are not limited to, cardiovascular disorders, renal disorders, hematological disorders, gastrointestinal and liver disorders, cancer disorders, fertility disorders, and metabolic diseases such as diabetes and obesity.

Peripheral disorders also include, in certain embodiments, diseases and conditions (other than primary neurological disorders) characterized by low levels of cAMP or cGMP in cells expressed PDE1, by inhibition of cAMP or cGMP signaling pathways in cells expressing PDE1, and by reduced dopamine D1 receptor signaling activity.

Cardiovascular Disorders

In certain embodiments, the peripheral disorder is a cardiovascular disorder. PDE1 enzymes and cyclic nucleotides are emerging as key mediators of pathological processes that underlie many vascular disorders, including hypertension and myocardial infarction. All three PDE1 isoforms are expressed in the human pulmonary artery, as well as the aorta and small mesenteric arteries (Schermuly et al., 2007, *Circulation* 115, 2331-2339; Murray et al., 2007, *Am. J. Physiol. Lung Cell. Mol. Physiol.*, 292, L294-L303). In addition, selective PDE1 inhibition induces vasodilation and lower blood pressure in rats (Laursen et al., 2017, *Br. J. Pharmacol.* 174, 2563-2575). Moreover, PDE1 enzymes constitute the majority of cAMP- and cGMP-hydrolytic activity in human myocardium, implicating them in the modulation of signaling pathways involved in heart failure.

Accordingly, the present invention includes the use of a compound or composition herein in a method of treating a cardiovascular disorder, comprising administration of an effective amount of a chemical entity or composition to a patient in need thereof.

Cardiovascular diseases within the scope of the present invention encompass, but are not limited to, angina pectoris, coronary artery disease, hypertension, congestive heart failure, myocardial infarction, ischemic diseases of the heart, atrial and ventricular arrhythmias, hypertensive vascular diseases, peripheral vascular diseases, pulmonary hypertension (PH) (or pulmonary arterial hypertension (PAH)), atherosclerosis, and other pulmonary and respiratory disorders.

In some embodiments, methods of treating a cardiovascular disorder in accord with the present invention comprise increasing cGMP concentration, cAMP concentration, or both, in any part of the heart muscle of a subject, the method comprising administering to the subject a chemical entity or composition described herein.

In other embodiments, chemical entities and compositions of the present invention may be useful in lowering the heart rate or blood pressure in an animal.

Renal Disorders

In certain embodiments, the peripheral disorder is a renal disease. PDE1 inhibitors are emerging therapeutic agents for progressive renal disease. See, e.g., Cheng et al., 2007, *Soc. Exp. Biol. Med.* 232, 38-51. Consistent with these findings, recent studies indicate that cAMP and cGMP regulate a variety of signaling pathways involved in the development and progression of renal disease, including pathways that modulate mitogenesis, inflammation, and extracellular matrix synthesis. See, e.g., Wang et al., 2010, *Kidney Int.* 77. 129-140; Wang et al., 2017, *PLoS One* 12, e0181087.

Accordingly, the present invention provides chemical entities or compositions in methods for treating a renal disorder, comprising administering an effective amount of the chemical entity or composition to a patient in need thereof. In a particular aspect, the renal disorder is selected from one or more of the group comprising renal artery stenosis, pyelonephritis, glomerulonephritis, kidney tumors, polycystic kidney disease, injury to the kidney, and damage resulting from radiation of the kidney, and autosomal dominant polycystic kidney disease (ADPKD).

Hematological Disorders

In certain embodiments, the peripheral disorder is a hematological disorder. PDE1B is highly expressed in the hematological system, including leukocytes (peripheral blood), bone marrow stromal cells, bone marrow CD33+ cells, cord blood CD34+ cells, neutrophils cord blood, neutrophils peripheral blood, spleen, spleen liver cirrhosis. Accordingly, the present invention includes methods to treat a hematological disorder, comprising administering a chemical entity or composition herein to a patient in need thereof. Hematological diseases within the scope of the present invention comprises disorders of the blood and all its constituents, including, but not limited to anemias, myeloproliferative disorders, hemorrhagic disorders, leukopenia, eosinophilic disorders, leukemias, lymphomas, plasma cell dyscrasias, and disorders of the spleen.

Gastrointestinal and Liver Diseases

In certain embodiments, the peripheral disorder is a gastrointestinal or liver disease. PDE1B shows differential expression between diseased (e.g., cancerous) and healthy stomach tissue, diseased (e.g., cancerous) versus healthy ileum tissue, diseased (cirrhotic) versus and healthy liver. Accordingly, the present invention includes methods to treat a gastrointestinal or liver disorder, comprising administering a compound or composition herein to a patient in need thereof. Gastrointestinal and liver diseases within the scope of the present invention comprise, but are not limited to, disorders of the esophagus, stomach, duodenum, pancreas, bowel, and liver.

Cancer Disorders

In certain embodiments, the peripheral disorder is a cancer disorder. PDE1B shows high expression in numerous cancer tissues, including tumors of the stomach, ileum, ovary, breast, and kidney, as well as differential expression between cancerous and healthy stomach, ileum, lung, ovary, breast, and kidney. Accordingly, the present invention includes methods to treat a cancer disorder, comprising administering a compound or composition herein to a patient in need thereof. Cancer disorders within the scope of the present invention comprise, but are not limited to, neoplasms, dysplasias, hyperplasias, and neoplasms, including cancers of the stomach, ileum, ovary, breast, and kidney.

Fertility Disorders

In certain embodiments, the peripheral disorder is a fertility disorder. PDE1 inhibitors, for example, have been implicated in the enhancement of progesterone signaling (e.g., WO 2008/070095). Accordingly, the present invention includes methods to treat a fertility disorder, comprising administering a compound or composition herein to a patient in need thereof. Fertility disorders within the scope of the present invention comprise female sexual dysfunction and disorders involving impairments in progesterone signaling, which include, but are not limited to, exercise amenorrhea, anovulation, menopause, menopausal symptoms, hypothyroidism, pre-menstrual syndrome, premature labor, infertility, irregular menstrual cycles, abnormal uterine bleeding, osteoporosis, autoimmune disease, multiple sclerosis, estrogen-induced endometrial hyperplasia and estrogen-induced endometrial carcinoma.

Treatment Combinations

Chemical entities and compositions of the present disclosure can be administered as a monotherapy or as part of a combination therapy. "Monotherapy" refers to a treatment regimen based on the delivery of one (e.g., one and only one) therapeutically effective chemical entity or composition thereof.

In a combination therapy, one or more chemical entities or compositions of the present invention can be co-administered or used in combination with one or more additional agents (or therapies), such as additional agents (or therapies) known in the art. Such administration may be simultaneous, sequential, or staggered. In certain embodiments, the additional agent (or therapies) is based on a different target or modality (e.g., is not a PDE1 inhibitor).

In some embodiments, the combination is administered as part of an adjunct (or adjunctive) therapy, in which one agent is given in addition to a primary agent to assist or maximize the effectiveness of the primary agent.

In specific embodiments, the combination is administered to treat schizophrenia, Parkinson's disease, Alzheimer's disease, Huntington's disease, anxiety and depressive disorders, or stroke. In some embodiments, a chemical entity or composition disclosed herein is administered as an adjunct therapy in conjunction with a dopamine precursor, such as levodopa, to treat Parkinson's disease or a related disorder.

Exemplary agents for treating schizophrenia include, but are not limited to, clozapine, aripiprazole, brexpiprazole, cariprazine, lurasidone, paliperidone, quetiapine, risperidone, olanzapine, ziprasidone, and iloperidone.

Exemplary agents for treating Parkinson's disease include, but are not limited to, dopamine preparations (including dopamine precursors such as levodopa), dopamine agonists, or COMT agents (drugs that inhibit the action of catechol-methyl transferase).

Exemplary agents for treating Alzheimer's disease include, but are not limited to, donepezil, rivastigmine, galantamine, marijuana-like cannabinoids, and memantine.

Exemplary agents for treating Huntington's disease (or other motor disorders) may include, but are not limited to, tetrabenazine, as well as antipsychotic drugs such as haloperidol, chlorpromazine, risperidone, and quetiapine, and anti-epileptic drugs such as levetiracetam and clonazepam, which may be beneficial in treating chorea or related motor disorders.

Exemplary agents for treating anxiety or depression include, but are not limited to, benzodiazepines and other anxiolytics; serotonin reuptake inhibitors (SSRIs), such as sertraline, fluoxetine, citalopram, escitalopram, paroxetine, fluvoxamine, and trazodone; serotonin and norepinephrine reuptake inhibitors (SNRIs), such as desvenlafaxine, duloxetine, levomilnacipran, and venlafaxine; tricyclic antidepressants (TCAs), such as amitriptyline, amoxapine, clomipramine, desipramine, doxepin, imipramine, nortriptyline, protriptyline, and trimipramine; monoamine oxidase inhibitors (MAOIs), such as isocarboxazid, phenelzine, selegiline, and tranylcypromine; and other classes of drugs, such as maprotiline, bupropion, vilazodone, nefazodone, trazodone, vortioxetine, and mirtazapine Exemplary agents for treating stroke include, but are not limited to, a thrombolytic agent (e.g., streptokinase, acylated plasminogen-streptokinase activator complex (APSAC), urokinase, single-chain urokinase-plasminogen activator (scu-PA), anti-inflammatory agents, thrombin-like enzymes, tissue plasminogen activator (t-PA); an anticoagulant (e.g., warfarin or heparin); an antiplatelet drug (e.g., aspirin); a glycoprotein IIb/IIIa inhibitor; a glycosaminoglycan; coumarin; GCSF; melatonin; an apoptosis inhibitor (e.g., caspase inhibitor), an anti-oxidant (e.g., NXY-059); and a neuroprotectant (e.g., an NMDA receptor antagonists or a cannabinoid antagonist).

The preceding list of additional active agents is meant to be exemplary rather than fully inclusive. Additional active agents not included in the above list may be administered in combination with a compound of Formula (I) such as those know for treating peripheral disorders described herein. The additional active agent will be dosed according to its approved prescribing information, though in some embodiments the additional active agent may be dosed at less the typically prescribed dose.

EXAMPLES

The present disclosure will be further illustrated by the following non-limiting Examples. These Examples are understood to be exemplary only, and they are not to be construed as limiting the scope of the one or more embodiments, and as defined by the appended claims.

Preparative Examples

Exemplary compounds will now be described by reference to the illustrative synthetic schemes for their general preparation below and the specific examples to follow.

One skilled in the art will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between −100° C. and the reflux temperature of the solvent. Reactions may be heated employing conventional heating or microwave heating. Reactions may also be conducted in sealed pressure vessels above the normal reflux temperature of the solvent.

Abbreviations

The specification includes numerous abbreviations, whose meanings are listed in the following Table:

TABLE 1

| Abbreviation | Definition |
| --- | --- |
| ACN | Acetonitrile |
| Ac₂O | Acetic anhydride |
| Boc | tert-Butyloxycarbonyl |
| Boc₂O | Di-tert-butyl dicarbonate |
| CAS | Chemical abstracts service |
| CCl₄ | Carbon tetrachloride |
| CDCl₃ | Deuterated chloroform |
| Celite ® | Diatomaceous earth |
| CHCl₃ | Chloroform |
| CH₂=CHBF₃K | Potassium vinyltrifluoroborate |
| CsF | Cesium fluoride |
| Cs₂CO₃ | Cesium carbonate |
| DCM, CH₂Cl₂ | Dichloromethane |
| DCE | Dichloroethane |
| DIPEA, DIEA | N,N-ethyldiisopropylamine or N,N-Diisopropylethylamine |
| DMA | N,N-Dimethylacetamide |
| DMF | N,N-Dimethylformamide |

TABLE 1-continued

| Abbreviation | Definition |
| --- | --- |
| DMSO | Dimethylsulfoxide |
| dppf | 1,1'-Bis(diphenylphosphino)ferrocene |
| EtOAc, or EA | Ethyl acetate |
| EtOH | Ethanol |
| FCC | Flash column chromatography |
| H₂ | Hydrogen |
| HATU | 1-[Bis(dimethylamino)methylene]-1H-1,2,3-triazolo[4,5-b]pyridinium 3-oxid hexafluorophosphate |
| HCl | Hydrochloric acid |
| HCO₂H | Formic acid |
| H₂O | Water |
| HPLC | High-performance liquid chromatography |
| IPA | Isopropyl alcohol |
| K₂CO₃ | Potassium carbonate |
| KF | Potassium fluoride |
| MeOH | Methanol |
| 2-MeTHF | 2-Methyltetrahydrofuran |
| MgSO₄ | Magnesium sulfate |
| N₂ | Nitrogen |
| NaCl | Sodium chloride, brine |
| Na₂CO₃ | Sodium carbonate |
| NaOMe | Sodium methoxide |
| NaOEt | Sodium ethoxide |
| Na₂SO₃ | Sodium sulfite |
| Na₂SO₄ | Sodium sulfate |
| NIS | N-Iodosuccinimide |
| Pd | Palladium |
| Pd/C | Palladium on carbon, 10% |
| Pd(dppf)Cl₂ | [1,1'-Bis(diphenylphosphino)ferrocene]dichloropalladium(II) |
| Pd(dppf)Cl₂•CH₂Cl₂ | [1,1'-P-Bis(diphenylphosphino)ferrocene]dichloropalladium(II), complex with dichloromethane |
| Pd(PPh₃)₄ | Tetrakis(triphenylphosphine)palladium(0) |
| PPh₃ | Triphenylphosphine |
| POCl₃ | Phosphorous oxychloride, phosphorous chloride |
| RT, rt | Room temperature |
| SFC | Supercritical fluid chromatography |
| SiO₂ | Silica gel |
| TEA, Et₃N | Triethylamine |
| TFA | Trifluoroacetic acid |
| THF | Tetrahydrofuran |
| ZnCN₂ | Zinc cyanide, dicyanozinc |

Synthetic Schemes

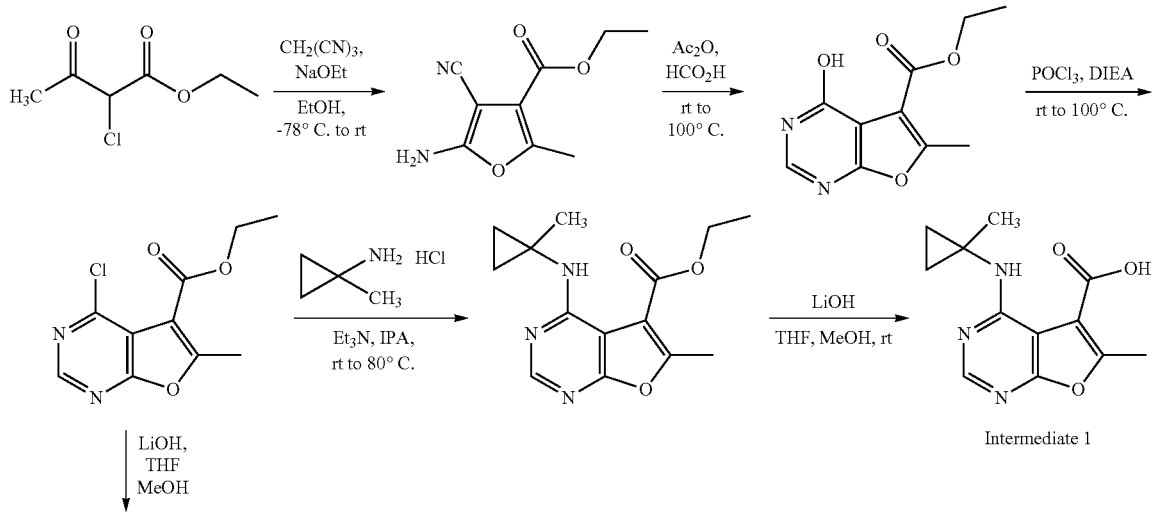

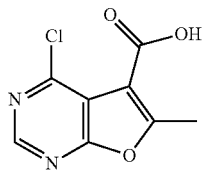

Intermediate 2

According to Scheme A, 6-methyl-4-((1-methylcyclopropyl)amino)furo[2,3-d]pyrimidine-5-carboxylic acid (Intermediate 1) can be synthesized from ethyl 2-chloro-3-oxobutanoate in 5 steps from commercially available starting materials. Treatment of ethyl 2-chloro-3-oxobutanoate with malonitrile, in a solvent such as ethanol, or the like, followed by a base such as sodium ethoxide, or the like, at a temperature ranging from −78° C. to rt, sometimes a temperature ranging from −10° C. to 10° C., provides ethyl 5-amino-4-cyano-2-methylfuran-3-carboxylate. Treatment of ethyl 5-amino-4-cyano-2-methylfuran-3-carboxylate with formic acid, followed by acetic anhydride, at a temperature ranging from rt to 100° C., for a time period of up to 48 hours, provides ethyl 4-hydroxy-6-methylfuro[2,3-d]pyrimidine-5-carboxylate. Subsequent chlorination, using conditions known to one of skill in the art, for instance treatment with phosphorous oxychloride, in the presence of a base such as N,N-diisopropylethylamine, or the like, with or without a solvent, at a temperature ranging from rt to 100° C., sometimes 85° C., provides ethyl 4-chloro-6-methylfuro[2,3-d]pyrimidine-5-carboxylate. A nucleophilic aromatic substitution reaction, using 1-methylcyclopropanamine hydrochloride as the amine, followed by hydrolysis of the ester, under conditions known to one of skill in the art, provides 6-methyl-4-((1-methylcyclopropyl)amino)furo[2,3-d]pyrimidine-5-carboxylic acid (Intermediate 1). For example, treatment of the arylchloride with 1-methylcyclopropylamine hydrochloride, in a solvent such as isopropanol, or the like, in the presence of a base such as triethylamine, at a temperature ranging from rt to 80° C., sometimes 45° C., provides ethyl 6-methyl-4-((1-methylcyclopropyl)amino)furo[2,3-d]pyrimidine-5-carboxylate. Subsequent base-catalyzed ester hydrolysis, using a base such as lithium hydroxide, or the like, in a solvent mixture such as tetrahydrofuran and methanol, or the like, at room temperature for several hours, provides 6-methyl-4-((1-methylcyclopropyl)amino)furo[2,3-d]pyrimidine-5-carboxylic acid (Intermediate 1).

In a similar fashion, base-catalyzed hydrolysis of ethyl 4-chloro-6-methylfuro[2,3-d]pyrimidine-5-carboxylate, under conditions known to one of skill in the art, such as those described above, provides 4-chloro-6-methylfuro[2,3-d]pyrimidine-5-carboxylic acid (Intermediate 2).

SCHEME B

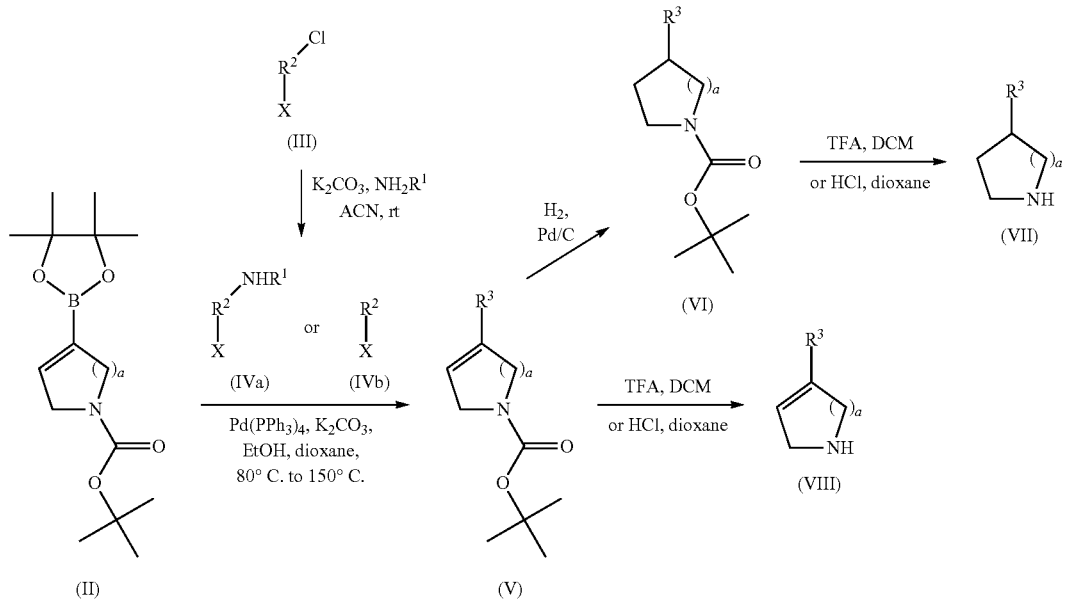

According to Scheme B, compounds of formula (VII) and (VIII) can be synthesized from the corresponding boronic acid pinacol ester starting material.

A compound of formula (IVa), where $R^1$ is $C_{1-6}$alkyl, $C_{1-6}$haloalyl, $C_{3-7}$cycloalkyl, can be synthesized by a nucleophilic aromatic substitution reaction of an amine and an aryl chloride of formula (III), where $R^2$ is an optionally substituted aryl or heteroaryl group and X is Cl, Br, or I. A subsequent Suzuki coupling of a boronic acid pinacol ester of formula (II) and a commercially available or synthetically accessible aryl halide or heteroaryl halide of formula (IVa) or (IVb), under conditions known to one of skill in the art, provides a compound of formula (V), where $R^3$ is an optionally substituted aryl or heteroaryl group (with the optional substitution including —NHR¹). For example, treatment of (II) with tetrakis(triphenylphosphine)palladium (0), in the presence of a base such as potassium carbonate or the like, in a solvent mixture such as ethanol and dioxane, or the like, at a temperature ranging from 80° C. to 150° C., provides a compound of formula (V), where a is 1 or 2 and R³ is an optionally substituted aryl or heteroaryl group. Subsequent reduction of the double bond in a catalytic hydrogenation, using conditions known to one of skill in the art, followed by removal of the tert-butoxycarbonyl protecting group under acidic conditions, provides a compound of formula (VII). For example, using a catalyst such as palladium on carbon, or the like, under an atmosphere of hydrogen, provides a compound of formula (VI). Subsequent treatment with a strong acid such as trifluoroacetic acid in a solvent such as dichloromethane, or the like, or hydrochloric acid in a solvent such as dioxane, or the like, provides an amine of formula (VII), where a is 1 or 2 and R³ is an optionally substituted aryl or heteroaryl group. Alternatively, treatment of a compound of formula (V) with a strong acid, under conditions known to one of skill in the art, as described above, provides a dihydropyrrole or tetrahydropyridine compound of formula (VIII), where a is 1 or 2 and R³ is an optionally substituted aryl or heteroaryl group.

aromatic substitution, under conditions known to one of skill in the art, followed by removal of the tert-butoxycarbonyl protecting group. For example, treatment of the aryl chloride with an amine, in the presence of a base such as N,N-diisopropylethylamine, or the like, in a solvent such as DMA or DMF, or the like, heated to a temperature ranging from 40° C. to 160° C., sometimes 80° C., provides a compound for formula (XII). Subsequent deprotection of the amine using conditions known to one of skill in the art, as previously described, provides an amino compound of formula (XIII), where b is 0 or 1; c is 1 or 2; B, D, E and G are C or N; and R⁴ and R⁵ are independently H or an optionally substituted $C_{1-6}$alkyl or $C_{3-7}$cycloalkyl group, or R⁴ and R⁵ come together to form an optionally substituted heterocycloalkyl group.

Treatment of a compound of formula (IX) with a strong acid, such as HCl or TFA, under conditions previously described, provides an amine compound of formula (XIV), where b is 0 or 1, c is 1 or 2, and B, D, E and G are C or N.

SCHEME C

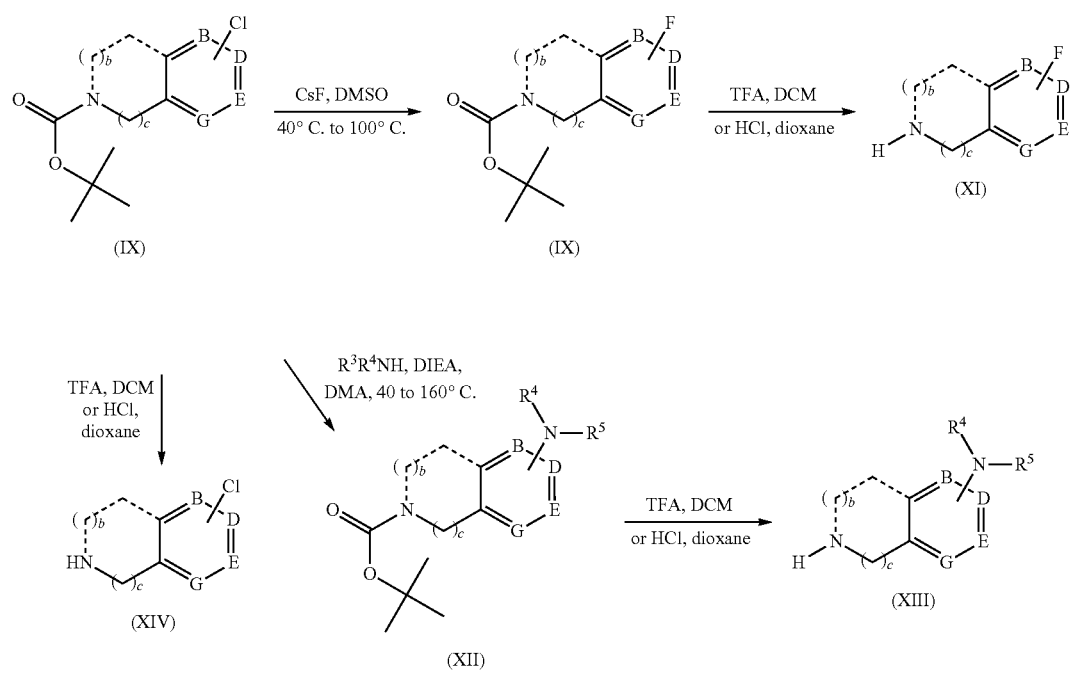

According to Scheme C, an aryl chloride can be converted to an aryl fluoride using conditions known to one of skill in the art. For instance, treatment of a compound of formula (IX) with cesium fluoride, in a solvent such as DMSO, or the like, at a temperature ranging from 40° C. to 100° C., sometimes 70° C., provides an aryl fluoride of formula (X). Subsequent removal of the t-butoxycarbonyl protecting group, as previously described, provides an amine of compound (XI), where b is 0 or 1, c is 1 or 2, and B, D, E and G are C or N.

Synthesis of an aryl amine of formula (XIII) from an aryl chloride of formula (IX) is achieved by a nucleophilic

SCHEME D

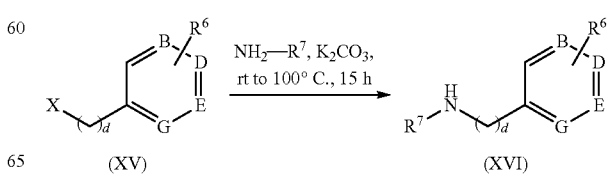

A nucleophilic substitution reaction of a compound of formula (XV), where X is Cl, Br or I, with an amine provides a compound of formula (XVI). For example, treatment of the alkyl halide with an amine, in the presence of a base such as potassium carbonate, or the like, in a solvent such as ACN, DMF, or DMA, or the like, at a temperature ranging from rt to 100° C., sometimes 40° C., for many hours, provides a compound of formula (XVI), where d is 0 or 1; B, D, E and G are C or N; $R^6$ is -halo, —OH, —CN or an optionally substituted amino, $C_{1-6}$alkyl, $C_{1-6}$haloalkyl, $C_{3-7}$cycloalkyl, aryl or heteroaryl group; and $R^7$ is an optionally substituted $C_{1-6}$alkyl, $C_{1-6}$haloalkyl or $C_{3-7}$cycloalkyl group.

SCHEME E

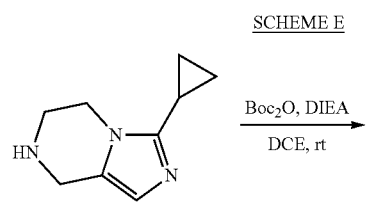

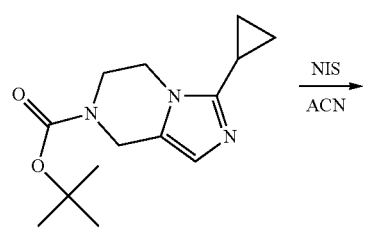

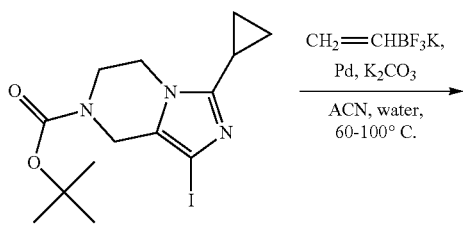

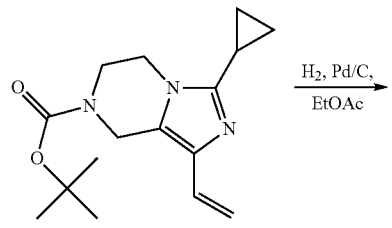

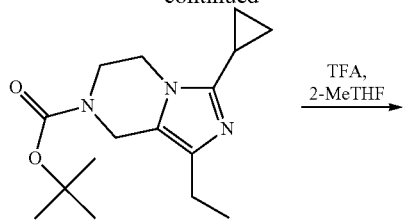

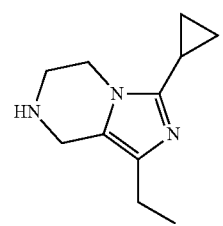

3-Cyclopropyl-1-ethyl-5,6,7,8-tetrahydroimidazo[1,5-a]pyrazine can be synthesized from commercially available or synthetically accessible 3-cyclopropyl-5,6,7,8-tetrahydroimidazo[1,5-a]pyrazine in 5 steps, as shown in Scheme E. Treatment of 3-cyclopropyl-1-ethyl-5,6,7,8-tetrahydroimidazo[1,5-a]pyrazine with di-tert-butyl dicarbonate, in the presence of a base such as N,N-diisopropylethylamine or the like, in a solvent such as DCE, or the like, at room temperature, provides tert-butyl 3-cyclopropyl-5,6-dihydroimidazo[1,5-a]pyrazine-7(8H)-carboxylate. Iodination of the imidazole, using conditions known to one of skill in the art, such as treatment with NIS, or the like, in a solvent such as ACN, or the like, provides tert-butyl 3-cyclopropyl-1-iodo-5,6-dihydroimidazo[1,5-a]pyrazine-7(8H)-carboxylate. A subsequent Suzuki coupling of the aryl iodide with potassium vinyltrifluoroborate, using palladium(0) as the catalyst, in the presence of a base such as potassium carbonate or sodium carbonate, or the like, in a solvent mixture such as ACN and water, or the like, heated to a temperature ranging from 60° C. to 110° C., sometimes 90° C., provides tert-butyl 3-cyclopropyl-1-vinyl-5,6-dihydroimidazo[1,5-a]pyrazine-7(8H)-carboxylate. Subsequent hydrogenation to reduce the alkene, followed by removal of the tert-butoxycarbonyl protecting group, provides the free amine compound. For example, catalytic hydrogenation under conditions known to one of skill in the art, such as treatment of tert-butyl 3-cyclopropyl-1-vinyl-5,6-dihydroimidazo[1,5-a]pyrazine-7(8H)-carboxylate with palladium on carbon, under an atmosphere of hydrogen, in a solvent such as ethyl acetate, or the like, provides tert-butyl 3-cyclopropyl-1-ethyl-5,6-dihydroimidazo[1,5-a]pyrazine-7(8H)-carboxylate. Treatment of the tert-butoxycarbonyl protected compound with trifluoroacetic acid, in a solvent such as 2-methyl tetrahydrofuran, provides 3-cyclopropyl-1-ethyl-5,6,7,8-tetrahydroimidazo[1,5-a]pyrazine.

SCHEME F

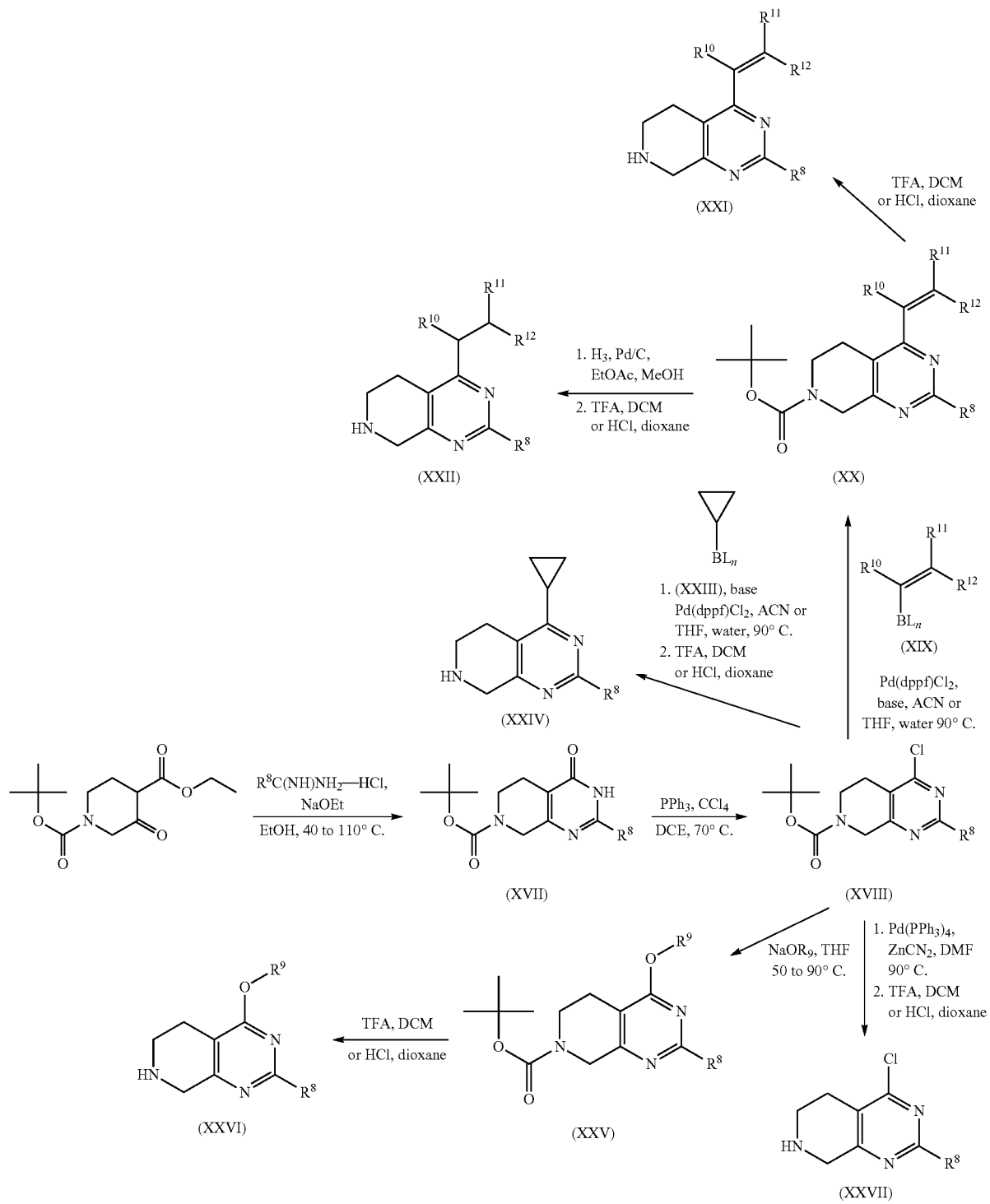

(XXVII)

A 4-chloro-5,6,7,8-tetrahydropyrido[3,4-d]pyrimidine compound of formula (XVIII) is synthetically accessible from commercially available 1-(tert-butyl) 4-ethyl 3-oxopiperidine-1,4-dicarboxylate in two steps. Treatment of 1-(tert-butyl) 4-ethyl 3-oxopiperidine-1,4-dicarboxylate with a substituted amidine, in the presence of a base such as sodium ethoxide or the like, in a solvent such as ethanol, at a temperature ranging from 40° C. to 100° C., sometimes 90° C., provides a tetrahydropyridopyrimidinone of formula (XVII), where $R^8$ is H or an optionally substituted $C_{1-6}$alkyl, $C_{1-6}$haloalkyl or $C_{3-7}$cycloalkyl group. Chlorination using conditions known to one of skill in the art, for example using carbon tetrachloride in the presence of triphenylphosphine, in a solvent such as dichloroethane or the like, at a temperature of 70° C., provides a compound of formula (XVIII). From this intermediate, several 4-substituted 5,6,7,8-tetrahydropyrido[3,4-d]pyrimidine compounds are synthetically accessible.

In one instance, a Suzuki coupling of an aryl chloride of formula (XVIII) with a boronic acid, boronic acid pinacol ester or potassium trifluoroborate salt of formula (XIX), where $BL_n$ is $B(OH)_2$, $B(O_2C_2(CH_3)_4)$, or $BF_3K$, under conditions known to one of skill in the art, provides a compound of formula (XX). For example, using conditions similar to the Suzuki coupling described in Scheme E, using [1,1'-bis(diphenylphosphino)ferrocene]palladium(II) dichloride as the catalyst and sodium carbonate as the base, provides a compound of formula (XX), where $R^8$ is H or an optionally substituted $C_{1-6}$alkyl, $C_{1-6}$haloalkyl or $C_{3-7}$cycloalkyl group, and $R^{10}$, $R^{11}$ and $R^{12}$ are independently H or $C_{1-6}$alkyl, or $R^9$ and $R^{10}$ taken together can form an optionally unsaturated $C_{4-6}$cycloalkyl or unsaturated $C_{4-6}$heterocycloalkyl group. Removal of the tert-butoxycarbonyl protecting group provides a compound of formula (XXI). Alternatively, reduction of an alkene of a compound of formula (XX) in a catalytic hydrogenation reaction, followed by deprotection of the tert-butoxycarbonyl protecting group, as described previously in Scheme B, provides a compound of formula (XXII), where $R^8$ is H or an optionally substituted $C_{1-6}$alkyl or $C_{3-7}$cycloalkyl group, and $R^{10}$, $R^{11}$ and $R^{12}$ are independently H or $C_{1-6}$alkyl or $R^{10}$ and $R^{11}$ taken together can form an optionally substituted saturated $C_{3-6}$cycloalkyl or saturated $C_{3-6}$heterocycloalkyl group. Alternatively, compounds of the formula (XXIV) can be prepared directly from (XVIII) using a Suzuki reaction with cyclopropylboronic acid, under conditions known to one of skill in the art.

In another instance, in a nucleophilic aromatic substitution reaction with an alkoxide, such as sodium methoxide, in a solvent such as THF or the like, at a temperature ranging from 50° C. to 90° C., sometimes 70° C., provides a compound of formula (XXV), where $R^8$ is H or an optionally substituted $C_{1-6}$alkyl, $C_{1-6}$haloalkyl or $C_{3-7}$cycloalkyl group, and $R^9$ is an optionally substituted $C_{1-6}$alkyl, $C_{1-6}$haloalkyl or $C_{3-7}$cycloalkyl group. Subsequent deprotection of the amine, as previously described, affords a compound of formula (XXVI).

In a metal-catalyzed cyanation reaction, under conditions known to one of skill in the art, by treatment of an aryl chloride of formula (XVIII) with dicyanozinc, in the presence of a transition metal catalyst such as tetrakis(triphenylphosphine)palladium(0), or the like, in a solvent such as DMF or DMA or the like, at a temperature of 90° C. for several hours, followed by removal of the tert-butoxycarbonyl group, as previously described, affords an amine of formula (XXVII), where $R^8$ is H or an optionally substituted $C_{1-6}$alkyl, $C_{1-6}$haloalkyl or $C_{3-7}$cycloalkyl group.

SCHEME G

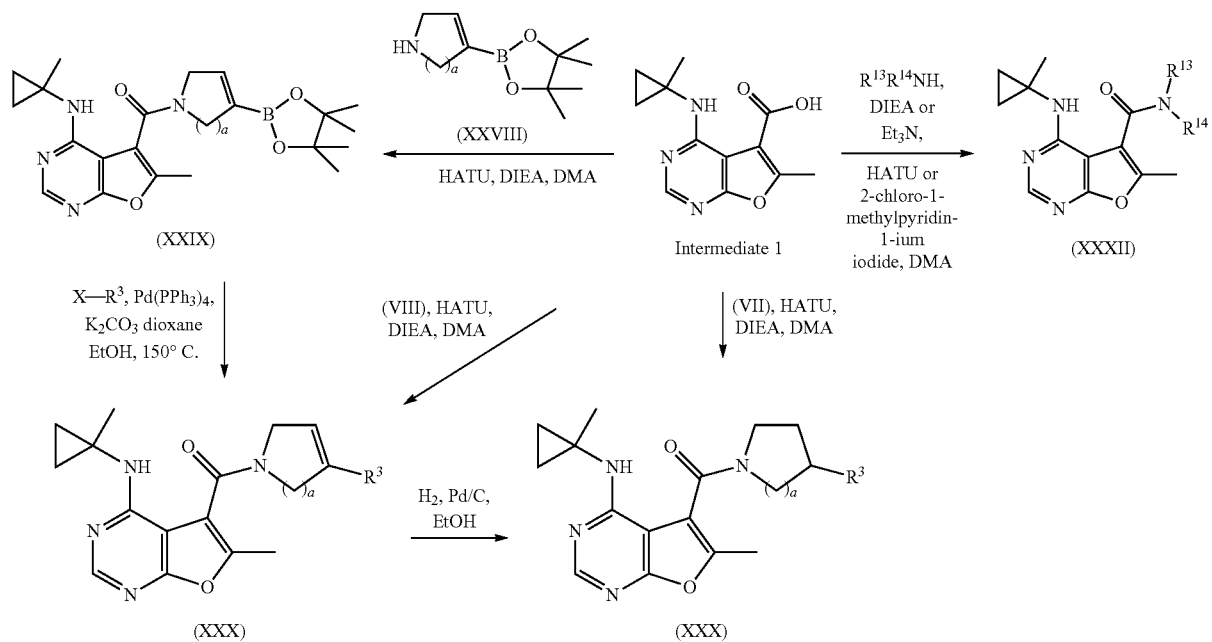

Various amide analogs can be synthesized from Intermediate 1, as shown in Scheme G.

A compound of formula (XXX), where $R^3$ is an optionally substituted aryl or heteroaryl group, can be synthesized in 1 or 2 steps from Intermediate 1, step-wise by an amide coupling with a compound of formula (XXVIII) followed by a Suzuki coupling, or in one step by an amide coupling with a bicyclic intermediate of formula (VIII). For example, an amide coupling of Intermediate 1 with an amine of formula (XXVIII), where a is 1 or 2, under conditions known to one of skill in the art, using a coupling reagent such as HATU or the like, in the presence of a base such as N,N-diisopropylethylamine, triethylamine, or the like, in a solvent such as DMA or DMF, or the like, provides a compound of formula (XXIX), where a is 1 or 2. Subsequently, a Suzuki coupling of a pinacol boronate ester with an aryl halide or heteroaryl halide of formula $X-R^3$, where X is Cl, Br or I and $R^3$ is an optionally substituted aryl or heteroaryl group, under conditions previously described in Scheme B, provides a compound of formula (XXX). Alternatively, a compound of formula (XXX) can be synthesized directly from Intermediate 1 in an amide coupling with a bicycle of formula (VIII), using conditions previously described.

Synthesis of a compound of formula (XXXI), where a is 1 or 2 and $R^3$ is an optionally substituted aryl or heteroaryl group, is achieved by either catalytic hydrogenation of an alkene of formula (XXX), under conditions previously described, or by an amide coupling of Intermediate 1 and a compound of formula (VII).

An amide coupling of Intermediate 1 with a amine, similar to conditions previously described, using a coupling agent such as HATU, or 2-chloro-1-methylpyridin-1-ium iodide or the like, in the presence of a base such as N,N-diisopropylethylamine, triethylamine, or the like, in a solvent such as DMF or DMA, for several hours at room temperature, provides a compound of formula (XXXII) where $R^{13}$ and $R^{14}$ are independently H or an optionally substituted $C_{1-6}$alkyl, $C_{1-6}$haloalkyl, $C_{1-4}$alkylaryl, or $C_{1-4}$alkyl-heteroaryl group; or $R^{13}$ and $R^{14}$ come together to form an optionally substituted N-containing heterocycloalkyl group or an optionally substituted N-containing heteroaryl group.

According to Scheme H, various amide analogs can be synthesized from Intermediate 1.

Formation of a fluoroalkoxy compound of formula (XXXV) is achieved in two steps from Intermediate 1. First an amide coupling of Intermediate 1 and an amine of (XXXIII), under conditions previously described, provides a hydroxyl-substituted compound of formula (XXXIV). Subsequent alkylation of the hydroxyl group, in a nucleophilic substitution reaction, using a fluoro alkyl methylbenzenesulfonate compound, in the presence of a base such as cesium carbonate, or the like, and a solvent such as DMF or DMA or the like, at a temperature ranging from 40° C. to 130° C., sometimes 70° C., provides a compound of formula (XXXV), where b is 0 or 1; c is 1 or 2; e is 1, 2 or 3; and B, D, E and G are C or N.

An aryl fluoride compound of formula (XXXVII) can be synthesized in a similar manner, either directly by an amide coupling of Intermediate 1 with an amine of formula (XI), or amide coupling with an aryl chloride of formula (XIV) followed by a fluorination reaction. For instance, an amide coupling of Intermediate 1 with an amine of formula (XI), in a manner previously described, provides a compound of formula (XXXVII), where b is 0 or 1; c is 1 or 2; and B, D,

SCHEME H

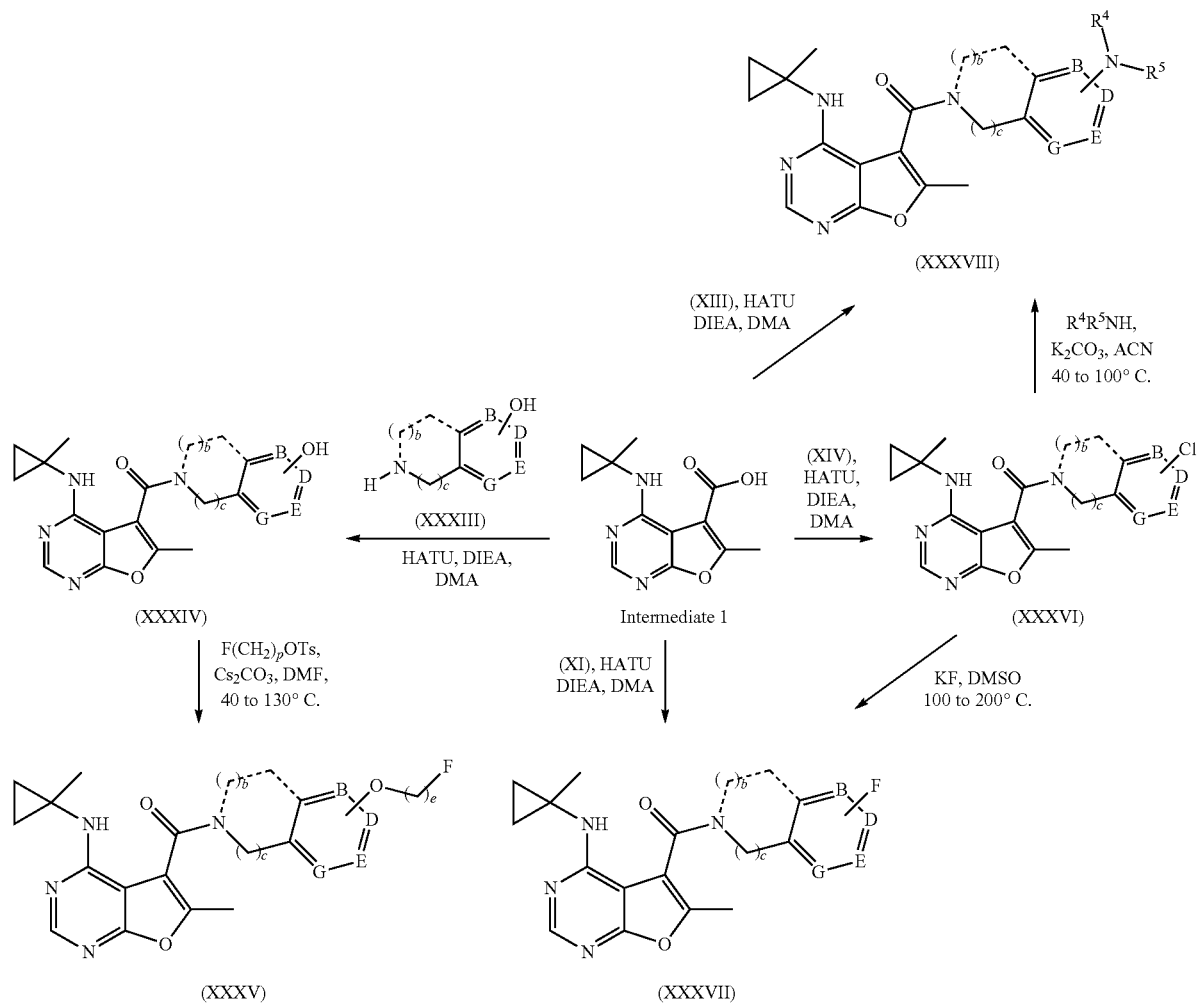

E and G are C or N. Alternatively, amide coupling of Intermediate 1 with an amine of formula (XIV), under conditions previously described, provides an aryl chloride of formula (XXXVI), where b is 0 or 1; c is 1 or 2; and B, D, E and G are C or N. A subsequent fluorination reaction of the aryl chloride, under conditions known to one of skill in the art, such as treatment with potassium fluoride, in a solvent such as DMSO or the like, at a temperature ranging from 100° C. to 200° C., sometimes 170° C., provides a compound of formula (XXXVII).

$C_{1-6}$alkyl or $C_{3-7}$cycloalkyl group, or $R^4$ and $R^5$ come together to form an optionally substituted N-containing heterocycloalkyl group. Alternatively, an amide coupling with an aryl chloride of formula (XIV), followed by a nucleophilic aromatic substitution reaction with a commercially available or synthetically accessible amine, in the presence of a base such as potassium carbonate, or the like, in a solvent such as ACN, at a temperature ranging from 40° C. to 100° C., sometimes 80° C., also provides a compound of formula (XXXVIII).

SCHEME I

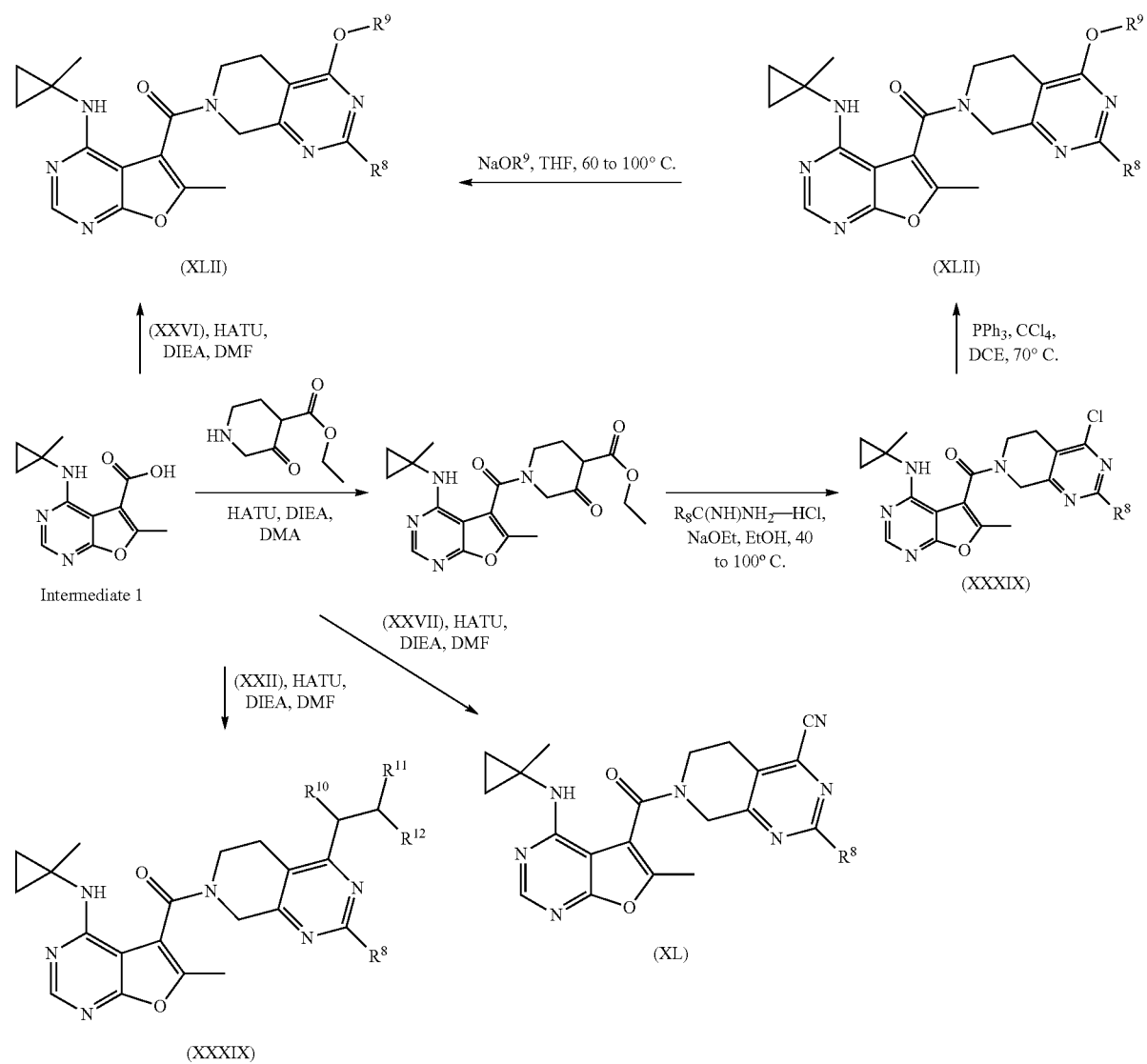

Various amide analogs can be synthesized from Intermediate 1, as shown in Scheme I.

An oxygen substituted compound of formula (XLIII) is afforded either by amide coupling of Intermediate 1 with an amine of formula (XXVI), the synthesis of which is described in Scheme F, or by an initial amide coupling with ethyl 3-oxopiperidine-4-carboxylate, followed by a three-step conversion to desired product. For example, amide coupling of Intermediate 1 with a commercially available or An aryl amine of formula (XXXVIII) can be synthesized directly through an amide coupling or in two steps by an amide coupling followed by nucleophilic aromatic substitution of the resulting aryl chloride. For example, treatment of Intermediate 1 with an amine of formula (XIII) in an amide coupling reaction, under conditions previously described, provides an amine of formula (XXXVIII), where b is 0 or 1; c is 1 or 2; and B, D, E and G are C or N; and $R^4$ and $R^5$ are independently H or an optionally substituted synthetically accessible amine of formula (XXVI), under conditions previously described, provides a compound of formula (XLIII), where $R^8$ is H or an optionally substituted $C_{1-6}$alkyl, $C_{1-6}$haloalkyl or $C_{3-7}$cycloalkyl group, and $R^9$ is H or an optionally substituted $C_{1-6}$alkyl, $C_{1-6}$haloalkyl or $C_{3-7}$cycloalkyl group. Alternatively, treatment of Intermediate 1 with ethyl 3-oxopiperidine-4-carboxylate in an amide coupling reaction, under conditions previously described, provides ethyl 1-(6-methyl-4-((1-methylcyclopropyl)amino) furo[2,3-d]pyrimidine-5-carbonyl)-3-oxopiperidine-4-carboxylate. Subsequent treatment with a substituted amidine, in the presence of a base such as sodium ethoxide or the like, in a solvent such as ethanol, at a temperature ranging from 40° C. to 100° C., sometimes 90° C., provides a tetrahydropyridopyrimidinone of formula (XLI), where $R^8$ is H or an optionally substituted $C_{1-6}$alkyl, $C_{1-6}$haloalkyl or $C_{3-7}$cycloalkyl group. Chlorination using conditions known to one of skill in the art, for example using carbon tetrachloride in the presence of triphenylphosphine, in a solvent such as dichloroethane or the like, at a temperature of 70° C., provides an aryl chloride of formula (XLII). A nucleophilic aromatic substitution reaction with an alkoxide, in a solvent such as THF, or the like, at a temperature ranging from 60° C. to 100° C., sometimes 90° C., also provides a compound of formula (XLIII).

In another embodiment, treatment of Intermediate 1 with an amine of formula (XXVII), under conditions previously described, provides a nitrile compound of formula (XL), where $R^8$ is H or an optionally substituted $C_{1-6}$alkyl, $C_{1-6}$haloalkyl or $C_{3-7}$cycloalkyl group. In a similar manner, treatment of Intermediate 1 with an amine of formula (XXII), under conditions previously described, provides a compound of formula (XXXIX), where $R^8$ is H or an optionally substituted $C_{1-6}$alkyl, $C_{1-6}$haloalkyl or $C_{3-7}$cycloalkyl group, and $R^{10}$, $R^{11}$ and $R^{12}$ are independently H or $C_{1-6}$alkyl or $R^{10}$ and $R^{11}$ taken together can form an optionally substituted saturated $C_{3-6}$cycloalkyl or saturated $C_{3-6}$heterocycloalkyl group.

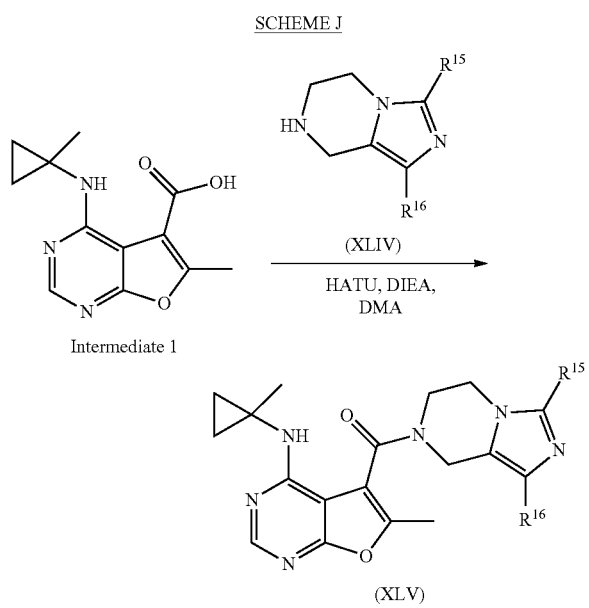

According to Scheme J, an amide coupling of a compound of Intermediate 1 and a 1,3-substituted-5,6,7,8-tetrahydroimidazo[1,5-a]pyrazine of formula (XLIV), under conditions previously described, provides a compound of formula (XLV), where $R^{15}$ and $R^{16}$ are an optionally substituted $C_{1-6}$alkyl, $C_{1-6}$haloalkyl, or $C_{3-6}$cycloalkyl group.

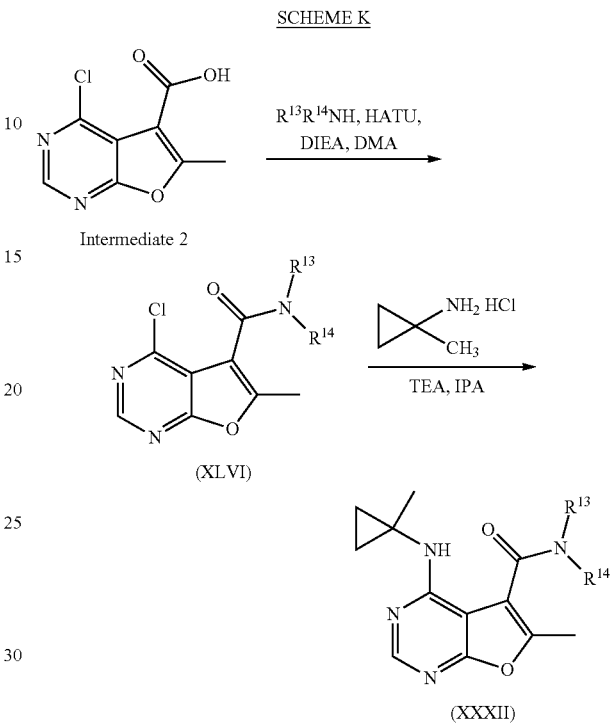

An amide of formula (XXXII) can be synthesized in two steps from Intermediate 2, by an amide coupling with a commercially available or synthetically accessible amine, followed by a nucleophilic aromatic substitution reaction with 1-methylcyclopropan-1-amine hydrochloride.

For instance, an amide coupling reaction of a carboxylic acid of Intermediate 2 with an amine, under conditions previously described, provides an amide of formula (XLVI), where $R^{13}$ and $R^{14}$ are independently H, $C_{1-6}$alkyl, $C_{1-6}$haloalkyl, $C_{1-4}$alkylaryl, or $C_{1-4}$alkyl-heteroaryl; or $R^{13}$ and $R^{14}$ come together to form an optionally substituted N-containing heterocycloalkyl group or an optionally substituted N-containing heteroaryl group. Subsequently, treatment with 1-methylcyclopropan-1-amine hydrochloride, in the presence of a base such as triethylamine, or the like, and a solvent such as IPA, provides an amide of formula (XXXII).

EXAMPLES

Chemistry:

In obtaining the compounds described in the examples below, and the corresponding analytical data, the following experimental and analytical protocols were followed unless otherwise indicated.

Unless otherwise stated, reaction mixtures were magnetically stirred at room temperature (rt) under an atmosphere of nitrogen. Where solutions were "dried," they were generally dried over a drying agent such as $Na_2SO_4$ or $MgSO_4$. Where mixtures, solutions, and extracts were "concentrated," they were typically concentrated on a rotary evaporator under reduced pressure.

Reactions under microwave irradiation conditions were carried out in a CEM Discover-SP with Activent microwave reaction apparatus, model number 909150, or Biotage Initiator, model number 355302.

Normal-phase flash column chromatography (FCC) was performed on Silica ($SiO_2$) using packed or prepackaged cartridges, eluting with the indicated solvents.

Analytical LC/MS were obtained on a Waters 2695 Separations Unit, 2487 Dual Absorbance Detector, Micromass ZQ fitted with ESI Probe, or a Waters Acquity™ Ultra performance LC (UPLC) with PDA eλ and SQ detectors. Alternatively, LC-MS was performed on a Waters Acquity UPLC-MS instrument equipped with a Acquity UPLC BEH C18 column (1.7 μm, 2.1×50 mm) and the solvent system A: 0.1% HCOOH in $H_2O$ and B: 0.1% HCOOH in ACN. Column temperature was 45° C. All compounds were run using the same elution gradient, i.e., 5% to 95% solvent B in 0.75 min with a flow rate of 1 mL/min.

Analytical SFC-MS was performed on a Waters $UPC^2$-MS instrument equipped with a Acquity $UPC^2$ BEH 2-ethylpyridine column (1.7 μm, 2.1×50 mm) and the solvent system A: $CO_2$ and B: 0.1% $NH_4OH$ in MeOH. Column temperature was 55° C. All compounds were run using the same elution gradient, i.e., 3% to 35% solvent B in 0.75 min with a flow rate of 2.5 mL/min.

Preparative HPLC was performed on a Shimadzu SIL-10AP system using a Waters SunFire™ OBD (5 μm, 30×100 mm) C18 column with a 15-minute gradient of 10-100% acetonitrile in water and 0.05% trifluoroacetic acid added as a modifier to both phases. Elution profiles were monitored by UV at 254 and 220 nm.

Some compounds were purified using a Waters Fractionlynx system equipped with a XBridge Prep C18 OBD column (5 μm, 19×50 mm) and the solvent system: $H_2O$: AcCN and 2% TFA in $H_2O$. Specific elution gradients were based on retention times obtained with an analytical UPLC-MS, however, in general all elution gradients of $H_2O$ and ACN were run over a 5.9 min run time with a flow rate of 40 mL/min. An autoblend method was used to ensure a concentration of 0.1% TFA throughout each run.

Some compounds were purified using a Waters Fractionlynx system equipped with a XBridge Prep C18 OBD column (5 μm, 30×100 mm) and the solvent system: $H_2O$: AcCN and 2% TFA in $H_2O$. Specific elution gradients were based on retention times obtained with an analytical UPLC-MS, however, in general all elution gradients of $H_2O$ and ACN were run over a 9 min run time with a flow rate of 60 mL/min. An autoblend method was used to ensure a concentration of 0.1% TFA throughout each run.

Preparative SFC-MS was run on a Waters Prep100 SFC-MS system equipped with a Viridis 2-ethylpyridine OBD column (5 μm, 30×100 mm) and the solvent system: $CO_2$: MeOH and 0.2% $NH_4OH$ in MeOH as a co-solvent. Specific elution gradients were based on retention times obtained with an analytical $UPC^2$-MS, however, in general all elution gradients of $CO_2$ and MeOH were run over a 3.6 min run time with a flow rate of 100 mL/min and a column temperature of 55° C. An autoblend method was used to ensure a concentration of 0.2% $NH_4OH$ throughout each run.

Nuclear magnetic resonance (NMR) spectra were obtained in an Agilent 300 MHz VNMR (Varian 300 MHz NMR) or a Varian 400 MHz or Bruker 400 MHz NMR. Samples were analyzed in either deuterated acetone (($CD_3)_2$ CO), chloroform ($CDCl_3$), MeOH-$d_4$ ($CD_3OD$), N,N-dimethylformamide-$d_7$ (DMF-$d_7$) or dimethyl sulfoxide-$d_6$ (DMSO-$d_6$). For ($CD_3)_2CO$ samples, the residual central resonance peak at 2.05 for $^1H$ was used for chemical shift assignment for $^1H$ NMR spectra. For $CDCl_3$ samples, the residual central resonance peak at 7.26 for $^1H$ was used for chemical shift assignment for $^1H$ NMR spectra. For $CD_3OD$ the residual central resonance peak at 3.31 for $^1H$ was used for chemical shift assignment and for DMF-$d_7$ the residual central resonance peaks at 2.92 or 2.75 for $^1H$ were used for chemical shift assignment. For DMSO-$d_6$ the residual central resonance peak at 2.50 ppm for $^1H$ was used for chemical shift assignment. The format of the $^1H$ NMR data below is: chemical shift in ppm downfield the tetramethylsilane reference (multiplicity, coupling constant J in Hz, integration), using conventional abbreviations for designation of major peaks: e.g. s, singlet; d, doublet; t, triplet; q, quartet; p, pentet; m, multiplet; br, broad.

Chemical names were generated using ChemDraw Ultra 12.0 (CambridgeSoft Corp., Cambridge, Mass.), ChemDraw Professional 15.1 (CambridgeSoft Corp., Cambridge, Mass.) or ChemAxon.

Intermediate 1. 6-Methyl-4-((1-methylcyclopropyl) amino)furo[2,3-d]pyrimidine-5-carboxylic acid

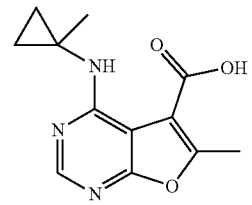 [SMILES: Cc1oc2ncnc(NC3(C)CC3)c2c1C(=O)O]

Step 1. Ethyl 5-amino-4-cyano-2-methylfuran-3-carboxylate. Sodium ethoxide (2.49 L, 21% w/w, 6.68 mol) was diluted with ethyl alcohol (3.00 L). The jacket temperature was set to −10° C. Separately, a solution of ethyl 2-chloro-3-oxobutanoate (840 mL, 6.08 mol) and malononitrile (401 g, 6.08 mol) were taken up in ethanol (2.00 L). The substrate solution was added, maintaining the internal temperature below 10° C. Upon complete addition, the jacket temperature was adjusted to 10° C. and the slurry was stirred overnight. A total of 2.90 L of solvent was removed by vacuum distillation. The temperature was then ramped to 45° C. and water (10 L) was charged to the reactor. The slurry was stirred overnight and cooled to 11° C. The solid was collected by vacuum filtration and then slurried/washed with additional water (10 L). The solid was air dried to afford the title product (1.058 kg, 90%). $^1H$ NMR (400 MHz, DMSO-$d_6$) δ 7.42 (s, 2H), 4.21 (q, J=7.1 Hz, 2H), 2.37 (s, 3H), 1.26 (t, J=7.2 Hz, 3H). [M+H]=195.

Step 2. Ethyl 4-hydroxy-6-methylfuro[2,3-d]pyrimidine-5-carboxylate. Formic acid (700 mL) was charged to a 5 L reactor, and then ethyl 5-amino-4-cyano-2-methylfuran-3-carboxylate (292 g, 1.50 mol) was added as a solid followed by additional formic acid (1.46 L). This mixture was cooled to 0° C. and acetic anhydride (1,752 mL, 6.0 V) was added drop-wise maintaining the internal temperature below 10° C. (addition was over 2 h). The reaction was warmed gradually until the jacket temperature reached 100° C. (internal temperature observed to be 97.5° C.). The reaction was held at this temperature overnight. After 48 h, the jacket temperature was cooled to 65° C. and 2.3 L of solvent was removed by vacuum distillation. The reactor was cooled and when the internal temperature was approximately 60° C., water (2.92 L) was added over 15 min and the reaction was stirred at this temperature for 2 h until solids become uniform. The slurry was then cooled to 10° C. and held overnight. The solids were collected by filtration and washed with water (5.84 L).

After an additional rinse with water (1.80 L), the solid cake was packed down then rinsed with heptane (300 mL). The solid cake was dried on the funnel for 5 h and then dried in the vacuum oven to provide the title compound as an off-white solid (285 g, 85%).

$^1$H NMR (400 MHz, CDCl$_3$) δ 8.19 (s, 1H), 4.42 (q, J=8.0 Hz, 2H), 2.71 (s, 3H), 1.43 (t, J=8.0 Hz, 3H). [M+H]=223.

Step 3. Ethyl 4-chloro-6-methylfuro[2,3-d]pyrimidine-5-carboxylate. In a 5 L vertical reactor was added ethyl 4-hydroxy-6-methylfuro[2,3-d]pyrimidine-5-carboxylate (252 g, 1.13 mol) and ACN (2.52 L). At room temperature, phosphorus oxychloride (212 mL, 2.27 mol) was added. The internal reaction temperature was brought to 0° C., then DIEA (198 mL, 1.13 mol) was added slowly. Upon complete addition, the jacket temperature was raised to 85° C. and the reaction was allowed to stir at that temperature. After 4 h, the reaction was judged complete by UPLC analysis. A portion of the ACN solvent (1.10 L) was removed by vacuum distillation. The internal reaction temperature was cooled to 0° C., cold water (2.52 L) was charged into the reactor and the mixture was stirred at 0° C. overnight. The slurry was filtered and rinsed with cold water (5.04 L) to give a tan solid. This material was dried overnight to afford the title compound (216 g, 79%). $^1$H NMR (400 MHz, CDCl$_3$) δ 8.80 (s, 1H), 4.43 (q, J=8.0 Hz, 2H), 2.80 (s, 3H), 1.45 (t, J=8.0 Hz, 3H). [M+H]=241.

Step 4. Ethyl 6-methyl-4-((1-methylcyclopropyl)amino)furo[2,3-d]pyrimidine-5-carboxylate. 1-Methylcyclopropanamine hydrochloride (124 g, 1.09 mol) was taken up in IPA (800 mL). Ethyl 4-chloro-6-methylfuro[2,3-d]pyrimidine-5-carboxylate (203 g, 0.84 mol) was added, followed by additional IPA (800 mL). TEA (352 mL, 2.53 mol) was added slowly at ambient temperature. The reaction was warmed to 45° C. and stirred overnight. Once the reaction was judged to be complete, water (2.40 L) was added over 30 minutes, the temperature was lowered to 10° C. and the reaction was stirred for 3 h. The solids were filtered, washed with water (2.40 L) and dried to afford the title compound (194 g, 84%). $^1$H NMR (400 MHz, CDCl$_3$) δ 8.62 (br s, 1H), 8.45 (s, 1H), 4.41 (q, J=7.1 Hz, 2H), 2.71 (s, 3H), 1.56 (s, 3H), 1.44 (t, J=7.1 Hz, 3H), 0.91-0.71 (m, 4H). [M+H]=276.

Step 5. 6-Methyl-4-((1-methylcyclopropyl)amino)furo[2,3-d]pyrimidine-5-carboxylic acid. Ethyl 6-methyl-4-((1-methylcyclopropyl)amino)furo[2,3-d]pyrimidine-5-carboxylate (128 g, 0.46 mol) was dissolved in THF (1.24 L) and lithium hydroxide (1.5 M, 1.24 L, 1.86 mol) was added slowly, followed by methanol (256 mL). The reaction was stirred at ambient temperature for 1.5 h. Upon reaction completion, a mixture of methanol/THF (~1.4 L) was removed by vacuum distillation. The reactor temperature was returned to 20° C. and water (1.92 L) was charged into the system. An addition funnel containing hydrochloric acid (12.1 M, 154 mL, 1.86 mol) was equipped to the reactor. The acid was added dropwise until reaching pH<4 during which time a white precipitate began to form. The slurry was stirred at ambient temperature for 1 h after the addition and then vacuum filtered. This solid was rinsed with water (1.92 L) and dried on the filter for an additional 2 h. The solid was then slurried in water (3.5 L) at 70° C. The solution was filtered and rinsed with ACN (4×1 L) and then pressed/packed and allowed to dry to provide the title compound (104 g, 90%) as a white solid. $^1$H NMR (400 MHz, DMSO-d$_6$) δ 13.87 (br s, 1H), 8.33 (s, 1H), 2.68 (s, 3H), 1.46 (s, 3H), 0.73 (s, 4H). [M+H]=248.

Intermediate 2. 4-Chloro-6-methylfuro[2,3-d]pyrimidine-5-carboxylic acid

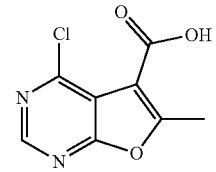

Aqueous lithium hydroxide (25 mL, 1.00 M, 25 mmol) was added to a solution of ethyl 4-chloro-6-methylfuro[2,3-d]pyrimidine-5-carboxylate (1.00 g, 4.16 mmol) in tetrahydrofuran (14 mL) and the mixture was stirred for 1 h. The mixture was acidified to pH 1 with concentrated hydrochloric acid (3 mL) and extracted twice with ethyl acetate. The combined organic extracts were washed with brine, dried (MgSO$_4$) and concentrated to provide the product as a yellow solid, which was used without further purification. $^1$H NMR (400 MHz, DMSO-d$_6$) δ 13.52 (br s, 1H), 8.81 (s, 1H), 2.70-2.77 (m, 3H). [M+H]=213.1.

Intermediate 3. 4-Fluoro-5,6,7,8-tetrahydropyrido[3,4-d]pyrimidine hydrochloride

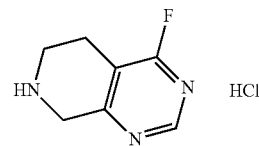 [SMILES: Fc1ncnc2c1CCNC2 ; Cl]

Step 1. tert-Butyl 4-fluoro-5,8-dihydropyrido[3,4-d]pyrimidine-7(6H)-carboxylate. A mixture of tert-butyl 4-chloro-5,6-dihydropyrido[3,4-d]pyrimidine-7(8H)-carboxylate (200 mg, 0.74 mmol) and cesium fluoride (169 mg, 1.11 mmol) in DMSO (3.7 mL) was heated at 70° C. for 3 h. The reaction mixture was diluted with methanol and was purified by preparative HPLC (elution with 10-60% ACN in water containing 0.05% TFA). Fractions containing product were combined, diluted with an aqueous solution of NaHCO$_3$ and extracted with ethyl acetate. Combined organics were dried over MgSO$_4$ and concentrated to afford the title compound (67 mg, 37%) as a yellow semi-solid. [M+H]=254.1.

Step 2. 4-Fluoro-5,6,7,8-tetrahydropyrido[3,4-d]pyrimidine hydrochloride. tert-Butyl 4-fluoro-5,8-dihydropyrido[3,4-d]pyrimidine-7(6H)-carboxylate (67 mg, 0.24 mmol) was dissolved in a solution of hydrogen chloride in dioxane (4 M, 0.62 mL, 2.5 mmol). The mixture was stirred for 30 min and then concentrated under vacuum to afford the title compound (46 mg, 100%) as a yellow solid.

Intermediate 4. 3-Fluoro-5-(1,2,3,6-tetrahydropyridin-4-yl)pyridine-2-carbonitrile

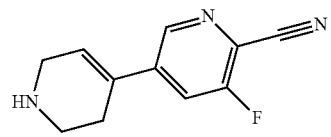 [SMILES: N#Cc1ncc(C2=CCNCC2)cc1F]

tert-Butyl 4-(4,4,5,5-tetramethyl-1,3,2-dioxaborolan-2-yl)-5,6-dihydropyridine-1(2H)-carboxylate (1.02 g, 3.30 mmol) and 5-bromo-3-fluoropyridine-2-carbonitrile (0.60 g, 3.0 mmol) were combined and dissolved in dioxane (7 mL) and ethanol (3 mL) and nitrogen gas was bubbled through the mixture. Water (2 mL), aqueous potassium carbonate (2.0 M, 4.5 mL, 9.0 mmol) and tetrakis(triphenylphosphine)palladium(0) (0.17 g, 0.15 mmol) were added and the mixture was heated at 150° C. for ten minutes in a microwave reactor. Much of the tert-butoxycarbonyl protecting group was also cleaved at this temperature. The mixture was poured into ethyl acetate (30 mL), the aqueous layer was removed and the organic layer was washed with brine (20 mL). The solution was then dried (MgSO$_4$) and concentrated under vacuum to afford a mixture of the title compound and the tert-butoxycarbonyl-protected title compound (0.36 g). [M+H]=204.1.

Intermediate 5. 5-Fluoro-6-methoxy-1',2',3',6'-tetrahydro-3,4'-bipyridine trifluoroacetate

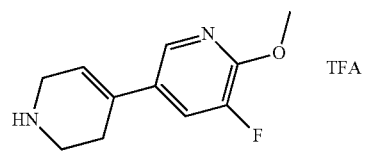

Step 1. tert-Butyl 4-(5-fluoro-6-methoxypyridin-3-yl)-1,2,3,6-tetrahydropyridine-1-carboxylate. tert-Butyl 4-(4,4,5,5-tetramethyl-1,3,2-dioxaborolan-2-yl)-5,6-dihydropyridine-1(2H)-carboxylate (1.02 g, 3.30 mmol) and 5-bromo-3-fluoro-2-methoxypyridine (0.62 g, 3.00 mmol) were combined and dissolved in dioxane (7 mL) and ethanol (3 mL) and nitrogen gas was bubbled through the mixture. Water (2 mL), aqueous potassium carbonate (2.0 M, 4.5 mL, 9.00 mmol) and tetrakis(triphenylphosphine)palladium(0) (0.17 g, 0.15 mmol) were added and the mixture was heated at 150° C. for 10 min by microwave. The mixture was poured into ethyl acetate (30 mL), the aqueous layer was removed and the organic layer was washed with brine (20 mL), dried (MgSO$_4$) and concentrated under vacuum. The residue was purified by flash chromatography (elution with 5-30% ethyl acetate in heptane) to afford the title compound (0.28 g, 30%) as a colorless oil. $^1$H NMR (400 MHz, CDCl$_3$) δ 7.96 (d, J=2.0 Hz, 1H), 7.38 (dd, J=2.0, 11.4 Hz, 1H), 6.00 (br s, 1H), 4.10 (d, J=2.8 Hz, 2H), 4.05 (s, 3H), 3.66 (t, J=5.7 Hz, 2H), 2.49 (br s, 2H), 1.51 (s, 10H). [M+H]=309.0.

Step 2. 5-Fluoro-6-methoxy-1',2',3',6'-tetrahydro-3,4'-bipyridine trifluoroacetate. tert-Butyl 4-(5-fluoro-6-methoxypyridin-3-yl)-1,2,3,6-tetrahydropyridine-1-carboxylate (280 mg, 0.91 mmol) was stirred in a mixture of DCM (3 mL) and TFA (3 mL) for 1 h and then concentrated under vacuum to afford the title compound (574 mg, 100%) as a yellow oil. $^1$H NMR (400 MHz, DMSO-d$_6$) δ 8.94 (br s, 2H), 8.12 (d, J=2.0 Hz, 1H), 7.91 (dd, J=2.1, 12.2 Hz, 1H), 6.27 (br s, 1H), 3.96 (s, 3H), 3.82-3.72 (m, 2H), 3.34 (d, J=5.6 Hz, 2H), 2.72-2.64 (m, 2H). [M+H]=209.1.

Intermediate 6. 2-(2,5-Dihydro-1H-pyrrol-3-yl)-5-fluoropyrimidine trifluoroacetate

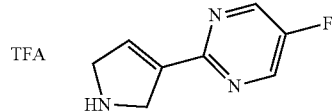 [SMILES: Fc1cnc(C2=CCNC2)nc1]

Step 1. tert-butyl 3-(5-fluoropyrimidin-2-yl)-2,5-dihydro-1H-pyrrole-1-carboxylate. The title compound was prepared in a manner analogous to Intermediate 5, Step 1 using the appropriate starting material substitutions. $^1$H NMR (400 MHz, CDCl$_3$) δ 8.59 (s, 2H), 6.96-6.75 (m, 1H), 4.59 (br s, 2H), 4.43 (br s, 2H), 1.54 (s, 9H). [M+H]=266.1.

Step 2. 2-(2,5-Dihydro-1H-pyrrol-3-yl)-5-fluoropyrimidine trifluoroacetate. The title compound was prepared in a manner analogous to Intermediate 5, Step 2 using the appropriate starting material substitutions. [M+H] was not observed.

Intermediate 7. 2-(1,2,3,6-Tetrahydropyridin-4-yl)pyrimidine-4-carbonitrile trifluoroacetate

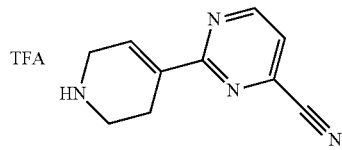 [SMILES: N#Cc1ccnc(C2=CCNCC2)n1]

Step 1. tert-Butyl 4-(4-cyanopyrimidin-2-yl)-5,6-dihydropyridine-1(2H)-carboxylate. The title compound was prepared in a manner analogous to Intermediate 5, Step 1 using the appropriate starting material substitutions. $^1$H NMR (400 MHz, CDCl$_3$) δ 8.91 (d, J=4.8 Hz, 1H), 7.44 (d, J=4.8 Hz, 1H), 7.37 (br s, 1H), 4.23 (d, J=2.6 Hz, 2H), 3.66 (t, J=5.6 Hz, 2H), 2.72 (br s, 2H), 1.52 (s, 9H). [M+H-t-Bu]=231.1.

Step 2. 2-(1,2,3,6-Tetrahydropyridin-4-yl)pyrimidine-4-carbonitrile trifluoroacetate. The title compound was prepared in a manner analogous to Intermediate 5, Step 2 using the appropriate starting material substitutions. $^1$H NMR (400 MHz, CD$_3$OD) δ 9.09-8.97 (m, 1H), 8.38-8.35 (m, 1H), 7.94 (dd, J=5.0, 13.0 Hz, 1H), 7.50-7.34 (m, 1H), 4.06-3.96 (m, 3H), 3.79-3.57 (m, 1H), 3.14-2.95 (m, 2H). [M+H]=187.1.

Intermediate 8. (R)-4-(3-Fluoropyrrolidin-1-yl)-5,6,7,8-tetrahydropyrido[3,4-d]pyrimidine hydrochloride

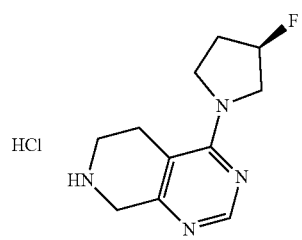 [SMILES: Cl ; F[C@@H]1CCN(c2ncnc3c2CCNC3)C1]

Step 1. (R)-tert-Butyl 4-(3-fluoropyrrolidin-1-yl)-5,6-dihydropyrido[3,4-d]pyrimidine-7(8H)-carboxylate. tert-Butyl 4-chloro-5,6-dihydropyrido[3,4-d]pyrimidine-7(8H)-carboxylate (226 mg, 0.84 mmol) in DMA (2.5 mL) was treated with (3R)-3-fluoropyrrolidine (1.58 g, 1.26 mmol) and DIEA (0.44 mL, 2.51 mmol) and the mixture was heated at 80° C. for 16 h. The mixture was cooled, concentrated under vacuum and the residue was purified by flash LC (elution with 0-75% A in B, where A is 10% methanol in ethyl acetate and B is heptane) to afford the title compound (212 mg, 78%) as a colorless semi-solid. [M+H]=323.1.

Step 2. (R)-4-(3-Fluoropyrrolidin-1-yl)-5,6,7,8-tetrahydropyrido[3,4-d]pyrimidine hydrochloride. (R)-tert-Butyl 4-(3-fluoropyrrolidin-1-yl)-5,6-dihydropyrido[3,4-d]pyrimidine-7(8H)-carboxylate (212 mg, 0.66 mmol) was dissolved in ethyl acetate (6 mL) and treated with hydrogen chloride in dioxane (4 M, 1.97 mL, 7.89 mmol). The mixture was stirred for 24 h and was then concentrated under vacuum to afford the title compound (192 mg, 99%) as a white solid. $^1$H NMR (400 MHz, CD$_3$OD) δ 8.65 (s, 1H), 5.58-5.33 (m, 1H), 4.47 (s, 2H), 4.40-4.04 (m, 4H), 3.76-3.69 (m, 1H), 3.56-3.35 (m, 3H), 2.54-2.12 (m, 2H). [M+H]= 223.1.

Intermediate 9. (S)-4-(3-Fluoropyrrolidin-1-yl)-5,6,7,8-tetrahydropyrido[3,4-d]pyrimidine hydrochloride

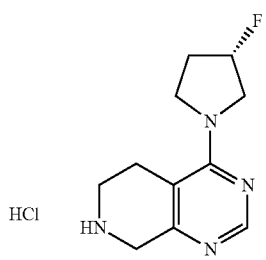 [SMILES: Cl ; F[C@H]1CCN(c2ncnc3c2CCNC3)C1]

Step 1. (S)-tert-Butyl 4-(3-fluoropyrrolidin-1-yl)-5,6-dihydropyrido[3,4-d]pyrimidine-7(8H)-carboxylate. The title compound was prepared in a manner analogous to Intermediate 8, Step 1 using the appropriate starting material substitutions. LCMS data was identical to that of Intermediate 8.

Step 2. (S)-4-(3-Fluoropyrrolidin-1-yl)-5,6,7,8-tetrahydropyrido[3,4-d]pyrimidine hydrochloride. The title compound was prepared in a manner analogous to Intermediate 8, Step 2 using the appropriate starting material substitutions. LCMS and $^1$H NMR data were identical to that of Intermediate 8.

Intermediate 10. 4-(5,6,7,8-Tetrahydropyrido[3,4-d]pyrimidin-4-yl)morpholine

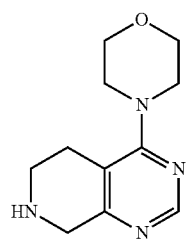 [SMILES: c1nc2c(c(N3CCOCC3)n1)CCNC2]

Step 1. tert-Butyl 4-morpholino-5,6-dihydropyrido[3,4-d]pyrimidine-7(8H)-carboxylate. The title compound was prepared in a manner analogous to Intermediate 8, Step 1 using the appropriate starting material substitutions. [M+H]= 321.1.

Step 2. 4-(5,6,7,8-Tetrahydropyrido[3,4-d]pyrimidin-4-yl)morpholine. The title compound was prepared in a manner analogous to Intermediate 8, Step 2 using the appropriate starting material substitutions. $^1$H NMR (400 MHz, CD$_3$OD) δ 8.69 (s, 1H), 4.50 (s, 2H), 4.13-4.01 (m, 4H), 3.89-3.80 (m, 4H), 3.52 (t, J=5.7 Hz, 2H), 3.15 (t, J=5.7 Hz, 2H). [M+H]=221.1.

Intermediate 11. 4-(3-Fluoroazetidin-1-yl)-5,6,7,8-tetrahydropyrido[3,4-d]pyrimidine

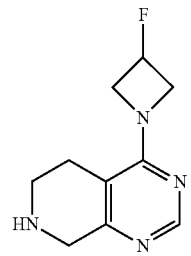

Step 1. tert-Butyl 4-(3-fluoroazetidin-1-yl)-5,6-dihydropyrido[3,4-d]pyrimidine-7(8H)-carboxylate. The title compound was prepared in a manner analogous to Intermediate 8, Step 1 using the appropriate starting material substitutions. [M+H]=309.0.

Step 2. 4-(3-Fluoroazetidin-1-yl)-5,6,7,8-tetrahydropyrido[3,4-d]pyrimidine. The title compound was prepared in a manner analogous to Intermediate 8, Step 2 using the appropriate starting material substitutions. $^1$H NMR (400 MHz, CD$_3$OD) δ 8.64 (s, 1H), 5.66-5.41 (m, 1H), 4.99 (br s, 2H), 4.73 (br s, 2H), 4.43 (s, 2H), 3.57 (t, J=6.2 Hz, 2H), 3.17 (t, J=6.1 Hz, 2H). [M+H]=209.1.

Intermediate 12. 2-Fluoro-4-(pyrrolidin-3-yl)pyridine hydrochloride

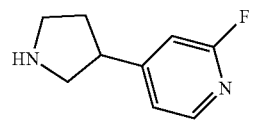 [SMILES: Fc1cc(C2CCNC2)ccn1]

Step 1. tert-Butyl 3-(2-fluoropyridin-4-yl)-2,5-dihydro-1H-pyrrole-1-carboxylate. tert-Butyl 3-(4,4,5,5-tetramethyl-1,3,2-dioxaborolan-2-yl)-2,5-dihydro-1H-pyrrole-1-carboxylate (434 mg, 1.47 mmol), 4-bromo-2-fluoropyridine (311 mg, 1.76 mmol), [1,1'-bis(diphenylphosphino)ferrocene]dichloropalladium(II) (54 mg, 0.07 mmol) and dioxane (23 mL) were combined. Aqueous sodium bicarbonate (1.2 M, 7.7 ml, 8.8 mmol) was added and the mixture was heated at 100° C. for 24 h. The mixture was cooled and diluted with ethyl acetate (75 mL) and brine (25 mL) and the layers were separated. The organic layer was dried (Na$_2$SO$_4$) and concentrated. The residue was purified by flash chromatography (elution with 0-75% ethyl acetate in heptane) to afford the title compound (341 mg, 88%) as an off-white solid. $^1$H NMR (400 MHz, CDCl$_3$) δ 8.41 (d, J=5.3 Hz, 1H), 8.22 (d, J=5.0 Hz, 1H), 7.23-7.13 (m, 1H), 6.86 (br s, 1H), 6.53-6.40 (m, 1H), 4.50 (dd, J=3.6, 19.3 Hz, 2H), 4.38 (d, J=18.5 Hz, 2H), 1.55-1.52 (m, 9H). [M+H]=265.1.

Step 2. 2-Fluoro-4-(pyrrolidin-3-yl)pyridine hydrochloride. A solution of tert-Butyl 3-(2-fluoropyridin-4-yl)-2,5-dihydro-1H-pyrrole-1-carboxylate (251 mg, 0.95 mmol) in methanol (7.5 mL) and ethyl acetate (7.5 mL) was flushed with nitrogen and palladium on activated carbon (81 mg, 0.38 mmol) was added. The mixture was stirred rapidly under a balloon of hydrogen for 3 h. The mixture was flushed with nitrogen, filtered through a pad of Celite® and concentrated under vacuum. The residue was suspended in ethyl acetate (5 mL) and a solution of hydrochloric acid in dioxane (4 M, 5.0 mL, 5.0 mmol) was added. The mixture was stirred for 1 h and concentrated under vacuum. The residue was taken up in a 1:1 mixture of dioxane-water and lyophilized to afford the title compound (294 mg, 90%) as a brown semi-solid. $^1$H NMR (400 MHz, CD$_3$OD) δ 8.21 (d, J=5.3 Hz, 1H), 7.37-7.30 (m, 1H), 7.13 (s, 1H), 3.91-3.54 (m, 5H), 3.54-3.39 (m, 2H), 2.24-2.10 (m, 1H). [M+H]=167.2.

Intermediate 13.
2-Fluoro-4-methyl-6-(pyrrolidin-3-yl)pyridine hydrochloride

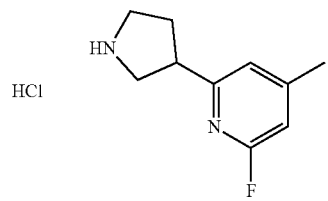

Step 1. tert-Butyl 4-(6-fluoro-4-methylpyridin-2-yl)-2,5-dihydro-1H-pyrrole-1-carboxylate. The title compound was prepared in a manner analogous to Intermediate 12, Step 1 using the appropriate starting material substitutions. $^1$H NMR (400 MHz, CDCl$_3$) δ 7.11-6.84 (m, 1H), 6.67 (s, 1H), 6.65-6.51 (m, 1H), 4.53 (br s, 2H), 4.42-4.29 (m, 2H), 2.42 (d, J=4.9 Hz, 3H), 1.56-1.51 (m, 9H). [M+H] was not observed.

Step 2. 2-Fluoro-4-methyl-6-(pyrrolidin-3-yl)pyridine hydrochloride. The title compound was prepared in a manner analogous to Intermediate 12, Step 2 using the appropriate starting material substitutions. $^1$H NMR (400 MHz, CD$_3$OD) δ 7.16 (s, 1H), 6.82 (s, 1H), 3.81-3.48 (m, 4H), 3.48-3.36 (m, 1H), 2.56-2.38 (m, 4H), 2.26-2.11 (m, 1H). [M+H]=181.1.

Intermediate 14.
3-Fluoro-2-methyl-6-(pyrrolidin-3-yl)pyridine hydrochloride

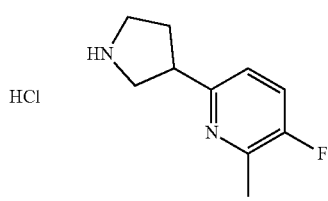

Step 1. tert-Butyl 4-(5-fluoro-6-methylpyridin-2-yl)-2,5-dihydro-1H-pyrrole-1-carboxylate. The title compound was prepared in a manner analogous to Intermediate 12, Step 1 using the appropriate starting material substitutions. [M+H-tert-butyl]=223.1.

Step 2. 3-Fluoro-2-methyl-6-(pyrrolidin-3-yl)pyridine hydrochloride. The title compound was prepared in a manner analogous to Intermediate 12, Step 2 using the appropriate starting material substitutions. $^1$H NMR (400 MHz, CD$_3$OD) δ 8.09 (t, J=8.7 Hz, 1H), 7.78 (dd, J=4.0, 8.8 Hz, 1H), 3.97 (quin, J=8.2 Hz, 1H), 3.81 (dd, J=8.3, 11.8 Hz, 1H), 3.73-3.54 (m, 2H), 3.48 (td, J=8.1, 11.5 Hz, 1H), 2.71 (d, J=2.6 Hz, 3H), 2.68-2.54 (m, 1H), 2.31 (qd, J=8.7, 13.2 Hz, 1H). [M+H]=181.1.

Intermediate 15.
5-Fluoro-4-methyl-2-(pyrrolidin-3-yl)pyrimidine hydrochloride

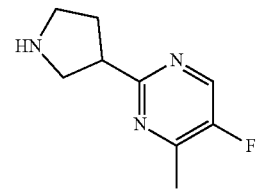

Step 1. tert-Butyl 4-(5-fluoro-4-methylpyrimidin-2-yl)-2,5-dihydro-1H-pyrrole-1-carboxylate. The title compound was prepared in a manner analogous to Intermediate 12, Step 1 using the appropriate starting material substitutions. $^1$H NMR (400 MHz, CDCl$_3$) δ 8.41 (s, 1H), 6.91-6.74 (m, 1H), 4.67-4.47 (m, 2H), 4.47-4.30 (m, 2H), 2.60-2.48 (m, 3H), 1.59-1.47 (m, 9H). [M+H-tert-butyl]=224.1.

Step 2. 3-Fluoro-2-methyl-6-(pyrrolidin-3-yl)pyridine hydrochloride. The title compound was prepared in a manner analogous to Intermediate 12, Step 2 using the appropriate starting material substitutions. $^1$H NMR (400 MHz, CD$_3$OD) δ 8.60 (d, J=1.8 Hz, 1H), 3.97-3.84 (m, 1H), 3.80-3.74 (m, 1H), 3.72-3.64 (m, 1H), 3.54-3.41 (m, 2H), 2.61-2.47 (m, 4H), 2.33 (qd, J=6.7, 13.8 Hz, 1H). [M+H]=182.1.

Intermediate 16.
2-(Pyrrolidin-3-yl)-6-(trifluoromethyl)pyridine hydrochloride

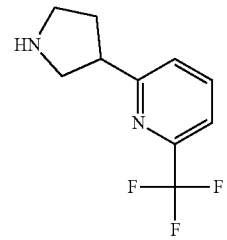

Step 1. tert-Butyl 4-(6-(trifluoromethyl)pyridin-2-yl)-2,5-dihydro-1H-pyrrole-1-carboxylate. The title compound was prepared in a manner analogous to Intermediate 12, Step 1 using the appropriate starting material substitutions. $^1$H NMR (400 MHz, CDCl$_3$) δ 7.86 (t, J=7.9 Hz, 1H), 7.63-7.40

(m, 2H), 6.68 (d, J=18.0 Hz, 1H), 4.61 (d, J=15.3 Hz, 2H), 4.51-4.29 (m, 2H), 1.54 (d, J=7.1 Hz, 9H). [M+H-tert-butyl]= 259.1.

Step 2. 2-(Pyrrolidin-3-yl)-6-(trifluoromethyl)pyridine hydrochloride. The title compound was prepared in a manner analogous to Intermediate 12, Step 2 using the appropriate starting material substitutions. $^1$H NMR (400 MHz, CD$_3$OD) δ 8.05 (t, J=7.9 Hz, 1H), 7.75 (d, J=7.7 Hz, 1H), 7.68 (d, J=7.8 Hz, 1H), 3.91 (quin, J=7.7 Hz, 1H), 3.80-3.63 (m, 2H), 3.63-3.53 (m, 1H), 3.46 (td, J=7.8, 11.5 Hz, 1H), 2.62-2.47 (m, 1H), 2.32-2.18 (m, 1H). [M+H]=217.2.

Intermediate 17.
2-(Pyrrolidin-3-yl)-4-(trifluoromethyl)pyridine hydrochloride

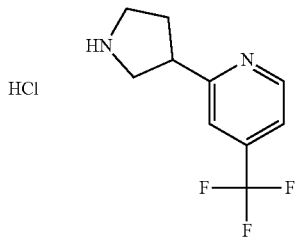 [SMILES: Cl ; FC(F)(F)c1ccnc(C2CCNC2)c1]

Step 1. tert-Butyl 4-(4-(trifluoromethyl)pyridin-2-yl)-2,5-dihydro-1H-pyrrole-1-carboxylate. The title compound was prepared in a manner analogous to Intermediate 12, Step 1 using the appropriate starting material substitutions. $^1$H NMR (400 MHz, CDCl$_3$) δ 8.78 (d, J=5.0 Hz, 1H), 7.69-7.48 (m, 1H), 7.48-7.38 (m, 1H), 6.66 (br s, 1H), 4.68-4.56 (m, 2H), 4.49-4.34 (m, 2H), 1.56-1.52 (m, 9H), 1.56-1.52 (m, 9H). [M+H-tert-butyl]=259.3.

Step 2. 2-(Pyrrolidin-3-yl)-4-(trifluoromethyl)pyridine hydrochloride. The title compound was prepared in a manner analogous to Intermediate 12, Step 2 using the appropriate starting material substitutions. $^1$H NMR (400 MHz, CD$_3$OD) δ 8.86 (d, J=5.3 Hz, 1H), 7.83 (s, 1H), 7.71 (d, J=5.1 Hz, 1H), 3.97 (quin, J=7.2 Hz, 1H), 3.72-3.66 (m, 2H), 3.64-3.53 (m, 1H), 3.47 (td, J=7.6, 11.6 Hz, 1H), 2.58 (dtd, J=6.1, 7.6, 13.4 Hz, 1H), 2.31-2.19 (m, 1H). [M+H]=217.2.

Intermediate 18. 4-Ethyl-5,6,7,8-tetrahydropyrido[3,4-d]pyrimidine hydrochloride

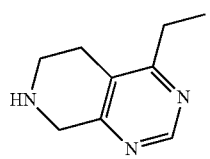

Step 1. tert-Butyl 4-vinyl-5,6-dihydropyrido[3,4-d]pyrimidine-7(8H)-carboxylate. A mixture of tert-butyl 4-chloro-5,6-dihydropyrido[3,4-d]pyrimidine-7(8H)-carboxylate (500 mg, 1.85 mmol), potassium vinyltrifluoroborate (372 mg, 2.78 mmol), [1,1'-bis(diphenylphosphino)ferrocene]dichloropalladium(II)complex with dichloromethane (76 mg, 0.09 mmol), ACN (7.4 mL), and aqueous sodium bicarbonate (1 M, 3.3 mL, 3.3 mmol) was degassed for 1 min with nitrogen and then heated to 90° C. for 2 h. The mixture was filtered through Celite®, diluted with ethyl acetate, washed with brine, dried (MgSO$_4$) and concentrated to a red oil. This material was adsorbed onto silica using DCM and flash chromatography (elution with 0-25% ethyl acetate in heptane) afforded the title compound (300 mg, 62%) as an oil. $^1$H NMR (400 MHz, CDCl$_3$) δ 8.97 (s, 1H), 6.91 (dd, J=10.64, 16.87 Hz, 1H), 6.68 (dd, J=1.83, 16.99 Hz, 1H), 5.77 (dd, J=1.83, 10.64 Hz, 1H), 4.65 (s, 2H), 3.75 (t, J=5.87 Hz, 2H), 2.89 (t, J=5.75 Hz, 2H), 1.51 (s, 9H). [M+H]=262.2.

Step 2. tert-Butyl 4-ethyl-5,6-dihydropyrido[3,4-d]pyrimidine-7(8H)-carboxylate. tert-Butyl 4-vinyl-5,6-dihydropyrido[3,4-d]pyrimidine-7(8H)-carboxylate (293 mg, 1.12 mmol) and 10% palladium on carbon (60 mg, 0.056 mol) in ethyl acetate (3.7 mL) and methanol (3.7 mL) were stirred under 180 psi of hydrogen for 16 h. The catalyst was filtered and the filtrate concentrated to afford the title compound (269 mg, 91%) as a solid. $^1$H NMR (400 MHz, CDCl$_3$) δ 8.93 (s, 1H), 4.63 (s, 2H), 3.74 (t, J=5.8 Hz, 2H), 2.86-2.72 (m, 4H), 1.51 (s, 9H), 1.31 (t, J=7.5 Hz, 3H). [M+H]=264.2.

Step 3. 4-Ethyl-5,6,7,8-tetrahydropyrido[3,4-d]pyrimidine hydrochloride. To a stirring solution of tert-butyl 4-ethyl-5,6-dihydropyrido[3,4-d]pyrimidine-7(8H)-carboxylate (269 mg, 1.0 mmol) in dioxane (5.1 mL) was added a solution of hydrogen chloride in dioxane (4 M, 1.28 mL, 5.1 mmol) and the solution was stirred for 18 h. The mixture was concentrated and the residue was taken up and concentrated twice from methanol and twice from DCM to afford the title compound (222 mg, 100%) as a solid.

Intermediate 19. 4-(Tetrahydro-2H-pyran-4-yl)-5,6,7,8-tetrahydropyrido[3,4-d]pyrimidine hydrochloride

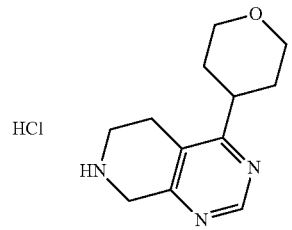 [SMILES: Cl ; c1nc2c(c(C3CCOCC3)n1)CCNC2]

Step 1. tert-Butyl 4-(3,6-dihydro-2H-pyran-4-yl)-5,6-dihydropyrido[3,4-d]pyrimidine-7(8H)-carboxylate. The title compound was prepared in a manner analogous to Intermediate 18, Step 1 using the appropriate starting material substitutions. $^1$H NMR (400 MHz, CDCl$_3$) δ 9.01 (s, 1H), 8.99 (s, 1H), 6.10 (br s, 1H), 5.96 (s, 1H), 5.66 (d, J=2.20 Hz, 1H), 4.68 (s, 3H), 4.37 (q, J=2.69 Hz, 2H), 3.96 (t, J=5.32 Hz, 2H), 3.67 (t, J=5.56 Hz, 2H), 2.92 (t, J=5.32 Hz, 2H), 2.59 (dd, J=2.57, 4.40 Hz, 2H), 1.52 (s, 13H), 1.29 (s, 2H), 1.26 (s, 1H. [M+H]=318.2.

Step 2. tert-Butyl 4-(tetrahydro-2H-pyran-4-yl)-5,6-dihydropyrido[3,4-d]pyrimidine-7(8H)-carboxylate. The title compound was prepared in a manner analogous to Intermediate 18, Step 2 using the appropriate starting material substitutions. $^1$H NMR (400 MHz, CDCl$_3$) δ 8.97 (s, 1H), 4.64 (s, 2H), 4.12 (dd, J=3.6, 11.2 Hz, 2H), 3.74 (t, J=5.9 Hz, 2H), 3.62-3.50 (m, 2H), 3.06 (tt, J=3.5, 11.6 Hz, 1H), 2.86 (t, J=5.7 Hz, 2H), 2.18-2.02 (m, 2H), 1.63 (dd, J=1.6, 13.2 Hz, 2H), 1.51 (s, 9H). [M+H-tert-butyl]=320.3.

Step 3. 4-(Tetrahydro-2H-pyran-4-yl)-5,6,7,8-tetrahydropyrido[3,4-d]pyrimidine hydrochloride. The title compound was prepared in a manner analogous to Intermediate 18, Step 3 using the appropriate starting material substitutions. ¹H NMR (400 MHz, DMSO-d₆) δ 9.86 (br s, 2H), 8.99 (s, 1H), 4.26 (t, J=4.59 Hz, 2H), 3.96 (dd, J=3.42, 11.25 Hz, 2H), 3.47-3.55 (m, 2H), 3.43 (d, J=6.97 Hz, 2H), 3.17 (tt, J=3.59, 11.51 Hz, 1H), 3.10 (t, J=6.05 Hz, 2H), 1.83 (dq, J=4.34, 12.41 Hz, 2H), 1.60 (d, J=11.25 Hz, 2H). [M+H]=220.2.

Intermediate 20. 4-(Prop-1-en-2-yl)-5,6,7,8-tetrahydropyrido[3,4-d]pyrimidine trifluoroacetate

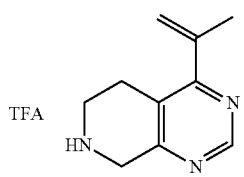

Step 1. tert-Butyl 4-(prop-1-en-2-yl)-5,6-dihydropyrido[3,4-d]pyrimidine-7(8H)-carboxylate. The title compound was prepared in a manner analogous to Intermediate 18, Step 1 using potassium trifluoro(prop-1-en-2-yl)borate and any appropriate starting material substitutions. [M+H]=276.3.

Step 2. 4-(Prop-1-en-2-yl)-5,6,7,8-tetrahydropyrido[3,4-d]pyrimidine trifluoroacetate. The title compound was prepared in a manner analogous to Intermediate 18, Step 3 using any appropriate starting material substitutions. [M+H]= 176.1.

Intermediate 21. 4-Cyclopropyl-5,6,7,8-tetrahydropyrido[3,4-d]pyrimidine trifluoroacetate

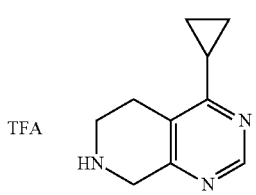 [SMILES: c1nc2c(c(C3CC3)n1)CCNC2]

Step 1. tert-Butyl 4-cyclopropyl-5,6-dihydropyrido[3,4-d]pyrimidine-7(8H)-carboxylate. The title compound was prepared in a manner analogous to Intermediate 18, Step 1 using cyclopropylboronic acid and any appropriate starting material substitutions. [M+H]=276.3.

Step 2. 4-Cyclopropyl-5,6,7,8-tetrahydropyrido[3,4-d]pyrimidine trifluoroacetate. The title compound was prepared in a manner analogous to Intermediate 18, Step 3 using any appropriate starting material substitutions. [M+H]=176.1.

Intermediate 22. 5,6,7,8-Tetrahydropyrido[3,4-d]pyrimidine-4-carbonitrile

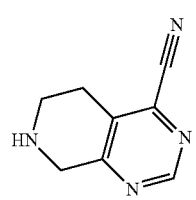 [SMILES: N#Cc1ncnc2c1CCNC2]

Step 1. tert-Butyl 4-cyano-5,6-dihydropyrido[3,4-d]pyrimidine-7(8H)-carboxylate. A mixture of tert-butyl 4-chloro-5,8-dihydropyrido[3,4-d]pyrimidine-7(6H)-carboxylate (500 mg, 1.85 mmol), DMF (10 mL), dicyanozinc (272 mg, 2.32 mmol) and tetrakis(triphenylphosphine)palladium(0) (214 mg, 0.19 mmol) was degassed by bubbling nitrogen through the mixture for 1 min then the mixture was heated at 90° C. for 2 h. The mixture was diluted with ethyl acetate, filtered through Celite®, washed with water and brine, dried (MgSO₄) and concentrated. The residue was adsorbed to silica and purified by flash chromatography (elution with 0-25% ethyl acetate in heptane) to provide the title compound (374 mg, 78%). ¹H NMR (400 MHz, CDCl₃) δ 9.14 (s, 1H), 4.74 (s, 2H), 3.81 (t, J=5.87 Hz, 2H), 3.08 (t, J=5.75 Hz, 2H), 1.52 (s, 9H).

Step 2. 5,6,7,8-Tetrahydropyrido[3,4-d]pyrimidine-4-carbonitrile. tert-Butyl 4-cyano-5,6-dihydropyrido[3,4-d]pyrimidine-7(8H)-carboxylate (20 mg, 0.08 mmol) was dissolved in DCM (0.20 mL) and TFA (0.20 mL) and the mixture was stirred for 1 h. It was diluted with DCM and washed with 1 M Na₂CO₃. The aqueous layer was extracted with 10% methanol in DCM, and the combined organics were dried (MgSO₄) and concentrated to afford the title compound (4.0 mg, 33%). ¹H NMR (400 MHz, CDCl₃) δ 9.08 (s, 1H), 4.15 (s, 2H), 3.26 (t, J=5.87 Hz, 2H), 3.04 (t, J=5.69 Hz, 2H), 2.07 (br s, 2H). [M+H]=161.3.

Intermediate 23. 4-Ethoxy-5,6,7,8-tetrahydropyrido[3,4-d]pyrimidine

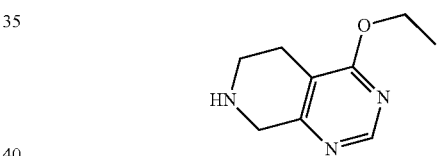

Step 1. tert-Butyl 4-ethoxy-5,6-dihydropyrido[3,4-d]pyrimidine-7(8H)-carboxylate. tert-Butyl 4-chloro-5,8-dihydropyrido[3,4-d]pyrimidine-7(6H)-carboxylate (700 mg, 2.60 mmol) was dissolved in tetrahydrofuran (7 mL). Sodium ethoxide (25% w/w, 1.12 mL, 3.9 mmol) was added and stirring was continued for 15 min. The reaction was quenched with aqueous ammonium chloride (3.5 mL) and water (20 mL) and extracted with ethyl acetate (3×20 mL). The combined organics were dried (MgSO₄), concentrated and the residue was purified by flash chromatography (elution with 0-60% ethyl acetate in heptane) to afford the title compound (729 mg, 100%) as a yellow oil. ¹H NMR (400 MHz, CDCl₃) δ 8.58 (s, 1H), 5.32 (s, 1H), 4.56 (s, 2H), 4.47 (q, J=7.05 Hz, 2H), 3.69 (t, J=5.81 Hz, 2H), 2.70 (t, J=5.38 Hz, 2H), 1.51 (s, 9H), 1.42 (s, 3H). [M+H]=280.0.

Step 2. 4-Ethoxy-5,6,7,8-tetrahydropyrido[3,4-d]pyrimidine. The title compound was prepared in a manner analogous to Intermediate 22, Step 2 using the appropriate starting material substitutions. ¹H NMR (400 MHz, CDCl₃) δ 8.54 (s, 1H), 4.46 (q, J=7.05 Hz, 2H), 3.99 (s, 2H), 3.16 (t, J=5.93 Hz, 2H), 2.64 (t, J=5.81 Hz, 2H), 1.42 (t, J=7.03 Hz, 3H). [M+H]=180.0.

Intermediate 24. 4-Propoxy-5,6,7,8-tetrahydropyrido[3,4-d]pyrimidine

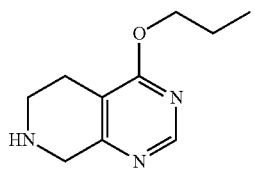

Step 1. tert-Butyl 4-propoxy-5,6-dihydropyrido[3,4-d]pyrimidine-7(8H)-carboxylate. The title compound was prepared in a manner analogous to Intermediate 23, Step 1 using the appropriate starting material substitutions. $^1$H NMR (400 MHz, CDCl$_3$) δ 8.58 (s, 1H), 5.32 (s, 1H), 4.56 (s, 2H), 4.36 (t, J=6.66 Hz, 2H), 3.70 (t, J=5.75 Hz, 2H), 2.70 (t, J=5.32 Hz, 2H), 1.78-1.87 (m, 2H), 1.61-1.66 (m, 2H), 1.51 (s, 9H), 1.04 (s, 3H). [M+H]=294.3.

Step 2. 4-Propoxy-5,6,7,8-tetrahydropyrido[3,4-d]pyrimidine. This material was prepared using the procedure described for Intermediate 23, step 2. $^1$H NMR (400 MHz, CDCl$_3$) δ 8.54 (s, 1H), 5.32-5.33 (m, 1H), 4.35 (t, J=6.60 Hz, 2H), 3.99 (s, 2H), 3.16 (t, J=5.93 Hz, 2H), 2.65 (t, J=5.81 Hz, 2H), 1.82 (sxt, J=7.12 Hz, 2H), 1.04 (t, J=7.40 Hz, 3H). [M+H]=194.2.

Intermediate 25. 4-Isobutoxy-5,6,7,8-tetrahydropyrido[3,4-d]pyrimidine

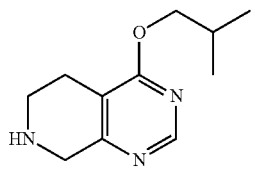

Step 1. tert-Butyl 4-isobutoxy-5,6-dihydropyrido[3,4-d]pyrimidine-7(8H)-carboxylate. The title compound was prepared in a manner analogous to Intermediate 23, Step 1 using the appropriate starting material substitutions. $^1$H NMR (400 MHz, CDCl$_3$) δ 8.58 (s, 1H), 4.57 (s, 2H), 4.17 (d, J=6.60 Hz, 2H), 3.70 (t, J=5.75 Hz, 2H), 2.72 (t, J=5.44 Hz, 2H), 2.08-2.18 (m, 1H), 1.51 (s, 9H), 1.04 (d, J=6.72 Hz, 6H). [M+H]=308.3.

Step 2. 4-Isobutoxy-5,6,7,8-tetrahydropyrido[3,4-d]pyrimidine. The title compound was prepared in a manner analogous to Intermediate 23, Step 2 using the appropriate starting material substitutions. $^1$H NMR (400 MHz, CDCl$_3$) δ 8.54 (s, 1H), 5.32 (s, 1H), 4.16 (d, J=6.60 Hz, 2H), 4.00 (s, 2H), 3.18 (t, J=5.93 Hz, 2H), 2.67 (t, J=5.81 Hz, 2H), 2.12 (dt, J=13.36, 6.71 Hz, 1H), 1.04 (d, J=6.72 Hz, 6H). [M+H]=208.2.

Intermediate 26. 4-(Cyclopropylmethoxy)-5,6,7,8-tetrahydropyrido[3,4-d]pyrimidine

Step 1. tert-Butyl 4-(cyclopropylmethoxy)-5,6-dihydropyrido[3,4-d]pyrimidine-7(8H)-carboxylate. The title compound was prepared in a manner analogous to Intermediate 23, Step 1 using the appropriate starting material substitutions. [M+H]=306.3.

Step 2. 4-(Cyclopropylmethoxy)-5,6,7,8-tetrahydropyrido[3,4-d]pyrimidine. The title compound was prepared in a manner analogous to Intermediate 23, Step 2 using the appropriate starting material substitutions. $^1$H NMR (400 MHz, CDCl$_3$) δ 8.51 (s, 1H), 4.23 (d, J=7.09 Hz, 2H), 3.97 (s, 2H), 3.12-3.18 (m, 2H), 2.61-2.69 (m, 2H), 1.24-1.34 (m, 1H), 0.57-0.65 (m, 2H), 0.37 (q, J=4.89 Hz, 2H). [M+H]=206.2.

Intermediate 27. 4-(2-Methoxyethoxy)-5,6,7,8-tetrahydropyrido[3,4-d]pyrimidine

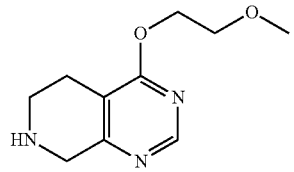

Step 1. tert-Butyl 4-(2-methoxyethoxy)-5,8-dihydropyrido[3,4-d]pyrimidine-7(6H)-carboxylate. The title compound was prepared in a manner analogous to Intermediate 23, Step 1 using the appropriate starting material substitutions. [M+H]=310.0.

Step 2. 4-(2-Methoxyethoxy)-5,6,7,8-tetrahydropyrido[3,4-d]pyrimidine. The title compound was prepared in a manner analogous to Intermediate 23, Step 2 using the appropriate starting material substitutions. $^1$H NMR (400 MHz, CDCl$_3$) δ 8.54 (s, 1H), 4.54-4.61 (m, 2H), 4.02 (s, 1H), 3.98-4.01 (m, 2H), 3.74-3.82 (m, 2H), 3.45 (s, 3H), 3.26-3.28 (m, 1H), 3.16 (t, J=5.93 Hz, 2H), 2.68 (t, J=5.81 Hz, 2H), 2.46 (s, 1H), 2.29 (s, 1H), 2.23 (s, 1H), 2.19 (s, 1H), 1.46 (s, 1H), 1.28 (s, 1H), 0.04-0.21 (m, 1H). [M+H]=210.2.

Intermediate 28. 4-Cyclobutoxy-5,6,7,8-tetrahydropyrido[3,4-d]pyrimidine

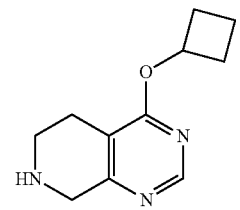 [SMILES: c1nc2c(c(OC3CCC3)n1)CCNC2]

Step 1. tert-Butyl 4-cyclobutoxy-5,8-dihydropyrido[3,4-d]pyrimidine-7(6H)-carboxylate. The title compound was prepared in a manner analogous to Intermediate 23, Step 1 using the appropriate starting material substitutions. [M+H]= 306.1.

Step 2. 4-Cyclobutoxy-5,6,7,8-tetrahydropyrido[3,4-d]pyrimidine. The title compound was prepared in a manner analogous to Intermediate 23, Step 2 using the appropriate starting material substitutions. $^1$H NMR (400 MHz, CDCl$_3$) δ 8.51 (s, 1H), 5.25-5.33 (m, 1H), 3.97 (s, 2H), 3.15 (t, J=5.87 Hz, 2H), 2.63 (t, J=5.81 Hz, 2H), 2.48 (br s, 2H), 2.10-2.21 (m, 2H), 1.80-1.94 (m, 1H), 1.75 (s, 4H). [M+H]= 206.1.

Intermediate 29. 4-Cyclopropoxy-5,6,7,8-tetrahydropyrido[3,4-d]pyrimidine

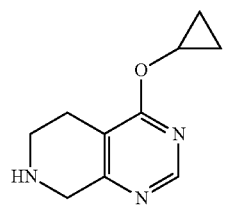 [SMILES: c1nc2c(c(OC3CC3)n1)CCNC2]

Step 1. tert-Butyl 4-cyclopropoxy-5,8-dihydropyrido[3,4-d]pyrimidine-7(6H)-carboxylate. The title compound was prepared in a manner analogous to Intermediate 23, Step 1 using the appropriate starting material substitutions. [M+H]= 292.0.

Step 2. 4-Cycloprooxy-5,6,7,8-tetrahydropyrido[3,4-d]pyrimidine. The title compound was prepared in a manner analogous to Intermediate 23, Step 2 using the appropriate starting material substitutions. $^1$H NMR (400 MHz, CDCl$_3$) δ 8.61 (s, 1H), 5.32 (s, 1H), 4.39 (tt, J=6.22, 3.13 Hz, 1H), 3.98 (s, 2H), 3.13 (t, J=5.93 Hz, 2H), 2.56 (t, J=5.75 Hz, 2H), 0.75-0.89 (m, 5H). [M+H]=192.1.

Intermediate 30. N-(2-Fluoroethyl)-2-(piperidin-4-yl)pyrimidin-4-amine hydrochloride

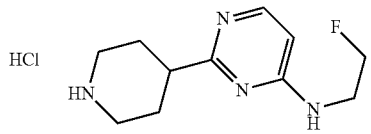 [SMILES: Cl ; FCCNc1ccnc(C2CCNCC2)n1]

Step 1. 2-Chloro-N-(2-fluoroethyl)pyrimidin-4-amine. 2-Fluoroethylamine hydrochloride (3.6 g, 36.5 mmol) and K$_2$CO$_3$ (13.8 g, 101 mmol) were added to a stirred solution of 2,4-dichloropyrimidine (5.0 g, 33.6 mmol) in ACN (250 mL) and stirring was continued for 6 h. The mixture was diluted with water (10 mL) and extracted with ethyl acetate (2×10 mL). The organic layer was evaporated under reduced pressure and the residue was purified by flash chromatography to afford the title compound (3.9 g, 66%) as a pale yellow solid. $^1$H NMR (500 MHz, DMSO-d$_6$) δ 8.24-7.88 (m, 2H), 6.52 (d, J=5.9 Hz, 1H), 4.59 (t, J=4.9 Hz, 1H), 4.49 (t, J=4.9 Hz, 1H), 3.67-3.51 (m, 2H). [M+H]=176.0.

Step 2. tert-Butyl 4-(4-(2-fluoroethylamino)pyrimidin-2-yl)-5,6-dihydropyridine-1(2H)-carboxylate. Solutions of tert-butyl 4-(4,4,5,5-tetramethyl-1,3,2-dioxaborolan-2-yl)-3,6-dihydropyridine-1(2H)-carboxylate (3.0 g, 9.7 mmol) in dioxane (15 mL) and sodium carbonate (5.42 g, 29 mmol) in water (20 mL) were combined and degassed with argon. PdCl$_2$(dppf).DCM (0.695 g, 0.85 mmol) and 2-chloro-N-(2-fluoroethyl)pyrimidin-4-amine (3.5 g, 11.6 mmol) were added and the resulting mixture was heated to 90° C. for 4 h. The reaction mixture was diluted with water (20 mL) and extracted with ethyl acetate (2×20 mL). The organic layer was concentrated under reduced pressure and the residue was purified by flash chromatography to afford the title compound (1.8 g, 58%) as an off-white solid. $^1$H NMR (400 MHz, CDCl$_3$) δ 8.18 (d, J=9.6 Hz, 1H), 7.05-6.99 (m 1H), 6.22 (d, J=9.6 Hz 1H), 5.02 (br s, 1H), 4.69-4.65 (dd, J=9.6, 4.8 Hz), 4.54-4.57 (dd, J=9.6, 4.8 Hz), 4.41 (t, J=7.2 Hz, 2H), 3.68-3.81 (m, 2H), 3.68 (br s, 2H), 2.66 (m, 2H), 1.48 (s, 9H). [M+H]=323.1.

Step 3. tert-Butyl 4-(4-(2-fluoroethylamino)pyrimidin-2-yl)piperidine-1-carboxylate. A stirred suspension of tert-butyl 4-(4-(2-fluoroethylamino)pyrimidin-2-yl)-5,6-dihydropyridine-1(2H)-carboxylate (1.8 g, 5.6 mmol) and 10% palladium on carbon (700 mg) in ethanol (20 mL) was stirred for 4 h under hydrogen. The reaction mixture was filtered through Celite® and the filtrate was concentrated under reduced pressure. The residue was purified by flash chromatography to afford the title compound (1.3 g, 72%) as a pale yellow liquid. $^1$H NMR (400 MHz, CDCl$_3$) δ 8.18 (d, J=5.9 Hz, 1H), 7.05 (s, 1H), 6.22 (d, J=5.9 Hz, 1H), 5.02 (d, J=17.6 Hz, 1H), 4.68 (t, J=4.8 Hz, 1H), 4.55 (q, J=4.4, 3.9 Hz, 1H), 4.21-4.05 (m, 2H), 3.77 (dd, J=27.1, 5.2 Hz, 2H), 3.60 (s, 2H), 2.66 (s, 2H), 1.48 (s, 9H), 1.25 (d, J=4.6 Hz, 4H). [M+H]=325.1.

Step 4. N-(2-Fluoroethyl)-2-(piperidin-4-yl)pyrimidin-4-amine hydrochloride. The title compound was prepared by treatment of tert-Butyl 4-(4-(2-fluoroethylamino)pyrimidin-2-yl)piperidine-1-carboxylate with HCl, in a manner analogous to Intermediate 12, step 2. $^1$H NMR (400 MHz, CDCl$_3$) δ 14.76 (s, 1H), 9.89 (d, J=7.5 Hz, 1H), 9.37-9.09 (m, 2H), 8.13 (d, J=7.1 Hz, 1H), 6.81 (d, J=7.0 Hz, 1H), 4.69 (t, J=4.9 Hz, 1H), 4.58 (t, J=4.9 Hz, 1H), 3.80 (dq, J=27.5, 5.2 Hz, 2H), 3.35 (d, J=12.9 Hz, 2H), 3.22 (ddt, J=11.1, 8.0, 3.9 Hz, 1H), 3.05-2.90 (m, 2H), 2.16-1.97 (m, 4H).

Intermediate 31. 2-Isopropyl-4-methoxy-5,6,7,8-tetrahydropyrido[3,4-d]pyrimidine trifluoroacetate

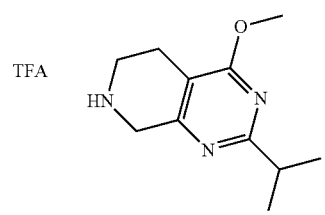

Step 1. tert-Butyl 2-isopropyl-4-oxo-3,4,5,6-tetrahydropyrido[3,4-d]pyrimidine-7(8H)-carboxylate. 2-Methylpropanimidamide hydrochloride (153 mg, 1.24 mmol) and sodium ethoxide (21% w/w, 0.62 mL, 1.66 mmol) were added to a stirred solution of 1-(tert-butyl) 4-ethyl 3-oxopiperidine-1,4-dicarboxylate (225 mg, 0.83 mmol) in ethanol (8.3 mL) and the reaction was refluxed for 20 h. The reaction was cooled to room temperature, diluted with DCM and washed with brine. The aqueous layer was extracted with DCM and the combined organics were washed with brine, dried over MgSO₄ and concentrated under vacuum. The residue was purified by column chromatography (elution with 0-100% ethyl acetate and heptane) to afford the title compound (189 mg, 78%) as a white solid. ¹H NMR (400 MHz, CD₃OD) δ 4.34 (s, 2H), 3.68-3.54 (m, 2H), 2.84 (spt, J=6.9 Hz, 1H), 2.51 (t, J=5.7 Hz, 2H), 1.49 (s, 9H), 1.28 (d, J=7.0 Hz, 6H). [M+H]=294.3.

Step 2. tert-Butyl 4-chloro-2-isopropyl-5,6-dihydropyrido[3,4-d]pyrimidine-7(8H)-carboxylate. A mixture of tert-Butyl 2-isopropyl-4-oxo-3,4,5,6-tetrahydropyrido[3,4-d]pyrimidine-7(8H)-carboxylate (180 mg, 0.61 mmol) and triphenylphosphine (320 mg, 1.23 mmol) in 1,2-dichloroethane (7.2 mL) was stirred for 15 min. Carbon tetrachloride (0.18 mL) was added and the reaction mixture was heated at 70° C. for 3 h. The solvents were removed in vacuo and the residue was purified by column chromatography (elution with 0-25% ethyl acetate and heptane) to afford the title compound (125 mg, 65%) as a colorless oil. [M+H]=312.3.

Step 3. tert-Butyl 2-isopropyl-4-methoxy-5,6-dihydropyrido[3,4-d]pyrimidine-7(8H)-carboxylate. tert-Butyl 4-chloro-2-isopropyl-5,6-dihydropyrido[3,4-d]pyrimidine-7(8H)-carboxylate (125 mg, 0.38 mmol) was dissolved in methanol (2.35 mL) and sodium methoxide (25% w/w, 0.34 mL, 1.51 mmol) was added. The mixture was heated to 70° C. for an hour, cooled and the solvent was evaporated. The residue was extracted with ethyl acetate and washed with saturated ammonium chloride. The organics were dried (MgSO₄) and the solvent was evaporated to afford the title compound (116 mg, 96%) as a colorless oil. [M+H]=308.4.

Step 4. 2-Isopropyl-4-methoxy-5,6,7,8-tetrahydropyrido[3,4-d]pyrimidine trifluoroacetate. tert-Butyl 2-isopropyl-4-methoxy-5,6-dihydropyrido[3,4-d]pyrimidine-7(8H)-carboxylate (111 mg, 0.22 mmol) was dissolved in DCM (1.3 mL) and TFA (0.67 mL) was added. The reaction mixture was stirred for one hour and concentrated under vacuum to afford the title compound (70 mg, 89%) as a yellow oil. [M+H]=208.2.

Intermediate 32. 2-Cyclopropyl-4-methoxy-5,6,7,8-tetrahydropyrido[3,4-d]pyrimidine trifluoroacetate

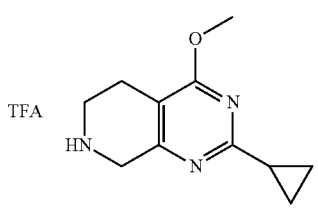

Step 1. tert-Butyl 2-cyclopropyl-4-oxo-3,4,5,6-tetrahydropyrido[3,4-d]pyrimidine-7(8H)-carboxylate. The title compound was prepared in a manner analogous to Intermediate 31, Step 1 using the appropriate starting material substitutions. ¹H NMR (400 MHz, CD₃OD) δ 4.24 (s, 2H), 3.66-3.54 (m, 2H), 2.49 (t, J=5.8 Hz, 2H), 1.90-1.80 (m, 1H), 1.48 (s, 9H), 1.16-1.01 (m, 4H). [M+H]=292.3.

Step 2. tert-Butyl 4-chloro-2-cyclopropyl-5,6-dihydropyrido[3,4-d]pyrimidine-7(8H)-carboxylate. The title compound was prepared in a manner analogous to Intermediate 31, Step 2 using the appropriate starting material substitutions. [M+H]=310.3.

Step 3. tert-Butyl 2-cyclopropyl-4-methoxy-5,6-dihydropyrido[3,4-d]pyrimidine-7(8H)-carboxylate. The title compound was prepared in a manner analogous to Intermediate 31, Step 3 using the appropriate starting material substitutions. [M+H]=306.3.

Step 4. 2-Cyclopropyl-4-methoxy-5,6,7,8-tetrahydropyrido[3,4-d]pyrimidine trifluoroacetate. The title compound was prepared in a manner analogous to Intermediate 31, Step 4 using the appropriate starting material substitutions. [M+H]=206.3.

Intermediate 33. N-((6-Methoxypyrimidin-4-yl)methyl)cyclopropanamine

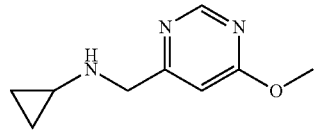

Cyclopropanamine (0.048 mL, 0.69 mmol) was added to a mixture of 4-(chloromethyl)-6-methoxypyrimidine (100 mg, 0.63 mmol) and potassium carbonate (131 mg, 0.95 mmol) in DMF (3.2 mL) and the mixture was heated at 40° C. for 15 h. The reaction was filtered and the solvent was removed under vacuum to afford a mixture of the title product and N,N-bis((6-methoxypyrimidin-4-yl)methyl)cyclopropanamine (113 mg). [M+H] was not observed.

Intermediate 34. N-((6-Methoxypyrimidin-4-yl)methyl)ethanamine

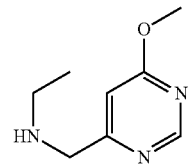

The title compound was prepared in a manner analogous to Intermediate 33, using the appropriate starting material substitutions. [M+H]=168.1.

Intermediate 35. 3-Cyclopropyl-1-ethyl-5,6,7,8-tetrahydroimidazo[1,5-a]pyrazine

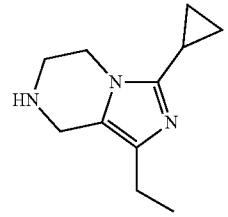

Step 1. tert-Butyl 3-Cyclopropyl-5,6-dihydroimidazo[1,5-a]pyrazine-7(8H)-carboxylate. To a stirred solution of 3-cyclopropyl-5,6,7,8-tetrahydroimidazo[1,5-a]pyrazine (7.0 g, 43 mmol) and DIEA (145 mL, 86 mmol) in 1,2-dichloroethane (70 mL) was added di-tert-butyl dicarbonate (12.2 g, 55.8 mmol) in portions. The mixture was stirred for 5 h, and then it was diluted with DCM, washed with water and brine, dried (MgSO$_4$) and concentrated to provide an oily residue. This material was purified by flash chromatography (elution with 10-100% ethyl acetate in heptane) to provide the title compound (4.13 g, 37%). $^1$H NMR (400 MHz, CDCl$_3$) δ 6.68 (s, 1H), 4.62 (s, 2H), 3.98-4.06 (m, 2H), 3.83 (t, J=5.44 Hz, 2H), 1.69-1.81 (m, 1H), 1.51 (s, 9H), 0.97-1.03 (m, 2H), 0.90-0.97 (m, 2H). [M+H]=264.3.

Step 2. tert-Butyl 3-cyclopropyl-1-iodo-5,6-dihydroimidazo[1,5-a]pyrazine-7(8H)-carboxylate. tert-Butyl 3-Cyclopropyl-5,6-dihydroimidazo[1,5-a]pyrazine-7(8H)-carboxylate (1.12 g, 4.25 mmol) and 1-iodopyrrolidine-2,5-dione (1.15 g, 5.10 mmol) were combined and diluted with ACN (11.2 mL). The mixture was stirred for 22 h and then it was diluted with ethyl acetate and washed sequentially with a 1 M aqueous solution of Na$_2$SO$_3$ and a 1 M aqueous solution of Na$_2$CO$_3$, then dried (MgSO$_4$) and concentrated. The residue was purified by flash chromatography (elution with 10-50% ethyl acetate in heptane) to afford the title compound (1.16 g, 71%) as a gum. $^1$H NMR (400 MHz, CDCl$_3$) δ 4.46 (s, 2H), 3.95-4.05 (m, 2H), 3.82 (t, J=5.32 Hz, 2H), 1.68-1.78 (m, 1H), 1.53 (s, 9H), 1.01-1.07 (m, 2H), 0.91-1.00 (m, 2H). [M+H]=390.2.

Step 3. tert-Butyl 3-cyclopropyl-1-vinyl-5,6-dihydroimidazo[1,5-a]pyrazine-7(8H)-carboxylate. A mixture of tert-butyl 3-cyclopropyl-1-iodo-5,6-dihydroimidazo[1,5-a]pyrazine-7(8H)-carboxylate (277 mg, 0.71 mmol), (R)-1-[(SP)-2-(dicyclohexylphosphino)ferrocenyl]ethyl-di-tert-butylphosphine palladium(II) dichloride (26 mg, 0.04 mmol), potassium fluoride/potassium vinyltrifluoroborate (1:1) (286 mg, 2.13 mmol), ACN (3.6 mL) and aqueous sodium bicarbonate (1 M, 1.8 mL, 1.8 mmol) were combined in a 20 mL vial and degassed with nitrogen for 1 min. The mixture was heated to 90° C. for 8 h. Some starting material persisted so additional potassium fluoride/potassium vinyltrifluoroborate (1:1) (286 mg, 2.13 mmol), palladium catalyst (26 mg, 0.04 mmol), ACN (3.6 mL) and sodium bicarbonate (1 M, 1.8 mL, 1.8 mmol) were added, the mixture was again degassed and heated at 90° C. for 16 h. The mixture was shaken with ethyl acetate and an aqueous solution of Na$_2$CO$_3$, and the resulting aqueous layer was extracted with ethyl acetate. The combined organics were dried (MgSO$_4$) and concentrated, and the residue was purified by flash chromatography (elution with 10-75% ethyl acetate in heptane) to provide the title compound (76 mg, 37%). $^1$H NMR (400 MHz, CDCl$_3$) δ 6.55 (dd, J=11.1, 17.5 Hz, 1H), 5.56 (dd, J=1.5, 17.6 Hz, 1H), 5.12 (dd, J=1.3, 11.1 Hz, 1H), 4.66 (s, 2H), 4.07-3.95 (m, 2H), 3.83 (t, J=5.3 Hz, 2H), 1.73 (tt, J=5.2, 8.2 Hz, 1H), 1.52 (s, 9H), 1.07-0.99 (m, 2H), 0.98-0.88 (m, 2H). [M+H]=290.3.

Step 4. tert-Butyl 3-cyclopropyl-1-ethyl-5,6-dihydroimidazo[1,5-a]pyrazine-7(8H)-carboxylate. A mixture of tert-Butyl 3-cyclopropyl-1-vinyl-5,6-dihydroimidazo[1,5-a]pyrazine-7(8H)-carboxylate (73 mg, 0.25 mmol), and palladium on activated carbon (27 mg, 0.03 mmol) in ethyl acetate (1.5 mL) was stirred under 180 psi of hydrogen for 16 h. The mixture was filtered through Celite® and concentrated under vacuum to provide the title compound (90 mg, 100%). $^1$H NMR (400 MHz, CDCl$_3$) δ 4.55 (s, 2H), 3.98 (t, J=6.1 Hz, 2H), 3.81 (t, J=5.4 Hz, 2H), 2.48 (q, J=7.6 Hz, 2H), 1.75-1.66 (m, 1H), 1.51 (s, 9H), 1.18 (t, J=7.6 Hz, 3H), 1.01-0.95 (m, 2H), 0.95-0.89 (m, 2H). [M+H]=292.3.

Step 5. 3-Cyclopropyl-1-ethyl-5,6,7,8-tetrahydroimidazo[1,5-a]pyrazine. tert-Butyl 3-cyclopropyl-1-ethyl-5,6-dihydroimidazo[1,5-a]pyrazine-7(8H)-carboxylate (90 mg, 0.31 mmol) was stirred in 2-methyltetrahydrofuran (0.45 mL) and TFA (0.45 mL) for 3 h. The solvent was evaporated and the residue diluted with 1 M Na$_2$CO$_3$. The solution was extracted with a 5:1 solution of DCM-methanol (3×25 mL) and the combined extracts were dried (MgSO$_4$) and concentrated to provide the title compound (54 mg, 91%) as a light yellow solid. $^1$H NMR (400 MHz, CDCl$_3$) δ 3.99 (s, 2H), 3.93 (t, J=5.6 Hz, 2H), 3.23 (t, J=5.6 Hz, 2H), 2.51-2.43 (m, 2H), 1.72 (tt, J=5.1, 8.2 Hz, 1H), 1.16 (t, J=7.6 Hz, 3H), 1.03-0.98 (m, 2H), 0.94-0.87 (m, 2H). [M+H]=192.2.

Example 1. (6-Methyl-4-((1-methylcyclopropyl)amino)furo[2,3-d]pyrimidin-5-yl)(4-phenylpiperazin-1-yl)methanone (or 6-methyl-N-(1-methylcyclopropyl)-5-(4-phenylpiperazine-1-carbonyl)furo[2,3-d]pyrimidin-4-amine)

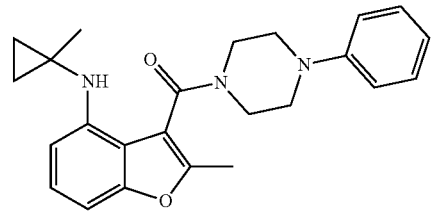 [SMILES: Cc1oc2cccc(NC3(C)CC3)c2c1C(=O)N1CCN(c2ccccc2)CC1]

Step 1. (4-Chloro-6-methylfuro[2,3-d]pyrimidin-5-yl)(4-phenylpiperazin-1-yl)methanone. 4-Chloro-6-methylfuro[2,3-d]pyrimidine-5-carboxylic acid (Intermediate 2, 500 mg, 1.65 mmol) and DIEA (0.57 ml, 3.3 mmol) were combined in DMA (8.2 mL) and treated with HATU (810 mg, 2.14 mmol) and 1-phenylpiperazine (0.26 mL, 1.73 mmol). The mixture was stirred for 1 h, diluted with water and extracted with ethyl acetate (2×50 mL). The combined organic layers were washed with brine and dried over MgSO$_4$. The solvent was evaporated and the residue was purified by column chromatography (elution with 0-80% ethyl acetate in heptane) to afford the title compound (320 mg, 54%) as a white solid. [M+H]=357.0.

Step 2. (6-Methyl-4-((1-methylcyclopropyl)amino)furo[2,3-d]pyrimidin-5-yl)(4-phenylpiperazin-1-yl)methanone. (4-Chloro-6-methylfuro[2,3-d]pyrimidin-5-yl)(4-phenylpiperazin-1-yl)methanone (25 mg, 0.07 mmol) was dissolved in DMA (0.70 mL) and was treated with DIEA (0.050 mL, 0.28 mmol) and 1-methylcyclopropanamine hydrochloride (0.01 g, 0.09 mmol). The mixture was stirred at 85° C. for 16 h and cooled. It was filtered and purified by preparative HPLC (elution with 20-80% ACN with 0.05% TFA). Fractions containing product were combined and lyophilized to afford the title compound (26 mg, 74%) as a white powder. $^1$H NMR (400 MHz, CD$_3$OD) δ 8.41 (s, 1H), 7.33-7.26 (m, 2H), 7.04 (d, J=7.8 Hz, 2H), 6.92 (t, J=7.3 Hz, 1H), 4.09-3.74 (m, 4H), 3.30-3.16 (m, 4H), 2.62-2.56 (m, 3H), 1.58-1.49 (m, 3H), 1.00-0.82 (m, 4H). [M+H]=392.3.

Example 2. (2-Cyclopropyl-7,8-dihydropyrido[4,3-d]pyrimidin-6(5H)-yl)(6-methyl-4-((1-methylcyclopropyl)amino)furo[2,3-d]pyrimidin-5-yl)methanone (or 5-{2-cyclopropyl-5H,6H,7H,8H-pyrido[4,3-d]pyrimidine-6-carbonyl}-6-methyl-N-(1-methylcyclopropyl)furo[2,3-d]pyrimidin-4-amine)

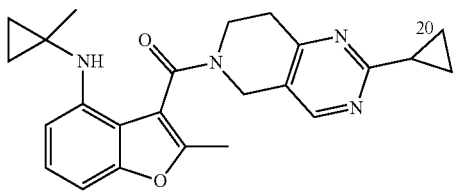 [SMILES: Cc1oc2cccc(NC3(C)CC3)c2c1C(=O)N1CCc2nc(C3CC3)ncc2C1]

DIEA (0.063 mL, 0.36 mmol) and 6-methyl-4-((1-methylcyclopropyl)amino)furo[2,3-d]pyrimidine-5-carboxylic acid (Intermediate 1, 25 mg, 0.09 mmol) were combined in DMA (0.91 ml). HATU (52 mg, 0.14 mmol) and 2-cyclopropyl-5,6,7,8-tetrahydropyrido[4,3-d]pyrimidine hydrochloride (25 mg, 0.12 mmol) were added and the mixture was stirred for 30 minutes. The mixture was filtered and purified by preparative HPLC (elution with 10-70% ACN with 0.05% TFA). Fractions containing product were combined and lyophilized to afford the title compound (33 mg, 70%) as a white powder. $^1$H NMR (400 MHz, CD$_3$OD) δ 8.57 (d, J=5.6 Hz, 1H), 8.35 (s, 1H), 8.27 (dt, J=1.6, 7.9 Hz, 1H), 7.68 (dt, J=1.1, 6.7 Hz, 1H), 7.61 (d, J=8.2 Hz, 1H), 4.65-3.49 (m, 4H), 2.57 (s, 3H), 2.43 (br s, 2H), 2.11 (t, J=3.4 Hz, 1H), 1.51 (s, 3H), 0.94-0.79 (m, 4H). [M+H]=390.3.

Example 3. N-(1-(fluoromethyl)cyclopropyl)-6-methyl-4-((1-methylcyclopropyl)amino)furo[2,3-d]pyrimidine-5-carboxamide

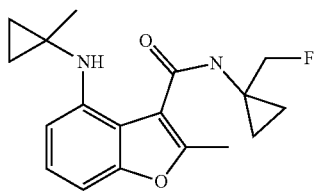 [SMILES: Cc1oc2cccc(NC3(C)CC3)c2c1C(=O)NC1(CF)CC1]

6-Methyl-4-((1-methylcyclopropyl)amino)furo[2,3-d]pyrimidine-5-carboxylic acid (Intermediate 1, 1.00 g, 4.04 mmol) and 1-(fluoromethyl)cyclopropanamine hydrochloride (0.63 g, 5.06 mmol) were taken up in DMA (5 mL). DIEA (2.12 mL, 12.1 mmol) was added, followed by 2-chloro-1-methylpyridin-1-ium iodide (1.34 g, 5.26 mmol). After 7 h of stirring, the reaction was judged to be complete and water (5 mL) was added. The reaction was stirred for 16 h during which time a solid formed. The slurry was further diluted with water (2 mL) and the solid was collected and rinsed with heptane to afford the title compound (1.09 g, 85%) as a white solid. $^1$H NMR (400 MHz, CDCl$_3$) δ 8.59 (br s, 1H), 8.46 (s, 1H), 6.39 (br s, 1H), 4.52 (d, J=48 Hz, 2H), 2.68 (s, 3H), 1.55 (s, 3H), 1.10 (s, 4H), 0.92-0.76 (m, 4H). [M+H]=319.3.

Example 4. (4-Methoxy-5,8-dihydropyrido[3,4-d]pyrimidin-7(6H)-yl)(6-methyl-4-((1-methylcyclopropyl)amino)furo[2,3-d]pyrimidin-5-yl)methanone (or 5-{4-methoxy-5H,6H,7H,8H-pyrido[3,4-d]pyrimidine-7-carbonyl}-6-methyl-N-(1-methylcyclopropyl)furo[2,3-d]pyrimidin-4-amine)

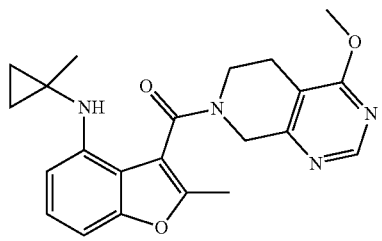 [SMILES: COc1ncnc2c1CCN(C(=O)c1c(C)oc3cccc(NC4(C)CC4)c13)C2]

6-Methyl-4-((1-methylcyclopropyl)amino)furo[2,3-d]pyrimidine-5-carboxylic acid (Intermediate 1, 3.80 g, 15.4 mmol), 4-methoxy-5,6,7,8-tetrahydropyrido[3,4-d]pyrimidine hydrochloride (4.08 g, 19.2 mmol) and HATU (8.77 g, 23.05 mmol) were combined and DMA (38 mL) was added. The slurry was cooled in an ice bath. DIEA (10.7 mL, 61.48 mmol) was added slowly, maintaining the internal temperature below 15° C. The reaction was judged to be complete after 1 h. The reaction was quenched with sodium hydroxide (0.1 N, 40 mL, 4.0 mmol) and then diluted with water (40 mL). The solution was stirred at ambient temperature overnight, during which time a solid formed. The solid was collected and rinsed with water to afford the title compound (4.45 g, 73%) as a white solid. $^1$H NMR (400 MHz, DMSO-d$_6$) δ 8.59 (s, 1H), 8.33 (s, 1H), 7.12 (br s, 1H), 4.68 (br s, 2H), 3.95 (s, 3H), 3.78 (d, J=11.7 Hz, 2H), 2.69 (br s, 2H), 2.47 (s, 3H), 1.38 (s, 3H), 0.70-0.57 (m, 4H). [M+H]=395.5.

Example 5. (4-Fluoro-5,8-dihydropyrido[3,4-d]pyrimidin-7(6H)-yl)(6-methyl-4-((1-methylcyclopropyl)amino)furo[2,3-d]pyrimidin-5-yl)methanone (or 5-{4-fluoro-5H,6H,7H,8H-pyrido[3,4-d]pyrimidine-7-carbonyl}-6-methyl-N-(1-methylcyclopropyl)furo[2,3-d]pyrimidin-4-amine)

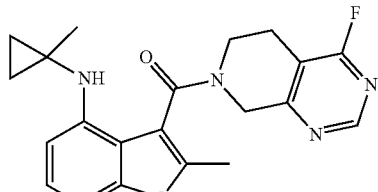

4-Fluoro-5,6,7,8-tetrahydropyrido[3,4-d]pyrimidine hydrochloride was coupled to 6-methyl-4-((1-methylcyclopropyl)amino)furo[2,3-d]pyrimidine-5-carboxylic acid (Intermediate 1), in a manner analogous to Example 2, to afford the title compound as a colorless oil. $^1$H NMR (400 MHz, CD$_3$OD) δ 8.72 (s, 1H), 8.44 (s, 1H), 4.93 (br s, 2H), 4.16-3.89 (m, 2H), 3.00-2.91 (m, 2H), 2.64-2.57 (m, 3H), 1.53-1.46 (m, 3H), 0.97-0.88 (m, 4H). [M+H]=383.0.

Example 6. 5-{4-chloro-5H,6H,7H,8H-pyrido[3,4-d]pyrimidine-7-carbonyl}-6-methyl-N-(1-methylcyclopropyl)furo[2,3-d]pyrimidin-4-amine

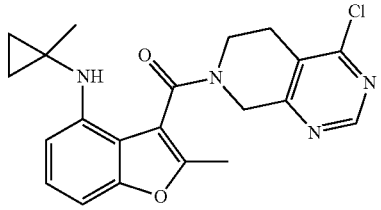 [SMILES: Cc1oc2cccc(NC3(C)CC3)c2c1C(=O)N1CCc2c(Cl)ncnc2C1]

4-chloro-5,6,7,8-tetrahydropyrido[3,4-d]pyrimidine hydrochloride was coupled to 6-methyl-4-((1-methylcyclopropyl)amino)furo[2,3-d]pyrimidine-5-carboxylic acid (Intermediate 1), in a manner analogous to Example 2, to afford the title compound as a colorless oil. $^1$H NMR (400 MHz, CD$_3$OD) δ 8.79 (s, 1H), 8.42 (s, 1H), 4.90 (br s, 2H), 4.02 (br s, 2H), 3.04-2.98 (m, 2H), 2.60 (s, 3H), 1.48 (s, 3H), 0.94-0.85 (m, 4H). [M+H]=398.93.

Example 7. 5-{4-[(2-Fluoroethyl)amino]-5H,6H,7H,8H-pyrido[3,4-d]pyrimidine-7-carbonyl}-6-methyl-N-(1-methylcyclopropyl)furo[2,3-d]pyrimidin-4-amine trifluoroacetate

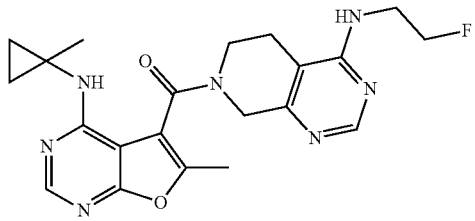 [SMILES: Cc1oc2ncnc(NC3(C)CC3)c2c1C(=O)N1CCc2c(ncnc2NCCF)C1]

To a stirred solution of 5-{4-chloro-5H,6H,7H,8H-pyrido[3,4-d]pyrimidine-7-carbonyl}-6-methyl-N-(1-methylcyclopropyl)furo[2,3-d]pyrimidin-4-amine (Example 6, 40 mg, 0.08 mmol) in ACN (0.78 mL) was added TEA (0.038 mL, 0.27 mmol) and 2-fluoroethanamine hydrochloride (12 mg, 0.12 mmol) and the mixture was heated at 60° C. for 20 h, then 80° C. for 3 h. Potassium carbonate (11 mg, 0.08 mmol) was added and heating at 80° C. was continued for 20 h. The mixture was cooled, diluted with methanol, filtered and purified by preparative HPLC (elution with 3-45% ACN in water containing 0.05% TFA). Fractions containing product were combined and lyophilized to afford the title compound (12 mg, 42%) as a yellow solid. $^1$H NMR (400 MHz, CD$_3$OD) δ 8.67 (s, 1H), 8.37 (s, 1H), 4.92-4.87 (m, 2H), 4.77-4.55 (m, 2H), 4.18-3.82 (m, 4H), 2.78-2.65 (m, 2H), 2.59 (s, 3H), 1.48 (s, 3H), 0.88-0.76 (m, 4H). [M+H]=426.0.

Example 8. N-((5-Chloropyrazin-2-yl)methyl)-6-methyl-4-((1-methylcyclopropyl)amino)furo[2,3-d]pyrimidine-5-carboxamide

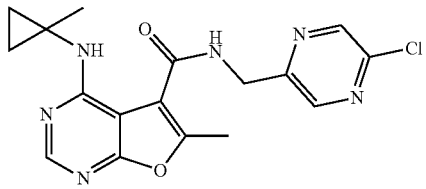 [SMILES: Cc1oc2ncnc(NC3(C)CC3)c2c1C(=O)NCc1cnc(Cl)cn1]

(5-Chloropyrazin-2-yl)methanamine hydrochloride was coupled to 6-methyl-4-((1-methylcyclopropyl)amino)furo[2,3-d]pyrimidine-5-carboxylic acid (Intermediate 1), in a manner analogous to Example 2, to afford the title compound as a colorless oil. $^1$H NMR (400 MHz, CD$_3$OD) δ 8.64 (d, J=1.5 Hz, 1H), 8.51 (d, J=1.2 Hz, 1H), 8.38 (s, 1H), 4.76 (s, 2H), 2.75 (s, 3H), 1.50 (s, 3H), 0.96-0.85 (m, 4H). [M+H]=372.93.

Example 9. N-((5-Fluoropyrazin-2-yl)methyl)-6-methyl-4-((1-methylcyclopropyl)amino)furo[2,3-d]pyrimidine-5-carboxamide

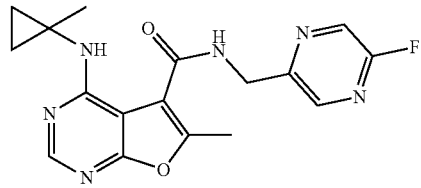 [SMILES: Cc1oc2ncnc(NC3(C)CC3)c2c1C(=O)NCc1cnc(F)cn1]

A mixture of N-((5-chloropyrazin-2-yl)methyl)-6-methyl-4-((1-methylcyclopropyl)amino)furo[2,3-d]pyrimidine-5-carboxamide (Example 8, 13 mg, 0.03 mmol) and potassium fluoride (16 mg, 0.27 mmol) in DMSO (0.89 mL) was heated at 100° C. for 20 h. The mixture was transferred to a microwave vial, ACN (1 mL) was added and the reaction mixture was heated by microwave at 110° C. for 15 min, 130° C. for 30 min, 150° C. for 1 h, 160° C. for 1 h and finally 170° C. for 1 h. The mixture was diluted with methanol, filtered and purified by prep HPLC (elution with 5-50% ACN in water containing 0.05% TFA). Fractions containing product were combined and lyophilized to afford the title compound (3.0 mg, 19%) as an orange solid. $^1$H NMR (400 MHz, CD$_3$OD) δ 8.49 (dd, J=1.2, 8.2 Hz, 1H), 8.36 (s, 1H), 8.34 (s, 1H), 4.77 (s, 2H), 2.76-2.74 (m, 3H), 1.50 (s, 3H), 0.94-0.86 (m, 4H). [M+H]=356.9.

Example 10. N-[(5-Hydroxypyridin-2-yl)methyl]-6-methyl-4-[(1-methylcyclopropyl)amino]furo[2,3-d]pyrimidine-5-carboxamide

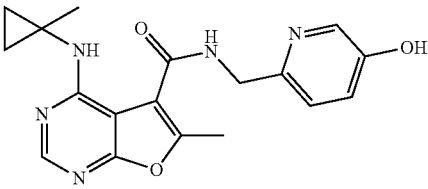 [SMILES: Cc1oc2ncnc(NC3(C)CC3)c2c1C(=O)NCc1ccc(O)cn1]

6-(Aminomethyl)pyridin-3-ol hydrochloride was coupled to 6-methyl-4-((1-methylcyclopropyl)amino)furo[2,3-d]pyrimidine-5-carboxylic acid (Intermediate 1), in a manner analogous to Example 2, to afford the title compound as a colorless oil. $^1$H NMR (400 MHz, CD$_3$OD) δ 8.35 (s, 1H), 8.21 (d, J=2.3 Hz, 1H), 7.83-7.72 (m, 2H), 4.76 (s, 2H), 2.75 (s, 3H), 1.48 (s, 3H), 0.89-0.84 (m, 4H).

Example 11. N-((5-(Fluoromethoxy)pyridin-2-yl)methyl)-6-methyl-4-((1-methylcyclopropyl)amino)furo[2,3-d]pyrimidine-5-carboxamide

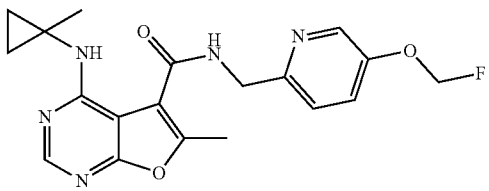 [SMILES: Cc1oc2ncnc(NC3(C)CC3)c2c1C(=O)NCc1ccc(OCF)cn1]

To a solution of N-[(5-hydroxypyridin-2-yl)methyl]-6-methyl-4-[(1-methylcyclopropyl)amino]furo[2,3-d]pyrimidine-5-carboxamide (Example 10, 100 mg, 0.16 mmol) in DMF (1.1 mL) was added cesium carbonate (107 mg, 0.33 mmol) and a solution of fluoromethyl 4-methylbenzene-1-sulfonate (67 mg, 0.33 mmol) in DMF (0.55 mL). After 1 h stirring at room temperature, the reaction mixture was heated at 70° C. for 45 min. The reaction was cooled, diluted with methanol, filtered and purified by prep HPLC (elution with 5-50% ACN in water containing 0.05% TFA). Fractions containing product were combined and lyophilized to afford the title compound (3.0 mg, 19%) as an orange solid. $^1$H NMR (400 MHz, CD$_3$OD) δ 8.39 (d, J=2.8 Hz, 1H), 8.37 (s, 1H), 7.68-7.58 (m, 1H), 7.49 (d, J=8.7 Hz, 1H), 5.95-5.72 (m, 2H), 4.71 (s, 2H), 2.76 (s, 3H), 1.51 (s, 3H), 0.96-0.84 (m, 4H). [M+H]=386.0.

Example 12. 3-Fluoro-5-(1-{6-methyl-4-[(1-methylcyclopropyl)amino]furo[2,3-d]pyrimidine-5-carbonyl}-1,2,3,6-tetrahydropyridin-4-yl)pyridine-2-carbonitrile

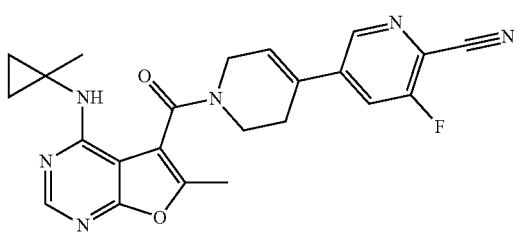 [SMILES: Cc1oc2ncnc(NC3(C)CC3)c2c1C(=O)N1CC=C(c2cnc(C#N)c(F)c2)CC1]

3-Fluoro-5-(1,2,3,6-tetrahydropyridin-4-yl)pyridine-2-carbonitrile (Intermediate 4) was coupled to 6-methyl-4-((1-methylcyclopropyl)amino)furo[2,3-d]pyrimidine-5-carboxylic acid (Intermediate 1), in a manner analogous to Example 2, to afford the title compound as a colorless oil. $^1$H NMR (400 MHz, CD$_3$OD) δ 8.73 (t, J=1.5 Hz, 1H), 8.33 (s, 1H), 7.96 (dd, J=1.7, 10.4 Hz, 1H), 6.58 (br s, 1H), 4.44 (br s, 2H), 4.14-3.74 (m, 2H), 2.73 (br s, 2H), 2.55 (s, 3H), 1.49 (s, 3H), 0.86-0.73 (m, 4H). [M+H]=433.0.

Example 13. 5-[4-(5-Fluoro-6-methoxypyridin-3-yl)-1,2,3,6-tetrahydropyridine-1-carbonyl]-6-methyl-N-(1-methylcyclopropyl)furo[2,3-d]pyrimidin-4-amine

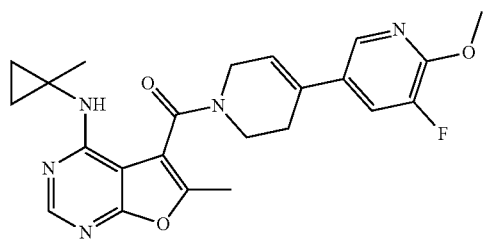 [SMILES: COc1ncc(C2=CCN(C(=O)c3c(C)oc4ncnc(NC5(C)CC5)c34)CC2)cc1F]

5-Fluoro-6-methoxy-1',2',3',6'-tetrahydro-3,4'-bipyridine trifluoroacetate (Intermediate 5) was coupled to 6-methyl-4-((1-methylcyclopropyl)amino)furo[2,3-d]pyrimidine-5-carboxylic acid (Intermediate 1), in a manner analogous to Example 2, to afford the title compound as a colorless oil. $^1$H NMR (400 MHz, CD$_3$OD) δ 8.31 (s, 1H), 8.02 (d, J=2.1 Hz, 1H), 7.64 (dd, J=2.1, 11.9 Hz, 1H), 6.18 (br s, 1H), 4.34 (br s, 2H), 4.01 (s, 4H), 2.67 (br s, 2H), 2.53 (s, 3H), 1.48 (s, 3H), 0.88-0.68 (m, 4H). [M+H]=438.0.

Example 14. 5-[4-(5-Fluoro-6-methoxypyridin-3-yl)piperidine-1-carbonyl]-6-methyl-N-(1-methylcyclopropyl)furo[2,3-d]pyrimidin-4-amine

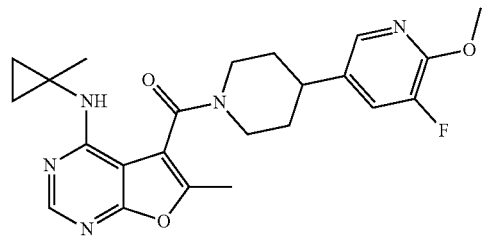 [SMILES: COc1ncc(C2CCN(C(=O)c3c(C)oc4ncnc(NC5(C)CC5)c34)CC2)cc1F]

A mixture of 5-[4-(5-fluoro-6-methoxypyridin-3-yl)-1,2,3,6-tetrahydropyridine-1-carbonyl]-6-methyl-N-(1-methylcyclopropyl)furo[2,3-d]pyrimidin-4-amine (Example 13, 85 mg, 0.19 mmol) and palladium on activated carbon (50 mg, 0.05 mmol) in ethanol (5 mL) were stirred under 1 atm of hydrogen for 1 h. The mixture was filtered through a pad of Celite®, concentrated, and the residue was purified by flash LC (elution with 30-100% ethyl acetate in heptane) to afford the title compound (21 mg, 25%) as a white solid. $^1$H NMR (400 MHz, CD$_3$OD) δ 8.32 (s, 1H), 7.85 (s, 1H), 7.44 (d, J=10.0 Hz, 1H), 3.98 (s, 3H), 3.61-3.02 (m, 4H), 2.94 (br s, 1H), 2.54 (s, 3H), 2.09-1.86 (m, 2H), 1.70 (d, J=14.1 Hz, 2H), 1.52 (s, 3H), 0.92-0.72 (m, 4H). [M+H]=440.0.

Example 15. 5-[4-(5-Fluoropyrimidin-2-yl)-1,2,3,6-tetrahydropyridine-1-carbonyl]-6-methyl-N-(1-methylcyclopropyl)furo[2,3-d]pyrimidin-4-amine

Example 16 and 17. 3-(Fluoromethyl)-7-{6-methyl-4-[(1-methylcyclopropyl)amino]furo[2,3-d]pyrimidine-5-carbonyl}-3H,4H,5H,6H,7H,8H-pyrido[3,4-d]pyrimidin-4-one and 5-[4-(fluoromethoxy)-5H,6H,7H,8H-pyrido[3,4-d]pyrimidine-7-carbonyl]-6-methyl-N-(1-methylcyclopropyl)furo[2,3-d]pyrimidin-4-amine

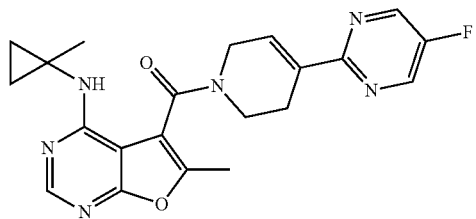

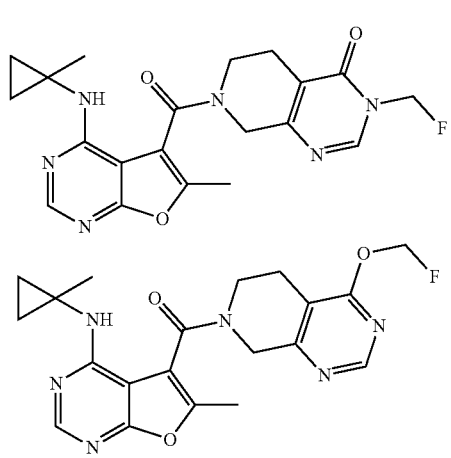

Step 1. 6-Methyl-N-(1-methylcyclopropyl)-5-[4-(tetramethyl-1,3,2-dioxaborolan-2-yl)-1,2,3,6-tetrahydropyridine-1-carbonyl]furo[2,3-d]pyrimidin-4-amine. The title compound was synthesized in a manner analogous to Example 2, using 6-Methyl-4-((1-methylcyclopropyl)amino)furo[2,3-d]pyrimidine-5-carboxylic acid (Intermediate 1) and 4-(tetramethyl-1,3,2-dioxaborolan-2-yl)-1,2,3,6-tetrahydropyridine as the starting materials. $^1$H NMR (400 MHz, CDCl$_3$) δ 8.45 (br s, 1H), 6.97 (br s, 1H), 6.49 (br s, 1H), 4.48-3.95 (m, 2H), 3.61 (br s, 2H), 2.45 (br s, 3H), 2.37 (br s, 2H), 2.04 (br s, 1H), 1.50 (br s, 3H), 1.36-1.17 (m, 14H), 0.96-0.59 (m, 4H). [M+H]=439.0.

Step 2. 5-[4-(5-Fluoropyrimidin-2-yl)-1,2,3,6-tetrahydropyridine-1-carbonyl]-6-methyl-N-(1-methylcyclopropyl)furo[2,3-d]pyrimidin-4-amine. 6-Methyl-N-(1-methylcyclopropyl)-5-[4-(tetramethyl-1,3,2-dioxaborolan-2-yl)-1,2,3,6-tetrahydropyridine-1-carbonyl]furo[2,3-d]pyrimidin-4-amine (64 mg, 0.15 mmol) and 2-bromo-5-fluoropyrimidine (31 mg, 0.18 mmol) were combined and dissolved in dioxane (0.8 mL) and ethyl alcohol (0.3 mL) with nitrogen bubbling through the mixture. Water (0.2 mL), aqueous sodium carbonate (2 M, 0.22 mL, 0.44 mmol) and tetrakis(triphenylphosphine)palladium(0) (8 mg, 0.01 mmol) were added and the mixture was heated at 120° C. for 15 min in a microwave reactor. The mixture was filtered and purified by preparative HPLC (elution with 15-75% ACN in water containing 0.05% TFA). Fractions containing product were poured into ethyl acetate (20 mL), washed with saturated sodium bicarbonate (20 mL), dried (MgSO$_4$) and concentrated. The residue was purified by flash LC (30-100% ethyl acetate in heptane) to afford the title compound (5.0 mg, 8%) as a white solid. $^1$H NMR (400 MHz, CD$_3$OD) δ 8.81 (d, J=1.5 Hz, 2H), 8.32 (s, 1H), 6.36 (br s, 1H), 4.39 (br s, 2H), 3.93 (br s, 2H), 2.72 (br s, 2H), 2.55 (s, 3H), 1.49 (s, 3H), 0.86-0.66 (m, 4H). [M+H]=409.0.

Step 1. 7-(6-Methyl-4-((1-methylcyclopropyl)amino)furo[2,3-d]pyrimidine-5-carbonyl)-5,6,7,8-tetrahydropyrido[3,4-d]pyrimidin-4(3H)-one. 5,6,7,8-Tetrahydropyrido[3,4-d]pyrimidin-4(3H)-one and 6-methyl-4-((1-methylcyclopropyl)amino)furo[2,3-d]pyrimidine-5-carboxylic acid (Intermediate 1) were coupled, in a manner analogous to Example 2, to afford the title compound as a solid. $^1$H NMR (400 MHz, CD$_3$OD) δ 8.46 (s, 1H), 8.30-8.21 (m, 1H), 4.72 (br s, 2H), 4.12-3.67 (m, 2H), 3.46 (br s, 6H), 3.25-3.06 (m, 8H), 2.82-2.74 (m, 2H), 2.68 (s, 3H), 1.53 (s, 4H), 1.08 (br s, 2H), 0.97 (s, 2H). [M+H]=381.0.

Step 2. 3-(Fluoromethyl)-7-{6-methyl-4-[(1-methylcyclopropyl)amino]furo[2,3-d]pyrimidine-5-carbonyl}-3H,4H,5H,6H,7H,8H-pyrido[3,4-d]pyrimidin-4-one and 5-[4-(fluoromethoxy)-5H,6H,7H,8H-pyrido[3,4-d]pyrimidine-7-carbonyl]-6-methyl-N-(1-methylcyclopropyl)furo[2,3-d]pyrimidin-4-amine. To a solution of 7-(6-methyl-4-((1-methylcyclopropyl)amino)furo[2,3-d]pyrimidine-5-carbonyl)-5,6,7,8-tetrahydropyrido[3,4-d]pyrimidin-4(3H)-one (38 mg, 0.06 mmol) in DMF (0.38 mL) was added cesium carbonate (38 mg, 0.12 mmol) and a solution of fluoromethyl 4-methylbenzene-1-sulfonate (24 mg, 0.12 mmol) in DMF (0.19 mL). After 1 h stirring at 60° C., the reaction mixture was cooled, diluted with methanol, filtered and purified by prep HPLC (elution with 15-50% ACN in water containing 0.05% TFA). Fractions containing the two products were lyophilized to afford Example 16 (6.2 mg, 20%) and Example 17 (8.9 mg, 29%), both as yellow solids. Example 16:

$^1$H NMR (400 MHz, CD$_3$OD) δ 8.44 (s, 1H), 8.41-8.37 (m, 1H), 6.08-5.90 (m, 2H), 4.65 (br s, 2H), 3.91 (br s, 2H), 2.72 (br s, 2H), 2.58 (s, 3H), 1.49 (s, 3H), 0.88 (d, J=10.6 Hz, 4H). [M+H]=413.1. Example 17: $^1$H NMR (400 MHz, CD$_3$OD) δ 8.64 (s, 1H), 8.41 (s, 1H), 6.27-6.04 (m, 2H), 4.92 (br s, 2H), 4.22-3.82 (m, 2H), 2.90 (t, J=5.3 Hz, 2H), 2.59 (s, 3H), 1.48 (s, 3H), 0.95-0.83 (m, 4H). [M+H]=413.0.

Example 18. 5-{4-[(3R)-3-Fluoropyrrolidin-1-yl]-5H,6H,7H,8H-pyrido[3,4-d]pyrimidine-7-carbonyl}-6-methyl-N-(1-methylcyclopropyl)furo[2,3-d]pyrimidin-4-amine

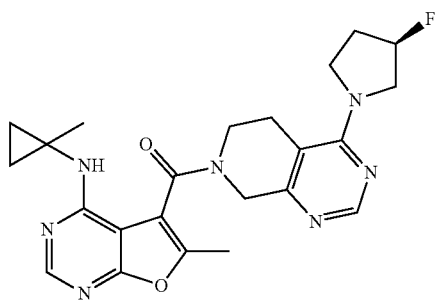 [SMILES: Cc1oc2ncnc(NC3(C)CC3)c2c1C(=O)N1CCc2c(ncnc2N2CC[C@@H](F)C2)C1]

(R)-4-(3-Fluoropyrrolidin-1-yl)-5,6,7,8-tetrahydropyrido[3,4-d]pyrimidine hydrochloride (Intermediate 8) and 6-methyl-4-((1-methylcyclopropyl)amino)furo[2,3-d]pyrimidine-5-carboxylic acid (Intermediate 1) were coupled, in a manner analogous to Example 2 to afford the title compound. $^1$H NMR (400 MHz, CD$_3$OD) δ 8.59 (s, 1H), 8.38 (s, 1H), 5.54-5.31 (m, 1H), 5.01 (br s, 1H), 4.74 (d, J=16.9 Hz, 1H), 4.34-4.16 (m, 3H), 4.16-3.99 (m, 2H), 3.63 (br s, 1H), 3.27 (br s, 1H), 3.22-3.10 (m, 1H), 2.61 (s, 3H), 2.52-2.34 (m, 1H), 2.34-2.07 (m, 1H), 1.50 (s, 3H), 0.95-0.77 (m, 4H). [M+H]=452.0.

Example 19. 7-{6-methyl-4-[(1-methylcyclopropyl)amino]furo[2,3-d]pyrimidine-5-carbonyl}-5,6,7,8-tetrahydro-1,7-naphthyridin-4-ol

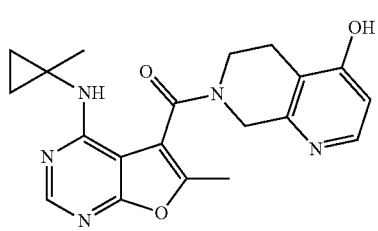 [SMILES: Cc1oc2ncnc(NC3(C)CC3)c2c1C(=O)N1CCc2c(O)ccnc2C1]

5,6,7,8-Tetrahydro-1,7-naphthyridin-4-ol hydrochloride was coupled to 6-methyl-4-((1-methylcyclopropyl)amino)furo[2,3-d]pyrimidine-5-carboxylic acid (Intermediate 1), in a manner analogous to Example 2, to afford the title compound as a colorless oil. $^1$H NMR (400 MHz, CD$_3$OD) δ 8.40-8.29 (m, 2H), 7.07 (d, J=6.8 Hz, 1H), 5.02 (br s, 2H), 3.97 (br s, 2H), 2.90 (br s, 2H), 2.58 (s, 3H), 1.46 (s, 3H), 0.86-0.75 (m, 4H). [M+H]=379.98.

Example 20. 5-[4-(2-Fluoroethoxy)-5,6,7,8-tetrahydro-1,7-naphthyridine-7-carbonyl]-6-methyl-N-(1-methylcyclopropyl)furo[2,3-d]pyrimidin-4-amine trifluoroacetate

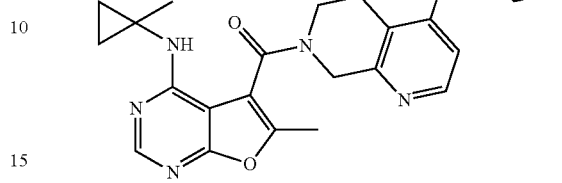

To a stirred solution of 7-{6-methyl-4-[(1-methylcyclopropyl)amino]furo[2,3-d]pyrimidine-5-carbonyl}-5,6,7,8-tetrahydro-1,7-naphthyridin-4-ol (Example 19, 20 mg, 0.04 mmol) in DMF (0.83 mL) was added cesium carbonate (27 mg, 0.08 mmol) and a solution of 2-fluoroethyl 4-methylbenzene-1-sulfonate (12 mg, 0.05 mmol) in DMF (0.2 mL). The reaction mixture was heated at 60° C. for 20 h, then the mixture was cooled, diluted with methanol, filtered and purified by prep HPLC (elution with 5-45% ACN in water containing 0.05% TFA). Fractions containing product were combined and lyophilized to afford the title compound (8.3 mg, 37%) as a white solid. $^1$H NMR (400 MHz, CD$_3$OD) δ 8.62 (d, J=6.7 Hz, 1H), 8.40 (s, 1H), 7.51 (d, J=7.0 Hz, 1H), 5.11 (br s, 2H), 4.94-4.89 (m, 1H), 4.82-4.77 (m, 1H), 4.73-4.67 (m, 1H), 4.65-4.60 (m, 1H), 4.00 (br s, 2H), 2.99 (t, J=5.6 Hz, 2H), 2.61 (s, 3H), 1.47 (s, 3H), 0.92-0.79 (m, 4H). [M+H]=426.1.

Example 21. 5-[3-(2-Fluoropyridin-4-yl)pyrrolidine-1-carbonyl]-6-methyl-N-(1-methylcyclopropyl)furo[2,3-d]pyrimidin-4-amine

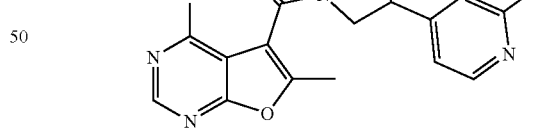

2-Fluoro-4-(pyrrolidin-3-yl)pyridine (Intermediate 12) and 6-Methyl-4-((1-methylcyclopropyl)amino)furo[2,3-d]pyrimidine-5-carboxylic acid (Intermediate 1) were coupled, in a manner analogous to Example 2, to provide the title compound. $^1$H NMR (400 MHz, CD$_3$OD) δ 8.57 (s, 1H), 8.31 (s, 1H), 4.79 (br s, 2H), 4.19-3.79 (m, 5H), 2.82 (br s, 2H), 2.53 (s, 3H), 1.46 (s, 3H), 0.81-0.68 (m, 4H). [M+H]=396.1.

Example 22. 2-Isopropyl-7-(6-methyl-4-((1-methyl-cyclopropyl)amino)furo[2,3-d]pyrimidine-5-carbonyl)-5,6,7,8-tetrahydropyrido[3,4-d]pyrimidin-4 (3H)-one (or 7-{6-methyl-4-[(1-methylcyclopropyl) amino]furo[2,3-d]pyrimidine-5-carbonyl}-2-(propan-2-yl)-3H,4H,5H,6H,7H,8H-pyrido[3,4-d] pyrimidin-4-one)

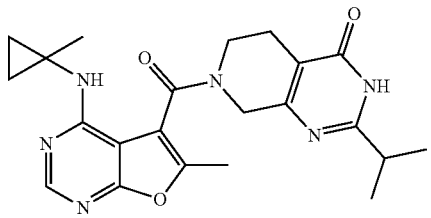 [SMILES: Cc1oc2ncnc(NC3(C)CC3)c2c1C(=O)N1CCc2c(nc(C(C)C)[nH]c2=O)C1]

Step 1. Ethyl 1-(6-methyl-4-((1-methylcyclopropyl) amino)furo[2,3-d]pyrimidine-5-carbonyl)-3-oxopiperidine-4-carboxylate. Ethyl 3-oxopiperidine-4-carboxylate and 6-methyl-4-((1-methylcyclopropyl)amino)furo[2,3-d]pyrimidine-5-carboxylic acid (Intermediate 1) were coupled in a manner analogous to Example 2 to afford the title compound as a solid. [M+H]=401.1.

Step 2. 2-Isopropyl-7-(6-methyl-4-((1-methylcyclopropyl)amino)furo[2,3-d]pyrimidine-5-carbonyl)-5,6,7,8-tetrahydropyrido[3,4-d]pyrimidin-4(3H)-one. To a stirred solution of isobutyrimidamide hydrochloride (92 mg, 0.75 mmol) and 1-(6-methyl-4-((1-methylcyclopropyl)amino) furo[2,3-d]pyrimidine-5-carbonyl)-3-oxopiperidine-4-carboxylate (200 mg, 0.50 mmol) in ethanol (5 mL) was added sodium ethoxide in ethanol (21% w/w, 0.37 mL, 1.0 mmol). The mixture was heated to reflux for 2 h, cooled to room temperature, diluted with DCM and washed with water. The aqueous layer was extracted with DCM and the combined organics were washed with brine, dried over MgSO$_4$ and concentrated under vacuum. The solvent was evaporated and the residue was dissolved in methanol and purified by prep HPLC (elution with 5-50% ACN in water containing 0.05% TFA). The fraction containing product was lyophilized to afford the title compound (19 mg, 7%) as an off-white solid. $^1$H NMR (400 MHz, CD$_3$OD) δ 8.42 (s, 1H), 4.63 (br s, 2H), 3.91 (br s, 2H), 2.87 (td, J=6.8, 13.6 Hz, 1H), 2.67 (br s, 2H), 2.60 (s, 3H), 1.50 (s, 3H), 1.29 (d, J=6.8 Hz, 6H), 0.93-0.86 (m, 4H). [M+H]=423.0.

Example 23. 5-{4-Ethyl-5H,6H,7H,8H-pyrido[3,4-d]pyrimidine-7-carbonyl}-6-methyl-N-(1-methylcyclopropyl)furo[2,3-d]pyrimidin-4-amine

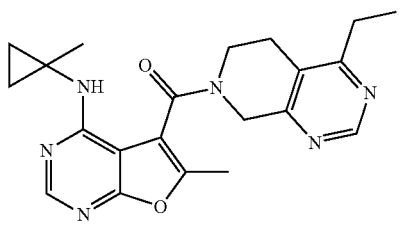 [SMILES: CCc1ncnc2c1CCN(C(=O)c1c(C)oc3ncnc(NC4(C)CC4)c13)C2]

4-Ethyl-5,6,7,8-tetrahydropyrido[3,4-d]pyrimidine hydrochloride (Intermediate 18) and 6-methyl-4-((1-methylcyclopropyl)amino)furo[2,3-d]pyrimidine-5-carboxylic acid (Intermediate 1) were coupled in a manner analogous to Example 2 to provide the title compound. $^1$H NMR (400 MHz, CDCl$_3$) δ 8.96 (s, 1H), 8.49 (s, 1H), 7.09 (br s, 1H), 4.82 (br s, 2H), 3.70-4.29 (m, 2H), 2.95 (t, J=5.62 Hz, 2H), 2.81 (q, J=7.50 Hz, 2H), 2.53 (s, 3H), 1.50 (s, 3H), 1.34 (t, J=7.52 Hz, 3H), 0.75-0.81 (m, 4H). [M+H]=393.4.

Example 24. 7-(6-Methyl-4-((1-methylcyclopropyl) amino)furo[2,3-d]pyrimidine-5-carbonyl)-5,6,7,8-tetrahydropyrido[3,4-d]pyrimidine-4-carbonitrile (or 7-{6-methyl-4-[(1-methylcyclopropyl)amino]furo[2,3-d]pyrimidine-5-carbonyl}-5H,6H,7H,8H-pyrido[3,4-d]pyrimidine-4-carbonitrile)

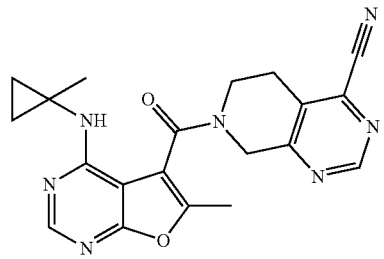 [SMILES: Cc1oc2ncnc(NC3(C)CC3)c2c1C(=O)N1CCc2c(C#N)ncnc2C1]

5,6,7,8-Tetrahydropyrido[3,4-d]pyrimidine-4-carbonitrile (Intermediate 22) and 6-methyl-4-((1-methylcyclopropyl) amino)furo[2,3-d]pyrimidine-5-carboxylic acid (Intermediate 1) were coupled in a manner analogous to Example 2, to afford the title compound. $^1$H NMR (400 MHz, CDCl$_3$) δ 9.18 (s, 1H), 8.50 (s, 1H), 7.00 (br s, 1H), 4.95 (br s, 2H), 3.76-4.48 (m, 2H), 3.21 (t, J=5.75 Hz, 2H), 2.56 (s, 3H), 1.52 (s, 3H), 0.80 (d, J=8.07 Hz, 4H). [M+H]=390.4.

Example 25. 5-{4-Ethoxy-5H,6H,7H,8H-pyrido[3,4-d]pyrimidine-7-carbonyl}-6-methyl-N-(1-methylcyclopropyl)furo[2,3-d]pyrimidin-4-amine

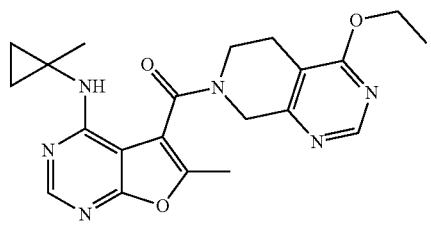 [SMILES: CCOc1ncnc2c1CCN(C(=O)c1c(C)oc3ncnc(NC4(C)CC4)c13)C2]

4-Ethoxy-5,6,7,8-tetrahydropyrido[3,4-d]pyrimidine (Intermediate 23) and 6-methyl-4-((1-methylcyclopropyl) amino)furo[2,3-d]pyrimidine-5-carboxylic acid (Intermediate 1) were coupled in a manner analogous to Example 2, to afford the title compound. $^1$H NMR (400 MHz, CDCl$_3$) δ 8.59 (s, 1H), 8.48 (s, 1H), 7.00 (br s, 1H), 4.75 (br s, 2H), 4.50 (q, J=7.09 Hz, 2H), 3.56-4.23 (m, 2H), 2.83 (t, J=5.62 Hz, 2H), 2.52 (s, 3H), 1.51 (s, 3H), 1.44 (t, J=7.09 Hz, 3H), 0.71-0.83 (m, 4H). [M+H]=409.4.

Example 26. (4-(4-((2-Fluoroethyl)amino)pyrimidin-2-yl)piperidin-1-yl)(6-methyl-4-((1-methylcyclopropyl)amino)furo[2,3-d]pyrimidin-5-yl)methanone (or N-(2-fluoroethyl)-2-(1-{6-methyl-4-[(1-methylcyclopropyl)amino]furo[2,3-d]pyrimidine-5-carbonyl}piperidin-4-yl)pyrimidin-4-amine)

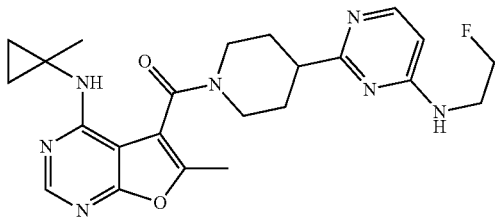 [SMILES: Cc1oc2ncnc(NC3(C)CC3)c2c1C(=O)N1CCC(c2nccc(NCCF)n2)CC1]

N-(2-Fluoroethyl)-2-(piperidin-4-yl)pyrimidin-4-amine hydrochloride (Intermediate 30) and 6-methyl-4-((1-methylcyclopropyl)amino)furo[2,3-d]pyrimidine-5-carboxylic acid (Intermediate 1) were coupled in a manner analogous to Example 2, to afford the title compound. [M+H]=454.3.

Example 27. 5-[4-Methoxy-2-(propan-2-yl)-5H,6H,7H,8H-pyrido[3,4-d]pyrimidine-7-carbonyl]-6-methyl-N-(1-methylcyclopropyl)furo[2,3-d]pyrimidin-4-amine

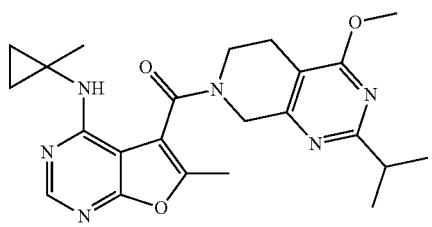 [SMILES: COc1nc(C(C)C)nc2c1CCN(C(=O)c1c(C)oc3ncnc(NC4(C)CC4)c13)C2]

2-Isopropyl-4-methoxy-5,6,7,8-tetrahydropyrido[3,4-d]pyrimidine trifluoroacetate (Intermediate 31) and 6-methyl-4-((1-methylcyclopropyl)amino)furo[2,3-d]pyrimidine-5-carboxylic acid (Intermediate 1) were coupled in a manner analogous to Example 2, to afford the title compound. $^1$H NMR (400 MHz, CD$_3$OD) δ 8.37 (s, 1H), 4.80 (br s, 2H), 4.23-3.77 (m, 5H), 3.10-2.99 (m, 1H), 2.79 (t, J=5.6 Hz, 2H), 2.57 (s, 3H), 1.46 (s, 3H), 1.32 (d, J=6.7 Hz, 6H), 0.83 (d, J=4.3 Hz, 4H). [M+H]=437.5.

Example 28. N-Cyclopropyl-N-[(6-methoxypyrimidin-4-yl)methyl]-6-methyl-4-[(1-methylcyclopropyl)amino]furo[2,3-d]pyrimidine-5-carboxamide

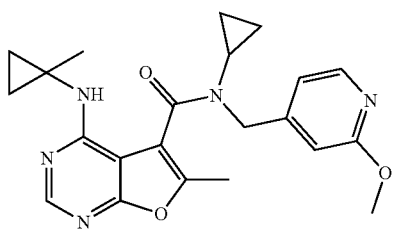 [SMILES: COc1cc(CN(C(=O)c2c(C)oc3ncnc(NC4(C)CC4)c23)C2CC2)ccn1]

N-((6-Methoxypyrimidin-4-yl)methyl)cyclopropanamine (Intermediate 33) and 6-methyl-4-((1-methylcyclopropyl)amino)furo[2,3-d]pyrimidine-5-carboxylic acid (Intermediate 1) were coupled in a manner analogous to Example 2, to afford the title compound. $^1$H NMR (400 MHz, CD$_3$OD) δ 8.81 (br s, 1H), 8.33 (s, 1H), 7.83-7.58 (m, 1H), 6.87 (s, 1H), 5.02-4.89 (m, 1H), 4.82-4.68 (m, 1H), 4.03 (s, 3H), 2.96 (br s, 1H), 2.55 (s, 3H), 1.56 (s, 3H), 0.83 (br s, 4H), 0.68 (br s, 4H). [M+H]=409.4.

Example 29. 5-{3-Cyclopropyl-1-ethyl-5H,6H,7H,8H-imidazo[1,5-a]pyrazine-7-carbonyl}-6-methyl-N-(1-methylcyclopropyl)furo[2,3-d]pyrimidin-4-amine

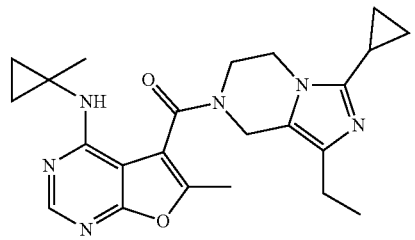 [SMILES: CCc1nc(C2CC2)n2c1CN(C(=O)c1c(C)oc3ncnc(NC4(C)CC4)c13)CC2]

3-Cyclopropyl-1-ethyl-5,6,7,8-tetrahydroimidazo[1,5-a]pyrazine (Intermediate 35) and 6-methyl-4-((1-methylcyclopropyl)amino)furo[2,3-d]pyrimidine-5-carboxylic acid (Intermediate 1) were coupled in a manner analogous to Example 2, to afford the title compound. $^1$H NMR (400 MHz, CDCl$_3$) δ 8.51 (s, 1H), 6.97 (br s, 1H), 4.77 (br s, 2H), 4.12 (br s, 4H), 2.51 (s, 3H), 2.46 (q, J=7.4 Hz, 2H), 1.80-1.70 (m, 1H), 1.53 (s, 3H), 1.16 (t, J=7.6 Hz, 3H), 1.02 (td, J=2.7, 5.1 Hz, 2H), 0.99-0.94 (m, 2H), 0.86-0.81 (m, 2H), 0.78 (s, 2H). [M+H]=421.3.

Example 30-Example 760 were prepared in a manner analogous to Example 2, with the appropriate starting material substitutions.

Example 30. 6-methyl-N-(1-methylcyclopropyl)-5-[(1R,5S,6S)-6-(pyridin-2-yl)-3-azabicyclo[3.1.0]hexane-3-carbonyl]furo[2,3-d]pyrimidin-4-amine

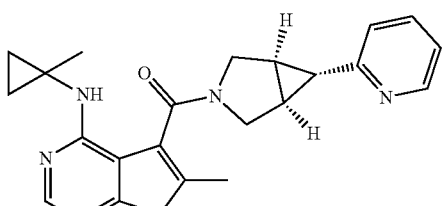

$^1$H NMR (400 MHz, CD$_3$OD) δ 8.57 (d, J=5.6 Hz, 1H), 8.35 (s, 1H), 8.27 (dt, J=1.6, 7.9 Hz, 1H), 7.68 (dt, J=1.1, 6.7 Hz, 1H), 7.61 (d, J=8.2 Hz, 1H), 4.65-3.49 (m, 4H), 2.57 (s, 3H), 2.43 (br s, 2H), 2.11 (t, J=3.4 Hz, 1H), 1.51 (s, 3H), 0.94-0.79 (m, 4H). [M+H]=390.3.

Example 31. 5-[3-(5-Fluoropyridin-2-yl)azetidine-1-carbonyl]-6-methyl-N-(1-methylcyclopropyl)furo[2,3-d]pyrimidin-4-amine

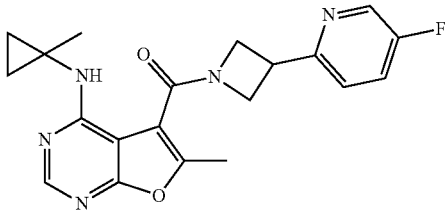 [SMILES: Cc1oc2ncnc(NC3(C)CC3)c2c1C(=O)N1CC(c2ccc(F)cn2)C1]

¹H NMR (400 MHz, CD₃OD) δ 8.50 (d, J=2.4 Hz, 1H), 8.44 (d, J=5.0 Hz, 1H), 8.41 (s, 1H), 7.66-7.58 (m, 1H), 4.75-4.66 (m, 2H), 4.50-4.37 (m, 2H), 4.37-4.26 (m, 1H), 2.64 (s, 3H), 1.53 (s, 3H), 1.02-0.85 (m, 4H). [M+H]=382.3.

Example 32. 4-(1-{6-Methyl-4-[(1-methylcyclopropyl)amino]furo[2,3-d]pyrimidine-5-carbonyl}azetidin-3-yl)benzonitrile

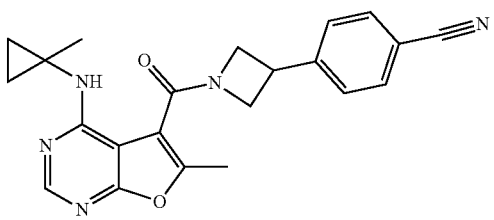 [SMILES: Cc1oc2ncnc(NC3(C)CC3)c2c1C(=O)N1CC(c2ccc(C#N)cc2)C1]

¹H NMR (400 MHz, CD₃OD) δ 8.38 (s, 1H), 7.80-7.73 (m, 2H), 7.60 (d, J=8.2 Hz, 2H), 4.75-4.63 (m, 2H), 4.32 (br s, 2H), 4.22-4.09 (m, 1H), 2.63 (s, 3H), 1.53 (s, 3H), 1.02-0.83 (m, 4H). [M+H]=388.4.

Example 33. 6-Methyl-N-(1-methylcyclopropyl)-5-[3-(1,3-thiazol-2-yl)azetidine-1-carbonyl]furo[2,3-d]pyrimidin-4-amine

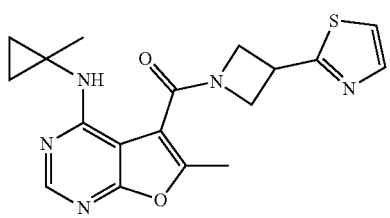 [SMILES: Cc1oc2ncnc(NC3(C)CC3)c2c1C(=O)N1CC(c2nccs2)C1]

¹H NMR (400 MHz, CD₃OD) δ 8.43-8.36 (m, 1H), 7.82 (d, J=3.4 Hz, 1H), 7.57 (d, J=3.3 Hz, 1H), 4.76-4.66 (m, 2H), 4.57-4.34 (m, 3H), 2.64 (s, 3H), 1.53 (s, 3H), 1.03-0.87 (m, 4H). [M+H]=370.3.

Example 34. N-[6-(Furan-3-yl)pyridin-3-yl]-6-methyl-4-[(1-methylcyclopropyl)amino]furo[2,3-d]pyrimidine-5-carboxamide

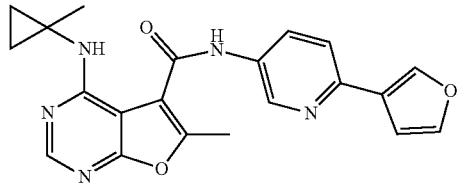 [SMILES: Cc1oc2ncnc(NC3(C)CC3)c2c1C(=O)Nc1ccc(-c2ccoc2)nc1]

¹H NMR (400 MHz, CD₃OD) δ 8.95 (d, J=2.2 Hz, 1H), 8.39 (s, 1H), 8.35-8.23 (m, 2H), 7.92 (d, J=8.7 Hz, 1H), 7.70 (t, J=1.7 Hz, 1H), 7.04 (dd, J=0.8, 1.9 Hz, 1H), 2.82-2.77 (m, 3H), 1.55-1.49 (m, 3H), 0.95-0.82 (m, 4H). [M+H]=390.3.

Example 35. 6-Methyl-N-(1-methylcyclopropyl)-5-[4-(1,3-thiazol-2-yl)piperazine-1-carbonyl]furo[2,3-d]pyrimidin-4-amine

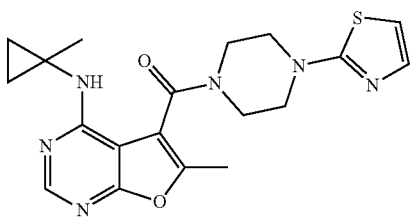 [SMILES: Cc1oc2ncnc(NC3(C)CC3)c2c1C(=O)N1CCN(c2nccs2)CC1]

¹H NMR (400 MHz, CD₃OD) δ 8.44-8.33 (m, 1H), 7.29 (d, J=4.0 Hz, 1H), 6.95 (d, J=4.0 Hz, 1H), 3.90 (br s, 4H), 3.69 (br s, 4H), 2.61-2.52 (m, 3H), 1.53-1.45 (m, 3H), 0.98-0.78 (m, 4H). [M+H]=399.3.

Example 36. 6-Methyl-N-(1-methylcyclopropyl)-5-[2-(trifluoromethyl)-5H,6H,7H-pyrrolo[3,4-d]pyrimidine-6-carbonyl]furo[2,3-d]pyrimidin-4-amine

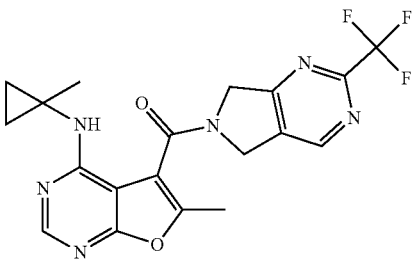 [SMILES: Cc1oc2ncnc(NC3(C)CC3)c2c1C(=O)N1Cc2cnc(C(F)(F)F)nc2C1]

¹H NMR (400 MHz, CD₃OD) δ 9.09-8.70 (m, 1H), 8.38 (s, 1H), 5.33-4.95 (m, 4H), 2.66 (s, 3H), 1.48 (s, 3H), 0.94-0.77 (m, 4H). [M+H]=419.3.

Example 37. 5-[2-(4-Fluorophenyl)-5H,6H,7H-pyrrolo[3,4-d]pyrimidine-6-carbonyl]-6-methyl-N-(1-methylcyclopropyl)furo[2,3-d]pyrimidin-4-amine

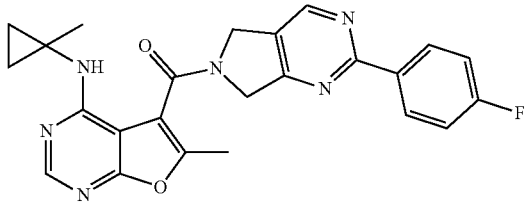 [SMILES: Cc1oc2ncnc(NC3(C)CC3)c2c1C(=O)N1Cc2cnc(-c3ccc(F)cc3)nc2C1]

¹H NMR (400 MHz, CD₃OD) δ 8.94-8.66 (m, 1H), 8.54-8.41 (m, 2H), 8.41-8.37 (m, 1H), 7.21 (t, J=8.0 Hz, 2H), 5.33-4.88 (m, 4H), 2.72-2.62 (m, 3H), 1.48 (s, 3H), 0.96-0.77 (m, 4H). [M+H]=445.4.

Example 38. 5-{3-[3-Fluoro-5-(trifluoromethyl)pyridin-2-yl]azetidine-1-carbonyl}-6-methyl-N-(1-methylcyclopropyl)furo[2,3-d]pyrimidin-4-amine

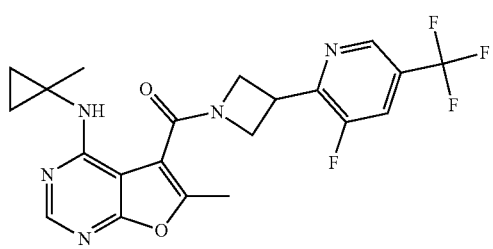 [SMILES: Cc1oc2ncnc(NC3(C)CC3)c2c1C(=O)N1CC(c2ncc(C(F)(F)F)cc2F)C1]

¹H NMR (400 MHz, CD₃OD) δ 8.79 (s, 1H), 8.37 (s, 1H), 7.99 (dd, J=1.7, 9.5 Hz, 1H), 4.73-4.62 (m, 2H), 4.61-4.32 (m, 3H), 2.63 (s, 3H), 1.53 (s, 3H), 1.02-0.81 (m, 4H). [M+H]=450.3.

Example 39. 6-Methyl-5-{2-methyl-5H,6H,7H,8H-pyrido[4,3-d]pyrimidine-6-carbonyl}-N-(1-methylcyclopropyl)furo[2,3-d]pyrimidin-4-amine

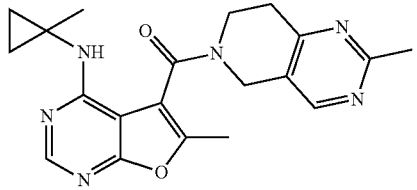 [SMILES: Cc1ncc2c(n1)CCN(C(=O)c1c(C)oc3ncnc(NC4(C)CC4)c13)C2]

¹H NMR (400 MHz, CD₃OD) δ 8.52 (br s, 1H), 8.39 (s, 1H), 4.89 (br s, 2H), 4.21-3.80 (m, 2H), 3.11-3.01 (m, 2H), 2.65 (s, 3H), 2.58 (s, 3H), 1.47 (s, 3H), 0.85 (s, 4H). [M+H]=379.3.

Example 40. 5-(5-Methoxy-1,2,3,4-tetrahydro-2,6-naphthyridine-2-carbonyl)-6-methyl-N-(1-methylcyclopropyl)furo[2,3-d]pyrimidin-4-amine

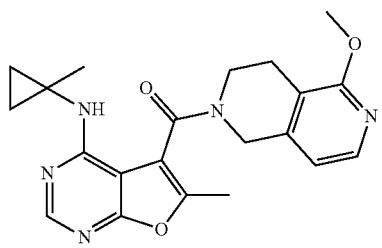 [SMILES: COc1nccc2c1CCN(C(=O)c1c(C)oc3ncnc(NC4(C)CC4)c13)C2]

¹H NMR (400 MHz, CD₃OD) δ 8.40 (s, 1H), 7.94 (d, J=5.4 Hz, 1H), 6.80 (br s, 1H), 4.83 (br s, 2H), 3.96 (s, 5H), 2.83 (t, J=5.0 Hz, 2H), 2.56 (s, 3H), 1.51-1.45 (m, 3H), 0.86 (s, 4H). [M+H]=394.3.

Example 41. 5-{2-tert-Butyl-5H,6H,7H,8H-pyrido[4,3-d]pyrimidine-6-carbonyl}-6-methyl-N-(1-methylcyclopropyl)furo[2,3-d]pyrimidin-4-amine

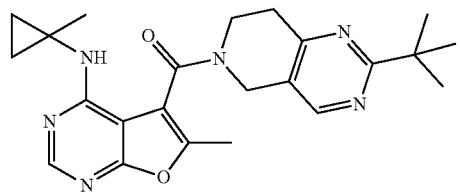 [SMILES: Cc1oc2ncnc(NC3(C)CC3)c2c1C(=O)N1CCc2nc(C(C)(C)C)ncc2C1]

¹H NMR (400 MHz, CD₃OD) δ 8.50 (br s, 1H), 8.38 (s, 1H), 4.86 (d, J=4.2 Hz, 2H), 4.03 (br s, 2H), 3.12-3.01 (m, 2H), 2.58 (s, 3H), 1.46 (s, 3H), 1.38 (s, 9H), 0.82 (s, 4H). [M+H]=421.4.

Example 42. 6-Methyl-N-(1-methylcyclopropyl)-5-[4-(pyridin-2-yl)piperazine-1-carbonyl]furo[2,3-d]pyrimidin-4-amine

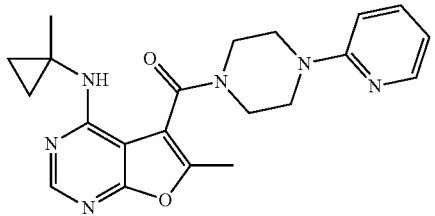 [SMILES: Cc1oc2ncnc(NC3(C)CC3)c2c1C(=O)N1CCN(c2ccccn2)CC1]

¹H NMR (400 MHz, CD₃OD) δ 8.45-8.39 (m, 1H), 8.09 (ddd, J=1.7, 7.2, 9.2 Hz, 1H), 8.02 (dd, J=1.3, 6.3 Hz, 1H), 7.41 (d, J=9.3 Hz, 1H), 7.14-6.98 (m, 1H), 3.96 (d, J=4.3 Hz, 4H), 3.92-3.81 (m, 4H), 2.63-2.55 (m, 3H), 1.52 (s, 3H), 1.00-0.86 (m, 4H). [M+H]=393.4.

Example 43. 5-[4-(5-Fluoropyridin-2-yl)piperazine-1-carbonyl]-6-methyl-N-(1-methylcyclopropyl)furo[2,3-d]pyrimidin-4-amine

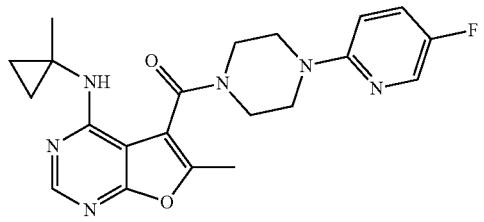 [SMILES: Cc1oc2ncnc(NC3(C)CC3)c2c1C(=O)N1CCN(c2ccc(F)cn2)CC1]

¹H NMR (400 MHz, CD₃OD) δ 8.46-8.41 (m, 1H), 8.09-8.00 (m, 1H), 7.52 (ddd, J=3.1, 7.9, 9.4 Hz, 1H), 6.97 (dd, J=3.4, 9.4 Hz, 1H), 3.84 (br s, 4H), 3.63 (br s, 4H), 2.59 (s, 3H), 1.52 (s, 3H), 1.03-0.84 (m, 4H). [M+H]=411.3.

Example 44. 6-Methyl-N-(1-methylcyclopropyl)-5-[4-(5-methylpyridin-2-yl)piperazine-1-carbonyl]furo[2,3-d]pyrimidin-4-amine

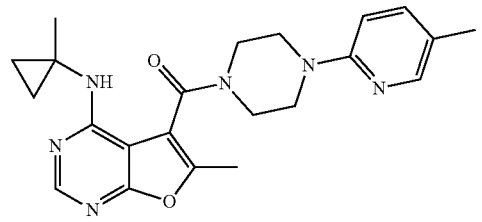 [SMILES: Cc1ccc(N2CCN(C(=O)c3c(C)oc4ncnc(NC5(C)CC5)c34)CC2)nc1]

¹H NMR (400 MHz, CD₃OD) δ 8.40 (s, 1H), 7.99 (dd, J=2.1, 9.4 Hz, 1H), 7.84 (s, 1H), 7.35 (d, J=9.4 Hz, 1H), 3.95 (br s, 4H), 3.83 (br s, 4H), 2.59 (s, 3H), 2.32 (s, 3H), 1.56-1.49 (m, 3H), 0.97-0.78 (m, 4H). [M+H]=407.4.

Example 45. 5-{2-Methoxy-5H,6H,7H,8H-pyrido[4,3-d]pyrimidine-6-carbonyl}-6-methyl-N-(1-methylcyclopropyl)furo[2,3-d]pyrimidin-4-amine

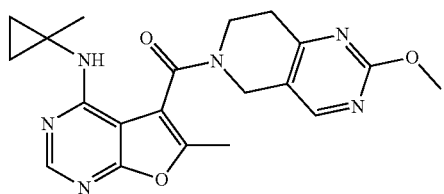 [SMILES: COc1ncc2c(n1)CCN(C(=O)c1c(C)oc3ncnc(NC4(C)CC4)c13)C2]

¹H NMR (400 MHz, CD₃OD) δ 8.49 (s, 1H), 8.41 (br s, 1H), 4.11-3.92 (m, 5H), 3.35 (d, J=1.7 Hz, 2H), 3.12-2.98 (m, 2H), 2.63 (s, 3H), 1.51 (s, 3H), 1.02-0.94 (m, 4H). [M+H]=395.3.

Example 46. 6-Methyl-4-[(1-methylcyclopropyl)amino]-N-[5-(morpholin-4-yl)pyridin-2-yl]furo[2,3-d]pyrimidine-5-carboxamide

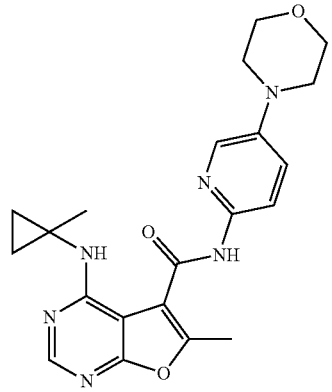 [SMILES: Cc1oc2ncnc(NC3(C)CC3)c2c1C(=O)Nc1ccc(N2CCOCC2)cn1]

¹H NMR (400 MHz, CD₃OD) δ 8.41 (s, 1H), 8.03 (d, J=2.9 Hz, 1H), 7.87 (d, J=9.3 Hz, 1H), 7.75 (dd, J=3.1, 9.3 Hz, 1H), 3.90-3.83 (m, 4H), 3.28-3.23 (m, 4H), 2.80 (s, 3H), 1.52 (s, 3H), 1.01-0.85 (m, 4H). [M+H]=409.4.

Example 47. 4-(4-{6-Methyl-4-[(1-methylcyclopropyl)amino]furo[2,3-d]pyrimidine-5-carbonyl}piperazin-1-yl)benzonitrile

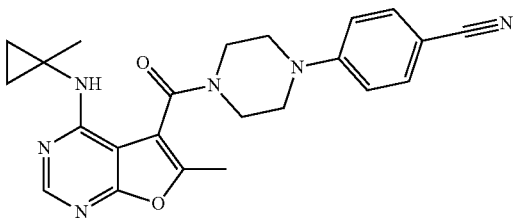 [SMILES: Cc1oc2ncnc(NC3(C)CC3)c2c1C(=O)N1CCN(c2ccc(C#N)cc2)CC1]

¹H NMR (400 MHz, CD₃OD) δ 8.39 (s, 1H), 7.62-7.50 (m, 2H), 7.05 (d, J=9.0 Hz, 2H), 3.85 (br s, 4H), 3.60-3.41 (m, 4H), 2.56 (s, 3H), 1.50 (s, 3H), 0.97-0.82 (m, 4H). [M+H]=417.4.

Example 48. N-[(4-Fluorophenyl)methyl]-6-methyl-4-[(1-methylcyclopropyl)amino]furo[2,3-d]pyrimidine-5-carboxamide

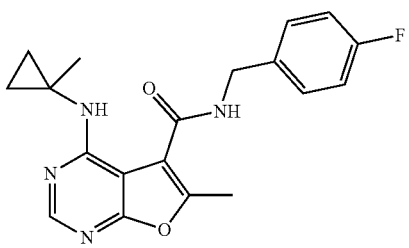 [SMILES: Cc1oc2ncnc(NC3(C)CC3)c2c1C(=O)NCc1ccc(F)cc1]

¹H NMR (400 MHz, CD₃OD) δ 8.33 (s, 1H), 7.46-7.36 (m, 2H), 7.14-7.02 (m, 2H), 4.63-4.53 (m, 2H), 2.65 (s, 3H), 1.50 (s, 3H), 0.92-0.81 (m, 4H). [M+H]=355.3.

Example 49. N-[(5-Fluoropyridin-2-yl)methyl]-6-methyl-4-[(1-methylcyclopropyl)amino]furo[2,3-d]pyrimidine-5-carboxamide

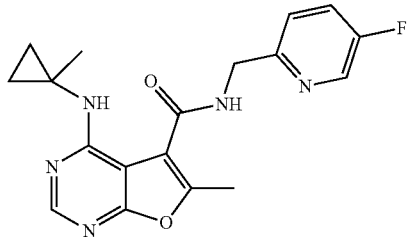 [SMILES: Cc1oc2ncnc(NC3(C)CC3)c2c1C(=O)NCc1ccc(F)cn1]

¹H NMR (400 MHz, CD₃OD) δ 8.46 (d, J=2.9 Hz, 1H), 8.38 (s, 1H), 7.70-7.61 (m, 1H), 7.52 (dd, J=4.4, 8.7 Hz, 1H), 4.73 (s, 2H), 2.77 (s, 3H), 1.52 (s, 3H), 0.99-0.83 (m, 4H). [M+H]=356.2.

Example 50. N-[2-(4-Fluorophenyl)ethyl]-6-methyl-4-[(1-methylcyclopropyl)amino]furo[2,3-d]pyrimidine-5-carboxamide

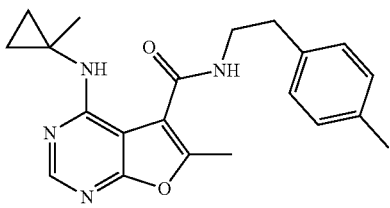 [SMILES: Cc1ccc(CCNC(=O)c2c(C)oc3ncnc(NC4(C)CC4)c23)cc1]

¹H NMR (400 MHz, CD₃OD) δ 8.32 (s, 1H), 8.19 (br s, 1H), 7.30 (dd, J=5.4, 8.6 Hz, 2H), 7.04 (t, J=8.8 Hz, 2H), 3.76-3.57 (m, 2H), 2.95 (t, J=7.1 Hz, 2H), 2.51 (s, 3H), 1.51 (s, 3H), 0.97-0.81 (m, 4H). [M+H]=369.3.

Example 51. N-[1-(5-Fluoropyridin-2-yl)ethyl]-6-methyl-4-[(1-methylcyclopropyl)amino]furo[2,3-d]pyrimidine-5-carboxamide

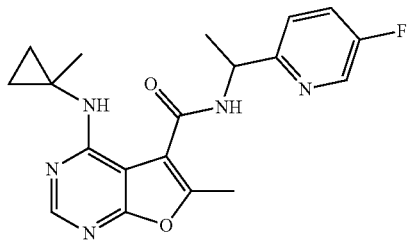 [SMILES: Cc1oc2ncnc(NC3(C)CC3)c2c1C(=O)NC(C)c1ccc(F)cn1]

¹H NMR (400 MHz, CD₃OD) δ 8.46 (d, J=2.8 Hz, 1H), 8.34 (s, 1H), 7.67-7.59 (m, 1H), 7.51 (dd, J=4.4, 8.7 Hz, 1H), 5.29 (q, J=7.0 Hz, 1H), 2.83-2.69 (m, 3H), 1.65-1.54 (m, 3H), 1.49 (s, 3H), 0.97-0.80 (m, 4H). [M+H]=370.3.

Example 52. N-[(4-Cyanophenyl)methyl]-6-methyl-4-[(1-methylcyclopropyl)amino]furo[2,3-d]pyrimidine-5-carboxamide

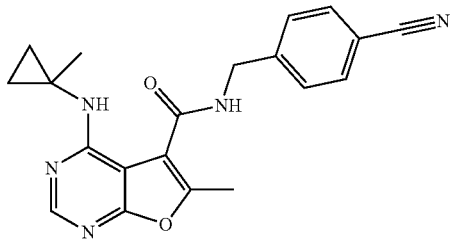 [SMILES: Cc1oc2ncnc(NC3(C)CC3)c2c1C(=O)NCc1ccc(C#N)cc1]

¹H NMR (400 MHz, CD₃OD) δ 8.36 (s, 1H), 7.74 (d, J=8.3 Hz, 2H), 7.57 (d, J=8.3 Hz, 2H), 4.68 (s, 2H), 2.79-2.68 (m, 3H), 1.56-1.46 (m, 3H), 0.94-0.82 (m, 4H). [M+H]=362.3.

Example 53. N-[(6-Methoxypyridin-2-yl)methyl]-6-methyl-4-[(1-methylcyclopropyl)amino]furo[2,3-d]pyrimidine-5-carboxamide

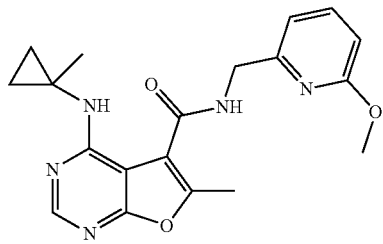 [SMILES: COc1cccc(CNC(=O)c2c(C)oc3ncnc(NC4(C)CC4)c23)n1]

¹H NMR (400 MHz, CD₃OD) δ 8.37 (s, 1H), 7.70-7.62 (m, 1H), 6.97 (d, J=7.3 Hz, 1H), 6.70 (d, J=8.2 Hz, 1H), 4.64 (s, 2H), 3.91 (s, 3H), 2.78 (s, 3H), 1.56-1.45 (m, 3H), 0.95-0.81 (m, 4H). [M+H]=368.3.

Example 54. N-[(6-Methoxypyridin-3-yl)methyl]-6-methyl-4-[(1-methylcyclopropyl)amino]furo[2,3-d]pyrimidine-5-carboxamide

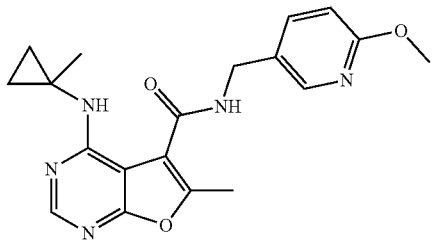 [SMILES: COc1ccc(CNC(=O)c2c(C)oc3ncnc(NC4(C)CC4)c23)cn1]

¹H NMR (400 MHz, CD₃OD) δ 8.37 (s, 1H), 8.18 (d, J=2.2 Hz, 1H), 7.77 (dd, J=2.4, 8.6 Hz, 1H), 6.84 (d, J=8.4 Hz, 1H), 4.54 (s, 2H), 3.92 (s, 3H), 2.72-2.64 (m, 3H), 1.51 (s, 3H), 0.97-0.86 (m, 4H). [M+H]=368.3.

Example 55. N-[(5-Methoxypyridin-2-yl)methyl]-6-methyl-4-[(1-methylcyclopropyl)amino]furo[2,3-d]pyrimidine-5-carboxamide

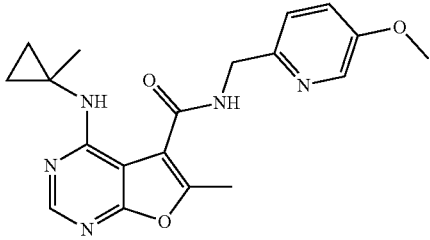 [SMILES: COc1ccc(CNC(=O)c2c(C)oc3ncnc(NC4(C)CC4)c23)nc1]

$^1$H NMR (400 MHz, CD$_3$OD) δ 8.38 (s, 1H), 8.35 (d, J=2.7 Hz, 1H), 7.76-7.70 (m, 1H), 7.67-7.62 (m, 1H), 4.75 (s, 2H), 3.96 (s, 3H), 2.77 (s, 3H), 1.51 (s, 3H), 0.94-0.86 (m, 4H). [M+H]=368.3.

Example 56. 5-[3-(4-Fluorophenyl)azetidine-1-carbonyl]-6-methyl-N-(1-methylcyclopropyl)furo[2,3-d]pyrimidin-4-amine

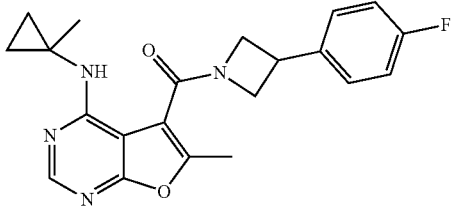 [SMILES: Cc1oc2ncnc(NC3(C)CC3)c2c1C(=O)N1CC(c2ccc(F)cc2)C1]

$^1$H NMR (400 MHz, CD$_3$OD) δ 8.36 (s, 1H), 7.45-7.37 (m, 2H), 7.14-7.06 (m, 2H), 4.72-4.60 (m, 2H), 4.26 (br s, 2H), 4.14-3.99 (m, 1H), 2.62 (s, 3H), 1.52 (s, 3H), 1.00-0.78 (m, 4H). [M+H]=381.3.

Example 57. 5-[3-(4-Fluorophenyl)pyrrolidine-1-carbonyl]-6-methyl-N-(1-methylcyclopropyl)furo[2,3-d]pyrimidin-4-amine

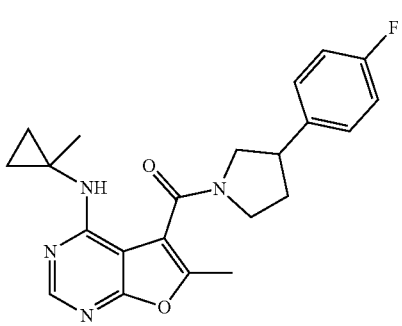 [SMILES: Cc1oc2ncnc(NC3(C)CC3)c2c1C(=O)N1CCC(c2ccc(F)cc2)C1]

$^1$H NMR (400 MHz, CD$_3$OD) δ 8.37 (s, 1H), 7.47-7.22 (m, 2H), 7.15-6.97 (m, 2H), 4.15-3.88 (m, 1H), 3.88-3.68 (m, 2H), 3.64-3.41 (m, 2H), 2.57 (d, J=14.8 Hz, 3H), 2.50-2.00 (m, 2H), 1.54-1.48 (m, 3H), 0.99-0.79 (m, 4H). [M+H]=395.4.

Example 58. 2-{6-Methyl-4-[(1-methylcyclopropyl)amino]furo[2,3-d]pyrimidine-5-carbonyl}-1,2,3,4-tetrahydroisoquinoline-6-carbonitrile

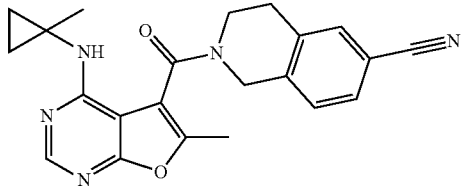 [SMILES: Cc1oc2ncnc(NC3(C)CC3)c2c1C(=O)N1CCc2cc(C#N)ccc2C1]

$^1$H NMR (400 MHz, CD$_3$OD) δ 8.39 (s, 1H), 7.61 (s, 1H), 7.56 (d, J=7.9 Hz, 1H), 7.37 (br s, 1H), 4.92 (br s, 2H), 3.94 (br s, 2H), 3.09-2.98 (m, 2H), 2.55 (s, 3H), 1.47 (s, 3H), 0.84 (br s, 4H). [M+H]=388.4.

Example 59. N-{[5-(Difluoromethoxy)pyridin-2-yl]methyl}-6-methyl-4-[(1-methylcyclopropyl)amino]furo[2,3-d]pyrimidine-5-carboxamide

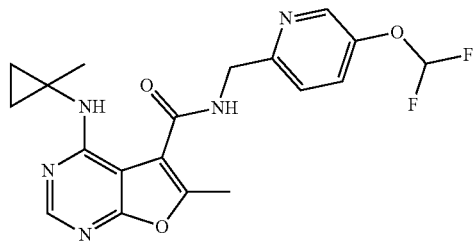 [SMILES: Cc1oc2ncnc(NC3(C)CC3)c2c1C(=O)NCc1ccc(OC(F)F)cn1]

$^1$H NMR (400 MHz, CD$_3$OD) δ 8.44 (d, J=2.7 Hz, 1H), 8.41 (s, 1H), 7.67 (dd, J=2.7, 8.6 Hz, 1H), 7.53 (d, J=8.6 Hz, 1H), 7.17-6.72 (m, 1H), 4.74 (s, 2H), 2.79 (s, 3H), 1.52 (s, 3H), 0.98-0.88 (m, 4H). [M+H]=404.3.

Example 60. 5-[4-(4-Fluorophenyl)piperidine-1-carbonyl]-6-methyl-N-(1-methylcyclopropyl)furo[2,3-d]pyrimidin-4-amine

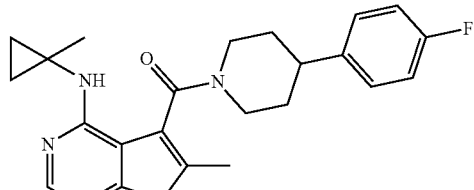

$^1$H NMR (400 MHz, CD$_3$OD) δ 8.36 (s, 1H), 7.26 (dd, J=5.6, 8.4 Hz, 2H), 7.02 (t, J=8.8 Hz, 2H), 5.08 (s, 1H), 4.74-3.39 (m, 1H), 3.22-2.65 (m, 3H), 2.55 (s, 3H), 1.95 (d, J=11.2 Hz, 2H), 1.68 (br s, 2H), 1.52 (s, 3H), 0.96-0.82 (m, 4H). [M+H]=409.4.

Example 61. 5-[4-(4-Fluorophenyl)piperazine-1-carbonyl]-6-methyl-N-(1-methylcyclopropyl)furo[2,3-d]pyrimidin-4-amine

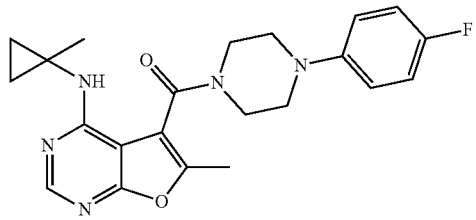 [SMILES: Cc1oc2ncnc(NC3(C)CC3)c2c1C(=O)N1CCN(c2ccc(F)cc2)CC1]

¹H NMR (400 MHz, CD₃OD) δ 8.38 (s, 1H), 7.05-6.97 (m, 4H), 3.85 (br s, 4H), 3.26-3.11 (m, 4H), 2.56 (s, 3H), 1.50 (s, 3H), 0.94-0.84 (m, 4H). [M+H]=410.4.

Example 62. 5-[4-Fluoro-4-(pyridin-2-yl)piperidine-1-carbonyl]-6-methyl-N-(1-methylcyclopropyl)furo[2,3-d]pyrimidin-4-amine

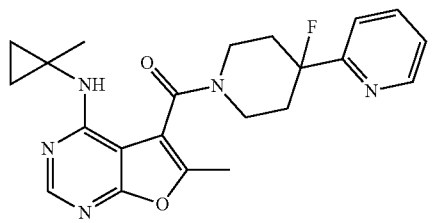 [SMILES: Cc1oc2ncnc(NC3(C)CC3)c2c1C(=O)N1CCC(F)(c2ccccn2)CC1]

¹H NMR (400 MHz, CD₃OD) δ 8.53 (d, J=4.9 Hz, 1H), 8.40 (s, 1H), 7.90 (dt, J=1.7, 7.8 Hz, 1H), 7.67 (d, J=7.9 Hz, 1H), 7.37 (ddd, J=1.0, 5.0, 7.5 Hz, 1H), 2.58 (s, 4H), 2.51-2.17 (m, 3H), 2.10-1.84 (m, 2H), 1.52 (s, 4H), 1.07-0.86 (m, 5H). [M+H]=410.4.

Example 63. 4-(4-Fluorophenyl)-1-{6-methyl-4-[(1-methylcyclopropyl)amino]furo[2,3-d]pyrimidine-5-carbonyl}piperidin-4-ol

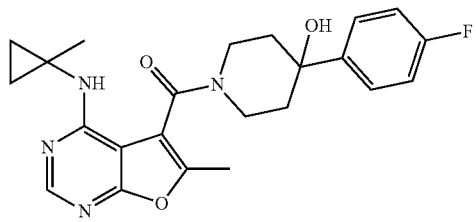

¹H NMR (400 MHz, CD₃OD) δ 8.38 (s, 1H), 7.53 (dd, J=5.2, 8.7 Hz, 2H), 7.07 (t, J=8.9 Hz, 2H), 4.72-3.41 (m, 4H), 2.56 (s, 3H), 2.17-1.94 (m, 2H), 1.87 (br s, 2H), 1.53 (s, 3H), 0.99-0.83 (m, 4H). [M+H]=425.4.

Example 64. 1-(3,4-Difluorophenyl)-4-{6-methyl-4-[(1-methylcyclopropyl)amino]furo[2,3-d]pyrimidine-5-carbonyl}piperazin-2-one

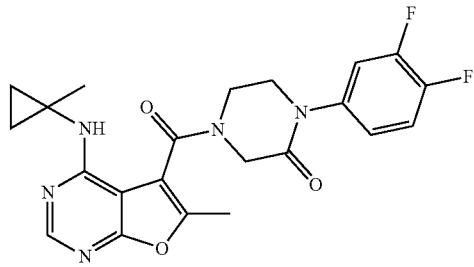 [SMILES: Cc1oc2ncnc(NC3(C)CC3)c2c1C(=O)N1CCN(c2ccc(F)c(F)c2)C(=O)C1]

¹H NMR (400 MHz, CD₃OD) δ 8.69 (s, 1H), 8.38 (s, 1H), 7.94 (dd, J=1.9, 8.4 Hz, 1H), 7.43 (d, J=8.3 Hz, 1H), 4.39 (br s, 1H), 4.07-3.62 (m, 3H), 2.58 (s, 3H), 2.32 (br s, 2H), 2.01 (t, J=3.2 Hz, 1H), 1.54 (s, 3H), 1.03-0.83 (m, 4H). [M+H]=442.4.

Example 65. 6-Methyl-N-(1-methylcyclopropyl)-5-[(1R,5S,6S)-6-[5-(trifluoromethyl)pyridin-2-yl]-3-azabicyclo[3.1.0]hexane-3-carbonyl]furo[2,3-d]pyrimidin-4-amine

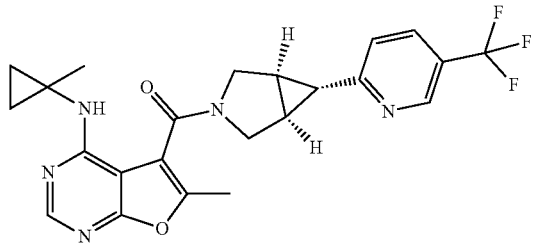 [SMILES: Cc1oc2ncnc(NC3(C)CC3)c2c1C(=O)N1C[C@@H]2[C@H](C1)[C@H]2c1ccc(C(F)(F)F)cn1]

¹H NMR (400 MHz, CD₃OD) δ 8.69 (s, 1H), 8.38 (s, 1H), 7.94 (dd, J=1.9, 8.4 Hz, 1H), 7.43 (d, J=8.3 Hz, 1H), 4.39 (br s, 1H), 4.07-3.62 (m, 3H), 2.58 (s, 3H), 2.32 (br s, 2H), 2.01 (t, J=3.2 Hz, 1H), 1.54 (s, 3H), 1.03-0.83 (m, 4H). [M+H]=458.4.

Example 66. N-[(3-Cyanophenyl)methyl]-6-methyl-4-[(1-methylcyclopropyl)amino]furo[2,3-d]pyrimidine-5-carboxamide

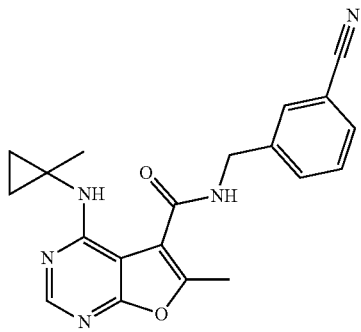 [SMILES: Cc1oc2ncnc(NC3(C)CC3)c2c1C(=O)NCc1cccc(C#N)c1]

¹H NMR (400 MHz, CD₃OD) δ 8.36 (s, 1H), 7.76 (s, 1H), 7.71 (d, J=7.8 Hz, 1H), 7.66 (d, J=7.8 Hz, 1H), 7.59-7.52 (m, 1H), 4.64 (s, 2H), 2.71 (s, 3H), 1.50 (s, 3H), 0.94-0.84 (m, 4H). [M+H]=362.3.

Example 67. 3-(4-Fluorophenyl)-1-{6-methyl-4-[(1-methylcyclopropyl)amino]furo[2,3-d]pyrimidine-5-carbonyl}pyrrolidin-3-ol

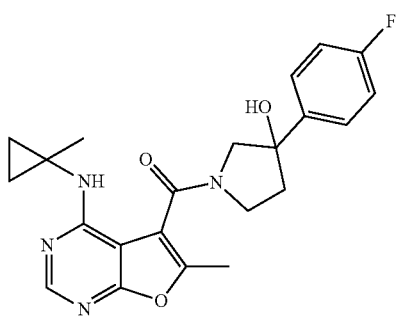 [SMILES: Cc1oc2ncnc(NC3(C)CC3)c2c1C(=O)N1CCC(O)(c2ccc(F)cc2)C1]

¹H NMR (400 MHz, CD₃OD) δ 8.39 (s, 1H), 7.68-7.46 (m, 2H), 7.10 (td, J=8.6, 17.3 Hz, 2H), 4.22-3.58 (m, 4H), 2.65-2.15 (m, 5H), 1.60-1.44 (m, 3H), 1.02-0.83 (m, 4H). [M+H]=411.3.

Example 68. N-[1-(4-Fluorophenyl)ethyl]-6-methyl-4-[(1-methylcyclopropyl)amino]furo[2,3-d]pyrimidine-5-carboxamide

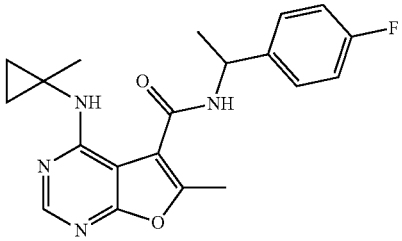 [SMILES: Cc1oc2ncnc(NC3(C)CC3)c2c1C(=O)NC(C)c1ccc(F)cc1]

¹H NMR (400 MHz, CD₃OD) δ 8.62 (d, J=7.7 Hz, 1H), 8.32 (s, 1H), 7.52-7.36 (m, 2H), 7.16-7.02 (m, 2H), 5.28-5.14 (m, 1H), 2.66 (s, 3H), 1.58 (d, J=7.0 Hz, 3H), 1.47 (s, 3H), 0.89-0.73 (m, 4H). [M+H]=369.3.

Example 69. N-[1-(4-Fluorophenyl)cyclopropyl]-6-methyl-4-[(1-methylcyclopropyl)amino]furo[2,3-d]pyrimidine-5-carboxamide

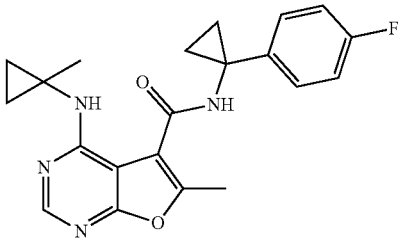 [SMILES: Cc1oc2ncnc(NC3(C)CC3)c2c1C(=O)NC1(c2ccc(F)cc2)CC1]

¹H NMR (400 MHz, CD₃OD) δ 9.08 (s, 1H), 8.34 (s, 1H), 7.41-7.34 (m, 2H), 7.10-7.00 (m, 2H), 2.67 (s, 3H), 1.48 (s, 3H), 1.39-1.31 (m, 4H), 0.83 (s, 4H). [M+H]=381.1.

Example 70. 6-Methyl-N-(1-methylcyclopropyl)-5-[3-(pyridin-2-yl)pyrrolidine-1-carbonyl]furo[2,3-d]pyrimidin-4-amine

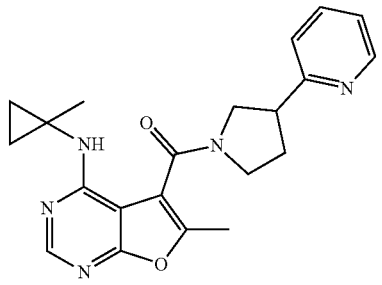 [SMILES: Cc1oc2ncnc(NC3(C)CC3)c2c1C(=O)N1CCC(c2ccccn2)C1]

¹H NMR (400 MHz, CD₃OD) δ 8.80-8.61 (m, 1H), 8.40 (s, 1H), 8.36-8.15 (m, 1H), 7.96-7.62 (m, 2H), 4.23-4.03 (m, 1H), 4.01-3.75 (m, 4H), 2.65-2.44 (m, 4H), 2.30 (d, J=18.2 Hz, 1H), 1.52 (s, 3H), 1.02-0.86 (m, 4H). [M+H]=378.3.

Example 71. 6-Methyl-N-(1-methylcyclopropyl)-5-[3-(pyridin-3-yl)pyrrolidine-1-carbonyl]furo[2,3-d]pyrimidin-4-amine

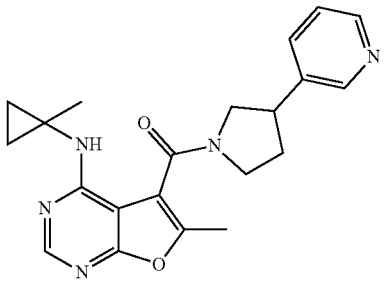 [SMILES: Cc1oc2ncnc(NC3(C)CC3)c2c1C(=O)N1CCC(c2cccnc2)C1]

¹H NMR (400 MHz, CD₃OD) δ 9.00-8.73 (m, 2H), 8.70-8.54 (m, 1H), 8.41 (s, 1H), 8.18-7.96 (m, 1H), 4.30-4.07 (m, 1H), 4.04-3.60 (m, 4H), 2.68-2.44 (m, 4H), 2.40-2.12 (m, 1H), 1.57-1.48 (m, 3H), 1.01-0.84 (m, 4H). [M+H]= 378.3.

Example 72. 6-Methyl-N-(1-methylcyclopropyl)-5-[3-(pyridin-4-yl)pyrrolidine-1-carbonyl]furo[2,3-d]pyrimidin-4-amine

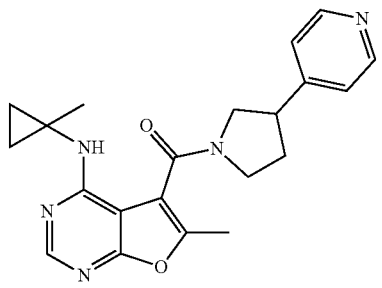 [SMILES: Cc1oc2ncnc(NC3(C)CC3)c2c1C(=O)N1CCC(c2ccncc2)C1]

¹H NMR (400 MHz, CD₃OD) δ 8.79 (br s, 2H), 8.36 (s, 1H), 8.18-7.92 (m, 2H), 4.31-4.03 (m, 1H), 3.82 (br s, 4H), 2.58 (br s, 4H), 2.39-2.08 (m, 1H), 1.50 (s, 3H), 0.96-0.78 (m, 4H). [M+H]=378.3.

Example 73. 6-Methyl-4-[(1-methylcyclopropyl)amino]-N-(1,3-thiazol-2-ylmethyl)furo[2,3-d]pyrimidine-5-carboxamide

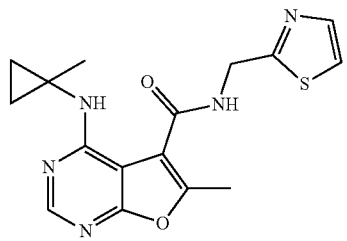 [SMILES: Cc1oc2ncnc(NC3(C)CC3)c2c1C(=O)NCc1nccs1]

¹H NMR (400 MHz, CD₃OD) δ 8.45-8.38 (m, 1H), 7.81-7.75 (m, 1H), 7.60-7.57 (m, 1H), 4.97-4.90 (m, 2H), 2.81-2.74 (m, 3H), 1.52 (s, 3H), 1.02-0.88 (m, 4H). [M+H]=344.2.

Example 74. 6-Methyl-4-[(1-methylcyclopropyl)amino]-N-(1,3-thiazol-5-ylmethyl)furo[2,3-d]pyrimidine-5-carboxamide

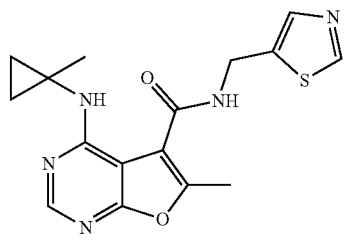 [SMILES: Cc1oc2ncnc(NC3(C)CC3)c2c1C(=O)NCc1cncs1]

¹H NMR (400 MHz, CD₃OD) δ 8.99 (s, 1H), 8.40 (s, 1H), 7.89 (s, 1H), 4.83 (s, 2H), 2.74-2.66 (m, 3H), 1.53 (s, 3H), 1.06-0.89 (m, 4H). [M+H]=344.2.

Example 75. 6-Methyl-4-[(1-methylcyclopropyl)amino]-N-(1,3-thiazol-4-ylmethyl)furo[2,3-d]pyrimidine-5-carboxamide

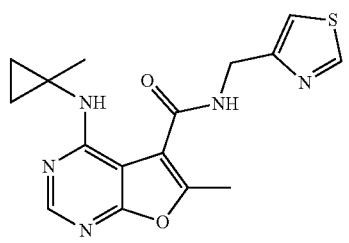 [SMILES: Cc1oc2ncnc(NC3(C)CC3)c2c1C(=O)NCc1cscn1]

¹H NMR (400 MHz, CD₃OD) δ 9.02 (d, J=2.0 Hz, 1H), 8.44-8.40 (m, 1H), 7.58-7.49 (m, 1H), 4.77 (s, 2H), 2.74 (s, 3H), 1.52 (s, 3H), 1.03-0.92 (m, 4H). [M+H]=344.2.

Example 76. 6-Methyl-4-[(1-methylcyclopropyl)amino]-N-(pyridin-2-ylmethyl)furo[2,3-d]pyrimidine-5-carboxamide

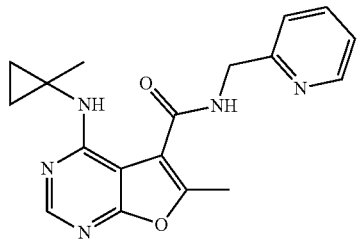 [SMILES: Cc1oc2ncnc(NC3(C)CC3)c2c1C(=O)NCc1ccccn1]

¹H NMR (400 MHz, CD₃OD) δ 8.71 (d, J=5.4 Hz, 1H), 8.40-8.37 (m, 1H), 8.30 (dt, J=1.5, 7.9 Hz, 1H), 7.86 (d, J=7.9 Hz, 1H), 7.80-7.71 (m, 1H), 4.87 (br s, 2H), 2.84-2.78 (m, 3H), 1.49 (s, 3H), 0.88 (d, J=3.4 Hz, 4H). [M+H]=338.2.

Example 77. 6-Methyl-4-[(1-methylcyclopropyl)amino]-N-[1-(pyridin-2-yl)ethyl]furo[2,3-d]pyrimidine-5-carboxamide

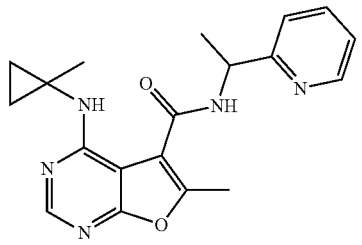 [SMILES: Cc1oc2ncnc(NC3(C)CC3)c2c1C(=O)NC(C)c1ccccn1]

¹H NMR (400 MHz, CD₃OD) δ 8.68 (d, J=4.6 Hz, 1H), 8.38-8.35 (m, 1H), 8.19 (dt, J=1.6, 7.8 Hz, 1H), 7.78 (d, J=7.9 Hz, 1H), 7.64 (ddd, J=1.0, 6.0, 7.0 Hz, 1H), 5.33 (q, J=7.0 Hz, 1H), 2.78 (s, 3H), 1.67 (d, J=7.1 Hz, 3H), 1.47 (s, 3H), 0.91-0.76 (m, 4H). [M+H]=352.3.

Example 78. 6-Methyl-4-[(1-methylcyclopropyl)amino]-N-[2-(pyridin-2-yl)propan-2-yl]furo[2,3-d]pyrimidine-5-carboxamide

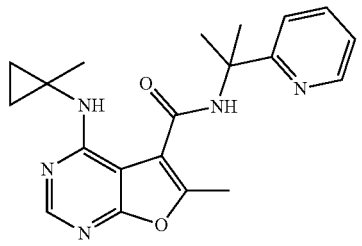 [SMILES: Cc1oc2ncnc(NC3(C)CC3)c2c1C(=O)NC(C)(C)c1ccccn1]

¹H NMR (400 MHz, CD₃OD) δ 8.65 (dd, J=0.9, 5.3 Hz, 1H), 8.40-8.34 (m, 1H), 8.20 (dt, J=1.6, 7.9 Hz, 1H), 7.87 (d, J=8.2 Hz, 1H), 7.68-7.57 (m, 1H), 2.81 (s, 3H), 1.86 (s, 6H), 1.46 (s, 3H), 0.90-0.78 (m, 4H). [M+H]=366.3.

Example 79. 6-Methyl-4-[(1-methylcyclopropyl)amino]-N-[1-(pyridin-2-yl)cyclopropyl]furo[2,3-d]pyrimidine-5-carboxamide

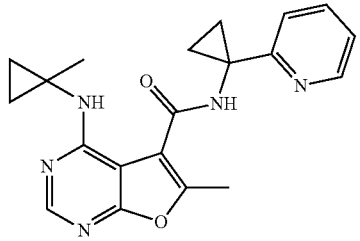 [SMILES: Cc1oc2ncnc(NC3(C)CC3)c2c1C(=O)NC1(c2ccccn2)CC1]

$^1$H NMR (400 MHz, CD$_3$OD) δ 8.59 (dd, J=0.9, 5.4 Hz, 1H), 8.43-8.36 (m, 1H), 8.14 (dt, J=1.7, 7.9 Hz, 1H), 7.65 (d, J=8.2 Hz, 1H), 7.57 (ddd, J=0.9, 6.0, 6.9 Hz, 1H), 2.75 (s, 3H), 1.82-1.73 (m, 2H), 1.67-1.59 (m, 2H), 1.52-1.46 (m, 3H), 0.85 (s, 4H). [M+H]=364.3.

Example 80. N,6-Dimethyl-4-[(1-methylcyclopropyl)amino]furo[2,3-d]pyrimidine-5-carboxamide

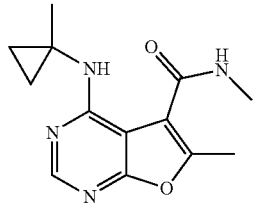 [SMILES: CNC(=O)c1c(C)oc2ncnc(NC3(C)CC3)c12]

$^1$H NMR (400 MHz, CD$_3$OD) δ 8.40 (s, 1H), 3.00-2.93 (m, 3H), 2.70 (s, 3H), 1.52 (s, 3H), 1.03-0.91 (m, 4H). [M+H]=261.1.

Example 81. N,N,6-Trimethyl-4-[(1-methylcyclopropyl)amino]furo[2,3-d]pyrimidine-5-carboxamide

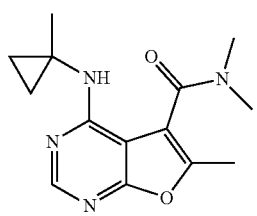 [SMILES: Cc1oc2ncnc(NC3(C)CC3)c2c1C(=O)N(C)C]

$^1$H NMR (400 MHz, CD$_3$OD) δ 8.40 (s, 1H), 3.15 (s, 6H), 2.58-2.48 (m, 3H), 1.51 (s, 3H), 1.00-0.85 (m, 4H). [M+H]=275.1.

Example 82. N-Ethyl-6-methyl-4-[(1-methylcyclopropyl)amino]furo[2,3-d]pyrimidine-5-carboxamide

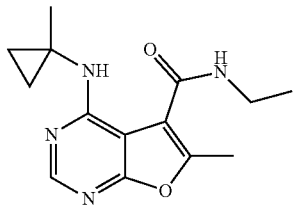 [SMILES: CCNC(=O)c1c(C)oc2ncnc(NC3(C)CC3)c12]

$^1$H NMR (400 MHz, CD$_3$OD) δ 8.38 (s, 1H), 3.52-3.39 (m, 2H), 2.73-2.66 (m, 3H), 1.52 (s, 3H), 1.26 (t, J=7.3 Hz, 3H), 1.01-0.89 (m, 4H). [M+H]=275.1.

Example 83. 6-Methyl-4-[(1-methylcyclopropyl)amino]-N-(oxetan-3-yl)furo[2,3-d]pyrimidine-5-carboxamide

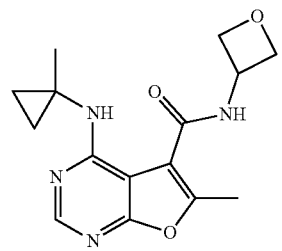 [SMILES: Cc1oc2ncnc(NC3(C)CC3)c2c1C(=O)NC1COC1]

$^1$H NMR (400 MHz, CD$_3$OD) δ 8.38 (s, 1H), 3.52-3.39 (m, 2H), 2.73-2.66 (m, 3H), 1.52 (s, 3H), 1.26 (t, J=7.3 Hz, 3H), 1.01-0.89 (m, 4H). [M+H]=303.1.

Example 84. N-(5-Fluoropyridin-2-yl)-6-methyl-4-[(1-methylcyclopropyl)amino]furo[2,3-d]pyrimidine-5-carboxamide

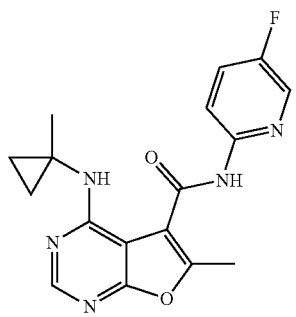 [SMILES: Cc1oc2ncnc(NC3(C)CC3)c2c1C(=O)Nc1ccc(F)cn1]

$^1$H NMR (400 MHz, CD$_3$OD) δ 8.39 (s, 1H), 8.28 (d, J=2.9 Hz, 1H), 8.21 (dd, J=4.0, 9.2 Hz, 1H), 7.68 (ddd, J=3.1, 8.0, 9.1 Hz, 1H), 2.78 (s, 3H), 1.51 (s, 3H), 0.96-0.92 (m, 2H), 0.90-0.86 (m, 2H). [M+H]=342.

Example 85. 5-[3-(4-Fluorophenyl)-3-methylpyrrolidine-1-carbonyl]-6-methyl-N-(1-methylcyclopropyl)furo[2,3-d]pyrimidin-4-amine

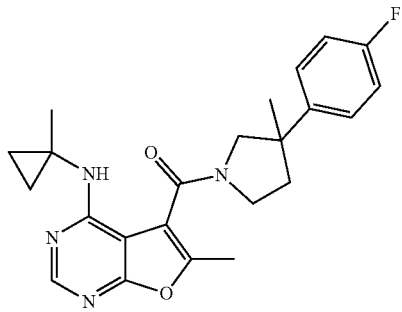 [SMILES: Cc1oc2ncnc(NC3(C)CC3)c2c1C(=O)N1CCC(C)(c2ccc(F)cc2)C1]

¹H NMR (400 MHz, CD₃OD) δ 8.39 (s, 1H), 7.40 (d, J=5.3 Hz, 1H), 7.27 (dd, J=5.3, 8.2 Hz, 1H), 7.15-7.04 (m, 1H), 7.04-6.94 (m, 1H), 4.04-3.54 (m, 4H), 4.04-3.54 (m, 4H), 2.62-2.49 (m, 3H), 2.48-2.14 (m, 2H), 1.51-1.43 (m, 4H), 1.30 (s, 2H), 0.96-0.75 (m, 4H). [M+H]=409.1.

Example 86. 6-Methyl-4-[(1-methylcyclopropyl)amino]-N-[1-(trifluoromethyl)cyclopropyl]furo[2,3-d]pyrimidine-5-carboxamide

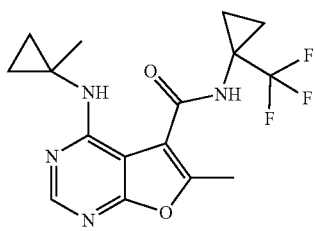 [SMILES: Cc1oc2ncnc(NC3(C)CC3)c2c1C(=O)NC1(C(F)(F)F)CC1]

¹H NMR (400 MHz, CD₃OD) δ 8.39 (s, 1H), 2.67 (s, 3H), 1.51 (s, 3H), 1.48-1.37 (m, 2H), 1.34-1.25 (m, 2H), 1.00-0.85 (m, 4H). [M+H]=355.1.

Example 87. N-[(4-Cyano-3-fluorophenyl)methyl]-6-methyl-4-[(1-methylcyclopropyl)amino]furo[2,3-d]pyrimidine-5-carboxamide

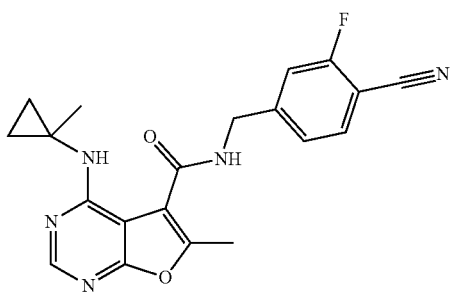 [SMILES: Cc1oc2ncnc(NC3(C)CC3)c2c1C(=O)NCc1ccc(C#N)c(F)c1]

¹H NMR (400 MHz, CD₃OD) δ 8.35 (s, 1H), 7.81-7.70 (m, 1H), 7.38 (d, J=9.0 Hz, 2H), 4.69-4.65 (m, 2H), 2.72 (s, 3H), 1.49 (s, 3H), 0.92-0.80 (m, 4H). [M+H]=380.

Example 88. N-[(3-Cyano-4-fluorophenyl)methyl]-6-methyl-4-[(1-methylcyclopropyl)amino]furo[2,3-d]pyrimidine-5-carboxamide

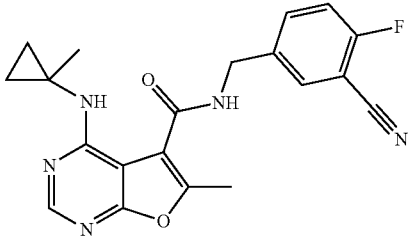 [SMILES: Cc1oc2ncnc(NC3(C)CC3)c2c1C(=O)NCc1ccc(F)c(C#N)c1]

¹H NMR (400 MHz, CD₃OD) δ 8.34 (s, 1H), 7.84-7.73 (m, 2H), 7.37 (t, J=8.9 Hz, 1H), 4.65-4.57 (m, 2H), 2.70 (s, 3H), 1.50 (s, 3H), 0.96-0.78 (m, 4H). [M+H]=380.0.

Example 89. 6-Methyl-N-(1-methylcyclopropyl)-4-[(1-methylcyclopropyl)amino]furo[2,3-d]pyrimidine-5-carboxamide

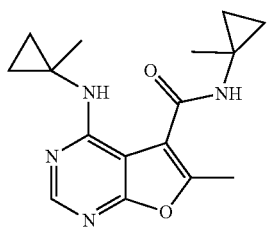 [SMILES: Cc1oc2ncnc(NC3(C)CC3)c2c1C(=O)NC1(C)CC1]

¹H NMR (400 MHz, CD₃OD) δ 8.52 (br s, 1H), 8.36 (s, 1H), 2.65-2.59 (m, 3H), 1.52 (s, 3H), 1.46 (s, 3H), 0.99-0.90 (m, 4H), 0.89-0.85 (m, 2H), 0.76-0.72 (m, 2H). [M+H]=301.1.

Example 90. 6-Methyl-4-[(1-methylcyclopropyl)amino]-N-(oxetan-3-ylmethyl)furo[2,3-d]pyrimidine-5-carboxamide

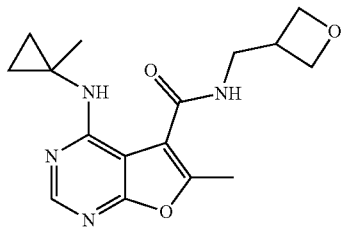 [SMILES: Cc1oc2ncnc(NC3(C)CC3)c2c1C(=O)NCC1COC1]

¹H NMR (400 MHz, CD₃OD) δ 8.46 (s, 1H), 8.28 (s, 1H), 4.88 (s, 2H), 4.60-4.51 (m, 2H), 3.72 (d, J=6.6 Hz, 2H), 3.38-3.34 (m, 1H), 2.65 (s, 3H), 1.51 (s, 3H), 0.88-0.73 (m, 4H). [M+H]=317.1.

Example 91. N-(1-Cyanocyclobutyl)-6-methyl-4-[(1-methylcyclopropyl)amino]furo[2,3-d]pyrimidine-5-carboxamide

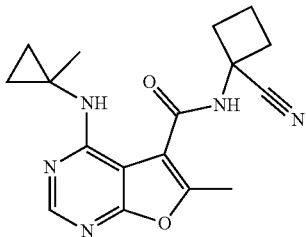 [SMILES: Cc1oc2ncnc(NC3(C)CC3)c2c1C(=O)NC1(C#N)CCC1]

$^1$H NMR (400 MHz, CD$_3$OD) δ 8.39 (s, 1H), 2.87-2.77 (m, 2H), 2.74 (s, 3H), 2.62-2.53 (m, 2H), 2.30-2.11 (m, 2H), 1.57-1.50 (m, 3H), 0.98-0.86 (m, 4H). [M+H]=326.1.

Example 92. 6-Methyl-4-[(1-methylcyclopropyl)amino]-N-(1,2-oxazol-3-ylmethyl)furo[2,3-d]pyrimidine-5-carboxamide

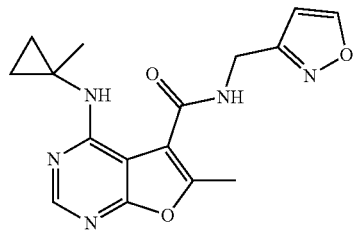 [SMILES: Cc1oc2ncnc(NC3(C)CC3)c2c1C(=O)NCc1ccon1]

$^1$H NMR (400 MHz, CD$_3$OD) δ 8.64 (d, J=1.7 Hz, 1H), 8.26 (s, 1H), 6.52 (d, J=1.7 Hz, 1H), 4.69 (s, 2H), 2.66 (s, 3H), 1.49 (s, 3H), 0.84-0.73 (m, 4H). [M+H]=328.1.

Example 93. 6-Methyl-4-[(1-methylcyclopropyl)amino]-N-[(3-methyloxetan-3-yl)methyl]furo[2,3-d]pyrimidine-5-carboxamide

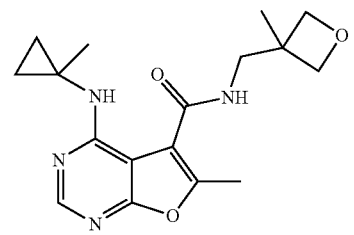 [SMILES: Cc1oc2ncnc(NC3(C)CC3)c2c1C(=O)NCC1(C)COC1]

$^1$H NMR (400 MHz, CD$_3$OD) δ 8.28 (s, 1H), 4.63 (d, J=6.1 Hz, 2H), 4.44 (d, J=6.0 Hz, 2H), 3.62 (s, 2H), 2.73-2.65 (m, 3H), 1.56-1.47 (m, 3H), 1.40 (s, 3H), 0.90-0.70 (m, 4H). [M+H]=331.1.

Example 94. N-[(3-Fluorooxetan-3-yl)methyl]-6-methyl-4-[(1-methylcyclopropyl)amino]furo[2,3-d]pyrimidine-5-carboxamide

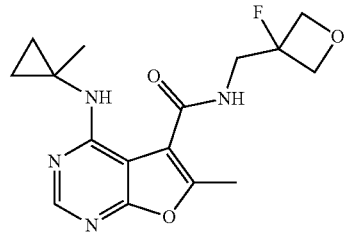 [SMILES: Cc1oc2ncnc(NC3(C)CC3)c2c1C(=O)NCC1(F)COC1]

$^1$H NMR (400 MHz, CD$_3$OD) δ 8.32 (s, 1H), 8.29-8.24 (m, 1H), 4.83-4.67 (m, 4H), 3.96 (d, J=19.4 Hz, 2H), 2.63 (s, 3H), 1.50 (s, 3H), 0.87-0.73 (m, 4H). [M+H]=335.1.

Example 95. N-(2-Methoxyethyl)-6-methyl-4-[(1-methylcyclopropyl)amino]furo[2,3-d]pyrimidine-5-carboxamide

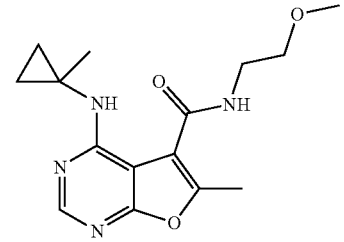 [SMILES: COCCNC(=O)c1c(C)oc2ncnc(NC3(C)CC3)c12]

$^1$H NMR (400 MHz, CDCl$_3$) δ 10.33 (br s, 1H), 8.60 (s, 1H), 6.76 (br s, 1H), 3.67 (q, J=5.1 Hz, 2H), 3.62-3.57 (m, 2H), 3.42 (s, 3H), 2.77-2.73 (m, 3H), 1.53 (s, 3H), 0.99-0.93 (m, 4H). [M+H]=305.1.

Example 96. 6-Methyl-4-[(1-methylcyclopropyl)amino]-N-[2-(morpholin-4-yl)ethyl]furo[2,3-d]pyrimidine-5-carboxamide

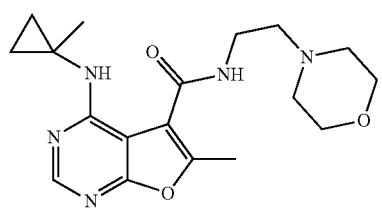 [SMILES: Cc1oc2ncnc(NC3(C)CC3)c2c1C(=O)NCCN1CCOCC1]

$^1$H NMR (400 MHz, CD$_3$OD) δ 8.52-8.34 (m, 1H), 4.25-3.58 (m, 8H), 3.48 (t, J=6.1 Hz, 2H), 3.33-3.13 (m, 2H), 2.76 (s, 3H), 1.54 (s, 3H), 1.02-0.90 (m, 4H). [M+H]=360.1.

Example 97. 6-Methyl-N-[(2-methyl-1,3-thiazol-4-yl)methyl]-4-[(1-methylcyclopropyl)amino]furo[2,3-d]pyrimidine-5-carboxamide

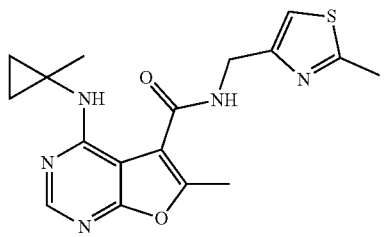

¹H NMR (400 MHz, CD₃OD) δ 8.43 (s, 1H), 7.31 (s, 1H), 4.69 (s, 2H), 2.76 (s, 3H), 2.73 (s, 3H), 1.54 (s, 3H), 1.10-0.90 (m, 4H). [M+H]=358.3.

Example 98. 6-Methyl-4-[(1-methylcyclopropyl)amino]-N-(1H-pyrrol-2-ylmethyl)furo[2,3-d]pyrimidine-5-carboxamide

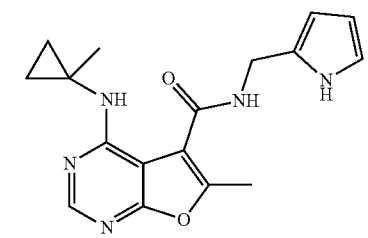 [SMILES: Cc1oc2ncnc(NC3(C)CC3)c2c1C(=O)NCc1ccc[nH]1]

¹H NMR (400 MHz, CD₃OD) δ 10.21 (br s, 1H), 8.38 (s, 1H), 6.77-6.62 (m, 1H), 6.09-5.97 (m, 2H), 4.57-4.51 (m, 2H), 2.66 (s, 3H), 1.53 (s, 3H), 1.04-0.88 (m, 4H). [M+H]=326.1.

Example 99. 6-Methyl-N-[(1-methyl-1H-pyrazol-3-yl)methyl]-4-[(1-methylcyclopropyl)amino]furo[2,3-d]pyrimidine-5-carboxamide

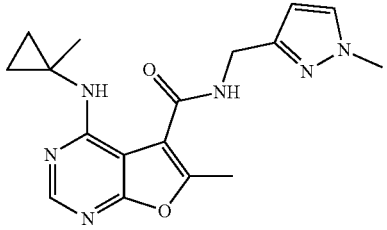 [SMILES: Cc1oc2ncnc(NC3(C)CC3)c2c1C(=O)NCc1ccn(C)n1]

¹H NMR (400 MHz, CD₃OD) δ 8.41 (s, 1H), 7.54 (d, J=2.1 Hz, 1H), 6.27 (d, J=2.2 Hz, 1H), 4.58 (s, 2H), 3.87 (s, 3H), 2.71 (s, 3H), 1.53 (s, 3H), 1.02-0.91 (m, 4H). [M+H]=341.1.

Example 100. 6-Methyl-4-[(1-methylcyclopropyl)amino]-N-(1,3-oxazol-4-ylmethyl)furo[2,3-d]pyrimidine-5-carboxamide

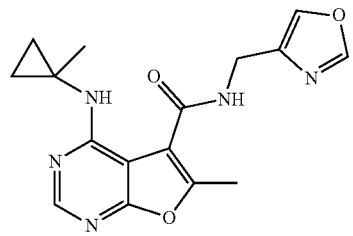 [SMILES: Cc1oc2ncnc(NC3(C)CC3)c2c1C(=O)NCc1cocn1]

¹H NMR (400 MHz, CD₃OD) δ 8.40 (s, 1H), 8.20 (s, 1H), 7.92 (d, J=0.9 Hz, 1H), 4.55 (s, 2H), 2.71 (s, 3H), 1.52 (s, 3H), 1.01-0.91 (m, 4H). [M+H]=328.

Example 101. 3-(4-Fluorophenyl)-1-{6-methyl-4-[(1-methylcyclopropyl)amino]furo[2,3-d]pyrimidine-5-carbonyl}azetidin-3-ol

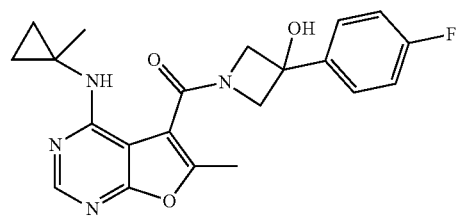 [SMILES: Cc1oc2ncnc(NC3(C)CC3)c2c1C(=O)N1CC(O)(c2ccc(F)cc2)C1]

¹H NMR (400 MHz, CD₃OD) δ 8.39 (s, 1H), 7.63-7.52 (m, 2H), 7.18-7.09 (m, 2H), 4.56 (d, J=11.1 Hz, 2H), 4.43-4.35 (m, 2H), 2.63 (s, 3H), 1.52 (s, 3H), 1.00-0.85 (m, 4H). [M+H]=397.1.

Example 102. 6-Methyl-N-[(1-methyl-1H-pyrazol-5-yl)methyl]-4-[(1-methylcyclopropyl)amino]furo[2,3-d]pyrimidine-5-carboxamide

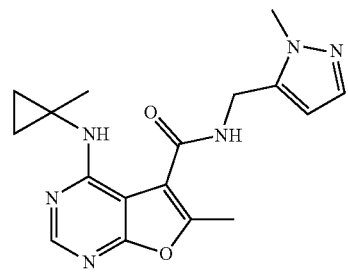 [SMILES: Cc1oc2ncnc(NC3(C)CC3)c2c1C(=O)NCc1ccnn1C]

¹H NMR (400 MHz, CD₃OD) δ 8.41 (s, 1H), 7.42 (d, J=2.0 Hz, 1H), 6.31 (d, J=1.8 Hz, 1H), 4.68 (s, 2H), 3.93 (s, 3H), 2.70 (s, 3H), 1.52 (s, 3H), 1.01-0.92 (m, 4H). [M+H]=341.1.

Example 103. 5-(3-Methoxy-3-phenylazetidine-1-carbonyl)-6-methyl-N-(1-methylcyclopropyl)furo[2,3-d]pyrimidin-4-amine

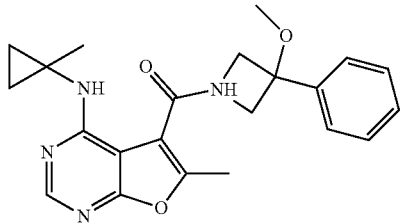 [SMILES: COC1(c2ccccc2)CN(C(=O)c2c(C)oc3ncnc(NC4(C)CC4)c23)C1]

$^1$H NMR (400 MHz, CD$_3$OD) δ 8.36 (s, 1H), 7.47-7.42 (m, 4H), 7.42-7.35 (m, 1H), 4.59-4.51 (m, 2H), 4.49-4.42 (m, 2H), 3.07 (s, 3H), 2.61 (s, 3H), 1.49 (s, 3H), 0.96-0.83 (m, 4H). [M+H]=393.2.

Example 104. 6-Methyl-N-(1-methylcyclobutyl)-4-[(1-methylcyclopropyl)amino]furo[2,3-d]pyrimidine-5-carboxamide

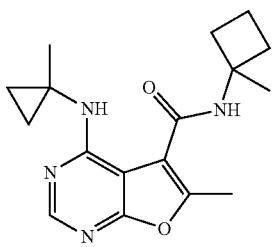 [SMILES: Cc1oc2ncnc(NC3(C)CC3)c2c1C(=O)NC1(C)CCC1]

$^1$H NMR (400 MHz, CD$_3$OD) δ 8.37 (s, 1H), 8.26 (br s, 1H), 2.69 (s, 3H), 2.46-2.35 (m, 2H), 2.21-2.09 (m, 2H), 2.01-1.89 (m, 2H), 1.58 (s, 3H), 1.52 (s, 3H), 0.99-0.86 (m, 4H). [M+H]=315.1.

Example 105. 6-Methyl-4-[(1-methylcyclopropyl)amino]-N-(3-methyloxetan-3-yl)furo[2,3-d]pyrimidine-5-carboxamide

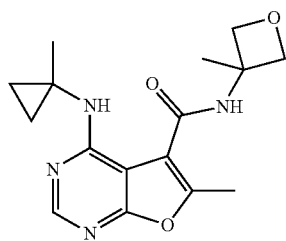 [SMILES: Cc1oc2ncnc(NC3(C)CC3)c2c1C(=O)NC1(C)COC1]

$^1$H NMR (400 MHz, CD$_3$OD) δ 8.25 (s, 1H), 4.86 (d, J=6.6 Hz, 2H), 4.53 (d, J=6.7 Hz, 2H), 2.67 (s, 3H), 1.74 (s, 3H), 1.49 (s, 3H), 0.83-0.72 (m, 4H). [M+H]=317.1.

Example 106. 6-Methyl-4-[(1-methylcyclopropyl)amino]-N-(oxolan-3-yl)furo[2,3-d]pyrimidine-5-carboxamide

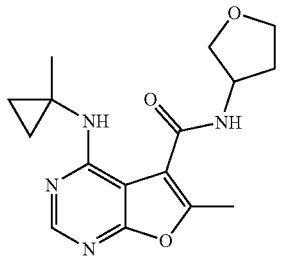 [SMILES: Cc1oc2ncnc(NC3(C)CC3)c2c1C(=O)NC1CCOC1]

$^1$H NMR (400 MHz, CD$_3$OD) δ 8.38 (s, 1H), 4.68-4.54 (m, 1H), 4.05-3.91 (m, 2H), 3.91-3.73 (m, 2H), 2.68 (s, 3H), 2.42-2.27 (m, 1H), 2.10-1.93 (m, 1H), 1.52 (s, 3H), 1.03-0.86 (m, 4H). [M+H]=317.1.

Example 107. 6-Methyl-4-[(1-methylcyclopropyl)amino]-N-(3-methyloxolan-3-yl)furo[2,3-d]pyrimidine-5-carboxamide

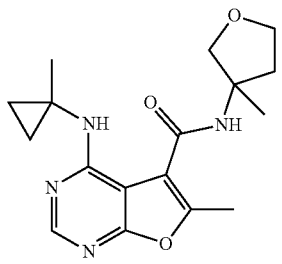 [SMILES: Cc1oc2ncnc(NC3(C)CC3)c2c1C(=O)NC1(C)CCOC1]

$^1$H NMR (400 MHz, CD$_3$OD) δ 8.39 (s, 1H), 8.17 (br s, 1H), 4.09 (d, J=9.2 Hz, 1H), 4.01-3.91 (m, 2H), 3.75 (d, J=9.2 Hz, 1H), 2.68 (s, 3H), 2.43 (td, J=6.6, 13.0 Hz, 1H), 2.07 (td, J=7.8, 12.9 Hz, 1H), 1.59 (s, 3H), 1.52 (s, 3H), 1.01-0.88 (m, 4H). [M+H]=331.1.

Example 108. 6-Methyl-4-[(1-methylcyclopropyl)amino]-N-(oxan-4-yl)furo[2,3-d]pyrimidine-5-carboxamide

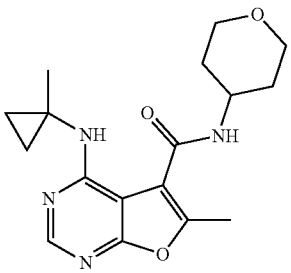 [SMILES: Cc1oc2ncnc(NC3(C)CC3)c2c1C(=O)NC1CCOCC1]

$^1$H NMR (400 MHz, CD$_3$OD) δ 8.38 (s, 1H), 8.18 (d, J=7.2 Hz, 1H), 4.24-4.08 (m, 1H), 4.05-3.91 (m, 2H), 3.54 (dt, J=1.9, 11.8 Hz, 2H), 2.69 (s, 3H), 1.95 (dd, J=2.1, 12.5

Hz, 2H), 1.69 (dq, J=4.4, 12.0 Hz, 2H), 1.51 (s, 3H), 1.00-0.89 (m, 4H). [M+H]=331.1.

Example 109. 6-Methyl-4-[(1-methylcyclopropyl)amino]-N-(4-methyloxan-4-yl)furo[2,3-d]pyrimidine-5-carboxamide

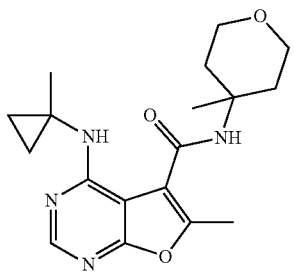 [SMILES: Cc1oc2ncnc(NC3(C)CC3)c2c1C(=O)NC1(C)CCOCC1]

¹H NMR (400 MHz, CD₃OD) δ 8.36 (s, 1H), 7.71 (br s, 1H), 3.86-3.66 (m, 4H), 2.73 (s, 3H), 2.24 (d, J=13.8 Hz, 2H), 1.77 (ddd, J=4.6, 8.8, 13.8 Hz, 2H), 1.54 (s, 3H), 1.51 (s, 3H), 0.99-0.83 (m, 4H). [M+H]=345.1.

Example 110. N-(2,2-Dimethyloxan-4-yl)-6-methyl-4-[(1-methylcyclopropyl)amino]furo[2,3-d]pyrimidine-5-carboxamide

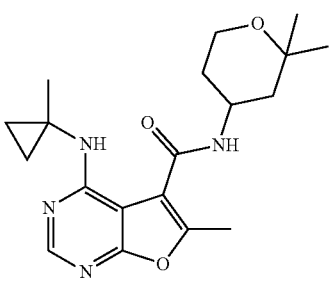 [SMILES: Cc1oc2ncnc(NC3(C)CC3)c2c1C(=O)NC1CCOC(C)(C)C1]

¹H NMR (400 MHz, CD₃OD) δ 8.39 (s, 1H), 8.10 (d, J=7.5 Hz, 1H), 4.44-4.27 (m, 1H), 3.89-3.72 (m, 2H), 2.68 (s, 3H), 2.00-1.87 (m, 2H), 1.64-1.43 (m, 5H), 1.34 (s, 3H), 1.26 (s, 3H), 1.00-0.87 (m, 4H). [M+H]=359.1.

Example 111. 6-Methyl-N-[(1-methyl-1H-pyrrol-2-yl)methyl]-4-[(1-methylcyclopropyl)amino]furo[2,3-d]pyrimidine-5-carboxamide

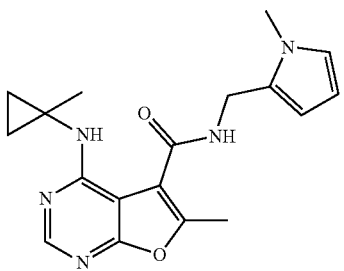 [SMILES: Cc1oc2ncnc(NC3(C)CC3)c2c1C(=O)NCc1cccn1C]

¹H NMR (400 MHz, CD₃OD) δ 8.36 (s, 1H), 6.66-6.63 (m, 1H), 6.10 (dd, J=1.7, 3.5 Hz, 1H), 5.99 (t, J=3.1 Hz, 1H), 4.59 (s, 2H), 3.67 (s, 3H), 2.62 (s, 3H), 1.52 (s, 3H), 0.97-0.87 (m, 4H). [M+H]=340.1.

Example 112. N-[(Dimethyl-1,3-oxazol-4-yl)methyl]-6-methyl-4-[(1-methylcyclopropyl)amino]furo[2,3-d]pyrimidine-5-carboxamide

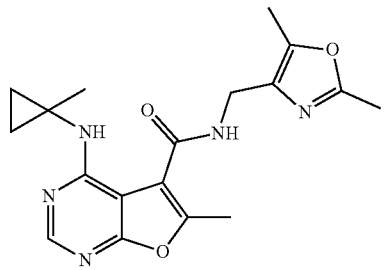 [SMILES: Cc1nc(CNC(=O)c2c(C)oc3ncnc(NC4(C)CC4)c23)c(C)o1]

¹H NMR (400 MHz, CD₃OD) δ 8.39 (s, 1H), 4.43-4.38 (m, 2H), 2.69 (s, 3H), 2.39 (s, 3H), 2.36 (s, 3H), 1.52 (s, 3H), 1.02-0.89 (m, 4H). [M+H]=356.1.

Example 113. 6-Methyl-N-[(5-methyl-1,2-oxazol-3-yl)methyl]-4-[(1-methylcyclopropyl)amino]furo[2,3-d]pyrimidine-5-carboxamide

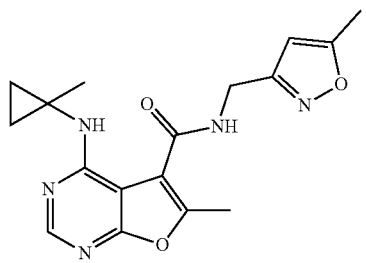 [SMILES: Cc1cc(CNC(=O)c2c(C)oc3ncnc(NC4(C)CC4)c23)no1]

¹H NMR (400 MHz, CD₃OD) δ 8.39 (s, 1H), 6.17 (s, 1H), 4.62 (s, 2H), 2.72 (s, 3H), 2.42 (d, J=0.6 Hz, 3H), 1.52 (s, 3H), 1.00-0.89 (m, 4H). [M+H]=342.1.

Example 114. 6-Methyl-4-[(1-methylcyclopropyl)amino]-N-[(1R,5S,6R)-3-oxabicyclo[3.1.0]hexan-6-yl]furo[2,3-d]pyrimidine-5-carboxamide

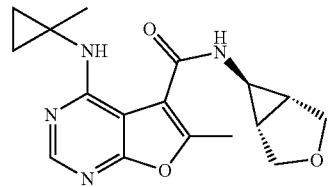 [SMILES: Cc1oc2ncnc(NC3(C)CC3)c2c1C(=O)N[C@H]1[C@@H]2COC[C@@H]21]

¹H NMR (400 MHz, CD₃OD) δ 8.38 (s, 1H), 4.03 (d, J=8.6 Hz, 2H), 3.81-3.72 (m, 2H), 2.69-2.63 (m, 4H), 1.99 (t, J=2.5 Hz, 2H), 1.52 (s, 3H), 1.02-0.88 (m, 4H). [M+H]=329.1.

Example 115. 6-Methyl-N-[(1-methyl-1H-imidazol-5-yl)methyl]-4-[(1-methylcyclopropyl)amino]furo[2,3-d]pyrimidine-5-carboxamide

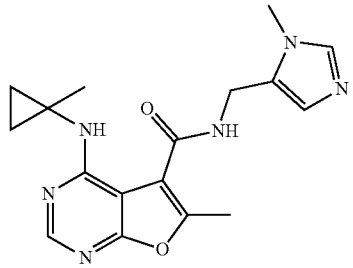 [SMILES: Cc1oc2ncnc(NC3(C)CC3)c2c1C(=O)NCc1cncn1C]

¹H NMR (400 MHz, CD₃OD) δ 8.39 (s, 1H), 8.26 (s, 1H), 7.66 (s, 1H), 7.00 (s, 1H), 4.63 (s, 2H), 3.76 (s, 3H), 2.59 (s, 3H), 1.49 (s, 3H), 0.84-0.73 (m, 4H). [M+H]=341.1.

Example 116. 6-Methyl-N-[(1-methyl-1H-imidazol-4-yl)methyl]-4-[(1-methylcyclopropyl)amino]furo[2,3-d]pyrimidine-5-carboxamide

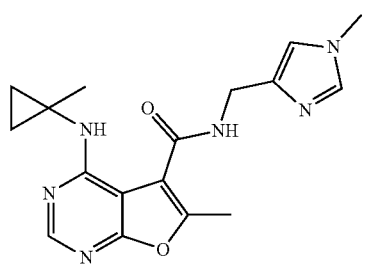 [SMILES: Cc1oc2ncnc(NC3(C)CC3)c2c1C(=O)NCc1cn(C)cn1]

¹H NMR (400 MHz, CD₃OD) δ 8.84 (s, 1H), 8.35 (s, 1H), 7.56 (s, 1H), 4.65 (s, 2H), 3.93 (s, 3H), 2.71 (s, 3H), 1.50 (s, 3H), 0.94-0.82 (m, 4H). [M+H]=341.1.

Example 117. 6-Methyl-N-(1-methylcyclopropyl)-5-(morpholine-4-carbonyl)furo[2,3-d]pyrimidin-4-amine

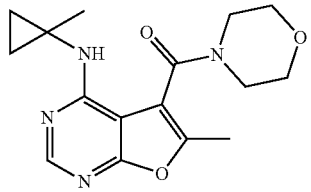 [SMILES: Cc1oc2ncnc(NC3(C)CC3)c2c1C(=O)N1CCOCC1]

¹H NMR (400 MHz, CD₃OD) δ 8.39 (s, 1H), 3.73 (br s, 8H), 2.54 (s, 3H), 1.52 (s, 3H), 1.00-0.85 (m, 4H). [M+H]=317.1.

Example 118. 6-Methyl-N-(1-methylcyclopropyl)-5-[2-(pyridin-2-yl)morpholine-4-carbonyl]furo[2,3-d]pyrimidin-4-amine

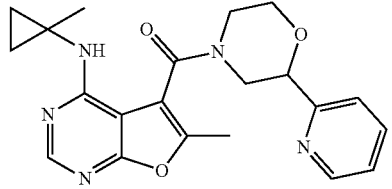

¹H NMR (400 MHz, CD₃OD) δ 8.58 (br s, 1H), 8.40 (s, 1H), 8.13 (br s, 1H), 7.81 (br s, 1H), 7.59 (br s, 1H), 4.98-4.85 (m, 2H), 4.65-3.35 (m, 5H), 2.56 (s, 3H), 1.51 (s, 3H), 1.00-0.82 (m, 4H). [M+H]=394.2.

Example 119. 6-Methyl-N-(1-methylcyclopropyl)-5-[2-(pyridin-4-yl)morpholine-4-carbonyl]furo[2,3-d]pyrimidin-4-amine

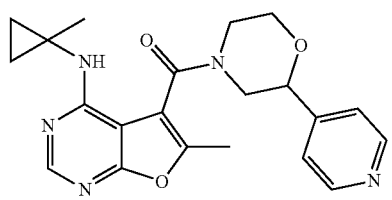 [SMILES: Cc1oc2ncnc(NC3(C)CC3)c2c1C(=O)N1CCOC(c2ccncc2)C1]

¹H NMR (400 MHz, CD₃OD) δ 8.83 (d, J=5.5 Hz, 2H), 8.37 (s, 1H), 8.11 (br s, 2H), 4.95 (br s, 1H), 4.81-4.36 (m, 1H), 4.31-3.37 (m, 4H), 3.28-2.75 (m, 1H), 2.55 (br s, 3H), 1.51 (s, 3H), 0.96-0.80 (m, 4H). [M+H]=394.2.

Example 120. 6-Methyl-N-(1-methylcyclopropyl)-5-[2-(pyridin-3-yl)morpholine-4-carbonyl]furo[2,3-d]pyrimidin-4-amine

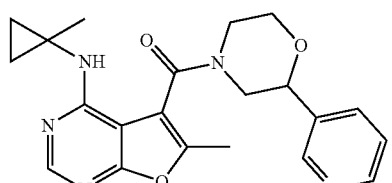

¹H NMR (400 MHz, CD₃OD) δ 8.87 (br s, 1H), 8.75 (d, J=5.4 Hz, 1H), 8.51 (br s, 1H), 8.36 (s, 1H), 7.94 (d, J=6.6 Hz, 1H), 5.02-4.86 (m, 2H), 4.72-3.35 (m, 5H), 2.55 (br s, 3H), 1.55-1.48 (m, 3H), 0.99-0.76 (m, 4H). [M+H]=394.2.

Example 121. 6-Methyl-5-[2-(1-methyl-1H-pyrazol-4-yl)morpholine-4-carbonyl]-N-(1-methylcyclopropyl)furo[2,3-d]pyrimidin-4-amine

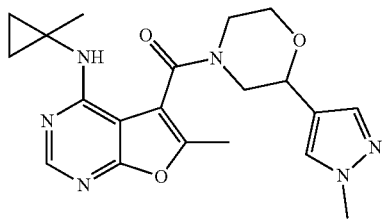 [SMILES: Cc1oc2ncnc(NC3(C)CC3)c2c1C(=O)N1CCOC(c2cnn(C)c2)C1]

¹H NMR (400 MHz, CD₃OD) δ 8.38 (s, 1H), 7.64 (br s, 1H), 7.49 (br s, 1H), 4.77-3.92 (m, 4H), 3.86 (s, 3H), 3.80-3.35 (m, 3H), 2.54 (s, 3H), 1.54-1.48 (m, 3H), 0.95-0.83 (m, 4H). [M+H]=397.2.

Example 122. 5-[2-(4-Fluorophenyl)morpholine-4-carbonyl]-6-methyl-N-(1-methylcyclopropyl)furo[2,3-d]pyrimidin-4-amine

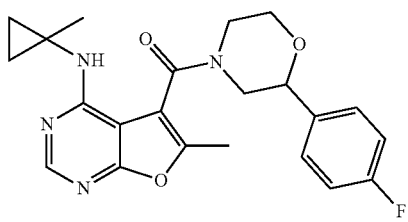 [SMILES: Cc1oc2ncnc(NC3(C)CC3)c2c1C(=O)N1CCOC(c2ccc(F)cc2)C1]

¹H NMR (400 MHz, CD₃OD) δ 8.39 (s, 1H), 7.46 (br s, 2H), 7.11 (t, J=8.4 Hz, 2H), 4.77-3.38 (m, 6H), 3.26-2.91 (m, 1H), 2.55 (br s, 3H), 1.56-1.49 (m, 3H), 0.99-0.84 (m, 4H). [M+H]=411.2.

Example 123. 5-[2-(4-Methoxyphenyl)morpholine-4-carbonyl]-6-methyl-N-(1-methylcyclopropyl)furo[2,3-d]pyrimidin-4-amine

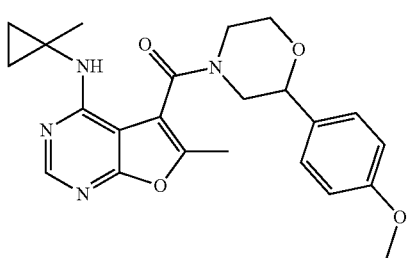 [SMILES: COc1ccc(C2CN(C(=O)c3c(C)oc4ncnc(NC5(C)CC5)c34)CCO2)cc1]

¹H NMR (400 MHz, CD₃OD) δ 8.34 (s, 1H), 7.45 (br s, 2H), 6.91 (d, J=7.9 Hz, 2H), 4.45 (d, J=12.1 Hz, 1H), 4.00 (d, J=13.1 Hz, 2H), 3.88-3.36 (m, 7H), 2.66-2.13 (m, 3H), 1.47 (br s, 3H), 0.79 (br s, 4H). [M+H]=423.2.

Example 124. N-Cyclopropyl-6-methyl-4-[(1-methylcyclopropyl)amino]furo[2,3-d]pyrimidine-5-carboxamide

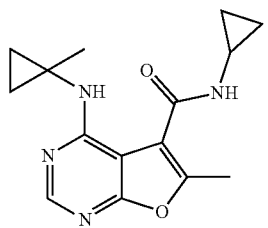 [SMILES: Cc1oc2ncnc(NC3(C)CC3)c2c1C(=O)NC1CC1]

¹H NMR (400 MHz, CD₃OD) δ 8.38 (s, 1H), 2.90 (tt, J=3.8, 7.4 Hz, 1H), 2.63 (s, 3H), 1.53 (s, 3H), 1.03-0.97 (m, 2H), 0.95-0.91 (m, 2H), 0.90-0.84 (m, 2H), 0.72-0.65 (m, 2H). [M+H]=287.1.

Example 125. N-(2-Fluoroethyl)-6-methyl-4-[(1-methylcyclopropyl)amino]furo[2,3-d]pyrimidine-5-carboxamide

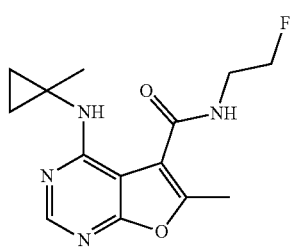 [SMILES: Cc1oc2ncnc(NC3(C)CC3)c2c1C(=O)NCCF]

¹H NMR (400 MHz, CD₃OD) δ 8.38 (s, 1H), 4.69-4.49 (m, 2H), 3.80-3.65 (m, 2H), 2.70 (s, 3H), 1.51 (s, 3H), 0.99-0.89 (m, 4H). [M+H]=293.1.

Example 126. 6-Methyl-4-[(1-methylcyclopropyl)amino]-N-[(1R,3R)-3-fluorocyclobutyl]furo[2,3-d]pyrimidine-5-carboxamide

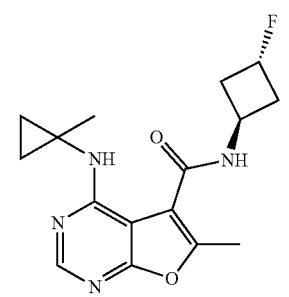 [SMILES: Cc1oc2ncnc(NC3(C)CC3)c2c1C(=O)N[C@H]1C[C@H](F)C1]

¹H NMR (400 MHz, CD₃OD) δ 8.37 (s, 1H), 5.37-5.13 (m, 1H), 4.73-4.62 (m, 1H), 2.73-2.59 (m, 5H), 2.58-2.44 (m, 2H), 1.51 (s, 3H), 0.98-0.85 (m, 4H). [M+H]=319.1.

Example 127. 6-Methyl-4-[(1-methylcyclopropyl)amino]-N-[(1S,3S)-3-fluorocyclobutyl]furo[2,3-d]pyrimidine-5-carboxamide

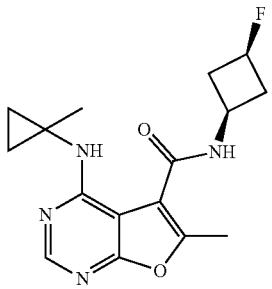 [SMILES: Cc1oc2ncnc(NC3(C)CC3)c2c1C(=O)N[C@H]1C[C@@H](F)C1]

¹H NMR (400 MHz, CD₃OD) δ 8.37 (s, 1H), 4.94 (quin, J=6.7 Hz, 1H), 4.82-4.74 (m, OH), 4.15-3.99 (m, 1H), 2.96-2.82 (m, 2H), 2.70 (s, 3H), 2.41-2.24 (m, 2H), 1.51 (s, 3H), 0.97-0.85 (m, 4H). [M+H]=319.1.

Example 128. N-(3,3-Difluorocyclobutyl)-6-methyl-4-[(1-methylcyclopropyl)amino]furo[2,3-d]pyrimidine-5-carboxamide

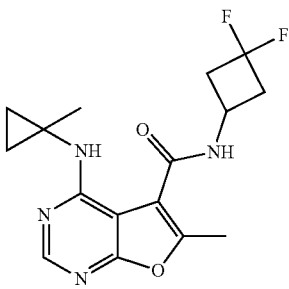 [SMILES: Cc1oc2ncnc(NC3(C)CC3)c2c1C(=O)NC1CC(F)(F)C1]

¹H NMR (400 MHz, CD₃OD) δ 8.35 (s, 1H), 4.44-4.28 (m, 1H), 3.13-2.95 (m, 2H), 2.84-2.70 (m, 2H), 2.70-2.66 (m, 3H), 1.50 (s, 3H), 0.96-0.85 (m, 4H). [M+H]=337.1.

Example 129. N-(4-Cyclopropyloxan-4-yl)-6-methyl-4-[(1-methylcyclopropyl)amino]furo[2,3-d]pyrimidine-5-carboxamide

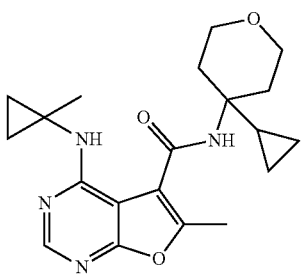 [SMILES: Cc1oc2ncnc(NC3(C)CC3)c2c1C(=O)NC1(C2CC2)CCOCC1]

¹H NMR (400 MHz, CD₃OD) δ 8.37 (s, 1H), 7.67 (s, 1H), 3.87-3.80 (m, 2H), 3.68 (dt, J=1.9, 11.8 Hz, 2H), 2.74 (s, 3H), 2.24 (d, J=12.2 Hz, 2H), 1.68 (ddd, J=4.7, 11.8, 14.0 Hz, 2H), 1.57-1.48 (m, 4H), 0.95-0.85 (m, 4H), 0.56-0.44 (m, 4H). [M+H]=371.1.

Example 130. 6-Methyl-4-[(1-methylcyclopropyl)amino]-N-(3-phenyloxetan-3-yl)furo[2,3-d]pyrimidine-5-carboxamide

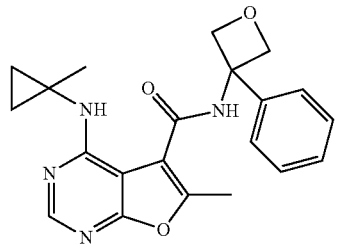 [SMILES: Cc1oc2ncnc(NC3(C)CC3)c2c1C(=O)NC1(c2ccccc2)COC1]

¹H NMR (400 MHz, CD₃OD) δ 8.37 (s, 1H), 7.64-7.57 (m, 2H), 7.48-7.39 (m, 2H), 7.39-7.30 (m, 1H), 5.14 (d, J=7.0 Hz, 2H), 4.96 (d, J=7.1 Hz, 2H), 2.83 (s, 3H), 1.44 (s, 3H), 0.85-0.77 (m, 4H). [M+H]=379.1.

Example 131. 5-{3-[4-(Difluoromethyl)phenyl]pyrrolidine-1-carbonyl}-6-methyl-N-(1-methylcyclopropyl)furo[2,3-d]pyrimidin-4-amine

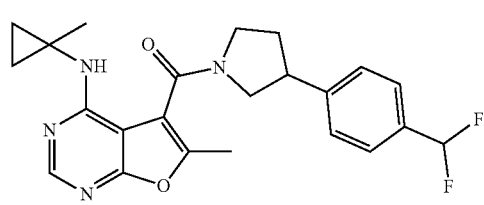 [SMILES: Cc1oc2ncnc(NC3(C)CC3)c2c1C(=O)N1CCC(c2ccc(C(F)F)cc2)C1]

¹H NMR (400 MHz, CD₃OD) δ 8.36 (s, 1H), 7.59-7.35 (m, 4H), 6.96-6.50 (m, 1H), 4.11-3.51 (m, 5H), 2.57 (d, J=14.4 Hz, 3H), 2.50-2.03 (m, 2H), 1.51 (s, 3H), 1.01-0.81 (m, 4H). [M+H]=427.1.

Example 132. 5-(3-Fluoro-3-phenylpyrrolidine-1-carbonyl)-6-methyl-N-(1-methylcyclopropyl)furo[2,3-d]pyrimidin-4-amine

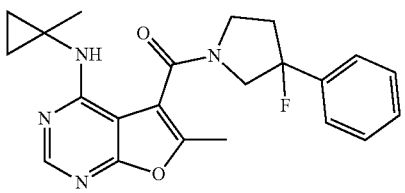 [SMILES: Cc1oc2ncnc(NC3(C)CC3)c2c1C(=O)N1CCC(F)(c2ccccc2)C1]

¹H NMR (400 MHz, CD₃OD) δ 8.42-8.37 (m, 1H), 7.60-7.34 (m, 5H), 4.27-3.83 (m, 4H), 2.59 (d, J=16.1 Hz, 5H), 1.52 (s, 3H), 1.00-0.87 (m, 4H). [M+H]=395.1.

Example 133. 5-[3-Fluoro-3-(4-fluorophenyl)pyrrolidine-1-carbonyl]-6-methyl-N-(1-methylcyclopropyl)furo[2,3-d]pyrimidin-4-amine

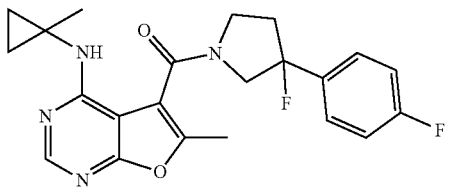 [SMILES: Cc1oc2ncnc(NC3(C)CC3)c2c1C(=O)N1CCC(F)(c2ccc(F)cc2)C1]

$^{1}$H NMR (400 MHz, CD$_{3}$OD) δ 8.37 (s, 1H), 7.57 (br s, 2H), 7.17 (br s, 2H), 4.24-3.79 (m, 4H), 2.57 (d, J=13.9 Hz, 5H), 1.50 (s, 3H), 0.97-0.81 (m, 4H). [M+H]=413.1.

Example 134. N-(2-Hydroxyethyl)-6-methyl-4-[(1-methylcyclopropyl)amino]furo[2,3-d]pyrimidine-5-carboxamide

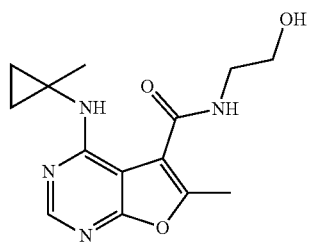 [SMILES: Cc1oc2ncnc(NC3(C)CC3)c2c1C(=O)NCCO]

$^{1}$H NMR (400 MHz, CD$_{3}$OD) δ 8.40 (s, 1H), 4.61 (t, J=5.2 Hz, 1H), 3.80 (t, J=5.2 Hz, 1H), 3.77-3.71 (m, 2H), 3.59-3.52 (m, 2H), 2.74-2.69 (m, 3H), 1.52 (s, 3H), 1.04-0.91 (m, 4H). [M+H]=291.1.

Example 135. N-(4-Hydroxy-2-methylbutan-2-yl)-6-methyl-4-[(1-methylcyclopropyl)amino]furo[2,3-d]pyrimidine-5-carboxamide

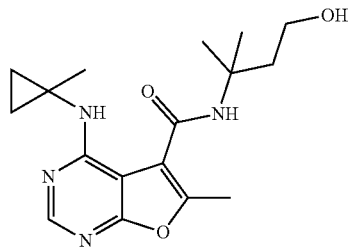 [SMILES: Cc1oc2ncnc(NC3(C)CC3)c2c1C(=O)NC(C)(C)CCO]

$^{1}$H NMR (400 MHz, CD$_{3}$OD) δ 8.39 (s, 1H), 8.22-8.09 (m, 1H), 4.53 (t, J=6.8 Hz, 1H), 3.80 (t, J=6.1 Hz, 2H), 2.72-2.68 (m, 3H), 2.45-2.21 (m, 1H), 2.21-1.96 (m, 2H), 1.54-1.49 (m, 9H), 1.02-0.92 (m, 4H). [M+H]=333.1.

Example 136. 6-Methyl-4-[(1-methylcyclopropyl)amino]-N-(propan-2-yl)furo[2,3-d]pyrimidine-5-carboxamide

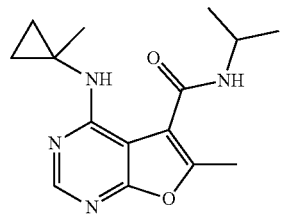 [SMILES: Cc1oc2ncnc(NC3(C)CC3)c2c1C(=O)NC(C)C]

$^{1}$H NMR (400 MHz, CD$_{3}$OD) δ 8.36 (s, 1H), 8.07 (d, J=6.2 Hz, 1H), 4.31-4.15 (m, 1H), 2.67 (s, 3H), 1.52 (s, 3H), 1.29 (d, J=6.6 Hz, 6H), 0.98-0.86 (m, 4H). [M+H]=289.1.

Example 137. 6-Methyl-4-[(1-methylcyclopropyl)amino]-N-(2-methylpropyl)furo[2,3-d]pyrimidine-5-carboxamide

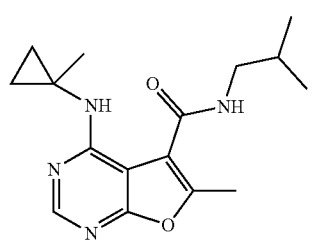 [SMILES: Cc1oc2ncnc(NC3(C)CC3)c2c1C(=O)NCC(C)C]

$^{1}$H NMR (400 MHz, CD$_{3}$OD) δ 8.33 (s, 1H), 8.25 (br s, 1H), 3.25 (t, J=6.4 Hz, 2H), 2.68 (s, 3H), 1.93 (quind, J=6.8, 13.5 Hz, 1H), 1.50 (s, 3H), 0.99 (d, J=6.7 Hz, 6H), 0.93-0.83 (m, 4H). [M+H]=303.1.

Example 138. N-tert-Butyl-6-methyl-4-[(1-methylcyclopropyl)amino]furo[2,3-d]pyrimidine-5-carboxamide

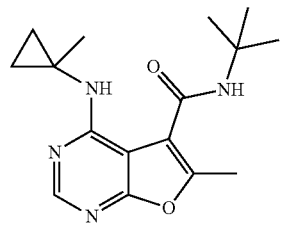 [SMILES: Cc1oc2ncnc(NC3(C)CC3)c2c1C(=O)NC(C)(C)C]

$^{1}$H NMR (400 MHz, CD$_{3}$OD) δ 8.30 (s, 1H), 7.72 (br s, 1H), 2.63 (s, 3H), 1.51 (s, 3H), 1.47 (s, 9H), 0.92-0.82 (m, 4H). [M+H]=303.1.

Example 139. 6-Methyl-4-[(1-methylcyclopropyl)amino]-N-(oxan-4-ylmethyl)furo[2,3-d]pyrimidine-5-carboxamide

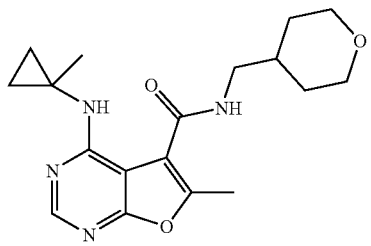 [SMILES: Cc1oc2ncnc(NC3(C)CC3)c2c1C(=O)NCC1CCOCC1]

¹H NMR (400 MHz, CD₃OD) δ 8.41 (s, 1H), 8.30 (br s, 1H), 3.99 (dd, J=2.9, 11.3 Hz, 2H), 3.45 (dt, J=2.1, 11.8 Hz, 2H), 3.39-3.34 (m, 2H), 2.73 (s, 3H), 2.01-1.88 (m, 1H), 1.72 (dd, J=1.8, 13.0 Hz, 2H), 1.54 (s, 3H), 1.46-1.32 (m, 2H), 1.04-0.90 (m, 4H). [M+H]=345.1.

Example 140. N-(4-Ethyloxan-4-yl)-6-methyl-4-[(1-methylcyclopropyl)amino]furo[2,3-d]pyrimidine-5-carboxamide

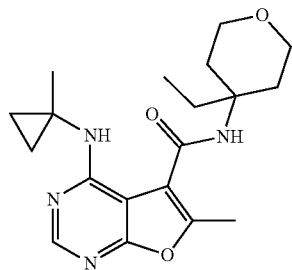 [SMILES: CCC1(NC(=O)c2c(C)oc3ncnc(NC4(C)CC4)c23)CCOCC1]

¹H NMR (400 MHz, CD₃OD) δ 8.32 (s, 1H), 7.68 (s, 1H), 3.86-3.78 (m, 2H), 3.75-3.64 (m, 2H), 2.72 (s, 3H), 2.24 (d, J=13.4 Hz, 2H), 2.05-1.94 (m, 2H), 1.76-1.65 (m, 2H), 1.54-1.46 (m, 3H), 0.89 (t, J=7.5 Hz, 3H), 0.84 (s, 4H). [M+H]=359.1.

Example 141. 6-Methyl-N-(1-methyl-1H-pyrazol-4-yl)-4-[(1-methylcyclopropyl)amino]furo[2,3-d]pyrimidine-5-carboxamide

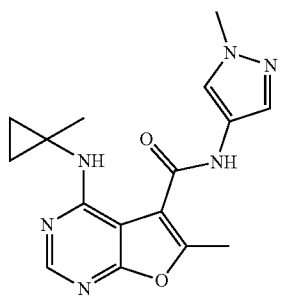 [SMILES: Cc1oc2ncnc(NC3(C)CC3)c2c1C(=O)Nc1cnn(C)c1]

¹H NMR (400 MHz, CD₃OD) δ 8.38 (s, 1H), 8.07 (s, 1H), 7.64 (s, 1H), 3.91 (s, 3H), 2.74 (s, 3H), 1.55-1.48 (m, 3H), 1.00-0.85 (m, 4H). [M+H]=327.1.

Example 142. 6-Methyl-N-(5-methyl-1,2-oxazol-3-yl)-4-[(1-methylcyclopropyl)amino]furo[2,3-d]pyrimidine-5-carboxamide

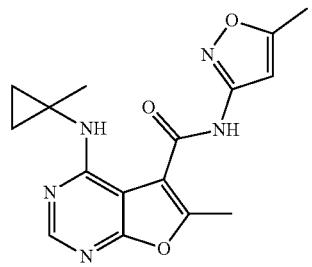 [SMILES: Cc1cc(NC(=O)c2c(C)oc3ncnc(NC4(C)CC4)c23)no1]

¹H NMR (400 MHz, CD₃OD) δ 8.37 (s, 1H), 6.71 (d, J=0.9 Hz, 1H), 2.73 (s, 3H), 2.46 (d, J=0.9 Hz, 3H), 1.52 (s, 3H), 0.95-0.89 (m, 2H), 0.88-0.82 (m, 2H). [M+H]=328.1.

Example 143. 6-Methyl-4-[(1-methylcyclopropyl)amino]-N-(1,3-thiazol-2-yl)furo[2,3-d]pyrimidine-5-carboxamide

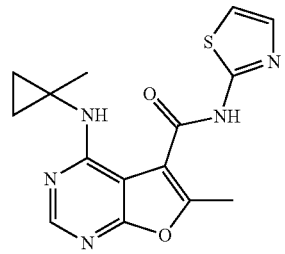 [SMILES: Cc1oc2ncnc(NC3(C)CC3)c2c1C(=O)Nc1nccs1]

¹H NMR (400 MHz, CD₃OD) δ 8.36 (s, 1H), 7.42 (d, J=4.4 Hz, 1H), 7.08 (d, J=4.4 Hz, 1H), 2.92 (s, 3H), 1.56 (s, 3H), 1.02-0.92 (m, 4H). [M+H]=330.

Example 144. N-(5-Methoxypyridin-2-yl)-6-methyl-4-[(1-methylcyclopropyl)amino]furo[2,3-d]pyrimidine-5-carboxamide

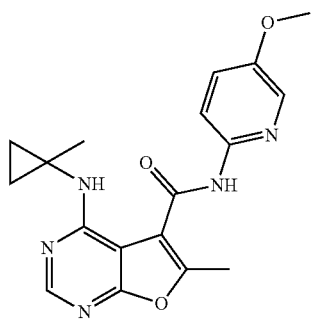 [SMILES: COc1ccc(NC(=O)c2c(C)oc3ncnc(NC4(C)CC4)c23)nc1]

¹H NMR (400 MHz, CD₃OD) δ 8.35 (s, 1H), 8.09-8.04 (m, 2H), 7.50 (dd, J=3.2, 9.0 Hz, 1H), 3.90 (s, 3H), 2.77 (s, 3H), 1.51 (s, 3H), 0.95-0.80 (m, 4H). [M+H]=354.1.

Example 145. N-(1-Ethylcyclopropyl)-6-methyl-4-[(1-methylcyclopropyl)amino]furo[2,3-d]pyrimidine-5-carboxamide

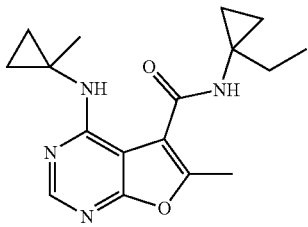 [SMILES: CCC1(NC(=O)c2c(C)oc3ncnc(NC4(C)CC4)c23)CC1]

$^1$H NMR (400 MHz, CD$_3$OD) δ 8.49 (br s, 1H), 8.37 (s, 1H), 2.65 (s, 3H), 1.74 (q, J=7.4 Hz, 2H), 1.53 (s, 3H), 1.03 (t, J=7.5 Hz, 3H), 0.99-0.91 (m, 4H), 0.89-0.84 (m, 2H), 0.80-0.74 (m, 2H). [M+H]=315.1.

Example 146. N-[1-(Hydroxymethyl)cyclopropyl]-6-methyl-4-[(1-methylcyclopropyl)amino]furo[2,3-d]pyrimidine-5-carboxamide

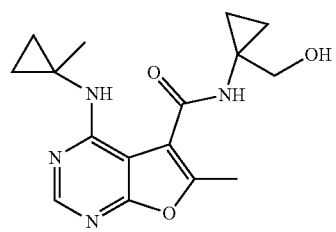 [SMILES: Cc1oc2ncnc(NC3(C)CC3)c2c1C(=O)NC1(CO)CC1]

$^1$H NMR (400 MHz, CD$_3$OD) δ 8.40 (s, 1H), 3.69 (s, 2H), 2.68 (s, 3H), 1.53 (s, 3H), 1.07-0.86 (m, 8H). [M+H]=317.

Example 147. 6-Methyl-4-[(1-methylcyclopropyl)amino]-N-[1-(propan-2-yl)cyclopropyl]furo[2,3-d]pyrimidine-5-carboxamide

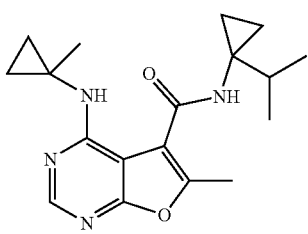 [SMILES: Cc1oc2ncnc(NC3(C)CC3)c2c1C(=O)NC1(C(C)C)CC1]

$^1$H NMR (400 MHz, CD$_3$OD) δ 8.41 (br s, 1H), 8.36 (s, 1H), 2.66 (s, 3H), 1.65 (spt, J=6.8 Hz, 1H), 1.51 (s, 3H), 1.03 (d, J=6.8 Hz, 6H), 0.98-0.78 (m, 8H). [M+H]=329.1.

Example 148. N-[1-(Methoxymethyl)cyclopropyl]-6-methyl-4-[(1-methylcyclopropyl)amino]furo[2,3-d]pyrimidine-5-carboxamide

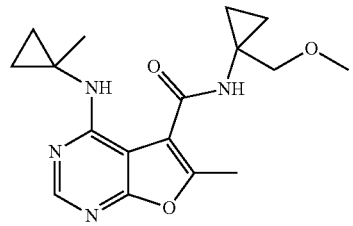 [SMILES: COCC1(NC(=O)c2c(C)oc3ncnc(NC4(C)CC4)c23)CC1]

$^1$H NMR (400 MHz, CD$_3$OD) δ 8.50 (br s, 1H), 8.35 (s, 1H), 3.56 (s, 2H), 3.41 (s, 3H), 2.64 (s, 3H), 1.52 (s, 3H), 0.99-0.86 (m, 8H). [M+H]=331.1.

Example 149. N-(1-Cyclopropylcyclopropyl)-6-methyl-4-[(1-methylcyclopropyl)amino]furo[2,3-d]pyrimidine-5-carboxamide

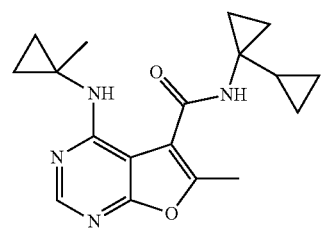 [SMILES: Cc1oc2ncnc(NC3(C)CC3)c2c1C(=O)NC1(C2CC2)CC1]

$^1$H NMR (400 MHz, CD$_3$OD) δ 8.61 (br s, 1H), 8.35 (s, 1H), 2.63 (s, 3H), 1.58-1.46 (m, 4H), 1.00-0.87 (m, 4H), 0.85-0.69 (m, 4H), 0.51-0.45 (m, 2H), 0.33-0.26 (m, 2H). [M+H]=327.1.

Example 150. N-(1-Cyclobutylcyclopropyl)-6-methyl-4-[(1-methylcyclopropyl)amino]furo[2,3-d]pyrimidine-5-carboxamide

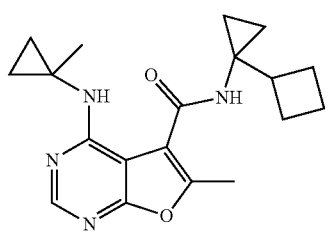 [SMILES: Cc1oc2ncnc(NC3(C)CC3)c2c1C(=O)NC1(C2CCC2)CC1]

$^1$H NMR (400 MHz, CD$_3$OD) δ 8.56 (br s, 1H), 8.34 (s, 1H), 2.85-2.74 (m, 1H), 2.63 (s, 3H), 2.04-1.89 (m, 2H), 1.87-1.75 (m, 3H), 1.74-1.65 (m, 1H), 1.51 (s, 3H), 0.97-0.86 (m, 4H), 0.86-0.79 (m, 4H). [M+H]=341.1.

Example 151. N-[3-(4-Fluorophenyl)cyclobutyl]-6-methyl-4-[(1-methylcyclopropyl)amino]furo[2,3-d]pyrimidine-5-carboxamide

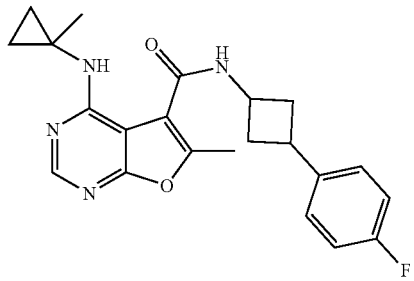 [SMILES: Cc1oc2ncnc(NC3(C)CC3)c2c1C(=O)NC1CC(c2ccc(F)cc2)C1]

¹H NMR (400 MHz, CD₃OD) δ 8.48-8.40 (m, 1H), 8.36 (s, 1H), 7.41-7.24 (m, 2H), 7.12-6.97 (m, 2H), 4.70-4.41 (m, 1H), 3.29-3.21 (m, 1H), 2.83 (dq, J=2.8, 7.9 Hz, 2H), 2.76-2.68 (m, 3H), 2.65-2.55 (m, 1H), 2.27-2.14 (m, 2H), 1.55-1.49 (m, 3H), 1.02-0.84 (m, 4H). [M+H]=395.2.

Example 152. 5-[4-(3-Fluoropyridin-2-yl)piperazine-1-carbonyl]-6-methyl-N-(1-methylcyclopropyl)furo[2,3-d]pyrimidin-4-amine

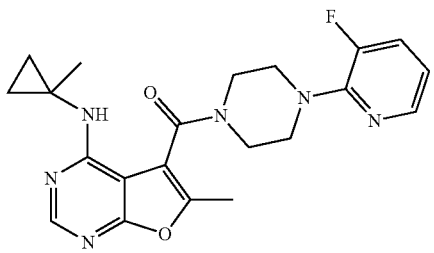 [SMILES: Cc1oc2ncnc(NC3(C)CC3)c2c1C(=O)N1CCN(c2ncccc2F)CC1]

¹H NMR (400 MHz, CD₃OD) δ 8.39 (s, 1H), 8.01 (d, J=4.8 Hz, 1H), 7.44 (ddd, J=1.4, 7.9, 13.2 Hz, 1H), 6.92 (ddd, J=3.2, 4.8, 8.0 Hz, 1H), 3.85 (br s, 4H), 3.55 (br s, 4H), 2.57 (s, 3H), 1.51 (s, 3H), 0.96-0.84 (m, 4H). [M+H]=411.2.

Example 153. 5-[4-(5-Fluoropyrimidin-2-yl)piperazine-1-carbonyl]-6-methyl-N-(1-methylcyclopropyl)furo[2,3-d]pyrimidin-4-amine

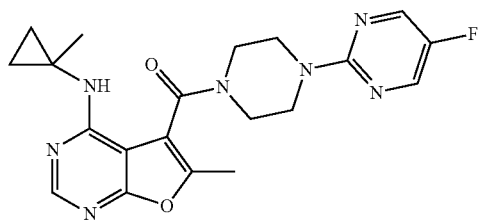 [SMILES: Cc1oc2ncnc(NC3(C)CC3)c2c1C(=O)N1CCN(c2ncc(F)cn2)CC1]

¹H NMR (400 MHz, CD₃OD) δ 8.36 (s, 1H), 8.32 (s, 2H), 4.05-3.56 (m, 8H), 2.55 (s, 3H), 1.50 (s, 3H), 0.94-0.78 (m, 4H). [M+H]=412.2.

Example 154. 5-[4-(6-Fluoropyridin-2-yl)piperazine-1-carbonyl]-6-methyl-N-(1-methylcyclopropyl)furo[2,3-d]pyrimidin-4-amine

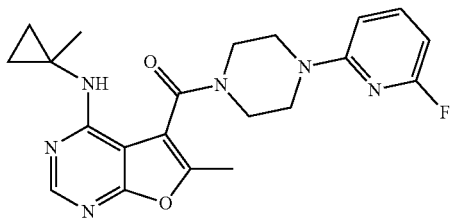 [SMILES: Cc1oc2ncnc(NC3(C)CC3)c2c1C(=O)N1CCN(c2cccc(F)n2)CC1]

¹H NMR (400 MHz, CD₃OD) δ 8.36 (s, 1H), 7.66 (q, J=8.2 Hz, 1H), 6.65 (dd, J=2.4, 8.2 Hz, 1H), 6.25 (dd, J=2.8, 7.8 Hz, 1H), 3.79 (br s, 4H), 3.66 (br s, 4H), 2.55 (s, 3H), 1.50 (s, 3H), 0.93-0.79 (m, 4H). [M+H]=411.2.

Example 155. 5-[(3aS,6aS)-Hexahydro-2H-furo[3,2-b]pyrrole-4-carbonyl]-6-methyl-N-(1-methylcyclopropyl)furo[2,3-d]pyrimidin-4-amine

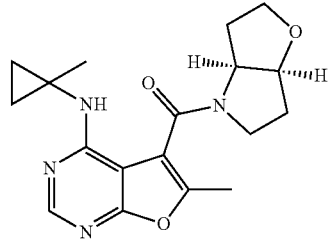 [SMILES: Cc1oc2ncnc(NC3(C)CC3)c2c1C(=O)N1CC[C@@H]2OCC[C@@H]21]

¹H NMR (400 MHz, CD₃OD) δ 8.39 (s, 1H), 4.89 (br s, 1H), 4.56 (t, J=4.3 Hz, 1H), 4.05-3.82 (m, 2H), 3.77-3.59 (m, 2H), 2.55 (s, 3H), 2.50-2.34 (m, 1H), 2.19-2.06 (m, 2H), 2.05-1.92 (m, 1H), 1.51 (s, 3H), 1.01-0.84 (m, 4H). [M+H]=343.1.

Example 156. 5-[4-(2-Fluorophenyl)-1,4-diazepane-1-carbonyl]-6-methyl-N-(1-methylcyclopropyl)furo[2,3-d]pyrimidin-4-amine

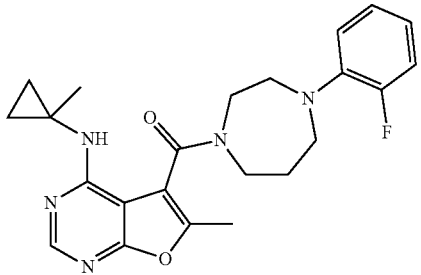 [SMILES: Cc1oc2ncnc(NC3(C)CC3)c2c1C(=O)N1CCCN(c2ccccc2F)CC1]

¹H NMR (400 MHz, CD₃OD) δ 8.33 (br s, 1H), 7.20-6.54 (m, 4H), 4.10-3.65 (m, 4H), 3.62-3.34 (m, 4H), 2.47 (br s, 3H), 2.24-1.74 (m, 2H), 1.40 (br s, 3H), 0.89-0.53 (m, 4H). [M+H]=424.1.

Example 157. 6-Methyl-N-(1-methylcyclopropyl)-5-(4-phenyl-1,4-diazepane-1-carbonyl)furo[2,3-d]pyrimidin-4-amine

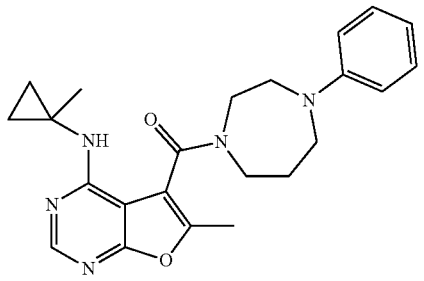 [SMILES: Cc1oc2ncnc(NC3(C)CC3)c2c1C(=O)N1CCCN(c2ccccc2)CC1]

$^1$H NMR (400 MHz, CD$_3$OD) δ 8.33 (s, 1H), 6.86 (t, J=7.6 Hz, 2H), 6.55 (d, J=7.8 Hz, 2H), 6.47-6.32 (m, 1H), 4.22-3.49 (m, 8H), 2.45 (s, 3H), 2.25-1.67 (m, 2H), 1.42 (s, 3H), 0.92-0.68 (m, 4H). [M+H]=406.1.

Example 158. 6-Methyl-N-(1-methylcyclopropyl)-5-[4-(pyridin-2-yl)-1,4-diazepane-1-carbonyl]furo[2,3-d]pyrimidin-4-amine

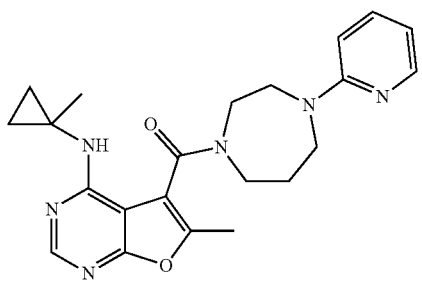

$^1$H NMR (400 MHz, CD$_3$OD) δ 8.31 (s, 1H), 7.83 (br s, 2H), 7.41-6.69 (m, 2H), 4.18-3.53 (m, 8H), 2.45 (s, 3H), 2.27-1.64 (m, 2H), 1.41 (s, 3H), 0.84-0.58 (m, 4H). [M+H]=407.1.

Example 159. 5-[4-(4-Methoxyphenyl)-1,4-diazepane-1-carbonyl]-6-methyl-N-(1-methylcyclopropyl)furo[2,3-d]pyrimidin-4-amine

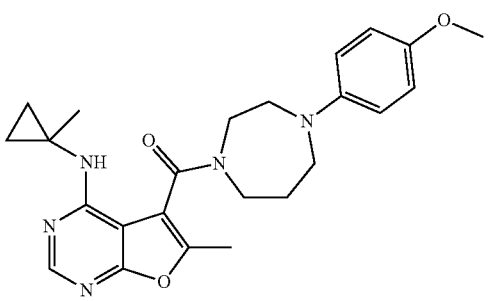 [SMILES: COc1ccc(N2CCCN(C(=O)c3c(C)oc4ncnc(NC5(C)CC5)c34)CC2)cc1]

$^1$H NMR (400 MHz, CD$_3$OD) δ 8.33 (s, 1H), 7.08-5.84 (m, 4H), 4.61-3.45 (m, 8H), 2.47 (s, 3H), 2.29-1.51 (m, 2H), 1.46-1.36 (m, 3H), 1.02-0.60 (m, 4H). [M+H]=436.1.

Example 160. 5-[4-(2-fluoropyridin-4-yl)piperazine-1-carbonyl]-6-methyl-N-(1-methylcyclopropyl)furo[2,3-d]pyrimidin-4-amine

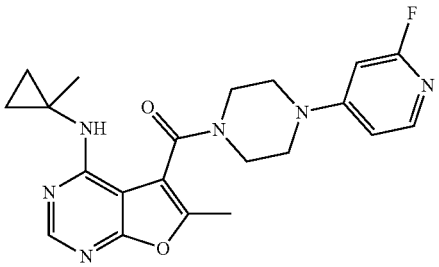 [SMILES: Cc1oc2ncnc(NC3(C)CC3)c2c1C(=O)N1CCN(c2ccnc(F)c2)CC1]

$^1$H NMR (400 MHz, CD$_3$OD) δ 8.39 (s, 1H), 7.85 (d, J=6.4 Hz, 1H), 6.86-6.80 (m, 1H), 6.51 (t, J=2.3 Hz, 1H), 3.85 (br s, 4H), 3.61 (br s, 4H), 2.57 (s, 3H), 1.50 (s, 3H), 0.94-0.81 (m, 4H). [M+H]=411.

Example 161. 5-[4-(6-Fluoropyrimidin-4-yl)piperazine-1-carbonyl]-6-methyl-N-(1-methylcyclopropyl)furo[2,3-d]pyrimidin-4-amine

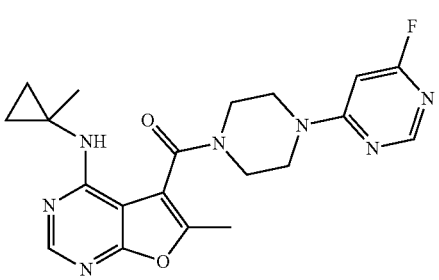 [SMILES: Cc1oc2ncnc(NC3(C)CC3)c2c1C(=O)N1CCN(c2cc(F)ncn2)CC1]

$^1$H NMR (400 MHz, CD$_3$OD) δ 8.41 (s, 1H), 8.30 (d, J=2.8 Hz, 1H), 6.42 (d, J=1.2 Hz, 1H), 3.82 (br s, 8H), 2.57 (s, 3H), 1.55-1.49 (m, 3H), 0.98-0.86 (m, 4H). [M+H]=412.

Example 162. 5-[4-(2-Fluoropyrimidin-4-yl)piperazine-1-carbonyl]-6-methyl-N-(1-methylcyclopropyl)furo[2,3-d]pyrimidin-4-amine

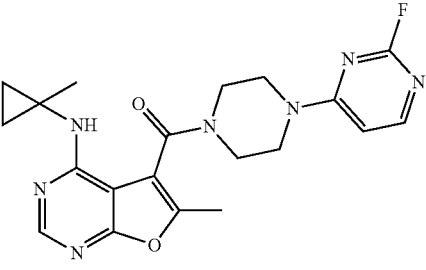 [SMILES: Cc1oc2ncnc(NC3(C)CC3)c2c1C(=O)N1CCN(c2ccnc(F)n2)CC1]

$^1$H NMR (400 MHz, CD$_3$OD) δ 8.40 (s, 1H), 8.09 (dd, J=2.7, 6.2 Hz, 1H), 6.74 (dd, J=4.4, 6.1 Hz, 1H), 3.83 (br s, 8H), 2.57 (s, 3H), 1.51 (s, 3H), 0.96-0.91 (m, 2H), 0.89-0.84 (m, 2H). [M+H]=412.

Example 163. N-[(3-Fluoropyridin-4-yl)methyl]-6-methyl-4-[(1-methylcyclopropyl)amino]furo[2,3-d]pyrimidine-5-carboxamide

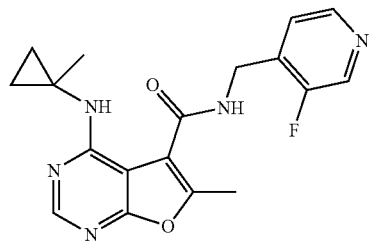 [SMILES: Cc1oc2ncnc(NC3(C)CC3)c2c1C(=O)NCc1ccncc1F]

¹H NMR (400 MHz, CD₃OD) δ 8.56 (d, J=1.5 Hz, 1H), 8.43 (d, J=5.0 Hz, 1H), 8.41 (s, 1H), 7.62 (t, J=5.8 Hz, 1H), 4.77 (s, 2H), 2.77 (s, 3H), 1.50 (s, 3H), 0.98-0.87 (m, 4H). [M+H]=356.

Example 164. N-[(2-Fluoropyridin-4-yl)methyl]-6-methyl-4-[(1-methylcyclopropyl)amino]furo[2,3-d]pyrimidine-5-carboxamide

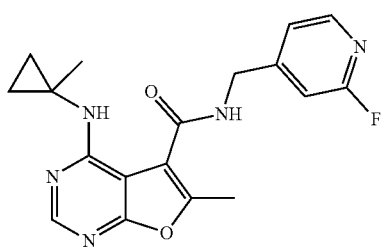 [SMILES: Cc1oc2ncnc(NC3(C)CC3)c2c1C(=O)NCc1ccnc(F)c1]

¹H NMR (400 MHz, CD₃OD) δ 8.26 (s, 1H), 8.18 (d, J=5.3 Hz, 1H), 7.32 (d, J=5.0 Hz, 1H), 7.06 (s, 1H), 4.66 (s, 2H), 2.69 (s, 3H), 1.47 (s, 3H), 0.79-0.71 (m, 4H). [M+H]=356.1.

Example 165. N-Cyclopentyl-6-methyl-4-[(1-methylcyclopropyl)amino]furo[2,3-d]pyrimidine-5-carboxamide

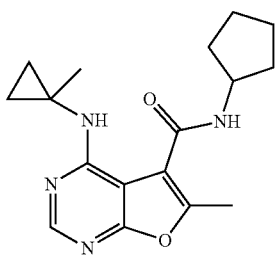 [SMILES: Cc1oc2ncnc(NC3(C)CC3)c2c1C(=O)NC1CCCC1]

[M+H]=315.2.

Example 166. 1-{6-Methyl-4-[(1-methylcyclopropyl)amino]furo[2,3-d]pyrimidine-5-carbonyl}pyrrolidin-3-ol

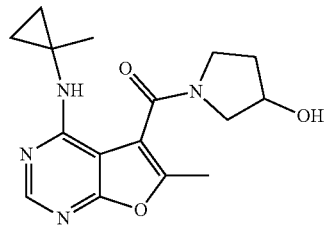 [SMILES: Cc1oc2ncnc(NC3(C)CC3)c2c1C(=O)N1CCC(O)C1]

[M+H]=317.2.

Example 167. 6-Methyl-4-[(1-methylcyclopropyl)amino]-N-pentylfuro[2,3-d]pyrimidine-5-carboxamide

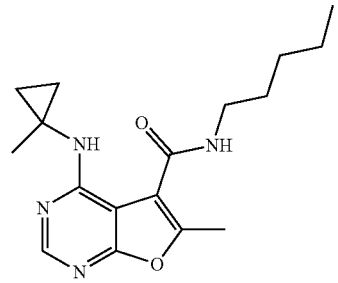 [SMILES: CCCCCNC(=O)c1c(C)oc2ncnc(NC3(C)CC3)c12]

[M+H]=317.4.

Example 168. 6-Methyl-N-(3-methylbutyl)-4-[(1-methylcyclopropyl)amino]furo[2,3-d]pyrimidine-5-carboxamide

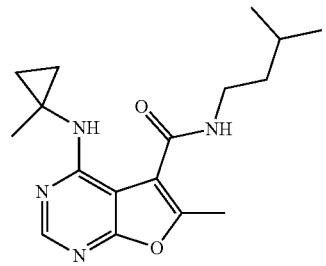 [SMILES: Cc1oc2ncnc(NC3(C)CC3)c2c1C(=O)NCCC(C)C]

[M+H]=317.4.

Example 169. 6-Methyl-4-[(1-methylcyclopropyl)amino]-N-(pentan-3-yl)furo[2,3-d]pyrimidine-5-carboxamide

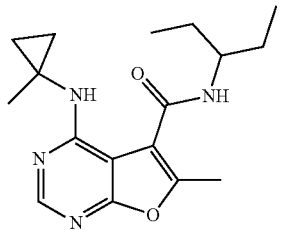 [SMILES: CCC(CC)NC(=O)c1c(C)oc2ncnc(NC3(C)CC3)c12]

[M+H]=317.4.

Example 170. 6-Methyl-N-(3-methylbutan-2-yl)-4-[(1-methylcyclopropyl)amino]furo[2,3-d]pyrimidine-5-carboxamide

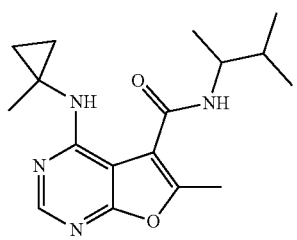 [SMILES: Cc1oc2ncnc(NC3(C)CC3)c2c1C(=O)NC(C)C(C)C]

[M+H]=317.2.

Example 171. N-(2-Rthoxyethyl)-6-methyl-4-[(1-methylcyclopropyl)amino]furo[2,3-d]pyrimidine-5-carboxamide

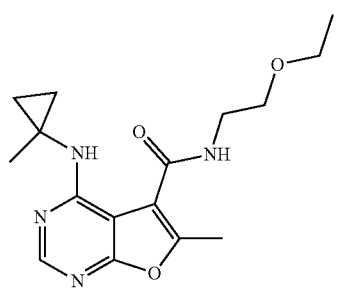 [SMILES: CCOCCNC(=O)c1c(C)oc2ncnc(NC3(C)CC3)c12]

[M+H]=319.2.

Example 172. 6-Methyl-4-[(1-methylcyclopropyl)amino]-N-(pyridin-4-yl)furo[2,3-d]pyrimidine-5-carboxamide

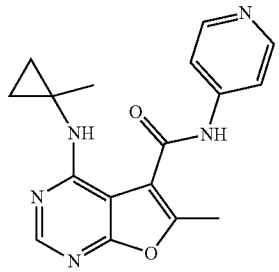 [SMILES: Cc1oc2ncnc(NC3(C)CC3)c2c1C(=O)Nc1ccncc1]

[M+H]=324.2.

Example 173. 6-Methyl-4-[(1-methylcyclopropyl)amino]-N-(pyridin-3-yl)furo[2,3-d]pyrimidine-5-carboxamide

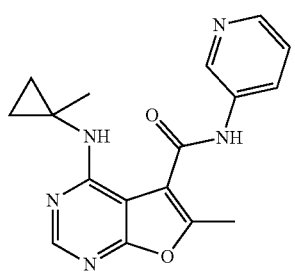 [SMILES: Cc1oc2ncnc(NC3(C)CC3)c2c1C(=O)Nc1cccnc1]

[M+H]=324.2.

Example 174. 6-Methyl-N-(1-methyl-1H-pyrazol-5-yl)-4-[(1-methylcyclopropyl)amino]furo[2,3-d]pyrimidine-5-carboxamide

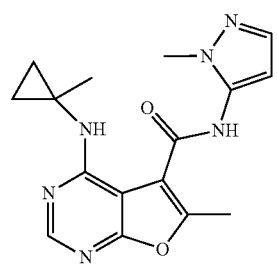 [SMILES: Cc1oc2ncnc(NC3(C)CC3)c2c1C(=O)Nc1ccnn1C]

$^1$H NMR (400 MHz, CD$_3$OD) δ 8.43 (s, 1H), 7.49 (d, J=2.1 Hz, 1H), 6.36 (d, J=2.1 Hz, 1H), 3.80 (s, 3H), 2.84 (s, 3H), 1.51 (s, 3H), 1.02-0.86 (m, 4H). [M+H]=327.2.

Example 175. 6-Methyl-4-[(1-methylcyclopropyl)amino]-N-(oxolan-2-ylmethyl)furo[2,3-d]pyrimidine-5-carboxamide

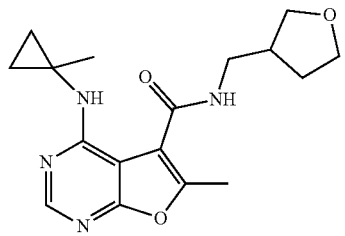 [SMILES: Cc1oc2ncnc(NC3(C)CC3)c2c1C(=O)NCC1CCOC1]

[M+H]=331.2.

Example 176. 6-Methyl-4-[(1-methylcyclopropyl)amino]-N-[2-(propan-2-yloxy)ethyl]furo[2,3-d]pyrimidine-5-carboxamide

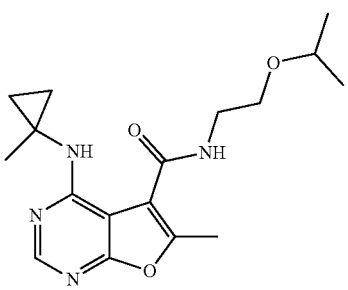 [SMILES: Cc1oc2ncnc(NC3(C)CC3)c2c1C(=O)NCCOC(C)C]

[M+H]=333.3.

Example 177. N-Benzyl-6-methyl-4-[(1-methylcyclopropyl)amino]furo[2,3-d]pyrimidine-5-carboxamide

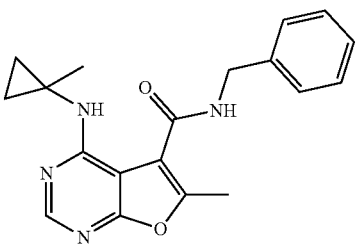 [SMILES: Cc1oc2ncnc(NC3(C)CC3)c2c1C(=O)NCc1ccccc1]

[M+H]=337.2.

Example 178. 6-Methyl-4-[(1-methylcyclopropyl)amino]-N-(2-methylphenyl)furo[2,3-d]pyrimidine-5-carboxamide

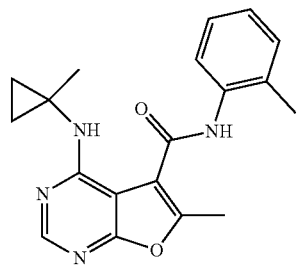 [SMILES: Cc1ccccc1NC(=O)c1c(C)oc2ncnc(NC3(C)CC3)c12]

[M+H]=337.2.

Example 179. 6-Methyl-4-[(1-methylcyclopropyl)amino]-N-(4-methylphenyl)furo[2,3-d]pyrimidine-5-carboxamide

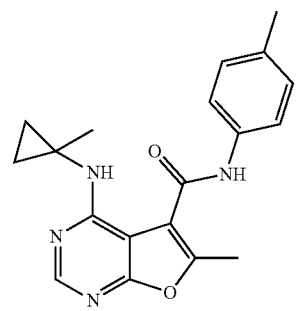 [SMILES: Cc1ccc(NC(=O)c2c(C)oc3ncnc(NC4(C)CC4)c23)cc1]

[M+H]=337.3.

Example 180. 6-Methyl-4-[(1-methylcyclopropyl)amino]-N-(3-methylphenyl)furo[2,3-d]pyrimidine-5-carboxamide

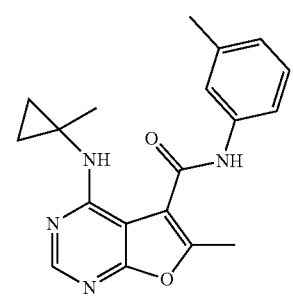 [SMILES: Cc1cccc(NC(=O)c2c(C)oc3ncnc(NC4(C)CC4)c23)c1]

[M+H]=337.2.

Example 181. 6-Methyl-4-[(1-methylcyclopropyl)amino]-N-(2-methylpyridin-3-yl)furo[2,3-d]pyrimidine-5-carboxamide

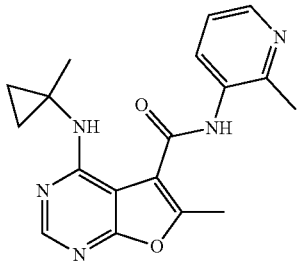 [SMILES: Cc1ncccc1NC(=O)c1c(C)oc2ncnc(NC3(C)CC3)c12]

[M+H]=338.2.

Example 182. 6-Methyl-4-[(1-methylcyclopropyl)amino]-N-[2-(1H-pyrrol-1-yl)ethyl]furo[2,3-d]pyrimidine-5-carboxamide

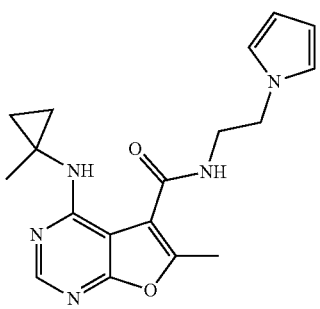 [SMILES: Cc1oc2ncnc(NC3(C)CC3)c2c1C(=O)NCCn1cccc1]

[M+H]=340.2.

Example 183. N-(3-Fluorophenyl)-6-methyl-4-[(1-methylcyclopropyl)amino]furo[2,3-d]pyrimidine-5-carboxamide

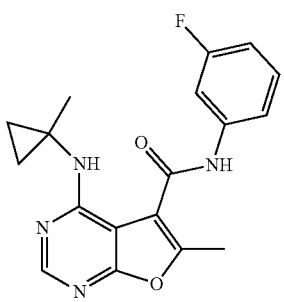 [SMILES: Cc1oc2ncnc(NC3(C)CC3)c2c1C(=O)Nc1cccc(F)c1]

[M+H]=341.4.

Example 184. 6-Methyl-4-[(1-methylcyclopropyl)amino]-N-{[4-(morpholin-4-yl)phenyl]methyl}furo[2,3-d]pyrimidine-5-carboxamide

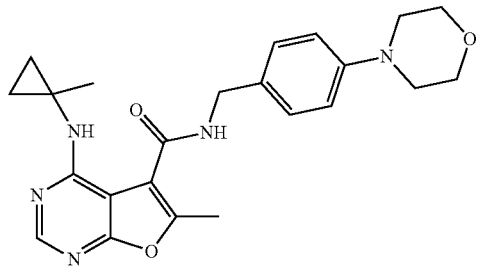 [SMILES: Cc1oc2ncnc(NC3(C)CC3)c2c1C(=O)NCc1ccc(N2CCOCC2)cc1]

[M+H]=422.6.

Example 185. N-[(2,3-Difluoro-4-methoxyphenyl)methyl]-6-methyl-4-[(1-methylcyclopropyl)amino]furo[2,3-d]pyrimidine-5-carboxamide

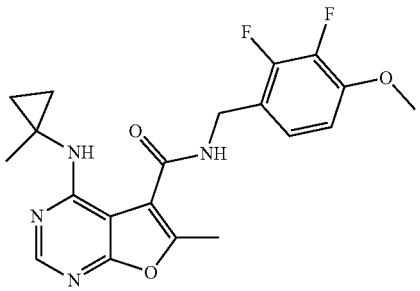

[M+H]=403.5.

Example 186. 5-[4-(4-Methoxyphenyl)piperazine-1-carbonyl]-6-methyl-N-(1-methylcyclopropyl)furo[2,3-d]pyrimidin-4-amine

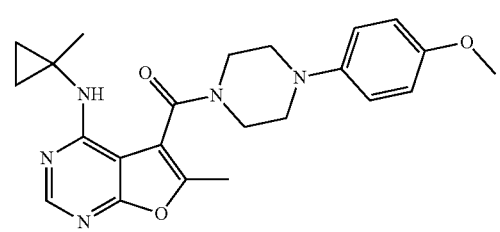 [SMILES: COc1ccc(N2CCN(C(=O)c3c(C)oc4ncnc(NC5(C)CC5)c34)CC2)cc1]

[M+H]=422.5.

Example 187. N-(2-Fluorophenyl)-6-methyl-4-[(1-methylcyclopropyl)amino]furo[2,3-d]pyrimidine-5-carboxamide

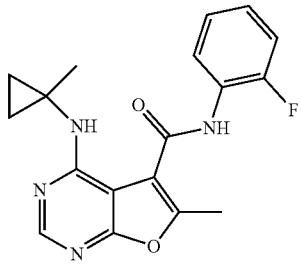 [SMILES: Cc1oc2ncnc(NC3(C)CC3)c2c1C(=O)Nc1ccccc1F]

[M+H]=341.2.

Example 188. N-[2-(Furan-2-yl)ethyl]-6-methyl-4-[(1-methylcyclopropyl)amino]furo[2,3-d]pyrimidine-5-carboxamide

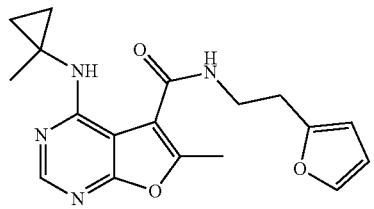 [SMILES: Cc1oc2ncnc(NC3(C)CC3)c2c1C(=O)NCCc1ccco1]

[M+H]=341.2.

Example 189. N-[2-(1H-Imidazol-1-yl)ethyl]-6-methyl-4-[(1-methylcyclopropyl)amino]furo[2,3-d]pyrimidine-5-carboxamide

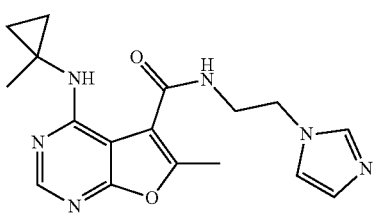 [SMILES: Cc1oc2ncnc(NC3(C)CC3)c2c1C(=O)NCCn1ccnc1]

[M+H]=341.2.

Example 190. 6-Methyl-4-[(1-methylcyclopropyl)amino]-N-(thiophen-2-ylmethyl)furo[2,3-d]pyrimidine-5-carboxamide

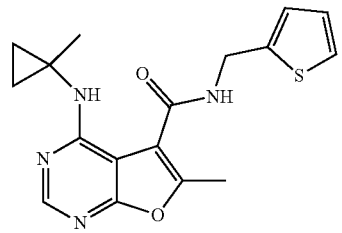 [SMILES: Cc1oc2ncnc(NC3(C)CC3)c2c1C(=O)NCc1cccs1]

[M+H]=343.2.

Example 191. 6-Methyl-4-[(1-methylcyclopropyl)amino]-N-(thiophen-3-ylmethyl)furo[2,3-d]pyrimidine-5-carboxamide

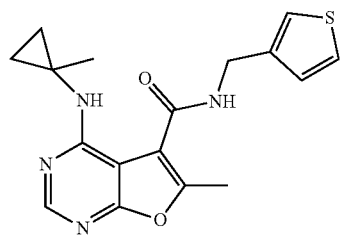 [SMILES: Cc1oc2ncnc(NC3(C)CC3)c2c1C(=O)NCc1ccsc1]

[M+H]=343.2.

Example 192. N-(Cyclohexylmethyl)-6-methyl-4-[(1-methylcyclopropyl)amino]furo[2,3-d]pyrimidine-5-carboxamide

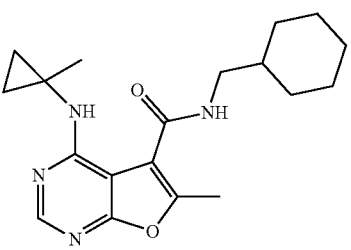 [SMILES: Cc1oc2ncnc(NC3(C)CC3)c2c1C(=O)NCC1CCCCC1]

[M+H]=343.3.

Example 193. 6-Methyl-4-[(1-methylcyclopropyl)amino]-N-(1-methylpiperidin-4-yl)furo[2,3-d]pyrimidine-5-carboxamide

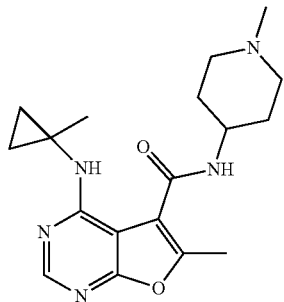 [SMILES: Cc1oc2ncnc(NC3(C)CC3)c2c1C(=O)NC1CCN(C)CC1]

[M+H]=344.3.

Example 194. 6-Methyl-4-[(1-methylcyclopropyl)amino]-N-(1-phenylethyl)furo[2,3-d]pyrimidine-5-carboxamide

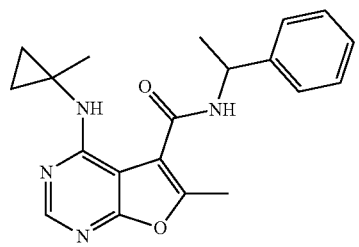 [SMILES: Cc1oc2ncnc(NC3(C)CC3)c2c1C(=O)NC(C)c1ccccc1]

[M+H]=351.3.

Example 195. 6-Methyl-4-[(1-methylcyclopropyl)amino]-N-(2-phenylethyl)furo[2,3-d]pyrimidine-5-carboxamide

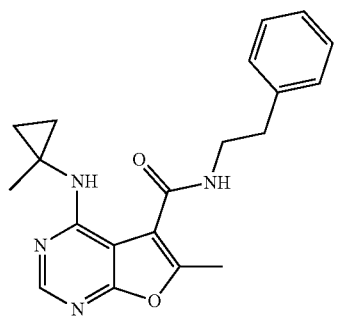 [SMILES: Cc1oc2ncnc(NC3(C)CC3)c2c1C(=O)NCCc1ccccc1]

[M+H]=351.3.

Example 196. 6-Methyl-4-[(1-methylcyclopropyl)amino]-N-[(4-methylphenyl)methyl]furo[2,3-d]pyrimidine-5-carboxamide

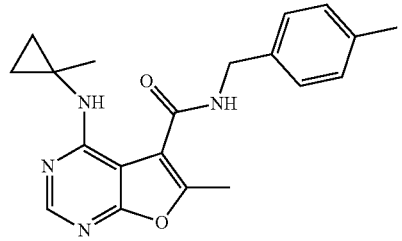 [SMILES: Cc1ccc(CNC(=O)c2c(C)oc3ncnc(NC4(C)CC4)c23)cc1]

[M+H]=351.3.

Example 197. N-(2,5-Dimethylphenyl)-6-methyl-4-[(1-methylcyclopropyl)amino]furo[2,3-d]pyrimidine-5-carboxamide

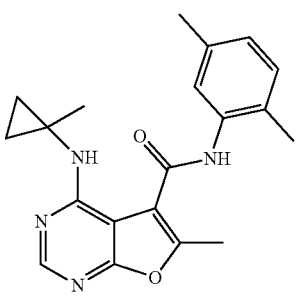 [SMILES: Cc1ccc(C)c(NC(=O)c2c(C)oc3ncnc(NC4(C)CC4)c23)c1]

[M+H]=351.3.

Example 198. 6-Methyl-4-[(1-methylcyclopropyl)amino]-N-[(3-methylphenyl)methyl]furo[2,3-d]pyrimidine-5-carboxamide

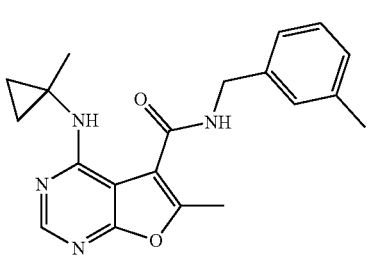 [SMILES: Cc1cccc(CNC(=O)c2c(C)oc3ncnc(NC4(C)CC4)c23)c1]

[M+H]=351.3.

Example 199. 6-Methyl-4-[(1-methylcyclopropyl)amino]-N-phenylfuro[2,3-d]pyrimidine-5-carboxamide

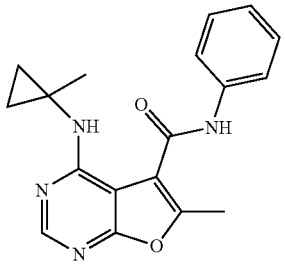 [SMILES: Cc1oc2ncnc(NC3(C)CC3)c2c1C(=O)Nc1ccccc1]

[M+H]=323.2.

Example 200. 5-[(1R,5S)-3-Azabicyclo[3.1.0]hexane-3-carbonyl]-6-methyl-N-(1-methylcyclopropyl)furo[2,3-d]pyrimidin-4-amine

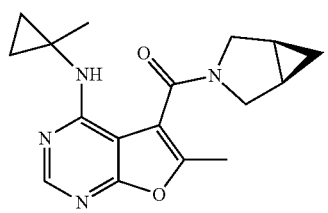 [SMILES: Cc1oc2ncnc(NC3(C)CC3)c2c1C(=O)N1C[C@H]2C[C@H]2C1]

[M+H]=313.4.

Example 201. 5-[(3aR,6aS)-Octahydrocyclopenta[c]pyrrole-2-carbonyl]-6-methyl-N-(1-methylcyclopropyl)furo[2,3-d]pyrimidin-4-amine

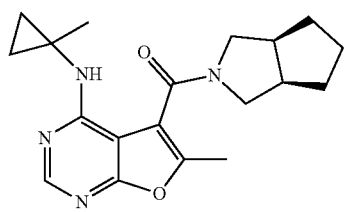 [SMILES: Cc1oc2ncnc(NC3(C)CC3)c2c1C(=O)N1C[C@H]2CCC[C@H]2C1]

[M+H]=341.5.

Example 202. N,N-Dimethyl-1-{6-methyl-4-[(1-methylcyclopropyl)amino]furo[2,3-d]pyrimidine-5-carbonyl}piperidin-4-amine

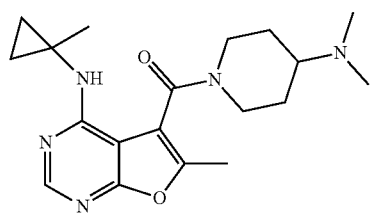 [SMILES: Cc1oc2ncnc(NC3(C)CC3)c2c1C(=O)N1CCC(N(C)C)CC1]

[M+H]=358.5.

Example 203. N-[(3-Methoxyphenyl)methyl]-N,6-dimethyl-4-[(1-methylcyclopropyl)amino]furo[2,3-d]pyrimidine-5-carboxamide

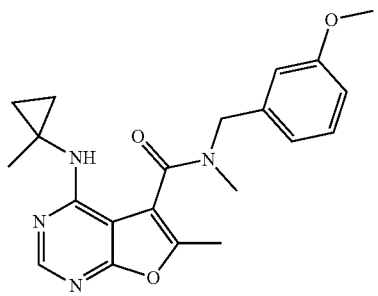

[M+H]=381.3.

Example 204. N-[2-(3-Chlorophenyl)ethyl]-6-methyl-4-[(1-methylcyclopropyl)amino]furo[2,3-d]pyrimidine-5-carboxamide

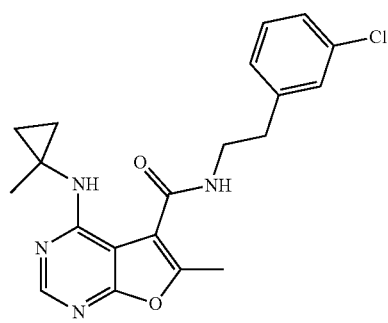 [SMILES: Cc1oc2ncnc(NC3(C)CC3)c2c1C(=O)NCCc1cccc(Cl)c1]

[M+H]=385.2.

Example 205. N-[2-(4-Methoxyphenyl)ethyl]-N,6-dimethyl-4-[(1-methylcyclopropyl)amino]furo[2,3-d]pyrimidine-5-carboxamide

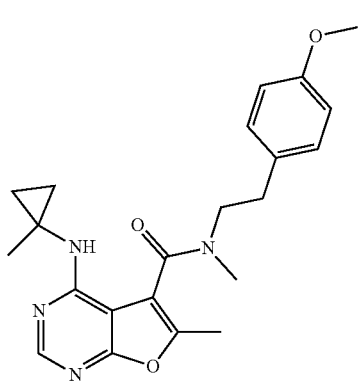

[M+H]=395.3.

Example 206. 6-Methyl-5-(4-methyl-1,4-diazepane-1-carbonyl)-N-(1-methylcyclopropyl)furo[2,3-d]pyrimidin-4-amine

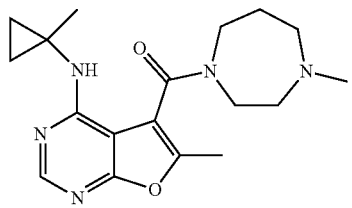 [SMILES: Cc1oc2ncnc(NC3(C)CC3)c2c1C(=O)N1CCCN(C)CC1]

[M+H]=344.3.

Example 207. N-[2-(5-Fluoro-1H-indol-3-yl)ethyl]-6-methyl-4-[(1-methylcyclopropyl)amino]furo[2,3-d]pyrimidine-5-carboxamide

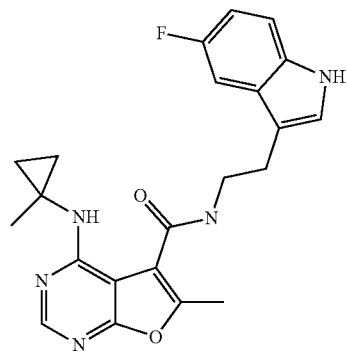 [SMILES: Cc1oc2ncnc(NC3(C)CC3)c2c1C(=O)NCCc1c[nH]c2ccc(F)cc12]

[M+H]=408.3.

Example 208. 6-Methyl-N-(1-methylcyclopropyl)-5-[(1R,5S,6S)-6-phenyl-3-azabicyclo[3.1.0]hexane-3-carbonyl]furo[2,3-d]pyrimidin-4-amine

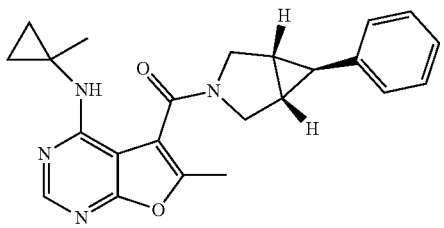 [SMILES: Cc1oc2ncnc(NC3(C)CC3)c2c1C(=O)N1C[C@@H]2[C@H](C1)[C@H]2c1ccccc1]

[M+H]=389.3.

Example 209. 5-[(1R,5S,6S)-6-(2-Methoxyphenyl)-3-azabicyclo[3.1.0]hexane-3-carbonyl]-6-methyl-N-(1-methylcyclopropyl)furo[2,3-d]pyrimidin-4-amine

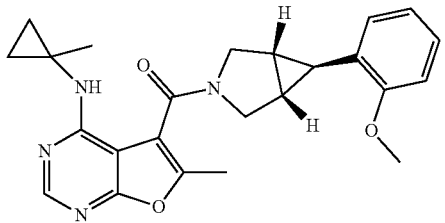 [SMILES: COc1ccccc1[C@H]1[C@@H]2CN(C(=O)c3c(C)oc4ncnc(NC5(C)CC5)c34)C[C@@H]21]

[M+H]=419.3.

Example 210. 6-Methyl-4-[(1-methylcyclopropyl)amino]-N-(prop-2-yn-1-yl)furo[2,3-d]pyrimidine-5-carboxamide

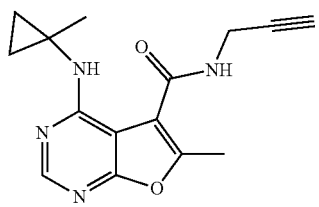 [SMILES: C#CCNC(=O)c1c(C)oc2ncnc(NC3(C)CC3)c12]

[M+H]=285.1.

Example 211. 6-Methyl-4-[(1-methylcyclopropyl)amino]-N-propylfuro[2,3-d]pyrimidine-5-carboxamide

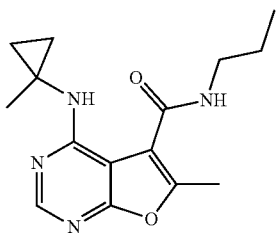 [SMILES: CCCNC(=O)c1c(C)oc2ncnc(NC3(C)CC3)c12]

$^1$H NMR (400 MHz, CDCl$_3$) δ 9.25-9.03 (m, 1H), 8.48 (s, 1H), 6.03-5.89 (m, 1H), 3.52-3.42 (m, 2H), 2.71 (s, 3H), 1.70 (d, J=7.2 Hz, 2H), 1.54 (s, 3H), 1.04 (t, J=7.5 Hz, 3H), 0.95-0.79 (m, 4H). [M+H]=289.2.

Example 212. N-Cyclobutyl-6-methyl-4-[(1-methyl-cyclopropyl)amino]furo[2,3-d]pyrimidine-5-carboxamide

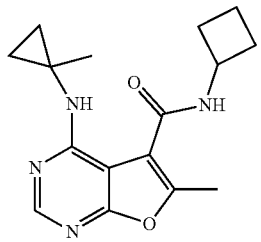 [SMILES: Cc1oc2ncnc(NC3(C)CC3)c2c1C(=O)NC1CCC1]

[M+H]=301.4.

Example 213. N-Butyl-6-methyl-4-[(1-methylcyclopropyl)amino]furo[2,3-d]pyrimidine-5-carboxamide

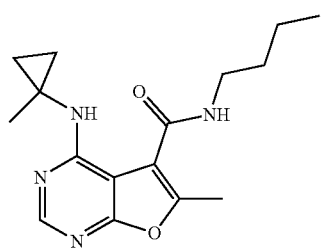 [SMILES: CCCCNC(=O)c1c(C)oc2ncnc(NC3(C)CC3)c12]

[M+H]=303.4.

Example 214. N,6-Dimethyl-4-[(1-methylcyclopropyl)amino]-N-(pyridin-2-ylmethyl)furo[2,3-d]pyrimidine-5-carboxamide

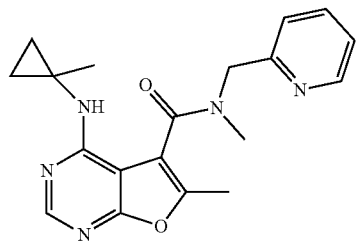 [SMILES: Cc1oc2ncnc(NC3(C)CC3)c2c1C(=O)N(C)Cc1ccccn1]

[M+H]=352.4.

Example 215. N,6-Dimethyl-4-[(1-methylcyclopropyl)amino]-N-(pyridin-3-ylmethyl)furo[2,3-d]pyrimidine-5-carboxamide

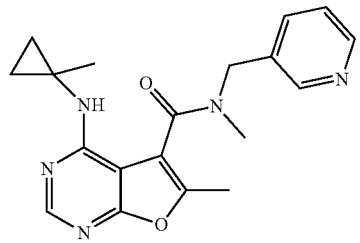 [SMILES: Cc1oc2ncnc(NC3(C)CC3)c2c1C(=O)N(C)Cc1cccnc1]

[M+H]=352.5.

Example 216. N-(3-Methoxyphenyl)-6-methyl-4-[(1-methylcyclopropyl)amino]furo[2,3-d]pyrimidine-5-carboxamide

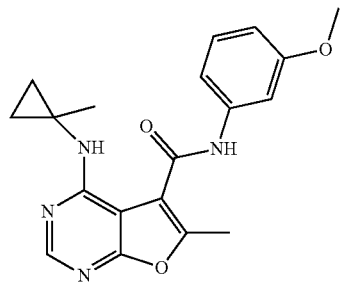 [SMILES: COc1cccc(NC(=O)c2c(C)oc3ncnc(NC4(C)CC4)c23)c1]

[M+H]=353.4.

Example 217. N-[(3-Fluorophenyl)methyl]-6-methyl-4-[(1-methylcyclopropyl)amino]furo[2,3-d]pyrimidine-5-carboxamide

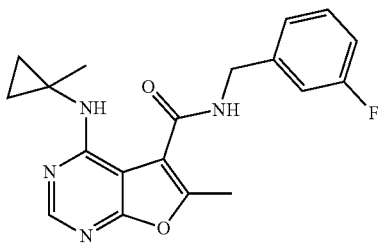 [SMILES: Cc1oc2ncnc(NC3(C)CC3)c2c1C(=O)NCc1cccc(F)c1]

[M+H]=355.4.

Example 218. N-[(2-Fluorophenyl)methyl]-6-methyl-4-[(1-methylcyclopropyl)amino]furo[2,3-d]pyrimidine-5-carboxamide

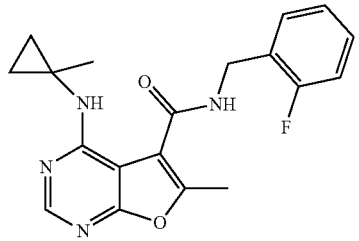 [SMILES: Cc1oc2ncnc(NC3(C)CC3)c2c1C(=O)NCc1ccccc1F]

[M+H]=355.4.

Example 219. N-(3-Fluoro-4-methylphenyl)-6-methyl-4-[(1-methylcyclopropyl)amino]furo[2,3-d]pyrimidine-5-carboxamide

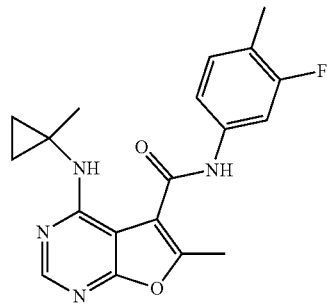 [SMILES: Cc1ccc(NC(=O)c2c(C)oc3ncnc(NC4(C)CC4)c23)cc1F]

[M+H]=355.4.

Example 220. N-[3-(1H-Imidazol-1-yl)propyl]-6-methyl-4-[(1-methylcyclopropyl)amino]furo[2,3-d]pyrimidine-5-carboxamide

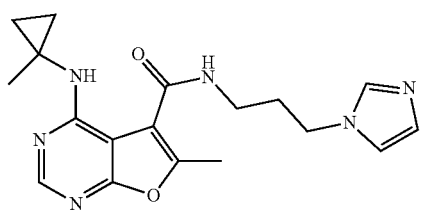 [SMILES: Cc1oc2ncnc(NC3(C)CC3)c2c1C(=O)NCCCn1ccnc1]

[M+H]=355.4.

Example 221. 5-[(8aS)-Octahydropyrrolo[1,2-a]piperazine-2-carbonyl]-6-methyl-N-(1-methylcyclopropyl)furo[2,3-d]pyrimidin-4-amine

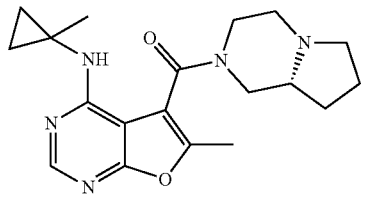 [SMILES: Cc1oc2ncnc(NC3(C)CC3)c2c1C(=O)N1CCN2CCC[C@@H]2C1]

[M+H]=356.5.

Example 222. 6-Methyl-4-[(1-methylcyclopropyl)amino]-N-[2-(thiophen-2-yl)ethyl]furo[2,3-d]pyrimidine-5-carboxamide

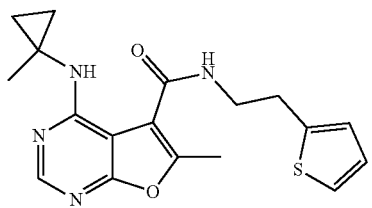 [SMILES: Cc1oc2ncnc(NC3(C)CC3)c2c1C(=O)NCCc1cccs1]

[M+H]=357.4.

Example 223. N,6-Dimethyl-4-[(1-methylcyclopropyl)amino]-N-(thiophen-3-ylmethyl)furo[2,3-d]pyrimidine-5-carboxamide

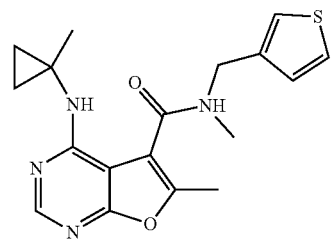 [SMILES: Cc1oc2ncnc(NC3(C)CC3)c2c1C(=O)N(C)Cc1ccsc1]

[M+H]=357.4.

Example 224. N,6-Dimethyl-4-[(1-methylcyclopropyl)amino]-N-(thiophen-2-ylmethyl)furo[2,3-d]pyrimidine-5-carboxamide

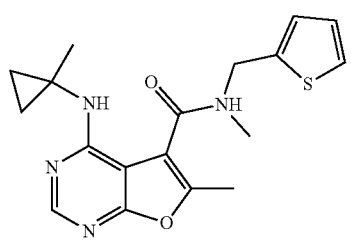 [SMILES: Cc1oc2ncnc(NC3(C)CC3)c2c1C(=O)N(C)Cc1cccs1]

[M+H]=357.4.

Example 225. N-(2-Cyclohexylethyl)-6-methyl-4-[(1-methylcyclopropyl)amino]furo[2,3-d]pyrimidine-5-carboxamide

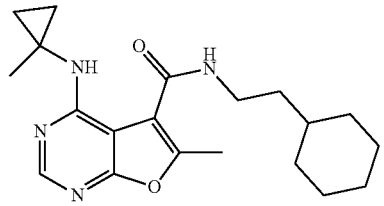 [SMILES: Cc1oc2ncnc(NC3(C)CC3)c2c1C(=O)NCCC1CCCCC1]

[M+H]=357.5.

Example 226. 1-(4-{6-Methyl-4-[(1-methylcyclopropyl)amino]furo[2,3-d]pyrimidine-5-carbonyl}piperazin-1-yl)ethan-1-one

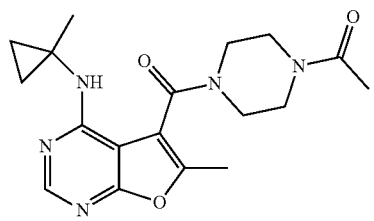 [SMILES: CC(=O)N1CCN(C(=O)c2c(C)oc3ncnc(NC4(C)CC4)c23)CC1]

[M+H]=358.4.

Example 227. N-(3,4-Difluorophenyl)-6-methyl-4-[(1-methylcyclopropyl)amino]furo[2,3-d]pyrimidine-5-carboxamide

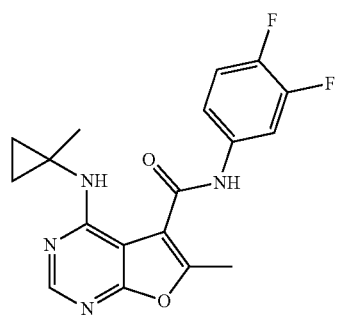 [SMILES: Cc1oc2ncnc(NC3(C)CC3)c2c1C(=O)Nc1ccc(F)c(F)c1]

[M+H]=359.4.

Example 228. N-(3,5-Difluorophenyl)-6-methyl-4-[(1-methylcyclopropyl)amino]furo[2,3-d]pyrimidine-5-carboxamide

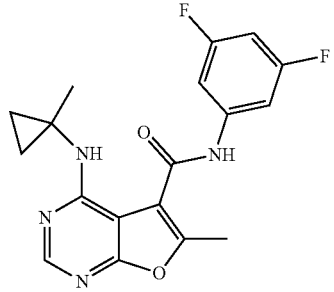 [SMILES: Cc1oc2ncnc(NC3(C)CC3)c2c1C(=O)Nc1cc(F)cc(F)c1]

[M+H]=359.4.

Example 229. N-(2,3-Dihydro-1H-inden-5-yl)-6-methyl-4-[(1-methylcyclopropyl)amino]furo[2,3-d]pyrimidine-5-carboxamide

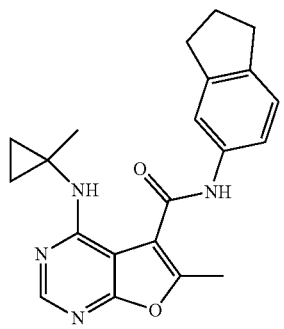 [SMILES: Cc1oc2ncnc(NC3(C)CC3)c2c1C(=O)Nc1ccc2c(c1)CCC2]

[M+H]=363.5.

Example 230. N-(2,3-Dihydro-1H-inden-1-yl)-6-methyl-4-[(1-methylcyclopropyl)amino]furo[2,3-d]pyrimidine-5-carboxamide

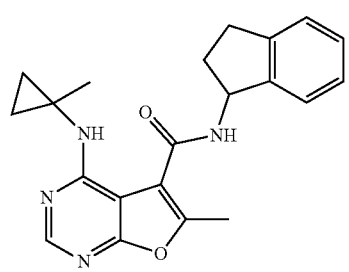 [SMILES: Cc1oc2ncnc(NC3(C)CC3)c2c1C(=O)NC1CCc2ccccc21]

[M+H]=363.4.

Example 231. N-(2,3-Dihydro-1H-inden-2-yl)-6-methyl-4-[(1-methylcyclopropyl)amino]furo[2,3-d]pyrimidine-5-carboxamide

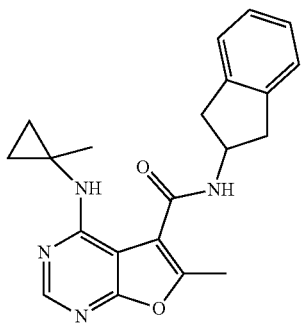 [SMILES: Cc1oc2ncnc(NC3(C)CC3)c2c1C(=O)NC1Cc2ccccc2C1]

[M+H]=363.5.

Example 232. N-(2,3-Dihydro-1H-inden-4-yl)-6-methyl-4-[(1-methylcyclopropyl)amino]furo[2,3-d]pyrimidine-5-carboxamide

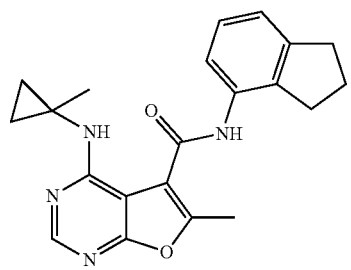 [SMILES: Cc1oc2ncnc(NC3(C)CC3)c2c1C(=O)Nc1cccc2c1CCC2]

[M+H]=363.5.

Example 233. 6-Methyl-N-(1-methylcyclopropyl)-5-(1,2,3,4-tetrahydroisoquinoline-2-carbonyl)furo[2,3-d]pyrimidin-4-amine

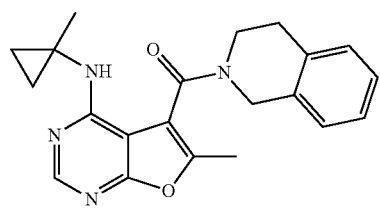 [SMILES: Cc1oc2ncnc(NC3(C)CC3)c2c1C(=O)N1CCc2ccccc2C1]

[M+H]=363.5.

Example 234. 6-Methyl-4-[(1-methylcyclopropyl)amino]-N-[4-(propan-2-yl)phenyl]furo[2,3-d]pyrimidine-5-carboxamide

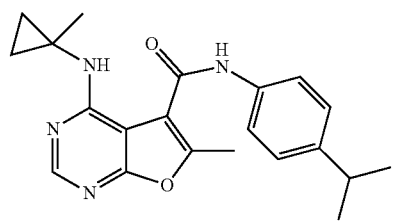

[M+H]=365.5.

Example 235. 6-Methyl-4-[(1-methylcyclopropyl)amino]-N-[2-(4-methylphenyl)ethyl]furo[2,3-d]pyrimidine-5-carboxamide

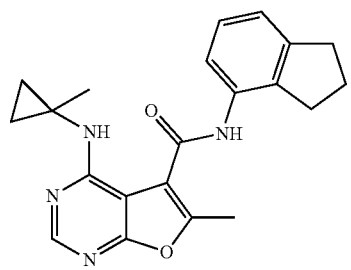 [SMILES: Cc1oc2ncnc(NC3(C)CC3)c2c1C(=O)Nc1cccc2c1CCC2]

[M+H]=365.5.

Example 236. 6-Methyl-4-[(1-methylcyclopropyl)amino]-N-[2-(2-methylphenyl)ethyl]furo[2,3-d]pyrimidine-5-carboxamide

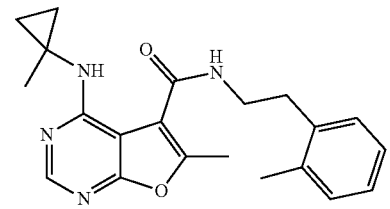

[M+H]=365.5.

Example 237. N-[(3,4-Dimethylphenyl)methyl]-6-methyl-4-[(1-methylcyclopropyl)amino]furo[2,3-d]pyrimidine-5-carboxamide

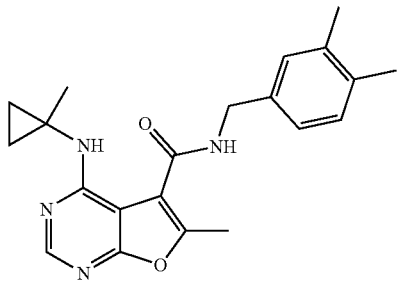 [SMILES: Cc1ccc(CNC(=O)c2c(C)oc3ncnc(NC4(C)CC4)c23)cc1C]

[M+H]=365.5.

Example 238. N-[(2,3-Dimethylphenyl)methyl]-6-methyl-4-[(1-methylcyclopropyl)amino]furo[2,3-d]pyrimidine-5-carboxamide

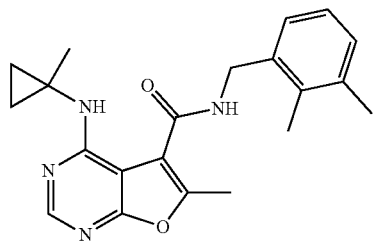 [SMILES: Cc1cccc(CNC(=O)c2c(C)oc3ncnc(NC4(C)CC4)c23)c1C]

[M+H]=365.5.

Example 239. 6-Methyl-4-[(1-methylcyclopropyl)amino]-N-(2-phenylpropan-2-yl)furo[2,3-d]pyrimidine-5-carboxamide

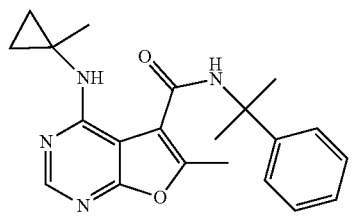

[M+H]=365.5.

Example 240. N,6-Dimethyl-4-[(1-methylcyclopropyl)amino]-N-(2-phenylethyl)furo[2,3-d]pyrimidine-5-carboxamide

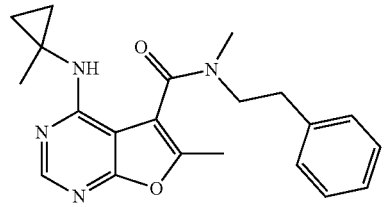 [SMILES: Cc1oc2ncnc(NC3(C)CC3)c2c1C(=O)N(C)CCc1ccccc1]

[M+H]=365.5.

Example 241. N-Benzyl-N-ethyl-6-methyl-4-[(1-methylcyclopropyl)amino]furo[2,3-d]pyrimidine-5-carboxamide

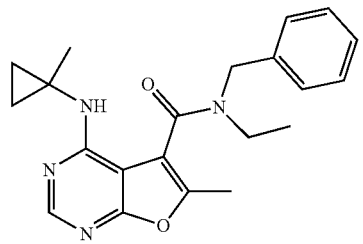 [SMILES: CCN(Cc1ccccc1)C(=O)c1c(C)oc2ncnc(NC3(C)CC3)c12]

[M+H]=365.5.

Example 242. N,6-Dimethyl-4-[(1-methylcyclopropyl)amino]-N-[2-(pyridin-2-yl)ethyl]furo[2,3-d]pyrimidine-5-carboxamide

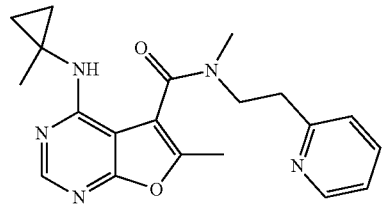 [SMILES: Cc1oc2ncnc(NC3(C)CC3)c2c1C(=O)N(C)CCc1ccccn1]

[M+H]=366.4.

Example 243. N-(2H-1,3-Benzodioxol-5-yl)-6-methyl-4-[(1-methylcyclopropyl)amino]furo[2,3-d]pyrimidine-5-carboxamide

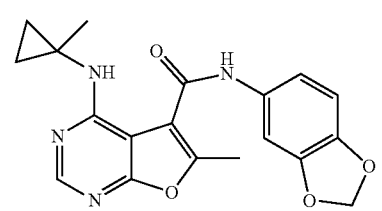

[M+H]=367.4.

Example 244. N-(4-Methoxy-2-methylphenyl)-6-methyl-4-[(1-methylcyclopropyl)amino]furo[2,3-d]pyrimidine-5-carboxamide

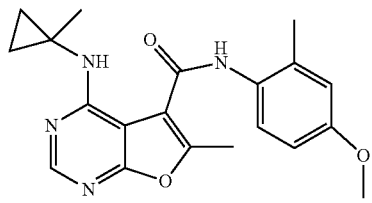

[M+H]=367.5.

Example 245. N-(3-Methoxy-2-methylphenyl)-6-methyl-4-[(1-methylcyclopropyl)amino]furo[2,3-d]pyrimidine-5-carboxamide

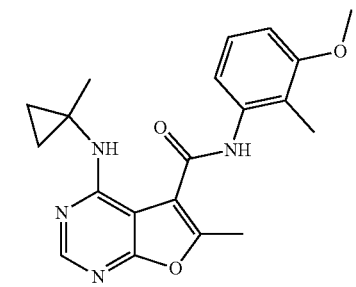 [SMILES: COc1cccc(NC(=O)c2c(C)oc3ncnc(NC4(C)CC4)c23)c1C]

[M+H]=367.4.

Example 246. N-[(3-Methoxyphenyl)methyl]-6-methyl-4-[(1-methylcyclopropyl)amino]furo[2,3-d]pyrimidine-5-carboxamide

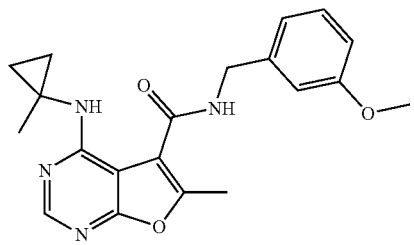 [SMILES: COc1cccc(CNC(=O)c2c(C)oc3ncnc(NC4(C)CC4)c23)c1]

[M+H]=367.5.

Example 247. 5-[2-(Furan-2-yl)pyrrolidine-1-carbonyl]-6-methyl-N-(1-methylcyclopropyl)furo[2,3-d]pyrimidin-4-amine

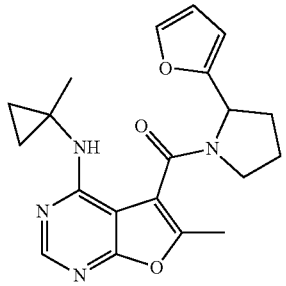 [SMILES: Cc1oc2ncnc(NC3(C)CC3)c2c1C(=O)N1CCCC1c1ccco1]

[M+H]=367.5.

Example 248. N-[(4-Fluorophenyl)methyl]-N,6-dimethyl-4-[(1-methylcyclopropyl)amino]furo[2,3-d]pyrimidine-5-carboxamide

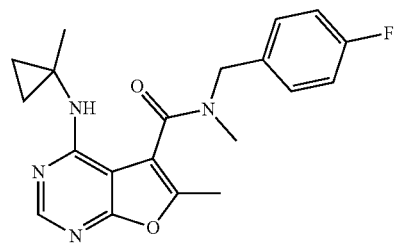 [SMILES: Cc1oc2ncnc(NC3(C)CC3)c2c1C(=O)N(C)Cc1ccc(F)cc1]

[M+H]=369.4.

Example 249. N-[(2-Fluorophenyl)methyl]-N,6-dimethyl-4-[(1-methylcyclopropyl)amino]furo[2,3-d]pyrimidine-5-carboxamide

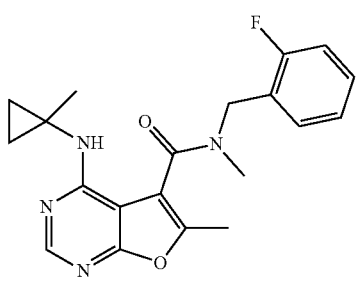 [SMILES: Cc1oc2ncnc(NC3(C)CC3)c2c1C(=O)N(C)Cc1ccccc1F]

[M+H]=369.5.

Example 250. N-[(3-Fluorophenyl)methyl]-N,6-dimethyl-4-[(1-methylcyclopropyl)amino]furo[2,3-d]pyrimidine-5-carboxamide

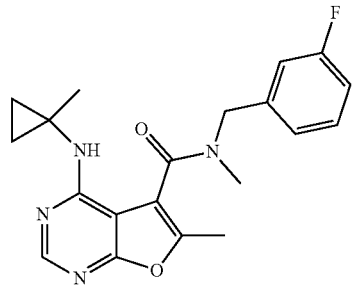 [SMILES: Cc1oc2ncnc(NC3(C)CC3)c2c1C(=O)N(C)Cc1cccc(F)c1]

[M+H]=369.4.

Example 251. N-[(3-Ethyl-1,2-oxazol-5-yl)methyl]-N,6-dimethyl-4-[(1-methylcyclopropyl)amino]furo[2,3-d]pyrimidine-5-carboxamide

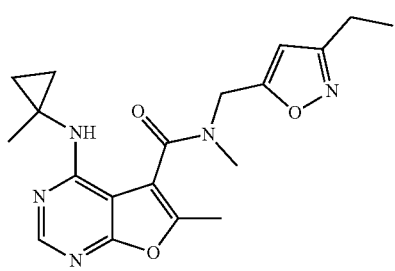 [SMILES: CCc1cc(CN(C)C(=O)c2c(C)oc3ncnc(NC4(C)CC4)c23)on1]

[M+H]=370.5.

Example 252. N-(5-Fluoro-2-methoxyphenyl)-6-methyl-4-[(1-methylcyclopropyl)amino]furo[2,3-d]pyrimidine-5-carboxamide

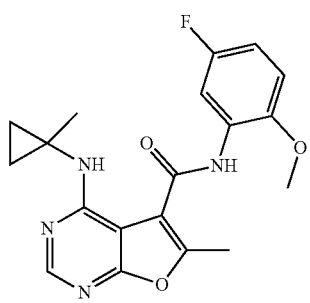 [SMILES: COc1ccc(F)cc1NC(=O)c1c(C)oc2ncnc(NC3(C)CC3)c12]

[M+H]=371.4.

Example 253. N-(4-Fluoro-3-methoxyphenyl)-6-methyl-4-[(1-methylcyclopropyl)amino]furo[2,3-d]pyrimidine-5-carboxamide

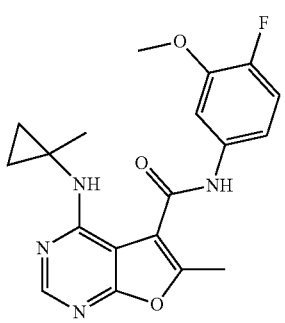 [SMILES: COc1cc(NC(=O)c2c(C)oc3ncnc(NC4(C)CC4)c23)ccc1F]

[M+H]=371.4.

Example 254. N-[(2-Chlorophenyl)methyl]-6-methyl-4-[(1-methylcyclopropyl)amino]furo[2,3-d]pyrimidine-5-carboxamide

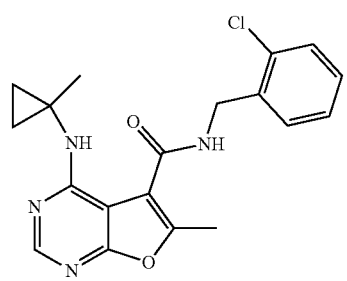 [SMILES: Cc1oc2ncnc(NC3(C)CC3)c2c1C(=O)NCc1ccccc1Cl]

[M+H]=371.4.

Example 255. N-(2-Chloro-4-methylphenyl)-6-methyl-4-[(1-methylcyclopropyl)amino]furo[2,3-d]pyrimidine-5-carboxamide

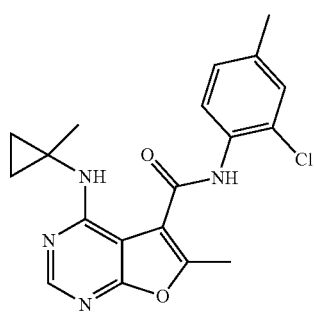 [SMILES: Cc1ccc(NC(=O)c2c(C)oc3ncnc(NC4(C)CC4)c23)c(Cl)c1]

[M+H]=371.4.

Example 256. N-(2-Chloro-5-methylphenyl)-6-methyl-4-[(1-methylcyclopropyl)amino]furo[2,3-d]pyrimidine-5-carboxamide

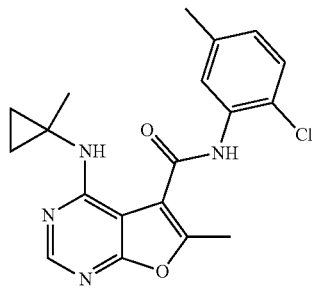 [SMILES: Cc1ccc(Cl)c(NC(=O)c2c(C)oc3ncnc(NC4(C)CC4)c23)c1]

[M+H]=371.4.

Example 257. 1-(4-{6-Methyl-4-[(1-methylcyclopropyl)amino]furo[2,3-d]pyrimidine-5-carbonyl}-1,4-diazepan-1-yl)ethan-1-one

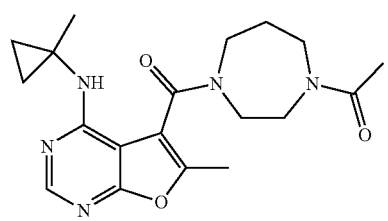 [SMILES: CC(=O)N1CCCN(C(=O)c2c(C)oc3ncnc(NC4(C)CC4)c23)CC1]

[M+H]=372.5.

Example 258. 5-(4-tert-Butylpiperazine-1-carbonyl)-6-methyl-N-(1-methylcyclopropyl)furo[2,3-d]pyrimidin-4-amine

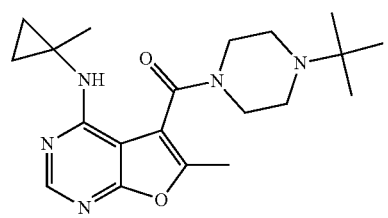 [SMILES: Cc1oc2ncnc(NC3(C)CC3)c2c1C(=O)N1CCN(C(C)(C)C)CC1]

[M+H]=372.5.

Example 259. 6-Methyl-4-[(1-methylcyclopropyl)amino]-N-[3-(morpholin-4-yl)propyl]furo[2,3-d]pyrimidine-5-carboxamide

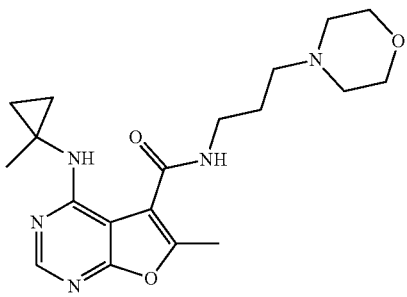 [SMILES: Cc1oc2ncnc(NC3(C)CC3)c2c1C(=O)NCCCN1CCOCC1]

[M+H]=374.5.

Example 260. 5-[4-(2-Methoxyethyl)piperazine-1-carbonyl]-6-methyl-N-(1-methylcyclopropyl)furo[2,3-d]pyrimidin-4-amine

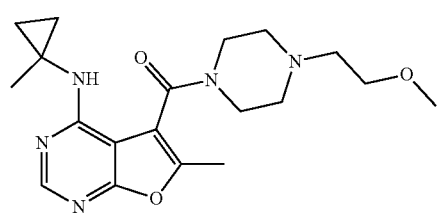

[M+H]=374.5.

Example 261. N-(4-Chloro-2-fluorophenyl)-6-methyl-4-[(1-methylcyclopropyl)amino]furo[2,3-d]pyrimidine-5-carboxamide

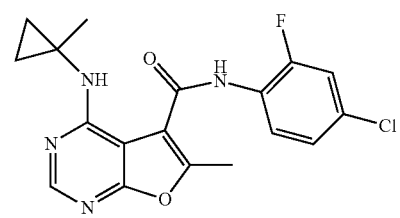 [SMILES: Cc1oc2ncnc(NC3(C)CC3)c2c1C(=O)Nc1ccc(Cl)cc1F]

[M+H]=375.4.

Example 262. 6-Methyl-N-(1-methyl-1H-indazol-5-yl)-4-[(1-methylcyclopropyl)amino]furo[2,3-d]pyrimidine-5-carboxamide

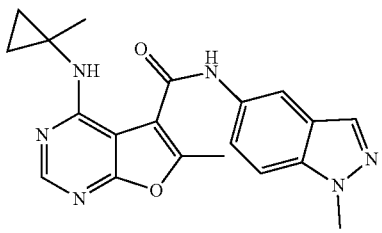 [SMILES: Cc1oc2ncnc(NC3(C)CC3)c2c1C(=O)Nc1ccc2c(cnn2C)c1]

[M+H]=377.4.

Example 263. N-(1,3-Benzothiazol-5-yl)-6-methyl-4-[(1-methylcyclopropyl)amino]furo[2,3-d]pyrimidine-5-carboxamide

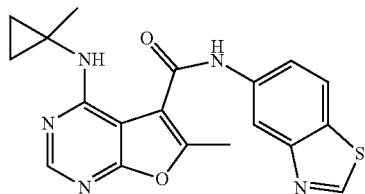 [SMILES: Cc1oc2ncnc(NC3(C)CC3)c2c1C(=O)Nc1ccc2scnc2c1]

[M+H]=380.4.

Example 264. N-(1,3-Benzothiazol-6-yl)-6-methyl-4-[(1-methylcyclopropyl)amino]furo[2,3-d]pyrimidine-5-carboxamide

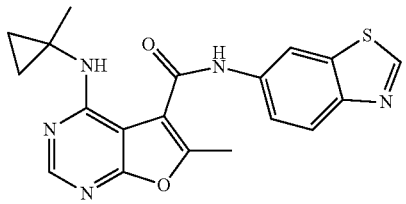 [SMILES: Cc1oc2ncnc(NC3(C)CC3)c2c1C(=O)Nc1ccc2ncsc2c1]

[M+H]=380.4.

Example 265. N-[(5-Cyclopropyl-1H-pyrazol-3-yl)methyl]-N,6-dimethyl-4-[(1-methylcyclopropyl)amino]furo[2,3-d]pyrimidine-5-carboxamide

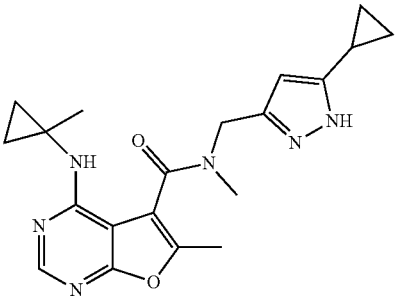 [SMILES: Cc1oc2ncnc(NC3(C)CC3)c2c1C(=O)N(C)Cc1cc(C2CC2)[nH]n1]

[M+H]=381.5.

Example 266. N-(2,2-Dimethyloxan-4-yl)-N-ethyl-6-methyl-4-[(1-methylcyclopropyl)amino]furo[2,3-d]pyrimidine-5-carboxamide

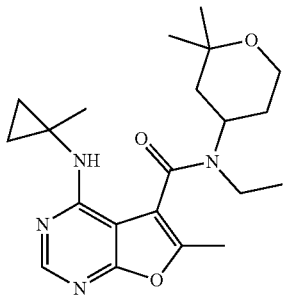 [SMILES: CCN(C(=O)c1c(C)oc2ncnc(NC3(C)CC3)c12)C1CCOC(C)(C)C1]

[M+H]=387.5.

Example 267. N-{[4-(Difluoromethoxy)phenyl]methyl}-6-methyl-4-[(1-methylcyclopropyl)amino]furo[2,3-d]pyrimidine-5-carboxamide

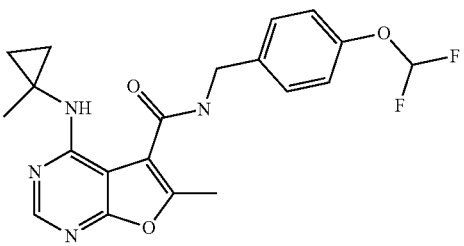 [SMILES: Cc1oc2ncnc(NC3(C)CC3)c2c1C(=O)NCc1ccc(OC(F)F)cc1]

[M+H]=403.4.

Example 268. N-[3-Methoxy-5-(trifluoromethyl) phenyl]-6-methyl-4-[(1-methylcyclopropyl)amino] furo[2,3-d]pyrimidine-5-carboxamide

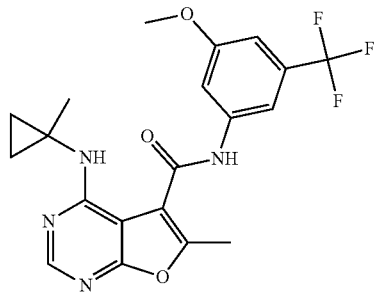 [SMILES: COc1cc(NC(=O)c2c(C)oc3ncnc(NC4(C)CC4)c23)cc(C(F)(F)F)c1]

[M+H]=421.5.

Example 269. 5-{5H,6H,7H,8H-Imidazo[1,2-a]pyrazine-7-carbonyl}-6-methyl-N-(1-methylcyclopropyl) furo[2,3-d]pyrimidin-4-amine

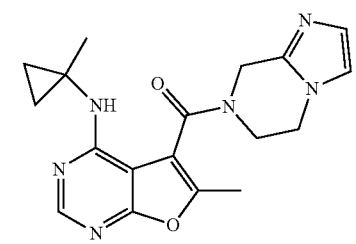 [SMILES: Cc1oc2ncnc(NC3(C)CC3)c2c1C(=O)N1CCn2ccnc2C1]

[M+H]=353.4.

Example 270. N-(Adamantan-1-yl)-6-methyl-4-[(1-methylcyclopropyl)amino]furo[2,3-d]pyrimidine-5-carboxamide

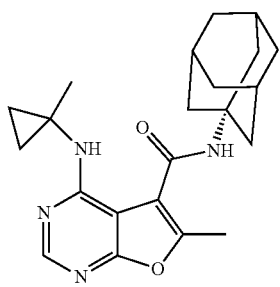

[M+H]=381.5.

Example 271. 5-[(4aS,8aR)-Decahydroisoquinoline-2-carbonyl]-6-methyl-N-(1-methylcyclopropyl)furo [2,3-d]pyrimidin-4-amine

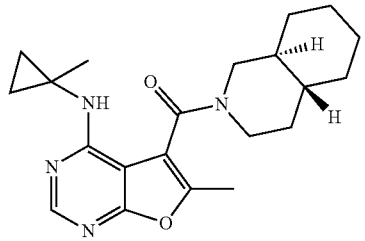

[M+H]=369.5.

Example 272. 6-Methyl-4-[(1-methylcyclopropyl) amino]-N-(6-methylpyridin-3-yl)furo[2,3-d]pyrimidine-5-carboxamide

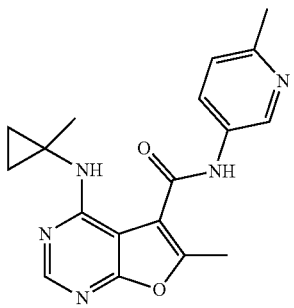 [SMILES: Cc1ccc(NC(=O)c2c(C)oc3ncnc(NC4(C)CC4)c23)cn1]

[M+H]=338.4.

Example 273. 6-Methyl-N-(1-methylcyclopropyl)-5-{4H,5H,6H,7H-thieno[3,2-c]pyridine-5-carbonyl}furo[2,3-d]pyrimidin-4-amine

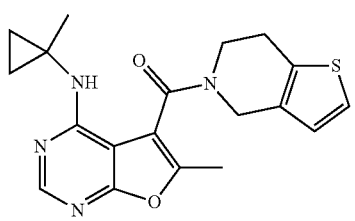 [SMILES: Cc1oc2ncnc(NC3(C)CC3)c2c1C(=O)N1CCc2sccc2C1]

[M+H]=369.4.

Example 274. 1-{6-Methyl-4-[(1-methylcyclopropyl)amino]furo[2,3-d]pyrimidine-5-carbonyl}-4-phenylpiperidine-4-carbonitrile

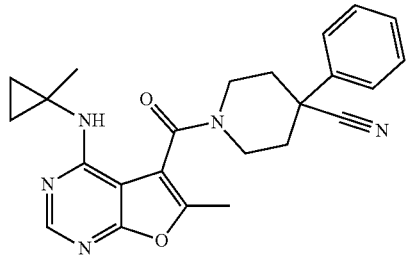 [SMILES: Cc1oc2ncnc(NC3(C)CC3)c2c1C(=O)N1CCC(C#N)(c2ccccc2)CC1]

[M+H]=416.5.

Example 275. N-{[1-(Ethoxymethyl)cyclopropyl]methyl}-6-methyl-4-[(1-methylcyclopropyl)amino]furo[2,3-d]pyrimidine-5-carboxamide

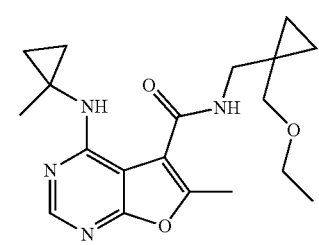 [SMILES: CCOCC1(CNC(=O)c2c(C)oc3ncnc(NC4(C)CC4)c23)CC1]

[M+H]=359.5.

Example 276. 6-Methyl-N-(1-methylcyclopropyl)-5-{5H,6H,7H-pyrrolo[3,4-b]pyridine-6-carbonyl}furo[2,3-d]pyrimidin-4-amine

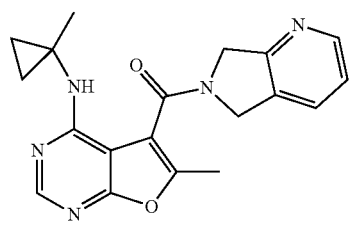 [SMILES: Cc1oc2ncnc(NC3(C)CC3)c2c1C(=O)N1Cc2cccnc2C1]

[M+H]=350.4.

Example 277. N-(Adamantan-2-yl)-6-methyl-4-[(1-methylcyclopropyl)amino]furo[2,3-d]pyrimidine-5-carboxamide

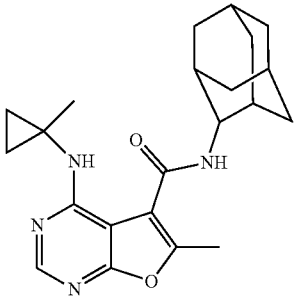 [SMILES: Cc1oc2ncnc(NC3(C)CC3)c2c1C(=O)NC1C2CC3CC(C2)CC1C3]

[M+H]=381.5.

Example 278. 5-{6,6-Dimethyl-3-azabicyclo[3.1.0]hexane-3-carbonyl}-6-methyl-N-(1-methylcyclopropyl)furo[2,3-d]pyrimidin-4-amine

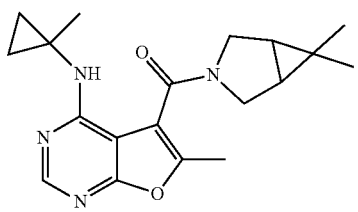 [SMILES: Cc1oc2ncnc(NC3(C)CC3)c2c1C(=O)N1CC2C(C1)C2(C)C]

[M+H]=341.5.

Example 279. 5-[(1R,5S,6S)-6-(4-Fluorophenyl)-3-azabicyclo[3.1.0]hexane-3-carbonyl]-6-methyl-N-(1-methylcyclopropyl)furo[2,3-d]pyrimidin-4-amine

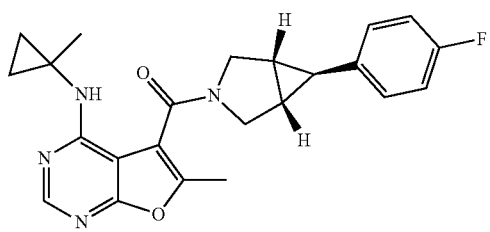 [SMILES: Cc1oc2ncnc(NC3(C)CC3)c2c1C(=O)N1C[C@@H]2[C@H](C1)[C@H]2c1ccc(F)cc1]

[M+H]=407.5.

Example 280. N-[(6-Fluoropyridin-2-yl)methyl]-6-methyl-4-[(1-methylcyclopropyl)amino]furo[2,3-d]pyrimidine-5-carboxamide

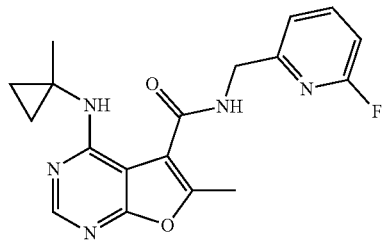 [SMILES: Cc1oc2ncnc(NC3(C)CC3)c2c1C(=O)NCc1cccc(F)n1]

¹H NMR (400 MHz, CD₃OD) δ 8.38 (s, 1H), 7.94 (q, J=8.1 Hz, 1H), 7.34 (dd, J=2.2, 7.3 Hz, 1H), 6.97 (dd, J=2.4, 8.1 Hz, 1H), 4.68 (s, 2H), 2.79 (s, 3H), 1.50 (s, 3H), 0.95-0.85 (m, 4H). [M+H]=355.90.

Example 281. N-[1-(5-Fluoropyridin-2-yl)cyclopropyl]-6-methyl-4-[(1-methylcyclopropyl)amino]furo[2,3-d]pyrimidine-5-carboxamide

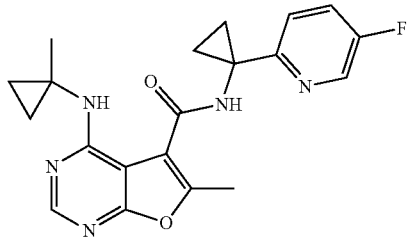 [SMILES: Cc1oc2ncnc(NC3(C)CC3)c2c1C(=O)NC1(c2ccc(F)cn2)CC1]

¹H NMR (400 MHz, CD₃OD) δ 8.40 (s, 1H), 8.36 (d, J=2.8 Hz, 1H), 7.51 (dt, J=2.9, 8.6 Hz, 1H), 7.39 (dd, J=4.2, 8.9 Hz, 1H), 2.74 (s, 3H), 1.70-1.62 (m, 2H), 1.49 (s, 3H), 1.44-1.36 (m, 2H), 0.91-0.85 (m, 4H). [M+H]=382.

Example 282. 5-[4-(6-Fluoropyridin-3-yl)piperazine-1-carbonyl]-6-methyl-N-(1-methylcyclopropyl)furo[2,3-d]pyrimidin-4-amine

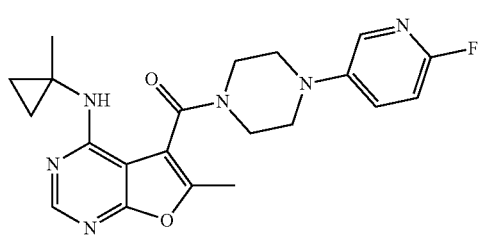 [SMILES: Cc1oc2ncnc(NC3(C)CC3)c2c1C(=O)N1CCN(c2ccc(F)nc2)CC1]

¹H NMR (400 MHz, CD₃OD) δ 8.41 (s, 1H), 7.86 (br s, 1H), 7.66 (ddd, J=3.1, 6.5, 9.2 Hz, 1H), 7.00 (dd, J=3.1, 9.0 Hz, 1H), 3.89 (br s, 4H), 3.29 (br s, 4H), 2.59 (s, 3H), 1.53 (s, 3H), 0.97-0.85 (m, 4H). [M+H]=411.

Example 283. 6-Methyl-5-(7-methyl-1,2,3,4-tetrahydro-2,6-naphthyridine-2-carbonyl)-N-(1-methylcyclopropyl)furo[2,3-d]pyrimidin-4-amine

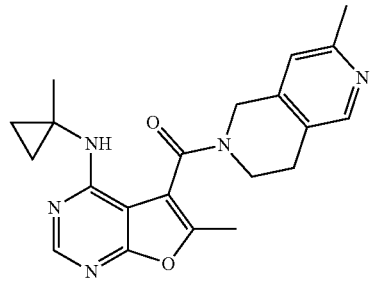 [SMILES: Cc1cc2c(cn1)CCN(C(=O)c1c(C)oc3ncnc(NC4(C)CC4)c13)C2]

¹H NMR (400 MHz, CD₃OD) δ 8.59 (s, 1H), 8.37 (s, 1H), 7.74 (br s, 1H), 5.11 (br s, 2H), 4.32-3.70 (m, 2H), 3.12 (t, J=5.4 Hz, 2H), 2.72 (s, 3H), 2.58 (s, 3H), 1.47 (s, 3H), 0.87-0.76 (m, 4H). [M+H]=378.1.

Example 284. 6-Methyl-5-(2-methyl-5,6,7,8-tetrahydro-1,6-naphthyridine-6-carbonyl)-N-(1-methylcyclopropyl)furo[2,3-d]pyrimidin-4-amine

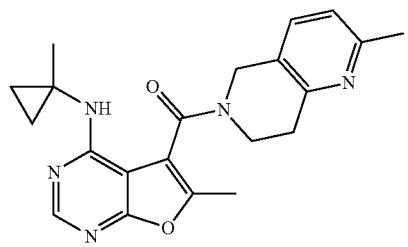 [SMILES: Cc1ccc2c(n1)CCN(C(=O)c1c(C)oc3ncnc(NC4(C)CC4)c13)C2]

¹H NMR (400 MHz, CD₃OD) δ 8.36 (s, 1H), 8.24 (d, J=7.8 Hz, 1H), 7.71 (d, J=8.2 Hz, 1H), 5.01 (br s, 2H), 4.09 (br s, 2H), 2.75 (s, 3H), 2.60-2.56 (m, 3H), 1.47 (s, 4H), 0.88-0.77 (m, 5H). [M+H]=378.

Example 285. 5-(5-Chloro-1,2,3,4-tetrahydro-2,6-naphthyridine-2-carbonyl)-6-methyl-N-(1-methylcyclopropyl)furo[2,3-d]pyrimidin-4-amine

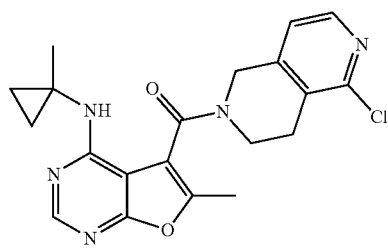 [SMILES: Cc1oc2ncnc(NC3(C)CC3)c2c1C(=O)N1CCc2c(ccnc2Cl)C1]

¹H NMR (400 MHz, CD₃OD) δ 8.38 (s, 1H), 8.19 (d, J=5.3 Hz, 1H), 7.25 (br s, 1H), 4.91 (br s, 2H), 4.01 (br s, 2H), 3.00 (t, J=5.3 Hz, 2H), 2.57 (s, 3H), 1.47 (s, 3H), 0.84 (s, 4H).
[M+H]=397.9.

Example 286. 5-(2-Chloro-5,6,7,8-tetrahydro-1,7-naphthyridine-7-carbonyl)-6-methyl-N-(1-methylcyclopropyl)furo[2,3-d]pyrimidin-4-amine

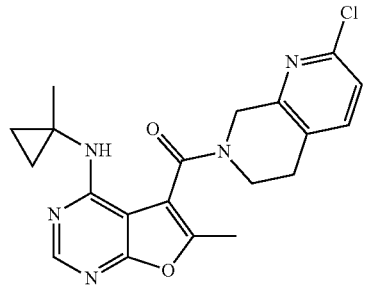 [SMILES: Cc1oc2ncnc(NC3(C)CC3)c2c1C(=O)N1CCc2ccc(Cl)nc2C1]

$^1$H NMR (400 MHz, CD$_3$OD) δ 8.38 (s, 1H), 7.66 (d, J=8.1 Hz, 1H), 7.31 (d, J=8.1 Hz, 1H), 4.85-4.73 (m, 2H), 4.14-3.77 (m, 2H), 2.99 (br s, 2H), 2.57 (s, 3H), 1.47 (s, 3H), 0.84 (d, J=5.1 Hz, 4H). [M+H]=397.9.

Example 287. 5-(2-Chloro-5,6,7,8-tetrahydro-1,6-naphthyridine-6-carbonyl)-6-methyl-N-(1-methylcyclopropyl)furo[2,3-d]pyrimidin-4-amine

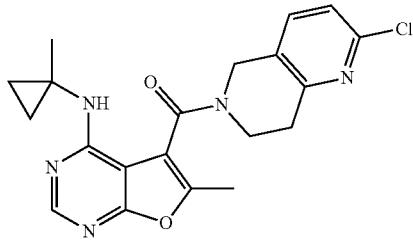 [SMILES: Cc1oc2ncnc(NC3(C)CC3)c2c1C(=O)N1CCc2nc(Cl)ccc2C1]

$^1$H NMR (400 MHz, CD$_3$OD) δ 8.37 (s, 1H), 7.63 (d, J=7.1 Hz, 1H), 7.31 (d, J=7.9 Hz, 1H), 4.87 (br s, 2H), 4.02 (br s, 2H), 3.06 (br s, 2H), 2.56 (s, 3H), 1.47 (s, 3H), 0.83 (s, 4H).
[M+H]=397.9.

Example 288. 5-{3-Chloro-5H,6H,7H,8H-pyrido[4,3-c]pyridazine-6-carbonyl}-6-methyl-N-(1-methylcyclopropyl)furo[2,3-d]pyrimidin-4-amine

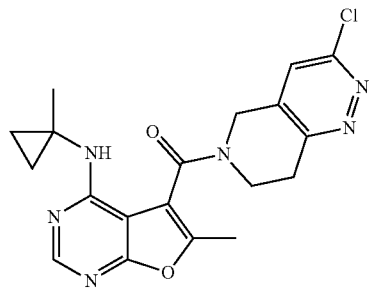

$^1$H NMR (400 MHz, CD$_3$OD) δ 8.39 (s, 1H), 7.69 (br s, 1H), 4.97 (br s, 2H), 4.07 (br s, 2H), 2.59 (s, 3H), 1.47 (s, 4H), 0.90-0.81 (m, 5H). [M+H]=398.9.

Example 289. 5-{2-Chloro-5H,6H,7H,8H-pyrido[4,3-d]pyrimidine-6-carbonyl}-6-methyl-N-(1-methylcyclopropyl)furo[2,3-d]pyrimidin-4-amine

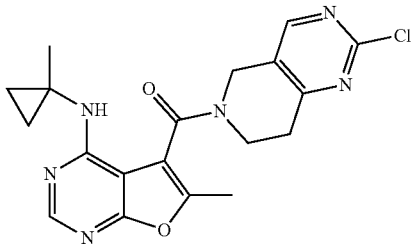 [SMILES: Cc1oc2ncnc(NC3(C)CC3)c2c1C(=O)N1CCc2nc(Cl)ncc2C1]

$^1$H NMR (400 MHz, CD$_3$OD) δ 8.51 (br s, 1H), 8.40 (s, 1H), 4.91 (br s, 2H), 4.02 (br s, 2H), 3.08 (t, J=5.4 Hz, 2H), 2.59 (s, 3H), 1.47 (s, 3H), 0.90-0.82 (m, 4H). [M+H]=398.9.

Example 290. 6-Methyl-N-(1-methylcyclopropyl)-5-[2-(oxan-4-yl)-5,6,7,8-tetrahydro-1,6-naphthyridine-6-carbonyl]furo[2,3-d]pyrimidin-4-amine

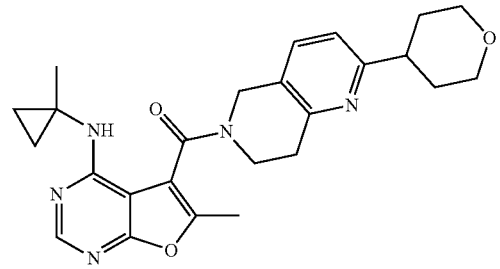 [SMILES: Cc1oc2ncnc(NC3(C)CC3)c2c1C(=O)N1CCc2nc(C3CCOCC3)ccc2C1]

$^1$H NMR (400 MHz, CD$_3$OD) δ 8.34 (s, 1H), 8.17 (d, J=7.9 Hz, 1H), 7.70 (d, J=8.3 Hz, 1H), 4.99 (br s, 2H), 4.39-3.78 (m, 4H), 3.57 (dt, J=2.9, 11.5 Hz, 2H), 3.19 (ddd, J=4.5, 11.1, 16.0 Hz, 1H), 2.57 (s, 3H), 1.98-1.83 (m, 4H), 1.46 (s, 3H), 0.78 (br s, 4H). [M+H]=448.

Example 291. N-[(2-Fluoropyridin-3-yl)methyl]-6-methyl-4-[(1-methylcyclopropyl)amino]furo[2,3-d]pyrimidine-5-carboxamide

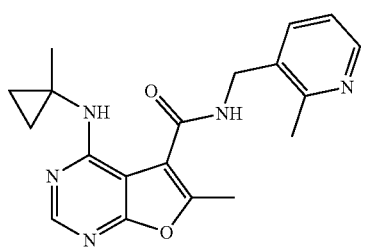 [SMILES: Cc1ncccc1CNC(=O)c1c(C)oc2ncnc(NC3(C)CC3)c12]

$^1$H NMR (400 MHz, CD$_3$OD) δ 8.36 (s, 1H), 8.15 (d, J=5.0 Hz, 1H), 7.99 (ddd, J=1.8, 7.5, 9.7 Hz, 1H), 7.34 (ddd, J=1.7, 5.1, 7.2 Hz, 1H), 4.65 (s, 2H), 2.71 (s, 3H), 1.51 (s, 3H), 0.97-0.83 (m, 4H). [M+H]=355.9.

Example 292. N-[(5-Fluoropyrimidin-2-yl)methyl]-6-methyl-4-[(1-methylcyclopropyl)amino]furo[2,3-d]pyrimidine-5-carboxamide

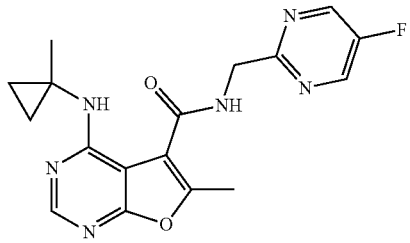 [SMILES: Cc1oc2ncnc(NC3(C)CC3)c2c1C(=O)NCc1ncc(F)cn1]

¹H NMR (400 MHz, CD₃OD) δ 8.75 (s, 2H), 8.38 (s, 1H), 4.84 (br s, 2H), 2.82 (s, 3H), 1.51 (s, 3H), 0.96-0.83 (m, 4H). [M+H]=356.9.

Example 293. N-[(6-Fluoropyridin-3-yl)methyl]-6-methyl-4-[(1-methylcyclopropyl)amino]furo[2,3-d]pyrimidine-5-carboxamide

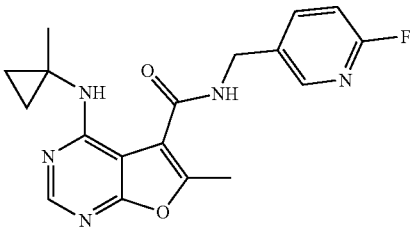 [SMILES: Cc1oc2ncnc(NC3(C)CC3)c2c1C(=O)NCc1ccc(F)nc1]

¹H NMR (400 MHz, CD₃OD) δ 8.75 (br s, 1H), 8.37 (s, 1H), 8.25 (d, J=2.2 Hz, 1H), 8.00 (dt, J=2.5, 8.1 Hz, 1H), 7.08 (dd, J=2.5, 8.5 Hz, 1H), 4.66-4.58 (m, 2H), 2.70 (s, 3H), 1.51 (s, 3H), 0.95-0.87 (m, 4H). [M+H]=355.9.

Example 294. 6-Methyl-N-(1-methylcyclopropyl)-5-[2-(propan-2-yl)-5H,6H,7H,8H-pyrido[3,4-d]pyrimidine-7-carbonyl]furo[2,3-d]pyrimidin-4-amine

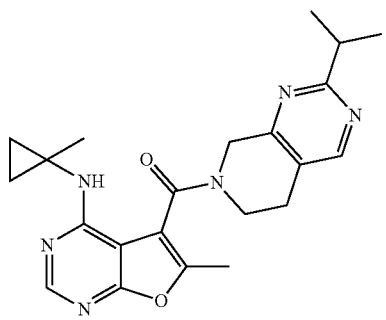 [SMILES: Cc1oc2ncnc(NC3(C)CC3)c2c1C(=O)N1CCc2cnc(C(C)C)nc2C1]

¹H NMR (400 MHz, CD₃OD) δ 8.56 (s, 1H), 8.40 (s, 1H), 4.95-4.86 (m, 2H), 3.99 (br s, 2H), 3.22-3.09 (m, 1H), 2.98 (br s, 2H), 2.59 (s, 3H), 1.48 (s, 3H), 1.31 (d, J=6.8 Hz, 6H), 0.90-0.83 (m, 4H). [M+H]=407.

Example 295. 5-[3-(4-Fluorophenyl)azepane-1-carbonyl]-6-methyl-N-(1-methylcyclopropyl)furo[2,3-d]pyrimidin-4-amine

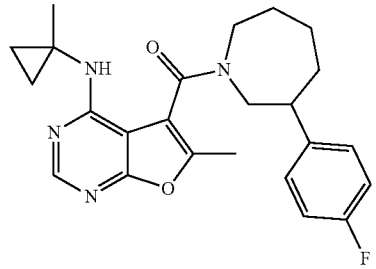 [SMILES: Cc1oc2ncnc(NC3(C)CC3)c2c1C(=O)N1CCCCC(c2ccc(F)cc2)C1]

¹H NMR (400 MHz, CD₃OD) δ 8.39 (s, 1H), 7.45-6.79 (m, 4H), 4.27-3.35 (m, 4H), 3.23-3.00 (m, 1H), 2.57-2.34 (m, 3H), 2.23-1.67 (m, 5H), 1.53 (s, 3H), 1.44-1.23 (m, 1H), 1.01-0.83 (m, 4H). [M+H]=423.

Example 296. 5-[4-(4-Fluorophenyl)azepane-1-carbonyl]-6-methyl-N-(1-methylcyclopropyl)furo[2,3-d]pyrimidin-4-amine

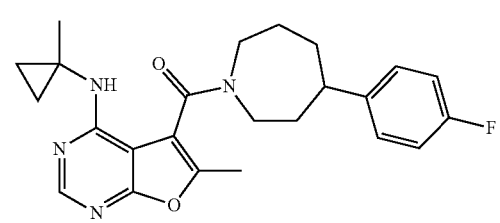 [SMILES: Cc1oc2ncnc(NC3(C)CC3)c2c1C(=O)N1CCCC(c2ccc(F)cc2)CC1]

¹H NMR (400 MHz, CD₃OD) δ 8.39 (s, 1H), 7.27-7.09 (m, 2H), 7.04-6.90 (m, 2H), 4.23-3.73 (m, 2H), 3.73-3.40 (m, 2H), 2.85-2.59 (m, 1H), 2.53 (s, 3H), 2.20-1.62 (m, 6H), 1.53 (s, 3H), 0.99-0.82 (m, 4H). [M+H]=423.

Example 297. N-[1-(2-Hydroxyethyl)cyclopropyl]-6-methyl-4-[(1-methylcyclopropyl)amino]furo[2,3-d]pyrimidine-5-carboxamide

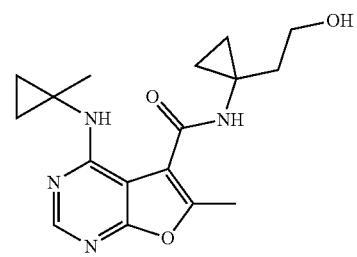 [SMILES: Cc1oc2ncnc(NC3(C)CC3)c2c1C(=O)NC1(CCO)CC1]

¹H NMR (400 MHz, CD₃OD) δ 8.43 (br s, 1H), 8.41-8.36 (m, 1H), 3.75 (t, J=6.5 Hz, 2H), 2.66 (s, 3H), 1.90 (t, J=6.6 Hz, 2H), 1.53 (s, 3H), 1.01-0.96 (m, 2H), 0.96-0.90 (m, 4H), 0.88-0.82 (m, 2H). [M+H]=331.

Example 298. N-[1-(3-Fluoro-4-methoxyphenyl)cyclopropyl]-6-methyl-4-[(1-methylcyclopropyl)amino]furo[2,3-d]pyrimidine-5-carboxamide

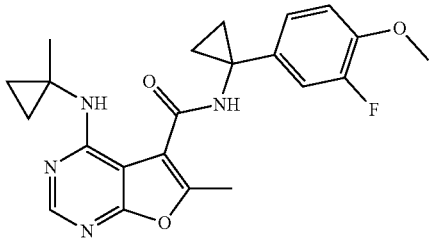 [SMILES: COc1ccc(C2(NC(=O)c3c(C)oc4ncnc(NC5(C)CC5)c34)CC2)cc1F]

¹H NMR (400 MHz, CD₃OD) δ 9.05 (s, 1H), 8.36 (s, 1H), 7.15-6.99 (m, 3H), 3.87-3.83 (m, 3H), 2.67 (s, 3H), 1.48 (s, 3H), 1.39-1.28 (m, 4H), 0.86 (s, 4H). [M+H]=411.

Example 299. 5-{2-Cyclopropyl-5H,6H,7H,8H-pyrido[3,4-d]pyrimidine-7-carbonyl}-6-methyl-N-(1-methylcyclopropyl)furo[2,3-d]pyrimidin-4-amine

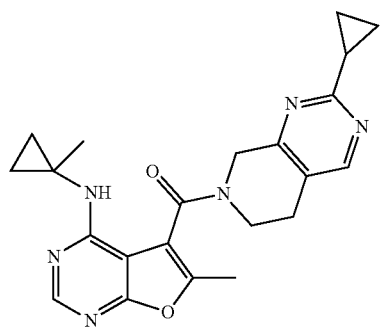 [SMILES: Cc1oc2ncnc(NC3(C)CC3)c2c1C(=O)N1CCc2cnc(C3CC3)nc2C1]

¹H NMR (400 MHz, CD₃OD) δ 8.45 (s, 1H), 8.38 (s, 1H), 4.81 (br s, 2H), 3.97 (br s, 2H), 2.94 (br s, 2H), 2.57 (s, 3H), 2.23-2.11 (m, 1H), 1.47 (s, 3H), 1.13-1.02 (m, 4H), 0.93-0.78 (m, 4H). [M+H]=405.1.

Example 300. 6-Methyl-4-[(1-methylcyclopropyl)amino]-N-[1-(oxan-4-yl)cyclopropyl]furo[2,3-d]pyrimidine-5-carboxamide

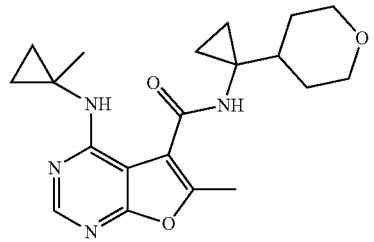 [SMILES: Cc1oc2ncnc(NC3(C)CC3)c2c1C(=O)NC1(C2CCOCC2)CC1]

¹H NMR (400 MHz, CD₃OD) δ 8.47 (s, 1H), 8.36 (s, 1H), 3.96 (dd, J=4.4, 11.5 Hz, 2H), 3.42-3.34 (m, 2H), 2.66 (s, 3H), 1.77-1.69 (m, 2H), 1.63-1.55 (m, 1H), 1.53-1.42 (m, 5H), 0.95-0.90 (m, 4H), 0.88 (s, 4H). [M+H]=371.1.

Example 301. 6-Methyl-N-(1-methylcyclopropyl)-5-[4-(pyridin-2-yl)piperidine-1-carbonyl]furo[2,3-d]pyrimidin-4-amine

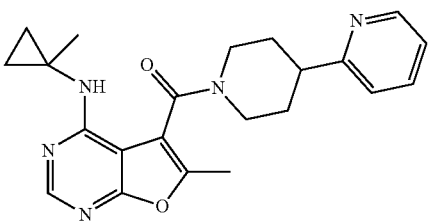 [SMILES: Cc1oc2ncnc(NC3(C)CC3)c2c1C(=O)N1CCC(c2ccccn2)CC1]

¹H NMR (400 MHz, CD₃OD) δ 8.77 (dd, J=1.0, 5.7 Hz, 1H), 8.52 (dt, J=1.6, 7.9 Hz, 1H), 8.42 (s, 1H), 8.00 (d, J=8.1 Hz, 1H), 7.90 (ddd, J=1.1, 6.0, 7.4 Hz, 1H), 4.81-3.88 (m, 2H), 3.60-3.34 (m, 2H), 3.30-3.08 (m, 1H), 2.60 (s, 3H), 2.27-2.10 (m, 2H), 1.95 (d, J=9.5 Hz, 2H), 1.54 (s, 3H), 1.00-0.87 (m, 4H). [M+H]=392.

Example 302. N-[1-(5-Fluoropyrimidin-2-yl)ethyl]-6-methyl-4-[(1-methylcyclopropyl)amino]furo[2,3-d]pyrimidine-5-carboxamide

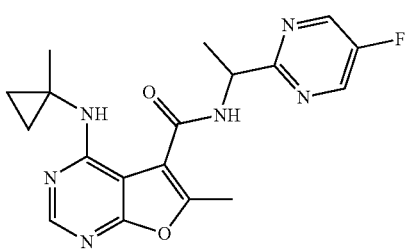 [SMILES: Cc1oc2ncnc(NC3(C)CC3)c2c1C(=O)NC(C)c1ncc(F)cn1]

¹H NMR (400 MHz, CD₃OD) δ 8.77 (s, 2H), 8.40 (s, 1H), 5.38 (q, J=7.0 Hz, 1H), 2.81 (s, 3H), 1.65 (d, J=7.0 Hz, 3H), 1.52 (s, 3H), 0.97-0.87 (m, 4H). [M+H]=371.

Example 303. 5-{2-Fluoro-5H,6H,7H,8H-pyrido[4,3-d]pyrimidine-6-carbonyl}-6-methyl-N-(1-methylcyclopropyl)furo[2,3-d]pyrimidin-4-amine

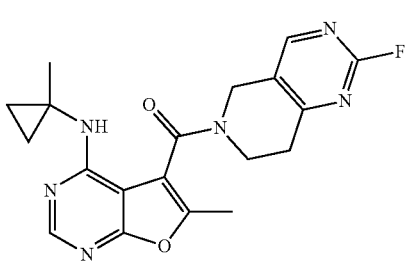 [SMILES: Cc1oc2ncnc(NC3(C)CC3)c2c1C(=O)N1CCc2nc(F)ncc2C1]

¹H NMR (400 MHz, CD₃OD) δ 8.52 (br s, 1H), 8.41 (s, 1H), 4.92 (br s, 2H), 4.04 (br s, 2H), 3.12-3.05 (m, 2H), 2.59 (s, 3H), 1.48 (s, 3H), 0.92-0.83 (m, 4H). [M+H]=383.

Example 304. N-[1-(3-Fluoro-4-methoxyphenyl)
ethyl]-6-methyl-4-[(1-methylcyclopropyl)amino]furo
[2,3-d]pyrimidine-5-carboxamide

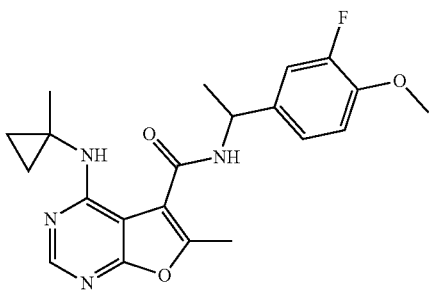 [SMILES: COc1ccc(C(C)NC(=O)c2c(C)oc3ncnc(NC4(C)CC4)c23)cc1F]

¹H NMR (400 MHz, CD₃OD) δ 8.66-8.53 (m, 1H), 8.35 (s, 1H), 7.19 (t, J=2.6 Hz, 1H), 7.16 (s, 1H), 7.11-7.04 (m, 1H), 5.23-5.11 (m, 1H), 3.86 (s, 3H), 2.66 (s, 3H), 1.57 (d, J=7.0 Hz, 3H), 1.48 (s, 3H), 0.93-0.80 (m, 4H). [M+H]=399.1.

Example 305. N-[(1S)-1-(2-Fluoro-4-methoxyphe-
nyl)ethyl]-6-methyl-4-[(1-methylcyclopropyl)amino]
furo[2,3-d]pyrimidine-5-carboxamide

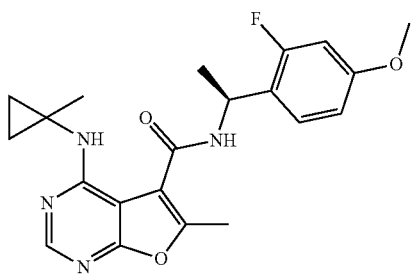 [SMILES: COc1ccc([C@H](C)NC(=O)c2c(C)oc3ncnc(NC4(C)CC4)c23)c(F)c1]

¹H NMR (400 MHz, CD₃OD) δ 8.60 (d, J=7.5 Hz, 1H), 8.36 (s, 1H), 7.21-7.14 (m, 2H), 7.14-7.04 (m, 1H), 5.24-5.14 (m, 1H), 3.87 (s, 3H), 2.68 (s, 3H), 1.58 (d, J=7.1 Hz, 3H), 1.49 (s, 3H), 0.96-0.83 (m, 4H). [M+H]=399.

Example 306. N-[(1R)-1-(2-Fluoro-4-methoxyphe-
nyl)ethyl]-6-methyl-4-[(1-methylcyclopropyl)amino]
furo[2,3-d]pyrimidine-5-carboxamide

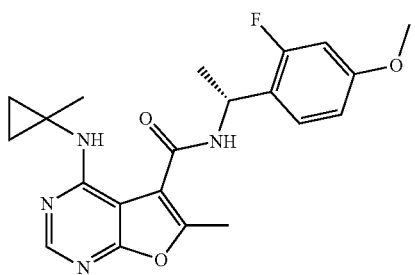 [SMILES: COc1ccc([C@@H](C)NC(=O)c2c(C)oc3ncnc(NC4(C)CC4)c23)c(F)c1]

¹H NMR (400 MHz, CD₃OD) δ 8.59 (d, J=7.1 Hz, 1H), 8.36 (s, 1H), 7.19 (t, J=2.6 Hz, 1H), 7.16 (s, 1H), 7.12-7.05 (m, 1H), 5.22-5.14 (m, 1H), 3.87 (s, 3H), 2.67 (s, 3H), 1.58 (d, J=7.1 Hz, 3H), 1.49 (s, 3H), 0.92-0.80 (m, 4H). [M+H]=399.

Example 307. 5-{2-Fluoro-5H,6H,7H,8H-pyrido[3,
4-d]pyrimidine-7-carbonyl}-6-methyl-N-(1-methyl-
cyclopropyl)furo[2,3-d]pyrimidin-4-amine

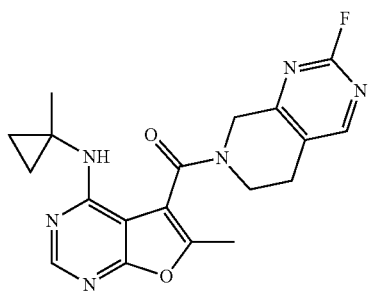 [SMILES: Cc1oc2ncnc(NC3(C)CC3)c2c1C(=O)N1CCc2cnc(F)nc2C1]

¹H NMR (400 MHz, CD₃OD) δ 8.56 (s, 1H), 8.41 (s, 1H), 4.88 (br s, 2H), 3.98 (br s, 2H), 2.99 (br s, 2H), 2.59 (s, 3H), 1.48 (s, 3H). [M+H]=383.

Example 308. 6-Methyl-N-(1-methylcyclopropyl)-5-
[4-(tetrachloropyridin-2-yl)piperazine-1-carbonyl]
furo[2,3-d]pyrimidin-4-amine

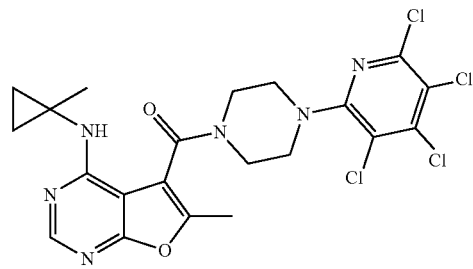 [SMILES: Cc1oc2ncnc(NC3(C)CC3)c2c1C(=O)N1CCN(c2nc(Cl)c(Cl)c(Cl)c2Cl)CC1]

¹H NMR (400 MHz, CDCl₃) δ 8.50 (s, 1H), 6.98 (s, 1H), 3.83 (br s, 4H), 3.47 (br s, 4H), 2.52 (s, 3H), 1.55 (s, 3H), 0.85 (br s, 2H), 0.79 (br s, 2H). [M+H]=531.1.

Example 309. 6-Methyl-N-(1-methylcyclopropyl)-5-
[4-(pyrimidin-2-yl)piperidine-1-carbonyl]furo[2,3-d]
pyrimidin-4-amine

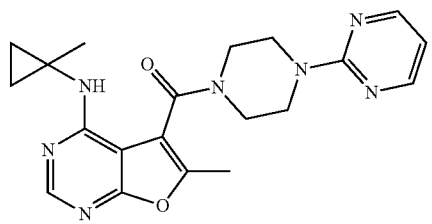 [SMILES: Cc1oc2ncnc(NC3(C)CC3)c2c1C(=O)N1CCN(c2ncccn2)CC1]

¹H NMR (400 MHz, CD₃OD) δ 8.77 (d, J=4.9 Hz, 2H), 8.42 (s, 1H), 7.37 (t, J=5.0 Hz, 1H), 3.26 (tt, J=3.8, 11.5 Hz, 2H), 2.59 (s, 3H), 2.20-1.86 (m, 4H), 1.55 (s, 3H), 1.04-0.86 (m, 4H). [M+H]=393.

Example 310. 6-Methyl-4-[(1-methylcyclopropyl)amino]-N-(5,6,7,8-tetrahydroquinolin-8-yl)furo[2,3-d]pyrimidine-5-carboxamide

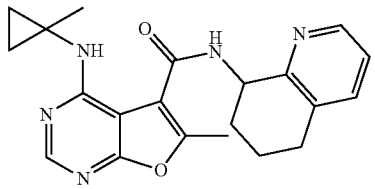 [SMILES: Cc1oc2ncnc(NC3(C)CC3)c2c1C(=O)NC1CCCc2cccnc21]

¹H NMR (400 MHz, CD₃OD) δ 8.60 (dd, J=1.3, 5.4 Hz, 1H), 8.38 (s, 1H), 8.24 (d, J=7.3 Hz, 1H), 7.77 (dd, J=5.5, 7.8 Hz, 1H), 5.62-5.46 (m, 1H), 3.07 (d, J=5.5 Hz, 2H), 2.71 (s, 3H), 2.43-2.26 (m, 1H), 2.26-1.95 (m, 3H), 1.54 (s, 3H), 1.00-0.82 (m, 4H). [M+H]=378.

Example 311. 6-Methyl-4-[(1-methylcyclopropyl)amino]-N-[1-(pyrazin-2-yl)cyclopropyl]furo[2,3-d]pyrimidine-5-carboxamide

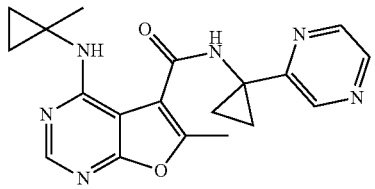 [SMILES: Cc1oc2ncnc(NC3(C)CC3)c2c1C(=O)NC1(c2cnccn2)CC1]

¹H NMR (400 MHz, CD₃OD) δ 8.60 (d, J=1.5 Hz, 1H), 8.56 (dd, J=1.6, 2.4 Hz, 1H), 8.42 (d, J=2.6 Hz, 1H), 8.40 (s, 1H), 2.77 (s, 3H), 1.81-1.71 (m, 2H), 1.58-1.44 (m, 5H), 0.95-0.79 (m, 4H). [M+H]=365.

Example 312. N-[(6-Chloropyridin-3-yl)methyl]-6-methyl-4-[(1-methylcyclopropyl)amino]furo[2,3-d]pyrimidine-5-carboxamide

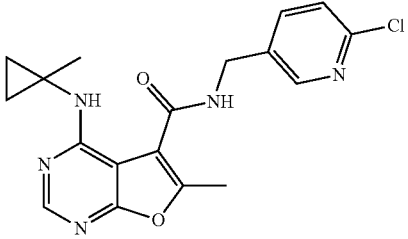 [SMILES: Cc1oc2ncnc(NC3(C)CC3)c2c1C(=O)NCc1ccc(Cl)nc1]

¹H NMR (400 MHz, CD₃OD) δ 8.42 (d, J=2.1 Hz, 1H), 8.38-8.34 (m, 1H), 7.91-7.85 (m, 1H), 7.47 (d, J=8.3 Hz, 1H), 4.62 (s, 2H), 2.70 (s, 3H), 1.50 (s, 3H), 0.94-0.84 (m, 4H).

[M+H]=371.9.

Example 313. N-[(2-Chloropyrimidin-5-yl)methyl]-6-methyl-4-[(1-methylcyclopropyl)amino]furo[2,3-d]pyrimidine-5-carboxamide

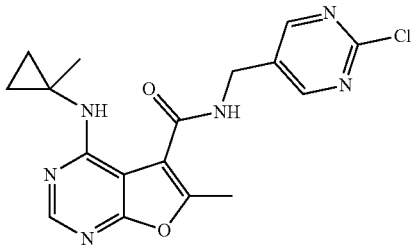 [SMILES: Cc1oc2ncnc(NC3(C)CC3)c2c1C(=O)NCc1cnc(Cl)nc1]

¹H NMR (400 MHz, CD₃OD) δ 8.75 (s, 2H), 8.37 (s, 1H), 4.62 (s, 2H), 2.72 (s, 3H), 1.50 (s, 3H), 0.95-0.87 (m, 4H). [M+H]=372.9.

Example 314. 5-(3-Fluoro-3-phenylazetidine-1-carbonyl)-6-methyl-N-(1-methylcyclopropyl)furo[2,3-d]pyrimidin-4-amine

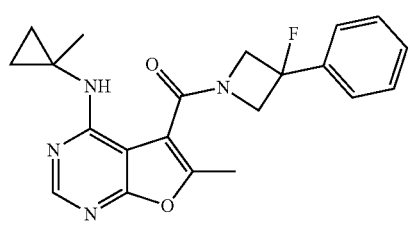 [SMILES: Cc1oc2ncnc(NC3(C)CC3)c2c1C(=O)N1CC(F)(c2ccccc2)C1]

¹H NMR (400 MHz, CD₃OD) δ 8.41-8.36 (m, 1H), 7.56-7.51 (m, 2H), 7.50-7.40 (m, 3H), 4.72 (s, 2H), 4.67 (s, 2H), 2.65 (s, 3H), 1.52 (s, 3H), 0.99-0.85 (m, 4H). [M+H]=381.1.

Example 315. 6-Methyl-4-[(1-methylcyclopropyl)amino]-N-[1-(pyrazin-2-yl)ethyl]furo[2,3-d]pyrimidine-5-carboxamide

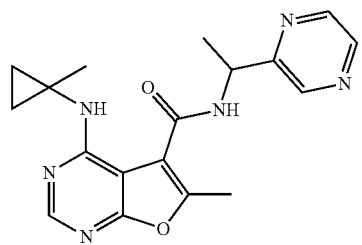 [SMILES: Cc1oc2ncnc(NC3(C)CC3)c2c1C(=O)NC(C)c1cnccn1]

¹H NMR (400 MHz, CD₃OD) δ 8.75 (d, J=1.5 Hz, 1H), 8.65 (dd, J=1.5, 2.5 Hz, 1H), 8.56 (d, J=2.6 Hz, 1H), 8.41-8.34 (m, 1H), 5.40 (q, J=7.1 Hz, 1H), 2.82-2.71 (m, 3H), 1.67 (d, J=7.0 Hz, 3H), 1.51 (s, 3H), 0.97-0.81 (m, 4H). [M+H]=353.

Example 316. N-{5H,6H,7H-Cyclopenta[b]pyridin-7-yl}-6-methyl-4-[(1-methylcyclopropyl)amino]furo[2,3-d]pyrimidine-5-carboxamide

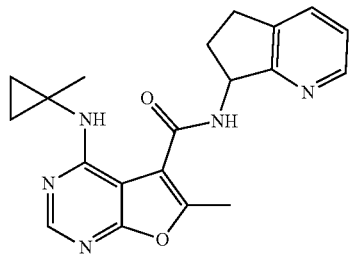 [SMILES: Cc1oc2ncnc(NC3(C)CC3)c2c1C(=O)NC1CCc2cccnc21]

¹H NMR (400 MHz, CD₃OD) δ 8.54 (d, J=5.3 Hz, 1H), 8.40 (s, 1H), 8.12 (d, J=7.7 Hz, 1H), 7.61 (dd, J=5.5, 7.6 Hz, 1H), 5.80 (t, J=8.4 Hz, 1H), 3.30-3.19 (m, 1H), 3.19-3.04 (m, 1H), 2.89-2.76 (m, 1H), 2.74 (s, 3H), 2.26 (qd, J=8.8, 13.0 Hz, 1H), 1.54 (s, 3H), 1.05-0.86 (m, 4H). [M+H]=364.

Example 317. 6-Methyl-4-[(1-methylcyclopropyl)amino]-N-[1-(pyrimidin-4-yl)ethyl]furo[2,3-d]pyrimidine-5-carboxamide

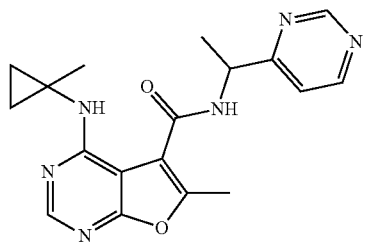 [SMILES: Cc1oc2ncnc(NC3(C)CC3)c2c1C(=O)NC(C)c1ccncn1]

¹H NMR (400 MHz, CD₃OD) δ 9.17 (d, J=1.2 Hz, 1H), 8.78 (d, J=5.3 Hz, 1H), 8.40 (s, 1H), 7.62 (dd, J=1.2, 5.3 Hz, 1H), 5.27 (q, J=7.1 Hz, 1H), 2.81 (s, 3H), 1.64 (d, J=7.1 Hz, 3H), 1.51 (s, 3H), 1.01-0.80 (m, 4H). [M+H]=353.

Example 318. N-[(3-Bromo-1,2-oxazol-5-yl)methyl]-6-methyl-4-[(1-methylcyclopropyl)amino]furo[2,3-d]pyrimidine-5-carboxamide

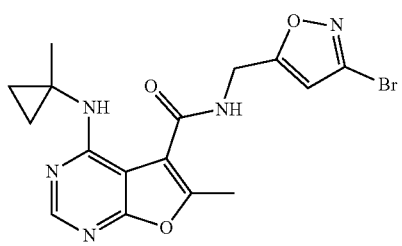 [SMILES: Cc1oc2ncnc(NC3(C)CC3)c2c1C(=O)NCc1cc(Br)no1]

¹H NMR (400 MHz, CD₃OD) δ 8.38 (s, 1H), 8.28 (s, 1H), 6.57 (s, 1H), 4.75 (s, 2H), 2.68 (s, 3H), 1.50 (s, 3H), 0.87-0.70 (m, 4H). [M+H]=405.8.

Example 319. 6-Methyl-N-[(3-methyl-1,2-oxazol-5-yl)methyl]-4-[(1-methylcyclopropyl)amino]furo[2,3-d]pyrimidine-5-carboxamide

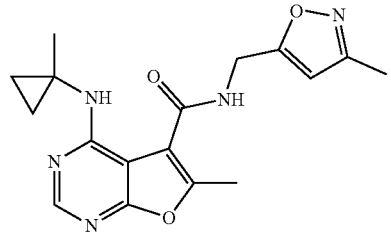 [SMILES: Cc1cc(CNC(=O)c2c(C)oc3ncnc(NC4(C)CC4)c23)on1]

¹H NMR (400 MHz, CD₃OD) δ 8.27 (s, 1H), 6.26 (s, 1H), 4.70 (s, 2H), 2.67 (s, 3H), 2.29 (s, 3H), 1.50 (s, 3H), 0.88-0.69 (m, 4H). [M+H]=342.0.

Example 320. 6-Methyl-5-[3-(1-methyl-1H-imidazol-2-yl)pyrrolidine-1-carbonyl]-N-(1-methylcyclopropyl)furo[2,3-d]pyrimidin-4-amine

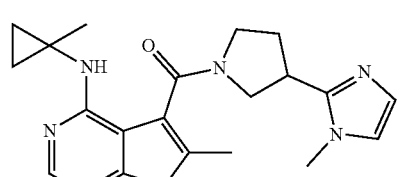

¹H NMR (400 MHz, CD₃OD) δ 8.38 (s, 1H), 7.54 (d, J=1.7 Hz, 2H), 4.31-3.71 (m, 8H), 2.60 (s, 4H), 2.32 (br s, 1H), 1.58-1.48 (m, 3H), 0.99-0.81 (m, 4H). [M+H]=381.

Example 321. 6-Methyl-5-[3-(1-methyl-1H-pyrazol-4-yl)pyrrolidine-1-carbonyl]-N-(1-methylcyclopropyl)furo[2,3-d]pyrimidin-4-amine

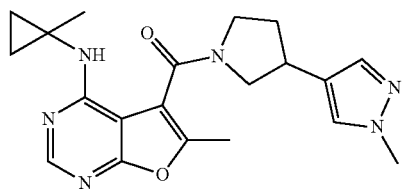 [SMILES: Cc1oc2ncnc(NC3(C)CC3)c2c1C(=O)N1CCC(c2cnn(C)c2)C1]

¹H NMR (400 MHz, CD₃OD) δ 8.41 (s, 1H), 7.65-7.31 (m, 2H), 4.07-3.36 (m, 8H), 2.57 (s, 3H), 2.49-2.27 (m, 1H), 2.21-1.96 (m, 1H), 1.58-1.46 (m, 3H), 1.02-0.85 (m, 4H). [M+H]=381.

Example 322. N-[(5-Ethyl-1,2-oxazol-3-yl)methyl]-6-methyl-4-[(1-methylcyclopropyl)amino]furo[2,3-d]pyrimidine-5-carboxamide

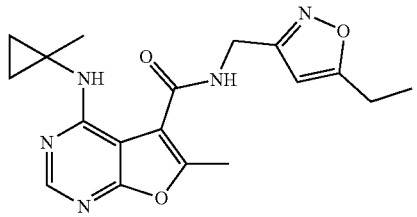 [SMILES: CCc1cc(CNC(=O)c2c(C)oc3ncnc(NC4(C)CC4)c23)no1]

$^1$H NMR (400 MHz, CD$_3$OD) δ 8.40 (s, 1H), 6.20 (s, 1H), 4.65 (s, 2H), 2.86-2.76 (m, 2H), 2.74 (s, 3H), 1.57-1.47 (m, 3H), 1.31 (t, J=7.6 Hz, 3H), 1.02-0.87 (m, 4H). [M+H]=356.

Example 323. N-[(5-Cyclopropyl-1,2-oxazol-3-yl)methyl]-6-methyl-4-[(1-methylcyclopropyl)amino]furo[2,3-d]pyrimidine-5-carboxamide

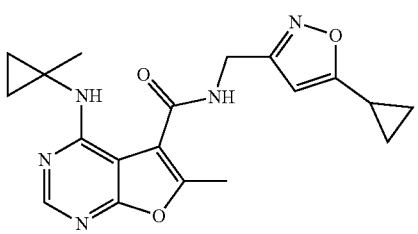 [SMILES: Cc1oc2ncnc(NC3(C)CC3)c2c1C(=O)NCc1cc(C2CC2)on1]

$^1$H NMR (400 MHz, CD$_3$OD) δ 8.40 (s, 1H), 6.12 (s, 1H), 4.62 (s, 2H), 2.73 (s, 3H), 2.12 (tt, J=5.0, 8.5 Hz, 1H), 1.54 (s, 3H), 1.17-1.03 (m, 2H), 1.03-0.86 (m, 6H). [M+H]=368.

Example 324. 6-Methyl-4-[(1-methylcyclopropyl)amino]-N-{[5-(propan-2-yl)-1,2-oxazol-3-yl]methyl}furo[2,3-d]pyrimidine-5-carboxamide

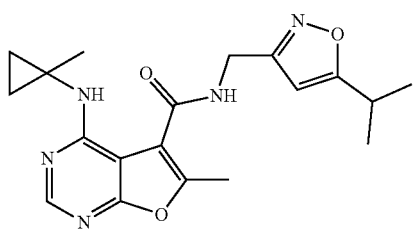 [SMILES: Cc1oc2ncnc(NC3(C)CC3)c2c1C(=O)NCc1cc(C(C)C)on1]

$^1$H NMR (400 MHz, CD$_3$OD) δ 8.39 (s, 1H), 6.19 (d, J=0.6 Hz, 1H), 4.65 (s, 2H), 3.19-3.03 (m, 1H), 2.79-2.67 (m, 3H), 1.53 (s, 3H), 1.33 (d, J=7.0 Hz, 6H), 1.02-0.85 (m, 4H).

[M+H]=370.

Example 325. N-{[5-(4-Fluorophenyl)-1,2-oxazol-3-yl]methyl}-6-methyl-4-[(1-methylcyclopropyl)amino]furo[2,3-d]pyrimidine-5-carboxamide

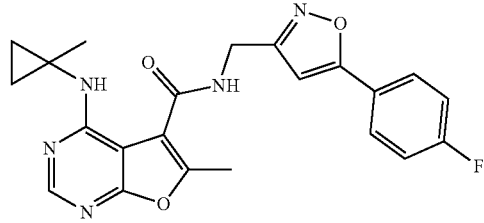 [SMILES: Cc1oc2ncnc(NC3(C)CC3)c2c1C(=O)NCc1cc(-c2ccc(F)cc2)on1]

$^1$H NMR (400 MHz, CD$_3$OD) δ 8.39 (s, 1H), 7.95-7.84 (m, 2H), 7.34-7.21 (m, 2H), 6.81 (s, 1H), 4.74 (s, 2H), 2.76 (s, 3H), 1.58-1.47 (m, 3H), 1.01-0.84 (m, 4H). [M+H]=422.

Example 326. N-{[5-(4-Methoxyphenyl)-1,2-oxazol-3-yl]methyl}-6-methyl-4-[(1-methylcyclopropyl)amino]furo[2,3-d]pyrimidine-5-carboxamide

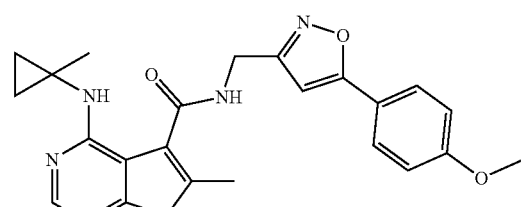

$^1$H NMR (400 MHz, CD$_3$OD) δ 8.37 (s, 1H), 7.78 (d, J=8.8 Hz, 2H), 7.06 (d, J=8.8 Hz, 2H), 6.68 (s, 1H), 4.71 (s, 2H), 3.87 (s, 3H), 2.75 (s, 3H), 1.52 (s, 3H), 0.99-0.80 (m, 4H).

[M+H]=434.

Example 327. 5-[4-(5-Methoxypyrimidin-2-yl)piperazine-1-carbonyl]-6-methyl-N-(1-methylcyclopropyl)furo[2,3-d]pyrimidin-4-amine

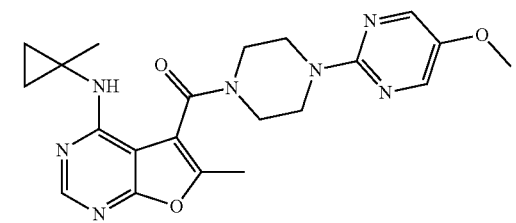 [SMILES: COc1cnc(N2CCN(C(=O)c3c(C)oc4ncnc(NC5(C)CC5)c34)CC2)nc1]

$^1$H NMR (400 MHz, CD$_3$OD) δ 8.41 (s, 1H), 8.19 (s, 2H), 4.00-3.67 (m, 11H), 2.58 (s, 3H), 1.53 (s, 3H), 1.00-0.84 (m, 4H). [M+H]=424.

Example 328. 3-[({6-Methyl-4-[(1-methylcyclopropyl)amino]furo[2,3-d]pyrimidin-5-yl}formamido)methyl]-1,2-oxazole-5-carboxamide

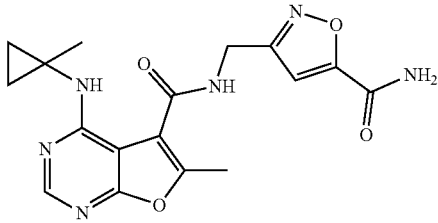 [SMILES: Cc1oc2ncnc(NC3(C)CC3)c2c1C(=O)NCc1cc(C(N)=O)on1]

$^1$H NMR (400 MHz, CD$_3$OD) δ 8.40 (s, 1H), 6.71 (s, 1H), 4.80 (s, 2H), 2.75 (s, 3H), 1.53 (s, 3H), 1.03-0.86 (m, 4H). [M+H]=370.9.

Example 329. 2-{6-Methyl-4-[(1-methylcyclopropyl)amino]furo[2,3-d]pyrimidine-5-carbonyl}-1,2,3,4-tetrahydroisoquinolin-5-ol

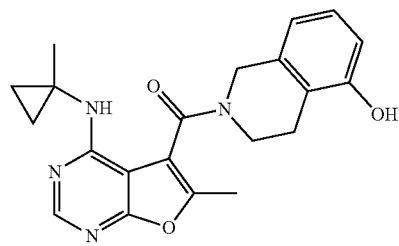 [SMILES: Cc1oc2ncnc(NC3(C)CC3)c2c1C(=O)N1CCc2c(O)cccc2C1]

$^1$H NMR (400 MHz, CD$_3$OD) δ 8.39 (s, 1H), 7.02 (t, J=7.8 Hz, 1H), 6.67 (d, J=7.9 Hz, 1H), 6.63 (d, J=6.4 Hz, 1H), 4.78 (br s, 2H), 3.93 (br s, 2H), 2.87 (t, J=5.7 Hz, 2H), 2.53 (s, 3H), 1.47 (s, 3H), 0.88-0.81 (m, 4H). [M+H]=379.

Example 330. 2-{6-Methyl-4-[(1-methylcyclopropyl)amino]furo[2,3-d]pyrimidine-5-carbonyl}-1,2,3,4-tetrahydroisoquinolin-6-ol

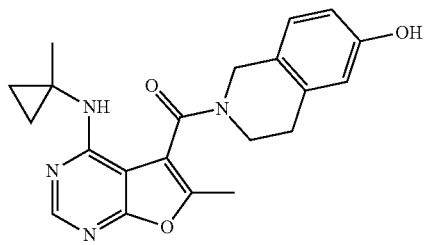 [SMILES: Cc1oc2ncnc(NC3(C)CC3)c2c1C(=O)N1CCc2cc(O)ccc2C1]

$^1$H NMR (400 MHz, CD$_3$OD) δ 8.40 (s, 1H), 6.96 (br s, 1H), 6.70-6.61 (m, 2H), 4.72 (br s, 2H), 3.90 (br s, 2H), 2.91 (br s, 2H), 2.54 (s, 3H), 1.47 (s, 3H), 0.85 (d, J=4.0 Hz, 4H). [M+H]=379.

Example 331. 2-{6-Methyl-4-[(1-methylcyclopropyl)amino]furo[2,3-d]pyrimidine-5-carbonyl}-1,2,3,4-tetrahydroisoquinolin-8-ol

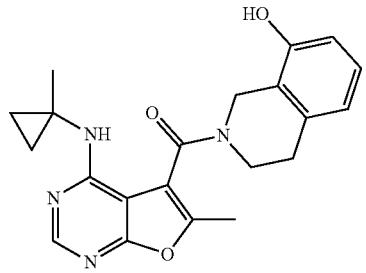 [SMILES: Cc1oc2ncnc(NC3(C)CC3)c2c1C(=O)N1CCc2cccc(O)c2C1]

$^1$H NMR (400 MHz, CD$_3$OD) δ 8.40 (s, 1H), 7.03 (t, J=7.8 Hz, 1H), 6.66 (dd, J=7.8, 17.2 Hz, 2H), 4.71 (br s, 2H), 3.93 (br s, 2H), 2.94 (br s, 2H), 2.54 (s, 3H), 1.47 (s, 3H), 0.91-0.81 (m, 4H). [M+H]=379.

Example 332. 2-{6-Methyl-4-[(1-methylcyclopropyl)amino]furo[2,3-d]pyrimidine-5-carbonyl}-1,2,3,4-tetrahydroisoquinolin-7-ol

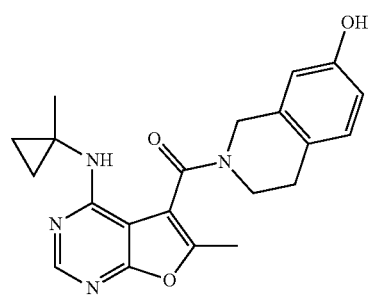 [SMILES: Cc1oc2ncnc(NC3(C)CC3)c2c1C(=O)N1CCc2ccc(O)cc2C1]

$^1$H NMR (400 MHz, CD$_3$OD) δ 8.39 (s, 1H), 7.00 (d, J=8.3 Hz, 1H), 6.65 (dd, J=2.5, 8.3 Hz, 1H), 6.57 (br s, 1H), 4.73 (br s, 2H), 3.88 (br s, 2H), 2.87 (br s, 2H), 2.53 (s, 3H), 1.46 (s, 3H), 0.85 (d, J=4.3 Hz, 4H). [M+H]=379.

Example 333. 6-{6-Methyl-4-[(1-methylcyclopropyl)amino]furo[2,3-d]pyrimidine-5-carbonyl}-5,6,7,8-tetrahydro-1,6-naphthyridin-3-ol

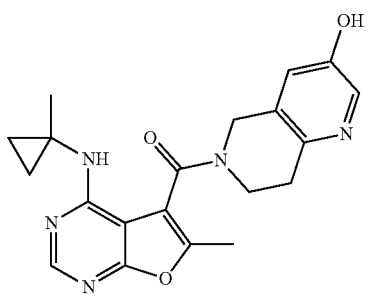 [SMILES: Cc1oc2ncnc(NC3(C)CC3)c2c1C(=O)N1CCc2ncc(O)cc2C1]

$^1$H NMR (400 MHz, CD$_3$OD) δ 8.35 (s, 1H), 8.14 (d, J=2.7 Hz, 1H), 7.73 (br s, 1H), 4.98 (br s, 2H), 4.42-3.79 (m,

2H), 3.20-3.13 (m, 2H), 2.57 (s, 3H), 1.52-1.44 (m, 3H), 0.85-0.76 (m, 4H). [M+H]=378.

Example 334. 5-[4-(3-Chloro-5-fluoropyridin-2-yl)piperidine-1-carbonyl]-6-methyl-N-(1-methylcyclopropyl)furo[2,3-d]pyrimidin-4-amine

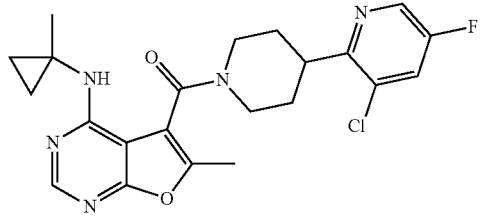 [SMILES: Cc1oc2ncnc(NC3(C)CC3)c2c1C(=O)N1CCC(c2ncc(F)cc2Cl)CC1]

$^1$H NMR (400 MHz, CD$_3$OD) δ 8.41 (d, J=2.3 Hz, 1H), 8.33 (s, 1H), 7.76 (dd, J=2.6, 8.3 Hz, 1H), 4.78-3.85 (m, 2H), 3.60 (br s, 2H), 3.43-2.93 (m, 3H), 2.54 (s, 3H), 1.93 (br s, 4H), 1.53 (s, 3H), 0.89 (br s, 2H), 0.81 (br s, 2H). [M+H]=444.

Example 335. 5-[3-(5-Chloropyrimidin-2-yl)pyrrolidine-1-carbonyl]-6-methyl-N-(1-methylcyclopropyl)furo[2,3-d]pyrimidin-4-amine

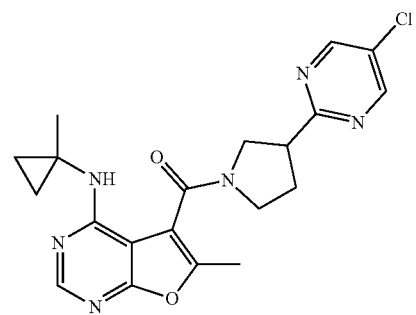 [SMILES: Cc1oc2ncnc(NC3(C)CC3)c2c1C(=O)N1CCC(c2ncc(Cl)cn2)C1]

$^1$H NMR (400 MHz, CD$_3$OD) δ 8.93-8.55 (m, 2H), 8.31 (s, 1H), 4.19-3.60 (m, 6H), 2.55 (s, 4H), 2.43 (br s, 2H), 1.51 (s, 4H), 0.91-0.67 (m, 5H). [M+H]=412.9.

Example 336. N-[(4-Fluoro-3-methoxyphenyl)methyl]-6-methyl-4-[(1-methylcyclopropyl)amino]furo[2,3-d]pyrimidine-5-carboxamide

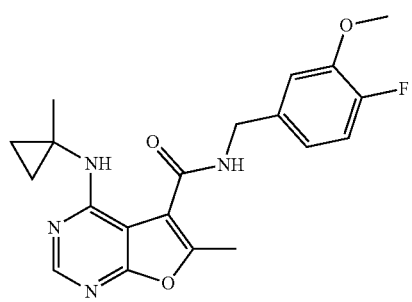 [SMILES: COc1cc(CNC(=O)c2c(C)oc3ncnc(NC4(C)CC4)c23)ccc1F]

$^1$H NMR (400 MHz, CD$_3$OD) δ 8.71 (br s, 1H), 8.33 (s, 1H), 7.14 (dd, J=2.0, 8.1 Hz, 1H), 7.06 (dd, J=8.3, 11.3 Hz, 1H), 6.93 (ddd, J=2.1, 4.2, 8.3 Hz, 1H), 4.59-4.52 (m, 2H), 3.88 (s, 3H), 2.67 (s, 3H), 1.50 (s, 3H), 0.93-0.81 (m, 4H). [M+H]=385.

Example 337. 6-{6-Methyl-4-[(1-methylcyclopropyl)amino]furo[2,3-d]pyrimidine-5-carbonyl}-1,2,5,6,7,8-hexahydro-2,6-naphthyridin-1-one

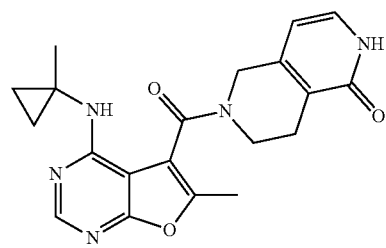 [SMILES: Cc1oc2ncnc(NC3(C)CC3)c2c1C(=O)N1CCc2c(cc[nH]c2=O)C1]

$^1$H NMR (400 MHz, CD$_3$OD) δ 8.41 (s, 1H), 7.30 (d, J=6.6 Hz, 1H), 6.26 (d, J=5.3 Hz, 1H), 4.71 (br s, 2H), 3.91 (br s, 2H), 2.70 (br s, 2H), 2.57 (s, 3H), 1.48 (s, 3H), 0.93-0.85 (m, 4H). [M+H]=380.

Example 338. 1-Methyl-2-{6-methyl-4-[(1-methylcyclopropyl)amino]furo[2,3-d]pyrimidine-5-carbonyl}-1,2,3,4-tetrahydroisoquinolin-7-ol

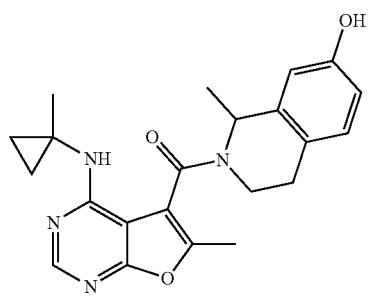 [SMILES: Cc1oc2ncnc(NC3(C)CC3)c2c1C(=O)N1CCc2ccc(O)cc2C1C]

$^1$H NMR (400 MHz, CD$_3$OD) δ 8.41 (s, 1H), 7.00 (d, J=8.4 Hz, 1H), 6.67 (dd, J=2.3, 8.3 Hz, 2H), 6.08-4.87 (m, 1H), 3.05-2.73 (m, 2H), 2.50 (br s, 4H), 1.70-1.27 (m, 7H), 0.82 (br s, 4H). [M+H]=393.1.

Example 339. 5-[3-(5-Fluoropyridin-3-yl)pyrrolidine-1-carbonyl]-6-methyl-N-(1-methylcyclopropyl)furo[2,3-d]pyrimidin-4-amine

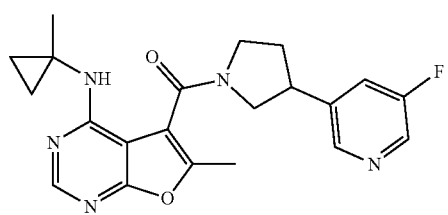 [SMILES: Cc1oc2ncnc(NC3(C)CC3)c2c1C(=O)N1CCC(c2cncc(F)c2)C1]

$^1$H NMR (400 MHz, CD$_3$OD) δ 8.40 (s, 1H), 7.00 (d, J=7.9 Hz, 1H), 6.67 (dd, J=2.3, 8.3 Hz, 2H), 6.10-5.04 (m,

1H), 4.82-3.35 (m, 2H), 3.08-2.70 (m, 2H), 2.50 (br s, 3H), 1.54 (br s, 3H), 1.45 (br s, 3H), 0.81 (br s, 4H). [M+H]=393.

Example 340. N-[(4-Fluoro-3-nitrophenyl)methyl]-6-methyl-4-[(1-methylcyclopropyl)amino]furo[2,3-d]pyrimidine-5-carboxamide

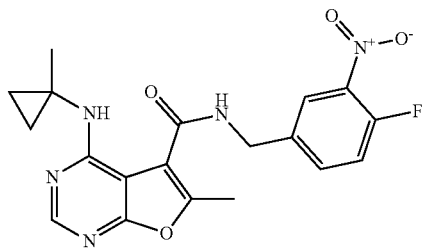 [SMILES: Cc1oc2ncnc(NC3(C)CC3)c2c1C(=O)NCc1ccc(F)c([N+](=O)[O-])c1]

$^1$H NMR (400 MHz, CD$_3$OD) δ 8.53-8.29 (m, 3H), 7.86-7.62 (m, 1H), 4.26-3.98 (m, 1H), 3.96-3.54 (m, 4H), 2.61 (d, J=10.8 Hz, 3H), 2.56-2.37 (m, 1H), 2.35-2.11 (m, 1H), 1.54 (s, 3H), 1.04-0.83 (m, 4H). [M+H]=396.0.

Example 341. N-[(4-Cyano-2-fluorophenyl)methyl]-6-methyl-4-[(1-methylcyclopropyl)amino]furo[2,3-d]pyrimidine-5-carboxamide

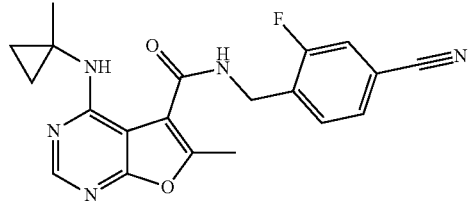 [SMILES: Cc1oc2ncnc(NC3(C)CC3)c2c1C(=O)NCc1ccc(C#N)cc1F]

$^1$H NMR (400 MHz, CD$_3$OD) δ 8.37 (s, 1H), 8.17 (dd, J=2.2, 7.1 Hz, 1H), 7.79 (ddd, J=2.4, 4.2, 8.6 Hz, 1H), 7.45 (dd, J=8.6, 10.9 Hz, 1H), 4.73-4.57 (m, 2H), 2.73 (s, 3H), 1.52 (s, 3H), 1.01-0.79 (m, 4H). [M+H]=400.0.

Example 342. 5-[4-(Cyclopropylamino)-5H,6H,7H,8H-pyrido[3,4-d]pyrimidine-7-carbonyl]-6-methyl-N-(1-methylcyclopropyl)furo[2,3-d]pyrimidin-4-amine

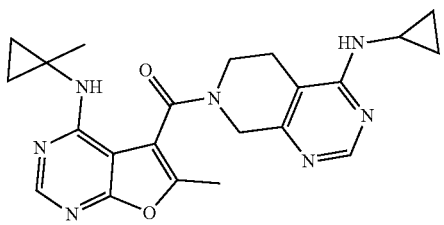 [SMILES: Cc1oc2ncnc(NC3(C)CC3)c2c1C(=O)N1CCc2c(ncnc2NC2CC2)C1]

$^1$H NMR (400 MHz, CD$_3$OD) δ 8.68 (s, 1H), 8.44-8.32 (m, 1H), 3.99 (br s, 2H), 3.24-3.11 (m, 1H), 2.66 (br s, 2H), 2.63-2.54 (m, 3H), 1.49 (s, 3H), 1.02-0.92 (m, 2H), 0.89-0.74 (m, 6H). [M+H]=420.

Example 343. 5-{4-[(Cyclopropylmethyl)amino]-5H,6H,7H,8H-pyrido[3,4-d]pyrimidine-7-carbonyl}-6-methyl-N-(1-methylcyclopropyl)furo[2,3-d]pyrimidin-4-amine

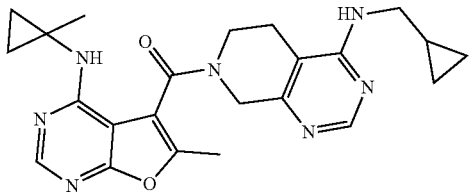 [SMILES: Cc1oc2ncnc(NC3(C)CC3)c2c1C(=O)N1CCc2c(ncnc2NCC2CC2)C1]

$^1$H NMR (400 MHz, CD$_3$OD) δ 8.62 (s, 1H), 8.36 (s, 1H), 4.34-3.73 (m, 2H), 3.55 (d, J=7.1 Hz, 2H), 2.70 (br s, 2H), 2.59 (s, 3H), 1.49 (s, 3H), 1.27-1.14 (m, 1H), 0.87-0.74 (m, 4H), 0.63-0.52 (m, 2H), 0.41-0.31 (m, 2H). [M+H]=434.1.

Example 344. 5-[4-(5-Chloropyrimidin-2-yl)piperidine-1-carbonyl]-6-methyl-N-(1-methylcyclopropyl)furo[2,3-d]pyrimidin-4-amine

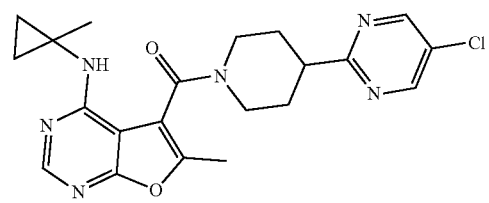 [SMILES: Cc1oc2ncnc(NC3(C)CC3)c2c1C(=O)N1CCC(c2ncc(Cl)cn2)CC1]

$^1$H NMR (400 MHz, CD$_3$OD) δ 8.78 (s, 2H), 8.41 (s, 1H), 3.30-3.21 (m, 1H), 2.57 (s, 3H), 2.14 (d, J=11.0 Hz, 2H), 1.92 (br s, 2H), 1.54 (s, 3H), 1.02-0.93 (m, 2H), 0.93-0.85 (m, 2H). [M+H]=427.

Example 345. 5-[4-(4-Methoxypyrimidin-2-yl)piperidine-1-carbonyl]-6-methyl-N-(1-methylcyclopropyl)furo[2,3-d]pyrimidin-4-amine

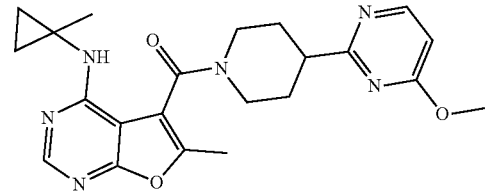 [SMILES: COc1ccnc(C2CCN(C(=O)c3c(C)oc4ncnc(NC5(C)CC5)c34)CC2)n1]

$^1$H NMR (400 MHz, CD$_3$OD) δ 8.49 (d, J=6.4 Hz, 1H), 8.42 (s, 1H), 6.92 (d, J=6.2 Hz, 1H), 4.09 (s, 3H), 3.25 (tt, J=3.8, 11.4 Hz, 1H), 2.59 (s, 3H), 2.16 (d, J=12.0 Hz, 2H), 1.98 (br s, 2H), 1.54 (s, 3H), 1.02-0.87 (m, 4H). [M+H]=423.

Example 346. 4-(1-{6-Methyl-4-[(1-methylcyclopropyl)amino]furo[2,3-d]pyrimidine-5-carbonyl}pyrrolidin-3-yl)phenol

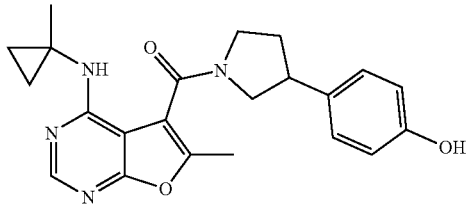 [SMILES: Cc1oc2ncnc(NC3(C)CC3)c2c1C(=O)N1CCC(c2ccc(O)cc2)C1]

¹H NMR (400 MHz, CD₃OD) δ 8.39 (s, 1H), 7.24-7.03 (m, 2H), 6.83-6.69 (m, 2H), 4.06-3.36 (m, 5H), 2.57 (d, J=15.2 Hz, 3H), 2.44-2.24 (m, 1H), 2.22-1.99 (m, 1H), 1.52 (s, 3H), 1.02-0.87 (m, 4H). [M+H]=393.

Example 347. 1-{6-Methyl-4-[(1-methylcyclopropyl)amino]furo[2,3-d]pyrimidine-5-carbonyl}-3-phenylpyrrolidin-3-ol

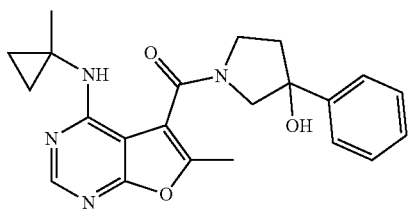 [SMILES: Cc1oc2ncnc(NC3(C)CC3)c2c1C(=O)N1CCC(O)(c2ccccc2)C1]

¹H NMR (400 MHz, CD₃OD) δ 8.38 (s, 1H), 7.67-7.46 (m, 2H), 7.45-7.24 (m, 3H), 4.22-3.65 (m, 4H), 2.68-2.40 (m, 4H), 2.36-2.17 (m, 1H), 1.51 (s, 3H), 1.02-0.83 (m, 4H). [M+H]=393.

Example 348. 5-[3-(5-Chloropyridin-2-yl)pyrrolidine-1-carbonyl]-6-methyl-N-(1-methylcyclopropyl)furo[2,3-d]pyrimidin-4-amine

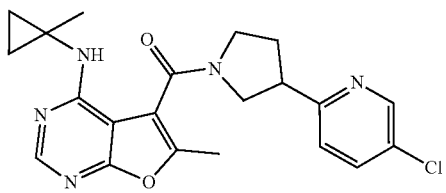 [SMILES: Cc1oc2ncnc(NC3(C)CC3)c2c1C(=O)N1CCC(c2ccc(Cl)cn2)C1]

¹H NMR (400 MHz, CD₃OD) δ 8.65-8.40 (m, 1H), 8.36 (s, 1H), 7.88-7.71 (m, 1H), 7.48-7.29 (m, 1H), 4.10-3.54 (m, 5H), 2.63-2.53 (m, 3H), 2.51-2.11 (m, 2H), 1.52 (s, 3H), 0.98-0.84 (m, 4H). [M+H]=412.

Example 349. 6-Methyl-4-[(1-methylcyclopropyl)amino]-N-[1-(pyrimidin-2-yl)cyclopropyl]furo[2,3-d]pyrimidine-5-carboxamide

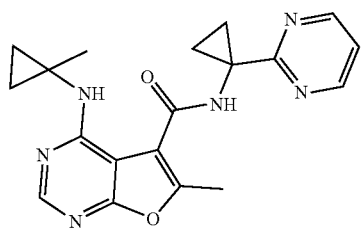 [SMILES: Cc1oc2ncnc(NC3(C)CC3)c2c1C(=O)NC1(c2ncccn2)CC1]

¹H NMR (400 MHz, CD₃OD) δ 8.72 (d, J=4.9 Hz, 2H), 8.42 (s, 1H), 7.30 (t, J=4.9 Hz, 1H), 2.74 (s, 3H), 1.85-1.77 (m, 2H), 1.57-1.46 (m, 5H), 0.94-0.83 (m, 4H). [M+H]=365.

Example 350. 6-Methyl-N-[1-(5-methyl-1,2-oxazol-3-yl)ethyl]-4-[(1-methylcyclopropyl)amino]furo[2,3-d]pyrimidine-5-carboxamide

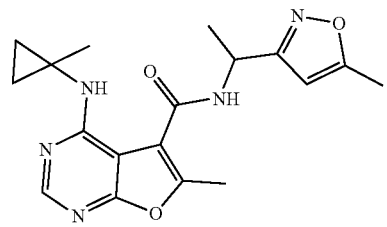 [SMILES: Cc1cc(C(C)NC(=O)c2c(C)oc3ncnc(NC4(C)CC4)c23)no1]

¹H NMR (400 MHz, CD₃OD) δ 8.39 (s, 1H), 6.21 (d, J=0.7 Hz, 1H), 5.36 (q, J=7.1 Hz, 1H), 2.73 (s, 3H), 2.44 (d, J=0.7 Hz, 3H), 1.63 (d, J=7.1 Hz, 3H), 1.53 (s, 3H), 1.04-0.84 (m, 4H). [M+H]=356.

Example 351. 5-[4-(2-Chloro-5-fluoropyrimidin-4-yl)piperidine-1-carbonyl]-6-methyl-N-(1-methylcyclopropyl)furo[2,3-d]pyrimidin-4-amine

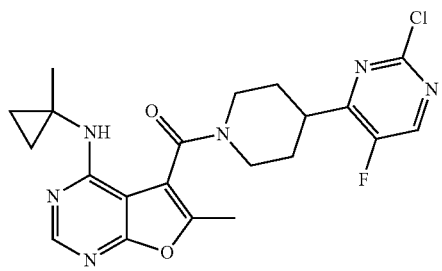

¹H NMR (400 MHz, CD₃OD) δ 8.59 (d, J=1.7 Hz, 1H), 8.42 (s, 1H), 3.55-3.45 (m, 1H), 3.33 (td, J=1.7, 3.2 Hz, 24H), 2.58 (s, 3H), 2.05-1.77 (m, 4H), 1.55 (s, 3H), 1.06-0.87 (m, 4H). [M+H]=445.0.

Example 352. 6-Methyl-N-{[5-(1-methyl-1H-pyrazol-4-yl)-1,2-oxazol-3-yl]methyl}-4-[(1-methylcyclopropyl)amino]furo[2,3-d]pyrimidine-5-carboxamide

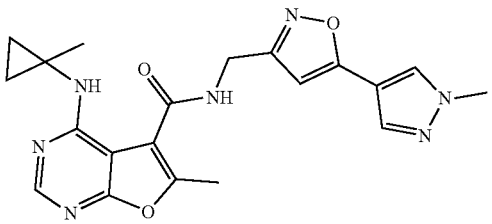 [SMILES: Cc1oc2ncnc(NC3(C)CC3)c2c1C(=O)NCc1cc(-c2cnn(C)c2)on1]

$^1$H NMR (400 MHz, CD$_3$OD) δ 8.39 (s, 1H), 8.13 (s, 1H), 7.88 (s, 1H), 6.53 (s, 1H), 4.70 (s, 2H), 3.97 (s, 3H), 2.75 (s, 3H), 1.53 (s, 3H), 0.99-0.84 (m, 4H). [M+H]=408.

Example 353. N-[1-(Hydroxymethyl)cyclobutyl]-6-methyl-4-[(1-methylcyclopropyl)amino]furo[2,3-d]pyrimidine-5-carboxamide

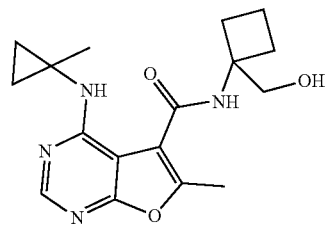 [SMILES: Cc1oc2ncnc(NC3(C)CC3)c2c1C(=O)NC1(CO)CCC1]

$^1$H NMR (400 MHz, CD$_3$OD) δ 8.32 (s, 1H), 8.09 (s, 1H), 3.86 (s, 2H), 2.67 (s, 3H), 2.40-2.30 (m, 2H), 2.29-2.20 (m, 2H), 2.05-1.81 (m, 2H), 1.48 (s, 3H), 0.93-0.81 (m, 4H). [M+H]=331.

Example 354. 5-[3-(6-Fluoropyridin-2-yl)azetidine-1-carbonyl]-6-methyl-N-(1-methylcyclopropyl)furo[2,3-d]pyrimidin-4-amine

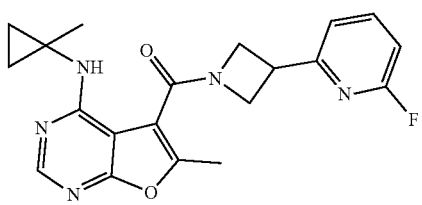 [SMILES: Cc1oc2ncnc(NC3(C)CC3)c2c1C(=O)N1CC(c2cccc(F)n2)C1]

$^1$H NMR (400 MHz, CD$_3$OD) δ 8.40 (s, 1H), 7.89 (q, J=8.2 Hz, 1H), 7.24 (dd, J=2.3, 7.3 Hz, 1H), 6.97 (dd, J=2.3, 8.2 Hz, 1H), 4.61 (t, J=9.0 Hz, 2H), 4.39 (br s, 2H), 4.09 (tt, J=5.8, 8.7 Hz, 1H), 2.65 (s, 3H), 1.54 (s, 3H), 1.05-0.88 (m, 4H). [M+H]=382.

Example 355. 2-(1-{6-Methyl-4-[(1-methylcyclopropyl)amino]furo[2,3-d]pyrimidine-5-carbonyl}piperidin-4-yl)pyrimidin-5-ol

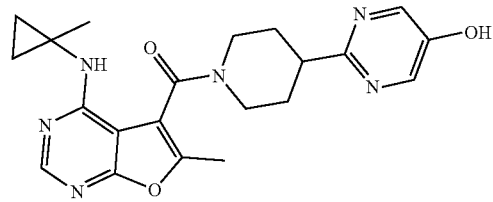 [SMILES: Cc1oc2ncnc(NC3(C)CC3)c2c1C(=O)N1CCC(c2ncc(O)cn2)CC1]

$^1$H NMR (400 MHz, CD$_3$OD) δ 8.44 (s, 1H), 8.31 (s, 2H), 3.18 (tt, J=3.8, 11.5 Hz, 1H), 2.59 (s, 3H), 2.16-2.02 (m, 2H), 1.90 (br s, 2H), 1.55 (s, 3H), 1.04-0.89 (m, 4H). [M+H]=409.1.

Example 356. 5-[4-(5-Fluoropyrimidin-2-yl)piperidine-1-carbonyl]-6-methyl-N-(1-methylcyclopropyl)furo[2,3-d]pyrimidin-4-amine

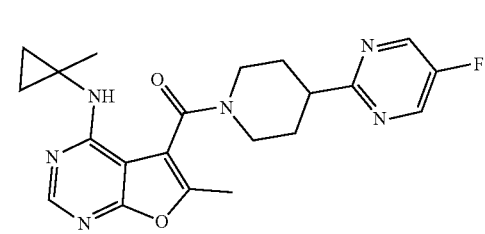 [SMILES: Cc1oc2ncnc(NC3(C)CC3)c2c1C(=O)N1CCC(c2ncc(F)cn2)CC1]

$^1$H NMR (400 MHz, CD$_3$OD) δ 8.70 (s, 2H), 8.42 (s, 1H), 3.31-3.24 (m, 1H), 2.58 (s, 3H), 2.24-2.04 (m, 2H), 1.93 (br s, 2H), 1.54 (s, 3H), 1.04-0.86 (m, 4H). [M+H]=411.1.

Example 357. 5-[4-(5-Fluoropyrimidin-2-yl)-2-methylpiperazine-1-carbonyl]-6-methyl-N-(1-methylcyclopropyl)furo[2,3-d]pyrimidin-4-amine

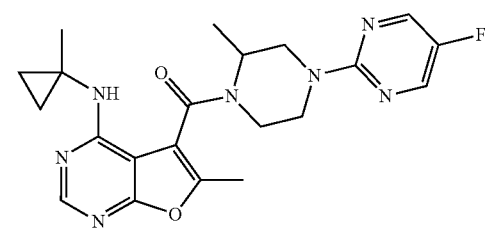 [SMILES: Cc1oc2ncnc(NC3(C)CC3)c2c1C(=O)N1CCN(c2ncc(F)cn2)CC1C]

$^1$H NMR (400 MHz, CD$_3$OD) δ 8.39 (s, 1H), 8.33 (s, 2H), 5.03 (br s, 1H), 4.52 (d, J=12.2 Hz, 2H), 4.29-3.57 (m, 2H), 3.54-3.02 (m, 21H), 2.55 (s, 3H), 1.51 (s, 3H), 1.37-0.89 (m, 4H), 0.85 (s, 3H). [M+H]=426.

Example 358. 5-[4-(5-Fluoropyrimidin-2-yl)-3-methylpiperazine-1-carbonyl]-6-methyl-N-(1-methylcyclopropyl)furo[2,3-d]pyrimidin-4-amine

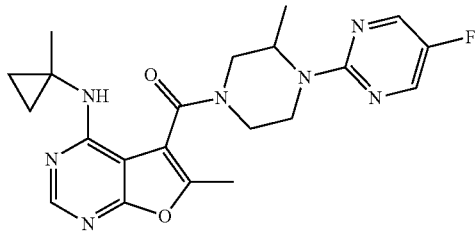 [SMILES: Cc1oc2ncnc(NC3(C)CC3)c2c1C(=O)N1CCN(c2ncc(F)cn2)C(C)C1]

$^1$H NMR (400 MHz, CD$_3$OD) δ 8.42 (s, 1H), 8.33 (s, 2H), 4.81-4.50 (m, 3H), 3.98 (br s, 1H), 3.74-3.47 (m, 1H), 3.36 (br s, 1H), 3.19-2.97 (m, 1H), 2.57 (s, 3H), 1.52 (s, 3H), 1.30 (d, J=6.5 Hz, 3H), 0.99-0.81 (m, 4H). [M+H]=426.1.

Example 359. 5-[4-(2-Fluoro-4-methanesulfonylphenyl)piperazine-1-carbonyl]-6-methyl-N-(1-methylcyclopropyl)furo[2,3-d]pyrimidin-4-amine

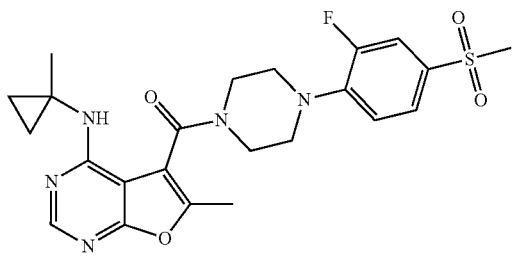 [SMILES: Cc1oc2ncnc(NC3(C)CC3)c2c1C(=O)N1CCN(c2ccc(S(C)(=O)=O)cc2F)CC1]

$^1$H NMR (400 MHz, CD$_3$OD) δ 8.42 (s, 1H), 7.77-7.59 (m, 2H), 7.26 (t, J=8.4 Hz, 1H), 3.91 (br s, 4H), 3.35 (d, J=1.6 Hz, 3H), 3.12 (s, 3H), 2.60 (s, 3H), 1.54 (s, 3H), 1.00-0.85 (m, 4H). [M+H]=487.9.

Example 360. 6-Methyl-N-(1-methylcyclopropyl)-5-[4-(5-methylpyrimidin-2-yl)piperidine-1-carbonyl]furo[2,3-d]pyrimidin-4-amine

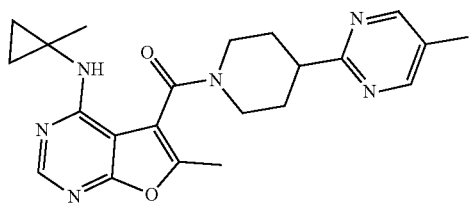 [SMILES: Cc1cnc(C2CCN(C(=O)c3c(C)oc4ncnc(NC5(C)CC5)c34)CC2)nc1]

$^1$H NMR (400 MHz, CD$_3$OD) δ 8.61 (s, 2H), 8.40 (s, 1H), 3.22 (tt, J=4.0, 11.6 Hz, 1H), 2.57 (s, 3H), 2.33 (s, 3H), 2.17-2.03 (m, 2H), 1.92 (br s, 2H), 1.54 (s, 3H), 1.02-0.93 (m, 2H), 0.93-0.84 (m, 2H). [M+H]=407.1.

Example 361. 5-[3-(3-Methoxyphenyl)pyrrolidine-1-carbonyl]-6-methyl-N-(1-methylcyclopropyl)furo[2,3-d]pyrimidin-4-amine

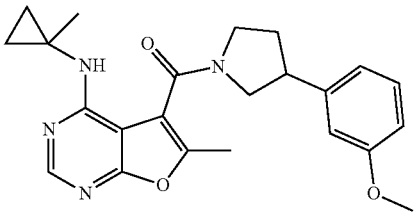 [SMILES: COc1cccc(C2CCN(C(=O)c3c(C)oc4ncnc(NC5(C)CC5)c34)C2)c1]

$^1$H NMR (400 MHz, CD$_3$OD) δ 8.39 (s, 1H), 7.24 (td, J=7.5, 15.2 Hz, 1H), 6.98-6.88 (m, 1H), 6.88-6.75 (m, 2H), 4.11-3.88 (m, 1H), 3.87-3.72 (m, 5H), 3.69-3.36 (m, 2H), 2.58 (d, J=13.9 Hz, 3H), 2.52-2.02 (m, 2H), 1.53 (s, 3H), 1.00-0.86 (m, 4H). [M+H]=407.09.

Example 362. 5-[4-(2-Chloro-5-fluoropyrimidin-4-yl)piperazine-1-carbonyl]-6-methyl-N-(1-methylcyclopropyl)furo[2,3-d]pyrimidin-4-amine

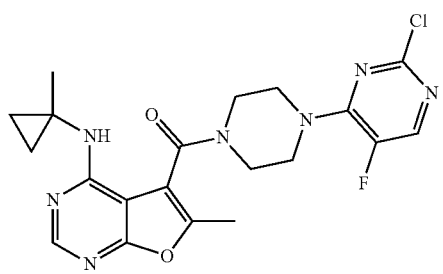 [SMILES: Cc1oc2ncnc(NC3(C)CC3)c2c1C(=O)N1CCN(c2nc(Cl)ncc2F)CC1]

$^1$H NMR (400 MHz, CD$_3$OD) δ 8.32 (s, 1H), 8.08 (d, J=6.4 Hz, 1H), 7.28 (s, 1H), 4.07-3.68 (m, 8H), 2.54 (s, 3H), 1.51 (s, 3H), 0.92-0.69 (m, 4H). [M+H]=446.0.

Example 363. N'-(5-Fluoropyrimidin-2-yl)-6-methyl-4-[(1-methylcyclopropyl)amino]furo[2,3-d]pyrimidine-5-carbohydrazide

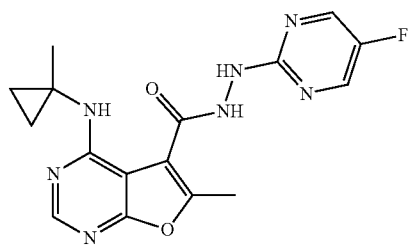 [SMILES: Cc1oc2ncnc(NC3(C)CC3)c2c1C(=O)NNc1ncc(F)cn1]

$^1$H NMR (400 MHz, CD$_3$OD) δ 8.45 (s, 3H), 2.81 (s, 3H), 1.54 (s, 3H), 1.06-0.83 (m, 4H). [M+H]=358.0.

Example 364. 5-[4-(6-Methoxypyridazin-3-yl)piperidine-1-carbonyl]-6-methyl-N-(1-methylcyclopropyl)furo[2,3-d]pyrimidin-4-amine

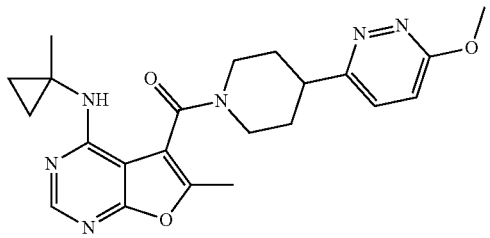 [SMILES: COc1ccc(C2CCN(C(=O)c3c(C)oc4ncnc(NC5(C)CC5)c34)CC2)nn1]

¹H NMR (400 MHz, CD₃OD) δ 8.32 (s, 1H), 7.58 (d, J=8.9 Hz, 1H), 7.16 (d, J=9.0 Hz, 1H), 4.08 (s, 3H), 3.73-2.96 (m, 7H), 2.54 (s, 3H), 2.15-2.04 (m, 2H), 2.07 (br s, 2H), 1.98-1.74 (m, 2H), 1.52 (s, 3H), 0.93-0.69 (m, 4H). [M+H]=423.1.

Example 365. 5-[4-(5-Methoxypyrazin-2-yl)piperidine-1-carbonyl]-6-methyl-N-(1-methylcyclopropyl)furo[2,3-d]pyrimidin-4-amine

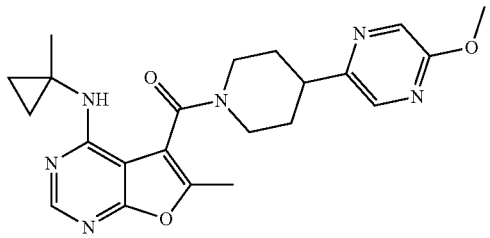

¹H NMR (400 MHz, CD₃OD) δ 8.32 (s, 1H), 8.16 (s, 1H), 8.09 (s, 1H), 4.59 (br s, 3H), 3.96 (s, 3H), 3.29-2.97 (m, 3H), 2.53 (br s, 3H), 2.16-1.68 (m, 4H), 1.53 (s, 3H), 0.96-0.70 (m, 4H). [M+H]=423.0.

Example 366. 5-[4-(5-Methoxypyridin-2-yl)piperidine-1-carbonyl]-6-methyl-N-(1-methylcyclopropyl)furo[2,3-d]pyrimidin-4-amine

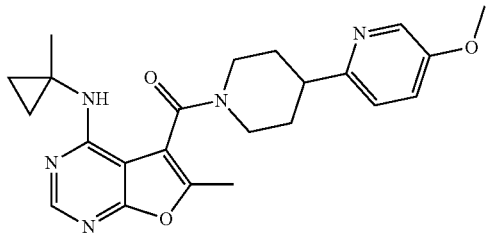 [SMILES: COc1ccc(C2CCN(C(=O)c3c(C)oc4ncnc(NC5(C)CC5)c34)CC2)nc1]

¹H NMR (400 MHz, CD₃OD) δ 8.32 (s, 1H), 8.17 (d, J=2.7 Hz, 1H), 7.42-7.33 (m, 1H), 7.28 (d, J=8.3 Hz, 1H), 4.79-3.98 (m, 2H), 3.87 (s, 3H), 3.23-2.85 (m, 2H), 2.54 (br s, 3H), 2.15-1.64 (m, 4H), 1.52 (s, 3H), 0.98-0.62 (m, 4H). [M+H]=422.1.

Example 367. 5-[3-(6-Methoxypyridin-2-yl)pyrrolidine-1-carbonyl]-6-methyl-N-(1-methylcyclopropyl)furo[2,3-d]pyrimidin-4-amine

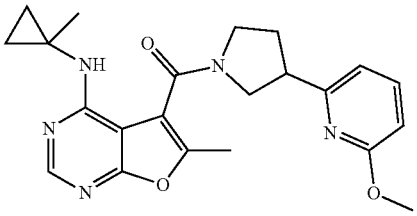 [SMILES: COc1cccc(C2CCN(C(=O)c3c(C)oc4ncnc(NC5(C)CC5)c34)C2)n1]

¹H NMR (400 MHz, CD₃OD) δ 8.36 (br s, 1H), 7.72-7.48 (m, 1H), 7.00-6.80 (m, 1H), 6.70-6.58 (m, 1H), 4.05-3.76 (m, 7H), 3.72-3.50 (m, 1H), 2.56 (br s, 3H), 2.46-2.20 (m, 2H), 1.50 (s, 3H), 0.86 (s, 4H). [M+H]=408.03.

Example 368. 5-[4-(4-Cyclopropylpyrimidin-2-yl)piperidine-1-carbonyl]-6-methyl-N-(1-methylcyclopropyl)furo[2,3-d]pyrimidin-4-amine

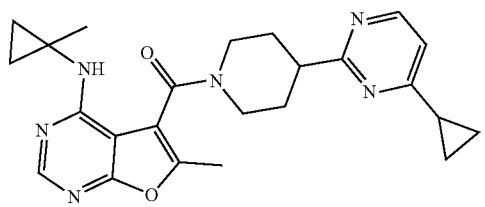 [SMILES: Cc1oc2ncnc(NC3(C)CC3)c2c1C(=O)N1CCC(c2nccc(C3CC3)n2)CC1]

¹H NMR (400 MHz, CD₃OD) δ 8.53 (d, J=5.6 Hz, 1H), 8.45 (s, 1H), 7.36 (d, J=5.5 Hz, 1H), 3.21 (tt, J=3.7, 11.4 Hz, 1H), 2.63-2.56 (m, 3H), 2.19 (quin, J=6.3 Hz, 1H), 2.10 (d, J=11.4 Hz, 2H), 1.92 (br s, 2H), 1.55 (s, 3H), 1.30-1.17 (m, 4H), 1.06-0.91 (m, 4H). [M+H]=433.03.

Example 369. 6-Methyl-N-(1-methylcyclopropyl)-5-[4-(4-propylpyrimidin-2-yl)piperidine-1-carbonyl]furo[2,3-d]pyrimidin-4-amine

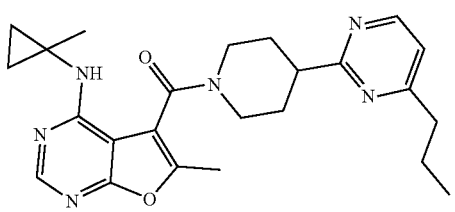 [SMILES: CCCc1ccnc(C2CCN(C(=O)c3c(C)oc4ncnc(NC5(C)CC5)c34)CC2)n1]

¹H NMR (400 MHz, CD₃OD) δ 8.60 (d, J=5.3 Hz, 1H), 8.41 (s, 1H), 7.25 (d, J=5.1 Hz, 1H), 3.23 (tt, J=3.8, 11.4 Hz, 2H), 2.83-2.72 (m, 2H), 2.58 (s, 3H), 2.08 (br s, 2H), 1.96 (br s, 2H), 1.79 (sxt, J=7.5 Hz, 2H), 1.61-1.49 (m, 3H), 1.05-0.85 (m, 7H). [M+H]=435.04.

Example 370. 5-[4-(5-Methoxypyrimidin-2-yl)piperidine-1-carbonyl]-6-methyl-N-(1-methylcyclopropyl)furo[2,3-d]pyrimidin-4-amine

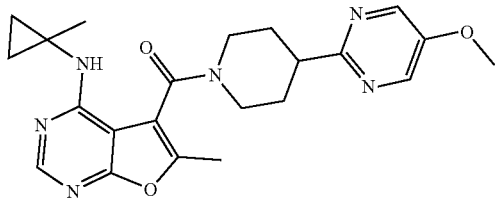 [SMILES: COc1cnc(C2CCN(C(=O)c3c(C)oc4ncnc(NC5(C)CC5)c34)CC2)nc1]

¹H NMR (400 MHz, CD₃OD) δ 8.46 (s, 2H), 8.40 (s, 1H), 3.95 (s, 3H), 3.21 (tt, J=3.8, 11.5 Hz, 1H), 2.57 (s, 3H), 2.08 (br s, 2H), 1.91 (br s, 2H), 1.54 (s, 3H), 1.01-0.85 (m, 4H). [M+H]=423.05.

Example 371. N-{1-[(4-Methoxyphenyl)methyl]cyclopropyl}-6-methyl-4-[(1-methylcyclopropyl)amino]furo[2,3-d]pyrimidine-5-carboxamide

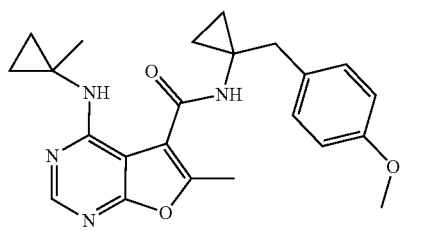 [SMILES: COc1ccc(CC2(NC(=O)c3c(C)oc4ncnc(NC5(C)CC5)c34)CC2)cc1]

¹H NMR (400 MHz, CD₃OD) δ 8.36 (s, 1H), 8.28 (s, 1H), 7.18 (d, J=8.6 Hz, 2H), 6.87-6.82 (m, 2H), 3.75 (s, 3H), 2.98 (s, 2H), 2.32-2.28 (m, 3H), 1.54 (s, 3H), 1.02-0.89 (m, 8H). [M+H]=407.04.

Example 372. 5-[3-(6-Bromopyridin-2-yl)pyrrolidine-1-carbonyl]-6-methyl-N-(1-methylcyclopropyl)furo[2,3-d]pyrimidin-4-amine

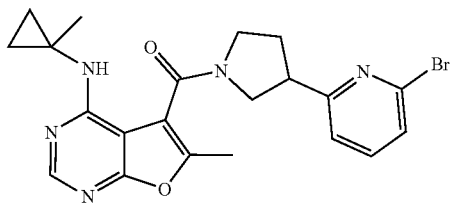 [SMILES: Cc1oc2ncnc(NC3(C)CC3)c2c1C(=O)N1CCC(c2cccc(Br)n2)C1]

¹H NMR (400 MHz, CD₃OD) δ 8.36 (s, 1H), 7.63 (dd, J=8.1, 12.7 Hz, 1H), 7.52-7.27 (m, 2H), 4.09-3.56 (m, 5H), 2.59 (d, J=7.7 Hz, 3H), 2.50-2.12 (m, 2H), 1.51 (s, 3H), 0.99-0.80 (m, 4H). [M+H]=458.10.

Example 373. 5-[3-(5-Bromopyridin-2-yl)pyrrolidine-1-carbonyl]-6-methyl-N-(1-methylcyclopropyl)furo[2,3-d]pyrimidin-4-amine

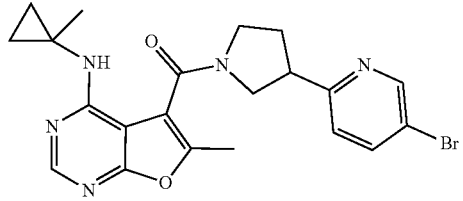 [SMILES: Cc1oc2ncnc(NC3(C)CC3)c2c1C(=O)N1CCC(c2ccc(Br)cn2)C1]

¹H NMR (400 MHz, CD₃OD) δ 8.71-8.46 (m, 1H), 8.36 (s, 1H), 8.01-7.84 (m, 1H), 7.43-7.23 (m, 1H), 4.08-3.88 (m, 2H), 3.86-3.53 (m, 3H), 2.56 (br s, 3H), 2.51-2.13 (m, 2H), 1.52 (s, 3H), 0.96-0.80 (m, 4H). [M+H]=458.10.

Example 374. N-(1-Fluoro-2-methylpropan-2-yl)-6-methyl-4-[(1-methylcyclopropyl)amino]furo[2,3-d]pyrimidine-5-carboxamide

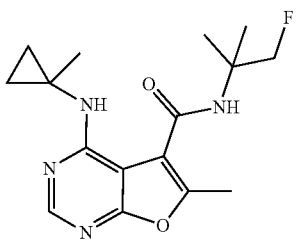 [SMILES: Cc1oc2ncnc(NC3(C)CC3)c2c1C(=O)NC(C)(C)CF]

¹H NMR (400 MHz, CD₃OD) δ 8.36 (s, 1H), 7.85 (br s, 1H), 4.69-4.50 (m, 2H), 2.67 (s, 3H), 1.52 (s, 3H), 1.47 (d, J=2.0 Hz, 6H), 0.96-0.87 (m, 4H). [M+H]=321.20.

Example 375. 1'-{6-Methyl-4-[(1-methylcyclopropyl)amino]furo[2,3-d]pyrimidine-5-carbonyl}-1,2-dihydrospiro[indole-3,3'-piperidine]-2-one

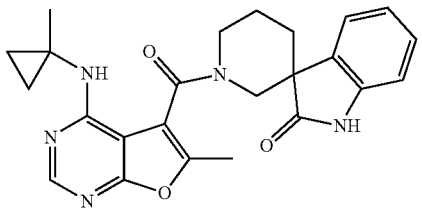 [SMILES: Cc1oc2ncnc(NC3(C)CC3)c2c1C(=O)N1CCCC2(C1)C(=O)Nc1ccccc12]

¹H NMR (400 MHz, CD₃OD) δ 8.52-8.25 (m, 1H), 7.46-6.74 (m, 5H), 4.63 (br s, 1H), 4.18-3.38 (m, 4H), 2.55 (br s, 2H), 2.42 (s, 2H), 2.29-1.90 (m, 3H), 1.69 (br s, 1H), 1.61 (br s, 2H), 1.57 (s, 2H), 1.22 (br s, 1H), 1.14-0.82 (m, 4H). [M+H]=432.3.

Example 376. 1-Methyl-1'-{6-methyl-4-[(1-methyl-cyclopropyl)amino]furo[2,3-d]pyrimidine-5-carbonyl}-1,2-dihydrospiro[indole-3,3'-piperidine]-2-one

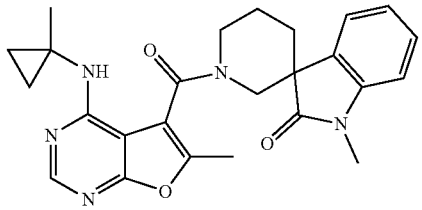 [SMILES: Cc1oc2ncnc(NC3(C)CC3)c2c1C(=O)N1CCCC2(C1)C(=O)N(C)c1ccccc12]

¹H NMR (400 MHz, CD₃OD) δ 8.59-8.21 (m, 1H), 7.66-6.82 (m, 5H), 4.57 (br s, 1H), 4.10 (br s, 1H), 3.97-3.70 (m, 1H), 3.69-3.57 (m, 1H), 3.39 (d, J=19.2 Hz, 1H), 2.97 (br s, 1H), 2.54 (br s, 2H), 2.40 (s, 2H), 2.20 (br s, 1H), 1.91 (d, J=12.3 Hz, 1H), 1.74-1.51 (m, 5H), 1.36-1.16 (m, 1H), 1.13-0.85 (m, 4H). [M+H]=446.3.

Example 377. 1'-{6-Methyl-4-[(1-methylcyclopropyl)amino]furo[2,3-d]pyrimidine-5-carbonyl}-2-oxo-1,2-dihydrospiro[indole-3,3'-pyrrolidine]-4'-carbonitrile

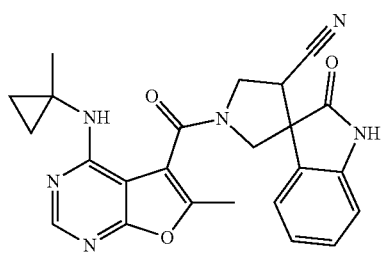 [SMILES: Cc1oc2ncnc(NC3(C)CC3)c2c1C(=O)N1CC(C#N)C2(C1)C(=O)Nc1ccccc12]

¹H NMR (400 MHz, DMSO-d₆) δ 10.90 (br s, 1H), 8.33 (br s, 1H), 7.47-6.82 (m, 5H), 4.44-3.71 (m, 11H), 2.59 (br s, 1H), 2.45 (br s, 2H), 1.49 (s, 3H), 0.80 (d, J=5.7 Hz, 4H). [M+H]=443.3.

Example 378. 5-({2,3-Dihydrospiro[indene-1,2'-morpholine]-4'-yl}carbonyl)-6-methyl-N-(1-methyl-cyclopropyl)furo[2,3-d]pyrimidin-4-amine

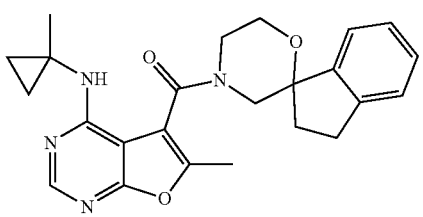 [SMILES: Cc1oc2ncnc(NC3(C)CC3)c2c1C(=O)N1CCOC2(CCc3ccccc32)C1]

¹H NMR (400 MHz, CD₃OD) δ 8.39 (s, 1H), 7.41 (d, J=6.0 Hz, 1H), 7.29 (br s, 3H), 4.33 (br s, 1H), 3.87 (br s, 4H), 3.04 (br s, 2H), 2.55 (br s, 4H), 2.14 (br s, 3H), 1.56 (s, 3H), 1.03-0.81 (m, 4H). [M+H]=419.3.

Example 379. 6-Methyl-N-(1-methylcyclopropyl)-5-({3H-spiro[2-benzofuran-1,3'-piperidine]-1'-yl}carbonyl)furo[2,3-d]pyrimidin-4-amine

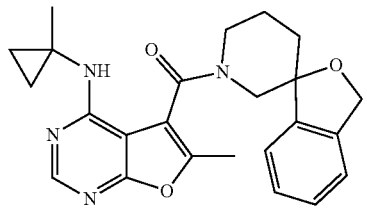 [SMILES: Cc1oc2ncnc(NC3(C)CC3)c2c1C(=O)N1CCCC2(C1)OCc1ccccc12]

¹H NMR (400 MHz, CD₃OD) δ 8.39 (s, 1H), 7.56-6.94 (m, 4H), 5.23 (br s, 1H), 4.84-4.38 (m, 1H), 4.33-3.75 (m, 1H), 3.73-3.37 (m, 2H), 3.26-3.00 (m, 1H), 2.42 (br s, 3H), 2.16 (br s, 2H), 2.01-1.67 (m, 2H), 1.58 (s, 3H), 1.13-0.81 (m, 4H). [M+H]=419.3.

Example 380. 6-Methyl-N-(1-methylcyclopropyl)-5-({3H-spiro[2-benzofuran-1,3'-pyrrolidine]-1'-yl}carbonyl)furo[2,3-d]pyrimidin-4-amine

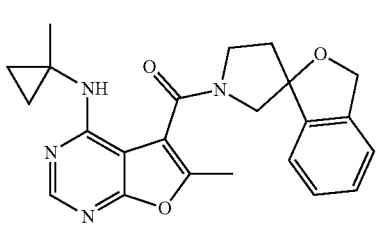 [SMILES: Cc1oc2ncnc(NC3(C)CC3)c2c1C(=O)N1CCC2(C1)OCc1ccccc12]

¹H NMR (400 MHz, CD₃OD) δ 8.39 (br s, 1H), 7.45-7.23 (m, 4H), 5.32-4.97 (m, 2H), 4.22-3.70 (m, 4H), 2.60 (d, J=19.8 Hz, 3H), 2.47 (d, J=10.1 Hz, 1H), 2.37-2.17 (m, 1H), 1.55 (s, 3H), 1.09-0.84 (m, 4H). [M+H]=405.3.

Example 381. 6-Methyl-N-(1-methylcyclopropyl)-5-[4-(pyrimidin-5-yl)piperazine-1-carbonyl]furo[2,3-d]pyrimidin-4-amine

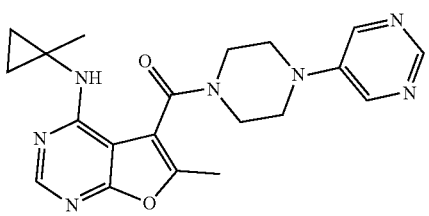 [SMILES: Cc1oc2ncnc(NC3(C)CC3)c2c1C(=O)N1CCN(c2cncnc2)CC1]

¹H NMR (400 MHz, CD₃OD) δ 8.65 (s, 1H), 8.56 (s, 2H), 8.43 (s, 1H), 3.91 (br s, 4H), 3.47 (br s, 4H), 2.60 (s, 3H), 1.53 (s, 3H), 0.99-0.86 (m, 4H). [M+H]=394.08.

Example 382. 4-(1-{6-Methyl-4-[(1-methylcyclopropyl)amino]furo[2,3-d]pyrimidine-5-carbonyl}piperidin-4-yl)benzamide

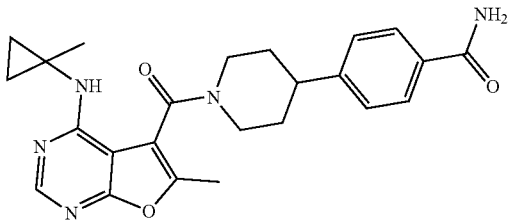 [SMILES: Cc1oc2ncnc(NC3(C)CC3)c2c1C(=O)N1CCC(c2ccc(C(N)=O)cc2)CC1]

¹H NMR (400 MHz, CD₃OD) δ 8.42 (s, 1H), 7.85 (d, J=8.3 Hz, 2H), 7.39 (d, J=8.2 Hz, 2H), 3.01 (t, J=12.1 Hz, 1H), 2.59 (s, 3H), 2.12-1.92 (m, 2H), 1.92-1.65 (m, 2H), 1.55 (s, 3H), 1.04-0.88 (m, 4H). [M+H]=434.11.

Example 383. 6-Methyl-N-(1-methylcyclopropyl)-5-[4-(6-methylpyridin-3-yl)piperidine-1-carbonyl]furo[2,3-d]pyrimidin-4-amine

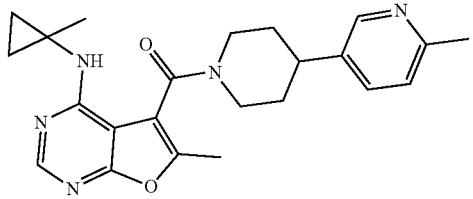 [SMILES: Cc1ccc(C2CCN(C(=O)c3c(C)oc4ncnc(NC5(C)CC5)c34)CC2)cn1]

¹H NMR (400 MHz, CD₃OD) δ 8.64 (s, 1H), 8.48 (dd, J=1.7, 8.4 Hz, 1H), 8.39 (s, 1H), 7.89 (d, J=8.4 Hz, 1H), 3.21 (t, J=12.2 Hz, 1H), 2.84-2.72 (m, 3H), 2.59 (s, 3H), 2.17-1.95 (m, 2H), 1.84 (d, J=10.3 Hz, 2H), 1.54 (s, 3H), 1.00-0.83 (m, 4H). [M+H]=406.10.

Example 384. 6-Methyl-N-(1-methylcyclopropyl)-5-[4-(4-methylphenyl)piperidine-1-carbonyl]furo[2,3-d]pyrimidin-4-amine

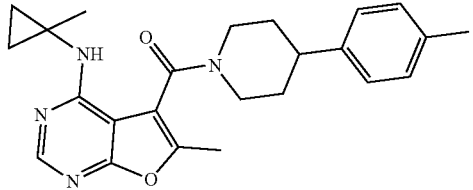 [SMILES: Cc1ccc(C2CCN(C(=O)c3c(C)oc4ncnc(NC5(C)CC5)c34)CC2)cc1]

¹H NMR (400 MHz, CD₃OD) δ 8.38 (s, 1H), 7.17-7.07 (m, 4H), 2.94-2.80 (m, 1H), 2.56 (s, 3H), 2.35-2.27 (m, 3H), 1.95 (d, J=11.4 Hz, 2H), 1.70 (br s, 2H), 1.54 (s, 3H), 1.01-0.82 (m, 4H). [M+H]=405.13.

Example 385. 4-(1-{6-Methyl-4-[(1-methylcyclopropyl)amino]furo[2,3-d]pyrimidine-5-carbonyl}piperidin-4-yl)benzonitrile

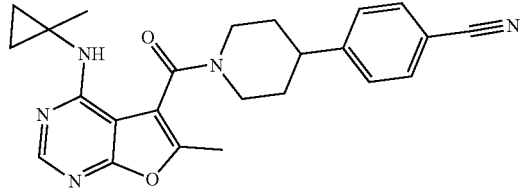 [SMILES: Cc1oc2ncnc(NC3(C)CC3)c2c1C(=O)N1CCC(c2ccc(C#N)cc2)CC1]

¹H NMR (400 MHz, CD₃OD) δ 8.39 (s, 1H), 7.70 (d, J=8.3 Hz, 2H), 7.49 (d, J=8.2 Hz, 2H), 3.04 (t, J=12.0 Hz, 1H), 2.58 (s, 3H), 2.12-1.90 (m, 2H), 1.90-1.65 (m, 2H), 1.54 (s, 3H), 1.01-0.83 (m, 4H). [M+H]=416.10.

Example 386. 6-Fluoro-1'-{6-methyl-4-[(1-methylcyclopropyl)amino]furo[2,3-d]pyrimidine-5-carbonyl}-1,2-dihydrospiro[3,1-benzoxazine-4,4'-piperidine]-2-one

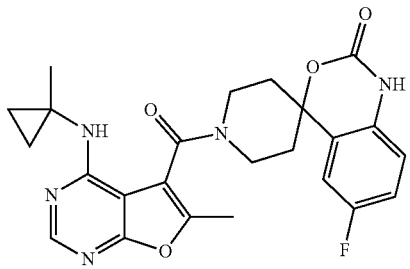 [SMILES: Cc1oc2ncnc(NC3(C)CC3)c2c1C(=O)N1CCC2(CC1)OC(=O)Nc1ccc(F)cc12]

¹H NMR (400 MHz, CD₃OD) δ 8.42 (s, 1H), 7.14 (d, J=8.9 Hz, 1H), 7.11-7.04 (m, 1H), 6.94 (dd, J=4.6, 8.8 Hz, 1H), 4.63 (br s, 1H), 4.76-3.39 (m, 4H), 2.61 (s, 3H), 2.33-2.08 (m, 4H), 1.55 (s, 3H), 1.07-0.83 (m, 4H). [M+H]=466.0.

Example 387. 6-Methyl-N-(1-methylcyclopropyl)-5-({spiro[indene-1,4'-piperidine]-1'-yl}carbonyl)furo[2,3-d]pyrimidin-4-amine

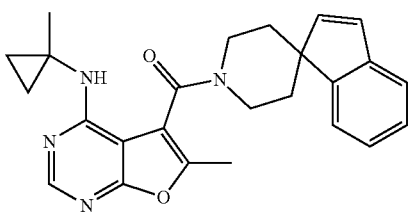 [SMILES: Cc1oc2ncnc(NC3(C)CC3)c2c1C(=O)N1CCC2(C=Cc3ccccc32)CC1]

¹H NMR (400 MHz, CD₃OD) δ 8.42 (s, 1H), 7.38 (br s, 1H), 7.34 (s, 1H), 7.29-7.16 (m, 2H), 7.08 (d, J=4.9 Hz, 1H), 6.88 (d, J=5.7 Hz, 1H), 4.77-3.42 (m, 4H), 2.63 (s, 3H), 2.16 (br s, 2H), 1.58 (s, 3H), 1.45 (d, J=11.4 Hz, 2H), 1.10-0.86 (m, 4H). [M+H]=415.1.

Example 388. 6-Methyl-N-(1-methylcyclopropyl)-5-({3H-spiro[2-benzothiophene-1,4'-piperidine]-1'-yl}carbonyl)furo[2,3-d]pyrimidin-4-amine

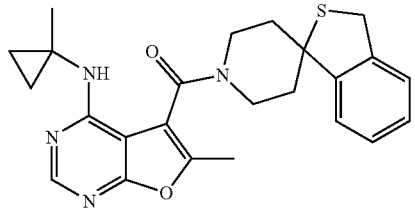 [SMILES: Cc1oc2ncnc(NC3(C)CC3)c2c1C(=O)N1CCC2(CC1)SCc1ccccc12]

$^1$H NMR (400 MHz, CD$_3$OD) δ 8.39 (s, 1H), 7.38-7.15 (m, 4H), 4.78-4.34 (m, 1H), 4.24 (s, 2H), 4.19-3.38 (m, 2H), 3.27-3.07 (m, 1H), 2.59 (s, 3H), 2.26 (br s, 2H), 2.00 (d, J=11.7 Hz, 2H), 1.56 (s, 3H), 1.02-0.83 (m, 4H). [M+H]=435.1.

Example 389. 5-[3-(3-Fluorophenyl)pyrrolidine-1-carbonyl]-6-methyl-N-(1-methylcyclopropyl)furo[2,3-d]pyrimidin-4-amine

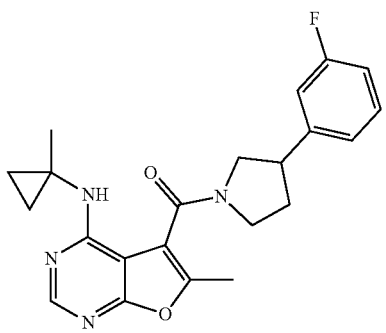 [SMILES: Cc1oc2ncnc(NC3(C)CC3)c2c1C(=O)N1CCC(c2cccc(F)c2)C1]

$^1$H NMR (400 MHz, CD$_3$OD) δ 8.36 (s, 1H), 7.35 (d, J=15.8 Hz, 1H), 7.25-6.88 (m, 3H), 4.11-3.90 (m, 1H), 3.88-3.44 (m, 4H), 2.57 (d, J=11.0 Hz, 3H), 2.50-1.98 (m, 2H), 1.51 (s, 3H), 0.97-0.82 (m, 4H). [M+H]=395.08.

Example 390. 6-Methyl-N-(1-methylcyclopropyl)-5-[4-(4-methylpyrimidin-2-yl)piperidine-1-carbonyl]furo[2,3-d]pyrimidin-4-amine

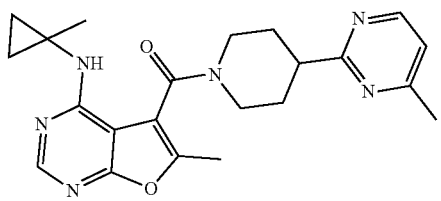 [SMILES: Cc1ccnc(C2CCN(C(=O)c3c(C)oc4ncnc(NC5(C)CC5)c34)CC2)n1]

$^1$H NMR (400 MHz, CD$_3$OD) δ 8.62 (d, J=5.3 Hz, 1H), 8.52-8.41 (m, 1H), 7.31 (d, J=5.3 Hz, 1H), 3.23 (tt, J=3.7, 11.5 Hz, 1H), 2.61 (s, 3H), 2.57 (s, 3H), 2.18-2.04 (m, 2H), 1.98 (br s, 2H), 1.59-1.53 (m, 3H), 1.08-0.92 (m, 4H). [M+H]=407.12.

Example 391. 5-[4-(4,5-Dimethylpyrimidin-2-yl)piperidine-1-carbonyl]-6-methyl-N-(1-methylcyclopropyl)furo[2,3-d]pyrimidin-4-amine

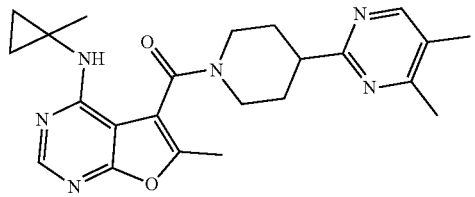 [SMILES: Cc1cnc(C2CCN(C(=O)c3c(C)oc4ncnc(NC5(C)CC5)c34)CC2)nc1C]

$^1$H NMR (400 MHz, CD$_3$OD) δ 8.50 (s, 1H), 8.44 (s, 1H), 3.27-3.17 (m, 1H), 2.57 (d, J=15.9 Hz, 6H), 2.32 (s, 3H), 2.08 (d, J=10.3 Hz, 2H), 1.96 (br s, 2H), 1.58-1.52 (m, 3H), 1.07-0.88 (m, 4H). [M+H]=421.13.

Example 392. 1'-{6-Methyl-4-[(1-methylcyclopropyl)amino]furo[2,3-d]pyrimidine-5-carbonyl}-1,2-dihydrospiro[indole-3,3'-pyrrolidine]-2-one

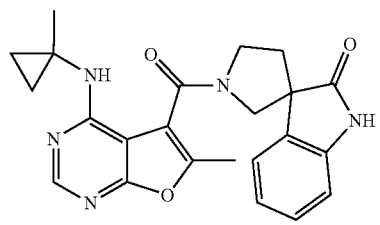 [SMILES: Cc1oc2ncnc(NC3(C)CC3)c2c1C(=O)N1CCC2(C1)C(=O)Nc1ccccc12]

$^1$H NMR (400 MHz, CD$_3$OD) δ 8.45 (d, J=18.5 Hz, 1H), 7.49-6.76 (m, 5H), 4.40-3.83 (m, 4H), 2.76-2.52 (m, 3H), 2.51-2.26 (m, 2H), 1.58 (s, 3H), 1.22-0.84 (m, 4H). [M+H]=418.1.

Example 393. 6-Methyl-N-(1-methylcyclopropyl)-5-[4-(5-methylpyrazin-2-yl)piperidine-1-carbonyl]furo[2,3-d]pyrimidin-4-amine

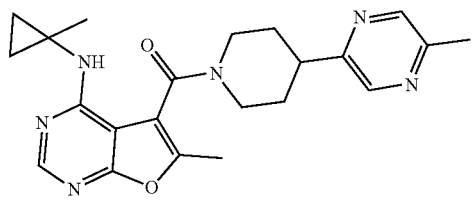 [SMILES: Cc1cnc(C2CCN(C(=O)c3c(C)oc4ncnc(NC5(C)CC5)c34)CC2)cn1]

$^1$H NMR (400 MHz, CD$_3$OD) δ 8.49 (s, 1H), 8.45 (s, 1H), 8.43 (s, 1H), 3.17 (ddd, J=3.6, 8.1, 11.7 Hz, 1H), 2.63-2.57 (m, 3H), 2.55 (s, 3H), 2.01 (br s, 2H), 1.91 (br s, 2H), 1.55 (s, 3H), 1.04-0.97 (m, 2H), 0.97-0.90 (m, 2H). [M+H]=407.08.

Example 394. 5-[4-(2-Methoxypyrimidin-5-yl)piperidine-1-carbonyl]-6-methyl-N-(1-methylcyclopropyl)furo[2,3-d]pyrimidin-4-amine

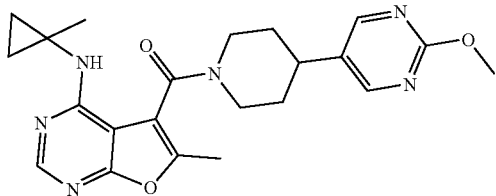 [SMILES: COc1ncc(C2CCN(C(=O)c3c(C)oc4ncnc(NC5(C)CC5)c34)CC2)cn1]

$^1$H NMR (400 MHz, CD$_3$OD) δ 8.53 (s, 2H), 8.46 (s, 1H), 4.08-3.95 (m, 3H), 3.04-2.92 (m, 1H), 2.61 (s, 3H), 2.01 (d, J=12.0 Hz, 2H), 1.89-1.69 (m, 2H), 1.56 (s, 3H), 1.09-0.91 (m, 4H). [M+H]=423.10.

Example 395. 6-Methyl-N-(1-methylcyclopropyl)-5-[3-(3-methylphenyl)pyrrolidine-1-carbonyl]furo[2,3-d]pyrimidin-4-amine

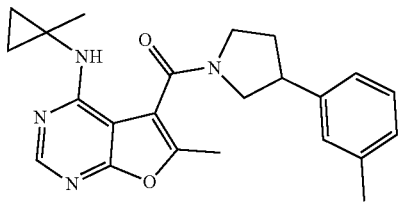 [SMILES: Cc1cccc(C2CCN(C(=O)c3c(C)oc4ncnc(NC5(C)CC5)c34)C2)c1]

$^1$H NMR (400 MHz, CD$_3$OD) δ 8.40 (s, 1H), 7.30-6.99 (m, 4H), 4.12-3.37 (m, 5H), 2.59 (d, J=15.7 Hz, 3H), 2.48-2.02 (m, 5H), 1.54 (s, 3H), 1.02-0.84 (m, 4H). [M+H]=391.09.

Example 396. 6-Methyl-N-(1-methylcyclopropyl)-5-{3-[3-(trifluoromethyl)phenyl]pyrrolidine-1-carbonyl}furo[2,3-d]pyrimidin-4-amine

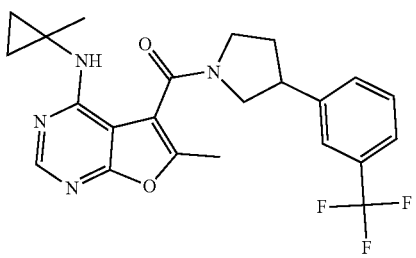 [SMILES: Cc1oc2ncnc(NC3(C)CC3)c2c1C(=O)N1CCC(c2cccc(C(F)(F)F)c2)C1]

$^1$H NMR (400 MHz, CD$_3$OD) δ 8.39 (s, 1H), 7.75-7.47 (m, 4H), 4.20-3.50 (m, 5H), 2.59 (d, J=13.1 Hz, 3H), 2.54-2.08 (m, 2H), 1.53 (s, 3H), 1.00-0.83 (m, 4H). [M+H]=445.05.

Example 397. 5-[3-(3,5-Dimethylphenyl)pyrrolidine-1-carbonyl]-6-methyl-N-(1-methylcyclopropyl)furo[2,3-d]pyrimidin-4-amine

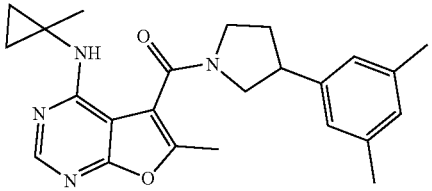 [SMILES: Cc1cc(C)cc(C2CCN(C(=O)c3c(C)oc4ncnc(NC5(C)CC5)c34)C2)c1]

$^1$H NMR (400 MHz, CD$_3$OD) δ 8.39 (s, 1H), 7.04-6.83 (m, 3H), 4.14-3.35 (m, 5H), 2.58 (d, J=15.0 Hz, 3H), 2.48-2.01 (m, 8H), 1.53 (s, 3H), 1.02-0.83 (m, 4H). [M+H]=405.11.

Example 398. 5-[3-(3-Fluorophenoxy)pyrrolidine-1-carbonyl]-6-methyl-N-(1-methylcyclopropyl)furo[2,3-d]pyrimidin-4-amine

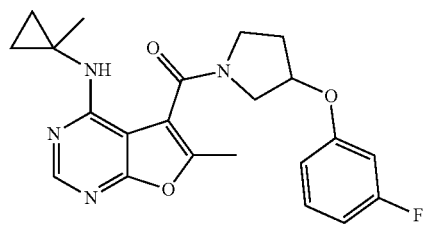 [SMILES: Cc1oc2ncnc(NC3(C)CC3)c2c1C(=O)N1CCC(Oc2cccc(F)c2)C1]

$^1$H NMR (400 MHz, CD$_3$OD) δ 8.35 (s, 1H), 7.39-7.11 (m, 1H), 6.70 (br s, 3H), 5.23-4.98 (m, 1H), 4.10-3.61 (m, 4H), 2.55 (br s, 3H), 2.28 (br s, 2H), 1.51 (s, 3H), 0.87 (d, J=16.5 Hz, 4H). [M+H]=411.06.

Example 399. 5-[3-(4-Fluorophenoxy)pyrrolidine-1-carbonyl]-6-methyl-N-(1-methylcyclopropyl)furo[2,3-d]pyrimidin-4-amine

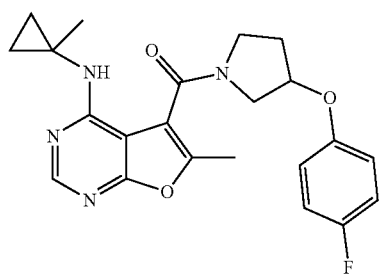 [SMILES: Cc1oc2ncnc(NC3(C)CC3)c2c1C(=O)N1CCC(Oc2ccc(F)cc2)C1]

$^1$H NMR (400 MHz, CD$_3$OD) δ 8.36 (s, 1H), 7.14-6.78 (m, 4H), 5.18-4.92 (m, 1H), 4.09-3.64 (m, 4H), 2.56 (br s, 3H), 2.27 (br s, 2H), 1.51 (s, 3H), 0.95-0.81 (m, 4H). [M+H]=411.07.

Example 400. N-(1-Cyclopropylethyl)-6-methyl-4-[(1-methylcyclopropyl)amino]furo[2,3-d]pyrimidine-5-carboxamide

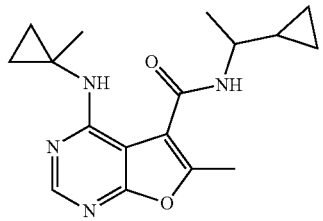 [SMILES: Cc1oc2ncnc(NC3(C)CC3)c2c1C(=O)NC(C)C1CC1]

$^1$H NMR (400 MHz, CD$_3$OD) δ 8.35 (s, 1H), 8.26 (d, J=7.7 Hz, 1H), 3.57-3.43 (m, 1H), 2.69 (s, 3H), 1.51 (s, 3H), 1.35 (d, J=6.7 Hz, 3H), 1.10-0.99 (m, 1H), 0.95-0.83 (m, 4H), 0.65-0.47 (m, 2H), 0.45-0.26 (m, 2H). [M+H]=315.06.

Example 401. N-(1-Cyclopropylpropyl)-6-methyl-4-[(1-methylcyclopropyl)amino]furo[2,3-d]pyrimidine-5-carboxamide

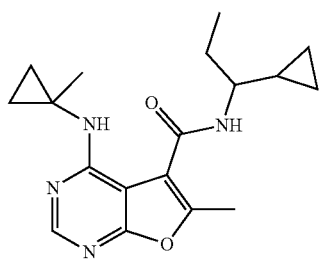 [SMILES: CCC(NC(=O)c1c(C)oc2ncnc(NC3(C)CC3)c12)C1CC1]

$^1$H NMR (400 MHz, CD$_3$OD) δ 8.37 (s, 1H), 8.26 (d, J=8.6 Hz, 1H), 3.40-3.34 (m, 1H), 2.71 (s, 3H), 1.91-1.68 (m, 2H), 1.53 (s, 3H), 1.10-0.96 (m, 4H), 0.95-0.86 (m, 4H), 0.72-0.61 (m, 1H), 0.58-0.47 (m, 1H), 0.44-0.33 (m, 2H). [M+H]=329.05.

Example 402. 6-Methyl-4-[(1-methylcyclopropyl)amino]-N-[1-(1-methylcyclopropyl)ethyl]furo[2,3-d]pyrimidine-5-carboxamide

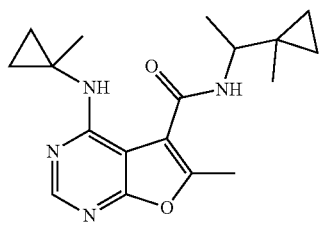 [SMILES: Cc1oc2ncnc(NC3(C)CC3)c2c1C(=O)NC(C)C1(C)CC1]

$^1$H NMR (400 MHz, CD$_3$OD) δ 8.37 (s, 1H), 8.10 (d, J=8.1 Hz, 1H), 3.82-3.69 (m, 1H), 2.70 (s, 3H), 1.51 (s, 3H), 1.28 (d, J=7.0 Hz, 3H), 1.14 (s, 3H), 0.99-0.87 (m, 4H), 0.70-0.62 (m, 1H), 0.55-0.46 (m, 1H), 0.42-0.29 (m, 2H). [M+H]=329.05.

Example 403. 5-{10-Azatricyclo[6.3.1.0$^{2,7}$]dodeca-2,4,6-triene-10-carbonyl}-6-methyl-N-(1-methylcyclopropyl)furo[2,3-d]pyrimidin-4-amine

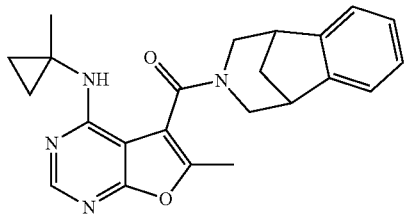 [SMILES: Cc1oc2ncnc(NC3(C)CC3)c2c1C(=O)N1CC2CC(C1)c1ccccc12]

$^1$H NMR (400 MHz, CD$_3$OD) δ 8.31 (s, 1H), 7.52-6.97 (m, 4H), 4.73 (br s, 1H), 3.81 (br s, 2H), 3.16 (br s, 2H), 2.58-2.41 (m, 1H), 2.37 (dd, J=5.1, 10.3 Hz, 2H), 2.14 (d, J=10.5 Hz, 1H), 1.47 (s, 3H), 0.77 (br s, 4H). [M+H]=389.1.

Example 404. 6-Methyl-N-(1-methylcyclopropyl)-5-[4-(propan-2-yl)-1H-pyrazole-1-carbonyl]furo[2,3-d]pyrimidin-4-amine

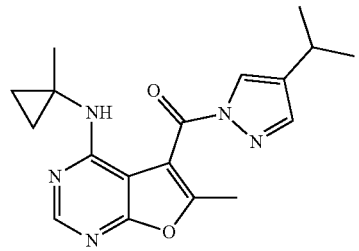 [SMILES: Cc1oc2ncnc(NC3(C)CC3)c2c1C(=O)n1cc(C(C)C)cn1]

$^1$H NMR (400 MHz, CD$_3$OD) δ 8.40 (s, 1H), 8.27 (s, 1H), 7.84 (s, 1H), 3.01-2.91 (m, 1H), 2.49 (s, 3H), 1.52-1.47 (m, 3H), 1.31 (d, J=6.8 Hz, 6H), 0.88-0.80 (m, 4H). [M+H]=340.06.

Example 405. 6-Methyl-N-(1-methylcyclopropyl)-5-(4-phenyl-1H-pyrazole-1-carbonyl)furo[2,3-d]pyrimidin-4-amine

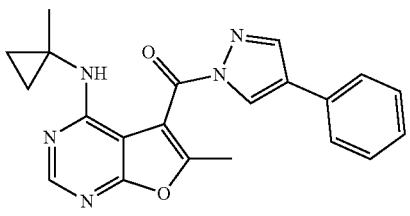 [SMILES: Cc1oc2ncnc(NC3(C)CC3)c2c1C(=O)n1cc(-c2ccccc2)cn1]

$^1$H NMR (400 MHz, CD$_3$OD) δ 8.85 (s, 1H), 8.42 (s, 1H), 8.31 (s, 1H), 7.73 (d, J=7.6 Hz, 2H), 7.50-7.40 (m, 2H), 7.38-7.33 (m, 1H), 2.55 (s, 3H), 1.50 (s, 3H), 0.91-0.79 (m, 4H).

[M+H]=374.05.

Example 406. 5-[4-(4-Methoxyphenyl)-1H-pyra-zole-1-carbonyl]-6-methyl-N-(1-methylcyclopropyl)furo[2,3-d]pyrimidin-4-amine

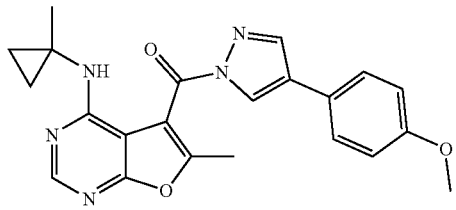 [SMILES: COc1ccc(-c2cnn(C(=O)c3c(C)oc4ncnc(NC5(C)CC5)c34)c2)cc1]

¹H NMR (400 MHz, CD₃OD) δ 8.73 (s, 1H), 8.42 (s, 1H), 8.24 (s, 1H), 7.64 (d, J=8.7 Hz, 2H), 7.00 (d, J=8.8 Hz, 2H), 3.83 (s, 3H), 2.54 (s, 3H), 1.50 (s, 3H), 0.92-0.79 (m, 4H). [M+H]=404.06.

Example 407. 5-[4-(4-Fluorophenyl)-1H-pyrazole-1-carbonyl]-6-methyl-N-(1-methylcyclopropyl)furo[2,3-d]pyrimidin-4-amine

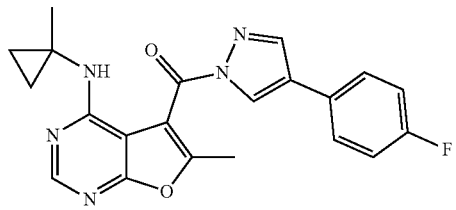 [SMILES: Cc1oc2ncnc(NC3(C)CC3)c2c1C(=O)n1cc(-c2ccc(F)cc2)cn1]

¹H NMR (400 MHz, CD₃OD) δ 8.56 (d, J=2.9 Hz, 1H), 8.45 (s, 1H), 7.95-7.88 (m, 2H), 7.23-7.15 (m, 2H), 7.13 (d, J=2.9 Hz, 1H), 2.60 (s, 3H), 1.44 (s, 3H), 0.84-0.75 (m, 4H). [M+H]=392.05.

Example 408. 6-Methyl-5-(4-methyl-1H-pyrazole-1-carbonyl)-N-(1-methylcyclopropyl)furo[2,3-d]pyrimidin-4-amine

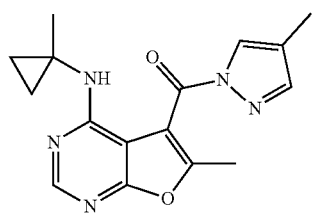 [SMILES: Cc1cnn(C(=O)c2c(C)oc3ncnc(NC4(C)CC4)c23)c1]

¹H NMR (400 MHz, CD₃OD) δ 8.41 (s, 1H), 8.25 (s, 1H), 7.75 (s, 1H), 2.49 (s, 3H), 2.18 (s, 3H), 1.49 (s, 3H), 0.91-0.82 (m, 4H). [M+H]=312.03.

Example 409. 6-Methyl-N-(1-methylcyclopropyl)-5-(trimethyl-1H-pyrazole-1-carbonyl)furo[2,3-d]pyrimidin-4-amine

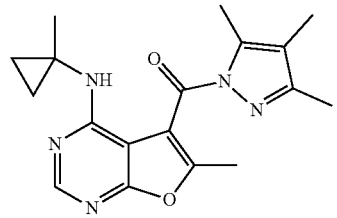 [SMILES: Cc1nn(C(=O)c2c(C)oc3ncnc(NC4(C)CC4)c23)c(C)c1C]

¹H NMR (400 MHz, CD₃OD) δ 8.39 (s, 1H), 2.56 (s, 3H), 2.39 (s, 3H), 2.19 (s, 3H), 2.02 (s, 3H), 1.49 (s, 3H), 0.83 (s, 4H). [M+H]=340.06.

Example 410. 6-Methyl-N-(1-methylcyclopropyl)-5-(1H-pyrazole-1-carbonyl)furo[2,3-d]pyrimidin-4-amine

¹H NMR (400 MHz, CD₃OD) δ 8.54 (d, J=2.9 Hz, 1H), 8.44 (s, 1H), 7.91 (d, J=1.2 Hz, 1H), 6.72 (dd, J=1.5, 2.8 Hz, 1H), 2.51 (s, 3H), 1.51 (s, 3H), 0.91-0.83 (m, 4H). [M+H]=298.05.

Example 411. 5-(3,5-Dimethyl-1H-pyrazole-1-carbonyl)-6-methyl-N-(1-methylcyclopropyl)furo[2,3-d]pyrimidin-4-amine

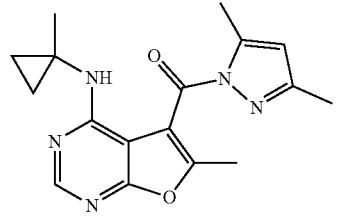 [SMILES: Cc1cc(C)n(C(=O)c2c(C)oc3ncnc(NC4(C)CC4)c23)n1]

¹H NMR (400 MHz, CD₃OD) δ 8.41 (s, 1H), 6.27 (s, 1H), 2.63 (s, 3H), 2.42-2.40 (m, 3H), 2.26-2.17 (m, 3H), 1.49 (s, 3H), 0.85 (s, 4H). [M+H]=326.05.

Example 412. 5-[4-(3-Methoxyphenyl)-1H-pyrazole-1-carbonyl]-6-methyl-N-(1-methylcyclopropyl)furo[2,3-d]pyrimidin-4-amine

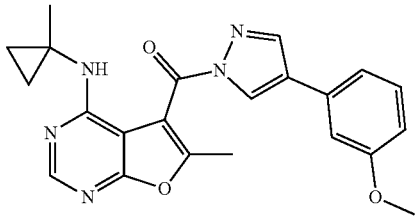 [SMILES: COc1cccc(-c2cnn(C(=O)c3c(C)oc4ncnc(NC5(C)CC5)c34)c2)c1]

$^1$H NMR (400 MHz, CD$_3$OD) δ 8.83 (s, 1H), 8.40 (s, 1H), 8.29 (s, 1H), 7.38-7.31 (m, 1H), 7.31-7.24 (m, 2H), 6.92 (dd, J=1.9, 8.0 Hz, 1H), 3.86 (s, 3H), 2.53 (s, 3H), 1.50 (s, 3H), 0.92-0.76 (m, 4H). [M+H]=404.05.

Example 413. 6-Methyl-4-[(1-methylcyclopropyl)amino]-N-[(1-methylcyclopropyl)methyl]furo[2,3-d]pyrimidine-5-carboxamide

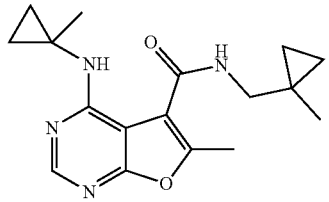 [SMILES: Cc1oc2ncnc(NC3(C)CC3)c2c1C(=O)NCC1(C)CC1]

$^1$H NMR (400 MHz, CD$_3$OD) δ 8.41 (s, 1H), 8.31 (br s, 1H), 2.74 (s, 3H), 1.52 (s, 3H), 1.16 (s, 4H), 1.05-0.93 (m, 5H), 0.58-0.54 (m, 2H), 0.41-0.36 (m, 2H). [M+H]=315.07.

Example 414. 5-{3-[(4-Fluorophenyl)methyl]pyrrolidine-1-carbonyl}-6-methyl-N-(1-methylcyclopropyl)furo[2,3-d]pyrimidin-4-amine

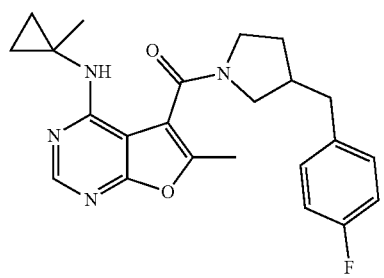

$^1$H NMR (400 MHz, CD$_3$OD) δ 8.42-8.37 (m, 1H), 7.38-7.12 (m, 2H), 7.10-6.89 (m, 2H), 3.89-3.52 (m, 3H), 3.47-3.34 (m, 1H), 3.47-3.34 (m, 1H), 2.93-2.58 (m, 3H), 2.54 (d, J=5.3 Hz, 3H), 2.20-1.96 (m, 1H), 1.75 (dd, J=9.7, 16.8 Hz, 1H), 1.52 (s, 3H), 1.01-0.82 (m, 4H). [M+H]=409.10.

Example 415. 5-[3,5-Dimethyl-4-(morpholin-4-ylmethyl)-1H-pyrazole-1-carbonyl]-6-methyl-N-(1-methylcyclopropyl)furo[2,3-d]pyrimidin-4-amine

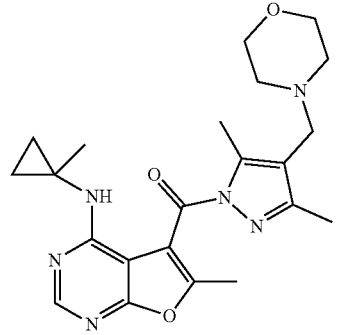 [SMILES: Cc1nn(C(=O)c2c(C)oc3ncnc(NC4(C)CC4)c23)c(C)c1CN1CCOCC1]

$^1$H NMR (400 MHz, CD$_3$OD) δ 8.38 (s, 2H), 4.34 (s, 3H), 2.74 (s, 4H), 2.38 (s, 4H), 2.35 (s, 4H), 1.50 (s, 4H), 0.81 (s, 6H). [M+H]=425.13.

Example 416. 6-Methyl-N-(1-methyl-1H-pyrazol-3-yl)-4-[(1-methylcyclopropyl)amino]furo[2,3-d]pyrimidine-5-carboxamide

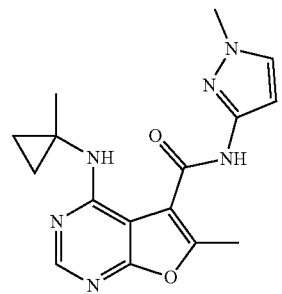 [SMILES: Cc1oc2ncnc(NC3(C)CC3)c2c1C(=O)Nc1ccn(C)n1]

$^1$H NMR (400 MHz, CD$_3$OD) δ 8.40 (s, 1H), 7.55 (d, J=2.3 Hz, 1H), 6.62 (d, J=2.3 Hz, 1H), 3.86 (s, 3H), 2.76 (s, 3H), 1.53 (s, 3H), 1.01-0.87 (m, 4H). [M+H]=326.99.

Example 417. N-(1,5-Dimethyl-1H-pyrazol-4-yl)-6-methyl-4-[(1-methylcyclopropyl)amino]furo[2,3-d]pyrimidine-5-carboxamide

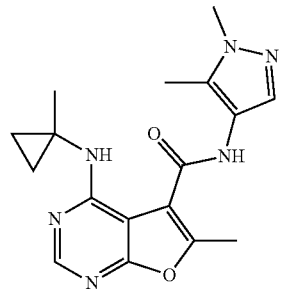 [SMILES: Cc1oc2ncnc(NC3(C)CC3)c2c1C(=O)Nc1cnn(C)c1C]

$^1$H NMR (400 MHz, CD$_3$OD) δ 8.44 (s, 1H), 7.62 (s, 1H), 3.82 (s, 3H), 2.82 (s, 3H), 2.29 (s, 3H), 1.52 (s, 3H), 1.02-0.92 (m, 4H). [M+H]=341.00.

Example 418. 6-Methyl-4-[(1-methylcyclopropyl)amino]-N-(trimethyl-1H-pyrazol-4-yl)furo[2,3-d]pyrimidine-5-carboxamide

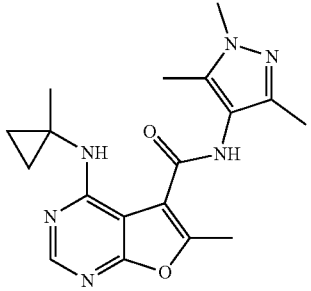 [SMILES: Cc1nn(C)c(C)c1NC(=O)c1c(C)oc2ncnc(NC3(C)CC3)c12]

$^1$H NMR (400 MHz, CD$_3$OD) δ 8.45 (s, 1H), 3.78 (s, 3H), 2.85 (s, 3H), 2.24 (s, 3H), 2.17 (s, 3H), 1.52 (s, 3H), 1.01-0.92 (m, 4H). [M+H]=355.07.

Example 419. 6-Methyl-4-[(1-methylcyclopropyl)amino]-N-[1-(pyridin-2-yl)-1H-pyrazol-4-yl]furo[2,3-d]pyrimidine-5-carboxamide

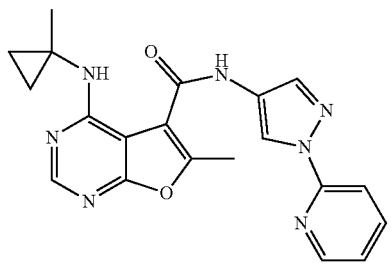 [SMILES: Cc1oc2ncnc(NC3(C)CC3)c2c1C(=O)Nc1cnn(-c2ccccn2)c1]

$^1$H NMR (400 MHz, CD$_3$OD) δ 9.01 (s, 1H), 8.46 (d, J=4.3 Hz, 1H), 8.40 (s, 1H), 8.03-7.92 (m, 3H), 7.32 (ddd, J=1.5, 5.1, 6.8 Hz, 1H), 2.79 (s, 3H), 1.54 (s, 3H), 1.01-0.86 (m, 4H).
[M+H]=390.28.

Example 420. N-[1-(2-Methoxyethyl)-3,5-dimethyl-1H-pyrazol-4-yl]-6-methyl-4-[(1-methylcyclopropyl)amino]furo[2,3-d]pyrimidine-5-carboxamide

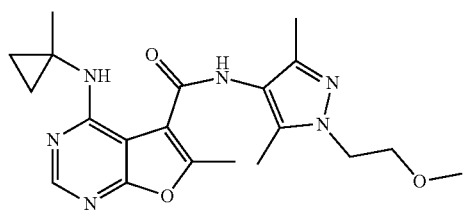 [SMILES: COCCn1nc(C)c(NC(=O)c2c(C)oc3ncnc(NC4(C)CC4)c23)c1C]

$^1$H NMR (400 MHz, CD$_3$OD) δ 8.41 (s, 1H), 4.22 (t, J=5.2 Hz, 2H), 3.72 (t, J=5.2 Hz, 2H), 3.31 (s, 3H), 2.83 (s, 3H), 2.25 (s, 3H), 2.18 (s, 3H), 1.51 (s, 3H), 0.99-0.86 (m, 4H).
[M+H]=399.02.

Example 421. 6-Methyl-4-[(1-methylcyclopropyl)amino]-N-{1-[2-(morpholin-4-yl)ethyl]-1H-pyrazol-4-yl}furo[2,3-d]pyrimidine-5-carboxamide

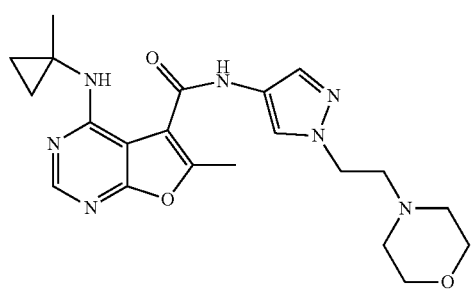 [SMILES: Cc1oc2ncnc(NC3(C)CC3)c2c1C(=O)Nc1cnn(CCN2CCOCC2)c1]

$^1$H NMR (400 MHz, CD$_3$OD) δ 8.35 (s, 1H), 8.27 (s, 1H), 7.74 (s, 1H), 4.64 (t, J=5.9 Hz, 2H), 3.93 (br s, 4H), 3.73 (t, J=6.0 Hz, 2H), 3.60-3.33 (m, 4H), 2.72 (s, 3H), 1.51 (s, 3H), 0.91-0.81 (m, 4H). [M+H]=426.23.

Example 422. 5-[4-(6-Methoxypyridin-2-yl)piperidine-1-carbonyl]-6-methyl-N-(1-methylcyclopropyl)furo[2,3-d]pyrimidin-4-amine

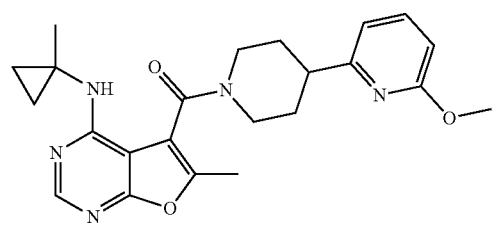 [SMILES: COc1cccc(C2CCN(C(=O)c3c(C)oc4ncnc(NC5(C)CC5)c34)CC2)n1]

$^1$H NMR (400 MHz, CD$_3$OD) δ 8.41 (s, 1H), 7.68-7.60 (m, 1H), 6.88 (d, J=7.2 Hz, 1H), 6.67 (d, J=8.2 Hz, 1H), 4.79-3.97 (m, 1H), 3.92 (s, 3H), 3.33 (td, J=1.6, 3.2 Hz, 13H), 3.09-2.95 (m, 1H), 2.58 (s, 3H), 2.03 (br s, 2H), 1.87 (br s, 2H), 1.54 (s, 3H), 1.06-0.82 (m, 4H). [M+H]=422.2.

Example 423. 5-[4-(5-Methoxy-4-methylpyrimidin-2-yl)piperidine-1-carbonyl]-6-methyl-N-(1-methylcyclopropyl)furo[2,3-d]pyrimidin-4-amine

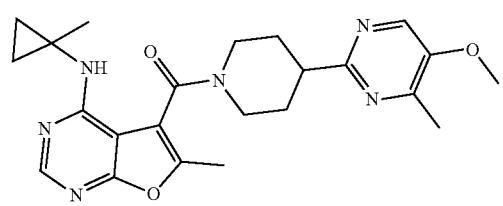 [SMILES: COc1cnc(C2CCN(C(=O)c3c(C)oc4ncnc(NC5(C)CC5)c34)CC2)nc1C]

$^1$H NMR (400 MHz, CD$_3$OD) δ 8.40 (s, 1H), 8.29 (s, 1H), 4.01-3.92 (m, 3H), 3.16 (tt, J=3.7, 11.5 Hz, 1H), 2.57 (s, 3H), 2.46 (s, 3H), 2.15-1.79 (m, 4H), 1.55 (s, 3H), 1.02-0.83 (m, 4H). [M+H]=436.95.

Example 424. 2-(4-Fluorophenyl)-7-{6-methyl-4-[(1-methylcyclopropyl)amino]furo[2,3-d]pyrimidine-5-carbonyl}-3H,4H,5H,6H,7H,8H-pyrido[3,4-d]pyrimidin-4-one

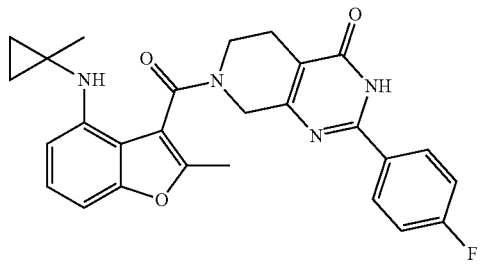 [SMILES: Cc1oc2cccc(NC3(C)CC3)c2c1C(=O)N1CCc2c(nc(-c3ccc(F)cc3)[nH]c2=O)C1]

¹H NMR (400 MHz, CD₃OD) δ 8.40 (s, 1H), 8.06 (br s, 2H), 7.27 (t, J=8.7 Hz, 2H), 4.70 (br s, 2H), 4.17-3.71 (m, 2H), 2.73 (br s, 2H), 2.60 (s, 3H), 1.49 (s, 3H), 0.95-0.82 (m, 4H). [M+H]=474.97.

Example 425. 2-(Methoxymethyl)-7-{6-methyl-4-[(1-methylcyclopropyl)amino]furo[2,3-d]pyrimidine-5-carbonyl}-3H,4H,5H,6H,7H,8H-pyrido[3,4-d]pyrimidin-4-one

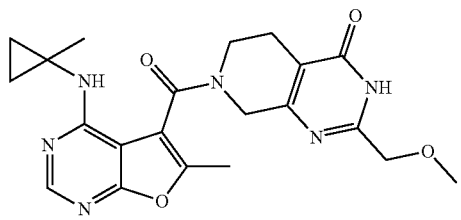 [SMILES: COCc1nc2c(c(=O)[nH]1)CCN(C(=O)c1c(C)oc3ncnc(NC4(C)CC4)c13)C2]

¹H NMR (400 MHz, CD₃OD) δ 8.40 (s, 1H), 4.61 (br s, 2H), 4.35 (s, 2H), 3.90 (br s, 2H), 3.45 (s, 3H), 2.67 (br s, 2H), 2.57 (s, 3H), 1.48 (s, 3H), 0.94-0.82 (m, 4H). [M+H]=425.30.

Example 426. 6-Methyl-4-[(1-methylcyclopropyl)amino]-N-(6-methylpyridin-2-yl)furo[2,3-d]pyrimidine-5-carboxamide

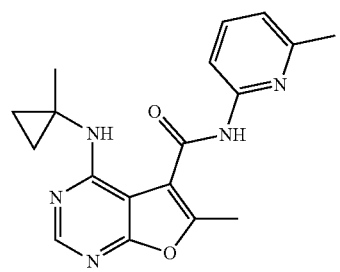 [SMILES: Cc1cccc(NC(=O)c2c(C)oc3ncnc(NC4(C)CC4)c23)n1]

¹H NMR (400 MHz, CD₃OD) δ 8.43 (s, 1H), 7.93-7.82 (m, 2H), 7.19 (d, J=7.6 Hz, 1H), 2.84 (s, 3H), 2.57 (s, 3H), 1.54 (s, 3H), 1.03-0.92 (m, 4H). [M+H]=338.31.

Example 427. 6-Methyl-4-[(1-methylcyclopropyl)amino]-N-(4-methylpyridin-2-yl)furo[2,3-d]pyrimidine-5-carboxamide

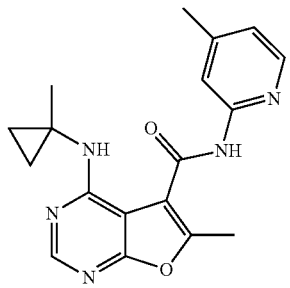 [SMILES: Cc1ccnc(NC(=O)c2c(C)oc3ncnc(NC4(C)CC4)c23)c1]

¹H NMR (400 MHz, CD₃OD) δ 8.43 (s, 1H), 8.28 (d, J=6.0 Hz, 1H), 7.66 (s, 1H), 7.36 (d, J=5.7 Hz, 1H), 2.82 (s, 3H), 2.57 (s, 3H), 1.53 (s, 3H), 1.02-0.89 (m, 4H). [M+H]=338.34.

Example 428. 6-Methyl-4-[(1-methylcyclopropyl)amino]-N-(3-methylpyridin-2-yl)furo[2,3-d]pyrimidine-5-carboxamide

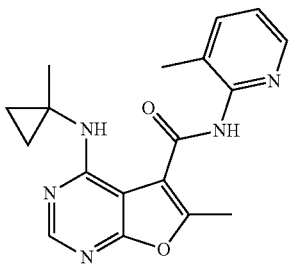 [SMILES: Cc1cccnc1NC(=O)c1c(C)oc2ncnc(NC3(C)CC3)c12]

¹H NMR (400 MHz, CD₃OD) δ 8.43 (s, 1H), 8.22 (d, J=5.3 Hz, 1H), 8.01 (d, J=7.3 Hz, 1H), 7.36-7.30 (m, 1H), 2.91 (s, 3H), 2.45 (s, 3H), 1.54 (s, 3H), 1.05-0.93 (m, 4H). [M+H]=338.32.

Example 429. N-[1-(2-Methoxyethyl)-1H-pyrazol-4-yl]-6-methyl-4-[(1-methylcyclopropyl)amino]furo[2,3-d]pyrimidine-5-carboxamide

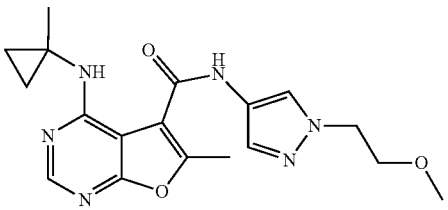 [SMILES: COCCn1cc(NC(=O)c2c(C)oc3ncnc(NC4(C)CC4)c23)cn1]

¹H NMR (400 MHz, CD₃OD) δ 8.49 (s, 1H), 8.11 (s, 1H), 7.72 (s, 1H), 4.35-4.29 (m, 2H), 3.75 (t, J=5.1 Hz, 2H), 3.34 (s, 3H), 2.80 (s, 3H), 1.55 (s, 3H), 1.12-1.01 (m, 4H). [M+H]=371.36.

Example 430. N-{Bicyclo[1.1.1]pentan-1-yl}-6-methyl-4-[(1-methylcyclopropyl)amino]furo[2,3-d]pyrimidine-5-carboxamide

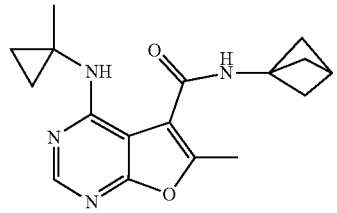 [SMILES: Cc1oc2ncnc(NC3(C)CC3)c2c1C(=O)NC12CC(C1)C2]

¹H NMR (400 MHz, CD₃OD) δ 8.38 (s, 1H), 2.67 (s, 3H), 2.53 (s, 1H), 2.23 (s, 6H), 1.54 (s, 3H), 1.02-0.86 (m, 4H). [M+H]=313.2.

Example 431. 6-Methyl-N-(1-methylcyclopropyl)-5-{4-[5-(trifluoromethyl)pyrimidin-2-yl]piperidine-1-carbonyl}furo[2,3-d]pyrimidin-4-amine

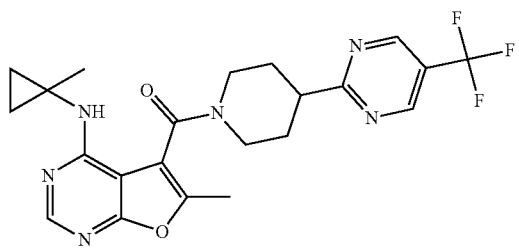 [SMILES: Cc1oc2ncnc(NC3(C)CC3)c2c1C(=O)N1CCC(c2ncc(C(F)(F)F)cn2)CC1]

¹H NMR (400 MHz, CD₃OD) δ 9.09 (s, 2H), 8.40 (s, 1H), 4.72-3.86 (m, 2H), 3.56-3.34 (m, 3H), 2.57 (s, 3H), 2.18 (br s, 2H), 2.09-1.82 (m, 2H), 1.54 (s, 3H), 1.00-0.86 (m, 4H). [M+H]=461.39.

Example 432. N-(1,4-Dimethyl-1H-pyrazol-3-yl)-6-methyl-4-[(1-methylcyclopropyl)amino]furo[2,3-d]pyrimidine-5-carboxamide

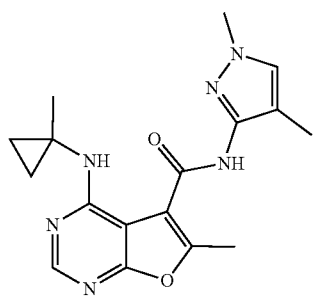 [SMILES: Cc1cn(C)nc1NC(=O)c1c(C)oc2ncnc(NC3(C)CC3)c12]

¹H NMR (400 MHz, CD₃OD) δ 8.39 (s, 1H), 7.43 (s, 1H), 3.84 (s, 3H), 2.79 (s, 3H), 2.01 (s, 3H), 1.51 (s, 3H), 0.98-0.85 (m, 4H). [M+H]=341.34.

Example 433. N-(Dimethyl-1,3-thiazol-2-yl)-6-methyl-4-[(1-methylcyclopropyl)amino]furo[2,3-d]pyrimidine-5-carboxamide

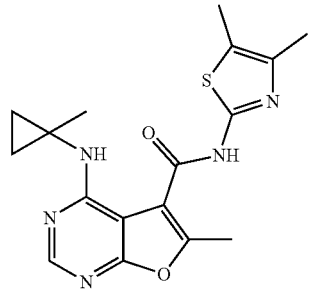 [SMILES: Cc1nc(NC(=O)c2c(C)oc3ncnc(NC4(C)CC4)c23)sc1C]

¹H NMR (400 MHz, CD₃OD) δ 8.35 (s, 1H), 2.94 (s, 3H), 2.26 (s, 3H), 2.24 (s, 3H), 1.57 (s, 3H), 1.05-1.00 (m, 2H), 0.99-0.95 (m, 2H). [M+H]=358.31.

Example 434. 6-Methyl-4-[(1-methylcyclopropyl)amino]-N-(6-methylpyridazin-3-yl)furo[2,3-d]pyrimidine-5-carboxamide

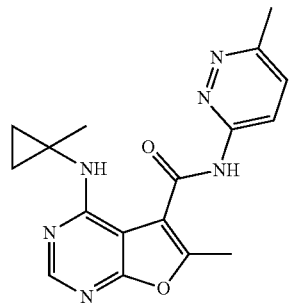 [SMILES: Cc1ccc(NC(=O)c2c(C)oc3ncnc(NC4(C)CC4)c23)nn1]

¹H NMR (400 MHz, CD₃OD) δ 8.51 (d, J=8.7 Hz, 1H), 8.42 (s, 1H), 7.94-7.88 (m, 1H), 2.82 (s, 3H), 2.73 (s, 3H), 1.53 (s, 3H), 1.01-0.88 (m, 4H). [M+H]=339.33.

Example 435. 6-Methyl-N-(1-methyl-1H-imidazol-4-yl)-4-[(1-methylcyclopropyl)amino]furo[2,3-d]pyrimidine-5-carboxamide

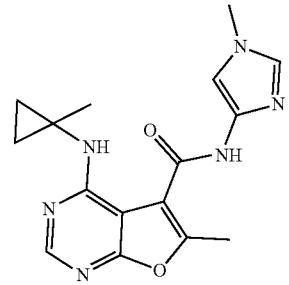 [SMILES: Cc1oc2ncnc(NC3(C)CC3)c2c1C(=O)Nc1cn(C)cn1]

¹H NMR (400 MHz, CD₃OD) δ 8.47 (s, 1H), 8.35 (s, 1H), 7.60 (d, J=1.6 Hz, 1H), 3.92 (s, 3H), 2.77 (s, 3H), 1.50 (s, 3H), 0.92-0.79 (m, 4H). [M+H]=327.33.

Example 436. N-(5-Fluoro-6-methylpyridin-2-yl)-6-methyl-4-[(1-methylcyclopropyl)amino]furo[2,3-d]pyrimidine-5-carboxamide

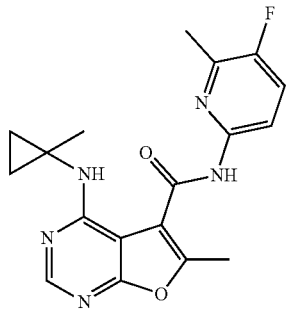 [SMILES: Cc1nc(NC(=O)c2c(C)oc3ncnc(NC4(C)CC4)c23)ccc1F]

¹H NMR (400 MHz, CD₃OD) δ 8.40 (s, 1H), 8.04 (dd, J=3.3, 8.9 Hz, 1H), 7.57 (t, J=8.9 Hz, 1H), 2.79 (s, 3H), 2.47 (d, J=2.8 Hz, 3H), 1.52 (s, 3H), 0.99-0.86 (m, 4H). [M+H]=356.33.

Example 437. 6-Methyl-4-[(1-methylcyclopropyl)amino]-N-(6-methylpyrazin-2-yl)furo[2,3-d]pyrimidine-5-carboxamide

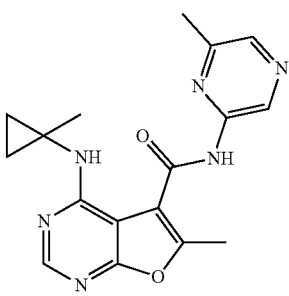 [SMILES: Cc1cncc(NC(=O)c2c(C)oc3ncnc(NC4(C)CC4)c23)n1]

¹H NMR (400 MHz, CD₃OD) δ 9.23 (s, 1H), 8.42 (s, 1H), 8.31 (s, 1H), 2.79 (s, 3H), 2.54 (s, 3H), 1.53 (s, 3H), 1.04-0.87 (m, 4H). [M+H]=339.34.

Example 438. 6-Methyl-4-[(1-methylcyclopropyl)amino]-N-(5-methylpyridin-2-yl)furo[2,3-d]pyrimidine-5-carboxamide

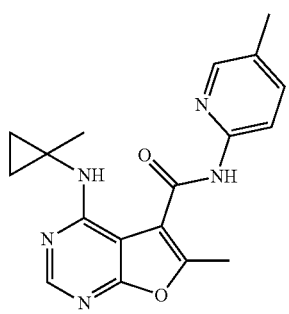 [SMILES: Cc1ccc(NC(=O)c2c(C)oc3ncnc(NC4(C)CC4)c23)nc1]

¹H NMR (400 MHz, CD₃OD) δ 8.41 (s, 1H), 8.24 (s, 1H), 7.94-7.87 (m, 2H), 2.81 (s, 3H), 2.40 (s, 3H), 1.53 (s, 3H), 1.01-0.88 (m, 4H). [M+H]=338.32.

Example 439. N-(1,5-Dimethyl-1H-pyrazol-3-yl)-6-methyl-4-[(1-methylcyclopropyl)amino]furo[2,3-d]pyrimidine-5-carboxamide

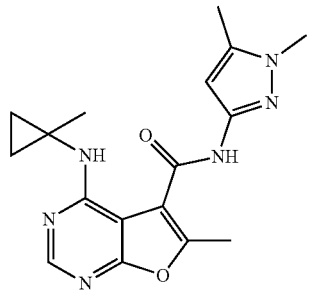 [SMILES: Cc1oc2ncnc(NC3(C)CC3)c2c1C(=O)Nc1cc(C)n(C)n1]

¹H NMR (400 MHz, CD₃OD) δ 8.37 (s, 1H), 6.43 (s, 1H), 3.74 (s, 3H), 2.75 (s, 3H), 2.32 (s, 3H), 1.52 (s, 3H), 0.98-0.85 (m, 4H). [M+H]=341.20.

Example 440. N-[1-(2-Methoxyethyl)-1H-pyrazol-3-yl]-6-methyl-4-[(1-methylcyclopropyl)amino]furo[2,3-d]pyrimidine-5-carboxamide

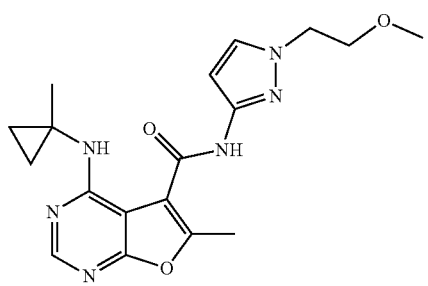 [SMILES: COCCn1ccc(NC(=O)c2c(C)oc3ncnc(NC4(C)CC4)c23)n1]

¹H NMR (400 MHz, CD₃OD) δ 8.45 (s, 1H), 7.62 (d, J=2.4 Hz, 1H), 6.65 (d, J=2.2 Hz, 1H), 4.27 (t, J=5.2 Hz, 2H), 3.76 (t, J=5.2 Hz, 2H), 3.35 (s, 3H), 2.80 (s, 3H), 1.55 (s, 3H), 1.07-0.93 (m, 4H). [M+H]=371.37.

Example 441. N-(5,6-Dimethylpyrazin-2-yl)-6-methyl-4-[(1-methylcyclopropyl)amino]furo[2,3-d]pyrimidine-5-carboxamide

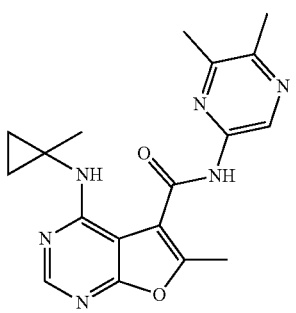 [SMILES: Cc1ncc(NC(=O)c2c(C)oc3ncnc(NC4(C)CC4)c23)nc1C]

¹H NMR (400 MHz, CD₃OD) δ 9.10 (s, 1H), 8.41 (s, 1H), 2.79 (s, 3H), 2.54 (d, J=5.5 Hz, 6H), 1.53 (s, 3H), 1.00-0.88 (m, 4H). [M+H]=353.35.

Example 442. N-(Dimethyl-1,3-oxazol-2-yl)-6-methyl-4-[(1-methylcyclopropyl)amino]furo[2,3-d]pyrimidine-5-carboxamide

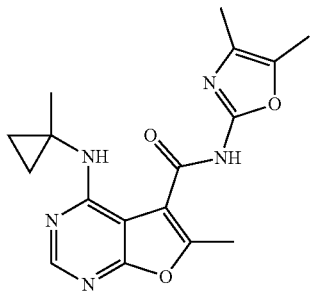 [SMILES: Cc1nc(NC(=O)c2c(C)oc3ncnc(NC4(C)CC4)c23)oc1C]

$^1$H NMR (400 MHz, CD$_3$OD) δ 8.36 (s, 1H), 2.88 (s, 3H), 2.25 (s, 3H), 2.14 (s, 3H), 1.55 (s, 3H), 1.12-0.95 (m, 4H). [M+H]=342.32.

Example 443. 6-Methyl-N-(4-methyl-1,3-thiazol-2-yl)-4-[(1-methylcyclopropyl)amino]furo[2,3-d]pyrimidine-5-carboxamide

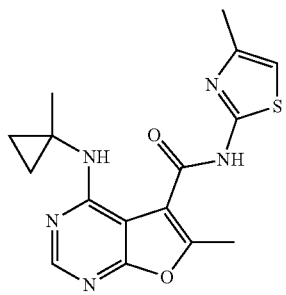 [SMILES: Cc1csc(NC(=O)c2c(C)oc3ncnc(NC4(C)CC4)c23)n1]

$^1$H NMR (400 MHz, CD$_3$OD) δ 8.37 (s, 1H), 6.61 (d, J=1.0 Hz, 1H), 2.95 (s, 3H), 2.33 (s, 3H), 1.57 (s, 3H), 1.07-0.95 (m, 4H). [M+H]=344.29.

Example 444. 4-(6-Fluoropyridin-2-yl)-1-{6-methyl-4-[(1-methylcyclopropyl)amino]furo[2,3-d]pyrimidine-5-carbonyl}piperidine-4-carbonitrile

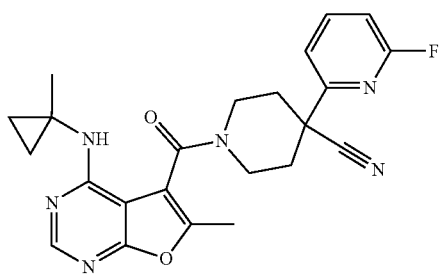 [SMILES: Cc1oc2ncnc(NC3(C)CC3)c2c1C(=O)N1CCC(C#N)(c2cccc(F)n2)CC1]

$^1$H NMR (400 MHz, CD$_3$OD) δ 8.39 (s, 1H), 8.06 (q, J=8.0 Hz, 1H), 7.64 (dd, J=2.2, 7.5 Hz, 1H), 7.10 (dd, J=2.7, 8.2 Hz, 1H), 4.35 (br s, 2H), 3.50 (br s, 2H), 2.59 (s, 3H), 2.28 (br s, 4H), 1.54 (s, 3H), 1.02-0.79 (m, 4H). [M+H]=435.4.

Example 445. 6-Methyl-4-[(1-methylcyclopropyl)amino]-N-[1-(propan-2-yl)-1H-pyrazol-3-yl]furo[2,3-d]pyrimidine-5-carboxamide

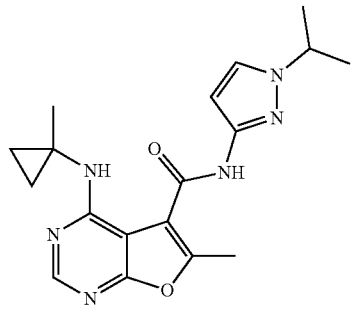 [SMILES: Cc1oc2ncnc(NC3(C)CC3)c2c1C(=O)Nc1ccn(C(C)C)n1]

$^1$H NMR (400 MHz, CD$_3$OD) δ 8.38 (s, 1H), 7.62 (d, J=2.3 Hz, 1H), 6.62 (d, J=2.2 Hz, 1H), 4.47 (spt, J=6.6 Hz, 1H), 2.77 (s, 3H), 1.52 (s, 3H), 1.50 (d, J=6.7 Hz, 6H), 1.00-0.84 (m, 4H). [M+H]=355.38.

Example 446. N-[1-(3-Fluoropyridin-2-yl)-1H-pyrazol-3-yl]-6-methyl-4-[(1-methylcyclopropyl)amino]furo[2,3-d]pyrimidine-5-carboxamide

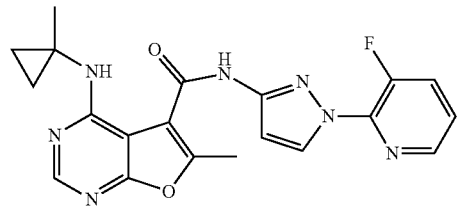 [SMILES: Cc1oc2ncnc(NC3(C)CC3)c2c1C(=O)Nc1ccn(-c2ncccc2F)n1]

$^1$H NMR (400 MHz, CD$_3$OD) δ 8.42 (d, J=2.4 Hz, 1H), 8.40 (s, 1H), 8.35 (d, J=5.0 Hz, 1H), 7.85 (dd, J=8.3, 11.1 Hz, 1H), 7.44 (td, J=4.0, 8.2 Hz, 1H), 7.08 (d, J=2.8 Hz, 1H), 2.80 (s, 3H), 1.54 (s, 3H), 1.00-0.87 (m, 4H). [M+H]=408.36.

Example 447. N-[1-(3-Fluoropyridin-2-yl)-1H-pyrazol-4-yl]-6-methyl-4-[(1-methylcyclopropyl)amino]furo[2,3-d]pyrimidine-5-carboxamide

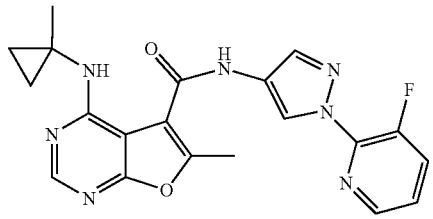 [SMILES: Cc1oc2ncnc(NC3(C)CC3)c2c1C(=O)Nc1cnn(-c2ncccc2F)c1]

$^1$H NMR (400 MHz, CD$_3$OD) δ 8.84 (s, 1H), 8.39 (s, 1H), 8.37 (d, J=4.6 Hz, 1H), 8.05 (s, 1H), 7.92-7.84 (m, 1H), 7.47 (td, J=4.1, 8.2 Hz, 1H), 2.79 (s, 3H), 1.54 (s, 3H), 1.00-0.87 (m, 4H). [M+H]=408.36.

Example 448. 6-Methyl-N-[(5-methyl-1,3-oxazol-2-yl)methyl]-4-[(1-methylcyclopropyl)amino]furo[2,3-d]pyrimidine-5-carboxamide

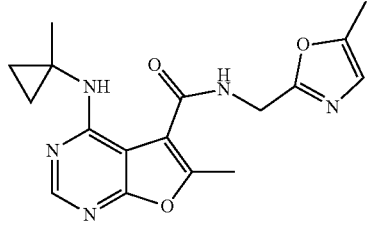 [SMILES: Cc1cnc(CNC(=O)c2c(C)oc3ncnc(NC4(C)CC4)c23)o1]

$^1$H NMR (400 MHz, CD$_3$OD) δ 8.39 (s, 1H), 6.79 (d, J=1.2 Hz, 1H), 4.69 (s, 2H), 2.75 (s, 3H), 2.35 (d, J=1.1 Hz, 3H), 1.53 (s, 3H), 1.00-0.81 (m, 4H). [M+H]=342.3.

Example 449. N-[(2-Methoxypyrimidin-4-yl)methyl]-6-methyl-4-[(1-methylcyclopropyl)amino]furo[2,3-d]pyrimidine-5-carboxamide

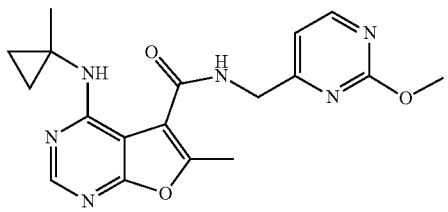 [SMILES: COc1nccc(CNC(=O)c2c(C)oc3ncnc(NC4(C)CC4)c23)n1]

$^1$H NMR (400 MHz, CD$_3$OD) δ 8.54 (d, J=5.0 Hz, 1H), 8.45 (s, 1H), 7.15 (d, J=5.1 Hz, 1H), 4.70 (s, 2H), 4.03 (s, 3H), 2.86 (s, 3H), 1.53 (s, 3H), 1.03-0.89 (m, 4H). [M+H]= 369.4.

Example 450. 6-Methyl-4-[(1-methylcyclopropyl)amino]-N-{[5-(trifluoromethyl)pyridin-2-yl]methyl}furo[2,3-d]pyrimidine-5-carboxamide

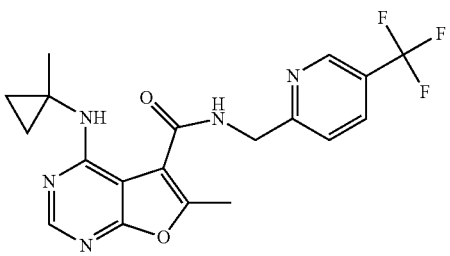 [SMILES: Cc1oc2ncnc(NC3(C)CC3)c2c1C(=O)NCc1ccc(C(F)(F)F)cn1]

$^1$H NMR (400 MHz, CD$_3$OD) δ 8.89 (s, 1H), 8.38 (s, 1H), 8.15 (dd, J=2.1, 8.3 Hz, 1H), 7.67 (d, J=8.2 Hz, 1H), 4.84 (s, 2H), 2.81 (s, 3H), 1.52 (s, 3H), 0.96-0.82 (m, 4H). [M+H]= 406.4.

Example 451. 6-Methyl-N-(4-methyl-1,3-oxazol-2-yl)-4-[(1-methylcyclopropyl)amino]furo[2,3-d]pyrimidine-5-carboxamide

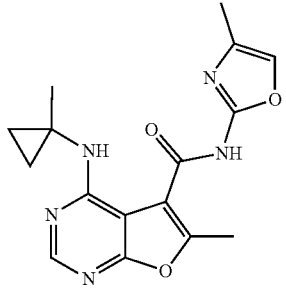 [SMILES: Cc1coc(NC(=O)c2c(C)oc3ncnc(NC4(C)CC4)c23)n1]

$^1$H NMR (400 MHz, CD$_3$OD) δ 8.34 (s, 1H), 7.32 (d, J=1.5 Hz, 1H), 2.87 (s, 3H), 2.21 (d, J=1.2 Hz, 3H), 1.54 (s, 3H), 1.07-1.02 (m, 2H), 0.96-0.92 (m, 2H). [M+H]=328.20.

Example 452. 6-Methyl-N-(3-methyl-1 2 4-oxadiazol-5-yl)-4-[(1-methylcyclopropyl)amino]furo[2,3-d]pyrimidine-5-carboxamide

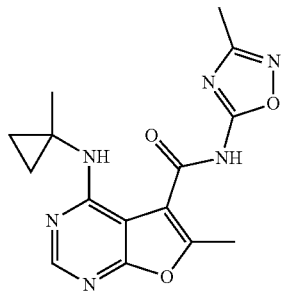 [SMILES: Cc1noc(NC(=O)c2c(C)oc3ncnc(NC4(C)CC4)c23)n1]

$^1$H NMR (400 MHz, CD$_3$OD) δ 8.40 (s, 1H), 2.85 (s, 3H), 2.40 (s, 3H), 1.53 (s, 3H), 1.09-0.90 (m, 4H). [M+H]= 329.30.

Example 453. 6-Methyl-N-(2-methyl-1,3-thiazol-4-yl)-4-[(1-methylcyclopropyl)amino]furo[2,3-d]pyrimidine-5-carboxamide

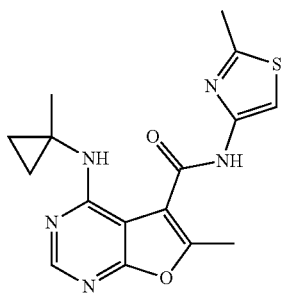 [SMILES: Cc1nc(NC(=O)c2c(C)oc3ncnc(NC4(C)CC4)c23)cs1]

$^1$H NMR (400 MHz, CD$_3$OD) δ 8.42 (s, 1H), 7.64 (s, 1H), 2.80 (s, 3H), 2.70 (s, 3H), 1.55 (s, 3H), 1.03-0.96 (m, 2H), 0.96-0.90 (m, 2H). [M+H]=344.22.

Example 454. 6-Methyl-N-(3-methyl-1,2,4-thiadi-azol-5-yl)-4-[(1-methylcyclopropyl)amino]furo[2,3-d]pyrimidine-5-carboxamide

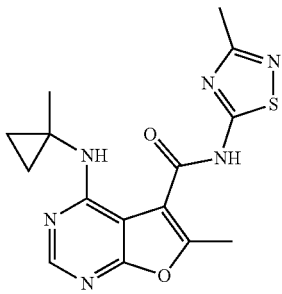 [SMILES: Cc1nsc(NC(=O)c2c(C)oc3ncnc(NC4(C)CC4)c23)n1]

$^1$H NMR (400 MHz, CD$_3$OD) δ 8.39 (s, 1H), 2.90 (s, 3H), 2.53 (s, 3H), 1.56 (s, 3H), 0.97 (d, J=19.4 Hz, 4H). [M+H]= 345.18.

Example 455. 6-Methyl-5-{4-methyl-5H,6H,7H,8H-pyrido[3,4-d]pyrimidine-7-carbonyl}-N-(1-methyl-cyclopropyl)furo[2,3-d]pyrimidin-4-amine

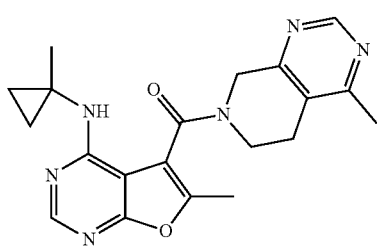 [SMILES: Cc1ncnc2c1CCN(C(=O)c1c(C)oc3ncnc(NC4(C)CC4)c13)C2]

$^1$H NMR (400 MHz, CD$_3$OD) δ 8.82 (s, 1H), 8.41 (s, 1H), 5.03-4.87 (m, 2H), 4.02 (br s, 2H), 3.01-2.92 (m, 2H), 2.59 (s, 3H), 2.54-2.49 (m, 3H), 1.48 (s, 3H), 0.96-0.83 (m, 4H). [M+H]=379.40.

Example 456. 6-Methyl-4-[(1-methylcyclopropyl)amino]-N-[1-(oxan-4-yl)-1H-pyrazol-4-yl]furo[2,3-d]pyrimidine-5-carboxamide

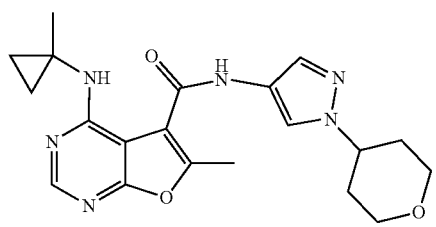 [SMILES: Cc1oc2ncnc(NC3(C)CC3)c2c1C(=O)Nc1cnn(C2CCOCC2)c1]

$^1$H NMR (400 MHz, CD$_3$OD) δ 8.40 (s, 1H), 8.16 (s, 1H), 7.69 (s, 1H), 4.51-4.38 (m, 1H), 4.08 (dd, J=2.6, 10.7 Hz, 2H), 3.59 (dt, J=2.9, 11.5 Hz, 2H), 2.75 (s, 3H), 2.16-2.01 (m, 4H), 1.53 (s, 3H), 1.01-0.88 (m, 4H). [M+H]=397.38.

Example 457. 6-Methyl-4-[(1-methylcyclopropyl)amino]-N-{[5-(trifluoromethyl)-1,2,4-oxadiazol-3-yl]methyl}furo[2,3-d]pyrimidine-5-carboxamide

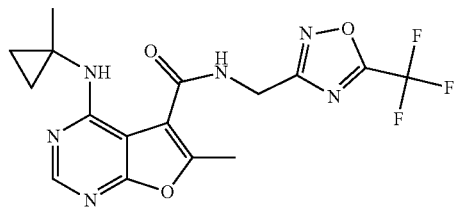 [SMILES: Cc1oc2ncnc(NC3(C)CC3)c2c1C(=O)NCc1noc(C(F)(F)F)n1]

$^1$H NMR (400 MHz, CD$_3$OD) δ 8.37 (s, 1H), 4.88 (s, 2H), 2.76 (s, 3H), 1.52 (s, 3H), 1.05-0.66 (m, 4H). [M+H]=397.3.

Example 458. 6-Methyl-4-[(1-methylcyclopropyl)amino]-N-[(4-methylpyrimidin-2-yl)methyl]furo[2,3-d]pyrimidine-5-carboxamide

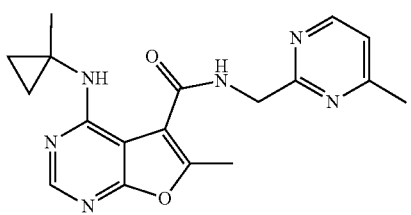 [SMILES: Cc1ccnc(CNC(=O)c2c(C)oc3ncnc(NC4(C)CC4)c23)n1]

$^1$H NMR (400 MHz, CD$_3$OD) δ 8.64 (d, J=5.1 Hz, 1H), 8.46 (s, 1H), 7.33 (d, J=5.3 Hz, 1H), 4.82 (s, 2H), 2.90 (s, 3H), 2.57 (s, 3H), 1.54 (s, 3H), 1.05-0.91 (m, 4H). [M+H]=353.4.

Example 459. N-[(4,6-Dimethylpyrimidin-2-yl)methyl]-6-methyl-4-[(1-methylcyclopropyl)amino]furo[2,3-d]pyrimidine-5-carboxamide

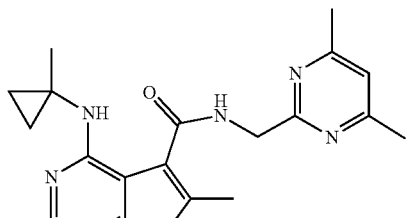

$^1$H NMR (400 MHz, CD$_3$OD) δ 8.43 (s, 1H), 7.23 (s, 1H), 4.78 (s, 2H), 2.92 (s, 3H), 2.52 (s, 6H), 1.53 (s, 3H), 1.04-0.86 (m, 4H). [M+H]=367.4.

Example 460. 6-Methyl-4-[(1-methylcyclopropyl)amino]-N-[(5-methylpyrazin-2-yl)methyl]furo[2,3-d]pyrimidine-5-carboxamide

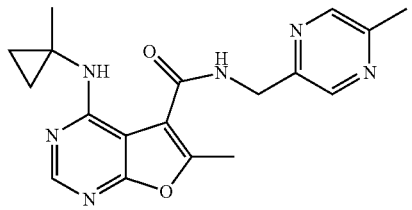 [SMILES: Cc1cnc(CNC(=O)c2c(C)oc3ncnc(NC4(C)CC4)c23)cn1]

$^1$H NMR (400 MHz, CD$_3$OD) δ 8.57 (s, 1H), 8.54 (s, 1H), 8.39 (s, 1H), 4.76 (s, 2H), 2.77 (s, 3H), 2.58 (s, 3H), 1.52 (s, 3H), 1.00-0.79 (m, 4H). [M+H]=353.4.

Example 461. 6-Methyl-N-[(5-methyl-1,2,4-oxadiazol-3-yl)methyl]-4-[(1-methylcyclopropyl)amino]furo[2,3-d]pyrimidine-5-carboxamide

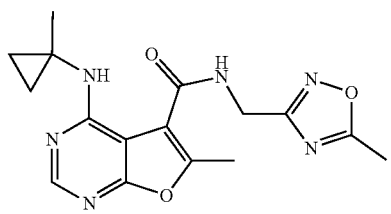 [SMILES: Cc1nc(CNC(=O)c2c(C)oc3ncnc(NC4(C)CC4)c23)no1]

$^1$H NMR (400 MHz, CD$_3$OD) δ 8.45 (s, 1H), 4.73 (s, 2H), 2.80 (s, 3H), 2.62 (s, 3H), 1.54 (s, 3H), 1.09-0.90 (m, 4H). [M+H]=343.3.

Example 462. Methyl 2-(1-{6-methyl-4-[(1-methylcyclopropyl)amino]furo[2,3-d]pyrimidine-5-carbonyl}azetidin-3-yl)pyrimidine-5-carboxylate

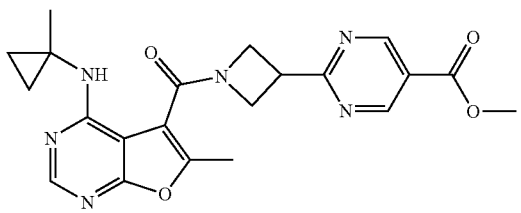 [SMILES: COC(=O)c1cnc(C2CN(C(=O)c3c(C)oc4ncnc(NC5(C)CC5)c34)C2)nc1]

$^1$H NMR (400 MHz, CD$_3$OD) δ 9.29 (s, 2H), 8.39 (s, 1H), 4.74-4.66 (m, 2H), 4.57 (br s, 2H), 4.32 (tt, J=5.8, 8.9 Hz, 1H), 4.00 (s, 3H), 2.65 (s, 3H), 1.55 (s, 3H), 1.02-0.84 (m, 4H).
[M+H]=423.4.

Example 463. 6-Methyl-4-[(1-methylcyclopropyl)amino]-N-{[6-(trifluoromethyl)-[1,2,4]triazolo[4,3-a]pyridin-3-yl]methyl}furo[2,3-d]pyrimidine-5-carboxamide

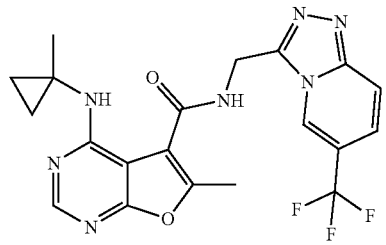 [SMILES: Cc1oc2ncnc(NC3(C)CC3)c2c1C(=O)NCc1nnc2ccc(C(F)(F)F)cn12]

$^1$H NMR (400 MHz, CD$_3$OD) δ 9.34 (s, 1H), 8.38 (s, 1H), 7.96 (d, J=9.7 Hz, 1H), 7.71 (dd, J=1.2, 9.7 Hz, 1H), 5.21 (s, 2H), 2.75 (s, 3H), 1.50 (s, 3H), 0.89 (s, 4H). [M+H]=446.3.

Example 464. N-[(5-Cyclopropyl-1,2,4-oxadiazol-3-yl)methyl]-6-methyl-4-[(1-methylcyclopropyl)amino]furo[2,3-d]pyrimidine-5-carboxamide

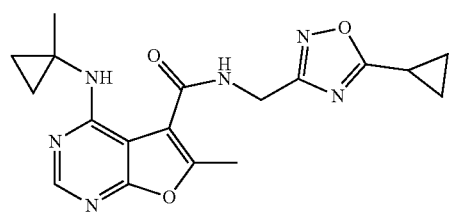 [SMILES: Cc1oc2ncnc(NC3(C)CC3)c2c1C(=O)NCc1noc(C2CC2)n1]

$^1$H NMR (400 MHz, CD$_3$OD) δ 8.38 (s, 1H), 4.68 (s, 2H), 2.76 (s, 3H), 2.30 (tt, J=4.8, 8.3 Hz, 1H), 1.53 (s, 3H), 1.35-1.24 (m, 2H), 1.22-1.13 (m, 2H), 1.01-0.83 (m, 4H). [M+H]=369.4.

Example 465. 6-Methyl-N-(1-methylcyclopropyl)-5-[4-(propan-2-yloxy)-5H,6H,7H,8H-pyrido[3,4-d]pyrimidine-7-carbonyl]furo[2,3-d]pyrimidin-4-amine

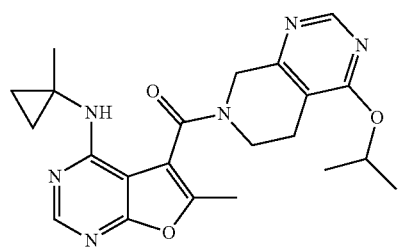 [SMILES: Cc1oc2ncnc(NC3(C)CC3)c2c1C(=O)N1CCc2c(ncnc2OC(C)C)C1]

$^1$H NMR (400 MHz, CD$_3$OD) δ 8.56 (s, 1H), 8.39 (s, 1H), 5.48 (td, J=6.2, 12.4 Hz, 1H), 4.78 (br s, 2H), 4.18-3.60 (m, 2H), 2.79 (br s, 2H), 2.57 (s, 3H), 1.47 (s, 3H), 1.38 (d, J=6.1 Hz, 6H), 0.84 (br s, 4H). [M+H]=423.44.

Example 466. 6-Methyl-4-[(1-methylcyclopropyl)amino]-N-[(4-methylpyridin-2-yl)methyl]furo[2,3-d]pyrimidine-5-carboxamide

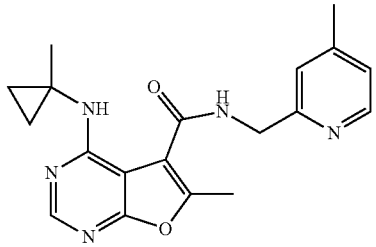 [SMILES: Cc1ccnc(CNC(=O)c2c(C)oc3ncnc(NC4(C)CC4)c23)c1]

$^1$H NMR (400 MHz, CDCl$_3$) δ 8.77 (s, 1H), 8.48 (d, J=5.6 Hz, 1H), 8.44 (s, 1H), 8.38 (br s, 1H), 7.56 (s, 1H), 7.37 (d, J=5.3 Hz, 1H), 4.81 (d, J=5.3 Hz, 2H), 2.76 (s, 3H), 2.57 (s, 3H), 1.52 (s, 3H), 0.90-0.72 (m, 4H). [M+H]=352.4.

Example 467. 6-Methyl-N-[(5-methyl-1,3-thiazol-2-yl)methyl]-4-[(1-methylcyclopropyl)amino]furo[2,3-d]pyrimidine-5-carboxamide

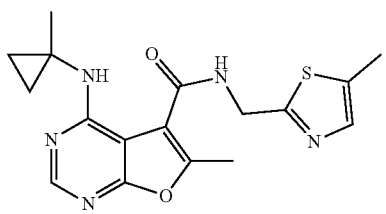 [SMILES: Cc1cnc(CNC(=O)c2c(C)oc3ncnc(NC4(C)CC4)c23)s1]

$^1$H NMR (400 MHz, CDCl$_3$) δ 8.73 (br s, 1H), 8.47 (s, 1H), 7.39 (s, 1H), 7.05 (br s, 1H), 4.89 (d, J=5.1 Hz, 2H), 2.75 (s, 3H), 2.49 (s, 3H), 1.55 (s, 3H), 0.93-0.75 (m, 4H). [M+H]=358.3.

Example 468. 6-Methyl-N-[(5-methyl-1,3,4-thiadiazol-2-yl)methyl]-4-[(1-methylcyclopropyl)amino]furo[2,3-d]pyrimidine-5-carboxamide

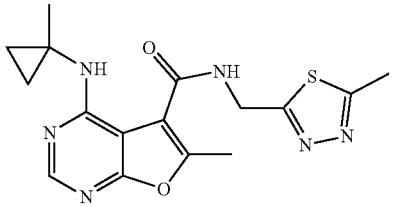 [SMILES: Cc1nnc(CNC(=O)c2c(C)oc3ncnc(NC4(C)CC4)c23)s1]

$^1$H NMR (400 MHz, CD$_3$OD) δ 8.42 (s, 1H), 4.98 (s, 2H), 2.78 (s, 3H), 2.76 (s, 3H), 1.54 (s, 3H), 1.04-0.86 (m, 4H). [M+H]=359.3.

Example 469. N,6-Dimethyl-N-(1-methyl-1H-pyrazol-4-yl)-4-[(1-methylcyclopropyl)amino]furo[2,3-d]pyrimidine-5-carboxamide

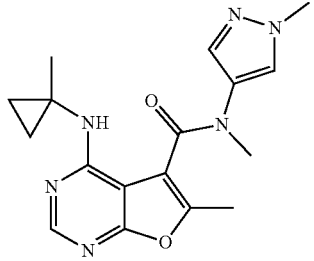 [SMILES: Cc1oc2ncnc(NC3(C)CC3)c2c1C(=O)N(C)c1cnn(C)c1]

$^1$H NMR (400 MHz, CD$_3$OD) δ 8.41 (s, 1H), 7.99-7.11 (m, 2H), 3.84 (s, 3H), 3.47 (s, 3H), 2.54-1.88 (m, 3H), 1.54 (s, 3H), 1.04-0.91 (m, 4H). [M+H]=341.36.

Example 470. N,6-Dimethyl-4-[(1-methylcyclopropyl)amino]-N-[1-(propan-2-yl)-1H-pyrazol-4-yl]furo[2,3-d]pyrimidine-5-carboxamide

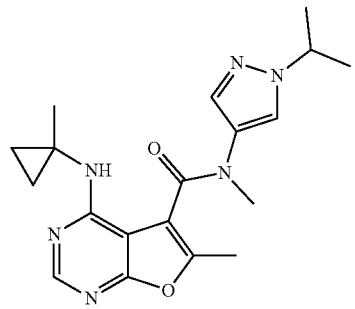 [SMILES: Cc1oc2ncnc(NC3(C)CC3)c2c1C(=O)N(C)c1cnn(C(C)C)c1]

$^1$H NMR (400 MHz, CD$_3$OD) δ 8.35 (s, 1H), 7.64 (s, 1H), 7.26 (s, 1H), 5.09-4.93 (m, 1H), 3.81 (s, 3H), 2.20 (s, 3H), 1.54 (s, 3H), 1.20 (d, J=6.7 Hz, 6H), 1.01-0.89 (m, 4H). [M+H]=369.3.

Example 471. 6-Methyl-N-(1-methylcyclopropyl)-5-{5H,6H,7H,8H-pyrido[3,4-d]pyrimidine-7-carbonyl}furo[2,3-d]pyrimidin-4-amine

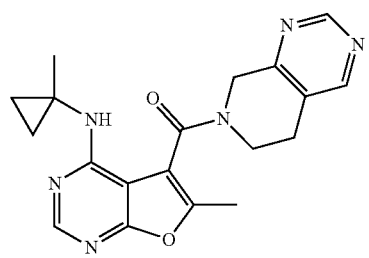 [SMILES: Cc1oc2ncnc(NC3(C)CC3)c2c1C(=O)N1CCc2cncnc2C1]

$^1$H NMR (400 MHz, CD$_3$OD) δ 8.97 (s, 1H), 8.65 (s, 1H), 8.46 (s, 1H), 4.92 (br s, 2H), 4.01 (br s, 2H), 3.06-2.99 (m, 2H), 2.62 (s, 3H), 1.49 (s, 3H), 1.01-0.92 (m, 4H). [M+H]=365.38.

Example 472. 6-Methyl-4-[(1-methylcyclopropyl)amino]-N-[1-(pyridin-2-ylmethyl)-1H-pyrazol-4-yl]furo[2,3-d]pyrimidine-5-carboxamide

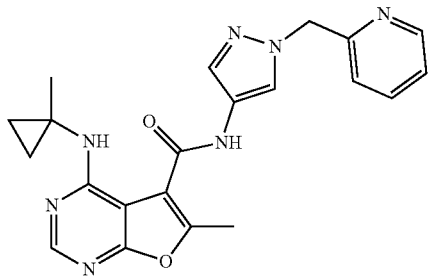 [SMILES: Cc1oc2ncnc(NC3(C)CC3)c2c1C(=O)Nc1cnn(Cc2ccccn2)c1]

$^1$H NMR (400 MHz, CD$_3$OD) δ 8.67 (d, J=4.8 Hz, 1H), 8.43 (s, 1H), 8.33 (s, 1H), 8.12 (dt, J=1.6, 7.8 Hz, 1H), 7.78 (s, 1H), 7.66-7.58 (m, 1H), 7.41 (d, J=7.9 Hz, 1H), 5.60 (s, 2H), 2.78 (s, 3H), 1.54 (s, 3H), 1.03-0.91 (m, 4H). [M+H]= 404.40.

Example 473. 6-Methyl-4-[(1-methylcyclopropyl)amino]-N-[1-(pyrimidin-2-yl)-1H-pyrazol-4-yl]furo[2,3-d]pyrimidine-5-carboxamide

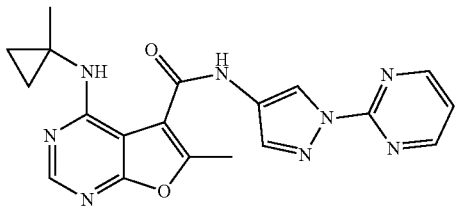 [SMILES: Cc1oc2ncnc(NC3(C)CC3)c2c1C(=O)Nc1cnn(-c2ncccn2)c1]

$^1$H NMR (400 MHz, CD$_3$OD) δ 9.10 (s, 1H), 8.84 (d, J=4.8 Hz, 2H), 8.42 (s, 1H), 8.07 (s, 1H), 7.43 (t, J=4.8 Hz, 1H), 2.80 (s, 3H), 1.55 (s, 3H), 1.03-0.89 (m, 4H). [M+H]= 391.37.

Example 474. 5-{4-[(4-Fluorophenyl)methyl]piperazine-1-carbonyl}-6-methyl-N-(1-methylcyclopropyl)furo[2,3-d]pyrimidin-4-amine

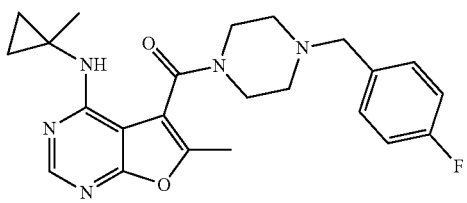 [SMILES: Cc1oc2ncnc(NC3(C)CC3)c2c1C(=O)N1CCN(Cc2ccc(F)cc2)CC1]

[M+H]=424.2.

Example 475. N-[1-(4-Methoxyphenyl)propyl]-6-methyl-4-[(1-methylcyclopropyl)amino]furo[2,3-d]pyrimidine-5-carboxamide

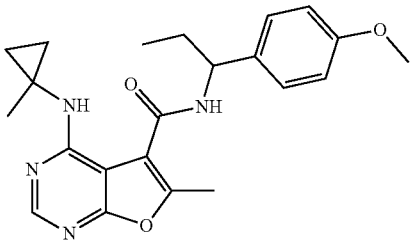 [SMILES: CCC(NC(=O)c1c(C)oc2ncnc(NC3(C)CC3)c12)c1ccc(OC)cc1]

[M+H]=395.2.

Example 476. N-[1-(3-Methoxyphenyl)ethyl]-N,6-dimethyl-4-[(1-methylcyclopropyl)amino]furo[2,3-d]pyrimidine-5-carboxamide

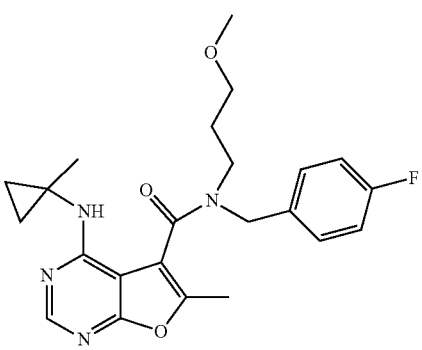 [SMILES: COCCCN(Cc1ccc(F)cc1)C(=O)c1c(C)oc2ncnc(NC3(C)CC3)c12]

[M+H]=395.2.

Example 477. N-[(4-Fluorophenyl)methyl]-N-(3-methoxypropyl)-6-methyl-4-[(1-methylcyclopropyl)amino]furo[2,3-d]pyrimidine-5-carboxamide

[M+H]=427.2.

Example 478. N-[(1S)-1-(3-Methoxyphenyl)ethyl]-6-methyl-4-[(1-methylcyclopropyl)amino]furo[2,3-d]pyrimidine-5-carboxamide

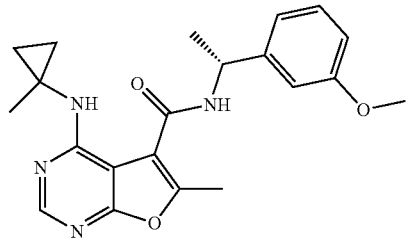

[M+H]=381.2.

Example 479. N-[(1R)-1-(3-Methoxyphenyl)ethyl]-6-methyl-4-[(1-methylcyclopropyl)amino]furo[2,3-d]pyrimidine-5-carboxamide

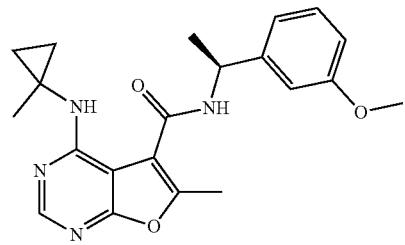 [SMILES: COc1cccc([C@H](C)NC(=O)c2c(C)oc3ncnc(NC4(C)CC4)c23)c1]

[M+H]=381.2.

Example 480. N-[(1S)-1-(4-Methoxyphenyl)ethyl]-6-methyl-4-[(1-methylcyclopropyl)amino]furo[2,3-d]pyrimidine-5-carboxamide

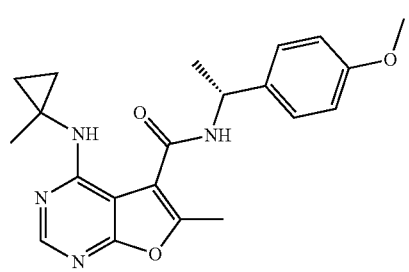

[M+H]=381.2.

Example 481. 5-[4-(4-Methoxypyrimidin-2-yl)piperazine-1-carbonyl]-6-methyl-N-(1-methylcyclopropyl)furo[2,3-d]pyrimidin-4-amine

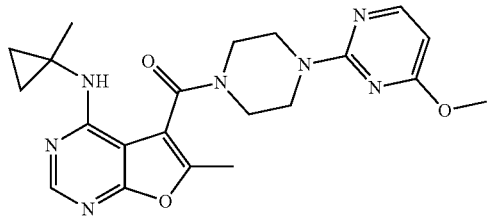 [SMILES: COc1ccnc(N2CCN(C(=O)c3c(C)oc4ncnc(NC5(C)CC5)c34)CC2)n1]

[M+H]=424.2.

Example 482. N-[(1S)-1-(2-Methoxyphenyl)ethyl]-6-methyl-4-[(1-methylcyclopropyl)amino]furo[2,3-d]pyrimidine-5-carboxamide

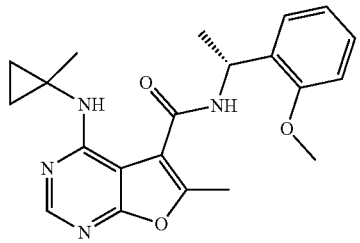 [SMILES: COc1ccccc1[C@@H](C)NC(=O)c1c(C)oc2ncnc(NC3(C)CC3)c12]

[M+H]=381.2.

Example 483. N-[(3-Fluoro-4-methoxyphenyl)methyl]-6-methyl-4-[(1-methylcyclopropyl)amino]furo[2,3-d]pyrimidine-5-carboxamide

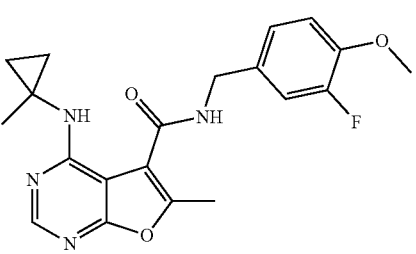

[M+H]=385.2.

Example 484. N-[(1R)-1-(4-Fluorophenyl)ethyl]-6-methyl-4-[(1-methylcyclopropyl)amino]furo[2,3-d]pyrimidine-5-carboxamide

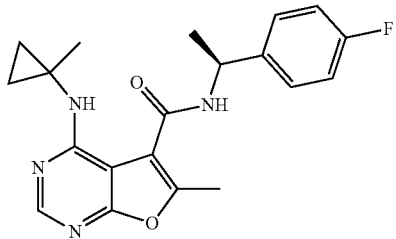 [SMILES: Cc1oc2ncnc(NC3(C)CC3)c2c1C(=O)N[C@@H](C)c1ccc(F)cc1]

[M+H]=369.2.

Example 485. N-[(1S)-1-(4-Fluorophenyl)ethyl]-6-methyl-4-[(1-methylcyclopropyl)amino]furo[2,3-d]pyrimidine-5-carboxamide

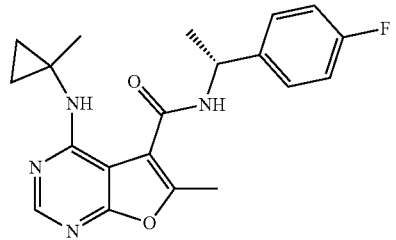 [SMILES: Cc1oc2ncnc(NC3(C)CC3)c2c1C(=O)N[C@H](C)c1ccc(F)cc1]

[M+H]=369.2.

Example 486. N-[1-(2,5-Difluorophenyl)ethyl]-6-methyl-4-[(1-methylcyclopropyl)amino]furo[2,3-d]pyrimidine-5-carboxamide

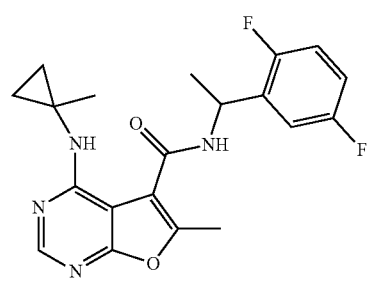 [SMILES: Cc1oc2ncnc(NC3(C)CC3)c2c1C(=O)NC(C)c1cc(F)ccc1F]

[M+H]=387.2.

Example 487. N-[(4-Hydroxy-3-methoxyphenyl)methyl]-6-methyl-4-[(1-methylcyclopropyl)amino]furo[2,3-d]pyrimidine-5-carboxamide

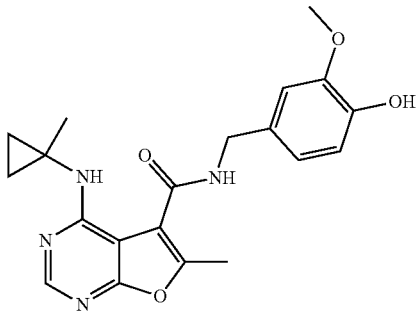 [SMILES: COc1cc(CNC(=O)c2c(C)oc3ncnc(NC4(C)CC4)c23)ccc1O]

[M+H]=383.2.

Example 488. N-[(3-Chloro-4-methoxyphenyl)methyl]-6-methyl-4-[(1-methylcyclopropyl)amino]furo[2,3-d]pyrimidine-5-carboxamide

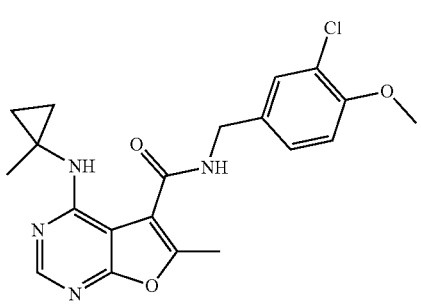

[M+H]=401.2.

Example 489. N-ethyl-N-[(4-Methoxyphenyl)methyl]-6-methyl-4-[(1-methylcyclopropyl)amino]furo[2,3-d]pyrimidine-5-carboxamide

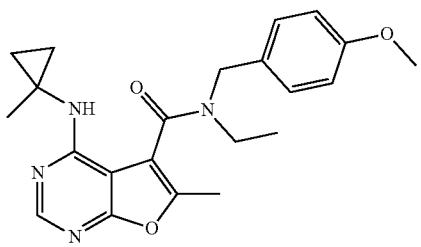

[M+H]=395.2.

Example 490. N-[1-(3-Methoxyphenyl)ethyl]-6-methyl-4-[(1-methylcyclopropyl)amino]furo[2,3-d]pyrimidine-5-carboxamide

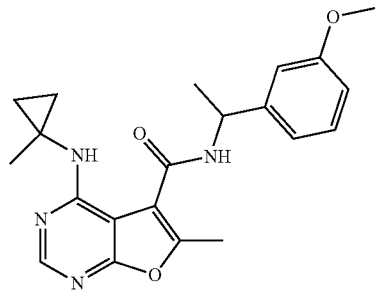

[M+H]=381.2.

Example 491. N-[2-Hydroxy-3-(4-methoxyphenoxy)propyl]-6-methyl-4-[(1-methylcyclopropyl)amino]furo[2,3-d]pyrimidine-5-carboxamide

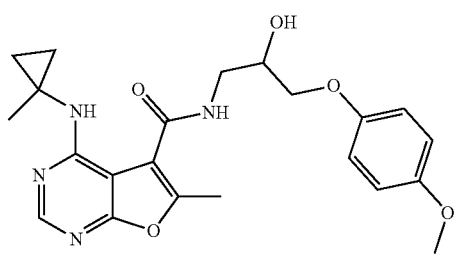 [SMILES: COc1ccc(OCC(O)CNC(=O)c2c(C)oc3ncnc(NC4(C)CC4)c23)cc1]

[M+H]=427.2.

Example 492. N-{[3-(4-Fluorophenyl)-1,2-oxazol-5-yl]methyl}-6-methyl-4-[(1-methylcyclopropyl)amino]furo[2,3-d]pyrimidine-5-carboxamide

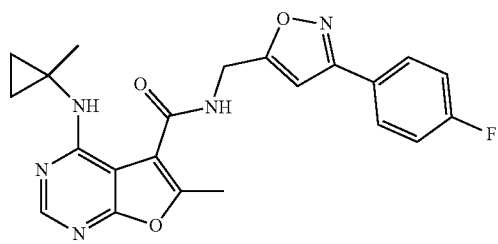 [SMILES: Cc1oc2ncnc(NC3(C)CC3)c2c1C(=O)NCc1cc(-c2ccc(F)cc2)no1]

[M+H]=422.2.

Example 493. N-[(7-Methoxy-2,3-dihydro-1,4-benzodioxin-6-yl)methyl]-6-methyl-4-[(1-methylcyclopropyl)amino]furo[2,3-d]pyrimidine-5-carboxamide

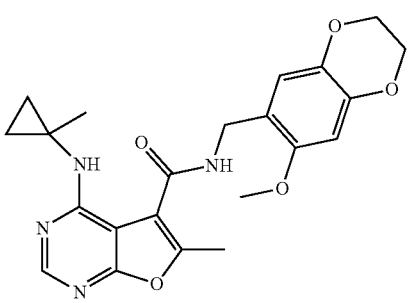 [SMILES: COc1cc2c(cc1CNC(=O)c1c(C)oc3ncnc(NC4(C)CC4)c13)OCCO2]

[M+H]=425.2.

Example 494. N-{[3-(2-fluorophenyl)-1,2-oxazol-5-yl]methyl}-6-methyl-4-[(1-methylcyclopropyl)amino]furo[2,3-d]pyrimidine-5-carboxamide

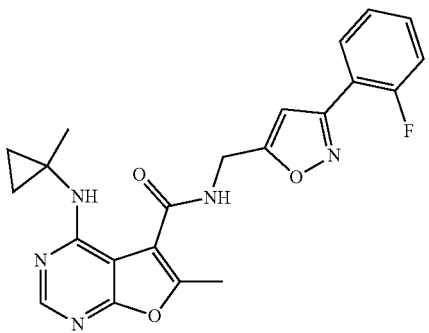 [SMILES: Cc1oc2ncnc(NC3(C)CC3)c2c1C(=O)NCc1cc(-c2ccccc2F)no1]

[M+H]=422.2.

Example 495. N-[(3,5-Dimethoxyphenyl)methyl]-6-methyl-4-[(1-methylcyclopropyl)amino]furo[2,3-d]pyrimidine-5-carboxamide

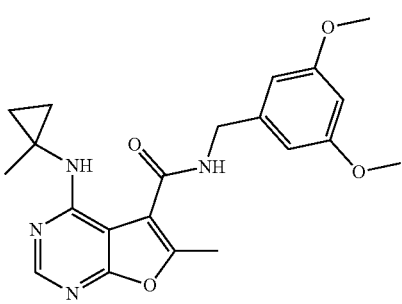

[M+H]=397.2.

Example 496. 5-{3-[(2-Fluorophenyl)methoxy]azetidine-1-carbonyl}-6-methyl-N-(1-methylcyclopropyl)furo[2,3-d]pyrimidin-4-amine

[M+H]=411.2.

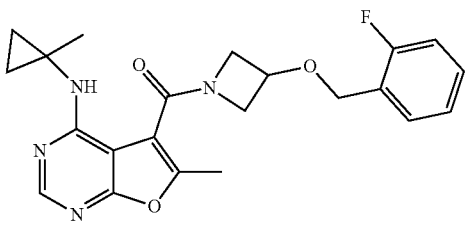 [SMILES: Cc1oc2ncnc(NC3(C)CC3)c2c1C(=O)N1CC(OCc2ccccc2F)C1]

Example 497. 5-{3-[(3-Fluorophenyl)methoxy]azetidine-1-carbonyl}-6-methyl-N-(1-methylcyclopropyl)furo[2,3-d]pyrimidin-4-amine

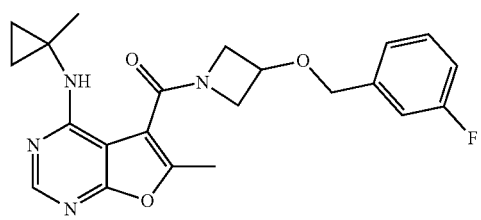 [SMILES: Cc1oc2ncnc(NC3(C)CC3)c2c1C(=O)N1CC(OCc2cccc(F)c2)C1]

[M+H]=411.2.

Example 498. N-[(4-Methoxy-3,5-dimethylpyridin-2-yl)methyl]-N,6-dimethyl-4-[(1-methylcyclopropyl)amino]furo[2,3-d]pyrimidine-5-carboxamide

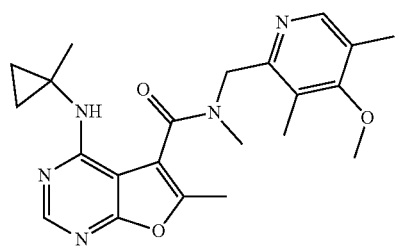 [SMILES: COc1c(C)cnc(CN(C)C(=O)c2c(C)oc3ncnc(NC4(C)CC4)c23)c1C]

[M+H]=410.2.

Example 499. 6-Methyl-N-(1-methylcyclopropyl)-5-[(1R,5S)-8-oxa-3-azabicyclo[3.2.1]octane-3-carbonyl]furo[2,3-d]pyrimidin-4-amine

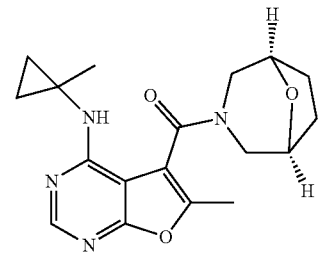 [SMILES: Cc1oc2ncnc(NC3(C)CC3)c2c1C(=O)N1C[C@H]2CC[C@@H](C1)O2]

[M+H]=343.1.

Example 500. N-[(2-Fluoro-6-methylphenyl)methyl]-6-methyl-4-[(1-methylcyclopropyl)amino]furo[2,3-d]pyrimidine-5-carboxamide

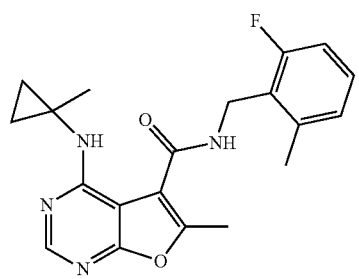 [SMILES: Cc1cccc(F)c1CNC(=O)c1c(C)oc2ncnc(NC3(C)CC3)c12]

[M+H]=369.2.

Example 501. N-[(2-Chloro-3-fluorophenyl)methyl]-6-methyl-4-[(1-methylcyclopropyl)amino]furo[2,3-d]pyrimidine-5-carboxamide

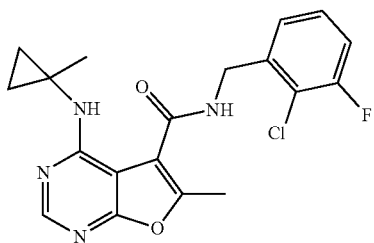 [SMILES: Cc1oc2ncnc(NC3(C)CC3)c2c1C(=O)NCc1cccc(F)c1Cl]

[M+H]=389.1.

Example 502. N-[1-(4-Methoxy-3-methylphenyl)ethyl]-6-methyl-4-[(1-methylcyclopropyl)amino]furo[2,3-d]pyrimidine-5-carboxamide

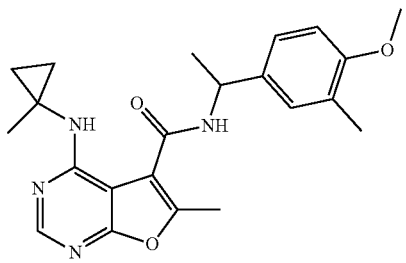

[M+H]=395.2.

Example 503. N-[(2,6-Difluorophenyl)methyl]-6-methyl-4-[(1-methylcyclopropyl)amino]furo[2,3-d]pyrimidine-5-carboxamide

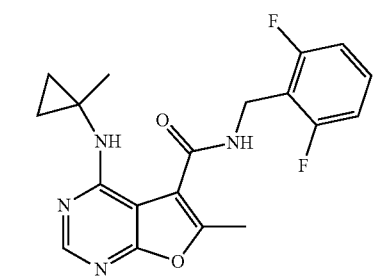 [SMILES: Cc1oc2ncnc(NC3(C)CC3)c2c1C(=O)NCc1c(F)cccc1F]

[M+H]=373.2.

Example 504. N-[(2,4-Difluorophenyl)methyl]-6-methyl-4-[(1-methylcyclopropyl)amino]furo[2,3-d]pyrimidine-5-carboxamide

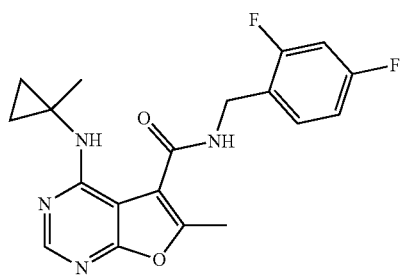 [SMILES: Cc1oc2ncnc(NC3(C)CC3)c2c1C(=O)NCc1ccc(F)cc1F]

[M+H]=373.2.

Example 505. N-[(3,4-Difluorophenyl)methyl]-6-methyl-4-[(1-methylcyclopropyl)amino]furo[2,3-d]pyrimidine-5-carboxamide

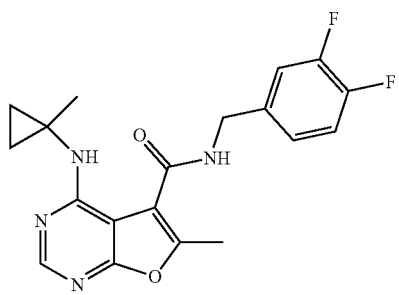 [SMILES: Cc1oc2ncnc(NC3(C)CC3)c2c1C(=O)NCc1ccc(F)c(F)c1]

[M+H]=373.2.

Example 506. 5-[2-(3-Fluorophenyl)pyrrolidine-1-carbonyl]-6-methyl-N-(1-methylcyclopropyl)furo[2,3-d]pyrimidin-4-amine

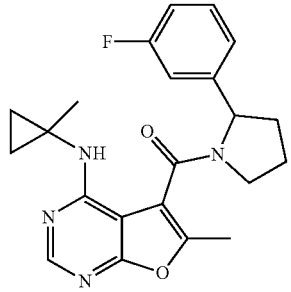 [SMILES: Cc1oc2ncnc(NC3(C)CC3)c2c1C(=O)N1CCCC1c1cccc(F)c1]

[M+H]=395.2.

Example 507. N-[(2-Chloro-4-fluorophenyl)methyl]-6-methyl-4-[(1-methylcyclopropyl)amino]furo[2,3-d]pyrimidine-5-carboxamide

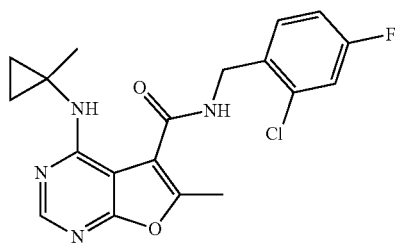 [SMILES: Cc1oc2ncnc(NC3(C)CC3)c2c1C(=O)NCc1ccc(F)cc1Cl]

[M+H]=389.1.

Example 508. N-[(4-Methoxyphenyl)methyl]-6-methyl-4-[(1-methylcyclopropyl)amino]-N-(prop-2-en-1-yl)furo[2,3-d]pyrimidine-5-carboxamide

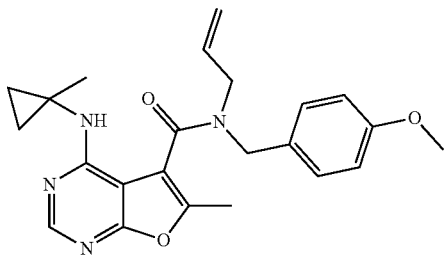 [SMILES: C=CCN(Cc1ccc(OC)cc1)C(=O)c1c(C)oc2ncnc(NC3(C)CC3)c12]

[M+H]=407.2.

Example 509. N-[(4-Ethoxy-3-methoxyphenyl)methyl]-6-methyl-4-[(1-methylcyclopropyl)amino]furo[2,3-d]pyrimidine-5-carboxamide

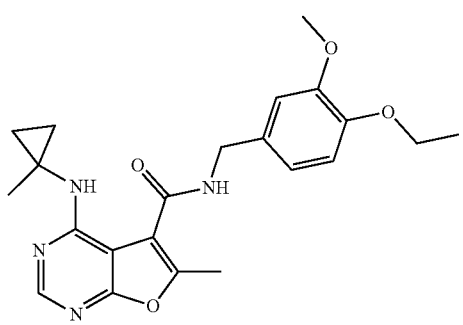 [SMILES: CCOc1ccc(CNC(=O)c2c(C)oc3ncnc(NC4(C)CC4)c23)cc1OC]

[M+H]=411.2.

Example 510. N-[1-(3-Fluoro-4-methoxyphenyl)ethyl]-N,6-dimethyl-4-[(1-methylcyclopropyl)amino]furo[2,3-d]pyrimidine-5-carboxamide

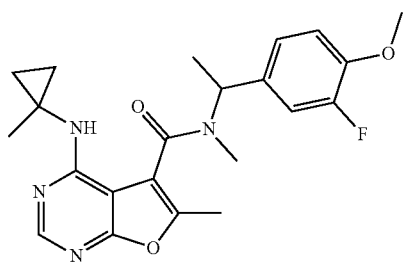

[M+H]=413.3.

Example 511. 7-Methoxy-1-methyl-2-{6-methyl-4-[(1-methylcyclopropyl)amino]furo[2,3-d]pyrimidine-5-carbonyl}-1,2,3,4-tetrahydroisoquinolin-6-ol

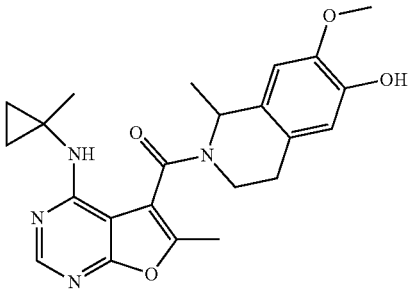 [SMILES: COc1cc2c(cc1O)CCN(C(=O)c1c(C)oc3ncnc(NC4(C)CC4)c13)C2C]

[M+H]=423.3.

Example 512. 5-[3-(4-Fluorophenoxy)azetidine-1-carbonyl]-6-methyl-N-(1-methylcyclopropyl)furo[2,3-d]pyrimidin-4-amine

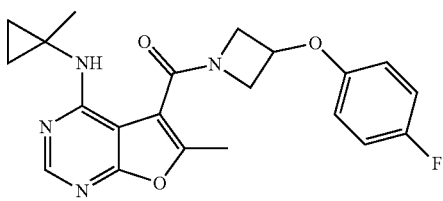 [SMILES: Cc1oc2ncnc(NC3(C)CC3)c2c1C(=O)N1CC(Oc2ccc(F)cc2)C1]

[M+H]=397.2.

Example 513. N-[1-(4-Fluorophenyl)-2-hydroxyethyl]-6-methyl-4-[(1-methylcyclopropyl)amino]furo[2,3-d]pyrimidine-5-carboxamide

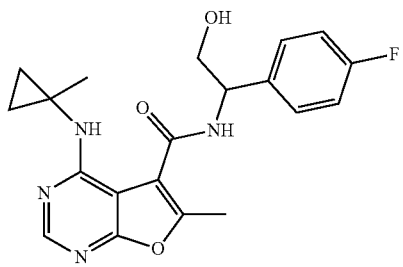 [SMILES: Cc1oc2ncnc(NC3(C)CC3)c2c1C(=O)NC(CO)c1ccc(F)cc1]

[M+H]=385.2.

Example 514. N-[2-(5-Fluoro-2-methyl-1H-indol-3-yl)ethyl]-6-methyl-4-[(1-methylcyclopropyl)amino]furo[2,3-d]pyrimidine-5-carboxamide

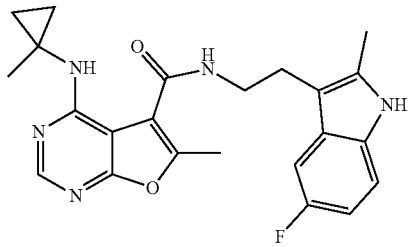 [SMILES: Cc1[nH]c2ccc(F)cc2c1CCNC(=O)c1c(C)oc2ncnc(NC3(C)CC3)c12]

[M+H]=422.3.

Example 515. N-[(1R)-1-(2,4-Difluorophenyl)ethyl]-6-methyl-4-[(1-methylcyclopropyl)amino]furo[2,3-d]pyrimidine-5-carboxamide

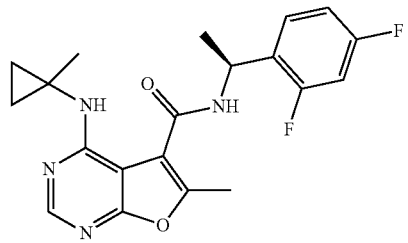 [SMILES: Cc1oc2ncnc(NC3(C)CC3)c2c1C(=O)N[C@@H](C)c1ccc(F)cc1F]

[M+H]=387.2.

Example 516. N-[(6-Chloro-2-fluoro-3-methoxyphenyl)methyl]-6-methyl-4-[(1-methylcyclopropyl)amino]furo[2,3-d]pyrimidine-5-carboxamide

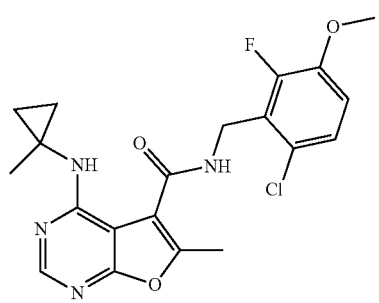

[M+H]=419.2.

Example 517. 5-[4-(3-Methoxyphenyl)piperidine-1-carbonyl]-6-methyl-N-(1-methylcyclopropyl)furo[2,3-d]pyrimidin-4-amine

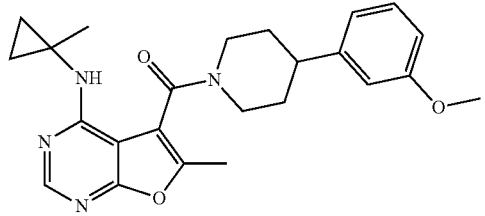 [SMILES: COc1cccc(C2CCN(C(=O)c3c(C)oc4ncnc(NC5(C)CC5)c34)CC2)c1]

[M+H]=421.3.

Example 518. N-[(1S)-1-(5-Fluoropyrimidin-2-yl)ethyl]-6-methyl-4-[(1-methylcyclopropyl)amino]furo[2,3-d]pyrimidine-5-carboxamide

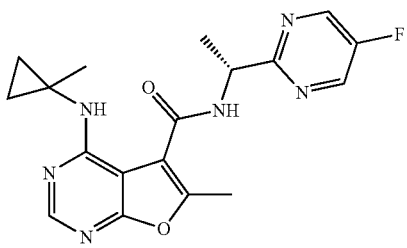 [SMILES: Cc1oc2ncnc(NC3(C)CC3)c2c1C(=O)N[C@H](C)c1ncc(F)cn1]

[M+H]=371.2.

Example 519. 5-[4-(4 6-Dimethoxypyrimidin-2-yl)piperidine-1-carbonyl]-6-methyl-N-(1-methylcyclopropyl)furo[2,3-d]pyrimidin-4-amine

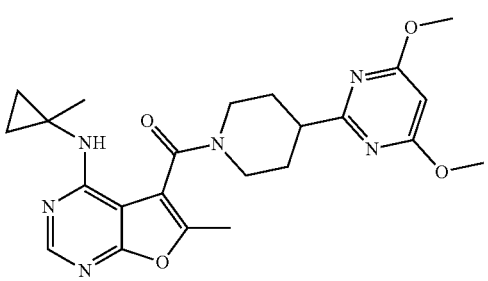 [SMILES: COc1cc(OC)nc(C2CCN(C(=O)c3c(C)oc4ncnc(NC5(C)CC5)c34)CC2)n1]

[M+H]=453.3.

Example 520. 6-Methyl-N-(2-methylbut-3-yn-2-yl)-4-[(1-methylcyclopropyl)amino]furo[2,3-d]pyrimidine-5-carboxamide

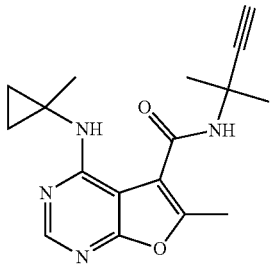 [SMILES: C#CC(C)(C)NC(=O)c1c(C)oc2ncnc(NC3(C)CC3)c12]

[M+H]=313.2.

Example 521. 5-[4-(4-Fluoro-2-methanesulfonylphenyl)piperazine-1-carbonyl]-6-methyl-N-(1-methylcyclopropyl)furo[2,3-d]pyrimidin-4-amine

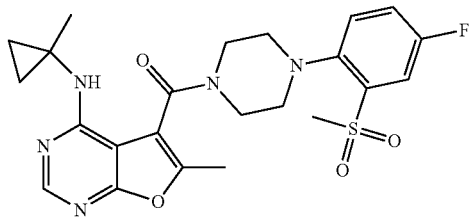 [SMILES: Cc1oc2ncnc(NC3(C)CC3)c2c1C(=O)N1CCN(c2ccc(F)cc2S(C)(=O)=O)CC1]

[M+H]=488.2.

Example 522. 5-[4-(2-Fluoro-4-methanesulfonylphenyl)-2-methylpiperazine-1-carbonyl]-6-methyl-N-(1-methylcyclopropyl)furo[2,3-d]pyrimidin-4-amine

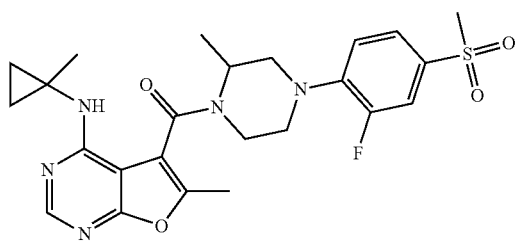 [SMILES: Cc1oc2ncnc(NC3(C)CC3)c2c1C(=O)N1CCN(c2ccc(S(C)(=O)=O)cc2F)CC1C]

[M+H]=502.2.

Example 523. 5-[4-(2-Fluoro-4-nitrophenyl)piperazine-1-carbonyl]-6-methyl-N-(1-methylcyclopropyl)furo[2,3-d]pyrimidin-4-amine

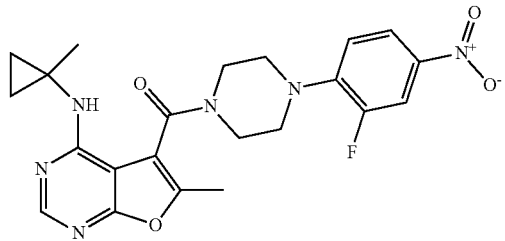 [SMILES: Cc1oc2ncnc(NC3(C)CC3)c2c1C(=O)N1CCN(c2ccc([N+](=O)[O-])cc2F)CC1]

[M+H]=455.2.

Example 524. N-[(4-Methoxy-2-methylphenyl)methyl]-6-methyl-4-[(1-methylcyclopropyl)amino]furo[2,3-d]pyrimidine-5-carboxamide

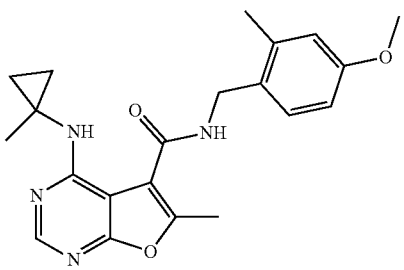

[M+H]=381.3.

Example 525. N-[(4-Fluoro-2-methoxyphenyl)methyl]-6-methyl-4-[(1-methylcyclopropyl)amino]furo[2,3-d]pyrimidine-5-carboxamide

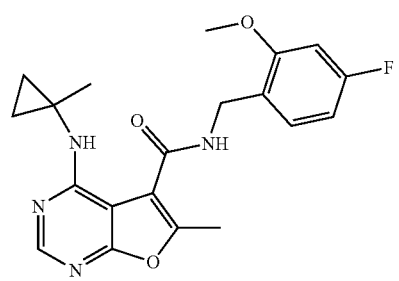 [SMILES: COc1cc(F)ccc1CNC(=O)c1c(C)oc2ncnc(NC3(C)CC3)c12]

[M+H]=385.2.

Example 526. N-[(3-Chloro-5-fluorophenyl)methyl]-6-methyl-4-[(1-methylcyclopropyl)amino]furo[2,3-d]pyrimidine-5-carboxamide

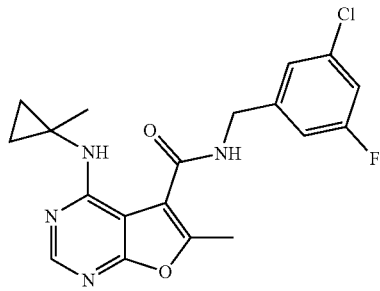 [SMILES: Cc1oc2ncnc(NC3(C)CC3)c2c1C(=O)NCc1cc(F)cc(Cl)c1]

[M+H]=389.2.

Example 527. 5-(7-Fluoro-1,2,3,4-tetrahydroisoquinoline-2-carbonyl)-6-methyl-N-(1-methylcyclopropyl)furo[2,3-d]pyrimidin-4-amine

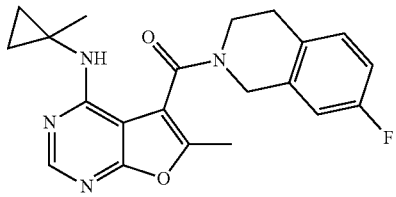 [SMILES: Cc1oc2ncnc(NC3(C)CC3)c2c1C(=O)N1CCc2ccc(F)cc2C1]

[M+H]=381.2.

Example 528. N-[(2-Methoxyphenyl)methyl]-N,6-dimethyl-4-[(1-methylcyclopropyl)amino]furo[2,3-d]pyrimidine-5-carboxamide

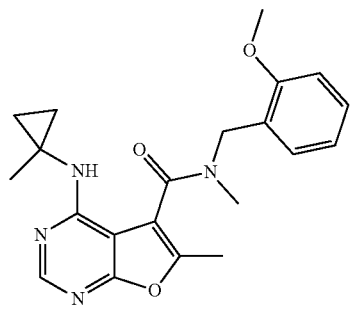 [SMILES: COc1ccccc1CN(C)C(=O)c1c(C)oc2ncnc(NC3(C)CC3)c12]

[M+H]=381.2.

Example 529. 5-[3-(3-Fluoropyridin-2-yl)pyrrolidine-1-carbonyl]-6-methyl-N-(1-methylcyclopropyl)furo[2,3-d]pyrimidin-4-amine

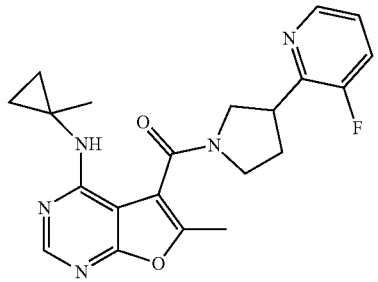 [SMILES: Cc1oc2ncnc(NC3(C)CC3)c2c1C(=O)N1CCC(c2ncccc2F)C1]

[M+H]=396.2.

Example 530. 5-[4-(6-Fluoro-5-methoxypyridin-2-yl)piperidine-1-carbonyl]-6-methyl-N-(1-methylcyclopropyl)furo[2,3-d]pyrimidin-4-amine

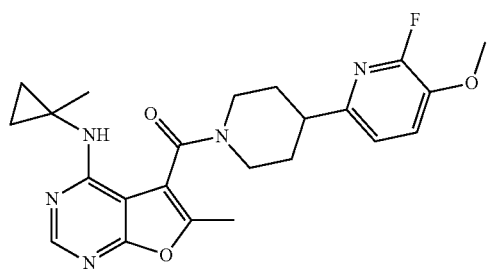 [SMILES: COc1ccc(C2CCN(C(=O)c3c(C)oc4ncnc(NC5(C)CC5)c34)CC2)nc1F]

[M+H]=440.3.

Example 531. 5-Fluoro-2-(1-{6-methyl-4-[(1-methylcyclopropyl)amino]furo[2,3-d]pyrimidine-5-carbonyl}piperidin-4-yl)-N-(propan-2-yl)pyrimidin-4-amine

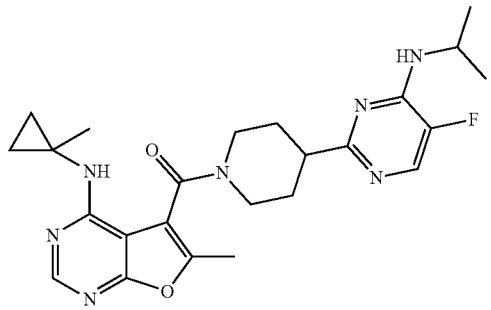 [SMILES: Cc1oc2ncnc(NC3(C)CC3)c2c1C(=O)N1CCC(c2ncc(F)c(NC(C)C)n2)CC1]

[M+H]=468.3.

Example 532. 5-[3-(6-Fluoropyridin-2-yl)pyrrolidine-1-carbonyl]-6-methyl-N-(1-methylcyclopropyl) furo[2,3-d]pyrimidin-4-amine

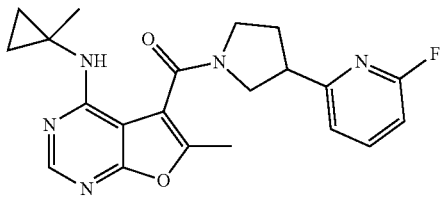 [SMILES: Cc1oc2ncnc(NC3(C)CC3)c2c1C(=O)N1CCC(c2cccc(F)n2)C1]

[M+H]=396.3.

Example 533. N-[(5-Cyano-2-fluorophenyl)methyl]-6-methyl-4-[(1-methylcyclopropyl)amino]furo[2,3-d]pyrimidine-5-carboxamide

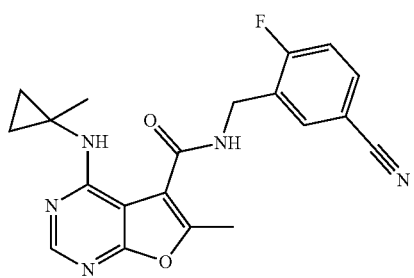 [SMILES: Cc1oc2ncnc(NC3(C)CC3)c2c1C(=O)NCc1cc(C#N)ccc1F]

[M+H]=380.2.

Example 534. N-[(4-Chloro-2-fluorophenyl)methyl]-6-methyl-4-[(1-methylcyclopropyl)amino]furo[2,3-d]pyrimidine-5-carboxamide

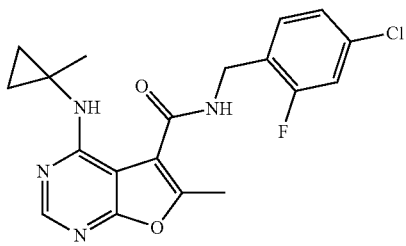 [SMILES: Cc1oc2ncnc(NC3(C)CC3)c2c1C(=O)NCc1ccc(Cl)cc1F]

[M+H]=389.1.

Example 535. 5-[4-(2,4-Difluorophenyl)piperazine-1-carbonyl]-6-methyl-N-(1-methylcyclopropyl)furo[2,3-d]pyrimidin-4-amine

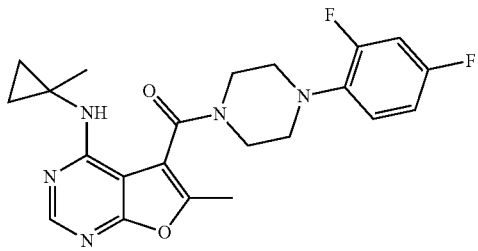 [SMILES: Cc1oc2ncnc(NC3(C)CC3)c2c1C(=O)N1CCN(c2ccc(F)cc2F)CC1]

[M+H]=428.2.

Example 536. 5-[3-(4-Fluorophenyl)piperazine-1-carbonyl]-6-methyl-N-(1-methylcyclopropyl)furo[2,3-d]pyrimidin-4-amine

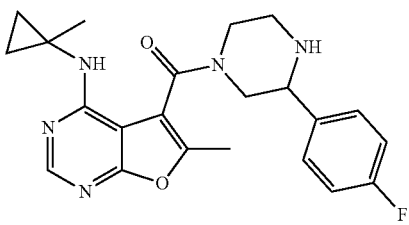 [SMILES: Cc1oc2ncnc(NC3(C)CC3)c2c1C(=O)N1CCNC(c2ccc(F)cc2)C1]

[M+H]=410.2.

Example 537. N-[1-(4-Fluorophenyl)propan-2-yl]-6-methyl-4-[(1-methylcyclopropyl)amino]furo[2,3-d]pyrimidine-5-carboxamide

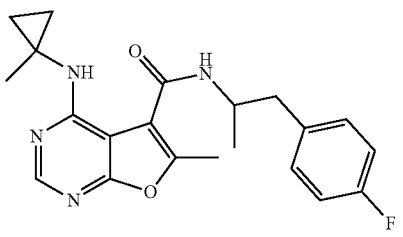 [SMILES: Cc1oc2ncnc(NC3(C)CC3)c2c1C(=O)NC(C)Cc1ccc(F)cc1]

[M+H]=383.2.

Example 538. N-[2-(3-Ethoxy-4-methoxyphenyl)ethyl]-6-methyl-4-[(1-methylcyclopropyl)amino]furo[2,3-d]pyrimidine-5-carboxamide

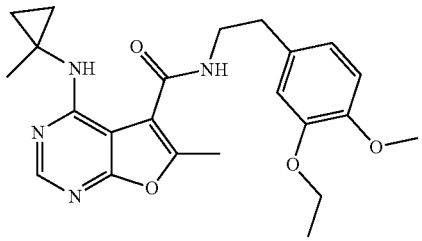

[M+H]=425.2.

Example 539. N-[2-(3,5-Difluorophenyl)ethyl]-6-methyl-4-[(1-methylcyclopropyl)amino]furo[2,3-d]pyrimidine-5-carboxamide

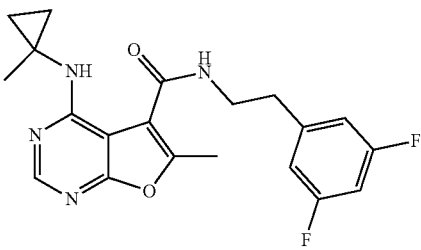 [SMILES: Cc1oc2ncnc(NC3(C)CC3)c2c1C(=O)NCCc1cc(F)cc(F)c1]

[M+H]=387.2.

Example 540. N-[2-(5-Chloro-2-fluorophenyl)ethyl]-6-methyl-4-[(1-methylcyclopropyl)amino]furo[2,3-d]pyrimidine-5-carboxamide

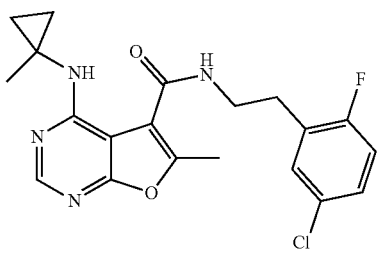 [SMILES: Cc1oc2ncnc(NC3(C)CC3)c2c1C(=O)NCCc1cc(Cl)ccc1F]

[M+H]=403.2.

Example 541. 5-{4-[(3-Fluorophenyl)methyl]piperazine-1-carbonyl}-6-methyl-N-(1-methylcyclopropyl)furo[2,3-d]pyrimidin-4-amine

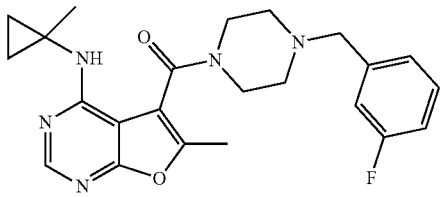 [SMILES: Cc1oc2ncnc(NC3(C)CC3)c2c1C(=O)N1CCN(Cc2cccc(F)c2)CC1]

[M+H]=424.2.

Example 542. N-[2-(2,5-Dimethoxyphenyl)ethyl]-6-methyl-4-[(1-methylcyclopropyl)amino]furo[2,3-d]pyrimidine-5-carboxamide

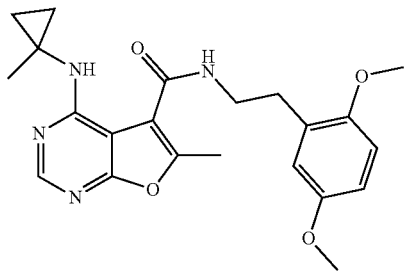

[M+H]=411.2.

Example 543. N-[2-(2,3-Dimethoxyphenyl)ethyl]-6-methyl-4-[(1-methylcyclopropyl)amino]furo[2,3-d]pyrimidine-5-carboxamide

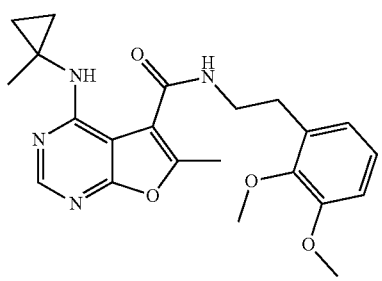 [SMILES: COc1cccc(CCNC(=O)c2c(C)oc3ncnc(NC4(C)CC4)c23)c1OC]

[M+H]=411.2.

Example 544. N-[2-(3-Chloro-4-fluorophenyl)ethyl]-6-methyl-4-[(1-methylcyclopropyl)amino]furo[2,3-d]pyrimidine-5-carboxamide

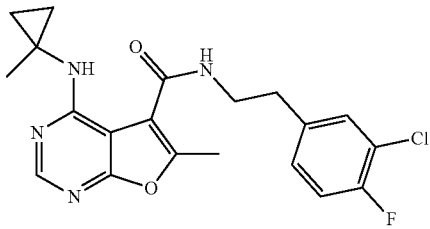 [SMILES: Cc1oc2ncnc(NC3(C)CC3)c2c1C(=O)NCCc1ccc(F)c(Cl)c1]

[M+H]=403.2.

Example 545. N-[2-(3,4-Dimethoxyphenyl)ethyl]-6-methyl-4-[(1-methylcyclopropyl)amino]furo[2,3-d]pyrimidine-5-carboxamide

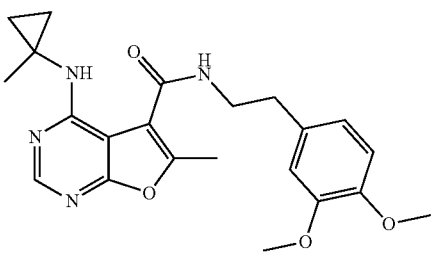

[M+H]=411.2.

Example 546. N-[1-(3,5-Difluorophenyl)ethyl]-6-methyl-4-[(1-methylcyclopropyl)amino]furo[2,3-d]pyrimidine-5-carboxamide

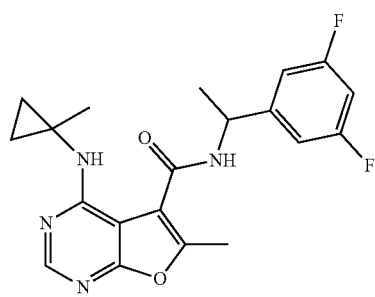 [SMILES: Cc1oc2ncnc(NC3(C)CC3)c2c1C(=O)NC(C)c1cc(F)cc(F)c1]

[M+H]=387.2.

Example 547. N-[(2-Fluoro-6-methoxyphenyl)methyl]-6-methyl-4-[(1-methylcyclopropyl)amino]furo[2,3-d]pyrimidine-5-carboxamide

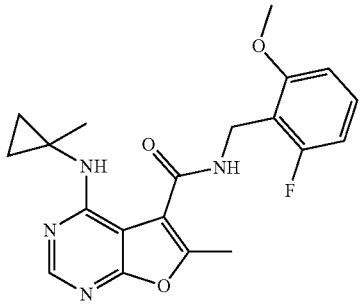 [SMILES: COc1cccc(F)c1CNC(=O)c1c(C)oc2ncnc(NC3(C)CC3)c12]

[M+H]=385.2.

Example 548. N-[1-(4-Fluorophenyl)propyl]-6-methyl-4-[(1-methylcyclopropyl)amino]furo[2,3-d]pyrimidine-5-carboxamide

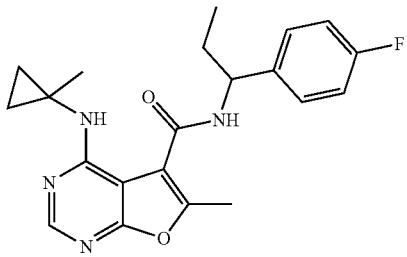 [SMILES: CCC(NC(=O)c1c(C)oc2ncnc(NC3(C)CC3)c12)c1ccc(F)cc1]

[M+H]=383.2.

Example 549. N-[(5-Chloro-2,4-difluorophenyl)methyl]-6-methyl-4-[(1-methylcyclopropyl)amino]furo[2,3-d]pyrimidine-5-carboxamide

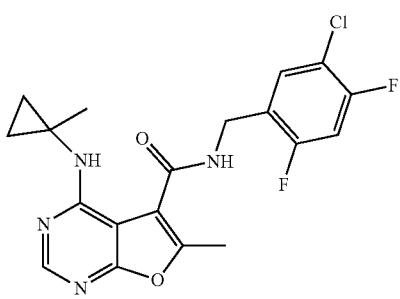 [SMILES: Cc1oc2ncnc(NC3(C)CC3)c2c1C(=O)NCc1cc(Cl)c(F)cc1F]

[M+H]=407.1.

Example 550. N-[(2-Fluoro-3-methylphenyl)
methyl]-6-methyl-4-[(1-methylcyclopropyl)amino]
furo[2,3-d]pyrimidine-5-carboxamide

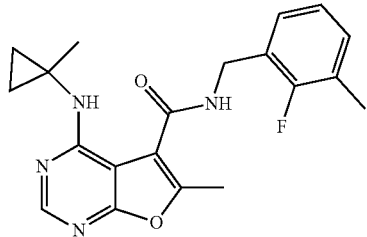 [SMILES: Cc1cccc(CNC(=O)c2c(C)oc3ncnc(NC4(C)CC4)c23)c1F]

[M+H]=369.2.

Example 551. N-[(2-Chloro-4-methoxyphenyl)
methyl]-6-methyl-4-[(1-methylcyclopropyl)amino]
furo[2,3-d]pyrimidine-5-carboxamide

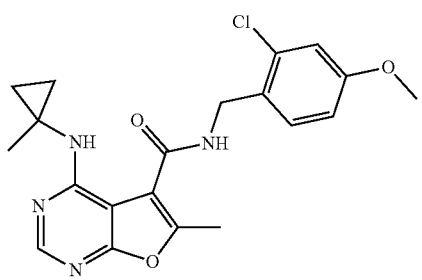

[M+H]=401.2.

Example 552. N-[(2-Ethoxy-6-fluorophenyl)
methyl]-6-methyl-4-[(1-methylcyclopropyl)amino]
furo[2,3-d]pyrimidine-5-carboxamide

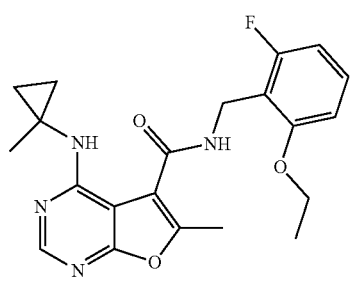 [SMILES: CCOc1cccc(F)c1CNC(=O)c1c(C)oc2ncnc(NC3(C)CC3)c12]

[M+H]=399.2.

Example 553. N-[(4-Fluoro-3-methylphenyl)
methyl]-6-methyl-4-[(1-methylcyclopropyl)amino]
furo[2,3-d]pyrimidine-5-carboxamide

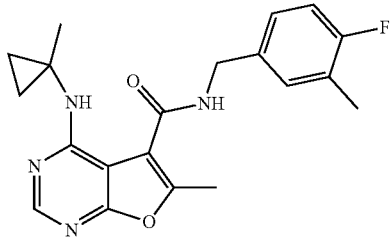 [SMILES: Cc1cc(CNC(=O)c2c(C)oc3ncnc(NC4(C)CC4)c23)ccc1F]

[M+H]=369.2.

Example 554. N-[(5-Fluoro-2-methylphenyl)
methyl]-6-methyl-4-[(1-methylcyclopropyl)amino]
furo[2,3-d]pyrimidine-5-carboxamide

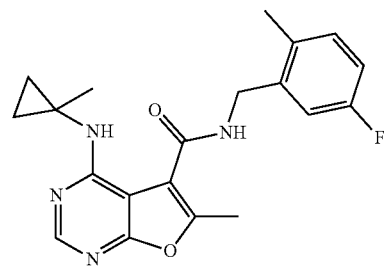 [SMILES: Cc1ccc(F)cc1CNC(=O)c1c(C)oc2ncnc(NC3(C)CC3)c12]

[M+H]=369.2.

Example 555. N-[1-(3,5-Dimethoxyphenyl)ethyl]-6-
methyl-4-[(1-methylcyclopropyl)amino]furo[2,3-d]
pyrimidine-5-carboxamide

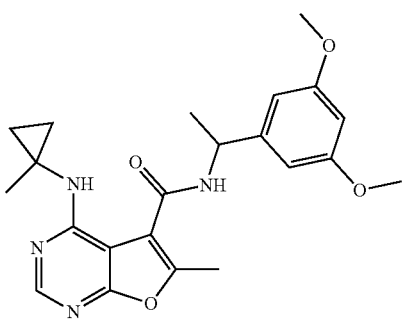

[M+H]=411.2.

Example 556. N-[(1R)-1-(3,4-Dimethoxyphenyl)ethyl]-6-methyl-4-[(1-methylcyclopropyl)amino]furo[2,3-d]pyrimidine-5-carboxamide

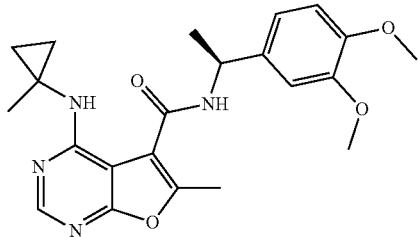

[M+H]=411.2.

Example 557. N-[2-(2-Methoxyphenoxy)ethyl]-6-methyl-4-[(1-methylcyclopropyl)amino]furo[2,3-d]pyrimidine-5-carboxamide

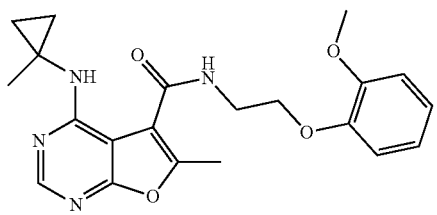 [SMILES: COc1ccccc1OCCNC(=O)c1c(C)oc2ncnc(NC3(C)CC3)c12]

[M+H]=397.2.

Example 558. N-[2-(2-Methoxyphenoxy)ethyl]-N,6-dimethyl-4-[(1-methylcyclopropyl)amino]furo[2,3-d]pyrimidine-5-carboxamide

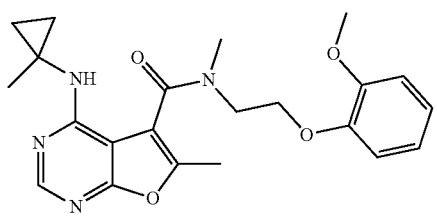 [SMILES: COc1ccccc1OCCN(C)C(=O)c1c(C)oc2ncnc(NC3(C)CC3)c12]

[M+H]=411.2.

Example 559. N-[2-(2-Fluorophenoxy)ethyl]-6-methyl-4-[(1-methylcyclopropyl)amino]furo[2,3-d]pyrimidine-5-carboxamide

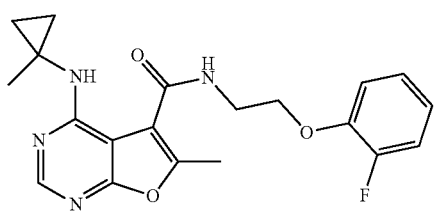 [SMILES: Cc1oc2ncnc(NC3(C)CC3)c2c1C(=O)NCCOc1ccccc1F]

[M+H]=385.2.

Example 560. N-[(1R)-1-(4-Methoxyphenyl)ethyl]-6-methyl-4-[(1-methylcyclopropyl)amino]furo[2,3-d]pyrimidine-5-carboxamide

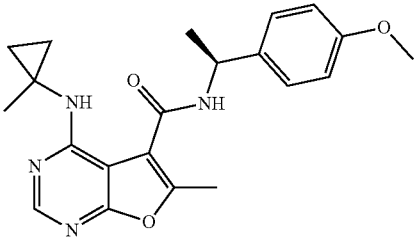

[M+H]=381.2.

Example 561. N-[(5-Chloro-2-fluorophenyl)methyl]-6-methyl-4-[(1-methylcyclopropyl)amino]furo[2,3-d]pyrimidine-5-carboxamide

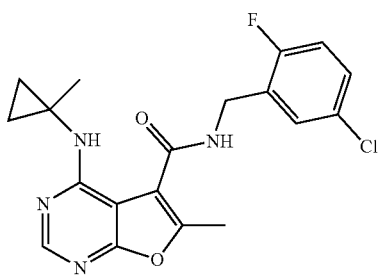 [SMILES: Cc1oc2ncnc(NC3(C)CC3)c2c1C(=O)NCc1cc(Cl)ccc1F]

[M+H]=389.1.

Example 562. N-[(3-Fluoro-4-methylphenyl)methyl]-6-methyl-4-[(1-methylcyclopropyl)amino]furo[2,3-d]pyrimidine-5-carboxamide

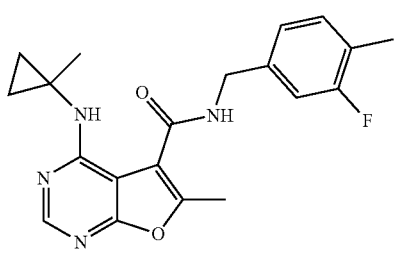 [SMILES: Cc1ccc(CNC(=O)c2c(C)oc3ncnc(NC4(C)CC4)c23)cc1F]

[M+H]=369.2.

Example 563. 6-Methyl-4-[(1-methylcyclopropyl)amino]-N-[(3-(5-trifluorophenyl)methyl]furo[2,3-d]pyrimidine-5-carboxamide

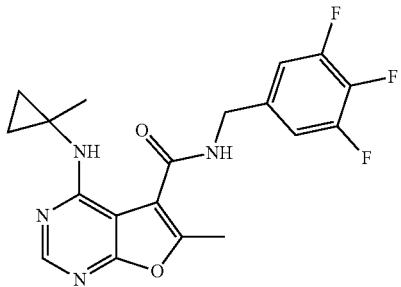 [SMILES: Cc1oc2ncnc(NC3(C)CC3)c2c1C(=O)NCc1cc(F)c(F)c(F)c1]

[M+H]=391.2.

Example 564. N-[(3-Chloro-2-fluorophenyl)methyl]-6-methyl-4-[(1-methylcyclopropyl)amino]furo[2,3-d]pyrimidine-5-carboxamide

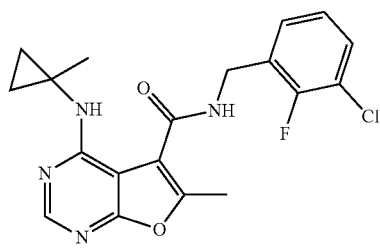 [SMILES: Cc1oc2ncnc(NC3(C)CC3)c2c1C(=O)NCc1cccc(Cl)c1F]

[M+H]=389.1.

Example 565. 5-[2-(4-Fluorophenyl)piperidine-1-carbonyl]-6-methyl-N-(1-methylcyclopropyl)furo[2,3-d]pyrimidin-4-amine

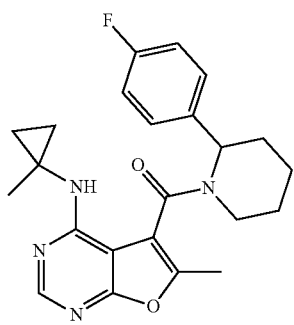 [SMILES: Cc1oc2ncnc(NC3(C)CC3)c2c1C(=O)N1CCCCC1c1ccc(F)cc1]

[M+H]=409.2.

Example 566. 5-[2-(3-Methoxyphenyl)pyrrolidine-1-carbonyl]-6-methyl-N-(1-methylcyclopropyl)furo[2,3-d]pyrimidin-4-amine

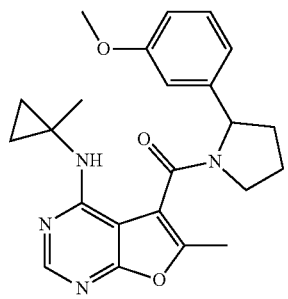 [SMILES: COc1cccc(C2CCCN2C(=O)c2c(C)oc3ncnc(NC4(C)CC4)c23)c1]

[M+H]=407.2.

Example 567. 5-[2-(3-Methoxyphenyl)piperidine-1-carbonyl]-6-methyl-N-(1-methylcyclopropyl)furo[2,3-d]pyrimidin-4-amine

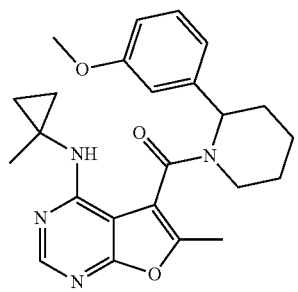 [SMILES: COc1cccc(C2CCCCN2C(=O)c2c(C)oc3ncnc(NC4(C)CC4)c23)c1]

[M+H]=421.6.

Example 568. N-[3-(5-Fluoro-1H-1,3-benzodiazol-2-yl)propyl]-6-methyl-4-[(1-methylcyclopropyl)amino]furo[2,3-d]pyrimidine-5-carboxamide

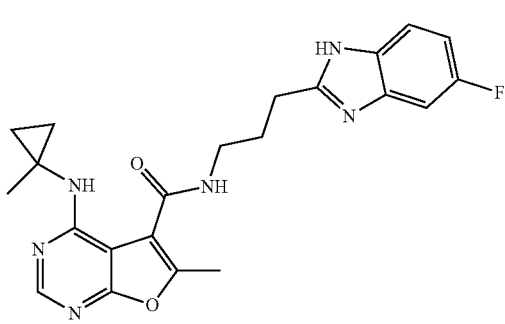 [SMILES: Cc1oc2ncnc(NC3(C)CC3)c2c1C(=O)NCCCc1nc2cc(F)ccc2[nH]1]

[M+H]=423.2.

Example 569. N-[(5-Fluoro-1H-indol-2-yl)methyl]-N,6-dimethyl-4-[(1-methylcyclopropyl)amino]furo[2,3-d]pyrimidine-5-carboxamide

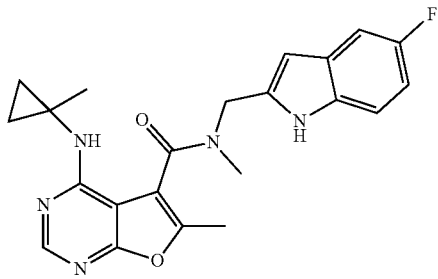 [SMILES: Cc1oc2ncnc(NC3(C)CC3)c2c1C(=O)N(C)Cc1cc2cc(F)ccc2[nH]1]

[M+H]=408.2.

Example 570. N-[(5-Methoxy-1H-indol-2-yl)methyl]-6-methyl-4-[(1-methylcyclopropyl)amino]furo[2,3-d]pyrimidine-5-carboxamide

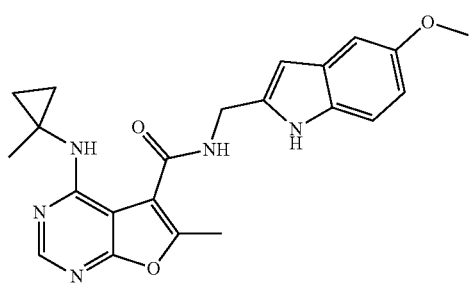

[M+H]=406.2.

Example 571. N-{[1-(4-Fluorophenyl)-1H-pyrazol-4-yl]methyl}-6-methyl-4-[(1-methylcyclopropyl)amino]furo[2,3-d]pyrimidine-5-carboxamide

[M+H]=421.2.

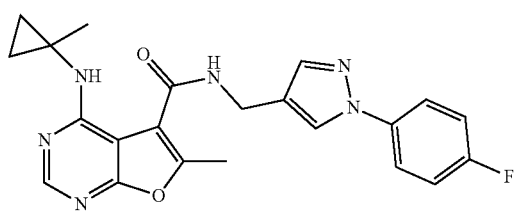 [SMILES: Cc1oc2ncnc(NC3(C)CC3)c2c1C(=O)NCc1cnn(-c2ccc(F)cc2)c1]

Example 572. N-{[1-(3-Fluorophenyl)-1H-pyrazol-4-yl]methyl}-6-methyl-4-[(1-methylcyclopropyl)amino]furo[2,3-d]pyrimidine-5-carboxamide

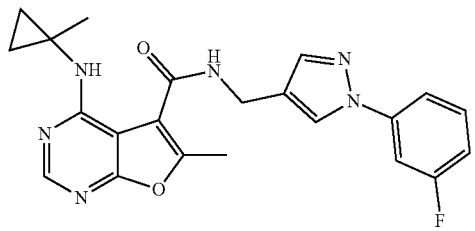 [SMILES: Cc1oc2ncnc(NC3(C)CC3)c2c1C(=O)NCc1cnn(-c2cccc(F)c2)c1]

[M+H]=421.2.

Example 573. N-(3-Hydroxypropyl)-N-[(4-methoxyphenyl)methyl]-6-methyl-4-[(1-methylcyclopropyl)amino]furo[2,3-d]pyrimidine-5-carboxamide

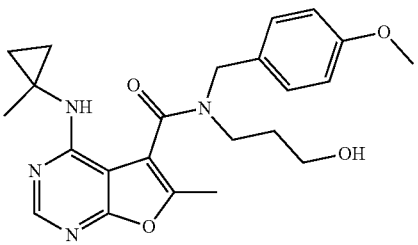

[M+H]=425.2.

Example 574. N-[(4-Fluorophenyl)methyl]-N-(3-hydroxypropyl)-6-methyl-4-[(1-methylcyclopropyl)amino]furo[2,3-d]pyrimidine-5-carboxamide

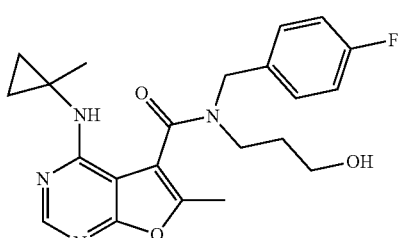

[M+H]=413.2.

Example 575. N-[(6-Fluoro-1H-1,3-benzodiazol-2-yl)methyl]-N,6-dimethyl-4-[(1-methylcyclopropyl)amino]furo[2,3-d]pyrimidine-5-carboxamide

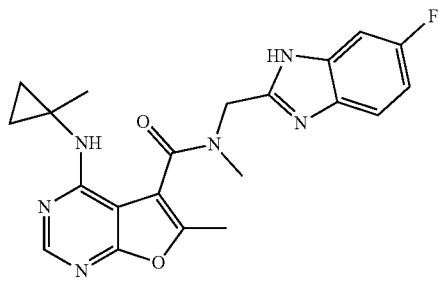 [SMILES: Cc1oc2ncnc(NC3(C)CC3)c2c1C(=O)N(C)Cc1nc2ccc(F)cc2[nH]1]

[M+H]=409.2.

Example 576. 5-[4-(2-Fluorophenoxy)piperidine-1-carbonyl]-6-methyl-N-(1-methylcyclopropyl)furo[2,3-d]pyrimidin-4-amine

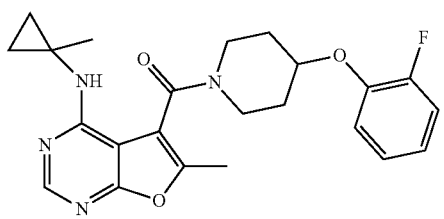 [SMILES: Cc1oc2ncnc(NC3(C)CC3)c2c1C(=O)N1CCC(Oc2ccccc2F)CC1]

[M+H]=425.2.

Example 577. 5-[4-(4-Fluorophenoxy)piperidine-1-carbonyl]-6-methyl-N-(1-methylcyclopropyl)furo[2,3-d]pyrimidin-4-amine

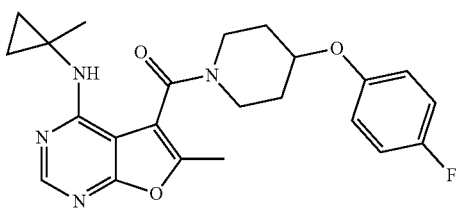 [SMILES: Cc1oc2ncnc(NC3(C)CC3)c2c1C(=O)N1CCC(Oc2ccc(F)cc2)CC1]

[M+H]=425.2.

Example 578. N-(2-Hydroxyethyl)-N-[(2-methoxyphenyl)methyl]-6-methyl-4-[(1-methylcyclopropyl)amino]furo[2,3-d]pyrimidine-5-carboxamide

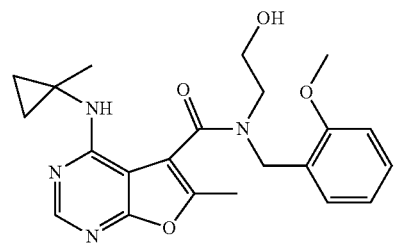 [SMILES: COc1ccccc1CN(CCO)C(=O)c1c(C)oc2ncnc(NC3(C)CC3)c12]

[M+H]=411.3.

Example 579. N-(2-Methoxyethyl)-N-[(2-methoxyphenyl)methyl]-6-methyl-4-[(1-methylcyclopropyl)amino]furo[2,3-d]pyrimidine-5-carboxamide

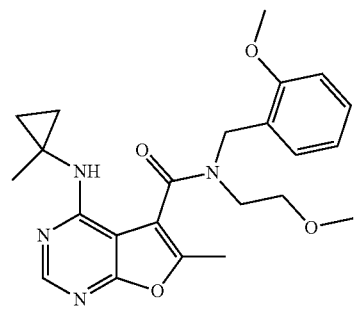

[M+H]=425.3.

Example 580. N-(2-Methoxyethyl)-N-[(3-methoxyphenyl)methyl]-6-methyl-4-[(1-methylcyclopropyl)amino]furo[2,3-d]pyrimidine-5-carboxamide

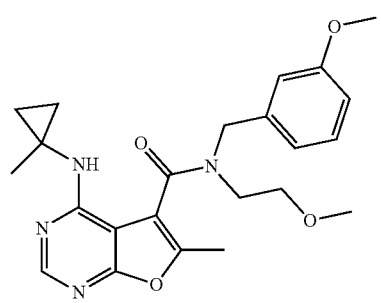

[M+H]=425.2.

Example 581. N-[1-(2-Methoxyphenyl)ethyl]-N,6-dimethyl-4-[(1-methylcyclopropyl)amino]furo[2,3-d]pyrimidine-5-carboxamide

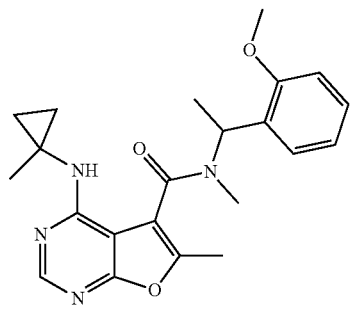 [SMILES: COc1ccccc1C(C)N(C)C(=O)c1c(C)oc2ncnc(NC3(C)CC3)c12]

[M+H]=395.3.

Example 582. N-{[3-(4-Fluorophenyl)-1H-pyrazol-4-yl]methyl}-6-methyl-4-[(1-methylcyclopropyl)amino]furo[2,3-d]pyrimidine-5-carboxamide

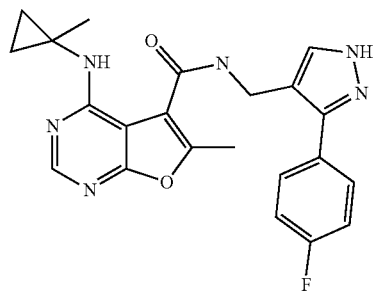 [SMILES: Cc1oc2ncnc(NC3(C)CC3)c2c1C(=O)NCc1c[nH]nc1-c1ccc(F)cc1]

[M+H]=421.3.

Example 583. N-[2-(5-Fluoro-1H-1,3-benzodiazol-2-yl)ethyl]-N,6-dimethyl-4-[(1-methylcyclopropyl)amino]furo[2,3-d]pyrimidine-5-carboxamide

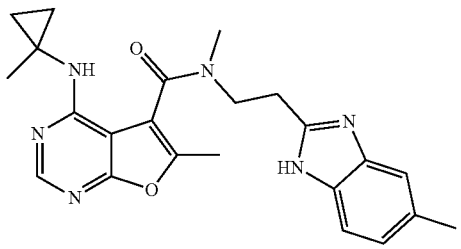

[M+H]=423.3.

Example 584. N-[(7-Fluoro-2-oxo-1,2-dihydroquinolin-3-yl)methyl]-6-methyl-4-[(1-methylcyclopropyl)amino]furo[2,3-d]pyrimidine-5-carboxamide

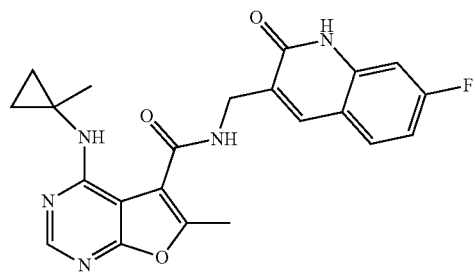 [SMILES: Cc1oc2ncnc(NC3(C)CC3)c2c1C(=O)NCc1cc2ccc(F)cc2[nH]c1=O]

[M+H]=422.2.

Example 585. N-[2-(4-Fluorophenoxy)ethyl]-6-methyl-4-[(1-methylcyclopropyl)amino]furo[2,3-d]pyrimidine-5-carboxamide

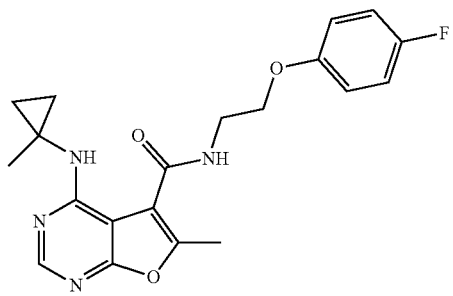 [SMILES: Cc1oc2ncnc(NC3(C)CC3)c2c1C(=O)NCCOc1ccc(F)cc1]

[M+H]=385.2.

Example 586. N-{2-[(4-Methoxyphenyl)sulfanyl]ethyl}-6-methyl-4-[(1-methylcyclopropyl)amino]furo[2,3-d]pyrimidine-5-carboxamide

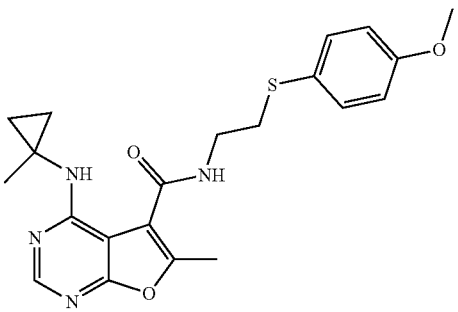

[M+H]=413.3.

Example 587. 5-[2-(3-Fluorophenyl)azepane-1-carbonyl]-6-methyl-N-(1-methylcyclopropyl)furo[2,3-d]pyrimidin-4-amine

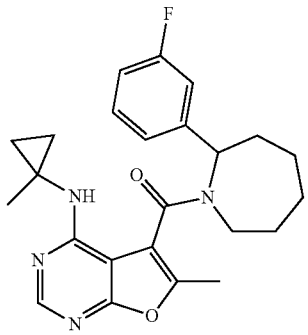 [SMILES: Cc1oc2ncnc(NC3(C)CC3)c2c1C(=O)N1CCCCCC1c1cccc(F)c1]

[M+H]=423.3.

Example 588. N-{[1-(4-Fluorophenyl)pyrrolidin-3-yl]methyl}-6-methyl-4-[(1-methylcyclopropyl)amino]furo[2,3-d]pyrimidine-5-carboxamide

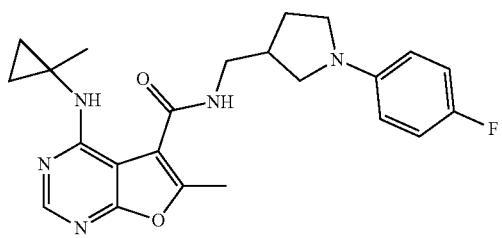 [SMILES: Cc1oc2ncnc(NC3(C)CC3)c2c1C(=O)NCC1CCN(c2ccc(F)cc2)C1]

[M+H]=424.3.

Example 589. 5-[3-(2-Methoxyphenoxy)azetidine-1-carbonyl]-6-methyl-N-(1-methylcyclopropyl)furo[2,3-d]pyrimidin-4-amine

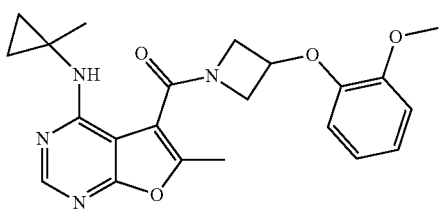 [SMILES: COc1ccccc1OC1CN(C(=O)c2c(C)oc3ncnc(NC4(C)CC4)c23)C1]

[M+H]=409.3.

Example 590. 5-[3-(3-Methoxyphenoxy)azetidine-1-carbonyl]-6-methyl-N-(1-methylcyclopropyl)furo[2,3-d]pyrimidin-4-amine

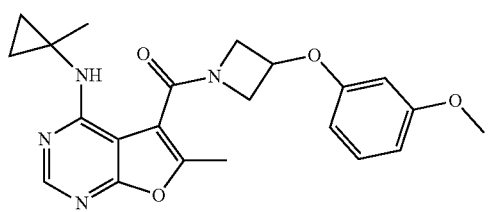 [SMILES: COc1cccc(OC2CN(C(=O)c3c(C)oc4ncnc(NC5(C)CC5)c34)C2)c1]

[M+H]=409.3.

Example 591. N-Ethyl-N-[(2-methoxyphenyl)methyl]-6-methyl-4-[(1-methylcyclopropyl)amino]furo[2,3-d]pyrimidine-5-carboxamide

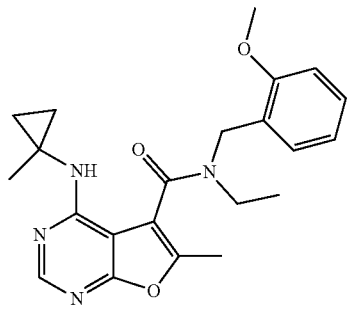 [SMILES: CCN(Cc1ccccc1OC)C(=O)c1c(C)oc2ncnc(NC3(C)CC3)c12]

[M+H]=395.3.

Example 592. N-{[3-Methoxy-4-(propan-2-yloxy)phenyl]methyl}-6-methyl-4-[(1-methylcyclopropyl)amino]furo[2,3-d]pyrimidine-5-carboxamide

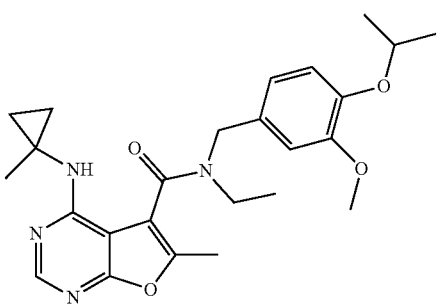 [SMILES: CCN(Cc1ccc(OC(C)C)c(OC)c1)C(=O)c1c(C)oc2ncnc(NC3(C)CC3)c12]

[M+H]=425.3.

Example 593. N-{[1-(3-Fluorophenyl)cyclopentyl]
methyl}-6-methyl-4-[(1-methylcyclopropyl)amino]
furo[2,3-d]pyrimidine-5-carboxamide

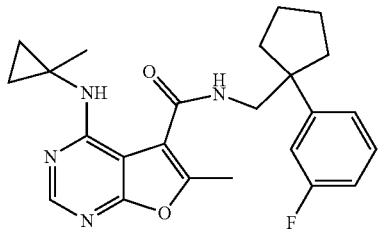 [SMILES: Cc1oc2ncnc(NC3(C)CC3)c2c1C(=O)NCC1(c2cccc(F)c2)CCCC1]

[M+H]=423.3.

Example 594. N-{[1-(2-Fluorophenyl)cyclopentyl]
methyl}-6-methyl-4-[(1-methylcyclopropyl)amino]
furo[2,3-d]pyrimidine-5-carboxamide

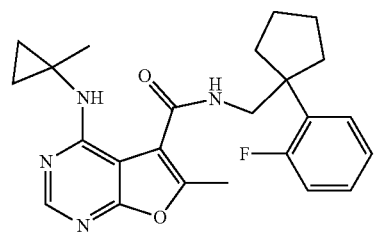 [SMILES: Cc1oc2ncnc(NC3(C)CC3)c2c1C(=O)NCC1(c2ccccc2F)CCCC1]

[M+H]=423.3.

Example 595. N-[1-(4-Ethoxy-3-fluorophenyl)
ethyl]-6-methyl-4-[(1-methylcyclopropyl)amino]furo
[2,3-d]pyrimidine-5-carboxamide

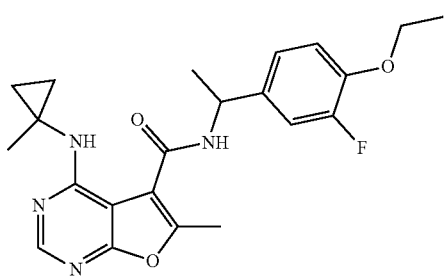 [SMILES: CCOc1ccc(C(C)NC(=O)c2c(C)oc3ncnc(NC4(C)CC4)c23)cc1F]

[M+H]=413.3.

Example 596. N-{[3-(3-Fluorophenyl)-1,2-oxazol-5-
yl]methyl}-6-methyl-4-[(1-methylcyclopropyl)
amino]furo[2,3-d]pyrimidine-5-carboxamide

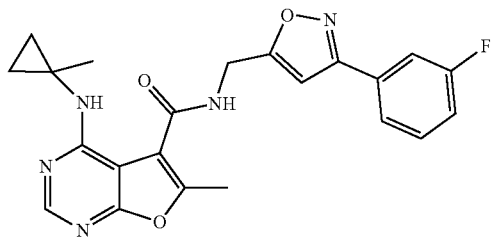 [SMILES: Cc1oc2ncnc(NC3(C)CC3)c2c1C(=O)NCc1cc(-c2cccc(F)c2)no1]

[M+H]=422.3.

Example 597. N-[1-(3,4-Dimethoxyphenyl)propyl]-
6-methyl-4-[(1-methylcyclopropyl)amino]furo[2,3-
d]pyrimidine-5-carboxamide

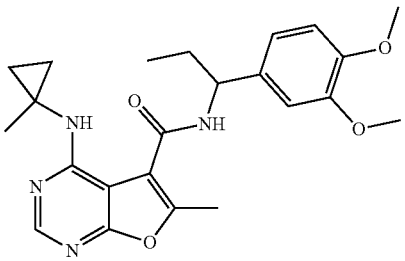

[M+H]=425.3.

Example 598. N-[1-(4-Methoxy-3,5-dimethylphe-
nyl)ethyl]-6-methyl-4-[(1-methylcyclopropyl)amino]
furo[2,3-d]pyrimidine-5-carboxamide

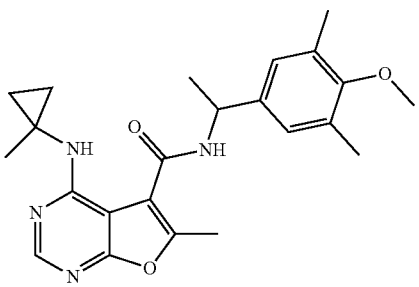

[M+H]=409.3.

Example 599. N-[2-Hydroxy-3-(3-methoxyphenoxy)propyl]-6-methyl-4-[(1-methylcyclopropyl)amino]furo[2,3-d]pyrimidine-5-carboxamide

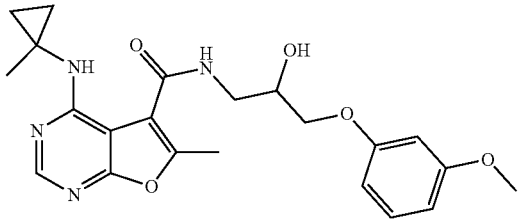

[M+H]=427.3.

Example 600. 5-(10-Methoxy-3,4,5,6-tetrahydro-2H-1,5-benzoxazocine-5-carbonyl)-6-methyl-N-(1-methylcyclopropyl)furo[2,3-d]pyrimidin-4-amine

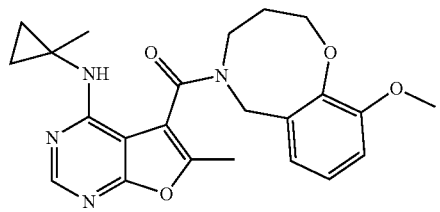 [SMILES: COc1cccc2c1OCCCN(C(=O)c1c(C)oc3ncnc(NC4(C)CC4)c13)C2]

[M+H]=423.2.

Example 601. N-Ethyl-N-[(3-Methoxyphenyl)methyl]-6-methyl-4-[(1-methylcyclopropyl)amino]furo[2,3-d]pyrimidine-5-carboxamide

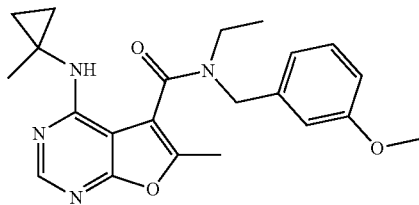

[M+H]=395.2.

Example 602. N-Ethyl-N-[2-(4-methoxyphenoxy)ethyl]-6-methyl-4-[(1-methylcyclopropyl)amino]furo[2,3-d]pyrimidine-5-carboxamide

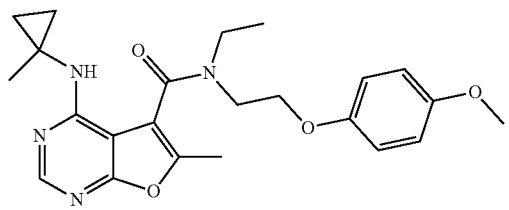

[M+H]=425.2.

Example 603. N-Cyclopropyl-N-[(2-methoxyphenyl)methyl]-6-methyl-4-[(1-methylcyclopropyl)amino]furo[2,3-d]pyrimidine-5-carboxamide

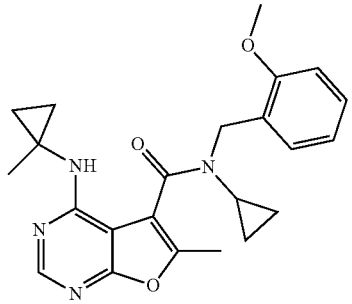 [SMILES: COc1ccccc1CN(C(=O)c1c(C)oc2ncnc(NC3(C)CC3)c12)C1CC1]

[M+H]=407.2.

Example 604. N-[(3-Hydroxy-4-methoxyphenyl)methyl]-N,6-dimethyl-4-[(1-methylcyclopropyl)amino]furo[2,3-d]pyrimidine-5-carboxamide

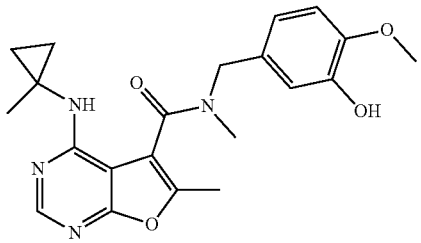

[M+H]=397.2.

Example 605. N-[3-(4-Methoxyphenoxy)propyl]-N,6-dimethyl-4-[(1-methylcyclopropyl)amino]furo[2,3-d]pyrimidine-5-carboxamide

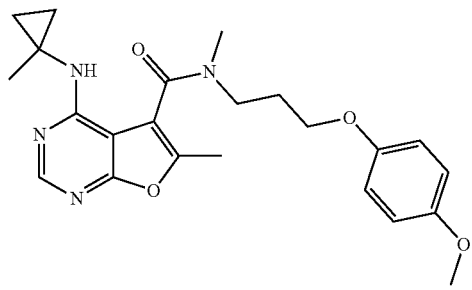 [SMILES: COc1ccc(OCCCN(C)C(=O)c2c(C)oc3ncnc(NC4(C)CC4)c23)cc1]

[M+H]=425.3.

Example 606. N-[(4-Methoxyphenyl)methyl]-6-methyl-4-[(1-methylcyclopropyl)amino]-N-(prop-2-yn-1-yl)furo[2,3-d]pyrimidine-5-carboxamide

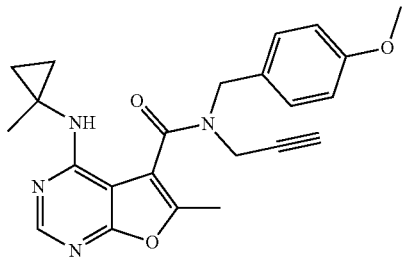

[M+H]=405.3.

Example 607. N-[(4-Fluorophenyl)methyl]-6-methyl-4-[(1-methylcyclopropyl)amino]-N-(prop-2-yn-1-yl)furo[2,3-d]pyrimidine-5-carboxamide

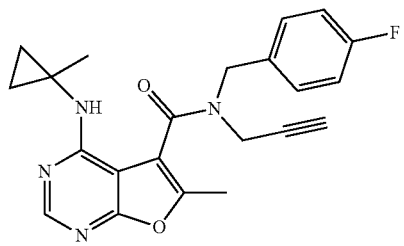 [SMILES: C#CCN(Cc1ccc(F)cc1)C(=O)c1c(C)oc2ncnc(NC3(C)CC3)c12]

[M+H]=393.2.

Example 608. N-[(5-Chloro-2-methoxyphenyl)methyl]-N,6-dimethyl-4-[(1-methylcyclopropyl)amino]furo[2,3-d]pyrimidine-5-carboxamide

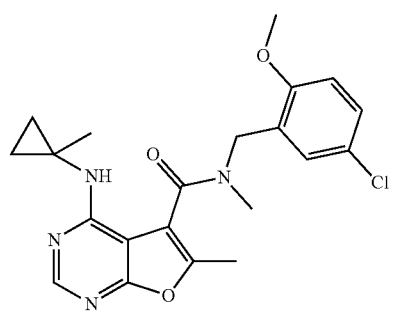 [SMILES: COc1ccc(Cl)cc1CN(C)C(=O)c1c(C)oc2ncnc(NC3(C)CC3)c12]

[M+H]=415.2.

Example 609. N-Ethyl-N-[(4-fluorophenyl)methyl]-6-methyl-4-[(1-methylcyclopropyl)amino]furo[2,3-d]pyrimidine-5-carboxamide

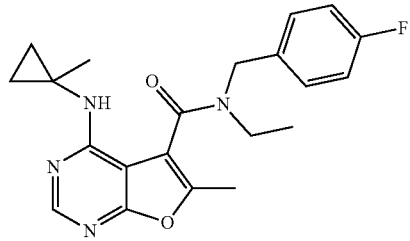 [SMILES: CCN(Cc1ccc(F)cc1)C(=O)c1c(C)oc2ncnc(NC3(C)CC3)c12]

[M+H]=383.3.

Example 610. N-[(2-Chloro-4,5-difluorophenyl)methyl]-6-methyl-4-[(1-methylcyclopropyl)amino]furo[2,3-d]pyrimidine-5-carboxamide

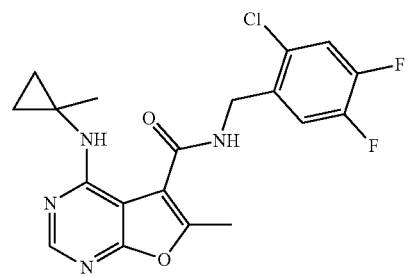 [SMILES: Cc1oc2ncnc(NC3(C)CC3)c2c1C(=O)NCc1cc(F)c(F)cc1Cl]

[M+H]=407.2.

Example 611. N-[(2-Fluoro-5-methylphenyl)methyl]-6-methyl-4-[(1-methylcyclopropyl)amino]furo[2,3-d]pyrimidine-5-carboxamide

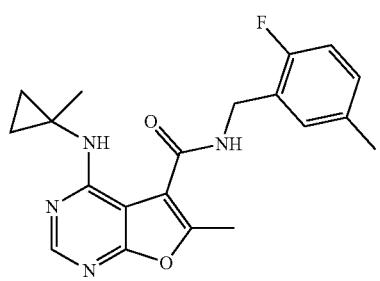 [SMILES: Cc1ccc(F)c(CNC(=O)c2c(C)oc3ncnc(NC4(C)CC4)c23)c1]

[M+H]=369.2.

Example 612. N-[(4-Chloro-2,6-difluorophenyl)methyl]-6-methyl-4-[(1-methylcyclopropyl)amino]furo[2,3-d]pyrimidine-5-carboxamide

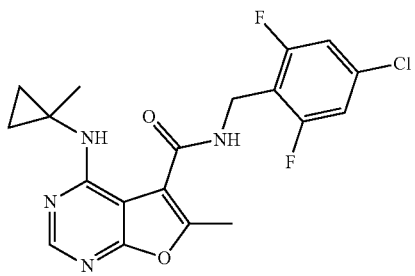 [SMILES: Cc1oc2ncnc(NC3(C)CC3)c2c1C(=O)NCc1c(F)cc(Cl)cc1F]

[M+H]=407.2.

Example 613. N-[1-(2-Methoxyphenyl)ethyl]-6-methyl-4-[(1-methylcyclopropyl)amino]furo[2,3-d]pyrimidine-5-carboxamide

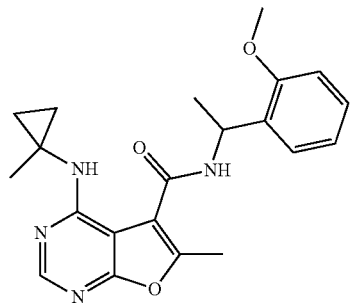 [SMILES: COc1ccccc1C(C)NC(=O)c1c(C)oc2ncnc(NC3(C)CC3)c12]

[M+H]=381.2.

Example 614. N-[(2-Fluoro-5-nitrophenyl)methyl]-6-methyl-4-[(1-methylcyclopropyl)amino]furo[2,3-d]pyrimidine-5-carboxamide

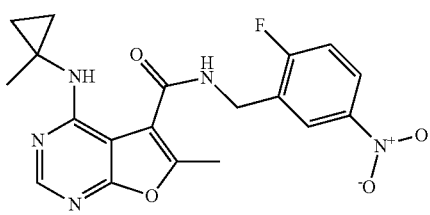

[M+H]=400.2.

Example 615. N-[(1R)-1-(5-Fluoropyrimidin-2-yl)ethyl]-6-methyl-4-[(1-methylcyclopropyl)amino]furo[2,3-d]pyrimidine-5-carboxamide

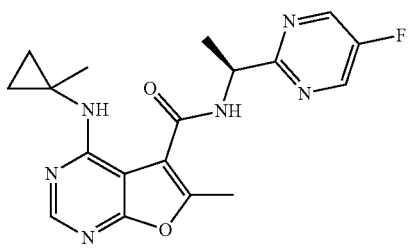 [SMILES: Cc1oc2ncnc(NC3(C)CC3)c2c1C(=O)N[C@@H](C)c1ncc(F)cn1]

[M+H]=371.2.

Example 616. N-Ethyl-N-[(3-fluorophenyl)methyl]-6-methyl-4-[(1-methylcyclopropyl)amino]furo[2,3-d]pyrimidine-5-carboxamide

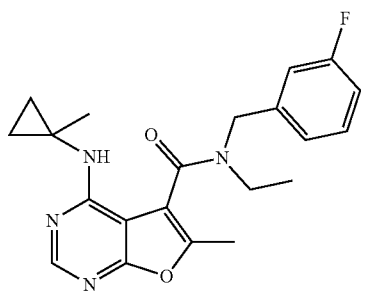 [SMILES: CCN(Cc1cccc(F)c1)C(=O)c1c(C)oc2ncnc(NC3(C)CC3)c12]

[M+H]=383.2.

Example 617. N-[2-(3,4-Dimethoxyphenyl)ethyl]-N,6-dimethyl-4-[(1-methylcyclopropyl)amino]furo[2,3-d]pyrimidine-5-carboxamide

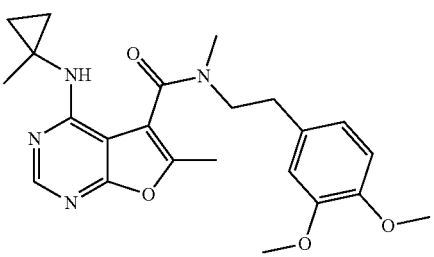

[M+H]=425.2.

Example 618. N-[1-(4-Fluorophenyl)ethyl]-N,6-dimethyl-4-[(1-methylcyclopropyl)amino]furo[2,3-d]pyrimidine-5-carboxamide

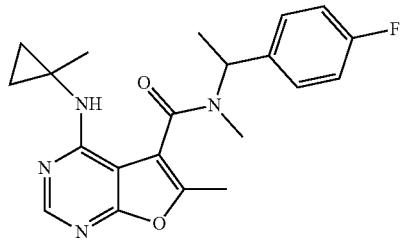 [SMILES: Cc1oc2ncnc(NC3(C)CC3)c2c1C(=O)N(C)C(C)c1ccc(F)cc1]

[M+H]=383.2.

Example 619. N-[2-(4-Methoxyphenyl)ethyl]-6-methyl-4-[(1-methylcyclopropyl)amino]furo[2,3-d]pyrimidine-5-carboxamide

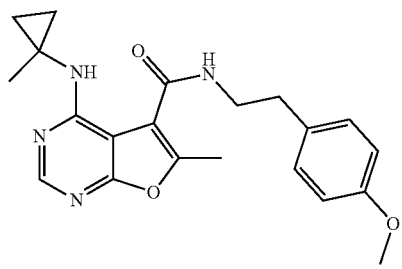 [SMILES: COc1ccc(CCNC(=O)c2c(C)oc3ncnc(NC4(C)CC4)c23)cc1]

[M+H]=381.2.

Example 620. 6-Methyl-4-[(1-methylcyclopropyl)amino]-N-[1-(pyridin-3-yl)-1H-pyrazol-4-yl]furo[2,3-d]pyrimidine-5-carboxamide

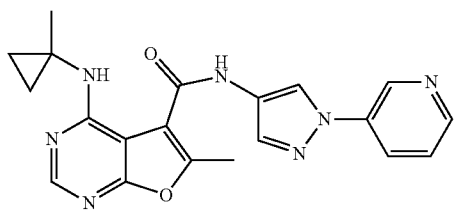 [SMILES: Cc1oc2ncnc(NC3(C)CC3)c2c1C(=O)Nc1cnn(-c2cccnc2)c1]

¹H NMR (400 MHz, CD₃OD) δ 9.19 (d, J=2.0 Hz, 1H), 8.86 (s, 1H), 8.59 (d, J=4.8 Hz, 1H), 8.53 (d, J=8.4 Hz, 1H), 8.41 (s, 1H), 8.01 (s, 1H), 7.82-7.73 (m, 1H), 2.79 (s, 3H), 1.54 (s, 3H), 1.03-0.88 (m, 4H). [M+H]=390.37.

Example 621. 6-Methyl-4-[(1-methylcyclopropyl)amino]-N-[1-(pyridin-4-yl)-1H-pyrazol-4-yl]furo[2,3-d]pyrimidine-5-carboxamide

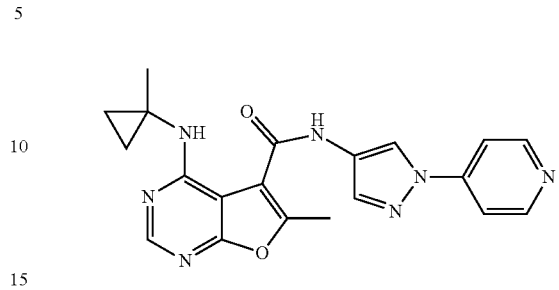

¹H NMR (400 MHz, CD₃OD) δ 9.10 (s, 1H), 8.81 (d, J=7.2 Hz, 2H), 8.44 (d, J=7.3 Hz, 2H), 8.38 (s, 1H), 8.17 (s, 1H), 2.78 (s, 3H), 1.52 (s, 3H), 0.97-0.84 (m, 4H). [M+H]=390.37.

Example 622. 5-{4-Methoxy-5H,6H,7H-pyrrolo[3,4-d]pyrimidine-6-carbonyl}-6-methyl-N-(1-methylcyclopropyl)furo[2,3-d]pyrimidin-4-amine

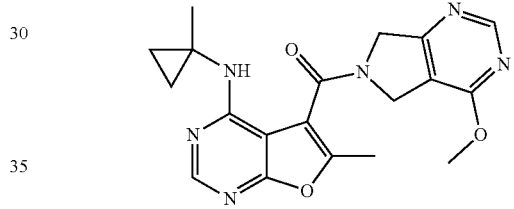

¹H NMR (400 MHz, CD₃OD) δ 8.72 (br s, 1H), 8.42 (s, 1H), 4.99 (br s, 4H), 4.15-3.99 (m, 3H), 2.65 (s, 3H), 1.49 (s, 3H), 0.96-0.83 (m, 4H). [M+H]=381.38.

Example 623. 6-Methyl-N-(1-methylcyclopropyl)-5-[2-(trifluoromethyl)-5H,6H,7H,8H-imidazo[1,2-a]pyrazine-7-carbonyl]furo[2,3-d]pyrimidin-4-amine

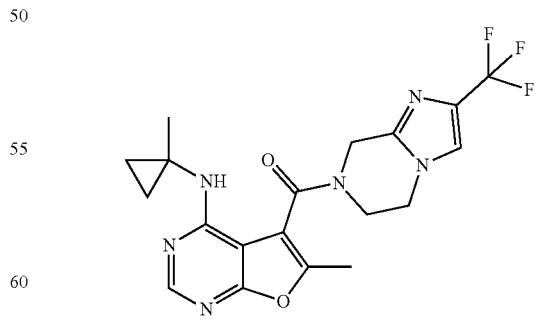

¹H NMR (400 MHz, CDCl₃) δ 8.50 (s, 1H), 7.30 (d, J=0.98 Hz, 1H), 6.97 (s, 1H), 4.95 (br s, 2H), 3.87-4.68 (m, 4H), 2.54 (s, 3H), 1.52 (s, 3H), 0.75-0.83 (m, 4H). [M+H]=421.4.

Example 624. 5-{3-Bromo-5H,6H,7H,8H-imidazo[1,2-a]pyrazine-7-carbonyl}-6-methyl-N-(1-methylcyclopropyl)furo[2,3-d]pyrimidin-4-amine

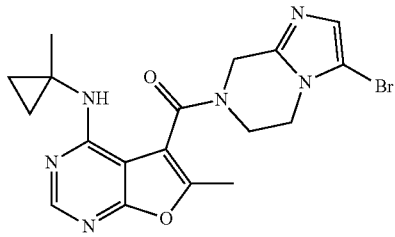 [SMILES: Cc1oc2ncnc(NC3(C)CC3)c2c1C(=O)N1CCn2c(Br)cnc2C1]

¹H NMR (400 MHz, CDCl₃) δ 8.50 (s, 1H), 7.05 (s, 1H), 6.97 (s, 1H), 4.88 (br s, 2H), 3.89-4.47 (m, 4H), 2.53 (s, 3H), 1.53 (s, 3H), 0.75-0.85 (m, 4H). [M+H]=431.3, 433.3.

Example 625. 6-Methyl-4-[(1-methylcyclopropyl)amino]-N-[(2-methylpyrimidin-4-yl)methyl]furo[2,3-d]pyrimidine-5-carboxamide

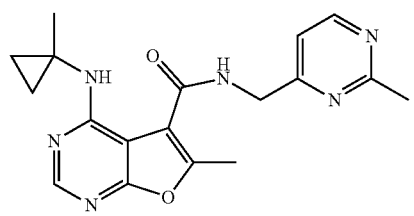 [SMILES: Cc1nccc(CNC(=O)c2c(C)oc3ncnc(NC4(C)CC4)c23)n1]

¹H NMR (400 MHz, CD₃OD) δ 8.66 (d, J=5.4 Hz, 1H), 8.41 (s, 1H), 7.39 (d, J=5.4 Hz, 1H), 4.73 (s, 2H), 2.86 (s, 3H), 2.72 (s, 3H), 1.52 (s, 3H), 1.00-0.84 (m, 5H). [M+H]=353.4.

Example 626. N-{[5-(Chlorodifluoromethyl)-1,2,4-oxadiazol-3-yl]methyl}-6-methyl-4-[(1-methylcyclopropyl)amino]furo[2,3-d]pyrimidine-5-carboxamide

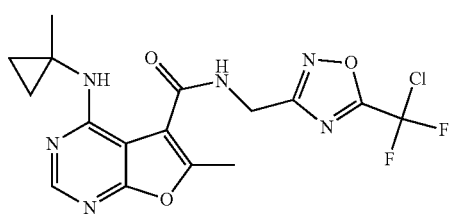 [SMILES: Cc1oc2ncnc(NC3(C)CC3)c2c1C(=O)NCc1noc(C(F)(F)Cl)n1]

¹H NMR (400 MHz, CD₃OD) δ 8.36 (s, 1H), 4.87 (br s, 2H), 2.76 (s, 3H), 1.52 (s, 3H), 1.03-0.74 (m, 4H). [M+H]=413.3.

Example 627. 6-Methyl-N-[(3-methyl-1 2 4-oxadiazol-5-yl)methyl]-4-[(1-methylcyclopropyl)amino]furo[2,3-d]pyrimidine-5-carboxamide

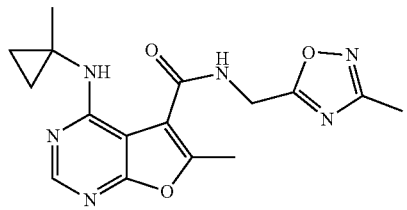 [SMILES: Cc1noc(CNC(=O)c2c(C)oc3ncnc(NC4(C)CC4)c23)n1]

¹H NMR (400 MHz, CD₃OD) δ 8.39 (s, 1H), 4.85 (br s, 2H), 2.78 (s, 3H), 2.39 (s, 3H), 1.52 (s, 3H), 0.97-0.84 (m, 4H). [M+H]=343.4.

Example 628. 6-Methyl-N-(1-methylcyclopropyl)-5-[4-(propan-2-yl)-5H,6H,7H,8H-pyrido[3,4-d]pyrimidine-7-carbonyl]furo[2,3-d]pyrimidin-4-amine

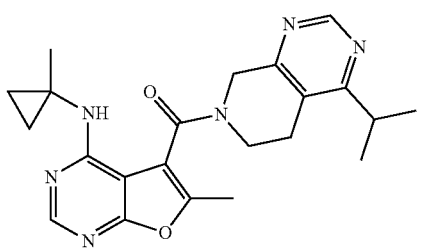

¹H NMR (400 MHz, CD₃OD) δ 8.89 (s, 1H), 8.31 (s, 1H), 5.22-4.86 (m, 2H), 4.40-3.62 (m, 2H), 3.30 (d, J=6.8 Hz, 1H), 3.02 (br s, 2H), 2.55 (s, 3H), 1.46 (s, 3H), 1.34-1.24 (m, 7H), 0.74 (s, 5H). [M+H]=407.4.

Example 629. 5-{4-Methoxy-5H,6H,7H,8H 9H-pyrimido[4,5-d]azepine-7-carbonyl}-6-methyl-N-(1-methylcyclopropyl)furo[2,3-d]pyrimidin-4-amine

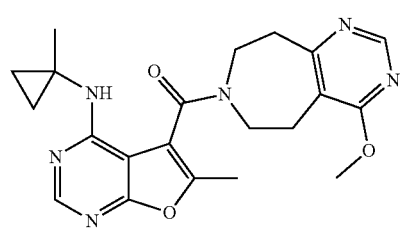 [SMILES: COc1ncnc2c1CCN(C(=O)c1c(C)oc3ncnc(NC4(C)CC4)c13)CC2]

¹H NMR (400 MHz, CD₃OD) δ 8.70 (s, 1H), 8.40 (s, 1H), 4.09 (br s, 3H), 4.04-3.81 (m, 4H), 3.32-2.93 (m, 4H), 2.54 (s, 3H), 1.51 (s, 3H), 0.89 (s, 4H). [M+H]=409.40.

Example 630. 6-Methyl-N-(1-methylcyclopropyl)-5-(5,6,7,8-tetrahydro-1,7-naphthyridine-7-carbonyl)furo[2,3-d]pyrimidin-4-amine

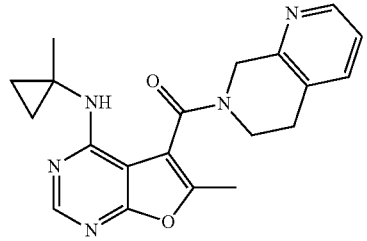

$^1$H NMR (400 MHz, CDCl$_3$) δ 8.48 (s, 1H), 8.46 (d, J=4.16 Hz, 1H), 7.54 (d, J=7.21 Hz, 1H), 7.20 (dd, J=4.77, 7.70 Hz, 1H), 7.08 (br s, 1H), 4.89 (br s, 2H), 4.06 (dd, J=6.05, 12.17 Hz, 2H), 2.94-3.08 (m, 2H), 2.53 (s, 3H), 1.50 (s, 3H), 0.69-0.85 (m, 4H). [M+H]=364.4.

Example 631. 6-Methyl-N-(1-methylcyclopropyl)-5-(5,6,7,8-tetrahydro-1,6-naphthyridine-6-carbonyl)furo[2,3-d]pyrimidin-4-amine

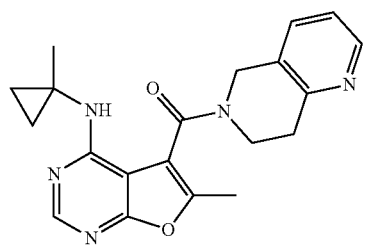 [SMILES: Cc1oc2ncnc(NC3(C)CC3)c2c1C(=O)N1CCc2cccnc2C1]

$^1$H NMR (400 MHz, CDCl$_3$) δ 8.52 (dd, J=1.59, 4.77 Hz, 1H), 8.49 (s, 1H), 7.47 (d, J=7.09 Hz, 1H), 7.22 (dd, J=4.83, 7.76 Hz, 1H), 6.95 (br s, 1H), 4.85 (br s, 2H), 4.03 (d, J=15.89 Hz, 2H), 3.17 (t, J=5.87 Hz, 2H), 2.52 (s, 3H), 1.50 (s, 3H), 0.77 (d, J=12.59 Hz, 4H). [M+H]=364.4.

Example 632. 6-Methyl-5-{2-methyl-4H,5H,6H,7H-pyrazolo[1,5-a]pyrazine-5-carbonyl}-N-(1-methylcyclopropyl)furo[2,3-d]pyrimidin-4-amine

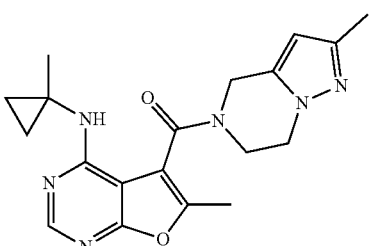

$^1$H NMR (400 MHz, CDCl$_3$) δ 8.49 (s, 1H), 6.91 (br s, 1H), 5.89 (s, 1H), 4.84 (br s, 2H), 4.26 (t, J=5.07 Hz, 2H), 3.88-4.23 (m, 2H), 2.51 (s, 3H), 2.29 (s, 3H), 1.52 (s, 3H), 0.78 (d, J=15.53 Hz, 4H). [M+H]=367.4.

Example 633. 6-Methyl-5-{2-methyl-5H,6H,7H,8H-imidazo[1,2-a]pyrazine-7-carbonyl}-N-(1-methylcyclopropyl)furo[2,3-d]pyrimidin-4-amine

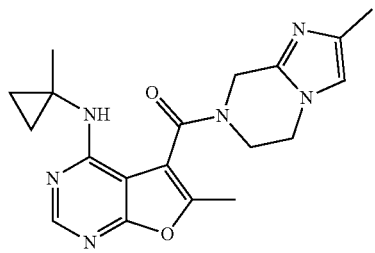 [SMILES: Cc1cn2c(n1)CN(C(=O)c1c(C)oc3ncnc(NC4(C)CC4)c13)CC2]

$^1$H NMR (400 MHz, CDCl$_3$) δ 8.39 (s, 1H), 6.61 (d, J=0.86 Hz, 1H), 4.82 (br s, 2H), 3.83-4.28 (m, 4H), 2.65 (s, 6H), 2.49 (s, 3H), 2.16 (d, J=0.86 Hz, 3H), 1.47 (s, 3H), 0.70-0.79 (m, 4H). [M+H]=367.4.

Example 634. 5-(6-Methoxy-1,2,3,4-tetrahydro-2,7-naphthyridine-2-carbonyl)-6-methyl-N-(1-methylcyclopropyl)furo[2,3-d]pyrimidin-4-amine

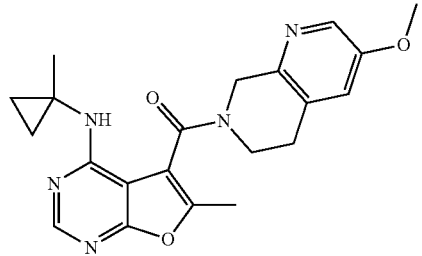 [SMILES: COc1cnc2c(c1)CCN(C(=O)c1c(C)oc3ncnc(NC4(C)CC4)c13)C2]

$^1$H NMR (400 MHz, CDCl$_3$) δ 8.49 (s, 1H), 7.96 (br s, 1H), 6.96 (br s, 1H), 6.61 (s, 1H), 4.77 (br s, 2H), 3.94 (s, 3H), 3.92 (d, J=1.47 Hz, 2H), 2.95 (t, J=5.44 Hz, 2H), 2.50 (s, 3H), 1.51 (s, 3H), 0.71-0.81 (m, 4H). [M+H]=394.4.

Example 635. 5-(2-Methoxy-5,6,7,8-tetrahydro-1,6-naphthyridine-6-carbonyl)-6-methyl-N-(1-methylcyclopropyl)furo[2,3-d]pyrimidin-4-amine

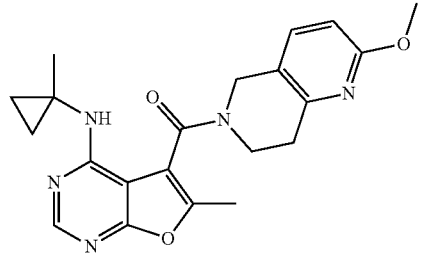 [SMILES: COc1ccc2c(n1)CCN(C(=O)c1c(C)oc3ncnc(NC4(C)CC4)c13)C2]

$^1$H NMR (400 MHz, CDCl$_3$) δ 8.49 (s, 1H), 7.31 (br s, 1H), 6.96 (br s, 1H), 6.65 (d, J=8.44 Hz, 1H), 4.73 (br s, 2H), 3.83-4.09 (m, 5H), 3.02 (br s, 2H), 2.50 (s, 3H), 1.51 (s, 3H), 0.77 (d, J=16.26 Hz, 4H). [M+H]=394.4.

Example 636. 5-{6-Methyl-4-[(1-methylcyclopropyl)amino]furo[2,3-d]pyrimidine-5-carbonyl}-4H,5H,6H,7H-pyrazolo[1,5-a]pyrazine-2-carbonitrile

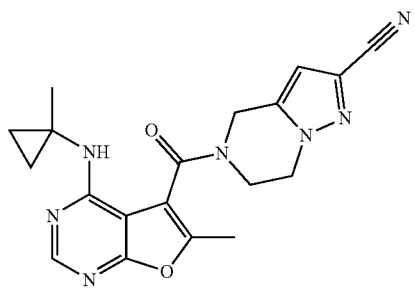 [SMILES: Cc1oc2ncnc(NC3(C)CC3)c2c1C(=O)N1CCn2nc(C#N)cc2C1]

¹H NMR (400 MHz, CDCl₃) δ 8.46-8.54 (m, 1H), 6.88 (s, 1H), 6.54 (s, 1H), 4.93 (br s, 2H), 4.39 (t, J=5.20 Hz, 2H), 3.85-4.30 (m, 2H), 2.54 (s, 3H), 1.52 (s, 3H), 0.79 (d, J=6.11 Hz, 4H). [M+H]=378.4.

Example 637. 6-Methyl-N-(1-methylcyclopropyl)-5-(1,2,3,4-tetrahydro-2 7-naphthyridine-2-carbonyl)furo[2,3-d]pyrimidin-4-amine

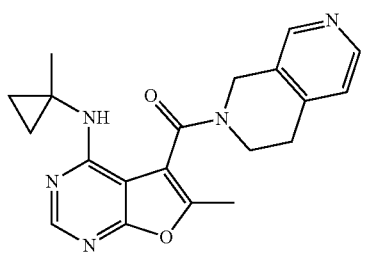 [SMILES: Cc1oc2ncnc(NC3(C)CC3)c2c1C(=O)N1CCc2ccncc2C1]

¹H NMR (400 MHz, CDCl₃) δ 8.49 (s, 1H), 8.46 (d, J=5.0 Hz, 1H), 8.42 (br s, 1H), 7.15 (d, J=5.0 Hz, 1H), 6.94 (br s, 1H), 4.86 (br s, 2H), 4.22-3.68 (m, 2H), 2.99 (t, J=5.4 Hz, 2H), 2.51 (s, 3H), 1.50 (s, 3H), 0.81-0.73 (m, 4H). [M+H]=364.4.

Example 638. 6-Methyl-N-(1-methylcyclopropyl)-5-[1-(oxan-4-yl)-3-(trifluoromethyl)-5H,6H,7H,8H-imidazo[1,5-a]pyrazine-7-carbonyl]furo[2,3-d]pyrimidin-4-amine

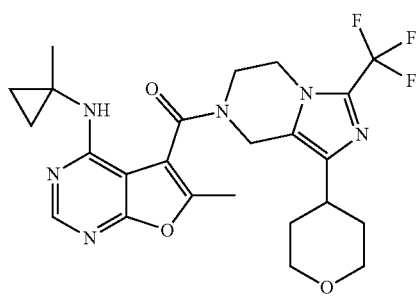 [SMILES: Cc1oc2ncnc(NC3(C)CC3)c2c1C(=O)N1CCn2c(C(F)(F)F)nc(C3CCOCC3)c2C1]

¹H NMR (400 MHz, CDCl₃) δ 8.44 (s, 1H), 6.94 (s, 1H), 4.88 (br s, 2H), 4.28-4.19 (m, 2H), 4.04 (dd, J=3.2, 11.2 Hz, 4H), 3.48 (t, J=11.7 Hz, 2H), 2.76 (t, J=11.8 Hz, 1H), 2.51 (s, 3H), 1.92 (dq, J=4.0, 12.4 Hz, 2H), 1.68 (d, J=12.7 Hz, 2H), 1.49 (s, 3H), 0.77 (d, J=8.7 Hz, 4H). [M+H]=505.5.

Example 639. 6-Methyl-5-[3-methyl-1-(oxan-4-yl)-5H,6H,7H,8H-imidazo[1,5-a]pyrazine-7-carbonyl]-N-(1-methylcyclopropyl)furo[2,3-d]pyrimidin-4-amine

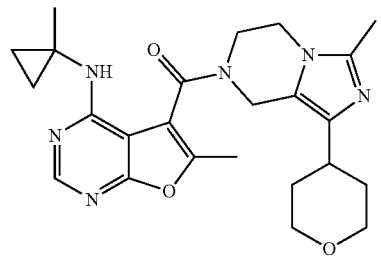 [SMILES: Cc1oc2ncnc(NC3(C)CC3)c2c1C(=O)N1CCn2c(C)nc(C3CCOCC3)c2C1]

¹H NMR (400 MHz, CDCl₃) δ 8.46 (s, 1H), 4.81 (s, 2H), 4.04 (dd, J=4.0, 11.1 Hz, 4H), 3.98-3.92 (m, 2H), 3.48 (dt, J=1.8, 11.9 Hz, 2H), 2.67 (t, J=11.9 Hz, 1H), 2.50 (s, 3H), 2.35 (s, 3H), 1.98-1.89 (m, 3H), 1.65 (d, J=11.5 Hz, 2H), 1.50 (s, 3H), 0.85-0.73 (m, 4H). [M+H]=451.5.

Example 640. 5-{5H,6H,7H,8H-Imidazo[1,5-a]pyrazine-7-carbonyl}-6-methyl-N-(1-methylcyclopropyl)furo[2,3-d]pyrimidin-4-amine

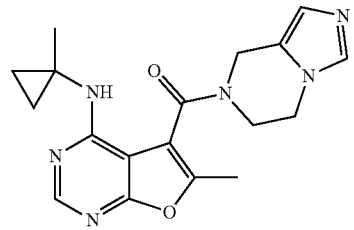 [SMILES: Cc1oc2ncnc(NC3(C)CC3)c2c1C(=O)N1CCn2cncc2C1]

¹H NMR (400 MHz, CDCl₃) δ 8.44 (s, 1H), 7.53 (s, 1H), 6.87 (s, 1H), 4.87 (br s, 2H), 4.22-4.16 (m, 2H), 4.10 (br s, 2H), 2.50 (s, 3H), 2.04 (br s, 1H), 1.49 (s, 3H), 0.83-0.71 (m, 4H). [M+H]=353.4.

Example 641. 5-{3-Bromo-4H,5H,6H,7H-pyrazolo[1,5-a]pyrazine-5-carbonyl}-6-methyl-N-(1-methylcyclopropyl)furo[2,3-d]pyrimidin-4-amine

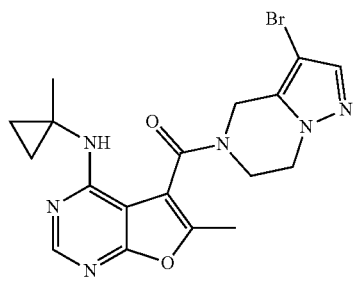 [SMILES: Cc1oc2ncnc(NC3(C)CC3)c2c1C(=O)N1CCn2ncc(Br)c2C1]

¹H NMR (400 MHz, CDCl₃) δ 8.55-8.49 (m, 1H), 7.54 (s, 1H), 6.94 (br s, 1H), 4.78 (s, 2H), 4.37-4.30 (m, 2H), 4.17 (br s, 2H), 2.53 (s, 3H), 1.53 (s, 3H), 0.87-0.76 (m, 4H). [M+H]=431.3.

Example 642. 5-(6-Chloro-1,2,3,4-tetrahydro-2,7-naphthyridine-2-carbonyl)-6-methyl-N-(1-methylcyclopropyl)furo[2,3-d]pyrimidin-4-amine

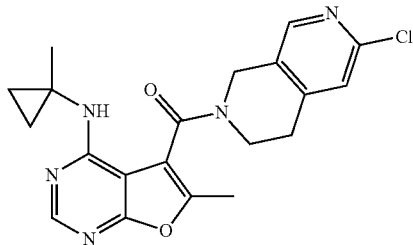 [SMILES: Cc1oc2ncnc(NC3(C)CC3)c2c1C(=O)N1CCc2cc(Cl)ncc2C1]

¹H NMR (400 MHz, CDCl₃) δ 8.49 (s, 1H), 8.20 (s, 1H), 7.21 (s, 1H), 6.93 (br s, 1H), 4.84 (br s, 2H), 3.92 (br s, 2H), 2.98 (t, J=5.6 Hz, 2H), 2.51 (s, 3H), 1.51 (s, 3H), 0.77 (d, J=10.9 Hz, 4H). [M+H]=398.3.

Example 643. N-Methoxy-N,6-dimethyl-4-[(1-methylcyclopropyl)amino]furo[2,3-d]pyrimidine-5-carboxamide

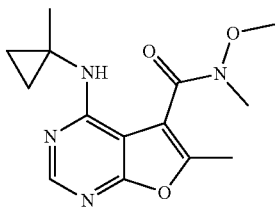 [SMILES: CON(C)C(=O)c1c(C)oc2ncnc(NC3(C)CC3)c12]

¹H NMR (400 MHz, CD₃OD) δ 8.40 (s, 1H), 3.65 (s, 3H), 3.46 (s, 3H), 2.58 (s, 3H), 1.53 (s, 3H), 0.99-0.82 (m, 4H). [M+H]=291.3.

Example 644. 6-Methyl-4-[(1-methylcyclopropyl)amino]-N-{[2-(propan-2-yl)pyrimidin-4-yl]methyl}furo[2,3-d]pyrimidine-5-carboxamide

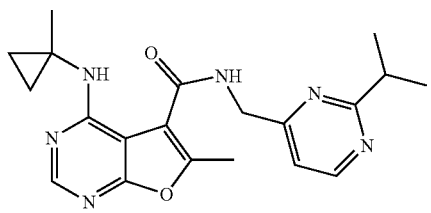 [SMILES: Cc1oc2ncnc(NC3(C)CC3)c2c1C(=O)NCc1ccnc(C(C)C)n1]

¹H NMR (400 MHz, CD₃OD) δ 8.68 (d, J=5.3 Hz, 1H), 8.43 (s, 1H), 7.38 (d, J=5.4 Hz, 1H), 4.76 (s, 2H), 3.22 (td, J=7.0, 13.8 Hz, 1H), 2.88 (s, 3H), 1.52 (s, 3H), 1.36 (d, J=6.8 Hz, 6H), 1.04-0.85 (m, 4H). [M+H]=381.4.

Example 645. N-(1-Cyclopropyl-1H-pyrazol-4-yl)-6-methyl-4-[(1-methylcyclopropyl)amino]furo[2,3-d]pyrimidine-5-carboxamide

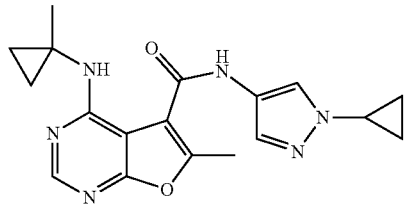 [SMILES: Cc1oc2ncnc(NC3(C)CC3)c2c1C(=O)Nc1cnn(C2CC2)c1]

¹H NMR (400 MHz, CD₃OD) δ 8.40 (s, 1H), 8.10 (s, 1H), 7.64 (s, 1H), 3.67 (td, J=3.5, 7.3 Hz, 1H), 2.75 (s, 3H), 1.53 (s, 3H), 1.16-1.04 (m, 4H), 1.01-0.87 (m, 4H). [M+H]=353.36.

Example 646. 6-Methyl-N-[(1-methyl-1H-pyrazol-4-yl)methyl]-4-[(1-methylcyclopropyl)amino]furo[2,3-d]pyrimidine-5-carboxamide

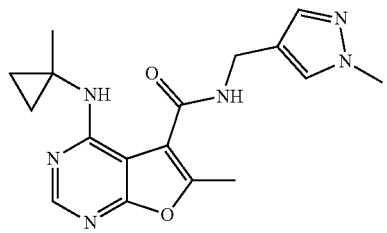 [SMILES: Cc1oc2ncnc(NC3(C)CC3)c2c1C(=O)NCc1cnn(C)c1]

¹H NMR (400 MHz, CD₃OD) δ 8.39 (s, 1H), 7.63 (s, 1H), 7.50 (s, 1H), 4.45 (s, 2H), 3.86 (s, 3H), 2.67 (s, 3H), 1.52 (s, 3H), 1.03-0.90 (m, 4H). [M+H]=341.36.

Example 647. 6-Methyl-4-[(1-methylcyclopropyl)amino]-N-(pyrimidin-5-ylmethyl)furo[2,3-d]pyrimidine-5-carboxamide

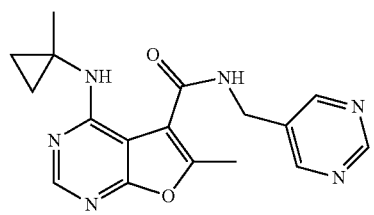 [SMILES: Cc1oc2ncnc(NC3(C)CC3)c2c1C(=O)NCc1cncnc1]

¹H NMR (400 MHz, CDCl₃) δ 9.13 (s, 1H), 8.89 (s, 2H), 8.40 (s, 1H), 4.68 (s, 2H), 2.75 (s, 3H), 1.53 (s, 3H), 1.00-0.85 (m, 5H). [M+H]=339.3.

Example 648. N-{5H,6H,7H-Cyclopenta[d]pyrimidin-2-ylmethyl}-6-methyl-4-[(1-methylcyclopropyl)amino]furo[2,3-d]pyrimidine-5-carboxamide

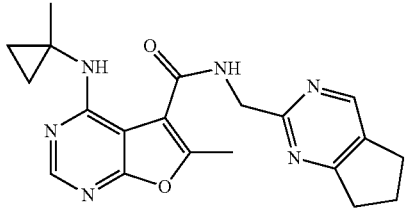 [SMILES: Cc1oc2ncnc(NC3(C)CC3)c2c1C(=O)NCc1ncc2c(n1)CCC2]

¹H NMR (400 MHz, CD₃OD) δ 8.58 (s, 1H), 8.43 (s, 1H), 4.81 (s, 2H), 3.09-2.99 (m, 4H), 2.87 (s, 3H), 2.22 (quin, J=7.7 Hz, 2H), 1.54 (s, 3H), 1.03-0.88 (m, 4H). [M+H]=379.4.

Example 649. 6-Methyl-N-{[4-methyl-6-(trifluoromethyl)pyrimidin-2-yl]methyl}-4-[(1-methylcyclopropyl)amino]furo[2,3-d]pyrimidine-5-carboxamide

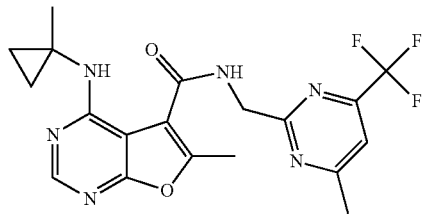 [SMILES: Cc1cc(C(F)(F)F)nc(CNC(=O)c2c(C)oc3ncnc(NC4(C)CC4)c23)n1]

¹H NMR (400 MHz, CD₃OD) δ 8.82 (br s, 1H), 8.38 (s, 1H), 7.72 (s, 1H), 4.92-4.88 (m, 2H), 2.88 (s, 3H), 2.69 (s, 3H), 1.52 (s, 3H), 0.95-0.82 (m, 4H). [M+H]=421.4.

Example 650. 6-Methyl-4-[(1-methylcyclopropyl)amino]-N-[1-(pyridin-2-yl)piperidin-4-yl]furo[2,3-d]pyrimidine-5-carboxamide

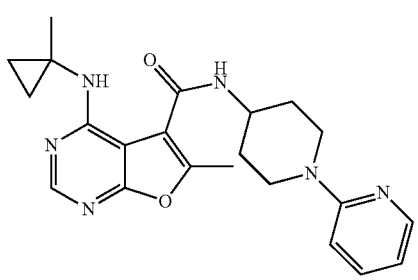 [SMILES: Cc1oc2ncnc(NC3(C)CC3)c2c1C(=O)NC1CCN(c2ccccn2)CC1]

NH NMR (400 MHz, CD₃OD) δ 8.40 (d, J=2.7 Hz, 1H), 8.34 (s, 1H), 8.18 (d, J=7.3 Hz, 1H), 8.13 (dd, J=2.6, 9.0 Hz, 1H), 8.09 (d, J=5.4 Hz, 1H), 7.83 (dd, J=5.4, 9.0 Hz, 1H), 4.27-4.17 (m, 1H), 4.03 (d, J=13.2 Hz, 2H), 3.21 (t, J=11.7 Hz, 2H), 2.66 (s, 3H), 2.17 (d, J=11.1 Hz, 2H), 1.78 (dq, J=4.0, 11.9 Hz, 2H), 1.51 (s, 3H), 0.96-0.83 (m, 4H). [M+H]=407.40.

Example 651. 6-Methyl-N-(2-methyl-1,3-benzoxazol-5-yl)-4-[(1-methylcyclopropyl)amino]furo[2,3-d]pyrimidine-5-carboxamide

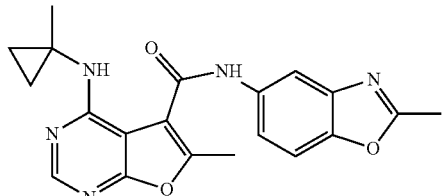

¹H NMR (400 MHz, CD₃OD) δ 8.39 (s, 1H), 8.02 (d, J=1.3 Hz, 1H), 7.63-7.53 (m, 2H), 2.78 (s, 3H), 2.66 (s, 3H), 1.52 (s, 3H), 0.99-0.83 (m, 4H). [M+H]=378.37.

Example 652. 6-Methyl-4-[(1-methylcyclopropyl)amino]-N-(pyrimidin-4-ylmethyl)furo[2,3-d]pyrimidine-5-carboxamide

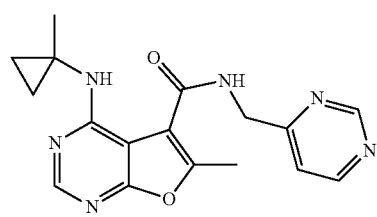 [SMILES: Cc1oc2ncnc(NC3(C)CC3)c2c1C(=O)NCc1ccncn1]

¹H NMR (400 MHz, CD₃OD) δ 9.18-9.12 (m, 1H), 8.76 (d, J=5.3 Hz, 1H), 8.50 (s, 1H), 8.28 (s, 1H), 7.56 (d, J=5.1 Hz, 1H), 4.74 (s, 2H), 2.76 (s, 3H), 1.49 (s, 3H), 0.88-0.68 (m, 4H). [M+H]=339.3.

Example 653. 6-Methyl-4-[(1-methylcyclopropyl)amino]-N-(pyrimidin-2-ylmethyl)furo[2,3-d]pyrimidine-5-carboxamide

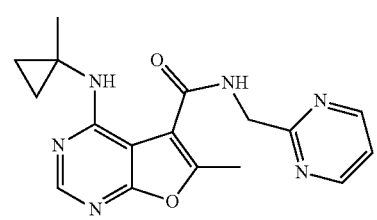 [SMILES: Cc1oc2ncnc(NC3(C)CC3)c2c1C(=O)NCc1ncccn1]

¹H NMR (400 MHz, CD₃OD) δ 8.82 (d, J=5.0 Hz, 2H), 8.51 (s, 1H), 8.28 (s, 1H), 7.43 (t, J=4.9 Hz, 1H), 4.84 (s, 2H), 2.77 (s, 3H), 1.51 (s, 3H), 0.86-0.67 (m, 4H). [M+H]=339.2.

Example 654. 6-Methyl-4-[(1-methylcyclopropyl)amino]-N-[(6-methylpyrimidin-4-yl)methyl]furo[2,3-d]pyrimidine-5-carboxamide

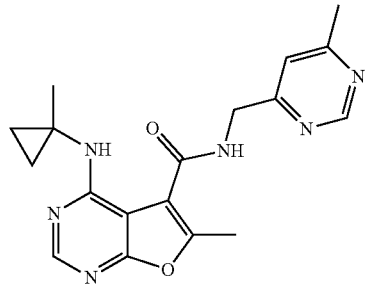 [SMILES: Cc1cc(CNC(=O)c2c(C)oc3ncnc(NC4(C)CC4)c23)ncn1]

¹H NMR (400 MHz, CD₃OD) δ 8.98 (d, J=1.2 Hz, 1H), 8.39 (s, 1H), 7.44 (s, 1H), 4.70 (s, 2H), 2.80 (s, 3H), 2.54 (s, 3H), 1.50 (s, 3H), 0.95-0.85 (m, 4H). [M+H]=353.20.

Example 655. 6-Methyl-4-[(1-methylcyclopropyl)amino]-N-[4-(morpholin-4-yl)phenyl]furo[2,3-d]pyrimidine-5-carboxamide

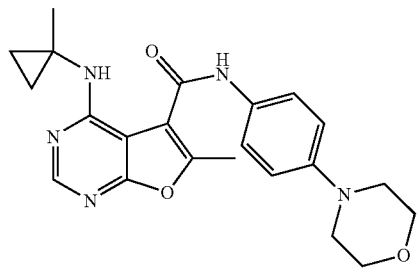 [SMILES: Cc1oc2ncnc(NC3(C)CC3)c2c1C(=O)Nc1ccc(N2CCOCC2)cc1]

¹H NMR (400 MHz, CD₃OD) δ 8.44 (s, 1H), 7.63 (d, J=8.9 Hz, 2H), 7.16 (d, J=8.9 Hz, 2H), 3.95-3.88 (m, 4H), 3.30-3.27 (m, 4H), 2.79 (s, 3H), 1.54 (s, 3H), 1.02-0.92 (m, 4H).
[M+H]=408.40.

Example 656. 6-Methyl-4-[(1-methylcyclopropyl)amino]-N-[6-(morpholin-4-yl)pyridazin-3-yl]furo[2,3-d]pyrimidine-5-carboxamide

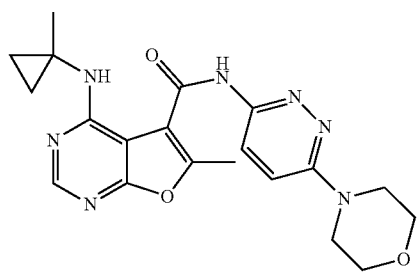 [SMILES: Cc1oc2ncnc(NC3(C)CC3)c2c1C(=O)Nc1ccc(N2CCOCC2)nn1]

¹H NMR (400 MHz, CD₃OD) δ 8.36 (s, 1H), 8.27 (d, J=9.7 Hz, 1H), 7.78 (d, J=10.1 Hz, 1H), 3.90-3.83 (m, 4H), 3.71-3.64 (m, 4H), 2.78 (s, 3H), 1.51 (s, 3H), 0.93-0.80 (m, 4H).
[M+H]=410.30.

Example 657. 6-Methyl-4-[(1-methylcyclopropyl)amino]-N-[2-(morpholin-4-yl)pyrimidin-5-yl]furo[2,3-d]pyrimidine-5-carboxamide

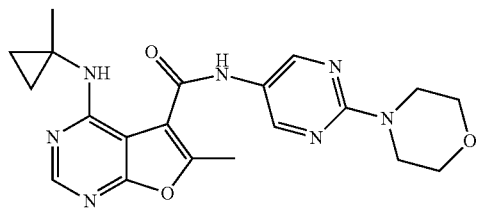 [SMILES: Cc1oc2ncnc(NC3(C)CC3)c2c1C(=O)Nc1cnc(N2CCOCC2)nc1]

¹H NMR (400 MHz, CD₃OD) δ 8.60 (s, 2H), 8.41 (s, 1H), 3.82-3.74 (m, 8H), 2.79 (s, 3H), 1.52 (s, 3H), 0.99-0.87 (m, 4H). [M+H]=410.30.

Example 658. 6-Methyl-4-[(1-methylcyclopropyl)amino]-N-[5-(morpholin-4-yl)pyrazin-2-yl]furo[2,3-d]pyrimidine-5-carboxamide

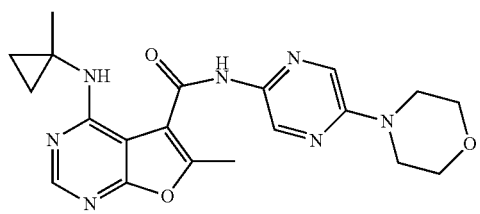 [SMILES: Cc1oc2ncnc(NC3(C)CC3)c2c1C(=O)Nc1cnc(N2CCOCC2)cn1]

¹H NMR (400 MHz, CD₃OD) δ 8.86 (d, J=1.3 Hz, 1H), 8.39 (s, 1H), 8.06 (d, J=1.3 Hz, 1H), 3.86-3.80 (m, 4H), 3.61-3.54 (m, 4H), 2.78 (s, 3H), 1.52 (s, 3H), 1.00-0.84 (m, 4H).

[M+H]=410.30.

Example 659. 6-Methyl-4-[(1-methylcyclopropyl)amino]-N-[(4-methylpyrimidin-5-yl)methyl]furo[2,3-d]pyrimidine-5-carboxamide

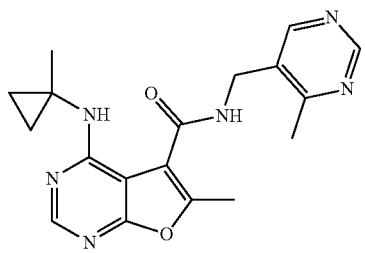 [SMILES: Cc1ncncc1CNC(=O)c1c(C)oc2ncnc(NC3(C)CC3)c12]

¹H NMR (400 MHz, CD₃OD) δ 8.95 (s, 1H), 8.74 (br s, 1H), 8.67 (s, 1H), 8.38 (s, 1H), 4.67 (s, 2H), 2.71 (s, 3H), 2.65 (s, 3H), 1.50 (s, 3H), 0.95-0.87 (m, 4H). [M+H]=353.27.

Example 660. 6-Methyl-4-[(1-methylcyclopropyl)amino]-N-[1-(pyrazin-2-yl)piperidin-4-yl]furo[2,3-d]pyrimidine-5-carboxamide

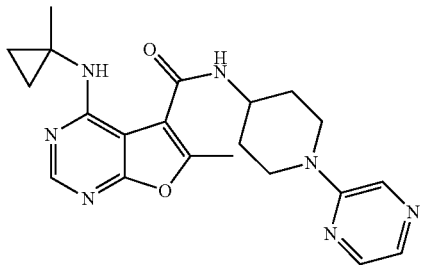 [SMILES: Cc1oc2ncnc(NC3(C)CC3)c2c1C(=O)NC1CCN(c2cnccn2)CC1]

¹H NMR (400 MHz, CD₃OD) δ 8.34 (s, 1H), 8.25 (d, J=1.3 Hz, 1H), 8.16 (d, J=7.5 Hz, 1H), 8.12 (dd, J=1.5, 2.7 Hz, 1H), 7.76 (d, J=2.7 Hz, 1H), 4.44 (d, J=13.6 Hz, 2H), 4.29-4.17 (m, 1H), 3.22-3.10 (m, 2H), 2.66 (s, 3H), 2.16-2.06 (m, 2H), 1.66 (dq, J=4.0, 12.0 Hz, 2H), 1.52 (s, 3H), 0.97-0.84 (m, 4H). [M+H]=408.36.

Example 661. 6-Methyl-4-[(1-methylcyclopropyl)amino]-N-[(6-oxo-1,6-dihydropyrimidin-4-yl)methyl]furo[2,3-d]pyrimidine-5-carboxamide

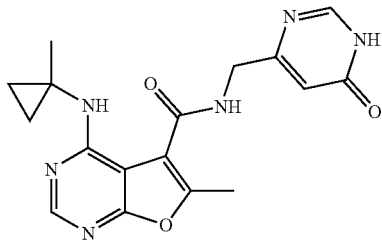 [SMILES: Cc1oc2ncnc(NC3(C)CC3)c2c1C(=O)NCc1cc(=O)[nH]cn1]

¹H NMR (400 MHz, CD₃OD) δ 8.40 (s, 1H), 8.21 (d, J=0.7 Hz, 1H), 6.40 (d, J=1.0 Hz, 1H), 4.49 (s, 2H), 2.79 (s, 3H), 1.51 (s, 3H), 0.97-0.90 (m, 4H). [M+H]=355.30.

Example 662. 6-Methyl-N-[(2-methyl-6-oxo-1,6-dihydropyrimidin-4-yl)methyl]-4-[(1-methylcyclopropyl)amino]furo[2,3-d]pyrimidine-5-carboxamide

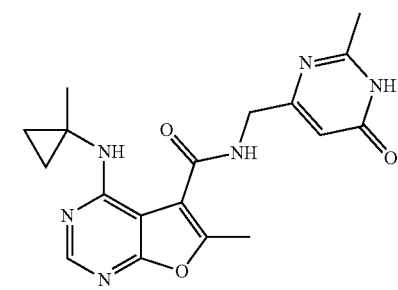 [SMILES: Cc1nc(CNC(=O)c2c(C)oc3ncnc(NC4(C)CC4)c23)cc(=O)[nH]1]

¹H NMR (400 MHz, CD₃OD) δ 8.39 (s, 1H), 6.23 (s, 1H), 4.44 (s, 2H), 2.79 (s, 3H), 2.42 (s, 3H), 1.50 (s, 3H), 0.96-0.87 (m, 4H). [M+H]=369.20.

Example 663. 5-{4-Methoxy-5H,6H,7H,8H-pyrido[4,3-d]pyrimidine-6-carbonyl}-6-methyl-N-(1-methylcyclopropyl)furo[2,3-d]pyrimidin-4-amine

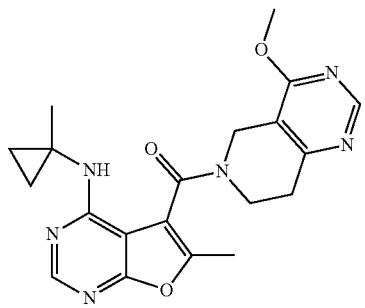 [SMILES: COc1ncnc2c1CN(C(=O)c1c(C)oc3ncnc(NC4(C)CC4)c13)CC2]

¹H NMR (400 MHz, CD₃OD) δ 8.69 (s, 1H), 8.41 (s, 1H), 4.73 (br s, 2H), 4.09 (s, 3H), 4.06-3.87 (m, 2H), 3.06-2.99 (m, 2H), 2.60 (s, 3H), 1.48 (s, 3H), 0.94-0.85 (m, 4H). [M+H]=395.30.

Example 664. 6-Methyl-4-[(1-methylcyclopropyl)amino]-N-{[5-(propan-2-yl)-1,3-oxazol-2-yl]methyl}furo[2,3-d]pyrimidine-5-carboxamide

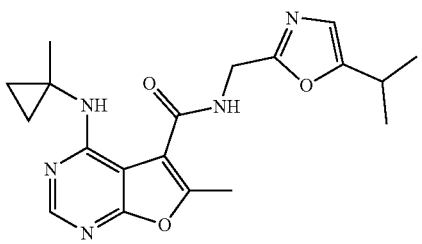 [SMILES: Cc1oc2ncnc(NC3(C)CC3)c2c1C(=O)NCc1ncc(C(C)C)o1]

¹H NMR (400 MHz, CD₃OD) δ 8.35 (s, 1H), 6.77 (d, J=1.0 Hz, 1H), 4.68 (s, 2H), 3.08-2.96 (m, 1H), 2.73 (s, 3H), 1.50 (s, 3H), 1.28 (d, J=6.8 Hz, 6H), 0.95-0.84 (m, 4H). [M+H]=370.32.

Example 665. 6-Methyl-4-[(1-methylcyclopropyl)amino]-N-[1-(pyrimidin-2-yl)piperidin-4-yl]furo[2,3-d]pyrimidine-5-carboxamide

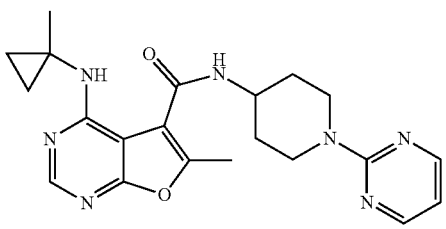 [SMILES: Cc1oc2ncnc(NC3(C)CC3)c2c1C(=O)NC1CCN(c2ncccn2)CC1]

¹H NMR (400 MHz, CD₃OD) δ 8.41 (d, J=4.5 Hz, 3H), 8.18 (d, J=7.3 Hz, 1H), 6.69 (t, J=4.9 Hz, 1H), 4.73 (d, J=13.4 Hz, 2H), 4.32-4.22 (m, 1H), 3.26-3.17 (m, 2H), 2.70 (s, 3H), 2.12 (dd, J=3.0, 12.8 Hz, 2H), 1.66 (dq, J=4.0, 12.0 Hz, 2H), 1.55 (s, 3H), 1.04-0.90 (m, 4H). [M+H]=408.40.

Example 666. N-[(6-Methoxypyrimidin-4-yl)methyl]-6-methyl-4-[(1-methylcyclopropyl)amino]furo[2,3-d]pyrimidine-5-carboxamide

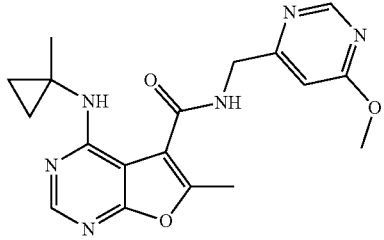 [SMILES: COc1cc(CNC(=O)c2c(C)oc3ncnc(NC4(C)CC4)c23)ncn1]

$^1$H NMR (400 MHz, CD$_3$OD) δ 8.73 (s, 1H), 8.39 (s, 1H), 6.86 (s, 1H), 4.63 (s, 2H), 4.01 (s, 3H), 2.78 (s, 3H), 1.50 (s, 3H), 0.90 (d, J=9.4 Hz, 4H). [M+H]=369.30.

Example 667. N-[(6-Methoxy-2-methylpyrimidin-4-yl)methyl]-6-methyl-4-[(1-methylcyclopropyl)amino]furo[2,3-d]pyrimidine-5-carboxamide

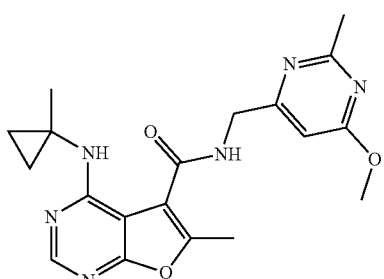

$^1$H NMR (400 MHz, CD$_3$OD) δ 8.38 (s, 1H), 6.76 (s, 1H), 4.63 (s, 2H), 4.03 (s, 3H), 2.80 (s, 3H), 2.64 (s, 3H), 1.49 (s, 3H), 0.95-0.83 (m, 4H). [M+H]=383.30.

Example 668. 6-Methyl-N-(1-methylcyclopropyl)-5-(1,2,3,4-tetrahydro-2,6-naphthyridine-2-carbonyl)furo[2,3-d]pyrimidin-4-amine

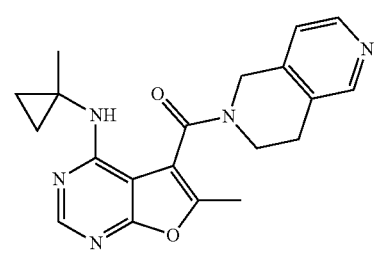 [SMILES: Cc1oc2ncnc(NC3(C)CC3)c2c1C(=O)N1CCc2cnccc2C1]

$^1$H NMR (400 MHz, CDCl$_3$) δ 8.50 (s, 2H), 8.47 (d, J=5.14 Hz, 1H), 7.08 (br s, 1H), 6.93 (br s, 1H), 4.83 (br s, 2H), 3.97 (d, J=19.20 Hz, 2H), 3.01 (t, J=5.44 Hz, 2H), 2.51 (s, 3H), 1.51 (s, 3H), 0.77 (d, J=13.69 Hz, 4H). [M+H]=364.3.

Example 669. 6-Methyl-4-[(1-methylcyclopropyl)amino]-N-[1-(pyridin-2-yl)pyrrolidin-3-yl]furo[2,3-d]pyrimidine-5-carboxamide

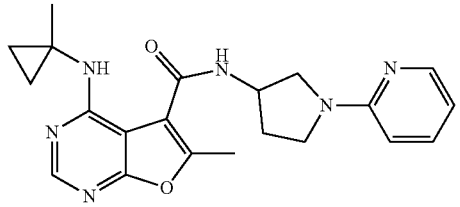 [SMILES: Cc1oc2ncnc(NC3(C)CC3)c2c1C(=O)NC1CCN(c2ccccn2)C1]

$^1$H NMR (400 MHz, CD$_3$OD) δ 8.33 (s, 1H), 8.03 (ddd, J=1.7, 7.2, 9.1 Hz, 1H), 7.93 (dd, J=0.9, 6.5 Hz, 1H), 7.16 (d, J=9.2 Hz, 1H), 6.98 (t, J=6.5 Hz, 1H), 4.93-4.86 (m, 1H), 4.05 (dd, J=6.6, 10.9 Hz, 1H), 3.88-3.72 (m, 2H), 3.66 (dd, J=4.9, 11.0 Hz, 1H), 2.66 (s, 3H), 2.61-2.49 (m, 1H), 2.35 (qd, J=6.6, 13.3 Hz, 1H), 1.51 (s, 3H), 0.93-0.81 (m, 4H). [M+H]=393.30.

Example 670. 6-Methyl-4-[(1-methylcyclopropyl)amino]-N-[1-(2-methylpyrimidin-4-yl)piperidin-4-yl]furo[2,3-d]pyrimidine-5-carboxamide

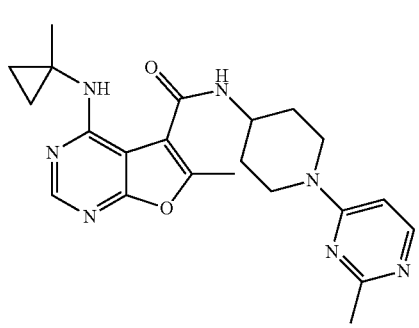 [SMILES: Cc1nccc(N2CCC(NC(=O)c3c(C)oc4ncnc(NC5(C)CC5)c34)CC2)n1]

$^1$H NMR (400 MHz, CD$_3$OD) δ 8.31 (s, 1H), 8.19 (d, J=7.6 Hz, 1H), 8.08 (d, J=7.6 Hz, 1H), 7.04 (d, J=7.7 Hz, 1H), 5.13 (d, J=11.0 Hz, 1H), 4.39-4.20 (m, 2H), 3.57-3.33 (m, 2H), 2.65 (s, 3H), 2.58 (s, 3H), 2.22 (br s, 2H), 1.68 (d, J=13.3 Hz, 2H), 1.51 (s, 3H), 0.91-0.80 (m, 4H). [M+H]=422.40.

Example 671. 6-Methyl-4-[(1-methylcyclopropyl)amino]-N-[1-(6-methylpyrimidin-4-yl)piperidin-4-yl]furo[2,3-d]pyrimidine-5-carboxamide

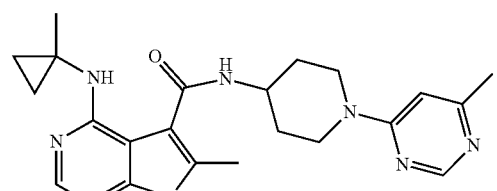

$^1$H NMR (400 MHz, CD$_3$OD) δ 8.59 (s, 1H), 8.30 (s, 1H), 8.18 (d, J=7.2 Hz, 1H), 7.05 (s, 1H), 5.09 (br s, 1H), 4.40-4.14 (m, 2H), 3.60-3.33 (m, 2H), 2.64 (s, 3H), 2.48 (s, 3H), 2.22 (d, J=12.2 Hz, 2H), 1.69 (d, J=10.5 Hz, 2H), 1.50 (s, 3H), 0.91-0.79 (m, 4H). [M+H]=422.40.

Example 672. N-[1-(2,6-Dimethylpyrimidin-4-yl)piperidin-4-yl]-6-methyl-4-[(1-methylcyclopropyl)amino]furo[2,3-d]pyrimidine-5-carboxamide

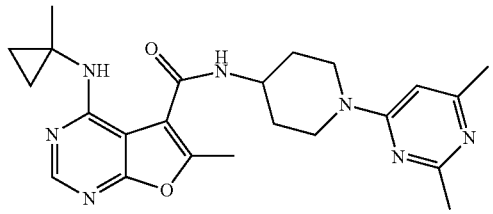 [SMILES: Cc1cc(N2CCC(NC(=O)c3c(C)oc4ncnc(NC5(C)CC5)c34)CC2)nc(C)n1]

¹H NMR (400 MHz, CD₃OD) δ 8.31 (s, 1H), 8.19 (d, J=7.2 Hz, 1H), 6.90 (s, 1H), 5.11 (d, J=12.7 Hz, 1H), 4.39-4.20 (m, 2H), 3.46 (t, J=12.5 Hz, 1H), 3.28 (br s, 1H), 2.64 (s, 3H), 2.56 (s, 3H), 2.44 (s, 3H), 2.29-2.12 (m, 2H), 1.68 (t, J=12.5 Hz, 2H), 1.51 (s, 3H), 0.90-0.80 (m, 4H). [M+H]=436.40.

Example 673. 6-Methyl-N-[(2-methyl-6-oxo-1,6-dihydropyrimidin-5-yl)methyl]-4-[(1-methylcyclopropyl)amino]furo[2,3-d]pyrimidine-5-carboxamide

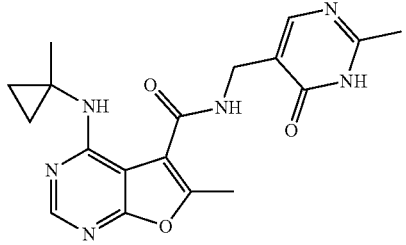 [SMILES: Cc1ncc(CNC(=O)c2c(C)oc3ncnc(NC4(C)CC4)c23)c(=O)[nH]1]

¹H NMR (400 MHz, CD₃OD) δ 8.36 (s, 1H), 7.95 (s, 1H), 4.39 (s, 2H), 2.70 (s, 3H), 2.46 (s, 3H), 1.50 (s, 3H), 0.97-0.85 (m, 4H). [M+H]=369.30.

Example 674. N-{[2-(1H-Imidazol-1-yl)pyridin-4-yl]methyl}-6-methyl-4-[(1-methylcyclopropyl)amino]furo[2,3-d]pyrimidine-5-carboxamide

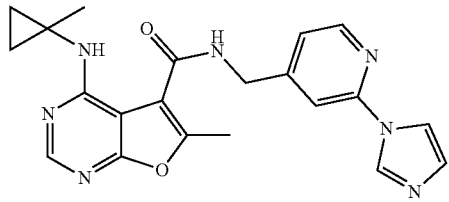 [SMILES: Cc1oc2ncnc(NC3(C)CC3)c2c1C(=O)NCc1ccnc(-n2ccnc2)c1]

¹H NMR (400 MHz, CD₃OD) δ 9.76 (s, 1H), 8.60 (d, J=5.1 Hz, 1H), 8.39 (s, 1H), 8.37 (s, 1H), 7.95 (s, 1H), 7.78 (s, 1H), 7.60 (d, J=5.1 Hz, 1H), 4.78 (s, 2H), 2.78 (s, 3H), 1.48 (s, 3H), 0.88-0.81 (m, 4H). [M+H]=404.30.

Example 675. 6-Methyl-4-[(1-methylcyclopropyl)amino]-N-{[2-(morpholin-4-yl)pyridin-4-yl]methyl}furo[2,3-d]pyrimidine-5-carboxamide

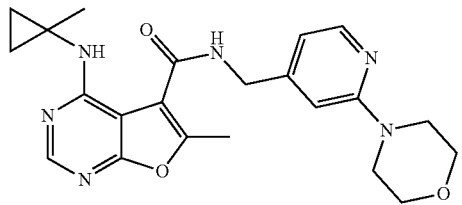 [SMILES: Cc1oc2ncnc(NC3(C)CC3)c2c1C(=O)NCc1ccnc(N2CCOCC2)c1]

¹H NMR (400 MHz, CD₃OD) δ 8.36 (s, 1H), 7.96 (d, J=6.5 Hz, 1H), 7.33 (s, 1H), 7.05 (dd, J=1.2, 6.6 Hz, 1H), 4.69 (s, 2H), 3.91-3.83 (m, 4H), 3.71-3.64 (m, 4H), 2.77 (s, 3H), 1.49 (s, 3H), 0.90-0.82 (m, 4H). [M+H]=423.40.

Example 676. N-[(4-Methoxy-2-methylpyrimidin-5-yl)methyl]-6-methyl-4-[(1-methylcyclopropyl)amino]furo[2,3-d]pyrimidine-5-carboxamide

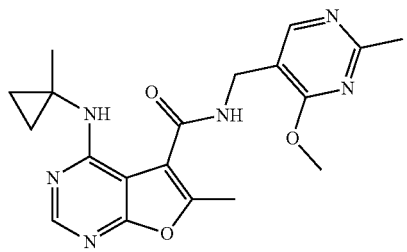 [SMILES: COc1nc(C)ncc1CNC(=O)c1c(C)oc2ncnc(NC3(C)CC3)c12]

¹H NMR (400 MHz, CD₃OD) δ 8.56 (s, 1H), 8.37 (s, 1H), 4.57 (s, 2H), 4.23 (s, 3H), 2.74 (s, 3H), 2.71 (s, 3H), 1.50 (s, 3H), 0.95-0.84 (m, 4H). [M+H]=383.28.

Example 677. N-[(2-Chloropyrimidin-4-yl)methyl]-6-methyl-4-[(1-methylcyclopropyl)amino]furo[2,3-d]pyrimidine-5-carboxamide

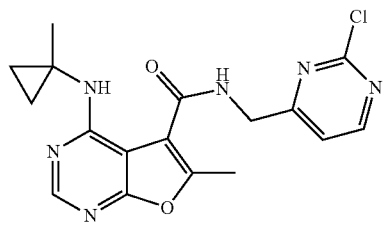 [SMILES: Cc1oc2ncnc(NC3(C)CC3)c2c1C(=O)NCc1ccnc(Cl)n1]

¹H NMR (400 MHz, CD₃OD) δ 8.65 (d, J=5.1 Hz, 1H), 8.37 (s, 1H), 7.50 (d, J=5.1 Hz, 1H), 4.73 (s, 2H), 2.82 (s, 3H), 1.50 (s, 3H), 0.93-0.84 (m, 4H). [M+H]=373.20.

Example 678. N-[(6-Fluoro-5-methoxypyridin-2-yl)methyl]-6-methyl-4-[(1-methylcyclopropyl)amino]furo[2,3-d]pyrimidine-5-carboxamide

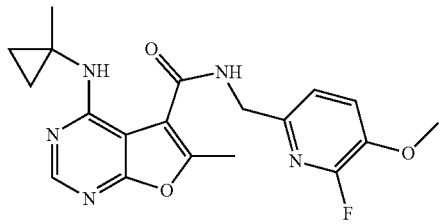 [SMILES: COc1ccc(CNC(=O)c2c(C)oc3ncnc(NC4(C)CC4)c23)nc1F]

¹H NMR (400 MHz, CD₃OD) δ 8.44 (s, 1H), 7.57 (dd, J=8.2, 10.1 Hz, 1H), 7.30 (d, J=8.1 Hz, 1H), 4.66-4.55 (m, 2H), 3.93 (s, 4H), 2.81 (s, 3H), 1.54 (s, 3H), 1.05-0.89 (m, 4H).
[M+H]=386.4.

Example 679. 6-Methyl-4-[(1-methylcyclopropyl)amino]-N-[(2-methylpyrimidin-5-yl)methyl]furo[2,3-d]pyrimidine-5-carboxamide

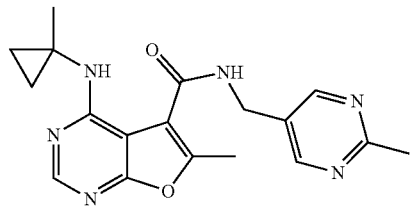 [SMILES: Cc1ncc(CNC(=O)c2c(C)oc3ncnc(NC4(C)CC4)c23)cn1]

¹H NMR (400 MHz, CD₃OD) δ 8.75 (s, 2H), 8.26 (s, 1H), 4.60 (s, 2H), 2.70 (s, 3H), 2.66 (s, 3H), 1.49 (s, 3H), 0.83-0.72 (m, 4H). [M+H]=353.4.

Example 680. 6-Methyl-4-[(1-methylcyclopropyl)amino]-N-{[4-(trifluoromethyl)pyrimidin-2-yl]methyl}furo[2,3-d]pyrimidine-5-carboxamide

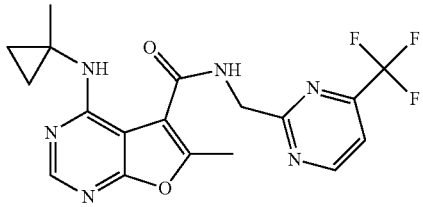 [SMILES: Cc1oc2ncnc(NC3(C)CC3)c2c1C(=O)NCc1nccc(C(F)(F)F)n1]

¹H NMR (400 MHz, CD₃OD) δ 9.13 (d, J=5.0 Hz, 1H), 8.38 (s, 1H), 7.82 (d, J=5.0 Hz, 1H), 4.96 (s, 2H), 2.86 (s, 3H), 1.51 (s, 3H), 0.93-0.79 (m, 4H). [M+H]=407.4.

Example 681. 2-Cyclopropyl-6-{6-methyl-4-[(1-methylcyclopropyl)amino]furo[2,3-d]pyrimidine-5-carbonyl}-3H,4H,5H,6H,7H-pyrrolo[3,4-d]pyrimidin-4-one

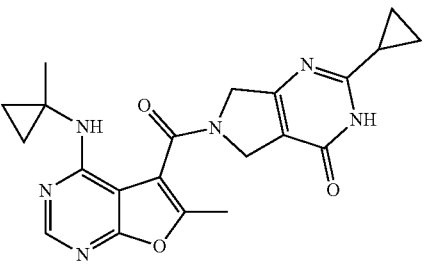 [SMILES: Cc1oc2ncnc(NC3(C)CC3)c2c1C(=O)N1Cc2nc(C3CC3)[nH]c(=O)c2C1]

¹H NMR (400 MHz, CD₃OD) δ 8.39 (s, 1H), 4.78 (br s, 2H), 4.65 (br s, 2H), 2.61 (s, 3H), 1.95 (br s, 1H), 1.49 (s, 3H), 1.24-1.07 (m, 4H), 0.95-0.82 (m, 4H). [M+H]=407.30.

Example 682. 6-{6-Methyl-4-[(1-methylcyclopropyl)amino]furo[2,3-d]pyrimidine-5-carbonyl}-2-(propan-2-yl)-3H,4H,5H,6H,7H-pyrrolo[3,4-d]pyrimidin-4-one

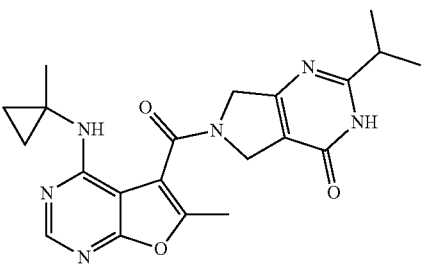 [SMILES: Cc1oc2ncnc(NC3(C)CC3)c2c1C(=O)N1Cc2nc(C(C)C)[nH]c(=O)c2C1]

¹H NMR (400 MHz, CD₃OD) δ 8.39 (s, 1H), 4.94-4.85 (m, 2H), 4.70 (d, J=15.2 Hz, 2H), 2.92 (br s, 1H), 2.62 (s, 3H), 1.49 (s, 3H), 1.30 (br s, 6H), 0.95-0.82 (m, 4H). [M+H]=409.30.

Example 683. 6-Methyl-N-(1-methylcyclopropyl)-5-{4H,5H,6H,7H-pyrazolo[1,5-a]pyrazine-5-carbonyl}furo[2,3-d]pyrimidin-4-amine

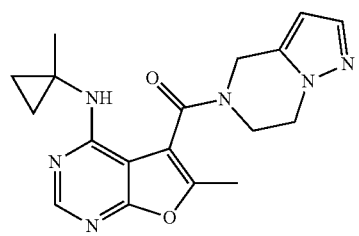 [SMILES: Cc1oc2ncnc(NC3(C)CC3)c2c1C(=O)N1CCn2nccc2C1]

¹H NMR (400 MHz, CDCl₃) δ 8.50 (s, 1H), 7.56 (d, J=1.96 Hz, 1H), 6.91 (br s, 1H), 6.12 (s, 1H), 4.91 (br s, 2H), 4.35 (t, J=5.26 Hz, 2H), 3.91-4.28 (m, 2H), 2.53 (s, 3H), 1.52 (s, 3H), 0.78 (d, J=14.43 Hz, 4H). [M+H]=353.3.

Example 684. 5-{3-Cyclopropyl-5H,6H,7H,8H-imidazo[1,5-a]pyrazine-7-carbonyl}-6-methyl-N-(1-methylcyclopropyl)furo[2,3-d]pyrimidin-4-amine

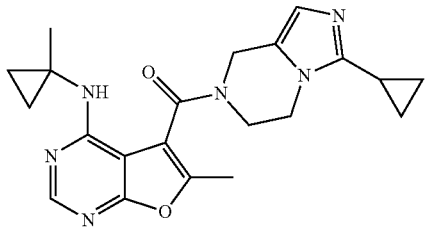 [SMILES: Cc1oc2ncnc(NC3(C)CC3)c2c1C(=O)N1CCn2c(cnc2C2CC2)C1]

¹H NMR (400 MHz, CDCl₃) δ 8.45 (s, 1H), 7.09 (br s, 1H), 6.81 (s, 1H), 4.87 (br s, 2H), 4.22 (br s, 2H), 2.63 (d, J=8.07 Hz, 2H), 2.48 (s, 3H), 1.80-1.91 (m, 1H), 1.51 (s, 3H), 1.05-1.11 (m, 4H), 0.82 (br s, 2H), 0.76 (s, 2H). [M+H]=393.3.

Example 685. N-[(6-Methoxypyrimidin-4-yl)methyl]-N,6-dimethyl-4-[(1-methylcyclopropyl)amino]furo[2,3-d]pyrimidine-5-carboxamide

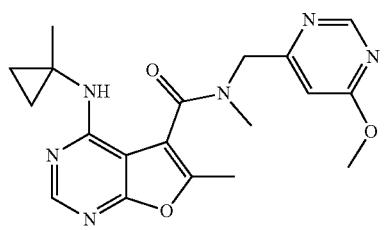 [SMILES: COc1cc(CN(C)C(=O)c2c(C)oc3ncnc(NC4(C)CC4)c23)ncn1]

¹H NMR (400 MHz, CD₃OD) δ 8.80 (br s, 1H), 8.43 (s, 1H), 6.89 (br s, 1H), 4.82-4.67 (m, 2H), 4.02 (br s, 3H), 3.16 (br s, 3H), 2.58 (s, 3H), 1.55 (s, 3H), 0.93 (br s, 4H). [M+H]=261.20.

Example 686. N-[(6-Cyclopropylpyrimidin-4-yl)methyl]-6-methyl-4-[(1-methylcyclopropyl)amino]furo[2,3-d]pyrimidine-5-carboxamide

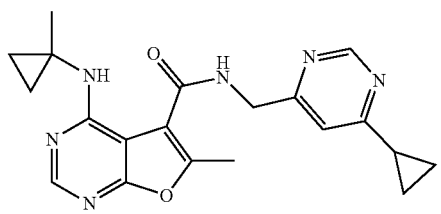 [SMILES: Cc1oc2ncnc(NC3(C)CC3)c2c1C(=O)NCc1cc(C2CC2)ncn1]

¹H NMR (400 MHz, CD₃OD) δ 8.88 (s, 1H), 8.41 (s, 1H), 7.39 (s, 1H), 4.67 (s, 2H), 2.81 (s, 3H), 2.10 (quin, J=6.4 Hz, 1H), 1.51 (s, 3H), 1.17-1.12 (m, 4H), 0.97-0.89 (m, 4H). [M+H]=379.40.

Example 687. 5-{2-Cyclopropyl-4-methoxy-5H,6H,7H-pyrrolo[3,4-d]pyrimidine-6-carbonyl}-6-methyl-N-(1-methylcyclopropyl)furo[2,3-d]pyrimidin-4-amine

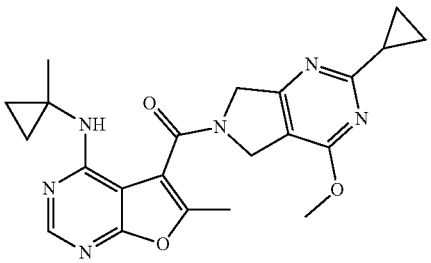 [SMILES: COc1nc(C2CC2)nc2c1CN(C(=O)c1c(C)oc3ncnc(NC4(C)CC4)c13)C2]

¹H NMR (400 MHz, CD₃OD) δ 8.40 (s, 1H), 4.90 (br s, 2H), 4.76 (br s, 2H), 4.08-3.93 (m, 3H), 2.62 (s, 3H), 2.15 (br s, 1H), 1.48 (s, 3H), 1.21-1.03 (m, 4H), 0.93-0.81 (m, 4H). [M+H]=421.41.

Example 688. 5-[4-Methoxy-2-(propan-2-yl)-5H,6H,7H-pyrrolo[3,4-d]pyrimidine-6-carbonyl]-6-methyl-N-(1-methylcyclopropyl)furo[2,3-d]pyrimidin-4-amine

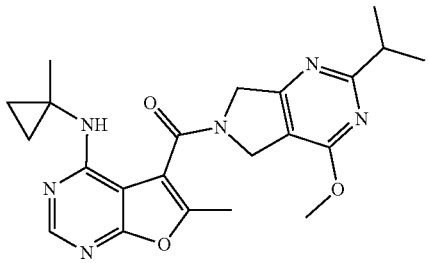 [SMILES: COc1nc(C(C)C)nc2c1CN(C(=O)c1c(C)oc3ncnc(NC4(C)CC4)c13)C2]

¹H NMR (400 MHz, CD₃OD) δ 8.40 (s, 1H), 4.93 (br s, 2H), 4.80 (br s, 2H), 4.19-3.98 (m, 3H), 3.13 (br s, 1H), 2.63 (s, 3H), 1.50-1.46 (m, 3H), 1.33 (d, J=4.5 Hz, 6H), 0.93-0.81 (m, 4H). [M+H]=423.42.

Example 689. N-[(2-Cyclopropylpyrimidin-4-yl)methyl]-6-methyl-4-[(1-methylcyclopropyl)amino]furo[2,3-d]pyrimidine-5-carboxamide

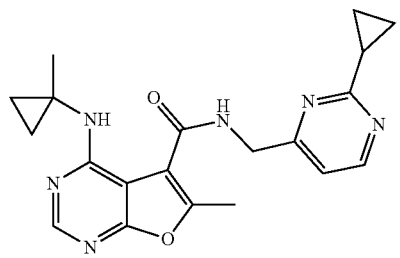 [SMILES: Cc1oc2ncnc(NC3(C)CC3)c2c1C(=O)NCc1ccnc(C2CC2)n1]

¹H NMR (400 MHz, CD₃OD) δ 8.59-8.52 (m, 1H), 8.41 (s, 1H), 7.28 (d, J=5.3 Hz, 1H), 4.68 (s, 2H), 2.83 (s, 3H), 2.29-2.18 (m, 1H), 1.50 (s, 3H), 1.15-1.09 (m, 4H), 0.97-0.88 (m, 4H). [M+H]=379.41.

Example 690. 5-{2-Chloro-5H,6H,7H,8H-pyrido[3,4-d]pyrimidine-7-carbonyl}-6-methyl-N-(1-methylcyclopropyl)furo[2,3-d]pyrimidin-4-amine

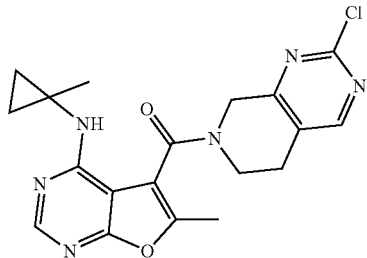 [SMILES: Cc1oc2ncnc(NC3(C)CC3)c2c1C(=O)N1CCc2cnc(Cl)nc2C1]

¹H NMR (400 MHz, CD₃OD) δ 8.54 (s, 1H), 8.38 (s, 1H), 4.94-4.86 (m, 2H), 3.97 (br s, 2H), 2.98 (t, J=5.3 Hz, 2H), 2.58 (s, 3H), 1.47 (s, 3H), 0.90-0.80 (m, 4H). [M+H]=399.29.

Example 691. N-[(5-tert-Butyl-1,3-oxazol-2-yl)methyl]-6-methyl-4-[(1-methylcyclopropyl)amino]furo[2,3-d]pyrimidine-5-carboxamide

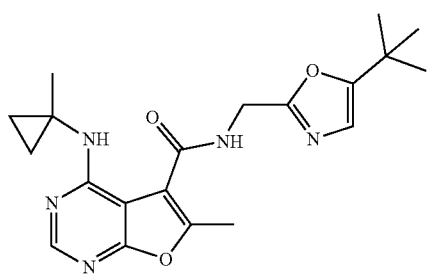 [SMILES: Cc1oc2ncnc(NC3(C)CC3)c2c1C(=O)NCc1ncc(C(C)(C)C)o1]

¹H NMR (400 MHz, CD₃OD) δ 8.23 (s, 1H), 6.65 (s, 1H), 4.58 (s, 2H), 2.62 (s, 3H), 1.40 (s, 3H), 1.22 (s, 9H), 0.87-0.69 (m, 4H). [M+H]=384.4.

Example 692. N,6-Dimethyl-4-[(1-methylcyclopropyl)amino]-N-(1,3-oxazol-2-ylmethyl)furo[2,3-d]pyrimidine-5-carboxamide

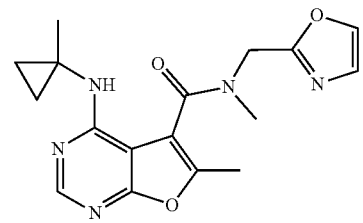 [SMILES: Cc1oc2ncnc(NC3(C)CC3)c2c1C(=O)N(C)Cc1ncco1]

¹H NMR (400 MHz, CD₃OD) δ 8.28 (s, 1H), 7.91-7.79 (m, 1H), 7.18-7.06 (m, 1H), 4.85-4.76 (m, 2H), 3.10-3.05 (m, 3H), 2.45-2.42 (m, 3H), 1.45-1.39 (m, 3H), 0.84-0.76 (m, 4H). [M+H]=342.3.

Example 693. N-[2-(2-Cyclopropylpyrimidin-5-yl)ethyl]-6-methyl-4-[(1-methylcyclopropyl)amino]furo[2,3-d]pyrimidine-5-carboxamide

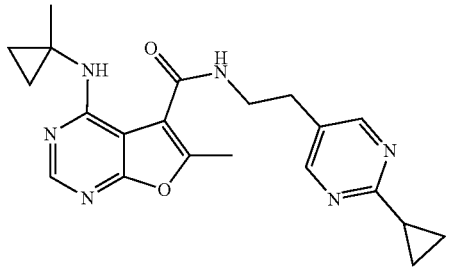 [SMILES: Cc1oc2ncnc(NC3(C)CC3)c2c1C(=O)NCCc1cnc(C2CC2)nc1]

¹H NMR (400 MHz, CD₃OD) δ 8.57 (s, 2H), 8.38 (s, 1H), 8.27 (br s, 1H), 3.75-3.68 (m, 2H), 2.96 (t, J=6.9 Hz, 2H), 2.62 (s, 3H), 2.29-2.15 (m, 1H), 1.52 (s, 3H), 1.13-1.06 (m, 4H), 1.01-0.89 (m, 4H). [M+H]=393.42.

Example 694. 5-{1-Chloro-3-cyclopropyl-5H,6H,7H,8H-imidazo[1,5-a]pyrazine-7-carbonyl}-6-methyl-N-(1-methylcyclopropyl)furo[2,3-d]pyrimidin-4-amine

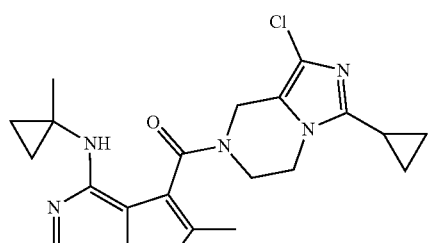

¹H NMR (400 MHz, CDCl₃) δ 8.51 (s, 1H), 6.99 (s, 1H), 4.73 (s, 2H), 4.13 (br s, 4H), 2.52 (s, 3H), 1.79-1.69 (m, 1H), 1.54 (s, 3H), 1.10-1.04 (m, 2H), 1.03-0.96 (m, 2H), 0.83 (br s, 2H), 0.78 (s, 2H). [M+H]=427.3.

Example 695. 5-{3-Cyclopropyl-1-iodo-5H,6H,7H,8H-imidazo[1,5-a]pyrazine-7-carbonyl}-6-methyl-N-(1-methylcyclopropyl)furo[2,3-d]pyrimidin-4-amine

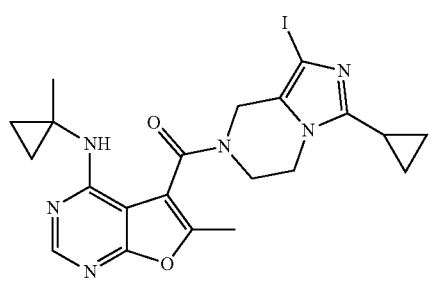 [SMILES: Cc1oc2ncnc(NC3(C)CC3)c2c1C(=O)N1CCn2c(C3CC3)nc(I)c2C1]

¹H NMR (400 MHz, CDCl₃) δ 8.51 (s, 1H), 7.00 (br s, 1H), 4.66 (s, 2H), 4.14 (br s, 4H), 2.52 (s, 3H), 1.81-1.71 (m,

1H), 1.54 (s, 3H), 1.10-1.05 (m, 2H), 1.04-0.96 (m, 2H), 0.87-0.81 (m, 2H), 0.79 (s, 2H). [M+H]=519.3.

Example 696. 6-Methyl-4-[(1-methylcyclopropyl)amino]-N-{[5-(trifluoromethyl)pyrimidin-2-yl]methyl}furo[2,3-d]pyrimidine-5-carboxamide

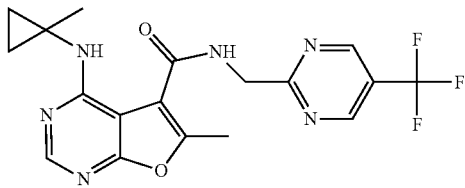 [SMILES: Cc1oc2ncnc(NC3(C)CC3)c2c1C(=O)NCc1ncc(C(F)(F)F)cn1]

¹H NMR (400 MHz, CD₃OD) δ 9.14 (s, 2H), 8.39 (s, 1H), 4.94 (s, 2H), 2.85 (s, 3H), 1.50 (s, 3H), 0.96-0.85 (m, 4H). [M+H]=407.4.

Example 697. 6-Methyl-4-[(1-methylcyclopropyl)amino]-N-[(6-methylpyridin-2-yl)methyl]furo[2,3-d]pyrimidine-5-carboxamide

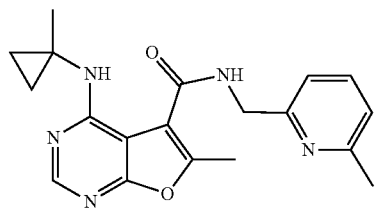 [SMILES: Cc1cccc(CNC(=O)c2c(C)oc3ncnc(NC4(C)CC4)c23)n1]

¹H NMR (400 MHz, CD₃OD) δ 8.34 (s, 1H), 8.29 (t, J=7.9 Hz, 1H), 7.72 (dd, J=8.0, 12.5 Hz, 2H), 2.80 (s, 3H), 2.79 (s, 3H), 1.49 (s, 3H), 0.96-0.86 (m, 1H), 0.82 (s, 4H). [M+H]=352.3.

Example 698. N-[(2-Methoxypyrimidin-5-yl)methyl]-6-methyl-4-[(1-methylcyclopropyl)amino]furo[2,3-d]pyrimidine-5-carboxamide

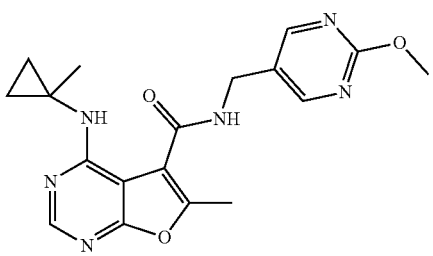 [SMILES: COc1ncc(CNC(=O)c2c(C)oc3ncnc(NC4(C)CC4)c23)cn1]

¹H NMR (400 MHz, CD₃OD) δ 8.63 (s, 2H), 8.39 (s, 1H), 4.55 (s, 2H), 4.01 (s, 3H), 2.71 (s, 3H), 1.51 (s, 3H), 0.94 (d, J=5.9 Hz, 4H). [M+H]=369.30.

Example 699. 5-{2-Methoxy-5H,6H,7H,8H-pyrido[3,4-d]pyrimidine-7-carbonyl}-6-methyl-N-(1-methylcyclopropyl)furo[2,3-d]pyrimidin-4-amine

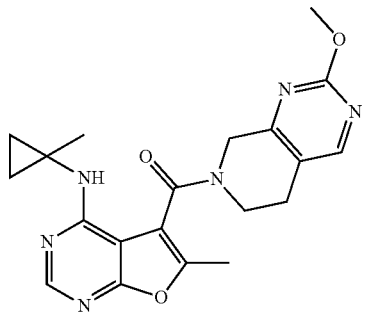 [SMILES: COc1ncc2c(n1)CN(C(=O)c1c(C)oc3ncnc(NC4(C)CC4)c13)CC2]

¹H NMR (400 MHz, CD₃OD) δ 8.41 (s, 2H), 4.83-4.76 (m, 2H), 4.05-3.87 (m, 5H), 2.92 (br s, 2H), 2.59 (s, 3H), 1.48 (s, 3H), 0.89 (d, J=7.6 Hz, 4H). [M+H]=395.30.

Example 700. N,6-Dimethyl-N-[(4-methyl-1,3-thiazol-2-yl)methyl]-4-[(1-methylcyclopropyl)amino]furo[2,3-d]pyrimidine-5-carboxamide

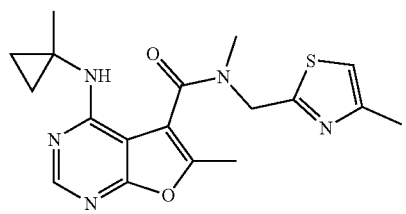 [SMILES: Cc1csc(CN(C)C(=O)c2c(C)oc3ncnc(NC4(C)CC4)c23)n1]

¹H NMR (400 MHz, CD₃OD) δ 8.39 (s, 1H), 7.19 (br s, 1H), 5.00 (s, 2H), 3.21 (s, 3H), 2.58 (s, 3H), 2.45 (s, 3H), 1.53 (s, 3H), 0.95-0.79 (m, 4H). [M+H]=372.4.

Example 701. N,6-Dimethyl-4-[(1-methylcyclopropyl)amino]-N-(1,3-thiazol-2-ylmethyl)furo[2,3-d]pyrimidine-5-carboxamide

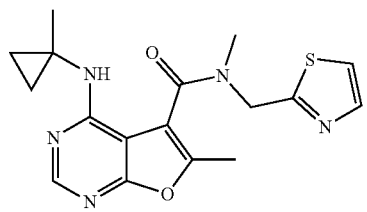 [SMILES: Cc1oc2ncnc(NC3(C)CC3)c2c1C(=O)N(C)Cc1nccs1]

¹H NMR (400 MHz, CD₃OD) δ 8.41 (s, 1H), 7.84 (br s, 1H), 7.67 (br s, 1H), 5.09 (br s, 2H), 3.19 (s, 3H), 2.57 (s, 3H), 1.55 (s, 3H), 1.03-0.80 (m, 4H). [M+H]=358.3.

Example 702. N,6-Dimethyl-N-[(5-methyl-1,3-thiazol-2-yl)methyl]-4-[(1-methylcyclopropyl)amino]furo[2,3-d]pyrimidine-5-carboxamide

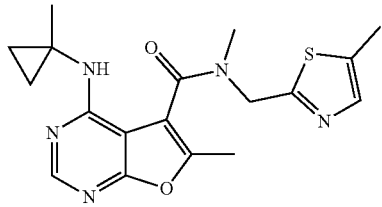 [SMILES: Cc1cnc(CN(C)C(=O)c2c(C)oc3ncnc(NC4(C)CC4)c23)s1]

¹H NMR (400 MHz, CD₃OD) δ 8.40 (s, 1H), 7.48 (br s, 1H), 4.99 (br s, 2H), 3.17 (s, 3H), 2.56 (s, 3H), 2.52 (s, 3H), 1.55 (s, 3H), 0.97-0.84 (m, 4H). [M+H]=372.4.

Example 703. 6-Methyl-N-[(4-methyl-1,3-thiazol-2-yl)methyl]-4-[(1-methylcyclopropyl)amino]furo[2,3-d]pyrimidine-5-carboxamide

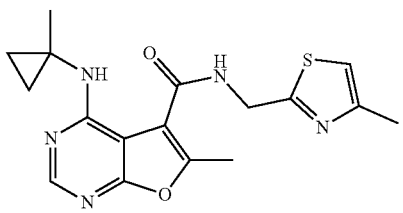 [SMILES: Cc1csc(CNC(=O)c2c(C)oc3ncnc(NC4(C)CC4)c23)n1]

¹H NMR (400 MHz, CD₃OD) δ 8.40 (s, 1H), 7.13 (d, J=1.0 Hz, 1H), 4.88 (s, 2H), 2.78 (s, 3H), 2.44 (d, J=0.9 Hz, 3H), 1.53 (s, 3H), 1.03-0.81 (m, 4H). [M+H]=358.3.

Example 704. 6-Methyl-4-[(1-methylcyclopropyl)amino]-N-{[4-(trifluoromethyl)-1,3-thiazol-2-yl]methyl}furo[2,3-d]pyrimidine-5-carboxamide

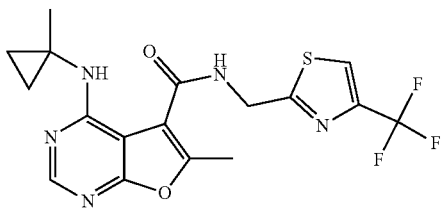 [SMILES: Cc1oc2ncnc(NC3(C)CC3)c2c1C(=O)NCc1nc(C(F)(F)F)cs1]

¹H NMR (400 MHz, CD₃OD) δ 8.37 (s, 1H), 8.18 (s, 1H), 4.94 (s, 2H), 2.77 (s, 3H), 1.52 (s, 3H), 1.08-0.74 (m, 4H). [M+H]=412.3.

Example 705. 6-Methyl-4-[(1-methylcyclopropyl)amino]-N-[(5-methylpyrimidin-2-yl)methyl]furo[2,3-d]pyrimidine-5-carboxamide

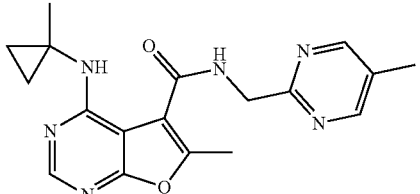

¹H NMR (400 MHz, CD₃OD) δ 8.67 (s, 2H), 8.46 (s, 1H), 4.83 (s, 2H), 2.87 (s, 3H), 2.37 (s, 3H), 1.54 (s, 3H), 1.04-0.93 (m, 4H). [M+H]=353.4.

Example 706. N-{[5-(Difluoromethyl)pyrimidin-2-yl]methyl}-6-methyl-4-[(1-methylcyclopropyl)amino]furo[2,3-d]pyrimidine-5-carboxamide

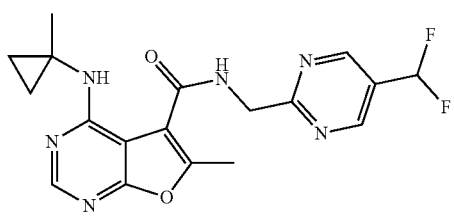 [SMILES: Cc1oc2ncnc(NC3(C)CC3)c2c1C(=O)NCc1ncc(C(F)F)cn1]

¹H NMR (400 MHz, CD₃OD) δ 8.99 (s, 2H), 8.41 (s, 1H), 7.29-6.78 (m, 1H), 4.93 (s, 2H), 2.86 (s, 3H), 1.52 (s, 3H), 0.98-0.85 (m, 4H). [M+H]=389.4.

Example 707. N-{[4-(Difluoromethyl)pyrimidin-2-yl]methyl}-6-methyl-4-[(1-methylcyclopropyl)amino]furo[2,3-d]pyrimidine-5-carboxamide

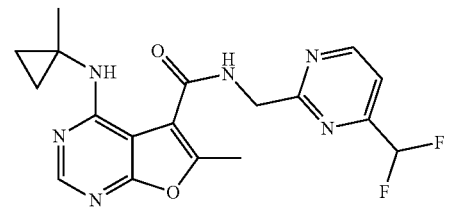 [SMILES: Cc1oc2ncnc(NC3(C)CC3)c2c1C(=O)NCc1nccc(C(F)F)n1]

¹H NMR (400 MHz, CD₃OD) δ 9.02 (d, J=5.0 Hz, 1H), 8.40 (s, 1H), 7.68 (d, J=5.0 Hz, 1H), 6.91-6.57 (m, 1H), 4.92 (s, 2H), 2.87 (s, 3H), 1.52 (s, 3H), 1.01-0.82 (m, 4H). [M+H]=389.4.

Example 708. N-[(2-Cyclopropylpyrimidin-5-yl)methyl]-6-methyl-4-[(1-methylcyclopropyl)amino]furo[2,3-d]pyrimidine-5-carboxamide

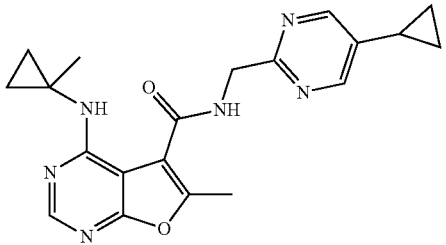 [SMILES: Cc1oc2ncnc(NC3(C)CC3)c2c1C(=O)NCc1ncc(C2CC2)cn1]

$^1$H NMR (400 MHz, CD$_3$OD) δ 8.67 (s, 2H), 8.37 (s, 1H), 4.56 (s, 2H), 2.71 (s, 3H), 2.22 (quin, J=6.4 Hz, 1H), 1.51 (s, 3H), 1.12-1.07 (m, 4H), 0.91 (d, J=4.2 Hz, 4H). [M+H]= 379.20.

Example 709. 5-{4-Methoxy-2-methyl-5H,6H,7H-pyrrolo[3,4-d]pyrimidine-6-carbonyl}-6-methyl-N-(1-methylcyclopropyl)furo[2,3-d]pyrimidin-4-amine

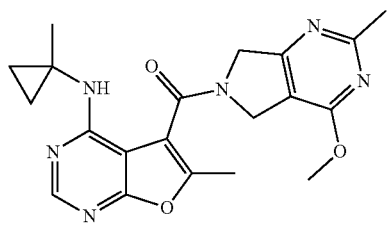 [SMILES: COc1nc(C)nc2c1CN(C(=O)c1c(C)oc3ncnc(NC4(C)CC4)c13)C2]

$^1$H NMR (400 MHz, CD$_3$OD) δ 8.36 (s, 1H), 4.92 (br s, 2H), 4.82-4.68 (m, 2H), 4.15-3.97 (m, 3H), 2.61 (s, 6H), 1.48 (s, 3H), 0.88-0.78 (m, 4H). [M+H]=395.30.

Example 710. 6-Methyl-4-[(1-methylcyclopropyl)amino]-N-[1-(pyrimidin-5-yl)ethyl]furo[2,3-d]pyrimidine-5-carboxamide

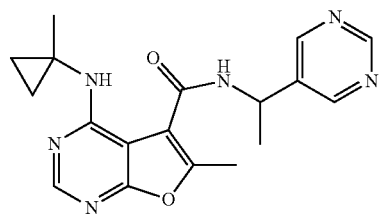 [SMILES: Cc1oc2ncnc(NC3(C)CC3)c2c1C(=O)NC(C)c1cncnc1]

$^1$H NMR (400 MHz, CD$_3$OD) δ 9.12 (s, 1H), 8.90 (s, 2H), 8.36 (s, 1H), 5.29 (q, J=7.2 Hz, 1H), 2.74 (s, 3H), 1.71 (d, J=7.1 Hz, 3H), 1.49 (s, 3H), 0.94-0.71 (m, 4H). [M+H]= 353.3.

Example 711. N-[(6-Methoxypyridazin-3-yl)methyl]-6-methyl-4-[(1-methylcyclopropyl)amino]furo[2,3-d]pyrimidine-5-carboxamide

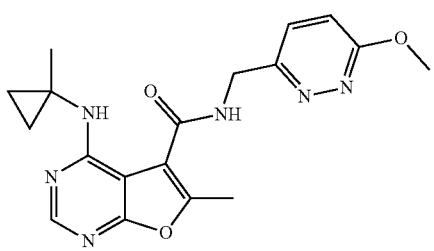 [SMILES: COc1ccc(CNC(=O)c2c(C)oc3ncnc(NC4(C)CC4)c23)nn1]

$^1$H NMR (400 MHz, CD$_3$OD) δ 8.42 (s, 1H), 7.69 (d, J=9.2 Hz, 1H), 7.24 (d, J=9.2 Hz, 1H), 4.82 (s, 2H), 4.10 (s, 3H), 2.77 (s, 3H), 1.53 (s, 3H), 1.00-0.90 (m, 4H). [M+H]= 369.30.

Example 712. 5-{4-Methoxy-2-methyl-5H,6H,7H,8H-pyrido[4,3-d]pyrimidine-6-carbonyl}-6-methyl-N-(1-methylcyclopropyl)furo[2,3-d]pyrimidin-4-amine

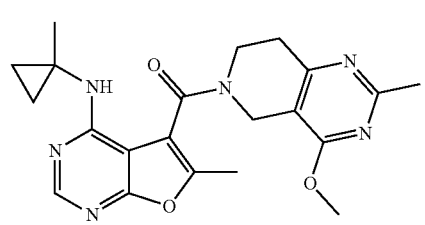 [SMILES: COc1nc(C)nc2c1CN(C(=O)c1c(C)oc3ncnc(NC4(C)CC4)c13)CC2]

$^1$H NMR (400 MHz, CD$_3$OD) δ 8.38 (s, 1H), 4.73 (br s, 2H), 4.17 (s, 3H), 4.03 (br s, 2H), 3.07 (t, J=5.4 Hz, 2H), 2.70 (s, 3H), 2.58 (s, 3H), 1.47 (s, 3H), 0.88-0.79 (m, 4H). [M+H]=409.23.

Example 713. 6-Methyl-4-[(1-methylcyclopropyl)amino]-N-(1,3-oxazol-2-ylmethyl)furo[2,3-d]pyrimidine-5-carboxamide

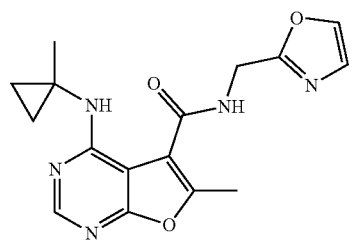 [SMILES: Cc1oc2ncnc(NC3(C)CC3)c2c1C(=O)NCc1ncco1]

$^1$H NMR (400 MHz, CD$_3$OD) δ 8.40 (s, 1H), 7.92 (d, J=0.7 Hz, 1H), 7.17 (d, J=0.6 Hz, 1H), 4.74 (s, 2H), 2.75 (s, 3H), 1.51 (s, 3H), 0.99-0.87 (m, 4H). [M+H]=328.20.

Example 714. N-[(5-Methoxy-1,3-benzoxazol-2-yl)methyl]-6-methyl-4-[(1-methylcyclopropyl)amino]furo[2,3-d]pyrimidine-5-carboxamide

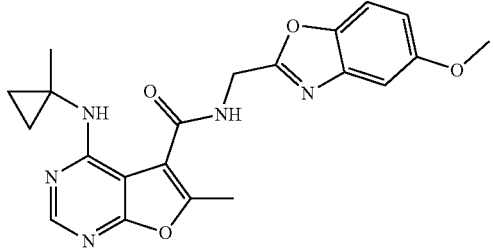 [SMILES: COc1ccc2oc(CNC(=O)c3c(C)oc4ncnc(NC5(C)CC5)c34)nc2c1]

¹H NMR (400 MHz, CD₃OD) δ 8.38 (s, 1H), 7.50 (d, J=8.9 Hz, 1H), 7.19 (d, J=2.4 Hz, 1H), 7.00 (dd, J=2.6, 8.9 Hz, 1H), 4.87 (s, 2H), 3.85 (s, 3H), 2.80 (s, 3H), 1.50 (s, 3H), 0.90-0.82 (m, 4H). [M+H]=408.20.

Example 715. 6-Methyl-N-[(1-methyl-1H-imidazol-2-yl)methyl]-4-[(1-methylcyclopropyl)amino]furo[2,3-d]pyrimidine-5-carboxamide

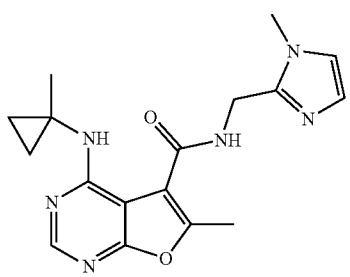 [SMILES: Cc1oc2ncnc(NC3(C)CC3)c2c1C(=O)NCc1nccn1C]

¹H NMR (400 MHz, CD₃OD) δ 8.32 (s, 1H), 7.56 (d, J=2.1 Hz, 1H), 7.52 (d, J=2.0 Hz, 1H), 4.88 (s, 2H), 3.98 (s, 3H), 2.74 (s, 3H), 1.48 (s, 3H), 0.83-0.79 (m, 4H). [M+H]=341.30.

Example 716. N-[(5-Chloropyrimidin-2-yl)methyl]-6-methyl-4-[(1-methylcyclopropyl)amino]furo[2,3-d]pyrimidine-5-carboxamide

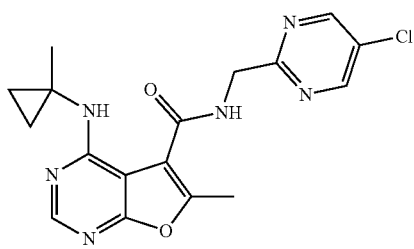 [SMILES: Cc1oc2ncnc(NC3(C)CC3)c2c1C(=O)NCc1ncc(Cl)cn1]

¹H NMR (400 MHz, CD₃OD) δ 8.82 (s, 2H), 8.39 (s, 1H), 4.84 (s, 2H), 2.83 (s, 3H), 1.51 (s, 3H), 0.96-0.86 (m, 4H). [M+H]=373.20.

Example 717. 6-Methyl-N-[(5-methyl-1,3,4-oxadiazol-2-yl)methyl]-4-[(1-methylcyclopropyl)amino]furo[2,3-d]pyrimidine-5-carboxamide

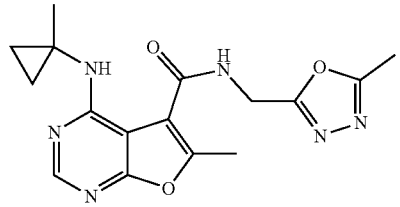 [SMILES: Cc1nnc(CNC(=O)c2c(C)oc3ncnc(NC4(C)CC4)c23)o1]

¹H NMR (400 MHz, CD₃OD) δ 8.41 (s, 1H), 4.83 (s, 2H), 2.78 (s, 3H), 2.57 (s, 3H), 1.53 (s, 3H), 1.05-0.85 (m, 4H). [M+H]=343.3.

Example 718. 6-Methyl-4-[(1-methylcyclopropyl)amino]-N-[(6-methylpyridazin-3-yl)methyl]furo[2,3-d]pyrimidine-5-carboxamide

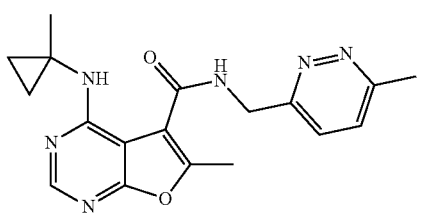 [SMILES: Cc1ccc(CNC(=O)c2c(C)oc3ncnc(NC4(C)CC4)c23)nn1]

¹H NMR (400 MHz, CD₃OD) δ 8.28 (s, 1H), 7.72-7.67 (m, 1H), 7.66-7.62 (m, 1H), 4.87 (s, 2H), 2.73 (s, 3H), 2.70 (s, 3H), 1.49 (s, 3H), 0.82-0.73 (m, 4H). [M+H]=353.4.

Example 719. N-{Imidazo[1,2-a]pyrazin-6-ylmethyl}-6-methyl-4-[(1-methylcyclopropyl)amino]furo[2,3-d]pyrimidine-5-carboxamide

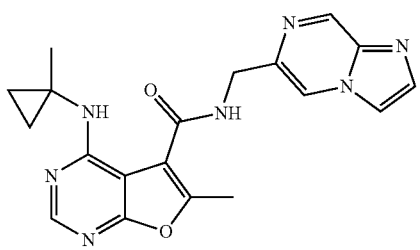 [SMILES: Cc1oc2ncnc(NC3(C)CC3)c2c1C(=O)NCc1cn2ccnc2cn1]

¹H NMR (400 MHz, CD₃OD) δ 9.26 (d, J=0.7 Hz, 1H), 8.78 (d, J=1.2 Hz, 1H), 8.40 (s, 1H), 8.26 (d, J=1.1 Hz, 1H), 8.09 (d, J=1.6 Hz, 1H), 4.81 (s, 2H), 2.78 (s, 3H), 1.50 (s, 3H), 0.97-0.87 (m, 4H). [M+H]=378.30.

Example 720. 6-Methyl-4-[(1-methylcyclopropyl)amino]-N-[1-(pyrimidin-4-yl)azetidin-3-yl]furo[2,3-d]pyrimidine-5-carboxamide

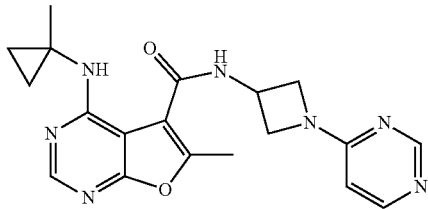 [SMILES: Cc1oc2ncnc(NC3(C)CC3)c2c1C(=O)NC1CN(c2ccncn2)C1]

$^1$H NMR (400 MHz, CD$_3$OD) δ 8.67 (d, J=1.1 Hz, 1H), 8.33 (s, 1H), 8.16 (dd, J=1.5, 7.3 Hz, 1H), 6.74 (dd, J=0.9, 7.4 Hz, 1H), 5.02 (tt, J=5.4, 8.0 Hz, 1H), 4.80-4.71 (m, 2H), 4.44 (d, J=5.7 Hz, 2H), 2.73 (s, 3H), 1.50 (s, 3H), 0.91-0.82 (m, 4H). [M+H]=380.30.

Example 721. 6-Methyl-4-[(1-methylcyclopropyl)amino]-N-[4-(oxan-4-yl)phenyl]furo[2,3-d]pyrimidine-5-carboxamide

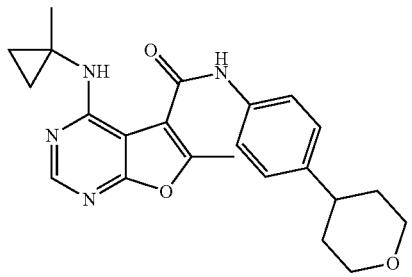 [SMILES: Cc1oc2ncnc(NC3(C)CC3)c2c1C(=O)Nc1ccc(C2CCOCC2)cc1]

$^1$H NMR (400 MHz, CD$_3$OD) δ 8.42 (s, 1H), 7.59 (d, J=8.6 Hz, 2H), 7.31 (d, J=8.6 Hz, 2H), 4.08-4.02 (m, 2H), 3.62-3.52 (m, 2H), 2.87-2.80 (m, 1H), 2.77 (s, 3H), 1.85-1.73 (m, 4H), 1.52 (s, 3H), 1.03-0.88 (m, 4H). [M+H]=407.36.

Example 722. 6-Methyl-4-[(1-methylcyclopropyl)amino]-N-{[4-(trifluoromethoxy)phenyl]methyl}furo[2,3-d]pyrimidine-5-carboxamide

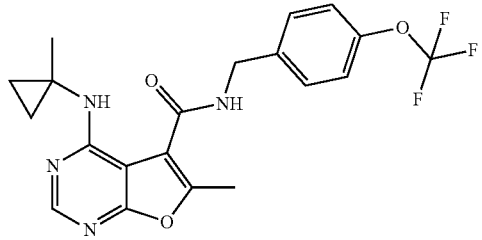 [SMILES: Cc1oc2ncnc(NC3(C)CC3)c2c1C(=O)NCc1ccc(OC(F)(F)F)cc1]

$^1$H NMR (400 MHz, CD$_3$OD) δ 8.35 (s, 1H), 7.49 (d, J=8.7 Hz, 2H), 7.27 (d, J=8.1 Hz, 2H), 4.62 (s, 2H), 2.68 (s, 3H), 1.50 (s, 3H), 0.94-0.83 (m, 4H). [M+H]=421.30.

Example 723. N-{[2-Fluoro-4-(trifluoromethoxy)phenyl]methyl}-6-methyl-4-[(1-methylcyclopropyl)amino]furo[2,3-d]pyrimidine-5-carboxamide

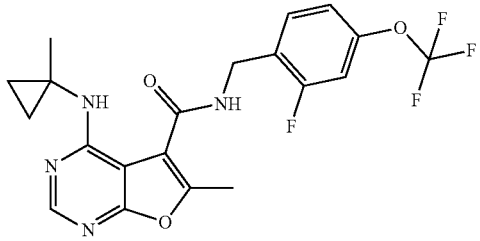 [SMILES: Cc1oc2ncnc(NC3(C)CC3)c2c1C(=O)NCc1ccc(OC(F)(F)F)cc1F]

$^1$H NMR (400 MHz, CD$_3$OD) δ 8.35 (s, 1H), 7.60-7.52 (m, 1H), 7.15 (t, J=7.3 Hz, 2H), 4.65 (s, 2H), 2.68 (s, 3H), 1.50 (s, 3H), 0.94-0.84 (m, 4H). [M+H]=439.30.

Example 724. N-[2-(5-Fluoro-1H-1,3-benzodiazol-2-yl)ethyl]-6-methyl-4-[(1-methylcyclopropyl)amino]furo[2,3-d]pyrimidine-5-carboxamide

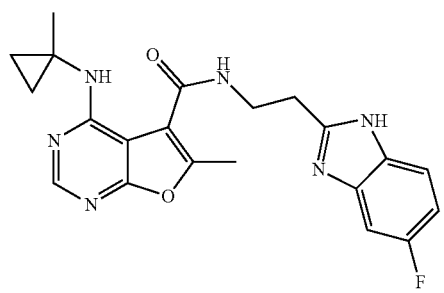 [SMILES: Cc1oc2ncnc(NC3(C)CC3)c2c1C(=O)NCCc1nc2cc(F)ccc2[nH]1]

$^1$H NMR (400 MHz, CD$_3$OD) δ 8.30 (s, 1H), 7.77 (dd, J=4.3, 9.0 Hz, 1H), 7.54 (dd, J=2.3, 8.2 Hz, 1H), 7.38 (dt, J=2.3, 9.2 Hz, 1H), 3.94 (t, J=6.4 Hz, 2H), 3.48 (t, J=6.4 Hz, 2H), 2.62 (s, 3H), 1.40 (s, 3H), 0.80-0.63 (m, 4H). [M+H]=409.30.

Example 725. N-[(6-Fluoro-1-methyl-1H-1,3-benzodiazol-2-yl)methyl]-6-methyl-4-[(1-methylcyclopropyl)amino]furo[2,3-d]pyrimidine-5-carboxamide

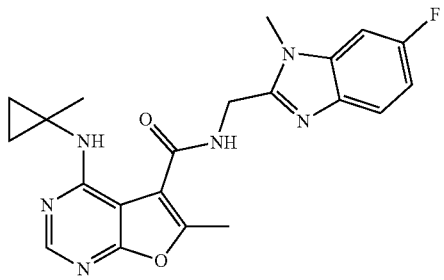 [SMILES: Cc1oc2ncnc(NC3(C)CC3)c2c1C(=O)NCc1nc2ccc(F)cc2n1C]

$^1$H NMR (400 MHz, CD$_3$OD) δ 8.37-8.35 (m, 1H), 7.80 (dd, J=4.3, 9.0 Hz, 1H), 7.73 (dd, J=2.0, 8.4 Hz, 1H), 7.40 (dt, J=2.2, 9.2 Hz, 1H), 5.14-5.09 (m, 2H), 4.10 (s, 3H), 2.80 (s, 3H), 1.46 (s, 3H), 0.84-0.78 (m, 4H). [M+H]=409.29.

Example 726. N-[(2-Ethylpyrimidin-4-yl)methyl]-6-methyl-4-[(1-methylcyclopropyl)amino]furo[2,3-d]pyrimidine-5-carboxamide

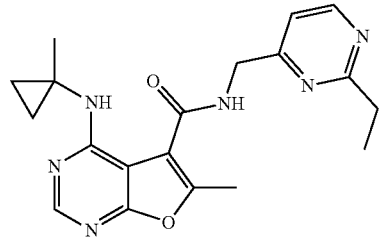 [SMILES: CCc1nccc(CNC(=O)c2c(C)oc3ncnc(NC4(C)CC4)c23)n1]

¹H NMR (400 MHz, CD₃OD) δ 8.67 (d, J=5.3 Hz, 1H), 8.42 (s, 1H), 7.39 (d, J=5.4 Hz, 1H), 4.74 (s, 2H), 3.02-2.94 (m, 2H), 2.85 (s, 3H), 1.51 (s, 3H), 1.40-1.32 (m, 3H), 0.97-0.89 (m, 4H). [M+H]=367.27.

Example 727. 6-Methyl-4-[(1-methylcyclopropyl)amino]-N-[5-(oxan-4-yl)pyridin-2-yl]furo[2,3-d]pyrimidine-5-carboxamide

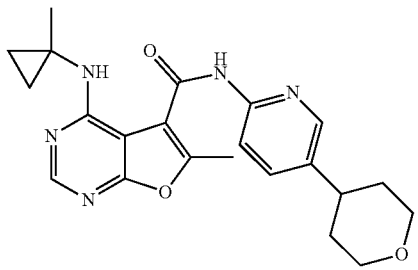 [SMILES: Cc1oc2ncnc(NC3(C)CC3)c2c1C(=O)Nc1ccc(C2CCOCC2)cn1]

¹H NMR (400 MHz, CD₃OD) δ 8.40 (s, 1H), 8.31 (s, 1H), 8.04 (d, J=8.6 Hz, 1H), 7.92 (dd, J=2.1, 8.6 Hz, 1H), 4.14-4.05 (m, 2H), 3.67-3.57 (m, 2H), 3.01-2.89 (m, 1H), 2.84-2.80 (m, 3H), 1.89-1.80 (m, 4H), 1.55-1.53 (m, 3H), 0.98-0.87 (m, 4H). [M+H]=408.29.

Example 728. N-[(Dimethyl-1,3-oxazol-2-yl)methyl]-6-methyl-4-[(1-methylcyclopropyl)amino]furo[2,3-d]pyrimidine-5-carboxamide

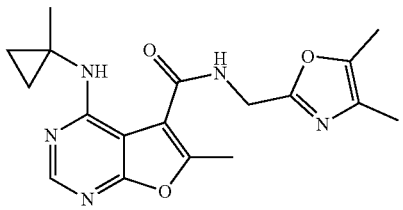 [SMILES: Cc1nc(CNC(=O)c2c(C)oc3ncnc(NC4(C)CC4)c23)oc1C]

¹H NMR (400 MHz, CD₃OD) δ 8.38 (s, 1H), 4.63 (s, 2H), 2.75 (s, 3H), 2.25 (s, 3H), 2.07 (d, J=0.6 Hz, 3H), 1.51 (s, 3H), 0.97-0.87 (m, 4H). [M+H]=356.20.

Example 729. N-[(5-Fluoro-1H-1,3-benzodiazol-2-yl)methyl]-6-methyl-4-[(1-methylcyclopropyl)amino]furo[2,3-d]pyrimidine-5-carboxamide

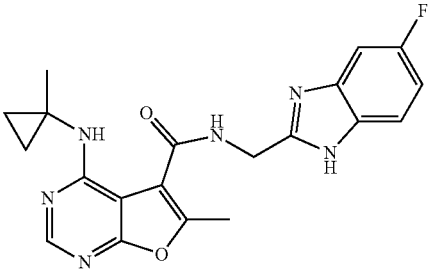 [SMILES: Cc1oc2ncnc(NC3(C)CC3)c2c1C(=O)NCc1nc2cc(F)ccc2[nH]1]

¹H NMR (400 MHz, CD₃OD) δ 8.35 (s, 1H), 7.78 (dd, J=4.3, 9.0 Hz, 1H), 7.54 (dd, J=2.3, 8.2 Hz, 1H), 7.37 (dt, J=2.4, 9.3 Hz, 1H), 5.05 (s, 2H), 2.81 (s, 3H), 1.46 (s, 3H), 0.80 (s, 4H). [M+H]=395.30.

Example 730. N-[2-(5-Fluoro-1,3-benzoxazol-2-yl)ethyl]-6-methyl-4-[(1-methylcyclopropyl)amino]furo[2,3-d]pyrimidine-5-carboxamide

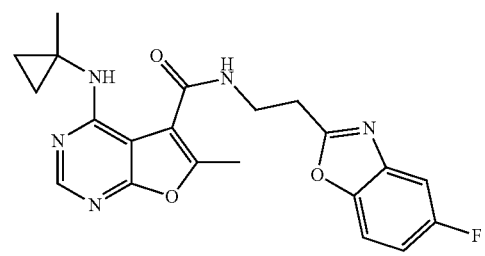 [SMILES: Cc1oc2ncnc(NC3(C)CC3)c2c1C(=O)NCCc1nc2cc(F)ccc2o1]

¹H NMR (400 MHz, CD₃OD) δ 8.45-8.38 (m, 1H), 8.34 (s, 1H), 7.59 (dd, J=4.3, 8.9 Hz, 1H), 7.38 (dd, J=2.6, 8.4 Hz, 1H), 7.16 (dt, J=2.6, 9.2 Hz, 1H), 3.97-3.90 (m, 2H), 3.29 (br s, 2H), 2.63 (s, 3H), 1.48 (s, 3H), 0.85 (s, 4H). [M+H]=410.30.

Example 731. N-[(5-Methoxypyrazin-2-yl)methyl]-6-methyl-4-[(1-methylcyclopropyl)amino]furo[2,3-d]pyrimidine-5-carboxamide

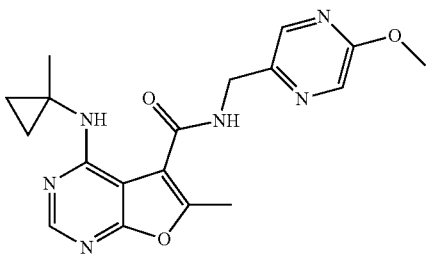 [SMILES: COc1cnc(CNC(=O)c2c(C)oc3ncnc(NC4(C)CC4)c23)cn1]

¹H NMR (400 MHz, CD₃OD) δ 8.37 (s, 1H), 8.23 (s, 1H), 8.20 (s, 1H), 4.67 (s, 2H), 3.97 (s, 3H), 2.72 (s, 3H), 1.51 (s, 3H), 0.96-0.86 (m, 4H). [M+H]=369.20.

Example 732. N-[(5-Cyclopropylpyrazin-2-yl)methyl]-6-methyl-4-[(1-methylcyclopropyl)amino]furo[2,3-d]pyrimidine-5-carboxamide

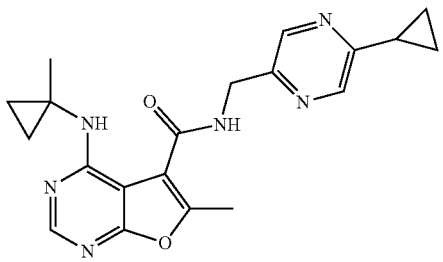 [SMILES: Cc1oc2ncnc(NC3(C)CC3)c2c1C(=O)NCc1cnc(C2CC2)cn1]

¹H NMR (400 MHz, CD₃OD) δ 8.51 (d, J=1.5 Hz, 1H), 8.49 (s, 1H), 8.37 (s, 1H), 4.71 (s, 2H), 2.74 (s, 3H), 2.23-2.12 (m, 1H), 1.51 (s, 3H), 1.13-1.01 (m, 4H), 0.95-0.84 (m, 4H).
[M+H]=379.30.

Example 733. N-[(5-Fluoro-1-methyl-1H-1,3-benzodiazol-2-yl)methyl]-6-methyl-4-[(1-methylcyclopropyl)amino]furo[2,3-d]pyrimidine-5-carboxamide

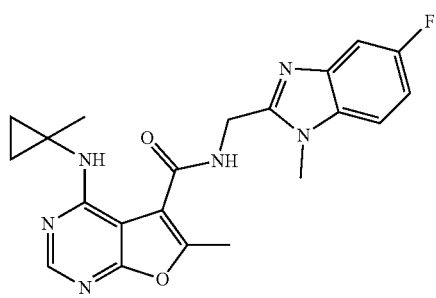 [SMILES: Cc1oc2ncnc(NC3(C)CC3)c2c1C(=O)NCc1nc2cc(F)ccc2n1C]

¹H NMR (400 MHz, CD₃OD) δ 8.35 (s, 1H), 7.90 (dd, J=4.3, 9.2 Hz, 1H), 7.55 (dd, J=2.4, 8.3 Hz, 1H), 7.43 (dt, J=2.4, 9.3 Hz, 1H), 5.10 (s, 2H), 4.13 (s, 3H), 2.80 (s, 3H), 1.46 (s, 3H), 0.80 (s, 4H). [M+H]=409.26.

Example 734. N-[2-(5-Fluoro-1-methyl-1H-1,3-benzodiazol-2-yl)ethyl]-6-methyl-4-[(1-methylcyclopropyl)amino]furo[2,3-d]pyrimidine-5-carboxamide

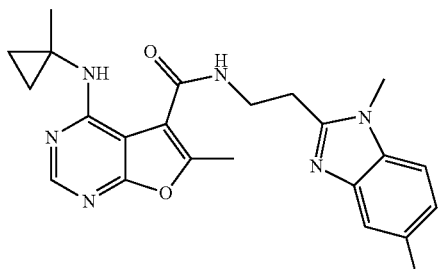

¹H NMR (400 MHz, CD₃OD) δ 8.30 (s, 1H), 7.90 (dd, J=4.2, 9.2 Hz, 1H), 7.55 (dd, J=2.3, 8.2 Hz, 1H), 7.44 (dt, J=2.3, 9.2 Hz, 1H), 4.09 (s, 3H), 3.93 (t, J=6.4 Hz, 2H), 3.55 (t, J=6.5 Hz, 2H), 2.66 (s, 3H), 1.40 (s, 3H), 0.80-0.60 (m, 4H). [M+H]=423.30.

Example 735. 6-Methyl-4-[(1-methylcyclopropyl)amino]-N-[6-(oxan-4-yl)pyridin-3-yl]furo[2,3-d]pyrimidine-5-carboxamide

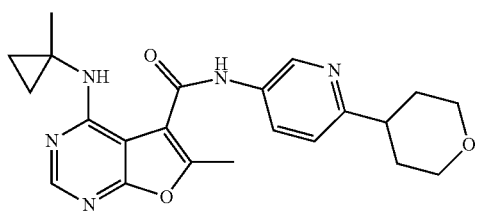

¹H NMR (400 MHz, CD₃OD) δ 9.16 (d, J=2.3 Hz, 1H), 8.51 (dd, J=2.3, 8.8 Hz, 1H), 8.40 (s, 1H), 7.91 (d, J=8.8 Hz, 1H), 4.11 (d, J=11.4 Hz, 2H), 3.68-3.54 (m, 2H), 3.29-3.20 (m, 1H), 2.79 (s, 3H), 2.01-1.89 (m, 4H), 1.51 (s, 3H), 0.95-0.83 (m, 4H). [M+H]=408.30.

Example 736. 6-Methyl-4-[(1-methylcyclopropyl)amino]-N-[5-(oxan-4-yl)pyrazin-2-yl]furo[2,3-d]pyrimidine-5-carboxamide

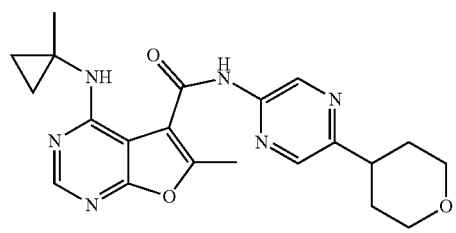 [SMILES: Cc1oc2ncnc(NC3(C)CC3)c2c1C(=O)Nc1cnc(C2CCOCC2)cn1]

¹H NMR (400 MHz, CD₃OD) δ 9.33 (s, 1H), 8.43 (s, 1H), 8.40-8.36 (m, 1H), 4.08 (dd, J=3.4, 11.2 Hz, 2H), 3.64-3.57 (m, 2H), 3.14-3.06 (m, 1H), 2.80 (s, 3H), 2.01-1.90 (m, 2H), 1.90-1.82 (m, 2H), 1.53 (s, 3H), 1.02-0.97 (m, 2H), 0.94-0.90 (m, 2H). [M+H]=409.3.

Example 737. 6-Methyl-4-[(1-methylcyclopropyl)amino]-N-{[6-(morpholin-4-yl)pyridin-2-yl]methyl}furo[2,3-d]pyrimidine-5-carboxamide

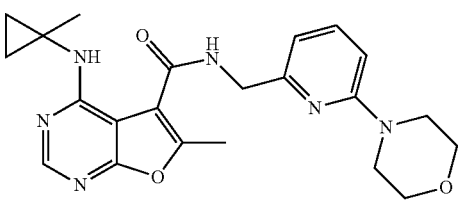 [SMILES: Cc1oc2ncnc(NC3(C)CC3)c2c1C(=O)NCc1cccc(N2CCOCC2)n1]

¹H NMR (400 MHz, DMSO-d₆) δ 8.72 (t, J=5.8 Hz, 1H), 8.41 (s, 1H), 8.26 (s, 1H), 7.56-7.46 (m, 1H), 6.69 (d, J=8.6 Hz, 1H), 6.60 (d, J=7.2 Hz, 1H), 4.40 (d, J=5.7 Hz, 2H), 3.67-3.57 (m, 4H), 3.45-3.33 (m, 4H), 2.60 (s, 3H), 1.36 (s, 3H), 0.68-0.58 (m, 4H). [M+H]=423.0.

Example 738. 6-Methyl-N-[(2-methyl-2H-1,2,3,4-tetrazol-5-yl)methyl]-4-[(1-methylcyclopropyl)amino]furo[2,3-d]pyrimidine-5-carboxamide

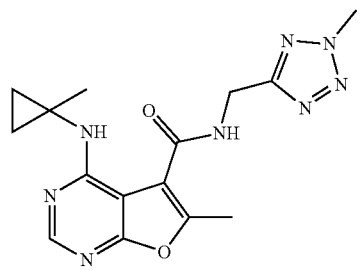 [SMILES: Cc1oc2ncnc(NC3(C)CC3)c2c1C(=O)NCc1nnn(C)n1]

$^1$H NMR (400 MHz, DMSO-d$_6$) δ 8.98 (t, J=5.7 Hz, 1H), 8.35-8.18 (m, 2H), 4.68 (d, J=5.9 Hz, 2H), 4.28 (s, 3H), 2.57 (s, 3H), 1.36 (s, 3H), 0.65 (d, J=4.5 Hz, 4H). [M+H]=343.0.

Example 739. 6-Methyl-4-[(1-methylcyclopropyl)amino]-N-{[2-(morpholin-4-yl)-1,3-thiazol-4-yl]methyl}furo[2,3-d]pyrimidine-5-carboxamide

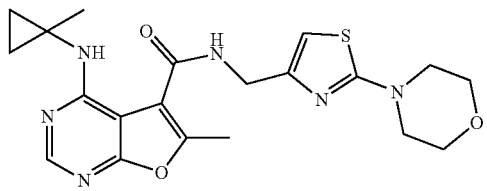 [SMILES: Cc1oc2ncnc(NC3(C)CC3)c2c1C(=O)NCc1csc(N2CCOCC2)n1]

$^1$H NMR (400 MHz, DMSO-d$_6$) δ 8.69 (t, J=5.8 Hz, 1H), 8.32 (s, 1H), 8.25 (s, 1H), 6.58 (s, 1H), 4.30 (d, J=5.5 Hz, 2H), 3.66-3.61 (m, 4H), 3.36-3.24 (m, 4H), 2.57 (s, 3H), 1.36 (s, 3H), 0.63 (d, J=6.5 Hz, 4H). [M+H]=429.91.

Example 740. 6-Methyl-N-[(2-methyl-2H-1,2,3-triazol-4-yl)methyl]-4-[(1-methylcyclopropyl)amino]furo[2,3-d]pyrimidine-5-carboxamide

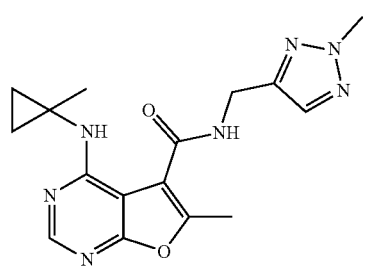 [SMILES: Cc1oc2ncnc(NC3(C)CC3)c2c1C(=O)NCc1cnn(C)n1]

$^1$H NMR (400 MHz, DMSO-d$_6$) δ 8.69 (t, J=5.8 Hz, 1H), 8.32 (s, 1H), 8.25 (s, 1H), 6.58 (s, 1H), 4.30 (d, J=5.5 Hz, 2H), 3.66-3.61 (m, 4H), 3.36-3.24 (m, 4H), 2.57 (s, 3H), 1.36 (s, 3H), 0.63 (d, J=6.5 Hz, 4H). [M+H]=342.0.

Example 741. 6-Methyl-N-[(1-methyl-1H-1,2,4-triazol-3-yl)methyl]-4-[(1-methylcyclopropyl)amino]furo[2,3-d]pyrimidine-5-carboxamide

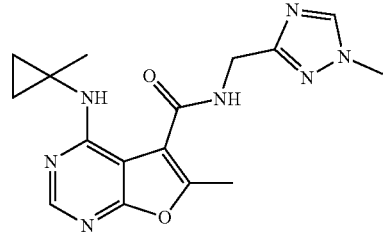 [SMILES: Cc1oc2ncnc(NC3(C)CC3)c2c1C(=O)NCc1ncn(C)n1]

$^1$H NMR (400 MHz, DMSO-d$_6$) δ 8.92-8.74 (m, 1H), 8.37 (s, 1H), 8.26 (s, 2H), 4.44 (d, J=5.9 Hz, 2H), 3.77 (s, 3H), 2.63-2.52 (m, 3H), 1.42-1.33 (m, 3H), 0.69-0.61 (m, 4H).

[M+H]=341.97.

Example 742. 5-{3-Bromo-5H,6H,7H-pyrrolo[3,4-b]pyridine-6-carbonyl}-6-methyl-N-(1-methylcyclopropyl)furo[2,3-d]pyrimidin-4-amine

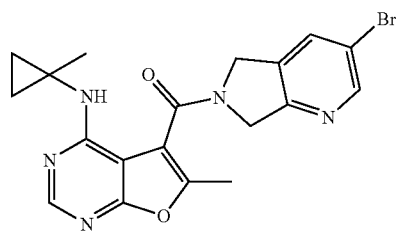 [SMILES: Cc1oc2ncnc(NC3(C)CC3)c2c1C(=O)N1Cc2cc(Br)cnc2C1]

$^1$H NMR (400 MHz, DMSO-d$_6$) δ 8.55 (d, J=10.1 Hz, 1H), 8.30 (s, 1H), 8.14-7.89 (m, 1H), 7.21 (br s, 1H), 4.96-4.63 (m, 4H), 2.48 (s, 3H), 1.34 (s, 3H), 0.60 (br s, 4H). [M+H]=429.7.

Example 743. 6-Methyl-N-[(2-methyl-1,3-thiazol-5-yl)methyl]-4-[(1-methylcyclopropyl)amino]furo[2,3-d]pyrimidine-5-carboxamide

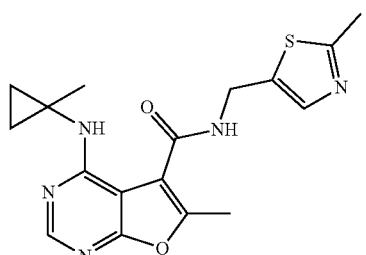

$^1$H NMR (400 MHz, DMSO-d$_6$) δ 8.94 (t, J=5.7 Hz, 1H), 8.39 (s, 1H), 8.27 (s, 1H), 7.51 (s, 1H), 4.56 (d, J=5.9 Hz, 2H), 2.53 (d, J=12.5 Hz, 6H), 1.38 (s, 3H), 0.68 (d, J=3.4 Hz, 4H).

[M+H]=358.0.

Example 744. 6-Methyl-N-[(2-methyl-1,3-oxazol-5-yl)methyl]-4-[(1-methylcyclopropyl)amino]furo[2,3-d]pyrimidine-5-carboxamide

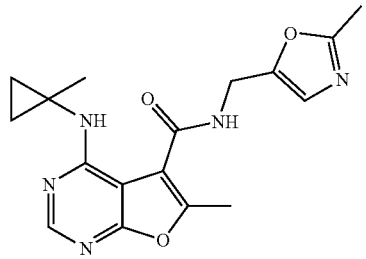 [SMILES: Cc1ncc(CNC(=O)c2c(C)oc3ncnc(NC4(C)CC4)c23)s1]

$^1$H NMR (400 MHz, DMSO-d$_6$) δ 8.81 (t, J=5.6 Hz, 1H), 8.45 (s, 1H), 8.29 (s, 1H), 6.87 (s, 1H), 4.45 (d, J=5.5 Hz, 2H), 2.53 (s, 3H), 2.32 (s, 3H), 1.38 (s, 3H), 0.67 (d, J=4.5 Hz, 4H).
[M+H]=342.1.

Example 745. 6-Methyl-4-[(1-methylcyclopropyl)amino]-N-{[6-(morpholin-4-yl)pyridazin-3-yl]methyl}furo[2,3-d]pyrimidine-5-carboxamide

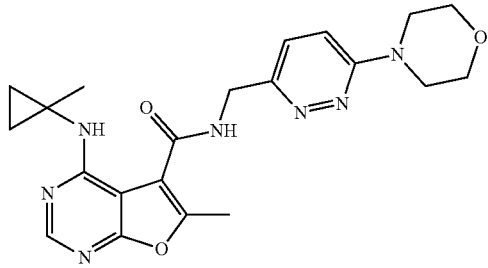 [SMILES: Cc1oc2ncnc(NC3(C)CC3)c2c1C(=O)NCc1ccc(N2CCOCC2)nn1]

$^1$H NMR (400 MHz, DMSO-d$_6$) δ 8.89-8.80 (m, 1H), 8.39 (br s, 1H), 8.27 (s, 1H), 7.85-7.74 (m, 1H), 4.59 (d, J=5.6 Hz, 3H), 3.74-3.67 (m, 3H), 3.60 (d, J=4.9 Hz, 5H), 2.60 (d, J=2.1 Hz, 3H), 1.42-1.34 (m, 3H), 0.70-0.57 (m, 4H). [M+H]=424.0.

Example 746. N-(Cyclopropylmethyl)-6-methyl-4-[(1-methylcyclopropyl)amino]furo[2,3-d]pyrimidine-5-carboxamide

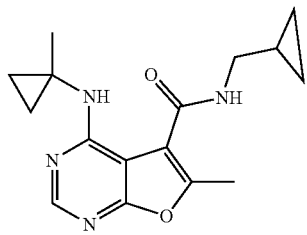 [SMILES: Cc1oc2ncnc(NC3(C)CC3)c2c1C(=O)NCC1CC1]

$^1$H NMR (400 MHz, CDCl$_3$) δ 8.57 (s, 1H), 6.41-6.32 (m, 1H), 3.30-3.21 (m, 2H), 2.73 (s, 4H), 1.49-1.43 (m, 3H), 1.11-0.82 (m, 5H), 0.64-0.43 (m, 2H), 0.35-0.14 (m, 2H). [M+H]=301.2.

Example 747. 6-Methyl-N-[(2-methyl-1,3-oxazol-4-yl)methyl]-4-[(1-methylcyclopropyl)amino]furo[2,3-d]pyrimidine-5-carboxamide

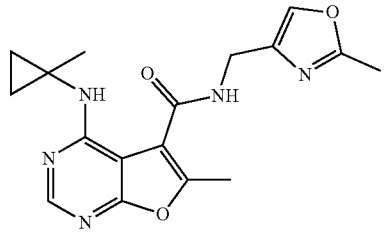

$^1$H NMR (400 MHz, CD$_3$OD) δ 8.34 (s, 1H), 7.66 (s, 1H), 4.82 (br s, 2H), 4.39 (d, J=0.9 Hz, 2H), 2.63 (s, 3H), 2.35 (s, 3H), 1.43 (s, 3H), 0.99-0.83 (m, 4H). [M+H]=342.2.

Example 748. 6-Methyl-N-(1-methylcyclopropyl)-5-[3-(oxan-4-yl)-5H,6H,7H-pyrrolo[3,4-b]pyridine-6-carbonyl]furo[2,3-d]pyrimidin-4-amine

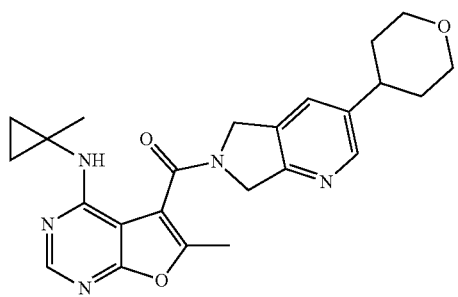 [SMILES: Cc1oc2ncnc(NC3(C)CC3)c2c1C(=O)N1Cc2cc(C3CCOCC3)cnc2C1]

$^1$H NMR (400 MHz, CD$_3$OD) δ 8.57-8.48 (m, 1H), 8.47 (s, 1H), 8.13-7.95 (m, 1H), 5.15 (br s, 2H), 5.01 (d, J=13.6 Hz, 2H), 4.06 (d, J=11.4 Hz, 2H), 3.67-3.52 (m, 2H), 3.12-2.95 (m, 1H), 2.68 (s, 3H), 1.82 (br s, 4H), 1.49 (s, 3H), 1.03-0.87 (m, 4H). [M+H]=434.0.

Example 749. 6-Methyl-4-[(1-methylcyclopropyl)amino]-N-[1-(1,3-oxazol-2-yl)ethyl]furo[2,3-d]pyrimidine-5-carboxamide

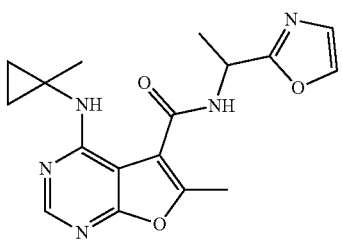 [SMILES: Cc1oc2ncnc(NC3(C)CC3)c2c1C(=O)NC(C)c1ncco1]

$^1$H NMR (400 MHz, CD$_3$OD) δ 8.33 (s, 1H), 7.82 (d, J=0.7 Hz, 1H), 7.08 (d, J=0.6 Hz, 1H), 5.30 (q, J=7.1 Hz, 1H), 2.64 (s, 3H), 1.58 (d, J=7.1 Hz, 3H), 1.42 (s, 3H), 0.93-0.82 (m, 4H). [M+H]=342.0.

Example 750. 6-Methyl-4-[(1-methylcyclopropyl)amino]-N-[1-(1,2-oxazol-3-yl)ethyl]furo[2,3-d]pyrimidine-5-carboxamide

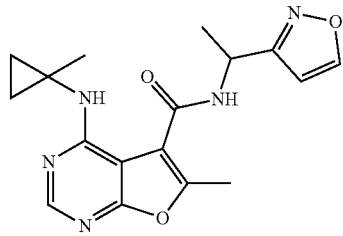 [SMILES: Cc1oc2ncnc(NC3(C)CC3)c2c1C(=O)NC(C)c1ccon1]

¹H NMR (400 MHz, CD₃OD) δ 8.55 (d, J=1.7 Hz, 1H), 8.32 (s, 1H), 6.46 (d, J=1.7 Hz, 1H), 5.33 (q, J=7.1 Hz, 1H), 2.63 (s, 3H), 1.55 (d, J=7.1 Hz, 3H), 1.42 (s, 3H), 0.93-0.79 (m, 4H). [M+H]=342.1.

Example 751. N-[(5-Fluoro-1,3-benzoxazol-2-yl)methyl]-6-methyl-4-[(1-methylcyclopropyl)amino]furo[2,3-d]pyrimidine-5-carboxamide

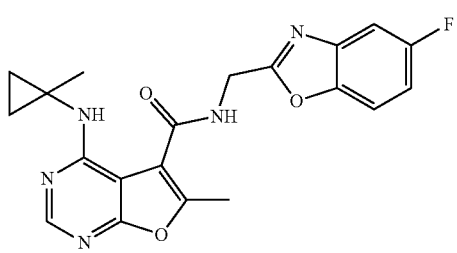 [SMILES: Cc1oc2ncnc(NC3(C)CC3)c2c1C(=O)NCc1nc2cc(F)ccc2o1]

¹H NMR (400 MHz, CD₃OD) δ 8.33 (s, 1H), 7.52 (dd, J=4.2, 9.0 Hz, 1H), 7.30 (dd, J=2.5, 8.4 Hz, 1H), 7.08 (dt, J=2.6, 9.2 Hz, 1H). [M+H]=396.0.

Example 752. 6-Methyl-4-[(1-methylcyclopropyl)amino]-N-[3-(pyrrolidin-1-yl)propyl]furo[2,3-d]pyrimidine-5-carboxamide

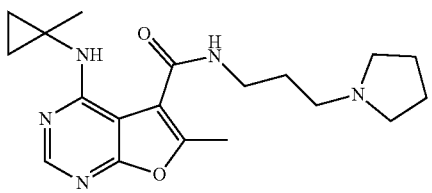 [SMILES: Cc1oc2ncnc(NC3(C)CC3)c2c1C(=O)NCCCN1CCCC1]

¹H NMR (400 MHz, CD₃OD) δ 8.31 (s, 1H), 3.68-3.54 (m, 2H), 3.43 (t, J=6.8 Hz, 2H), 3.25-3.17 (m, 3H), 3.07-2.93 (m, 2H), 2.64 (s, 3H), 2.17-1.85 (m, 6H), 1.42 (s, 3H), 0.93-0.79 (m, 4H). [M+H]=358.0.

Example 753. 6-Methyl-4-[(1-methylcyclopropyl)amino]-N-[6-(morpholin-4-yl)pyridin-3-yl]furo[2,3-d]pyrimidine-5-carboxamide

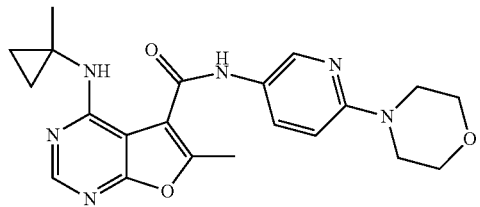 [SMILES: Cc1oc2ncnc(NC3(C)CC3)c2c1C(=O)Nc1ccc(N2CCOCC2)nc1]

¹H NMR (400 MHz, CD₃OD) δ 8.45 (d, J=2.6 Hz, 1H), 8.28 (s, 1H), 8.03 (d, J=2.6 Hz, 1H), 7.27 (d, J=9.8 Hz, 1H), 3.80-3.74 (m, 4H), 3.59-3.51 (m, 4H), 2.67 (s, 3H), 1.41 (s, 3H), 0.83-0.73 (m, 4H). [M+H]=409.2.

Example 754. 6-Methyl-4-[(1-methylcyclopropyl)amino]-N-(3,3,3-trifluoropropyl)furo[2,3-d]pyrimidine-5-carboxamide

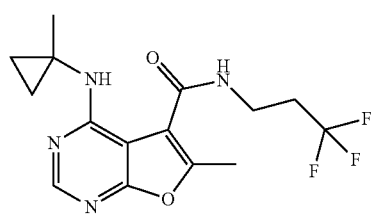 [SMILES: Cc1oc2ncnc(NC3(C)CC3)c2c1C(=O)NCCC(F)(F)F]

¹H NMR (400 MHz, CDCl₃) δ 8.74-8.61 (m, 1H), 8.45 (s, 1H), 6.45-6.31 (m, 1H), 3.77 (d, J=6.2 Hz, 2H), 2.66 (s, 3H), 2.58-2.40 (m, 2H), 1.54 (s, 3H), 0.96-0.73 (m, 4H). [M+H]=343.1.

Example 755. N-[(2,2-Difluorocyclopropyl)methyl]-6-methyl-4-[(1-methylcyclopropyl)amino]furo[2,3-d]pyrimidine-5-carboxamide

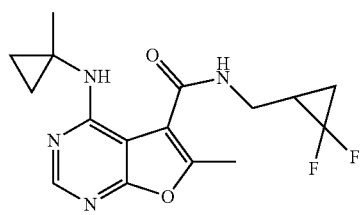 [SMILES: Cc1oc2ncnc(NC3(C)CC3)c2c1C(=O)NCC1CC1(F)F]

¹H NMR (400 MHz, CDCl₃) δ 8.56-8.46 (m, 1H), 8.36 (s, 1H), 6.28-6.11 (m, 1H), 3.93-3.79 (m, 1H), 3.30-3.16 (m, 1H), 2.58 (s, 3H), 2.03-1.83 (m, 1H), 1.50-1.43 (m, 3H), 1.30-1.07 (m, 2H), 0.86-0.60 (m, 4H). [M+H]=337.1.

Example 756. N-(2-{[Dimethyl(oxo)-λ⁶-sulfanylidene]amino}ethyl)-6-methyl-4-[(1-methylcyclopropyl)amino]furo[2,3-d]pyrimidine-5-carboxamide

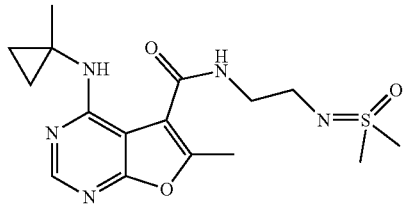 [SMILES: Cc1oc2ncnc(NC3(C)CC3)c2c1C(=O)NCCN=S(C)(C)=O]

¹H NMR (400 MHz, CD₃OD) δ 8.41-8.20 (m, 1H), 3.66 (s, 6H), 3.55 (dd, J=5.3, 11.9 Hz, 4H), 3.21 (s, 2H), 2.65 (s, 3H), 1.42 (s, 3H), 0.95-0.78 (m, 4H). [M+H]=366.1.

Example 757. 6-Methyl-4-[(1-methylcyclopropyl)amino]-N-(2-{8-oxa-3-azabicyclo[3.2.1]octan-3-yl}pyrimidin-5-yl)furo[2,3-d]pyrimidine-5-carboxamide

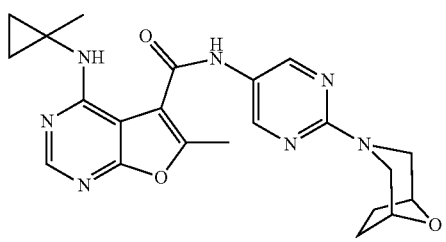 [SMILES: Cc1oc2ncnc(NC3(C)CC3)c2c1C(=O)Nc1cnc(N2CC3CCC(C2)O3)nc1]

¹H NMR (400 MHz, CDCl₃) δ 8.51-8.28 (m, 3H), 4.46-4.32 (m, 2H), 4.25-4.05 (m, 2H), 3.20-3.06 (m, 2H), 2.73 (br s, 3H), 1.93-1.87 (m, 2H), 1.73-1.64 (m, 2H), 1.42 (s, 3H), 0.84-0.66 (m, 4H). [M+H]=436.3.

Example 758. N-[2-(3,3-Dimethylmorpholin-4-yl)pyrimidin-5-yl]-6-methyl-4-[(1-methylcyclopropyl)amino]furo[2,3-d]pyrimidine-5-carboxamide

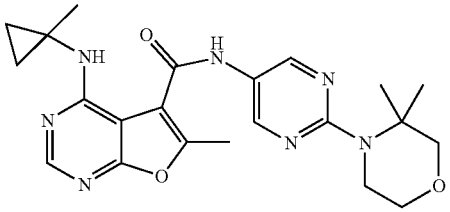 [SMILES: Cc1oc2ncnc(NC3(C)CC3)c2c1C(=O)Nc1cnc(N2CCOCC2(C)C)nc1]

¹H NMR (400 MHz, CDCl₃) δ 8.63-8.54 (m, 2H), 8.48-8.41 (m, 1H), 3.94-3.79 (m, 4H), 3.54-3.45 (m, 2H), 2.78 (s, 3H), 1.54-1.50 (m, 9H), 0.88-0.75 (m, 4H). [M+H]=438.28.

Example 759. N-{2-[(2R,6S)-2,6-Dimethylmorpholin-4-yl]pyrimidin-5-yl}-6-methyl-4-[(1-methylcyclopropyl)amino]furo[2,3-d]pyrimidine-5-carboxamide

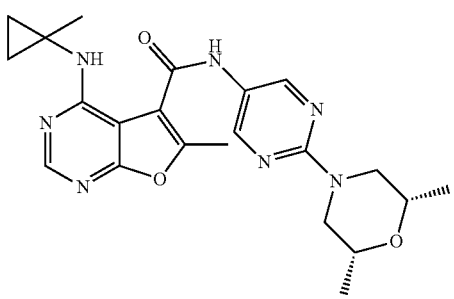 [SMILES: Cc1oc2ncnc(NC3(C)CC3)c2c1C(=O)Nc1cnc(N2C[C@@H](C)O[C@@H](C)C2)nc1]

¹H NMR (400 MHz, CDCl₃) δ 8.76 (s, 2H), 8.53 (s, 1H), 4.53 (d, J=12.1 Hz, 2H), 3.73-3.62 (m, 2H), 2.82 (s, 3H), 2.74 (dd, J=10.8, 13.3 Hz, 2H), 1.50 (s, 3H), 1.28 (d, J=6.2 Hz, 6H), 1.04-0.92 (m, 4H). [M+H]=438.

Example 760. 6-Methyl-N-[(4-methyl-1,3-oxazol-2-yl)methyl]-4-[(1-methylcyclopropyl)amino]furo[2,3-d]pyrimidine-5-carboxamide

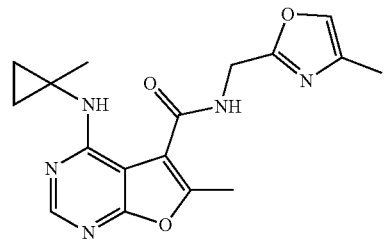 [SMILES: Cc1coc(CNC(=O)c2c(C)oc3ncnc(NC4(C)CC4)c23)n1]

¹H NMR (400 MHz, CD₃OD) δ 8.43 (s, 1H), 7.60 (d, J=1.3 Hz, 1H), 4.69 (s, 2H), 2.77 (s, 3H), 2.15 (d, J=1.3 Hz, 3H), 1.52 (s, 3H), 1.06-0.90 (m, 4H). [M+H]=342.1.

Example 761 was prepared in a manner analogous to Example 3, with the appropriate starting material substitutions.

Example 761. 6-Methyl-4-[(1-methylcyclopropyl)amino]furo[2,3-d]pyrimidine-5-carboxamide

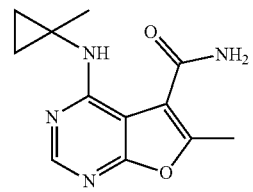 [SMILES: Cc1oc2ncnc(NC3(C)CC3)c2c1C(N)=O]

¹H NMR (400 MHz, DMSO-d₆) d=8.73 (s, 1H), 8.35-8.24 (m, 1H), 7.90 (br s, 1H), 7.73 (br s, 1H), 2.62 (s, 3H), 1.45 (s, 3H), 0.76-0.65 (m, 4H). [M+H]=247.

Example 762 was prepared in a manner analogous to Example 7, with the appropriate starting material substitutions.

Example 762. 6-Methyl-N-(1-methylcyclopropyl)-5-{4-[(propan-2-yl)amino]-5H,6H,7H,8H-pyrido[3,4-d]pyrimidine-7-carbonyl}furo[2,3-d]pyrimidin-4-amine

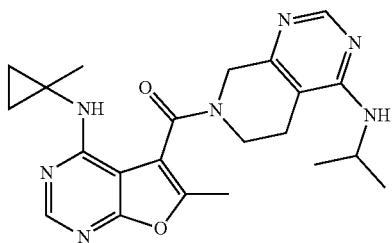 [SMILES: Cc1oc2ncnc(NC3(C)CC3)c2c1C(=O)N1CCc2c(ncnc2NC(C)C)C1]

$^1$H NMR (400 MHz, CD$_3$OD) δ 8.62 (s, 1H), 8.37 (s, 1H), 4.83 (br s, 2H), 4.72-4.62 (m, 1H), 4.15-3.70 (m, 2H), 2.67 (t, J=5.3 Hz, 2H), 2.60-2.55 (m, 3H), 1.47 (s, 3H), 1.32 (d, J=6.6 Hz, 6H), 0.85-0.79 (m, 4H). [M+H]=421.99.

Example 763-Example 773 were prepared in a manner analogous to Example 11, with the appropriate starting material substitutions.

Example 763. 5-[4-(Fluoromethoxy)-5,6,7,8-tetrahydro-1,7-naphthyridine-7-carbonyl]-6-methyl-N-(1-methylcyclopropyl)furo[2,3-d]pyrimidin-4-amine

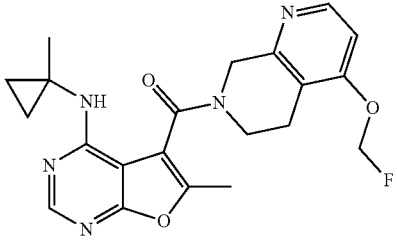 [SMILES: Cc1oc2ncnc(NC3(C)CC3)c2c1C(=O)N1CCc2c(cccc2OCF)C1]

$^1$H NMR (400 MHz, CD$_3$OD) δ 8.61 (d, J=6.4 Hz, 1H), 8.38 (s, 1H), 7.52 (d, J=6.5 Hz, 1H), 6.17-5.96 (m, 2H), 5.06 (br s, 2H), 4.27-3.69 (m, 2H), 3.03-2.96 (m, 2H), 2.59 (s, 3H), 1.47 (s, 3H), 0.89-0.79 (m, 4H). [M+H]=412.20.

Example 764. 5-[5-(Fluoromethoxy)-1,2,3,4-tetrahydroisoquinoline-2-carbonyl]-6-methyl-N-(1-methylcyclopropyl)furo[2,3-d]pyrimidin-4-amine

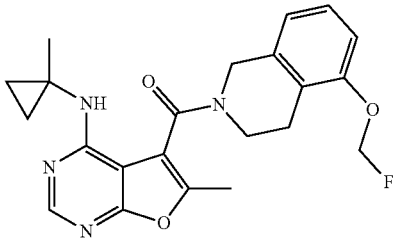

$^1$H NMR (400 MHz, CD$_3$OD) δ 8.35 (s, 1H), 7.26-7.16 (m, 1H), 7.03 (d, J=8.1 Hz, 1H), 6.93 (br s, 1H), 5.87-5.69 (m, 2H), 4.97-4.84 (m, 2H), 3.93 (br s, 2H), 2.93 (br s, 2H), 2.52 (s, 3H), 1.44 (s, 3H), 0.79 (s, 4H). [M+H]=411.04.

Example 765. 5-[6-(Fluoromethoxy)-1,2,3,4-tetrahydroisoquinoline-2-carbonyl]-6-methyl-N-(1-methylcyclopropyl)furo[2,3-d]pyrimidin-4-amine

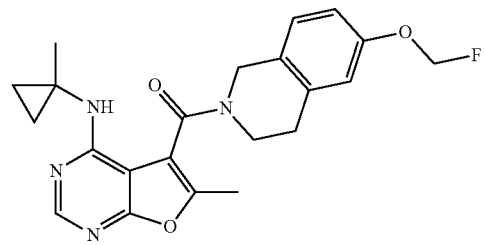 [SMILES: Cc1oc2ncnc(NC3(C)CC3)c2c1C(=O)N1CCc2cc(OCF)ccc2C1]

$^1$H NMR (400 MHz, CD$_3$OD) δ 8.37 (s, 1H), 7.13 (br s, 1H), 7.00-6.89 (m, 2H), 5.85-5.61 (m, 2H), 4.79 (br s, 2H), 3.92 (br s, 2H), 2.98 (br s, 2H), 2.53 (s, 3H), 1.46 (s, 3H), 0.82 (br s, 4H). [M+H]=411.05.

Example 766. 5-[8-(Fluoromethoxy)-1,2,3,4-tetrahydroisoquinoline-2-carbonyl]-6-methyl-N-(1-methylcyclopropyl)furo[2,3-d]pyrimidin-4-amine

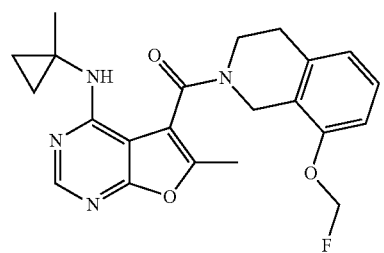 [SMILES: Cc1oc2ncnc(NC3(C)CC3)c2c1C(=O)N1CCc2cccc(OCF)c2C1]

$^1$H NMR (400 MHz, CD$_3$OD) δ 8.37 (s, 1H), 7.30-7.20 (m, 1H), 7.03 (d, J=7.9 Hz, 1H), 6.98 (d, J=7.3 Hz, 1H), 5.90-5.67 (m, 2H), 4.80 (br s, 2H), 3.93 (br s, 2H), 2.99 (br s, 2H), 2.53 (s, 3H), 1.46 (s, 3H), 0.82 (d, J=4.6 Hz, 4H). [M+H]=411.06.

Example 767. 5-[7-(Fluoromethoxy)-1,2,3,4-tetrahydroisoquinoline-2-carbonyl]-6-methyl-N-(1-methylcyclopropyl)furo[2,3-d]pyrimidin-4-amine

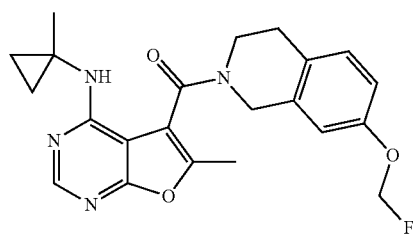 [SMILES: Cc1oc2ncnc(NC3(C)CC3)c2c1C(=O)N1CCc2ccc(OCF)cc2C1]

$^1$H NMR (400 MHz, CD$_3$OD) δ 8.39 (s, 1H), 7.19 (d, J=8.4 Hz, 1H), 7.01-6.87 (m, 2H), 5.80-5.61 (m, 2H), 4.84-4.69 (m, 2H), 3.92 (br s, 2H), 2.95 (br s, 2H), 2.55 (s, 3H), 1.47 (s, 3H), 0.83 (br s, 4H). [M+H]=411.06.

Example 768. 5-[3-(Fluoromethoxy)-5,6,7,8-tetrahydro-1,6-naphthyridine-6-carbonyl]-6-methyl-N-(1-methylcyclopropyl)furo[2,3-d]pyrimidin-4-amine

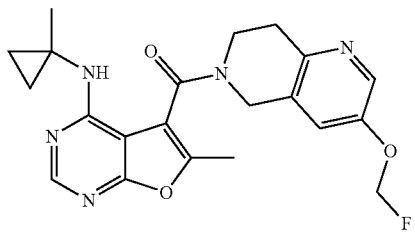

¹H NMR (400 MHz, CD₃OD) δ 8.41 (s, 1H), 8.35 (d, J=2.6 Hz, 1H), 7.67 (br s, 1H), 5.96-5.74 (m, 2H), 4.97 (br s, 2H), 4.08 (d, J=13.3 Hz, 2H), 3.13 (t, J=5.4 Hz, 2H), 2.60 (s, 3H), 1.49 (s, 3H), 0.86 (s, 4H). [M+H]=412.06.

Example 769. 5-[5-(Fluoromethoxy)-1,2,3,4-tetrahydro-2,6-naphthyridine-2-carbonyl]-6-methyl-N-(1-methylcyclopropyl)furo[2,3-d]pyrimidin-4-amine

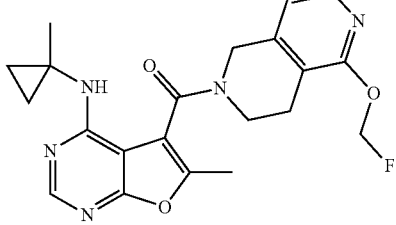

¹H NMR (400 MHz, CD₃OD) δ 8.39 (s, 1H), 8.00 (d, J=5.3 Hz, 1H), 6.96 (br s, 1H), 6.21-5.97 (m, 2H), 5.02-4.90 (m, 2H), 4.14-3.75 (m, 2H), 2.94-2.82 (m, 2H), 2.58-2.51 (m, 3H), 1.49-1.43 (m, 3H), 0.84 (br s, 4H). [M+H]=412.06.

Example 770. 5-{4-[5-(Fluoromethoxy)pyrimidin-2-yl]piperidine-1-carbonyl}-6-methyl-N-(1-methylcyclopropyl)furo[2,3-d]pyrimidin-4-amine

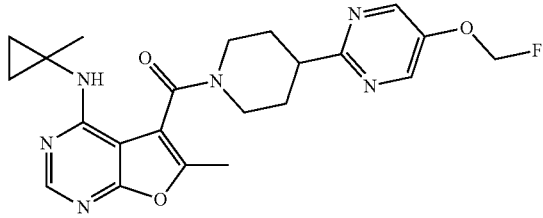 [SMILES: Cc1oc2ncnc(NC3(C)CC3)c2c1C(=O)N1CCC(c2ncc(OCF)cn2)CC1]

¹H NMR (400 MHz, CD₃OD) δ 8.60 (s, 2H), 8.40 (s, 1H), 5.98-5.71 (m, 2H), 3.26 (tt, J=3.8, 11.5 Hz, 1H), 2.57 (s, 3H), 2.12 (d, J=10.4 Hz, 2H), 1.92 (br s, 2H), 1.54 (s, 3H), 1.01-0.93 (m, 2H), 0.93-0.84 (m, 2H). [M+H]=441.07.

Example 771. 5-{3-[4-(Fluoromethoxy)phenyl]pyrrolidine-1-carbonyl}-6-methyl-N-(1-methylcyclopropyl)furo[2,3-d]pyrimidin-4-amine

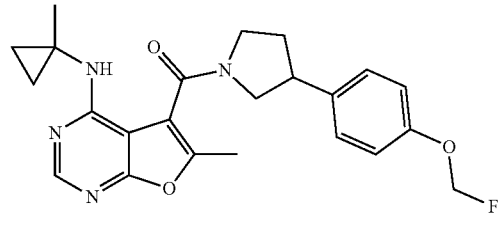 [SMILES: Cc1oc2ncnc(NC3(C)CC3)c2c1C(=O)N1CCC(c2ccc(OCF)cc2)C1]

¹H NMR (400 MHz, CD₃OD) δ 8.37 (s, 1H), 7.40-7.22 (m, 2H), 7.07 (d, J=18.1 Hz, 2H), 5.87-5.62 (m, 2H), 4.04 (br s, 1H), 3.86-3.71 (m, 2H), 3.65-3.41 (m, 2H), 2.57 (d, J=14.4 Hz, 3H), 2.49-1.99 (m, 2H), 1.52 (s, 3H), 0.96-0.82 (m, 4H). [M+H]=425.05.

Example 772. 5-[7-(Fluoromethoxy)-1-methyl-1,2,3,4-tetrahydroisoquinoline-2-carbonyl]-6-methyl-N-(1-methylcyclopropyl)furo[2,3-d]pyrimidin-4-amine

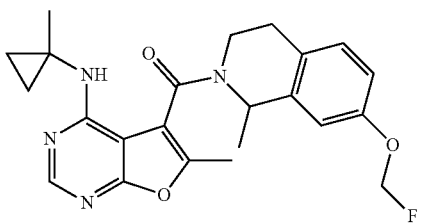 [SMILES: Cc1oc2ncnc(NC3(C)CC3)c2c1C(=O)N1CCc2ccc(OCF)cc2C1C]

¹H NMR (400 MHz, CD₃OD) δ 8.40 (s, 1H), 7.18 (d, J=8.3 Hz, 1H), 7.08-6.89 (m, 2H), 5.98-5.51 (m, 3H), 4.84-3.34 (m, 2H), 3.09-2.79 (m, 2H), 2.63-2.48 (m, 3H), 1.57 (br s, 3H), 1.46 (br s, 3H), 0.81 (br s, 4H). [M+H]=425.10.

Example 773. 5-[4-(Fluoromethoxy)-2-(methoxymethyl)-5H,6H,7H,8H-pyrido[3,4-d]pyrimidine-7-carbonyl]-6-methyl-N-(1-methylcyclopropyl)furo[2,3-d]pyrimidin-4-amine

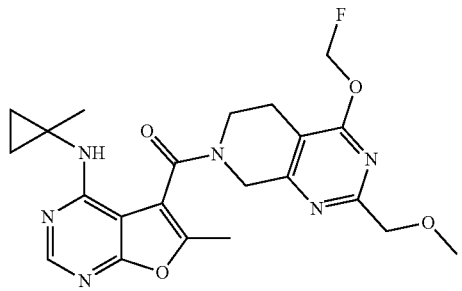 [SMILES: COCc1nc2c(c(OCF)n1)CCN(C(=O)c1c(C)oc3ncnc(NC4(C)CC4)c13)C2]

¹H NMR (400 MHz, CD₃OD) δ 8.41 (s, 1H), 6.29-6.06 (m, 2H), 4.96-4.86 (m, 2H), 4.54 (s, 2H), 4.00 (br s, 2H), 3.48 (s, 3H), 2.88 (br s, 2H), 2.62-2.54 (m, 3H), 1.48 (s, 3H), 0.88 (d, J=5.0 Hz, 4H). [M+H]=457.40.

Example 774-Example 775 were prepared in a manner analogous to Example 13, with the appropriate starting material substitutions.

Example 774. 5-[3-(5-Fluoropyrimidin-2-yl)-2,5-dihydro-1H-pyrrole-1-carbonyl]-6-methyl-N-(1-methylcyclopropyl)furo[2,3-d]pyrimidin-4-amine

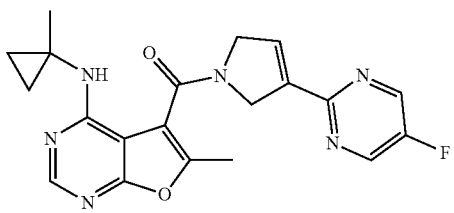 [SMILES: Cc1oc2ncnc(NC3(C)CC3)c2c1C(=O)N1CC=C(c2ncc(F)cn2)C1]

$^1$H NMR (400 MHz, CD$_3$OD) δ 8.96-8.50 (m, 2H), 8.31 (s, 1H), 7.14-6.70 (m, 1H), 2.60 (br s, 3H), 1.48 (s, 3H), 0.91-0.66 (m, 4H). [M+H]=395.0.

Example 775. 2-(1-{6-Methyl-4-[(1-methylcyclopropyl)amino]furo[2,3-d]pyrimidine-5-carbonyl}-1,2,3,6-tetrahydropyridin-4-yl)pyrimidine-4-carbonitrile

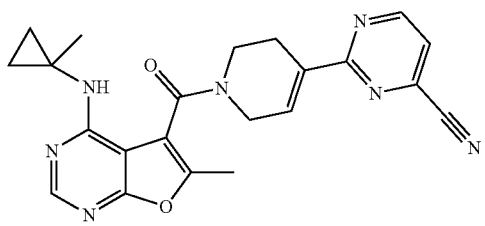 [SMILES: Cc1oc2ncnc(NC3(C)CC3)c2c1C(=O)N1CC=C(c2nccc(C#N)n2)CC1]

$^1$H NMR (400 MHz, CD$_3$OD) δ 9.17-8.84 (m, 1H), 8.36 (s, 1H), 7.83-7.60 (m, 1H), 4.47 (br s, 1H), 3.91 (br s, 2H), 2.85 (br s, 1H), 2.59-2.52 (m, 3H), 2.52-2.26 (m, 1H), 1.51-1.47 (m, 3H), 0.93-0.77 (m, 4H). [M+H]=416.05.

Example 776-Example 782 were prepared in a manner analogous to Example 14, with the appropriate starting material substitutions.

Example 776. 6-Methyl-5-[4-(1-methyl-1H-pyrazol-3-yl)piperidine-1-carbonyl]-N-(1-methylcyclopropyl)furo[2,3-d]pyrimidin-4-amine

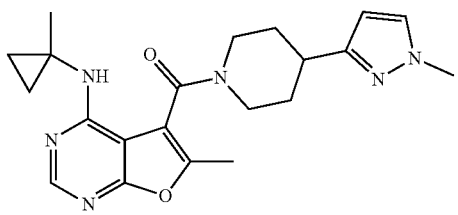 [SMILES: Cc1oc2ncnc(NC3(C)CC3)c2c1C(=O)N1CCC(c2ccn(C)n2)CC1]

$^1$H NMR (400 MHz, CD$_3$OD) δ 8.32 (s, 1H), 7.48 (d, J=2.1 Hz, 1H), 6.13 (br s, 1H), 4.80-3.90 (m, 2H), 3.85 (s, 3H), 3.39-3.08 (m, 6H), 3.00 (t, J=11.4 Hz, 1H), 2.52 (s, 3H), 2.14-1.95 (m, 2H), 1.91-1.61 (m, 2H), 1.51 (s, 3H), 0.91-0.71 (m, 4H). [M+H]=395.1.

Example 777. 6-Methyl-5-[4-(1-methyl-1H-1,2,4-triazol-3-yl)piperidine-1-carbonyl]-N-(1-methylcyclopropyl)furo[2,3-d]pyrimidin-4-amine

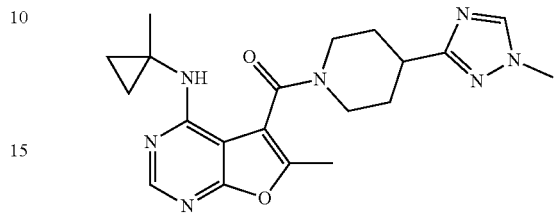

$^1$H NMR (400 MHz, CD$_3$OD) δ 8.47 (s, 1H), 8.43 (s, 1H), 4.77-3.98 (m, 2H), 3.92 (s, 3H), 3.33 (td, J=1.6, 3.2 Hz, 4H), 3.15 (tt, J=3.7, 11.1 Hz, 1H), 2.58 (s, 3H), 2.22-2.04 (m, 2H), 1.86 (br s, 2H), 1.54 (s, 3H), 1.03-0.85 (m, 4H). [M+H]=396.1.

Example 778. 6-Methyl-5-[4-(1-methyl-1H-1,2,3-triazol-4-yl)piperidine-1-carbonyl]-N-(1-methylcyclopropyl)furo[2,3-d]pyrimidin-4-amine

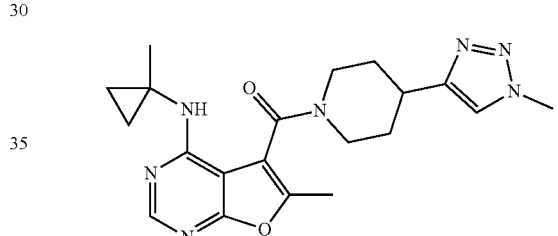

$^1$H NMR (400 MHz, CD$_3$OD) δ 8.43 (s, 1H), 7.79 (s, 1H), 4.78-4.12 (m, 2H), 4.09 (s, 3H), 3.50 (d, J=1.7 Hz, 1H), 3.29-3.20 (m, 1H), 3.13 (tt, J=3.7, 11.5 Hz, 1H), 2.58 (s, 3H), 2.22-2.06 (m, 2H), 1.92-1.67 (m, 2H), 1.54 (s, 3H), 1.04-0.85 (m, 4H). [M+H]=396.1.

Example 779. 5-[4-(1,5-Dimethyl-1H-pyrazol-3-yl)piperidine-1-carbonyl]-6-methyl-N-(1-methylcyclopropyl)furo[2,3-d]pyrimidin-4-amine

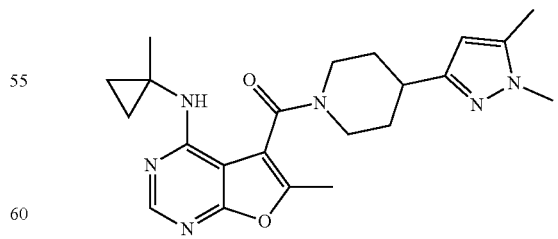

$^1$H NMR (400 MHz, CD$_3$OD) δ 8.42 (s, 1H), 6.01 (s, 1H), 4.76-3.84 (m, 2H), 3.76 (s, 3H), 3.57-3.07 (m, 10H), 3.02-2.90 (m, 1H), 2.57 (s, 3H), 2.29 (s, 3H), 2.04 (d, J=11.6 Hz, 2H), 1.70 (d, J=7.8 Hz, 2H), 1.54 (s, 3H), 1.05-0.82 (m, 4H). [M+H]=409.1.

Example 780. 5-[4-(2,4-Dimethyl-1H-imidazol-5-yl)piperidine-1-carbonyl]-6-methyl-N-(1-methylcyclopropyl)furo[2,3-d]pyrimidin-4-amine

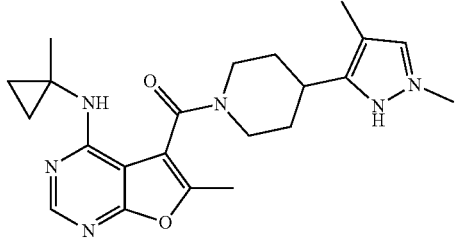

¹H NMR (400 MHz, CD₃OD) δ 8.37 (s, 1H), 4.78-3.85 (m, 1H), 3.65-3.28 (m, 16H), 3.58-3.23 (m, 16H), 3.16 (t, J=12.2 Hz, 2H), 2.58 (br s, 3H), 2.57 (s, 4H), 2.31 (s, 3H), 1.95 (br s, 2H), 1.87-1.64 (m, 2H), 1.53 (s, 3H), 0.97-0.78 (m, 5H). [M+H]=409.1.

Example 781. 6-Methyl-N-(1-methylcyclopropyl)-5-{4-[1-(propan-2-yl)-1H-pyrazol-3-yl]piperidine-1-carbonyl}furo[2,3-d]pyrimidin-4-amine

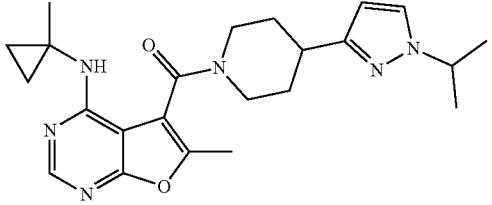 [SMILES: Cc1oc2ncnc(NC3(C)CC3)c2c1C(=O)N1CCC(c2ccn(C(C)C)n2)CC1]

¹H NMR (400 MHz, CD₃OD) δ 8.43 (s, 1H), 7.58 (d, J=2.3 Hz, 1H), 6.15 (d, J=2.1 Hz, 1H), 4.49 (quind, J=6.7, 13.4 Hz, 1H), 4.39-3.73 (m, 1H), 3.56-3.11 (m, 11H), 3.10-2.95 (m, 1H), 2.58 (s, 3H), 2.12-1.97 (m, 2H), 1.89-1.64 (m, 2H), 1.54 (s, 3H), 1.48 (d, J=6.7 Hz, 6H), 1.10-0.84 (m, 4H). [M+H]=423.2.

Example 782. 6-Methyl-5-[4-(1-methyl-1H-pyrazol-4-yl)piperidine-1-carbonyl]-N-(1-methylcyclopropyl)furo[2,3-d]pyrimidin-4-amine

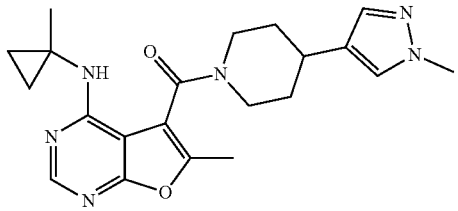 [SMILES: Cc1oc2ncnc(NC3(C)CC3)c2c1C(=O)N1CCC(c2cnn(C)c2)CC1]

¹H NMR (400 MHz, CD₃OD) δ 8.42 (s, 1H), 7.50 (s, 1H), 7.40 (s, 1H), 4.76-3.91 (m, 2H), 3.86 (s, 3H), 3.48-3.03 (m, 9H), 2.98-2.82 (m, 1H), 2.57 (s, 3H), 2.16-2.00 (m, 2H), 1.63 (br s, 2H), 1.53 (s, 3H), 1.01-0.80 (m, 4H). [M+H]=395.2.

Example 783-Example 785 were prepared in a manner analogous to Example 15, with the appropriate starting material substitutions.

Example 783. 5-[4-(2-Fluoro-1,3-thiazol-5-yl)-1,2,3,6-tetrahydropyridine-1-carbonyl]-6-methyl-N-(1-methylcyclopropyl)furo[2,3-d]pyrimidin-4-amine

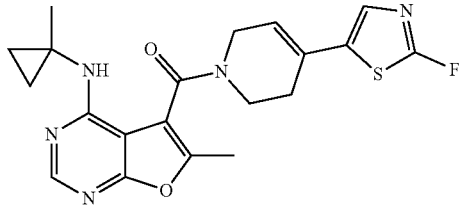 [SMILES: Cc1oc2ncnc(NC3(C)CC3)c2c1C(=O)N1CC=C(c2cnc(F)s2)CC1]

¹H NMR (400 MHz, CD₃OD) δ 8.31 (s, 1H), 7.23 (s, 1H), 6.08 (br s, 1H), 4.32 (br s, 2H), 4.09-3.61 (m, 2H), 2.66 (br s, 2H), 2.53 (s, 3H), 1.48 (s, 3H), 0.85-0.66 (m, 4H). [M+H]=414.0.

Example 784. 5-[4-(5-Methoxypyrazin-2-yl)-1,2,3,6-tetrahydropyridine-1-carbonyl]-6-methyl-N-(1-methylcyclopropyl)furo[2,3-d]pyrimidin-4-amine

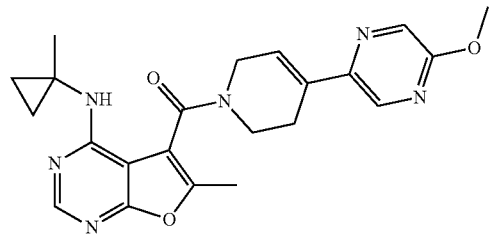

¹H NMR (400 MHz, CD₃OD) δ 8.38 (s, 1H), 8.32 (d, J=1.1 Hz, 1H), 8.18 (d, J=1.2 Hz, 1H), 6.63 (br s, 1H), 4.40 (br s, 2H), 4.08-3.82 (m, 5H), 2.78 (br s, 2H), 2.57 (s, 3H), 1.50 (s, 3H), 0.94-0.76 (m, 4H). [M+H]=421.1.

Example 785. 5-[4-(5-Methoxypyridin-2-yl)-1,2,3,6-tetrahydropyridine-1-carbonyl]-6-methyl-N-(1-methylcyclopropyl)furo[2,3-d]pyrimidin-4-amine

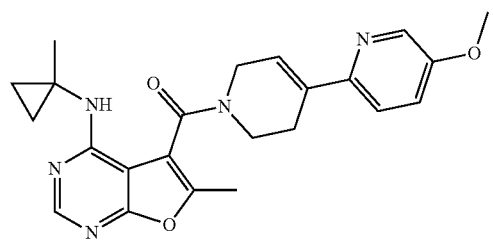 [SMILES: COc1cnc(C2=CCN(C(=O)c3c(C)oc4ncnc(NC5(C)CC5)c34)CC2)cn1]

¹H NMR (400 MHz, CD₃OD) δ 8.31 (s, 1H), 8.19 (d, J=2.8 Hz, 1H), 7.52 (d, J=8.8 Hz, 1H), 7.37 (dd, J=3.0, 8.9 Hz, 1H), 6.48 (br s, 1H), 4.36 (br s, 2H), 3.88 (s, 4H), 2.76 (br s, 2H), 2.53 (s, 3H), 1.46 (s, 3H), 0.86-0.64 (m, 4H). [M+H]=420.1.

Example 786-Example 796 were prepared in a manner analogous to Example 18, with the appropriate starting material substitutions.

Example 786. 5-{4-[(3S)-3-Fluoropyrrolidin-1-yl]-5H,6H,7H,8H-pyrido[3,4-d]pyrimidine-7-carbonyl}-6-methyl-N-(1-methylcyclopropyl)furo[2,3-d]pyrimidin-4-amine

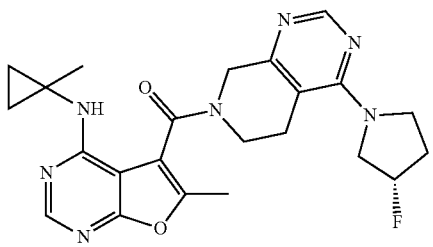 [SMILES: Cc1oc2ncnc(NC3(C)CC3)c2c1C(=O)N1CCc2c(ncnc2N2CC[C@H](F)C2)C1]

$^1$H NMR (400 MHz, CD$_3$OD) δ 8.59 (s, 1H), 8.37 (s, 1H), 5.53-5.30 (m, 1H), 5.01 (br s, 1H), 4.74 (d, J=18.0 Hz, 1H), 4.36-3.99 (m, 5H), 3.62 (br s, 1H), 3.27 (br s, 1H), 3.21-3.09 (m, 1H), 2.61 (s, 3H), 2.42 (dt, J=6.4, 15.2 Hz, 1H), 2.33-2.08 (m, 1H), 1.50 (s, 3H), 0.91-0.78 (m, 4H). [M+H]=452.01.

Example 787. 6-Methyl-N-(1-methylcyclopropyl)-5-[4-(morpholin-4-yl)-5H,6H,7H,8H-pyrido[3,4-d]pyrimidine-7-carbonyl]furo[2,3-d]pyrimidin-4-amine

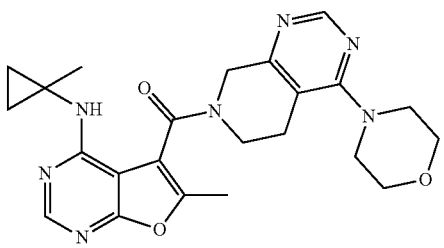 [SMILES: Cc1oc2ncnc(NC3(C)CC3)c2c1C(=O)N1CCc2c(ncnc2N2CCOCC2)C1]

$^1$H NMR (400 MHz, CD$_3$OD) δ 8.63 (s, 1H), 8.38 (s, 1H), 4.89 (br s, 2H), 4.06-3.72 (m, 10H), 2.94 (br s, 2H), 2.61 (s, 3H), 1.50 (s, 3H), 0.94-0.77 (m, 4H). [M+H]=450.07.

Example 788. 5-[4-(3-Fluoroazetidin-1-yl)-5H,6H,7H,8H-pyrido[3,4-d]pyrimidine-7-carbonyl]-6-methyl-N-(1-methylcyclopropyl)furo[2,3-d]pyrimidin-4-amine

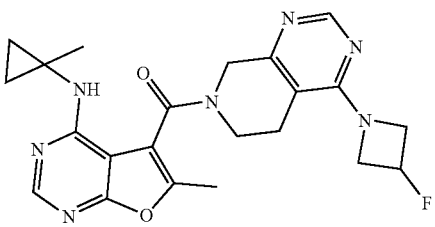 [SMILES: Cc1oc2ncnc(NC3(C)CC3)c2c1C(=O)N1CCc2c(ncnc2N2CC(F)C2)C1]

$^1$H NMR (400 MHz, CD$_3$OD) δ 8.56 (s, 1H), 8.37 (s, 1H), 5.65-5.35 (m, 1H), 5.01-4.89 (m, 2H), 4.87-4.82 (m, 2H), 4.75-4.57 (m, 2H), 3.94 (br s, 2H), 2.97 (t, J=5.2 Hz, 2H), 2.59 (s, 3H), 1.50 (s, 3H), 0.93-0.77 (m, 4H). [M+H]=438.08.

Example 789. 5-{2-Chloro-4-[(propan-2-yl)amino]-5H,6H,7H,8H-pyrido[3,4-d]pyrimidine-7-carbonyl}-6-methyl-N-(1-methylcyclopropyl)furo[2,3-d]pyrimidin-4-amine

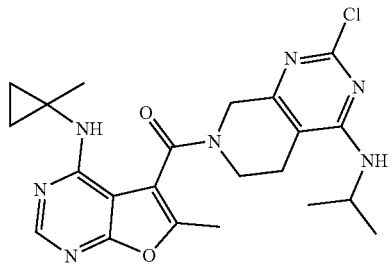 [SMILES: Cc1oc2ncnc(NC3(C)CC3)c2c1C(=O)N1CCc2c(nc(Cl)nc2NC(C)C)C1]

$^1$H NMR (400 MHz, CD$_3$OD) δ 8.29 (s, 1H), 4.55 (br s, 2H), 4.37 (td, J=6.5, 13.1 Hz, 1H), 4.10-3.62 (m, 2H), 2.58-2.51 (m, 2H), 2.50 (s, 3H), 1.43 (s, 3H), 1.24 (d, J=6.5 Hz, 6H), 0.71 (br s, 4H). [M+H]=456.04.

Example 790. 5-{4-[Cyclopropyl(methyl)amino]-5H,6H,7H,8H-pyrido[3,4-d]pyrimidine-7-carbonyl}-6-methyl-N-(1-methylcyclopropyl)furo[2,3-d]pyrimidin-4-amine

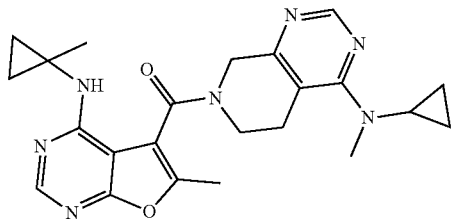 [SMILES: Cc1oc2ncnc(NC3(C)CC3)c2c1C(=O)N1CCc2c(ncnc2N(C)C2CC2)C1]

$^1$H NMR (400 MHz, CD$_3$OD) δ 8.58 (s, 1H), 8.36 (s, 1H), 4.91 (br s, 2H), 3.86 (br s, 2H), 3.35 (s, 4H), 3.25 (br s, 2H), 2.68-2.56 (m, 3H), 1.51 (s, 3H), 1.06-0.94 (m, 2H), 0.94-0.76 (m, 6H). [M+H]=434.11.

Example 791. 5-[4-(Dimethylamino)-5H,6H,7H,8H-pyrido[3,4-d]pyrimidine-7-carbonyl]-6-methyl-N-(1-methylcyclopropyl)furo[2,3-d]pyrimidin-4-amine

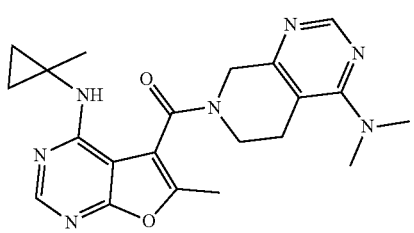 [SMILES: Cc1oc2ncnc(NC3(C)CC3)c2c1C(=O)N1CCc2c(ncnc2N(C)C)C1]

$^1$H NMR (400 MHz, CD$_3$OD) δ 8.57 (s, 1H), 8.37 (s, 1H), 3.88 (br s, 2H), 3.43 (s, 6H), 3.11 (br s, 2H), 2.69-2.54 (m, 3H), 1.51 (s, 3H), 0.91-0.76 (m, 4H). [M+H]=408.05.

Example 792. 6-Methyl-5-[4-(methylamino)-5H,6H,7H,8H-pyrido[3,4-d]pyrimidine-7-carbonyl]-N-(1-methylcyclopropyl)furo[2,3-d]pyrimidin-4-amine

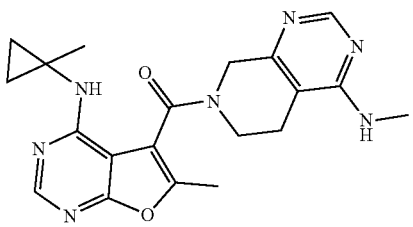 [SMILES: CNc1ncnc2c1CCN(C(=O)c1c(C)oc3ncnc(NC4(C)CC4)c13)C2]

$^1$H NMR (400 MHz, CD$_3$OD) δ 8.65 (s, 1H), 8.36 (s, 1H), 4.86-4.80 (m, 2H), 4.02 (br s, 2H), 3.18 (s, 3H), 2.66 (br s, 2H), 2.59 (s, 3H), 1.49 (s, 3H), 0.82 (d, J=10.9 Hz, 4H). [M+H]=394.02.

Example 793. 6-Methyl-5-{4-[methyl(oxan-4-yl)amino]-5H,6H,7H,8H-pyrido[3,4-d]pyrimidine-7-carbonyl}-N-(1-methylcyclopropyl)furo[2,3-d]pyrimidin-4-amine

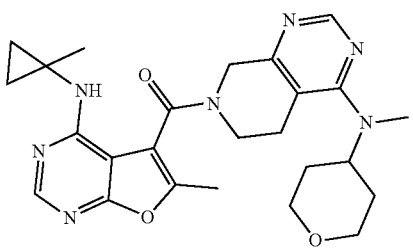 [SMILES: Cc1oc2ncnc(NC3(C)CC3)c2c1C(=O)N1CCc2c(ncnc2N(C)C2CCOCC2)C1]

$^1$H NMR (400 MHz, CD$_3$OD) δ 8.60 (s, 1H), 8.37 (s, 1H), 4.96-4.89 (m, 2H), 4.83 (br s, 1H), 4.07 (dd, J=4.3, 11.4 Hz, 2H), 4.01-3.69 (m, 2H), 3.64-3.50 (m, 2H), 3.26 (s, 3H), 3.06 (br s, 2H), 2.61 (s, 3H), 2.03 (dq, J=4.5, 12.2 Hz, 2H), 1.78 (dd, J=2.1, 12.1 Hz, 2H), 1.51 (s, 3H), 0.92-0.77 (m, 4H). [M+H]=478.05.

Example 794. 6-Methyl-N-(1-methylcyclopropyl)-5-{4-[(oxan-4-yl)amino]-5H,6H,7H,8H-pyrido[3,4-d]pyrimidine-7-carbonyl}furo[2,3-d]pyrimidin-4-amine

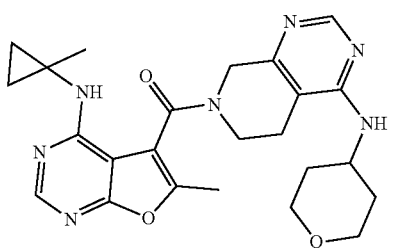 [SMILES: Cc1oc2ncnc(NC3(C)CC3)c2c1C(=O)N1CCc2c(ncnc2NC2CCOCC2)C1]

$^1$H NMR (400 MHz, CD$_3$OD) δ 8.65 (s, 1H), 8.37 (s, 1H), 5.00-4.88 (m, 2H), 4.67-4.51 (m, 1H), 4.24-3.84 (m, 4H), 3.61-3.47 (m, 2H), 2.70 (br s, 2H), 2.60 (s, 3H), 1.99-1.88 (m, 2H), 1.80 (dq, J=4.5, 12.2 Hz, 2H), 1.49 (s, 3H), 0.82 (d, J=6.0 Hz, 4H). [M+H]=464.05.

Example 795. 5-(4-{[1-(Methoxymethyl)cyclopropyl]amino}-5H,6H,7H,8H-pyrido[3,4-d]pyrimidine-7-carbonyl)-6-methyl-N-(1-methylcyclopropyl)furo[2,3-d]pyrimidin-4-amine

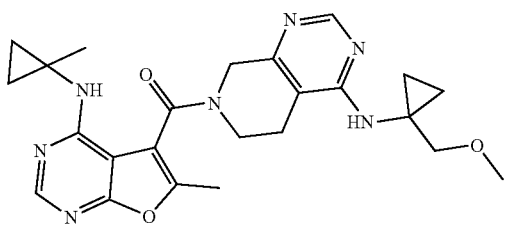 [SMILES: COCC1(Nc2ncnc3c2CCN(C(=O)c2c(C)oc4ncnc(NC5(C)CC5)c24)C3)CC1]

$^1$H NMR (400 MHz, CD$_3$OD) δ 8.67 (s, 1H), 8.36 (s, 1H), 4.20-3.76 (m, 2H), 3.61 (s, 2H), 3.37 (s, 3H), 2.66 (br s, 2H), 2.59 (s, 3H), 1.54-1.42 (m, 3H), 1.09-0.94 (m, 4H), 0.81 (d, J=6.8 Hz, 4H). [M+H]=463.99.

Example 796. 6-Methyl-N-(1-methylcyclopropyl)-5-{4-[(1-methylcyclopropyl)amino-5H,6H,7H,8H-pyrido[3,4-d]pyrimidine-7-carbonyl}furo[2,3-d]pyrimidin-4-amine

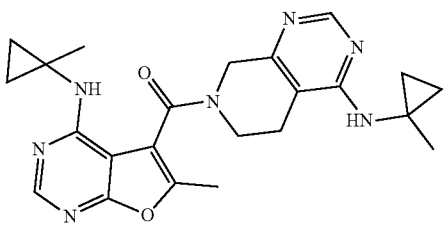 [SMILES: Cc1oc2ncnc(NC3(C)CC3)c2c1C(=O)N1CCc2c(ncnc2NC2(C)CC2)C1]

$^1$H NMR (400 MHz, CD$_3$OD) δ 8.69 (s, 1H), 8.37 (s, 1H), 4.87-4.78 (m, 2H), 3.98 (br s, 2H), 2.63 (br s, 2H), 2.59 (s, 3H), 1.50 (d, J=9.7 Hz, 6H), 1.01-0.75 (m, 8H). [M+H]=434.09.

Example 797 was prepared in a manner analogous to Example 20, with the appropriate starting material substitutions.

Example 797. 5-{3-[4-(2-Fluoroethoxy)phenyl]pyrrolidine-1-carbonyl}-6-methyl-N-(1-methylcyclopropyl)furo[2,3-d]pyrimidin-4-amine

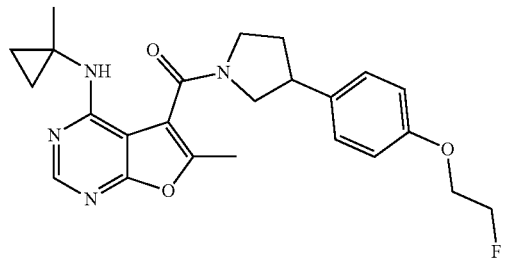 [SMILES: Cc1oc2ncnc(NC3(C)CC3)c2c1C(=O)N1CCC(c2ccc(OCCF)cc2)C1]

¹H NMR (400 MHz, CD₃OD) δ 8.39 (s, 1H), 7.38-7.15 (m, 2H), 7.02-6.87 (m, 2H), 4.84-4.59 (m, 2H), 4.33-4.11 (m, 2H), 4.05-3.40 (m, 5H), 2.58 (d, J=14.9 Hz, 3H), 2.46-2.00 (m, 2H), 1.53 (s, 3H), 0.98-0.84 (m, 4H). [M+H]=439.02.

Example 798-Example 802 were prepared in a manner analogous to Example 21, with the appropriate starting material substitutions.

Example 798. 5-[3-(6-Fluoro-4-methylpyridin-2-yl)pyrrolidine-1-carbonyl]-6-methyl-N-(1-methylcyclopropyl)furo[2,3-d]pyrimidin-4-amine

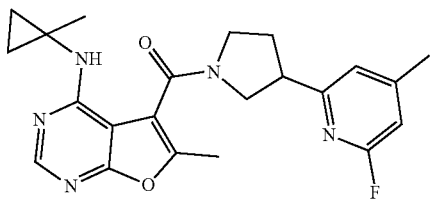 [SMILES: Cc1cc(F)nc(C2CCN(C(=O)c3c(C)oc4ncnc(NC5(C)CC5)c34)C2)c1]

¹H NMR (400 MHz, CD₃OD) δ 8.39 (s, 1H), 7.24-7.03 (m, 1H), 6.89-6.68 (m, 1H), 4.05-3.49 (m, 5H), 2.60 (d, J=6.8 Hz, 3H), 2.50-2.12 (m, 5H), 1.53 (s, 3H), 1.02-0.82 (m, 4H). [M+H]=410.11.

Example 799. 5-[3-(5-Fluoro-6-methylpyridin-2-yl)pyrrolidine-1-carbonyl]-6-methyl-N-(1-methylcyclopropyl)furo[2,3-d]pyrimidin-4-amine

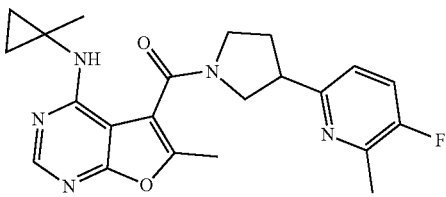 [SMILES: Cc1nc(C2CCN(C(=O)c3c(C)oc4ncnc(NC5(C)CC5)c34)C2)ccc1F]

¹H NMR (400 MHz, CD₃OD) δ 8.44 (s, 1H), 7.63-7.41 (m, 1H), 7.41-7.18 (m, 1H), 4.11-3.57 (m, 5H), 2.62 (d, J=8.9 Hz, 3H), 2.57-2.13 (m, 5H), 1.54 (s, 3H), 1.08-0.89 (m, 4H). [M+H]=410.12.

Example 800. 5-[3-(5-Fluoro-4-methylpyrimidin-2-yl)pyrrolidine-1-carbonyl]-6-methyl-N-(1-methylcyclopropyl)furo[2,3-d]pyrimidin-4-amine

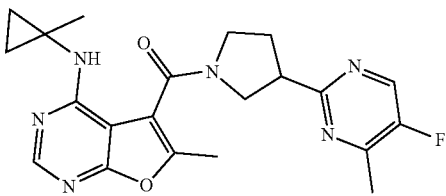

¹H NMR (400 MHz, CD₃OD) δ 8.61-8.38 (m, 2H), 4.17-3.66 (m, 5H), 2.62 (s, 3H), 2.59-2.21 (m, 5H), 1.54 (s, 3H), 1.08-0.88 (m, 4H). [M+H]=411.32.

Example 801. 6-Methyl-N-(1-methylcyclopropyl)-5-{3-[6-(trifluoromethyl)pyridin-2-yl]pyrrolidine-1-carbonyl}furo[2,3-d]pyrimidin-4-amine

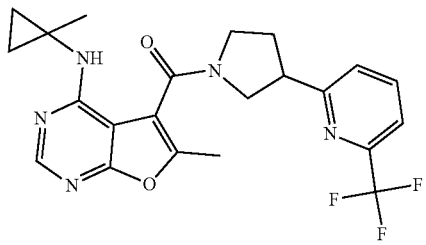 [SMILES: Cc1oc2ncnc(NC3(C)CC3)c2c1C(=O)N1CCC(c2cccc(C(F)(F)F)n2)C1]

¹H NMR (400 MHz, CD₃OD) δ 8.47-8.32 (m, 1H), 8.10-7.91 (m, 1H), 7.80-7.55 (m, 2H), 4.15-3.67 (m, 5H), 2.65-2.56 (m, 3H), 2.56-2.16 (m, 2H), 1.57-1.49 (m, 3H), 1.02-0.84 (m, 4H). [M+H]=446.53.

Example 802. 6-Methyl-N-(1-methylcyclopropyl)-5-{3-[4-(trifluoromethyl)pyridin-2-yl]pyrrolidine-1-carbonyl}furo[2,3-d]pyrimidin-4-amine

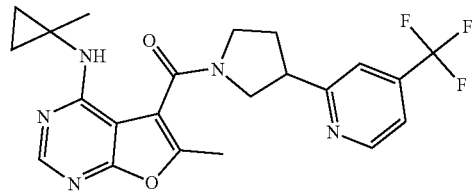 [SMILES: Cc1oc2ncnc(NC3(C)CC3)c2c1C(=O)N1CCC(c2cc(C(F)(F)F)ccn2)C1]

¹H NMR (400 MHz, CD₃OD) δ 8.92-8.67 (m, 1H), 8.46-8.34 (m, 1H), 7.82-7.45 (m, 2H), 4.18-3.66 (m, 5H), 2.66-2.18 (m, 5H), 1.54 (s, 3H), 1.03-0.83 (m, 4H). [M+H]=446.31.

Example 803 was prepared in a manner analogous to Example 23, with the appropriate starting material substitutions.

Example 803. 6-Methyl-N-(1-methylcyclopropyl)-5-[4-(oxan-4-yl)-5H,6H,7H,8H-pyrido[3,4-d]pyrimidine-7-carbonyl]furo[2,3-d]pyrimidin-4-amine

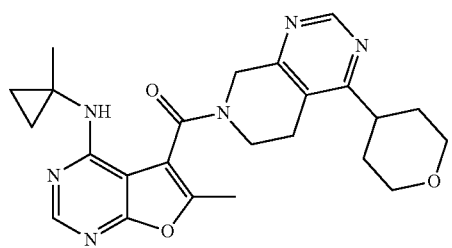 [SMILES: Cc1oc2ncnc(NC3(C)CC3)c2c1C(=O)N1CCc2c(ncnc2C2CCOCC2)C1]

¹H NMR (400 MHz, CDCl₃) δ 8.99 (s, 1H), 8.49 (s, 1H), 7.10 (br s, 1H), 4.83 (br s, 2H), 4.09-4.19 (m, 3H), 3.57 (dt, J=1.71, 11.92 Hz, 2H), 3.03-3.16 (m, 1H), 3.00 (t, J=5.56 Hz, 2H), 2.54 (s, 3H), 2.08-2.22 (m, 2H), 1.64 (d, J=12.96 Hz, 3H), 1.50 (s, 3H), 0.77 (br s, 4H). [M+H]=449.4.

Example 804-Example 805 were prepared in a manner analogous to Example 24, with the appropriate starting material substitutions.

Example 804. 6-Methyl-N-(1-methylcyclopropyl)-5-[4-(prop-1-en-2-yl)-5H,6H,7H,8H-pyrido[3,4-d]pyrimidine-7-carbonyl]furo[2,3-d]pyrimidin-4-amine

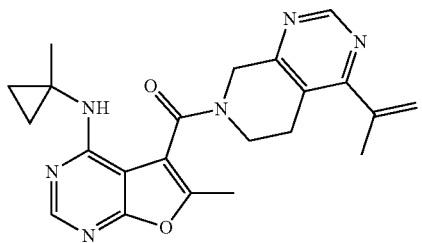 [SMILES: C=C(C)c1ncnc2c1CCN(C(=O)c1c(C)oc3ncnc(NC4(C)CC4)c13)C2]

$^1$H NMR (400 MHz, CD$_3$OD) δ 8.92 (s, 1H), 8.40 (s, 1H), 5.60 (s, 1H), 5.25 (s, 1H), 4.91 (br s, 2H), 3.94 (br s, 2H), 3.10-2.99 (m, 2H), 2.59 (s, 3H), 2.14 (s, 3H), 1.48 (s, 3H), 0.92-0.83 (m, 4H). [M+H]=405.42.

Example 805. 5-{4-Cyclopropyl-5H,6H,7H,8H-pyrido[3,4-d]pyrimidine-7-carbonyl}-6-methyl-N-(1-methylcyclopropyl)furo[2,3-d]pyrimidin-4-amine

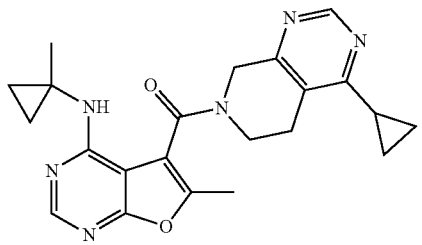 [SMILES: Cc1oc2ncnc(NC3(C)CC3)c2c1C(=O)N1CCc2c(ncnc2C2CC2)C1]

$^1$H NMR (400 MHz, CD$_3$OD) δ 8.72 (s, 1H), 8.41 (s, 1H), 4.84-4.70 (m, 2H), 4.26-3.76 (m, 2H), 3.11 (br s, 2H), 2.59 (s, 3H), 2.19 (d, J=5.0 Hz, 1H), 1.48 (s, 3H), 1.26-1.09 (m, 4H), 0.88 (d, J=6.2 Hz, 4H). [M+H]=405.42.

Example 806-Example 811 were prepared in a manner analogous to Example 25, with the appropriate starting material substitutions.

Example 806. 6-Methyl-N-(1-methylcyclopropyl)-5-{4-propoxy-5H,6H,7H,8H-pyrido[3,4-d]pyrimidine-7-carbonyl}furo[2,3-d]pyrimidin-4-amine

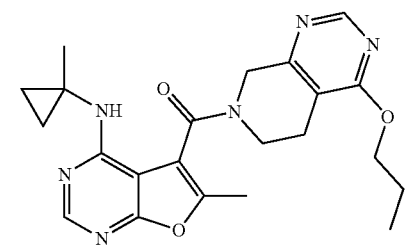 [SMILES: CCCOc1ncnc2c1CCN(C(=O)c1c(C)oc3ncnc(NC4(C)CC4)c13)C2]

$^1$H NMR (400 MHz, CDCl$_3$) δ 8.59 (s, 1H), 8.48 (s, 1H), 7.00 (br s, 1H), 4.75 (br s, 2H), 4.39 (t, J=6.66 Hz, 2H), 3.52-4.18 (m, 2H), 2.84 (t, J=5.01 Hz, 2H), 2.51 (s, 3H), 1.84 (sxt, J=7.12 Hz, 2H), 1.51 (s, 3H), 1.05 (t, J=7.46 Hz, 3H), 0.71-0.82 (m, 4H). [M+H]=423.4.

Example 807. 6-Methyl-N-(1-methylcyclopropyl)-5-[4-(2-methylpropoxy)-5H,6H,7H,8H-pyrido[3,4-d]pyrimidine-7-carbonyl]furo[2,3-d]pyrimidin-4-amine

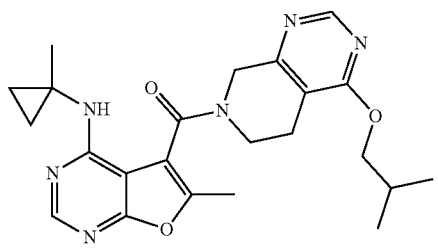 [SMILES: Cc1oc2ncnc(NC3(C)CC3)c2c1C(=O)N1CCc2c(ncnc2OCC(C)C)C1]

$^1$H NMR (400 MHz, CDCl$_3$) δ 8.59 (s, 1H), 8.48 (s, 1H), 7.00 (br s, 1H), 4.75 (br s, 2H), 4.20 (d, J=6.72 Hz, 2H), 3.53-4.13 (m, 2H), 2.78-2.88 (m, 2H), 2.52 (s, 3H), 2.14 (quind, J=6.71, 13.37 Hz, 1H), 1.51 (s, 3H), 1.05 (d, J=6.72 Hz, 6H), 0.71-0.83 (m, 4H). [M+H]=437.4.

Example 808. 5-[4-(Cyclopropylmethoxy)-5H,6H,7H,8H-pyrido[3,4-d]pyrimidine-7-carbonyl]-6-methyl-N-(1-methylcyclopropyl)furo[2,3-d]pyrimidin-4-amine

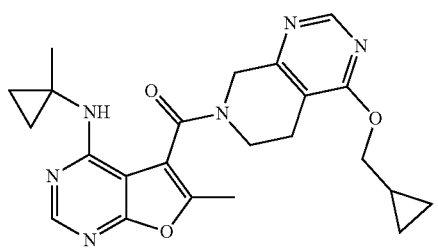 [SMILES: Cc1oc2ncnc(NC3(C)CC3)c2c1C(=O)N1CCc2c(ncnc2OCC2CC2)C1]

$^1$H NMR (400 MHz, CDCl$_3$) δ 8.57 (s, 1H), 8.49 (s, 1H), 7.00 (br s, 1H), 4.75 (br s, 2H), 4.28 (d, J=7.09 Hz, 2H), 3.47-4.16 (m, 2H), 2.86 (t, J=5.69 Hz, 2H), 2.52 (s, 3H), 1.51 (s, 3H), 1.26-1.37 (m, 1H), 0.72-0.83 (m, 4H), 0.59-0.69 (m, 2H), 0.32-0.43 (m, 2H). [M+H]=435.4.

Example 809. 5-[4-(2-Methoxyethoxy)-5H,6H,7H,8H-pyrido[3,4-d]pyrimidine-7-carbonyl]-6-methyl-N-(1-methylcyclopropyl)furo[2,3-d]pyrimidin-4-amine

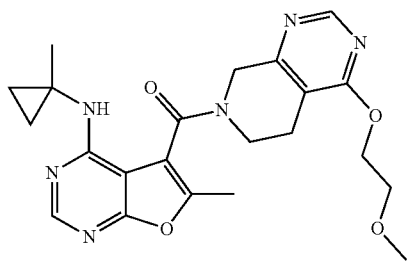 [SMILES: COCCOc1ncnc2c1CCN(C(=O)c1c(C)oc3ncnc(NC4(C)CC4)c13)C2]

$^1$H NMR (400 MHz, CDCl$_3$) δ 8.59 (s, 1H), 8.49 (s, 1H), 7.04 (br s, 1H), 4.76 (br s, 2H), 4.57-4.63 (m, 2H), 3.80-4.33 (m, 2H), 3.78 (dd, J=3.91, 5.38 Hz, 2H), 3.45 (s, 3H), 2.88 (t, J=5.62 Hz, 2H), 2.52 (s, 3H), 1.52 (s, 3H), 0.74-0.85 (m, 4H). [M+H]=439.4.

Example 810. 5-{4-Cyclobutoxy-5H,6H,7H,8H-pyrido[3,4-d]pyrimidine-7-carbonyl}-6-methyl-N-(1-methylcyclopropyl)furo[2,3-d]pyrimidin-4-amine

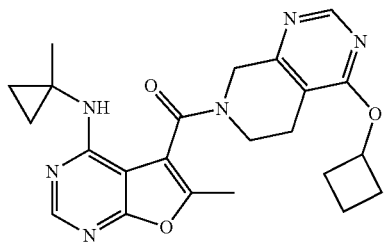 [SMILES: Cc1oc2ncnc(NC3(C)CC3)c2c1C(=O)N1CCc2c(ncnc2OC2CCC2)C1]

$^1$H NMR (400 MHz, CDCl$_3$) δ 8.57 (s, 1H), 8.48 (s, 1H), 7.00 (br s, 1H), 5.32 (quin, J=7.43 Hz, 1H), 4.74 (br s, 2H), 3.62-4.33 (m, 2H), 2.82-2.86 (m, 2H), 2.48-2.58 (m, 5H), 2.13-2.27 (m, 2H), 1.83-1.96 (m, 1H), 1.66-1.80 (m, 1H), 1.51 (s, 3H), 0.73-0.83 (m, 4H). [M+H]=435.4.

Example 811. 5-{4-Cyclopropoxy-5H,6H,7H,8H-pyrido[3,4-d]pyrimidine-7-carbonyl}-6-methyl-N-(1-methylcyclopropyl)furo[2,3-d]pyrimidin-4-amine

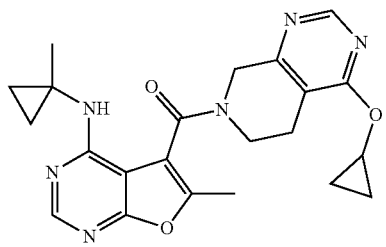 [SMILES: Cc1oc2ncnc(NC3(C)CC3)c2c1C(=O)N1CCc2c(ncnc2OC2CC2)C1]

$^1$H NMR (400 MHz, CDCl$_3$) δ 8.67 (s, 1H), 8.48 (s, 1H), 6.99 (br s, 1H), 4.76 (br s, 2H), 4.45 (tt, J=3.13, 6.22 Hz, 1H), 3.59-4.30 (m, 2H), 2.77 (t, J=5.69 Hz, 2H), 2.51 (s, 3H), 1.51 (s, 3H), 0.82-0.95 (m, 4H), 0.72-0.81 (m, 4H). [M+H]=421.4.

Example 812 was prepared in a manner analogous to Example 27, with the appropriate starting material substitutions.

Example 812. 5-{2-Cyclopropyl-4-methoxy-5H,6H,7H,8H-pyrido[3,4-d]pyrimidine-7-carbonyl}-6-methyl-N-(1-methylcyclopropyl)furo[2,3-d]pyrimidin-4-amine

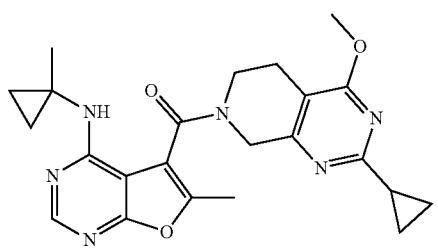 [SMILES: COc1nc(C2CC2)nc2c1CCN(C(=O)c1c(C)oc3ncnc(NC4(C)CC4)c13)C2]

$^1$H NMR (400 MHz, CD$_3$OD) δ 8.35 (s, 1H), 4.76 (br s, 2H), 4.08-3.72 (m, 5H), 2.75 (t, J=5.4 Hz, 2H), 2.55 (s, 3H), 2.15-2.07 (m, 1H), 1.46 (s, 3H), 1.23-1.05 (m, 4H), 0.80 (d, J=4.3 Hz, 4H). [M+H]=435.43.

Example 813 was prepared in a manner analogous to Example 28, with the appropriate starting material substitutions.

Example 813. N-Ethyl-N-[(6-methoxypyrimidin-4-yl)methyl]-6-methyl-4-[(1-methylcyclopropyl)amino]furo[2,3-d]pyrimidine-5-carboxamide

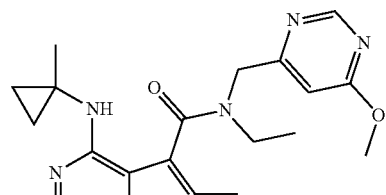

$^1$H NMR (400 MHz, CD$_3$OD) δ 8.85 (br s, 1H), 8.32 (br s, 1H), 7.80 (br s, 1H), 6.91 (br s, 1H), 4.83-4.59 (m, 2H), 4.02 (br s, 3H), 3.46 (br s, 2H), 2.48 (s, 3H), 1.55 (s, 3H), 1.12 (br s, 3H), 0.82 (br s, 4H). [M+H]=397.40.

Example 814 was prepared in a manner analogous to Example 29, with the appropriate starting material substitutions.

Example 814. 5-{1,3-Dimethyl-5H,6H,7H,8H-imidazo[1,5-a]pyrazine-7-carbonyl}-6-methyl-N-(1-methylcyclopropyl)furo[2,3-d]pyrimidin-4-amine

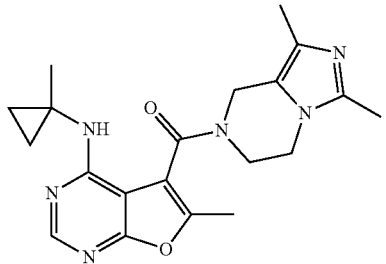 [SMILES: Cc1nc(C)n2c1CN(C(=O)c1c(C)oc3ncnc(NC4(C)CC4)c13)CC2]

$^1$H NMR (400 MHz, CDCl$_3$) δ 8.50 (s, 1H), 6.99 (s, 1H), 4.76 (s, 2H), 4.14-3.95 (m, 4H), 2.51 (s, 3H), 2.41 (s, 3H), 2.14 (s, 3H), 1.53 (s, 3H), 0.86-0.80 (m, 2H), 0.79-0.72 (m, 2H). [M+H]=381.3.

PHARMACOLOGICAL EXAMPLES

The present disclosure will be further illustrated by the following pharmacological examples. These examples are understood to be exemplary only and are not intended to limit the scope of the invention disclosed herein.

Enzymatic Assay

PDE1B inhibition was determined by an IMAP TR-FRET assay. The IMAP TR-FRET PDE assay was optimized for concentration of enzyme, Calmodulin, cAMP or cGMP substrate, DMSO tolerance, and incubation time.

Into each well of a solid white 1536 well plate (Corning) was dispensed 250 μg full-length recombinant NH-terminal GST tagged human PDE1B enzyme (BPS Bioscience Cat #60011, San Diego, Calif.) in 2.5 μL IMAP BSA reaction buffer (Molecular Devices, Sunnyvale, Calif.) containing 10 U/ml Calmodulin and 2.5 mM CaCl$_2$ (Sigma Aldrich.) After a brief centrifugation, 30 nL of compound was added by transfer from 1 mM stock in DMSO using a Kalypsys 1536 Pintool. Plates were incubated for 5 minutes at room temperature before dispensing 1.5 μL of 533 nM 5-carboxy fluorescein (FAM)-labeled cAMP (Molecular Devices, Sunnyvale, Calif.) for a final concentration of 200 nM. After a brief centrifugation, the plates were incubated for 30 minutes at room temperature. The assay was terminated by adding 5 μL IMAP binding reagent/Tb complex (Molecular Devices, Sunnyvale, Calif.) to each well.

Plates were incubated for 1 hour at room temperature and were read on a Viewlux multimode plate reader (Perkin Elmer). The instrument was set to excite using the DUG11 filter and measure using 490/10 nm and 520/10 nm filters. Ratios of acceptor and donor were then calculated.

Data Analysis

For IC$_{50}$ calculations, the values of % efficacy versus a series of compound concentrations were then plotted using non-linear regression analysis of sigmoidal dose-response curves generated with the equation Y=[B+(T−B)]/[1+10 ((Log EC$_{50}$−X)×Hill Slope)], where Y=percent activity, B=minimum percent efficacy, T=maximum percent efficacy, X=logarithm of compound and Hill Slope=slope factor or Hill coefficient. The IC$_{50}$ value was determined by the concentration causing a half-maximal percent efficacy.

Results

Table 2 presents the negative log of the half-maximal molar inhibitory concentration (pIC$_{50}$), with respect to PDE1B activity, for Formula I compounds.

TABLE 2

| PDE1b (pIC$_{50}$) | Example Numbers |
|---|---|
| >8 | 1, 11, 12, 13, 14, 20, 21, 25, 26, 27, 41, 42, 43, 44, 47, 51, 54, 55, 56, 57, 59, 60, 61, 62, 63, 66, 67, 69, 85, 88, 101, 103, 122, 131, 132, 133, 135, 145, 147, 150, 152, 154, 185, 194, 196, 209, 217, 237, 238, 267, 270, 296, 298, 301, 304, 306, 309, 312, 322, 323, 329, 334, 335, 338, 340, 341, 343, 344, 345, 346, 348, 351, 354, 355, 360, 361, 365, 366, 367, 368, 369, 370, 372, 373, 382, 384, 385, 387, 388, 389, 390, 395, 396, 397, 398, 422, 450, 454, 460, 464, 467, 475, 481, 483, 488, 493, 502, 532, 533, 536, 556, 557, 559, 560, 572, 574, 585, 590, 614, 648, 649, 666, 667, 686, 698, 704, 705, 708, 714, 716, 743, 751, 762, 763, 764, 765, 772, 775, 776, 779, 783, 784, 785, 789, 798, 799, 800, 801, 802, 807, 808, 810, 812 |
| 7-8 | 2, 3, 4, 5, 6, 7, 8, 9, 10, 15, 16, 17, 18, 22, 23, 28, 30, 31,32, 33, 34, 35, 38, 39, 40, 45, 48, 49, 50, 52, 53, 58, 64, 68, 70, 71, 72, 73, 74, 75, 76, 77, 78, 79, 82, 86, 87, 89, 91, 92, 93, 96, 97, 98, 99, 100, 102, 104, 105, 106, 107, 108, 109, 110, 111, 112, 113, 114, 116, 118, 124, 125, 126, 129, 130, 136, 137, 138, 139, 140, 141, 142, 143, 144, 146, 148, 149, 151, 153, 155, 156, 160, 161, 162, 163, 164, 165, 167, 168, 169, 170, 175, 176, 177, 178, 180, 181, 184, 186, 188, 190, 191, 192, 195, 198, 203, 204, 207, 208, 210, 211, 212, 213, 218, 220, 222, 223, 224, 225, 230, 233, 235, 236, 239, 244, 246, 248, 249, 250, 251, 253, 254, 256, 262, 263, 265, 269, 271, 273, 274, 275, 278, 279, 280, 281, 282, 283, 284, 285, 286, 287, 289, 290, 291, 292, 293, 294, 295, 297, 299, 300, 302, 305, 307, 308, 311, 313, 314, 315, 317, 318, 319, 320, 321, 324, 325, 326, 327, 328, 330, 331, 332, 336, 337, 339, 342, 347, 349, 350, 352, 353, 356, 357, 358, 359, 362, 364, 371, 374, 377, 380, 381, 383, 386, 391, 392, 393, 394, 399, 400, 401, 402, 404, 407, 409, 411, 412, 413, 414, 415, 416, 417, 418, 419, 420, 421, 423, 424, 426, 429, 430, 431, 432, 433, 436, 440, 441, 442, 443, 444, 445, 446, 447, 448, 449, 451, 452, 453, 455, 456, 457, 458, 459, 461, 463, 465, 466, 468, 471, 472, 473, 480, 482, 484, 487, 489, 495, 498, 508, 509, 510, 513, 520, 521, 522, 524, 525, 528, 529, 530, 534, 545, 547, 551, 552, 558, 568, 569, 570, 571, 573, 580, 584, 589, 595, 600, 604, 606, 613, 615, 619, 620, 621, 623, 624, 625, 626, 627, 628, 630, 632, 634, 635, 642, 644, |

TABLE 2-continued

| PDE1b (pIC$_{50}$) | Example Numbers |
|---|---|
| | 645, 646, 650, 651, 652, 653, 654, 655, 657, 658, 659, 660, 661, 662, 664, 665, 668, 669, 673, 674, 675, 676, 677, 678, 679, 680, 683, 687, 688, 689, 690, 691, 694, 695, 696, 697, 700, 702, 703, 706, 707, 710, 711, 712, 713, 715, 717, 718, 719, 722, 723, 724, 725, 726, 727, 728, 729, 730, 731, 732, 733, 734, 736, 737, 738, 739, 740, 741, 742, 744, 745, 746, 747, 750, 754, 755, 757, 758, 760, 766, 767, 768, 769, 770, 771, 773, 774, 777, 778, 781, 782, 786, 787, 788, 790, 791, 792, 793, 794, 795, 796, 797, 803, 804, 805, 806, 809, 811 |
| 6-7 | 19, 24, 29, 36, 37, 46, 65, 80, 81, 83, 90, 94, 95, 115, 117, 119, 120, 121, 123, 127, 128, 134, 157, 158, 159, 171, 174, 189, 214, 215, 260, 288, 303, 310, 316, 333, 363, 375, 376, 378, 379, 403, 405, 406, 408, 410, 425, 427, 428, 434, 435, 437, 438, 439, 462, 469, 470, 499, 518, 575, 583, 622, 629, 631, 633, 636, 637, 638, 639, 640, 641, 643, 647, 656, 663, 670, 671, 672, 681, 682, 684, 685, 692, 693, 699, 701, 709, 720, 721, 735, 748, 749, 753, 756, 759, 761, 780, 813, 814 |
| <6 | 193, 752 |

PDE1 Selectivity of Compounds

Assay Conditions

The selectivity of compounds of the present invention was determined using a panel of recombinant human PDEs and an in vitro enzymatic assay (BPS Bioscience). A series of dilutions of each test compound were prepared with 10% DMSO in assay buffer and 5 µL of the dilution was added to a 50 µL reaction so that the final concentration of DMSO is 1% in all of reactions.

The enzymatic reactions were conducted at room temperature for 60 minutes in a 50 µL mixture containing PDE assay buffer, 100 nM FAM-cAMP, or 100 nM FAM-cGMP, a recombinant PDE enzyme and the test compound.

After the enzymatic reaction, 100 µL of a binding solution (1:100 dilution of the binding agent with the binding agent diluent) was added to each reaction and the reaction was performed at room temperature for 60 minutes.

Fluorescence intensity was measured at an excitation of 485 nm and an emission of 528 nm using a Tecan Infinite M1000 microplate reader.

Data Analysis

PDE activity assays were performed in duplicate at each concentration. Fluorescence intensity is converted to fluorescence polarization using the Tecan Magellan6 software. The fluorescence polarization data were analyzed using the computer software, Graphpad Prism. The fluorescence polarization (FPt) in absence of the compound in each data set was defined as 100% activity. In the absence of PDE and the compound, the value of fluorescent polarization (FPb) in each data set was defined as 0% activity. The percent activity in the presence of the compound was calculated according to the following equation: % activity=(FP−FPb)/(FPt−FPb)×100%, where FP=the fluorescence polarization in the presence of the compound.

For IC$_{50}$ calculations, the values of % activity versus a series of compound concentrations were then plotted using non-linear regression analysis of Sigmoidal dose-response curve generated with the equation Y=[B+(T−B)]/[1+10((Log EC$_{50}$−X)×Hill Slope)], where Y=percent activity, B=minimum percent activity, T=maximum percent activity, X=logarithm of compound and Hill Slope=slope factor or Hill coefficient. The IC$_{50}$ value was determined by the concentration causing a half-maximal percent activity.

Results

Exemplary compounds of the present invention displayed selectivity for PDE1 enzymes versus isoforms from many, if not all, other PDE families. In addition, exemplary compounds showed greater specificity for PDE1B compared to PDE1A and PDE1C.

BIOLOGICAL EXAMPLES

The present disclosure will be further illustrated by the following biological examples. These examples are understood to be exemplary only, and not to limit the scope of the invention disclosed herein.

Biological Example 1

Effect of Exemplary Compounds on Memory and Catalepsy

The studies here evaluated the effect of exemplary compounds of the present invention on memory and haloperidol induced catalepsy in mice and rats.

Methods

Subjects

Outbred hooded Long Evans rats (400 g average weight, sourced from Taconic Farms or Envigo) were used for rat fear conditioning, object recognition, and catalepsy. Upon arrival, rats were house in standard cages in groups of two. Experiments were always conducted during the light phase of the cycle. The animals received food and water ad libitum except during training and testing. All procedures were consistent with National Institutes of Health (NIH) guidelines and approved by the DNS/Helicon Institutional Animal Care and Use Committee.

Drug Administration

PDE1 inhibitors and positive control were dosed in a vehicle containing 10% NMP, 40% PEG (MW400) and 50% water, unless specified otherwise. For subcutaneous dosing (s.c.), all drugs were administered at a volume of 10 mL per kg 30 min prior to behavior training unless specified otherwise. For oral dosing (p.o.), animals were dosed at the indicated amount 60 minutes prior to training.

Fear Conditioning

Rationale

Contextual fear conditioning is a form of associative learning in which animals learn to recognize a training environment (conditioned stimulus, CS) that has been previously paired with an aversive stimulus such as foot shock (unconditioned stimulus, US). When exposed to the same context at a later time, conditioned animals show a variety of conditional fear responses, including freezing behavior. See, e.g., Fanselow, 1984, *Behav. Neurosci.* 98, 269-277;

Fanselow, 1984, *Behav. Neurosci.* 98, 79-95; Phillips and LeDoux, 1992, *Behav. Neurosci.* 106, 274-285.

Contextual conditioning has been used to investigate the neural substrates mediating fear-motivated learning. See, e.g., Phillips and LeDoux, 1992, *Behav. Neurosci.* 106, 274-285; Kim et al., 1993, *Behav. Neurosci.* 107, 1093-1098. Studies in mice and rats have provided evidence for functional interaction between hippocampal and non-hippocampal systems during contextual conditioning training. See, e.g., Maren et al., 1997, *Behav. Brain Res.* 88, 261-274; Maren et al., 1997, *Neurobiol. Learn. Mem.* 67, 142-149; Frankland et al., 1998, *Behav. Neurosci.* 112, 863-874. Specifically, post-training lesions of the hippocampus (but not pre-training lesions) greatly reduced contextual fear, implying that: 1) the hippocampus is essential for contextual memory but not for contextual learning per se and 2) in the absence of the hippocampus during training, non-hippocampal systems can support contextual conditioning.

Contextual conditioning has been extensively used to study the impact of various mutations on hippocampus-dependent learning and memory and strain differences in mice. See, e.g., Bourtchouladze et al., 1994, *Cell* 79, 59-68; Bourtchouladze et al., 1998, *Learn Mem.* 5, 365-374; Kogan et al., 1997, *Current Biology* 7, 1-11; Silva et al., 1996, *Current Biology* 6, 1509-1518; Abel et al., 1997, *Cell* 88, 615-626; Giese et al., 1998, *Science* 279, 870-873; Logue et al., 1997, *Neuroscience* 80, 1075-1086; Chen et al., 1996, *Behav. Neurosci.* 110, 1177-1180; Nguyen et al., 2000, *Learn Mem.* 7, 170-179.

Because robust learning can be triggered with a few minutes training session, contextual conditioning has been especially useful to study the biology of temporally distinct processes of short- and long-term memory. See, e.g., Kim et al., 1993, *Behav. Neurosci.* 107, 1093-1098; Abel et al., 1997, *Cell* 88, 615-626; Bourtchouladze et al., 1994, *Cell* 79, 59-68; Bourtchouladze et al., 1998, *Learn. Mem.* 5, 365-374. As such, contextual conditioning provides an excellent model to evaluate the role of various novel genes in hippocampal-dependent memory formation.

Protocol

Previous investigations had established that training with 1× or 2× CS-US pairings induces sub-maximal (weak) memory in wild-type mice. See, e.g., U.S.2009/0053140; Tully et al., 2003, *Nat. Rev. Drug Discov.* 2, 267-77; Bourtchouladze et al., 1998, *Learn. Mem.* 5, 365-374. Accordingly, contextual conditioning in this study was performed as described by Bourtchouladze et al., 1994, *Cell* 79, 59-68.

An automated fear conditioning system (Colburn Instruments) was used for contextual conditioning and a manual setup (Med Associates) for trace fear conditioning. Rats were placed in the conditioning chamber and allowed to explore for 2 min. A total of two foot-shocks were delivered (0.4-0.6 mA, 2 s duration) with an inter-trial interval of 1 min. These training conditions generate sub-maximal, or weak, memory in control rats, thereby allowing one to evaluate whether a PDE1b compound of the present invention can enhance memory formation.

Freezing was scored for 30 s after the last foot-shock (immediate freezing). Freezing was scored for 30 s after the last foot-shock (immediate freezing). The rats were then returned to their home-cage. Memory was tested after 24 h (LTM) for 3 min by scoring freezing behavior using automated algorithms (Med Associates).

Object Recognition Memory

Rationale

Novel Object Recognition (NOR) is an assay of recognition learning and memory retrieval, which takes advantage of the spontaneous preference of rodents to investigate a novel object compared with a familiar one.

The NOR test has been employed extensively to assess the potential cognitive-enhancing properties of novel compounds derived from high-throughput screening. Object recognition is an ethologically relevant task that does not result from negative reinforcement (foot shock). This task relies on the natural curiosity of rodents to explore novel objects in their environments more than familiar ones. Obviously, for an object to be "familiar," the animal must have attended to it before and remembered that experience. Hence, animals with better memory will attend and explore a new object more than an object familiar to them. During testing, the animal is presented with the training object and a second, novel one. Memory of the training object renders it familiar to the animal, and it then spends more time exploring the new novel object rather than the familiar one. See Bourtchouladze et al., 2003, *Proc. Natl. Acad. Sci. USA* 100, 10518-10522).

Studies indicate that the NOR procedure involves several brain regions, including the cortex and the hippocampus. Recent neuroimaging studies in humans demonstrated that memory in object recognition depends on prefrontal cortex (PFC). See Delbert et al., 1999, *Neurology* 52, 1413-1417. Consistent with these findings, rats with the PFC lesions show poor working memory when they are required to discriminate between familiar and novel objects. See Mitchell, 1998, *Behav. Brain Res.* 97, 107-113. Other studies on monkeys and rodents suggest that the hippocampus is important for novel object recognition. See, e.g., Teng et al., 2000, *J. Neurosci* 20, 3853-3863; Mumby, 2001, *Brain Res.* 127, 159-181. Hence, object recognition provides an excellent behavioral model to evaluate drug-compound effects on cognitive task associated with function of the hippocampus and cortex.

Protocol

The novel object recognition task was performed as described by Bevins and Besheer, (2006, *Nat. Protocol.* 1, 1306-1311) using a standard novel object recognition system for rats (Stoelting). Objects were placed in the center of the box, testing was carried out in low light, and time exploring objects was assessed using Ethovision Software. All videos were reviewed by trained observers.

For two consecutive days, rats were habituated to the chamber for 5 min with 5 min of handling immediately following exposure to the apparatus. The next day, rats treated with 10% NMP, 40% PEG400, 50% water vehicle or drug 60 min before training were exposed to either two white blocks or two grey balls (~4 cm in width/diameter) for 3 min. Approximately 24 h after training, rats were exposed to one familiar object and one novel object (grey ball is replaced with a white block and vice versa) and the time exploring each object was measured. Memory was scored by calculation of a discrimination index $((T_N-T_F)/(T_N+T_F))*100$; between group comparison) and by comparison of the time exploring the novel versus familiar object on the test day (within group comparison).

Catalepsy

Rationale

Catalepsy in rats can be defined as a drug-induced state where the animal may be placed in an unnatural body position and will remain in this position for a significantly longer time than vehicle-treated rats (Wadenberg, et al., 1996, *Neurosci. Biobehav. Rev.*, 20, 325-339). The blockade of brain dopamine receptors by classic neuroleptic antipsychotics (e.g., haloperidol) produces extrapyramidal motor side-effects (including catalepsy) in a significant proportion of patients (Baldessarini, et al. "Drugs and the treatment of psychiatric disorders" *The pharmacological basis of therapeutics* Goodman, et al., (eds.) New York: Pergamon Press, 383-435). The neuroleptic-induced cataleptic state is a generally accepted animal model of the akinesia and rigidity observed in Parkinson's Disease (Sanberg, et al., 1998, *Behavioral Neuroscience*, 102, 748-759).

Protocol

Catalepsy was assessed with bar test 60 minutes after Haloperidol injection. The fore paws of the rats were placed on a horizontal bar positioned at 10 cm above the floor. Time spent in cataleptic posture, which was defined as an immobile posture while keeping both forelimbs on the bar, was measured with a maximum limit of 180 seconds. Automation of catalepsy scoring was performed using the Kinder Scientific Loco Chambers and data was recorded using Kinder Scientific Motor Monitor software.

Statistical Analyses

All behavioral experiments were designed and performed in a balanced fashion: (i) For each experimental condition (e.g. a specific dose-effect) an equal number of experimental and control animals were used; (ii) Each experimental condition may be replicated several times, and (iii) Replicate days were added to generate final number of subjects. In each experiment, the experimenter was unaware (blind) to the treatment of the subjects during training and testing. Data were analyzed by ANOVA using JMP or Prism software, followed by contrast analysis or Dunnett's multiple comparison tests, the results of which are shown.

Results

Exemplary compounds of Formula I were found to significantly enhance 24 hour memory, in the object recognition assay. Control experiments showed that compound administration did not significantly affect the cumulative distance traveled or amount of time spent exploring the left and right halves of the box. Significant effects were seen at several concentrations, depending on the compound, including concentrations of 0.03 mg/kg, 0.1 mg/kg, 0.3 mg/kg, and 1 mg/kg.

Exemplary compounds were also found to enhance contextual memory in the fear conditioning assay. Significant effects were seen at several concentrations, depending on the compound, including 0.03 mg/kg, 0.1 mg/kg, 0.3 mg/kg and 1.0 mg/kg.

Exemplary compounds were also found to reverse haloperidol-induced catalepsy. Significant effects were seen at several concentrations, depending on the compound, ranging from 0.01 to 1.0 mg/kg, p.o.

Biological Example 2

Effect of Exemplary Compounds on Cardiac Function

Exemplary compounds of the present invention are evaluated in several models of cardiovascular function, including the telemeterized rat and Beagle dog. Each test compound (or vehicle) is administered by oral gavage, and animals are evaluated after each dose for any abnormal clinical signs. Hemodynamic (Heart rate, systolic, diastolic, and mean arterial pressure) and electrocardiographic parameters (PR interval, QRS duration, QT/QTc interval, RR interval) are recorded following dosing.

Results for Several Exemplary Compounds.

Administration of several compounds of the present disclosure lead to changes in blood pressure and increases in heart rate.)

It will be understood by one skilled in the art that the described embodiments herein do not limit the scope of the invention. The specification, including the examples, is intended to be exemplary only, and it will be apparent to those skilled in the art that various modifications and variations can be made in the present invention without departing from the scope or spirit of the invention as defined by the appended claims.

Furthermore, while certain details in the present disclosure are provided to convey a thorough understanding of the invention as defined by the appended claims, it will be apparent to those skilled in the art that certain embodiments may be practiced without these details. Moreover, in certain instances, well-known methods, procedures, or other specific details have not been described to avoid unnecessarily obscuring aspects of the invention defined by the appended claims.

What is claimed is:

1. A compound of Formula (I):

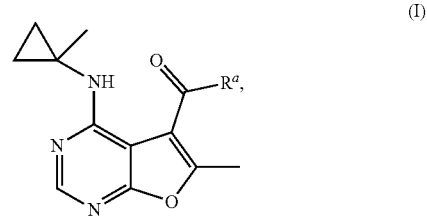

or a pharmaceutically acceptable salt thereof,
wherein,
$R^a$ is -$L^1$-$L^3$, -$L^1$-$L^2$-$L^3$, or —N($L^4$)-$L^5$;
$L^1$ is selected from the group consisting of: —N($R^b$)—, —N($R^b$)—(C($R^b$)$_2$)$_m$—, —N($R^b$)(CH$_2$)$_m$O—, —NHNH—, 3-15-membered heterocycloalkyl, and 5-10-membered heteroaryl, said 3-15-membered heterocycloalkyl or 5-10-membered heteroaryl optionally substituted with one to four $R^{1A}$, where each $R^{1A}$ is independently selected from the group consisting of: halo, —OH, =O, —NH$_2$, —NHC$_{1-4}$alkyl, —N(C$_{1-4}$alkyl)$_2$, —NO$_2$, —SO$_2$CH$_3$, —CN, —C$_{1-6}$alkyl, —C$_{1-6}$ haloalkyl, —C$_{1-6}$alkyl-OH, —C$_{1-6}$alkoxy, —C$_{1-6}$ haloalkoxy, —C$_{1-6}$alkyl-O—C$_{1-4}$alkyl, —C(O)C$_{1-6}$alkyl, —COOC$_{1-6}$alkyl, —C(O)NH$_2$, and —C$_{3-7}$cycloalkyl;
each m is independently 0, 1, 2, or 3;
each $R^b$ is independently —H, —OH, —C$_{1-6}$alkyl, —C$_{1-6}$haloalkyl, —C$_{1-6}$alkyl-OH, —C$_{1-6}$alkyl-O—C$_{1-4}$alkyl, —C(O)C$_{1-6}$alkyl, —C$_{3-7}$cycloalkyl, —C$_{2-6}$alkenyl, or —C$_{2-6}$alkynyl;
$L^2$ is selected from the group consisting of: —N($R^c$)—, —N($R^c$)(CH$_2$)$_m$, —O—, —S—, —C$_{1-6}$alkyl, —C$_{1-6}$haloalkyl, —C$_{1-6}$alkoxy, —C$_{1-6}$haloalkoxy, —C$_{2-6}$alkenyl, —C$_{2-6}$alkynyl, —C(O)C$_{1-6}$alkyl, —CHR$^c$—, —(CH$_2$)$_m$NH—, —(CH$_2$)$_m$O—, —(CH$_2$)$_m$S—, —C$_{3-10}$cycloalkyl, 3-15-membered heterocycloalkyl, phenyl, benzyl, and 5-10-membered heteroaryl, said —C$_{1-6}$alkyl, —C$_{3-10}$cycloalkyl, 3-15-membered heterocycloalkyl, phenyl, and 5-10-membered heteroaryl optionally substituted with one to four $R^{1B}$, where each $R^{1B}$ is independently selected from the group consisting of: halo, —OH, =O, —NH$_2$, —NHC$_{1-4}$alkyl, —N(C$_{1-4}$alkyl)$_2$, —NO$_2$, —SO$_2$CH$_3$, —CN, —C$_{1-6}$alkyl, —C$_{1-6}$haloalkyl, —C$_{1-6}$alkyl-OH, —C$_{1-6}$alkoxy, —C$_{1-6}$haloalkoxy, —C$_{1-6}$alkyl-O—C$_{1-4}$alkyl, —C(O)C$_{1-6}$alkyl, —COOC$_{1-6}$alkyl, —C(O)NH$_2$, —C$_{3-7}$cycloalkyl, 3-15-membered heterocycloalkyl, phenyl, benzyl, and 5-10-membered heteroaryl;

each R$^c$ is independently —H, —C$_{1-6}$alkyl, —C$_{1-6}$haloalkyl, —C$_{1-6}$alkyl-OH, —C$_{1-6}$alkyl-O—C$_{1-4}$alkyl, —C(O)C$_{1-6}$alkyl, —C$_{3-7}$cycloalkyl, —C$_{2-6}$alkenyl, or —C$_{2-6}$alkynyl;

L$^3$ is selected from the group consisting of: —H, —OH, —CN, —NH$_2$, —NHC$_{1-4}$alkyl, —N(C$_{1-4}$alkyl)$_2$, —N(R$^{1DD}$)$_2$, —N=S(=O)(CH$_3$)$_2$, —NO$_2$, —SO$_2$CH$_3$, halo, —C$_{1-6}$alkyl, —C$_{1-6}$haloalkyl, —C$_{1-6}$alkoxy, —C$_{1-6}$haloalkoxy, —C$_{2-6}$alkenyl, —C$_{2-6}$alkynyl, —C(O)C$_{1-6}$alkyl, —C(O)NH$_2$, —C$_{1-6}$alkyl-O—C$_{1-4}$alkyl, —C$_{3-10}$cycloalkyl, 3-15-membered heterocycloalkyl, phenyl, benzyl, and 5-10-membered heteroaryl, said —C$_{1-6}$alkyl, —C$_{3-10}$cycloalkyl, 3-15-membered heterocycloalkyl, phenyl, benzyl, and 5-10-membered heteroaryl optionally substituted with one to four R$^{1C}$, where each R$^{1C}$ is independently selected from the group consisting of: halo, —OH, =O, —NH$_2$, —NHC$_{1-4}$alkyl, —N(C$_{1-4}$alkyl)$_2$, —NO$_2$, —SO$_2$CH$_3$, —CN, —C$_{1-6}$alkyl, —C$_{1-6}$haloalkyl, —C$_{1-6}$alkyl-OH, —C$_{1-6}$alkoxy, —C$_{1-6}$haloalkoxy, —C$_{1-6}$alkyl-O—C$_{1-4}$alkyl, —C(O)C$_{1-6}$alkyl, —COOC$_{1-6}$alkyl, —C(O)NH$_2$, —C$_{3-7}$cycloalkyl, 3-15-membered heterocycloalkyl, phenyl and 5-10-membered heteroaryl;

each R$^{1DD}$ is independently selected from the group consisting of: —H, —C$_{1-6}$alkyl, —C$_{1-6}$haloalkyl, —C$_{1-6}$alkyl-OH, —C$_{1-6}$alkyl-O—C$_{1-4}$alkyl, —C(O)C$_{1-6}$alkyl, —COOC$_{1-6}$alkyl, —C$_{3-7}$cycloalkyl, 3-15-membered heterocycloalkyl, phenyl and 5-10-membered heteroaryl;

L$^4$ and L$^5$ are taken together with the nitrogen to which they are attached form a 3-15-membered heterocycloalkyl or 5-10-membered heteroaryl ring, optionally substituted with one to four R$^{1D}$, where each R$^{1D}$ is independently selected from the group consisting of: L$^6$, =O, —C$_{1-6}$alkyl-OH, —C$_{1-6}$alkyl-O—C$_{1-4}$alkyl, and —COOC$_{1-6}$alkyl; and L$^6$ is selected from the group consisting of: —H, —OH, —CN, —NH$_2$, —NHC$_{1-4}$alkyl, —N(C$_{1-4}$alkyl)$_2$, —N=S(=O)(CH$_3$)$_2$, —NO$_2$, —SO$_2$CH$_3$, halo, —C$_{1-6}$alkyl, —C$_{1-6}$haloalkyl, —C$_{1-6}$alkoxy, —C$_{1-6}$haloalkoxy, —C$_{2-6}$alkenyl, —C$_{2-6}$alkynyl, —C(O)C$_{1-6}$alkyl, —C(O)NH$_2$, —C$_{3-10}$cycloalkyl, —C$_{1-6}$alkyl-O—C$_{1-4}$alkyl, 3-15-membered heterocycloalkyl, phenyl, benzyl, and 5-10-membered heteroaryl, said —C$_{1-6}$alkyl, —C$_{3-10}$cycloalkyl, 3-15-membered heterocycloalkyl, phenyl, benzyl, and 5-10-membered heteroaryl optionally substituted with one to four R$^{1E}$, where each R$^{1E}$ is independently selected from the group consisting of: halo, —OH, =O, —NH$_2$, —NHC$_{1-4}$alkyl, —N(C$_{1-4}$ alkyl)$_2$, —NO$_2$, —SO$_2$CH$_3$, —CN, —C$_{1-6}$alkyl, —C$_{1-6}$haloalkyl, —C$_{1-6}$alkyl-OH, —C$_{1-6}$alkoxy, —C$_{1-6}$haloalkoxy, —C$_{1-6}$alkyl-O—C$_{1-4}$alkyl, —C(O)C$_{1-6}$alkyl, —COOC$_{1-6}$alkyl, —C(O)NH$_2$, —C$_{3-7}$cycloalkyl, 3-15-membered heterocycloalkyl, phenyl and 5-10-membered heteroaryl.

2. A compound as in claim 1, having the structure of Formula (Ia):

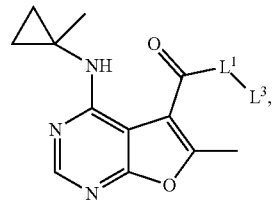

(Ia)

or a pharmaceutically acceptable salt thereof.

3. A compound, or pharmaceutically acceptable salt thereof, of claim 1, wherein L$^1$ is —N(R$^b$)— or —N(R$^b$)—(C(R$^b$)$_2$)$_m$—;

each m is independently 0, 1, 2, or 3; and each R$^b$ is independently —H, —C$_{1-6}$alkyl, —C$_{1-6}$haloalkyl, or —C$_{3-7}$cycloalkyl.

4. A compound, or pharmaceutically acceptable salt thereof, of claim 1, wherein L$^1$ is —NH— or —NHCH$_2$—.

5. A compound, or pharmaceutically acceptable salt thereof, of claim 1, wherein L$^3$ is selected from the group consisting of: —C$_{3-10}$cycloalkyl, 3-10-membered heterocycloalkyl, phenyl, and 5-10-membered heteroaryl, said —C$_{3-10}$cycloalkyl, 3-10-membered heterocycloalkyl, phenyl, and 5-10-membered heteroaryl optionally substituted with one to three R$^{1C}$.

6. A compound, or pharmaceutically acceptable salt thereof, of claim 1, wherein L$^3$ is selected from the group consisting of: azetidine, pyrrolidine, piperidine, azepane, dihydropyrrole, tetrahydropyridine, imidazoline, piperazine, diazepane, morpholine, oxetane, tetrahydrofuran, tetrahydropyran, benzo[d][1,3]dioxole, 2,3-dihydrobenzo[b][1,4]dioxine, tetrahydroquinoline, tetrahydroisoquinoline, quinolin-2(1H)-one, decahydroisoquinoline, decahydroquinoline, 6,7-dihydro-5H-cyclopenta[b]pyridine, 6,7-dihydro-5H-cyclopenta[d]pyrimidine, 2,3-dihydrobenzo[b][1,4]dioxine, pyrimidinone, 3-oxabicyclo[3.1.0]hexane, 3-azabicyclo[3.1.0]hexane, 8-oxa-3-azabicyclo[3.2.1]octane, pyrimidin-4(3H)-one, octahydrocyclopentapyrrole, 6,7-dihydro-5H-pyrrolo[3,4-d]pyrimidine, 6,7-dihydro-5H-pyrrolo[3,2-d]pyrimidine, 5,6,7,8-tetrahydropyrido[4,3-c]pyridazine, 5,6,7,8-tetrahydropyrido[3,4-c]pyridazine, 5,6,7,8-tetrahydropyrido[3,2-c]pyridazine, 5,6,7,8-tetrahydropyrido[4,3-d]pyrimidine, 5,6,7,8-tetrahydropyrido[3,4-d]pyrimidine, tetrahydronaphthyridine, 6,7-dihydro-5H-pyrrolo[3,4-b]pyridine, 2,3-dihydro-1H-pyrrolo[3,4-c]pyridine, and isoindoline, each optionally substituted with one to three R$^{1C}$, where each R$^{1C}$ is independently selected from the group consisting of: halo, —OH, =O, —NH$_2$, —NHC$_{1-4}$alkyl, —N(C$_{1-4}$alkyl)$_2$, —NO$_2$, —SO$_2$CH$_3$, —CN, —C$_{1-6}$alkyl, —C$_{1-6}$haloalkyl, —C$_{1-6}$alkyl-OH, —C$_{1-6}$alkoxy, —C$_{1-6}$haloalkoxy, —C$_{1-6}$alkyl-O—C$_{1-4}$alkyl, —C(O)C$_{1-6}$alkyl, —COOC$_{1-6}$alkyl, —C(O)NH$_2$, and —C$_{3-7}$cycloalkyl.

7. A compound, or pharmaceutically acceptable salt thereof, of claim 1, wherein L$^3$ is selected from the group consisting of: azetidine, pyrrolidine, piperidine, azepane, imidazoline, piperazine, diazepane, morpholine, oxetane, tetrahydrofuran, tetrahydropyran, benzo[d][1,3]dioxole, 2,3-dihydrobenzo[b][1,4]dioxine, tetrahydroquinoline, tetrahydroisoquinoline, quinolin-2(1H)-one, decahydroisoquinoline, decahydroquinoline, 6,7-dihydro-5H-cyclopenta[b]pyridine, 6,7-dihydro-5H-cyclopenta[d]pyrimidine, 2,3-dihydrobenzo[b][1,4]dioxine, pyrimidinone, 3-oxabicyclo[3.1.0]hexane, 3-azabicyclo[3.1.0]hexane, 8-oxa-3-azabicyclo[3.2.1]octane, and pyrimidin-4(3H)-one, each optionally substituted with one to three R¹ᶜ, where each R¹ᶜ is independently selected from the group consisting of: —F, —Cl, —Br, —I, —OH, =O, —NH₂, —NHC₁₋₄alkyl, —N(C₁₋₄alkyl)₂, —CN, —C₁₋₄alkyl, —C₁₋₄haloalkyl, —C₁₋₄alkyl-OH, —C₁₋₄alkoxy, —C₁₋₄haloalkoxy, —C₁₋₄alkyl-O—C₁₋₄alkyl, and —C₃₋₆cycloalkyl.

8. A compound, or pharmaceutically acceptable salt thereof, of claim 1, wherein L³ is phenyl, optionally substituted with one to three R¹ᶜ.

9. A compound, or pharmaceutically acceptable salt thereof, of claim 1, wherein L³ is selected from the group consisting of: pyridine, pyridazine, pyrazine, pyrimidine, pyrrole, furan, thiophene, pyrazole, imidazole, thiazole, isothiazole, oxazole, isoxazole, triazole, oxadiazole, thiadiazole, tetrazole, indole, indazole, benzimidazole, benzoxazole, benzothiazole, [1,2,4]triazolo[4,3-a]pyridine, and imidazo[1,2-a]pyrazine, each optionally substituted with one to three R¹ᶜ, where each R¹ᶜ is independently selected from the group consisting of: —F, —Cl, —Br, —I, —OH, =O, —NH₂, —NHC₁₋₄alkyl, —N(C₁₋₄alkyl)₂, —CN, —C₁₋₆alkyl, —C₁₋₆haloalkyl, —C₁₋₆alkyl-OH, —C₁₋₆alkoxy, —C₁₋₆ haloalkoxy, —C₁₋₆alkyl-O—C₁₋₄alkyl, —C(O)C₁₋₆alkyl, —COOC₁₋₆alkyl, —C(O)NH₂, and —C₃₋₇cycloalkyl.

10. A compound, or pharmaceutically acceptable salt thereof, of claim 1, wherein L³ is selected from the group consisting of: pyridine, pyridazine, pyrazine, and pyrimidine, each optionally substituted with one to three R¹ᶜ, where each R¹ᶜ is independently selected from the group consisting of: —F, —Cl, —Br, —I, —OH, =O, —NH₂, —NHC₁₋₄alkyl, —N(C₁₋₄alkyl)₂, —CN, —C₁₋₄alkyl, —C₁₋₄ haloalkyl, —C₁₋₄alkyl-OH, —C₁₋₄alkoxy, —C₁₋₄haloalkoxy, and —C₃₋₆cycloalkyl.

11. A compound, or pharmaceutically acceptable salt thereof, of claim 1, wherein L³ is selected from the group consisting of: pyrrole, pyrazole, imidazole, thiazole, oxazole, and isoxazole, each optionally substituted with one to three R¹ᶜ, where each R¹ᶜ is independently selected from the group consisting of: —F, —Cl, —Br, —I, —OH, =O, —NH₂, —NHC₁₋₄alkyl, —N(C₁₋₄alkyl)₂, —CN, —C₁₋₄alkyl, —C₁₋₄haloalkyl, —C₁₋₄alkyl-OH, —C₁₋₄alkoxy, —C₁₋₄ haloalkoxy, and —C₃₋₆cycloalkyl.

12. A compound, or pharmaceutically acceptable salt thereof, of claim 1, wherein each Rᵇ is independently —H, —C₁₋₃alkyl, —C₁₋₃haloalkyl, —C₁₋₃alkyl-OH, —C₁₋₃alkyl-O—C₁₋₃alkyl, or —C₃₋₅cycloalkyl.

13. A compound, or pharmaceutically acceptable salt thereof, of claim 1, wherein each R¹ᶜ is independently selected from the group consisting of: —F, —Cl, —OH, —C₁₋₄alkyl, —C₁₋₄haloalkyl, —C₁₋₄alkyl-OH, —C₁₋₄ alkoxy, and —C₁₋₄haloalkoxy.

14. A compound, or pharmaceutically acceptable salt thereof, of claim 1, wherein m is 0.

15. A compound, or pharmaceutically acceptable salt thereof, of claim 1, wherein m is 1.

16. A compound, or pharmaceutically acceptable salt thereof, of claim 1, wherein m is 2.

17. A compound selected from the group consisting of:
N-[6-(furan-3-yl)pyridin-3-yl]-6-methyl-4-[(1-methylcyclopropyl)amino]furo[2,3-d]pyrimidine-5-carboxamide;
6-methyl-4-[(1-methylcyclopropyl)amino]-N-[5-(morpholin-4-yl)pyridin-2-yl]furo[2,3-d][2,3-d]pyrimidine-5-carboxamide;
6-methyl-4-[(1-methylcyclopropyl)amino]-N-(oxetan-3-yl)furo[2,3-d]pyrimidine-5-carboxamide;
N-(5-fluoropyridin-2-yl)-6-methyl-4-[(1-methylcyclopropyl)amino]furo[2,3-d]pyrimidine-5-carboxamide;
N-(1-cyanocyclobutyl)-6-methyl-4-[(1-methylcyclopropyl)amino]furo[2,3-d]pyrimidine-5-carboxamide;
6-methyl-4-[(1-methylcyclopropyl)amino]-N-(pyridin-4-yl)furo[2,3-d]pyrimidine-5-carboxamide;
6-methyl-4-[(1-methylcyclopropyl)amino]-N-(pyridin-3-yl)furo[2,3-d]pyrimidine-5-carboxamide;
6-methyl-N-(1-methyl-1H-pyrazol-5-yl)-4-[(1-methylcyclopropyl)amino]furo[2,3-d]pyrimidine-5-carboxamide;
6-methyl-4-[(1-methylcyclopropyl)amino]-N-(5,6,7,8-tetrahydroquinolin-8-yl)furo[2,3-d]pyrimidine-5-carboxamide;
6-methyl-N-(1-methyl-1H-pyrazol-3-yl)-4-[(1-methylcyclopropyl)amino]furo[2,3-d]pyrimidine-5-carboxamide;
N-(1,5-dimethyl-1H-pyrazol-4-yl)-6-methyl-4-[(1-methylcyclopropyl)amino]furo[2,3-d]pyrimidine-5-carboxamide;
6-methyl-4-[(1-methylcyclopropyl)amino]-N-(trimethyl-1H-pyrazol-4-yl)furo[2,3-d]pyrimidine-5-carboxamide;
6-methyl-4-[(1-methylcyclopropyl)amino]-N-[1-(pyridin-2-yl)-1H-pyrazol-4-yl]furo[2,3-d]pyrimidine-5-carboxamide;
N-[1-(2-methoxyethyl)-3,5-dimethyl-1H-pyrazol-4-yl]-6-methyl-4-[(1-methylcyclopropyl)amino]furo[2,3-d]pyrimidine-5-carboxamide;
6-methyl-4-[(1-methylcyclopropyl)amino]-N-{1-[2-(morpholin-4-yl)ethyl]-1H-pyrazol-4-yl}furo[2,3-d]pyrimidine-5-carboxamide;
6-methyl-4-[(1-methylcyclopropyl)amino]-N-(6-methylpyridin-2-yl)furo[2,3-d]pyrimidine-5-carboxamide;
6-methyl-4-[(1-methylcyclopropyl)amino]-N-(4-methylpyridin-2-yl)furo[2,3-d]pyrimidine-5-carboxamide;
6-methyl-4-[(1-methylcyclopropyl)amino]-N-(3-methylpyridin-2-yl)furo[2,3-d]pyrimidine-5-carboxamide;
N-[1-(2-methoxyethyl)-1H-pyrazol-4-yl]-6-methyl-4-[(1-methylcyclopropyl)amino]furo[2,3-d]pyrimidine-5-carboxamide;
N-(1,4-dimethyl-1H-pyrazol-3-yl)-6-methyl-4-[(1-methylcyclopropyl)amino]furo[2,3-d]pyrimidine-5-carboxamide;
N-(dimethyl-1,3-thiazol-2-yl)-6-methyl-4-[(1-methylcyclopropyl)amino]furo[2,3-d]pyrimidine-5-carboxamide;
6-methyl-4-[(1-methylcyclopropyl)amino]-N-(6-methylpyridazin-3-yl)furo[2,3-d]pyrimidine-5-carboxamide;
6-methyl-N-(1-methyl-1H-imidazol-4-yl)-4-[(1-methylcyclopropyl)amino]furo[2,3-d]pyrimidine-5-carboxamide;
N-(5-fluoro-6-methylpyridin-2-yl)-6-methyl-4-[(1-methylcyclopropyl)amino]furo[2,3-d]pyrimidine-5-carboxamide;
6-methyl-4-[(1-methylcyclopropyl)amino]-N-(6-methylpyrazin-2-yl)furo[2,3-d]pyrimidine-5-carboxamide;
6-methyl-4-[(1-methylcyclopropyl)amino]-N-(5-methylpyridin-2-yl)furo[2,3-d]pyrimidine-5-carboxamide;
N-(1,5-dimethyl-1H-pyrazol-3-yl)-6-methyl-4-[(1-methylcyclopropyl)amino]furo[2,3-d]pyrimidine-5-carboxamide;
N-[1-(2-methoxyethyl)-1H-pyrazol-3-yl]-6-methyl-4-[(1-methylcyclopropyl)amino]furo[2,3-d]pyrimidine-5-carboxamide;
N-(5,6-dimethylpyrazin-2-yl)-6-methyl-4-[(1-methylcyclopropyl)amino]furo[2,3-d]pyrimidine-5-carboxamide;

N-(dimethyl-1,3-oxazol-2-yl)-6-methyl-4-[(1-methylcyclopropyl)amino]furo[2,3-d]pyrimidine-5-carboxamide;

6-methyl-N-(4-methyl-1,3-thiazol-2-yl)-4-[(1-methylcyclopropyl)amino]furo[2,3-d]pyrimidine-5-carboxamide;

6-methyl-4-[(1-methylcyclopropyl)amino]-N-[1-(propan-2-yl)-1H-pyrazol-3-yl]furo[2,3-d]pyrimidine-5-carboxamide;

N-[1-(3-fluoropyridin-2-yl)-1H-pyrazol-3-yl]-6-methyl-4-[(1-methylcyclopropyl)amino]furo[2,3-d]pyrimidine-5-carboxamide;

N-[1-(3-fluoropyridin-2-yl)-1H-pyrazol-4-yl]-6-methyl-4-[(1-methylcyclopropyl)amino]furo[2,3-d]pyrimidine-5-carboxamide;

6-methyl-N-(4-methyl-1,3-oxazol-2-yl)-4-[(1-methylcyclopropyl)amino]furo[2,3-d]pyrimidine-5-carboxamide;

6-methyl-N-(3-methyl-1,2,4-oxadiazol-5-yl)-4-[(1-methylcyclopropyl)amino]furo[2,3-d]pyrimidine-5-carboxamide;

6-methyl-N-(2-methyl-1,3-thiazol-4-yl)-4-[(1-methylcyclopropyl)amino]furo[2,3-d]pyrimidine-5-carboxamide;

6-methyl-N-(3-methyl-1,2,4-thiadiazol-5-yl)-4-[(1-methylcyclopropyl)amino]furo[2,3-d]pyrimidine-5-carboxamide;

6-methyl-4-[(1-methylcyclopropyl)amino]-N-[1-(oxan-4-yl)-1H-pyrazol-4-yl]furo[2,3-d]pyrimidine-5-carboxamide;

N,6-dimethyl-N-(1-methyl-1H-pyrazol-4-yl)-4-[(1-methylcyclopropyl)amino]furo[2,3-d]pyrimidine-5-carboxamide;

N,6-dimethyl-4-[(1-methylcyclopropyl)amino]-N-[1-(propan-2-yl)-1H-pyrazol-4-yl]furo[2,3-d]pyrimidine-5-carboxamide;

6-methyl-4-[(1-methylcyclopropyl)amino]-N-[1-(pyridin-2-ylmethyl)-1H-pyrazol-4-yl]furo[2,3-d]pyrimidine-5-carboxamide;

6-methyl-4-[(1-methylcyclopropyl)amino]-N-[1-(pyrimidin-2-yl)-1H-pyrazol-4-yl]furo[2,3-d]pyrimidine-5-carboxamide;

6-methyl-4-[(1-methylcyclopropyl)amino]-N-[1-(pyridin-3-yl)-1H-pyrazol-4-yl]furo[2,3-d]pyrimidine-5-carboxamide;

6-methyl-4-[(1-methylcyclopropyl)amino]-N-[1-(pyridin-4-yl)-1H-pyrazol-4-yl]furo[2,3-d]pyrimidine-5-carboxamide;

N-(1-cyclopropyl-1H-pyrazol-4-yl)-6-methyl-4-[(1-methylcyclopropyl)amino]furo[2,3-d]pyrimidine-5-carboxamide;

6-methyl-4-[(1-methylcyclopropyl)amino]-N-[1-(pyridin-2-yl)piperidin-4-yl]furo[2,3-d]pyrimidine-5-carboxamide;

6-methyl-N-(2-methyl-1,3-benzoxazol-5-yl)-4-[(1-methylcyclopropyl)amino]furo[2,3-d]pyrimidine-5-carboxamide;

6-methyl-4-[(1-methylcyclopropyl)amino]-N-[4-(morpholin-4-yl)phenyl]furo[2,3-d]pyrimidine-5-carboxamide;

6-methyl-4-[(1-methylcyclopropyl)amino]-N-[6-(morpholin-4-yl)pyridazin-3-yl]furo[2,3-d]pyrimidine-5-carboxamide;

6-methyl-4-[(1-methylcyclopropyl)amino]-N-[2-(morpholin-4-yl)pyrimidin-5-yl]furo[2,3-d]pyrimidine-5-carboxamide;

6-methyl-4-[(1-methylcyclopropyl)amino]-N-[5-(morpholin-4-yl)pyrazin-2-yl]furo[2,3-d]pyrimidine-5-carboxamide;

6-methyl-4-[(1-methylcyclopropyl)amino]-N-[1-(pyrazin-2-yl)piperidin-4-yl]furo[2,3-d]pyrimidine-5-carboxamide;

6-methyl-4-[(1-methylcyclopropyl)amino]-N-[1-(pyrimidin-2-yl)piperidin-4-yl]furo[2,3-d]pyrimidine-5-carboxamide;

6-methyl-4-[(1-methylcyclopropyl)amino]-N-[1-(pyridin-2-yl)pyrrolidin-3-yl]furo[2,3-d]pyrimidine-5-carboxamide;

6-methyl-4-[(1-methylcyclopropyl)amino]-N-[1-(2-methylpyrimidin-4-yl)piperidin-4-yl]furo[2,3-d]pyrimidine-5-carboxamide;

6-methyl-4-[(1-methylcyclopropyl)amino]-N-[1-(6-methylpyrimidin-4-yl)piperidin-4-yl]furo[2,3-d]pyrimidine-5-carboxamide;

N-[1-(2,6-dimethylpyrimidin-4-yl)piperidin-4-yl]-6-methyl-4-[(1-methylcyclopropyl)amino]furo[2,3-d]pyrimidine-5-carboxamide;

6-methyl-4-[(1-methylcyclopropyl)amino]-N-[1-(pyrimidin-4-yl)azetidin-3-yl]furo[2,3-d]pyrimidine-5-carboxamide;

6-methyl-4-[(1-methylcyclopropyl)amino]-N-[4-(oxan-4-yl)phenyl]furo[2,3-d]pyrimidine-5-carboxamide;

6-methyl-4-[(1-methylcyclopropyl)amino]-N-[5-(oxan-4-yl)pyridin-2-yl]furo[2,3-d]pyrimidine-5-carboxamide;

6-methyl-4-[(1-methylcyclopropyl)amino]-N-[6-(oxan-4-yl)pyridin-3-yl]furo[2,3-d]pyrimidine-5-carboxamide;

6-methyl-4-[(1-methylcyclopropyl)amino]-N-[5-(oxan-4-yl)pyrazin-2-yl]furo[2,3-d]pyrimidine-5-carboxamide;

6-methyl-4-[(1-methylcyclopropyl)amino]-N-[6-(morpholin-4-yl)pyridin-3-yl]furo[2,3-d]pyrimidine-5-carboxamide;

6-methyl-4-[(1-methylcyclopropyl)amino]-N-(2-{8-oxa-3-azabicyclo[3.2.1]octan-3-yl}pyrimidin-5-yl)furo[2,3-d]pyrimidine-5-carboxamide;

N-[2-(3,3-dimethylmorpholin-4-yl)pyrimidin-5-yl]-6-methyl-4-[(1-methylcyclopropyl)amino]furo[2,3-d]pyrimidine-5-carboxamide;

N-{2-[(2R,6S)-2,6-dimethylmorpholin-4-yl]pyrimidin-5-yl}-6-methyl-4-[(1-methylcyclopropyl)amino]furo[2,3-d]pyrimidine-5-carboxamide;

6-methyl-4-[(1-methylcyclopropyl)amino]-N-(3-methyloxetan-3-yl)furo[2,3-d]pyrimidine-5-carboxamide;

6-methyl-4-[(1-methylcyclopropyl)amino]-N-(oxolan-3-yl)furo[2,3-d]pyrimidine-5-carboxamide;

6-methyl-4-[(1-methylcyclopropyl)amino]-N-(3-methyloxolan-3-yl)furo[2,3-d]pyrimidine-5-carboxamide;

6-methyl-4-[(1-methylcyclopropyl)amino]-N-(oxan-4-yl)furo[2,3-d]pyrimidine-5-carboxamide 6-methyl-4-[(1-methylcyclopropyl)amino]-N-(4-methyloxan-4-yl)furo[2,3-d]pyrimidine-5-carboxamide;

N-(2,2-dimethyloxan-4-yl)-6-methyl-4-[(1-methylcyclopropyl)amino]furo[2,3-d]pyrimidine-5-carboxamide;

6-methyl-4-[(1-methylcyclopropyl)amino]-N-[(1R,5S,6R)-3-oxabicyclo[3.1.0]hexan-6-yl]furo[2,3-d]pyrimidine-5-carboxamide;

N-(4-cyclopropyloxan-4-yl)-6-methyl-4-[(1-methylcyclopropyl)amino]furo[2,3-d]pyrimidine-5-carboxamide;

6-methyl-4-[(1-methylcyclopropyl)amino]-N-(3-phenyloxetan-3-yl)furo[2,3-d]pyrimidine-5-carboxamide;

N-(4-ethyloxan-4-yl)-6-methyl-4-[(1-methylcyclopropyl)amino]furo[2,3-d]pyrimidine-5-carboxamide;

6-methyl-N-(1-methyl-1H-pyrazol-4-yl)-4-[(1-methylcyclopropyl)amino]furo[2,3-d]pyrimidine-5-carboxamide;
6-methyl-N-(5-methyl-1,2-oxazol-3-yl)-4-[(1-methylcyclopropyl)amino]furo[2,3-d]pyrimidine-5-carboxamide;
6-methyl-4-[(1-methylcyclopropyl)amino]-N-(1,3-thiazol-2-yl)furo[2,3-d]pyrimidine-5-carboxamide;
N-(5-methoxypyridin-2-yl)-6-methyl-4-[(1-methylcyclopropyl)amino]furo[2,3-d]pyrimidine-5-carboxamide;
6-methyl-4-[(1-methylcyclopropyl)amino]-N-(2-methylphenyl)furo[2,3-d]pyrimidine-5-carboxamide;
6-methyl-4-[(1-methylcyclopropyl)amino]-N-(4-methylphenyl)furo[2,3-d]pyrimidine-5-carboxamide;
6-methyl-4-[(1-methylcyclopropyl)amino]-N-(3-methylphenyl)furo[2,3-d]pyrimidine-5-carboxamide;
6-methyl-4-[(1-methylcyclopropyl)amino]-N-(2-methylpyridin-3-yl)furo[2,3-d]pyrimidine-5-carboxamide;
N-(3-fluorophenyl)-6-methyl-4-[(1-methylcyclopropyl)amino]furo[2,3-d]pyrimidine-5-carboxamide;
N-(2-fluorophenyl)-6-methyl-4-[(1-methylcyclopropyl)amino]furo[2,3-d]pyrimidine-5-carboxamide;
6-methyl-4-[(1-methylcyclopropyl)amino]-N-(1-methylpiperidin-4-yl)furo[2,3-d]pyrimidine-5-carboxamide;
N-(2,5-dimethylphenyl)-6-methyl-4-[(1-methylcyclopropyl)amino]furo[2,3-d]pyrimidine-5-carboxamide;
6-methyl-4-[(1-methylcyclopropyl)amino]-N-phenylfuro[2,3-d]pyrimidine-5-carboxamide
N-(3-methoxyphenyl)-6-methyl-4-[(1-methylcyclopropyl)amino]furo[2,3-d]pyrimidine-5-carboxamide;
N-(3-fluoro-4-methylphenyl)-6-methyl-4-[(1-methylcyclopropyl)amino]furo[2,3-d]pyrimidine-5-carboxamide;
N-(3,4-difluorophenyl)-6-methyl-4-[(1-methylcyclopropyl)amino]furo[2,3-d]pyrimidine-5-carboxamide;
N-(3,5-difluorophenyl)-6-methyl-4-[(1-methylcyclopropyl)amino]furo[2,3-d]pyrimidine-5-carboxamide;
N-(2,3-dihydro-1H-inden-5-yl)-6-methyl-4-[(1-methylcyclopropyl)amino]furo[2,3-d]pyrimidine-5-carboxamide;
N-(2,3-dihydro-1H-inden-1-yl)-6-methyl-4-[(1-methylcyclopropyl)amino]furo[2,3-d]pyrimidine-5-carboxamide;
N-(2,3-dihydro-1H-inden-2-yl)-6-methyl-4-[(1-methylcyclopropyl)amino]furo[2,3-d]pyrimidine-5-carboxamide;
N-(2,3-dihydro-1H-inden-4-yl)-6-methyl-4-[(1-methylcyclopropyl)amino]furo[2,3-d]pyrimidine-5-carboxamide;
6-methyl-4-[(1-methylcyclopropyl)amino]-N-[4-(propan-2-yl)phenyl]furo[2,3-d]pyrimidine-5-carboxamide;
N-(2H-1,3-benzodioxol-5-yl)-6-methyl-4-[(1-methylcyclopropyl)amino]furo[2,3-d]pyrimidine-5-carboxamide;
N-(4-methoxy-2-methylphenyl)-6-methyl-4-[(1-methylcyclopropyl)amino]furo[2,3-d]pyrimidine-5-carboxamide;
N-(3-methoxy-2-methylphenyl)-6-methyl-4-[(1-methylcyclopropyl)amino]furo[2,3-d]pyrimidine-5-carboxamide;
N-(5-fluoro-2-methoxyphenyl)-6-methyl-4-[(1-methylcyclopropyl)amino]furo[2,3-d]pyrimidine-5-carboxamide;
N-(4-fluoro-3-methoxyphenyl)-6-methyl-4-[(1-methylcyclopropyl)amino]furo[2,3-d]pyrimidine-5-carboxamide;
N-(2-chloro-4-methylphenyl)-6-methyl-4-[(1-methylcyclopropyl)amino]furo[2,3-d]pyrimidine-5-carboxamide;
N-(2-chloro-5-methylphenyl)-6-methyl-4-[(1-methylcyclopropyl)amino]furo[2,3-d]pyrimidine-5-carboxamide;
N-(4-chloro-2-fluorophenyl)-6-methyl-4-[(1-methylcyclopropyl)amino]furo[2,3-d]pyrimidine-5-carboxamide;
6-methyl-N-(1-methyl-1H-indazol-5-yl)-4-[(1-methylcyclopropyl)amino]furo[2,3-d]pyrimidine-5-carboxamide;
N-(1,3-benzothiazol-5-yl)-6-methyl-4-[(1-methylcyclopropyl)amino]furo[2,3-d]pyrimidine-5-carboxamide;
N-(1,3-benzothiazol-6-yl)-6-methyl-4-[(1-methylcyclopropyl)amino]furo[2,3-d]pyrimidine-5-carboxamide;
N-(2,2-dimethyloxan-4-yl)-N-ethyl-6-methyl-4-[(1-methylcyclopropyl)amino]furo[2,3-d]pyrimidine-5-carboxamide;
N-[3-methoxy-5-(trifluoromethyl)phenyl]-6-methyl-4-[(1-methylcyclopropyl)amino]furo[2,3-d]pyrimidine-5-carboxamide;
N-(adamantan-1-yl)-6-methyl-4-[(1-methylcyclopropyl)amino]furo[2,3-d]pyrimidine-5-carboxamide;
6-methyl-4-[(1-methylcyclopropyl)amino]-N-(6-methylpyridin-3-yl)furo[2,3-d]pyrimidine-5-carboxamide;
N-(adamantan-2-yl)-6-methyl-4-[(1-methylcyclopropyl)amino]furo[2,3-d]pyrimidine-5-carboxamide;
N-{5H,6H,7H-cyclopenta[b]pyridin-7-yl}-6-methyl-4-[(1-methylcyclopropyl)amino]furo[2,3-d]pyrimidine-5-carboxamide;
N-[1-(fluoromethyl)cyclopropyl]-6-methyl-4-[(1-methylcyclopropyl)amino]furo[2,3-d]pyrimidine-5-carboxamide;
N-[1-(4-fluorophenyl)cyclopropyl]-6-methyl-4-[(1-methylcyclopropyl)amino]furo[2,3-d]pyrimidine-5-carboxamide;
6-methyl-4-[(1-methylcyclopropyl)amino]-N-[1-(pyridin-2-yl)cyclopropyl]furo[2,3-d]pyrimidine-5-carboxamide;
6-methyl-4-[(1-methylcyclopropyl)amino]-N-[1-(trifluoromethyl)cyclopropyl]furo[2,3-d]pyrimidine-5-carboxamide;
6-methyl-N-(1-methylcyclopropyl)-4-[(1-methylcyclopropyl)amino]furo[2,3-d]pyrimidine-5-carboxamide;
6-methyl-N-(1-methylcyclobutyl)-4-[(1-methylcyclopropyl)amino]furo[2,3-d]pyrimidine-5-carboxamide;
N-cyclopropyl-6-methyl-4-[(1-methylcyclopropyl)amino]furo[2,3-d]pyrimidine-5-carboxamide;
6-methyl-4-[(1-methylcyclopropyl)amino]-N-[(1R,3R)-3-fluorocyclobutyl]furo[2,3-d]pyrimidine-5-carboxamide;
6-methyl-4-[(1-methylcyclopropyl)amino]-N-[(1S,3S)-3-fluorocyclobutyl]furo[2,3-d]pyrimidine-5-carboxamide;
N-(3,3-difluorocyclobutyl)-6-methyl-4-[(1-methylcyclopropyl)amino]furo[2,3-d]pyrimidine-5-carboxamide;
N-(1-ethylcyclopropyl)-6-methyl-4-[(1-methylcyclopropyl)amino]furo[2,3-d]pyrimidine-5-carboxamide;
N-[1-(hydroxymethyl)cyclopropyl]-6-methyl-4-[(1-methylcyclopropyl)amino]furo[2,3-d]pyrimidine-5-carboxamide;
6-methyl-4-[(1-methylcyclopropyl)amino]-N-[1-(propan-2-yl)cyclopropyl]furo[2,3-d]pyrimidine-5-carboxamide;

N-[1-(methoxymethyl)cyclopropyl]-6-methyl-4-[(1-methylcyclopropyl)amino]furo[2,3-d]pyrimidine-5-carboxamide;
N-(1-cyclopropylcyclopropyl)-6-methyl-4-[(1-methylcyclopropyl)amino]furo[2,3-d]pyrimidine-5-carboxamide;
N-(1-cyclobutylcyclopropyl)-6-methyl-4-[(1-methylcyclopropyl)amino]furo[2,3-d]pyrimidine-5-carboxamide;
N-[3-(4-fluorophenyl)cyclobutyl]-6-methyl-4-[(1-methylcyclopropyl)amino]furo[2,3-d]pyrimidine-5-carboxamide;
N-cyclopentyl-6-methyl-4-[(1-methylcyclopropyl)amino]furo[2,3-d]pyrimidine-5-carboxamide;
N-cyclobutyl-6-methyl-4-[(1-methylcyclopropyl)amino]furo[2,3-d]pyrimidine-5-carboxamide;
N-[1-(5-fluoropyridin-2-yl)cyclopropyl]-6-methyl-4-[(1-methylcyclopropyl)amino]furo[2,3-d]pyrimidine-5-carboxamide;
N-[1-(2-hydroxyethyl)cyclopropyl]-6-methyl-4-[(1-methylcyclopropyl)amino]furo[2,3-d]pyrimidine-5-carboxamide;
N-[1-(3-fluoro-4-methoxyphenyl)cyclopropyl]-6-methyl-4-[(1-methylcyclopropyl)amino]furo[2,3-d]pyrimidine-5-carboxamide;
6-methyl-4-[(1-methylcyclopropyl)amino]-N-[1-(oxan-4-yl)cyclopropyl]furo[2,3-d]pyrimidine-5-carboxamide;
6-methyl-4-[(1-methylcyclopropyl)amino]-N-[1-(pyrazin-2-yl)cyclopropyl]furo[2,3-d]pyrimidine-5-carboxamide;
6-methyl-4-[(1-methylcyclopropyl)amino]-N-[1-(pyrimidin-2-yl)cyclopropyl]furo[2,3-d]pyrimidine-5-carboxamide;
N-[1-(hydroxymethyl)cyclobutyl]-6-methyl-4-[(1-methylcyclopropyl)amino]furo[2,3-d]pyrimidine-5-carboxamide;
N-{bicyclo[1.1.1]pentan-1-yl}-6-methyl-4-[(1-methylcyclopropyl)amino]furo[2,3-d]pyrimidine-5-carboxamide;
N-{1-[(4-methoxyphenyl)methyl]cyclopropyl}-6-methyl-4-[(1-methylcyclopropyl)amino]furo[2,3-d]pyrimidine-5-carboxamide;
N-[(5-chloropyrazin-2-yl)methyl]-6-methyl-4-[(1-methylcyclopropyl)amino]furo[2,3-d]pyrimidine-5-carboxamide;
N-[(5-fluoropyrazin-2-yl)methyl]-6-methyl-4-[(1-methylcyclopropyl)amino]furo[2,3-d]pyrimidine-5-carboxamide;
N-[(5-hydroxypyridin-2-yl)methyl]-6-methyl-4-[(1-methylcyclopropyl)amino]furo[2,3-d]pyrimidine-5-carboxamide;
N-{[5-(fluoromethoxy)pyridin-2-yl]methyl}-6-methyl-4-[(1-methylcyclopropyl)amino]furo[2,3-d]pyrimidine-5-carboxamide;
N-cyclopropyl-N-[(6-methoxypyrimidin-4-yl)methyl]-6-methyl-4-[(1-methylcyclopropyl)amino]furo[2,3-d]pyrimidine-5-carboxamide;
N-[(4-fluorophenyl)methyl]-6-methyl-4-[(1-methylcyclopropyl)amino]furo[2,3-d]pyrimidine-5-carboxamide;
N-[(5-fluoropyridin-2-yl)methyl]-6-methyl-4-[(1-methylcyclopropyl)amino]furo[2,3-d]pyrimidine-5-carboxamide;
N-[(4-cyanophenyl)methyl]-6-methyl-4-[(1-methylcyclopropyl)amino]furo[2,3-d]pyrimidine-5-carboxamide;
N-[(6-methoxypyridin-2-yl)methyl]-6-methyl-4-[(1-methylcyclopropyl)amino]furo[2,3-d]pyrimidine-5-carboxamide;
N-[(6-methoxypyridin-3-yl)methyl]-6-methyl-4-[(1-methylcyclopropyl)amino]furo[2,3-d]pyrimidine-5-carboxamide;
N-[(5-methoxypyridin-2-yl)methyl]-6-methyl-4-[(1-methylcyclopropyl)amino]furo[2,3-d]pyrimidine-5-carboxamide;
N-{[5-(difluoromethoxy)pyridin-2-yl]methyl}-6-methyl-4-[(1-methylcyclopropyl)amino]furo[2,3-d]pyrimidine-5-carboxamide;
N-[(3-cyanophenyl)methyl]-6-methyl-4-[(1-methylcyclopropyl)amino]furo[2,3-d]pyrimidine-5-carboxamide;
6-methyl-4-[(1-methylcyclopropyl)amino]-N-(1,3-thiazol-2-ylmethyl)furo[2,3-d]pyrimidine-5-carboxamide;
6-methyl-4-[(1-methylcyclopropyl)amino]-N-(1,3-thiazol-5-ylmethyl)furo[2,3-d]pyrimidine-5-carboxamide;
6-methyl-4-[(1-methylcyclopropyl)amino]-N-(1,3-thiazol-4-ylmethyl)furo[2,3-d]pyrimidine-5-carboxamide;
6-methyl-4-[(1-methylcyclopropyl)amino]-N-(pyridin-2-ylmethyl)furo[2,3-d]pyrimidine-5-carboxamide;
N-ethyl-6-methyl-4-[(1-methylcyclopropyl)amino]furo[2,3-d]pyrimidine-5-carboxamide;
N-[(4-cyano-3-fluorophenyl)methyl]-6-methyl-4-[(1-methylcyclopropyl)amino]furo[2,3-d]pyrimidine-5-carboxamide;
N-[(3-cyano-4-fluorophenyl)methyl]-6-methyl-4-[(1-methylcyclopropyl)amino]furo[2,3-d]pyrimidine-5-carboxamide;
6-methyl-4-[(1-methylcyclopropyl)amino]-N-(oxetan-3-ylmethyl)furo[2,3-d]pyrimidine-5-carboxamide;
6-methyl-4-[(1-methylcyclopropyl)amino]-N-(1,2-oxazol-3-ylmethyl)furo[2,3-d]pyrimidine-5-carboxamide;
6-methyl-4-[(1-methylcyclopropyl)amino]-N-[(3-methyloxetan-3-yl)methyl]furo[2,3-d]pyrimidine-5-carboxamide;
N-[(3-fluorooxetan-3-yl)methyl]-6-methyl-4-[(1-methylcyclopropyl)amino]furo[2,3-d]pyrimidine-5-carboxamide;
6-methyl-N-[(2-methyl-1,3-thiazol-4-yl)methyl]-4-[(1-methylcyclopropyl)amino]furo[2,3-d]pyrimidine-5-carboxamide;
6-methyl-4-[(1-methylcyclopropyl)amino]-N-(1H-pyrrol-2-ylmethyl)furo[2,3-d]pyrimidine-5-carboxamide;
6-methyl-N-[(1-methyl-1H-pyrazol-3-yl)methyl]-4-[(1-methylcyclopropyl)amino]furo[2,3-d]pyrimidine-5-carboxamide;
6-methyl-4-[(1-methylcyclopropyl)amino]-N-(1,3-oxazol-4-ylmethyl)furo[2,3-d]pyrimidine-5-carboxamide;
6-methyl-N-[(1-methyl-1H-pyrazol-5-yl)methyl]-4-[(1-methylcyclopropyl)amino]furo[2,3-d]pyrimidine-5-carboxamide;
6-methyl-N-[(1-methyl-1H-pyrrol-2-yl)methyl]-4-[(1-methylcyclopropyl)amino]furo[2,3-d]pyrimidine-5-carboxamide;
N-[(dimethyl-1,3-oxazol-4-yl)methyl]-6-methyl-4-[(1-methylcyclopropyl)amino]furo[2,3-d]pyrimidine-5-carboxamide;
6-methyl-N-[(5-methyl-1,2-oxazol-3-yl)methyl]-4-[(1-methylcyclopropyl)amino]furo[2,3-d]pyrimidine-5-carboxamide;

6-methyl-N-[(1-methyl-1H-imidazol-5-yl)methyl]-4-[(1-methylcyclopropyl)amino]furo[2,3-d]pyrimidine-5-carboxamide;

6-methyl-N-[(1-methyl-1H-imidazol-4-yl)methyl]-4-[(1-methylcyclopropyl)amino]furo[2,3-d]pyrimidine-5-carboxamide;

6-methyl-4-[(1-methylcyclopropyl)amino]-N-(oxan-4-ylmethyl)furo[2,3-d]pyrimidine-5-carboxamide;

N-[(3-fluoropyridin-4-yl)methyl]-6-methyl-4-[(1-methylcyclopropyl)amino]furo[2,3-d]pyrimidine-5-carboxamide;

N-[(2-fluoropyridin-4-yl)methyl]-6-methyl-4-[(1-methylcyclopropyl)amino]furo[2,3-d]pyrimidine-5-carboxamide;

6-methyl-4-[(1-methylcyclopropyl)amino]-N-(oxolan-2-ylmethyl)furo[2,3-d]pyrimidine-5-carboxamide;

N-benzyl-6-methyl-4-[(1-methylcyclopropyl)amino]furo[2,3-d]pyrimidine-5-carboxamide 6-methyl-4-[(1-methylcyclopropyl)amino]-N-{[4-(morpholin-4-yl)phenyl]methyl}furo[2,3-d]pyrimidine-5-carboxamide;

N-[(2,3-difluoro-4-methoxyphenyl)methyl]-6-methyl-4-[(1-methylcyclopropyl)amino]furo[2,3-d]pyrimidine-5-carboxamide;

6-methyl-4-[(1-methylcyclopropyl)amino]-N-(thiophen-2-ylmethyl)furo[2,3-d]pyrimidine-5-carboxamide;

6-methyl-4-[(1-methylcyclopropyl)amino]-N-(thiophen-3-ylmethyl)furo[2,3-d]pyrimidine-5-carboxamide;

N-(cyclohexylmethyl)-6-methyl-4-[(1-methylcyclopropyl)amino]furo[2,3-d]pyrimidine-5-carboxamide;

6-methyl-4-[(1-methylcyclopropyl)amino]-N-[(4-methylphenyl)methyl]furo[2,3-d]pyrimidine-5-carboxamide;

6-methyl-4-[(1-methylcyclopropyl)amino]-N-[(3-methylphenyl)methyl]furo[2,3-d]pyrimidine-5-carboxamide;

N-[(3-methoxyphenyl)methyl]-N,6-dimethyl-4-[(1-methylcyclopropyl)amino]furo[2,3-d]pyrimidine-5-carboxamide;

N,6-dimethyl-4-[(1-methylcyclopropyl)amino]-N-(pyridin-2-ylmethyl)furo[2,3-d]pyrimidine-5-carboxamide;

N,6-dimethyl-4-[(1-methylcyclopropyl)amino]-N-(pyridin-3-ylmethyl)furo[2,3-d]pyrimidine-5-carboxamide;

N-[(3-fluorophenyl)methyl]-6-methyl-4-[(1-methylcyclopropyl)amino]furo[2,3-d]pyrimidine-5-carboxamide;

N-[(2-fluorophenyl)methyl]-6-methyl-4-[(1-methylcyclopropyl)amino]furo[2,3-d]pyrimidine-5-carboxamide;

N,6-dimethyl-4-[(1-methylcyclopropyl)amino]-N-(thiophen-3-ylmethyl)furo[2,3-d]pyrimidine-5-carboxamide;

N,6-dimethyl-4-[(1-methylcyclopropyl)amino]-N-(thiophen-2-ylmethyl)furo[2,3-d]pyrimidine-5-carboxamide;

N-[(3,4-dimethylphenyl)methyl]-6-methyl-4-[(1-methylcyclopropyl)amino]furo[2,3-d]pyrimidine-5-carboxamide;

N-[(2,3-dimethylphenyl)methyl]-6-methyl-4-[(1-methylcyclopropyl)amino]furo[2,3-d]pyrimidine-5-carboxamide;

N-benzyl-N-ethyl-6-methyl-4-[(1-methylcyclopropyl)amino]furo[2,3-d]pyrimidine-5-carboxamide;

N-[(3-methoxyphenyl)methyl]-6-methyl-4-[(1-methylcyclopropyl)amino]furo[2,3-d]pyrimidine-5-carboxamide;

N-[(4-fluorophenyl)methyl]-N,6-dimethyl-4-[(1-methylcyclopropyl)amino]furo[2,3-d]pyrimidine-5-carboxamide;

N-[(2-fluorophenyl)methyl]-N,6-dimethyl-4-[(1-methylcyclopropyl)amino]furo[2,3-d]pyrimidine-5-carboxamide;

N-[(3-fluorophenyl)methyl]-N,6-dimethyl-4-[(1-methylcyclopropyl)amino]furo[2,3-d]pyrimidine-5-carboxamide;

N-[(3-ethyl-1,2-oxazol-5-yl)methyl]-N,6-dimethyl-4-[(1-methylcyclopropyl)amino]furo[2,3-d]pyrimidine-5-carboxamide;

N-[(2-chlorophenyl)methyl]-6-methyl-4-[(1-methylcyclopropyl)amino]furo[2,3-d]pyrimidine-5-carboxamide;

N-[(5-cyclopropyl-1H-pyrazol-3-yl)methyl]-N,6-dimethyl-4-[(1-methylcyclopropyl)amino]furo[2,3-d]pyrimidine-5-carboxamide;

N-{[4-(difluoromethoxy)phenyl]methyl}-6-methyl-4-[(1-methylcyclopropyl)amino]furo[2,3-d]pyrimidine-5-carboxamide;

N-[(6-fluoropyridin-2-yl)methyl]-6-methyl-4-[(1-methylcyclopropyl)amino]furo[2,3-d]pyrimidine-5-carboxamide;

N-[(2-fluoropyridin-3-yl)methyl]-6-methyl-4-[(1-methylcyclopropyl)amino]furo[2,3-d]pyrimidine-5-carboxamide;

N-[(5-fluoropyrimidin-2-yl)methyl]-6-methyl-4-[(1-methylcyclopropyl)amino]furo[2,3-d]pyrimidine-5-carboxamide;

N-[(6-fluoropyridin-3-yl)methyl]-6-methyl-4-[(1-methylcyclopropyl)amino]furo[2,3-d]pyrimidine-5-carboxamide;

N-[(6-chloropyridin-3-yl)methyl]-6-methyl-4-[(1-methylcyclopropyl)amino]furo[2,3-d]pyrimidine-5-carboxamide;

N-[(2-chloropyrimidin-5-yl)methyl]-6-methyl-4-[(1-methylcyclopropyl)amino]furo[2,3-d]pyrimidine-5-carboxamide;

N-[(3-bromo-1,2-oxazol-5-yl)methyl]-6-methyl-4-[(1-methylcyclopropyl)amino]furo[2,3-d]pyrimidine-5-carboxamide;

6-methyl-N-[(3-methyl-1,2-oxazol-5-yl)methyl]-4-[(1-methylcyclopropyl)amino]furo[2,3-d]pyrimidine-5-carboxamide;

N-[(5-ethyl-1,2-oxazol-3-yl)methyl]-6-methyl-4-[(1-methylcyclopropyl)amino]furo[2,3-d]pyrimidine-5-carboxamide;

N-[(5-cyclopropyl-1,2-oxazol-3-yl)methyl]-6-methyl-4-[(1-methylcyclopropyl)amino]furo[2,3-d]pyrimidine-5-carboxamide;

6-methyl-4-[(1-methylcyclopropyl)amino]-N-{[5-(propan-2-yl)-1,2-oxazol-3-yl]methyl}furo[2,3-d]pyrimidine-5-carboxamide;

N-{[5-(4-fluorophenyl)-1,2-oxazol-3-yl]methyl}-6-methyl-4-[(1-methylcyclopropyl)amino]furo[2,3-d]pyrimidine-5-carboxamide;

N-{[5-(4-methoxyphenyl)-1,2-oxazol-3-yl]methyl}-6-methyl-4-[(1-methylcyclopropyl)amino]furo[2,3-d]pyrimidine-5-carboxamide;

3-[({6-methyl-4-[(1-methylcyclopropyl)amino]furo[2,3-d]pyrimidin-5-yl}formamido)methyl]-1,2-oxazole-5-carboxamide;

N-[(4-fluoro-3-methoxyphenyl)methyl]-6-methyl-4-[(1-methylcyclopropyl)amino]furo[2,3-d]pyrimidine-5-carboxamide;

N-[(4-fluoro-3-nitrophenyl)methyl]-6-methyl-4-[(1-methylcyclopropyl)amino]furo[2,3-d]pyrimidine-5-carboxamide;

N-[(4-cyano-2-fluorophenyl)methyl]-6-methyl-4-[(1-methylcyclopropyl)amino]furo[2,3-d]pyrimidine-5-carboxamide;

6-methyl-N-{[5-(1-methyl-1H-pyrazol-4-yl)-1,2-oxazol-3-yl]methyl}-4-[(1-methylcyclopropyl)amino]furo[2,3-d]pyrimidine-5-carboxamide;

6-methyl-N-[(5-methyl-1,3-oxazol-2-yl)methyl]-4-[(1-methylcyclopropyl)amino]furo[2,3-d]pyrimidine-5-carboxamide;

N-[(2-methoxypyrimidin-4-yl)methyl]-6-methyl-4-[(1-methylcyclopropyl)amino]furo[2,3-d]pyrimidine-5-carboxamide;

6-methyl-4-[(1-methylcyclopropyl)amino]-N-{[5-(trifluoromethyl)pyridin-2-yl]methyl}furo[2,3-d]pyrimidine-5-carboxamide;

6-methyl-4-[(1-methylcyclopropyl)amino]-N-{[5-(trifluoromethyl)-1,2,4-oxadiazol-3-yl]methyl}furo[2,3-d]pyrimidine-5-carboxamide;

6-methyl-4-[(1-methylcyclopropyl)amino]-N-[(4-methylpyrimidin-2-yl)methyl]furo[2,3-d]pyrimidine-5-carboxamide;

N-[(4,6-dimethylpyrimidin-2-yl)methyl]-6-methyl-4-[(1-methylcyclopropyl)amino]furo[2,3-d]pyrimidine-5-carboxamide;

6-methyl-4-[(1-methylcyclopropyl)amino]-N-[(5-methylpyrazin-2-yl)methyl]furo[2,3-d]pyrimidine-5-carboxamide;

6-methyl-N-[(5-methyl-1,2,4-oxadiazol-3-yl)methyl]-4-[(1-methylcyclopropyl)amino]furo[2,3-d]pyrimidine-5-carboxamide;

6-methyl-4-[(1-methylcyclopropyl)amino]-N-{[6-(trifluoromethyl)-[1,2,4]triazolo[4,3-a]pyridin-3-yl]methyl}furo[2,3-d]pyrimidine-5-carboxamide;

N-[(5-cyclopropyl-1,2,4-oxadiazol-3-yl)methyl]-6-methyl-4-[(1-methylcyclopropyl)amino]furo[2,3-d]pyrimidine-5-carboxamide;

6-methyl-4-[(1-methylcyclopropyl)amino]-N-[(4-methylpyridin-2-yl)methyl]furo[2,3-d]pyrimidine-5-carboxamide;

6-methyl-N-[(5-methyl-1,3-thiazol-2-yl)methyl]-4-[(1-methylcyclopropyl)amino]furo[2,3-d]pyrimidine-5-carboxamide;

6-methyl-N-[(5-methyl-1,3,4-thiadiazol-2-yl)methyl]-4-[(1-methylcyclopropyl)amino]furo[2,3-d]pyrimidine-5-carboxamide;

N-[(4-fluorophenyl)methyl]-N-(3-methoxypropyl)-6-methyl-4-[(1-methylcyclopropyl)amino]furo[2,3-d]pyrimidine-5-carboxamide;

N-[(3-fluoro-4-methoxyphenyl)methyl]-6-methyl-4-[(1-methylcyclopropyl)amino]furo[2,3-d]pyrimidine-5-carboxamide;

N-[(4-hydroxy-3-methoxyphenyl)methyl]-6-methyl-4-[(1-methylcyclopropyl)amino]furo[2,3-d]pyrimidine-5-carboxamide;

N-[(3-chloro-4-methoxyphenyl)methyl]-6-methyl-4-[(1-methylcyclopropyl)amino]furo[2,3-d]pyrimidine-5-carboxamide;

N-ethyl-N-[(4-methoxyphenyl)methyl]-6-methyl-4-[(1-methylcyclopropyl)amino]furo[2,3-d]pyrimidine-5-carboxamide;

N-{[3-(4-fluorophenyl)-1,2-oxazol-5-yl]methyl}-6-methyl-4-[(1-methylcyclopropyl)amino]furo[2,3-d]pyrimidine-5-carboxamide;

N-[(7-methoxy-2,3-dihydro-1,4-benzodioxin-6-yl)methyl]-6-methyl-4-[(1-methylcyclopropyl)amino]furo[2,3-d]pyrimidine-5-carboxamide;

N-{[3-(2-fluorophenyl)-1,2-oxazol-5-yl]methyl}-6-methyl-4-[(1-methylcyclopropyl)amino]furo[2,3-d]pyrimidine-5-carboxamide;

N-[(3,5-dimethoxyphenyl)methyl]-6-methyl-4-[(1-methylcyclopropyl)amino]furo[2,3-d]pyrimidine-5-carboxamide;

N-[(4-methoxy-3,5-dimethylpyridin-2-yl)methyl]-N,6-dimethyl-4-[(1-methylcyclopropyl)amino]furo[2,3-d]pyrimidine-5-carboxamide;

N-[(2-fluoro-6-methylphenyl)methyl]-6-methyl-4-[(1-methylcyclopropyl)amino]furo[2,3-d]pyrimidine-5-carboxamide;

N-[(2-chloro-3-fluorophenyl)methyl]-6-methyl-4-[(1-methylcyclopropyl)amino]furo[2,3-d]pyrimidine-5-carboxamide;

N-[(2,6-difluorophenyl)methyl]-6-methyl-4-[(1-methylcyclopropyl)amino]furo[2,3-d]pyrimidine-5-carboxamide;

N-[(2,4-difluorophenyl)methyl]-6-methyl-4-[(1-methylcyclopropyl)amino]furo[2,3-d]pyrimidine-5-carboxamide;

N-[(3,4-difluorophenyl)methyl]-6-methyl-4-[(1-methylcyclopropyl)amino]furo[2,3-d]pyrimidine-5-carboxamide;

N-[(2-chloro-4-fluorophenyl)methyl]-6-methyl-4-[(1-methylcyclopropyl)amino]furo[2,3-d]pyrimidine-5-carboxamide;

N-[(4-methoxyphenyl)methyl]-6-methyl-4-[(1-methylcyclopropyl)amino]-N-(prop-2-en-1-yl)furo[2,3-d]pyrimidine-5-carboxamide;

N-[(4-ethoxy-3-methoxyphenyl)methyl]-6-methyl-4-[(1-methylcyclopropyl)amino]furo[2,3-d]pyrimidine-5-carboxamide;

N-[2-(5-fluoro-2-methyl-1H-indol-3-yl)ethyl]-6-methyl-4-[(1-methylcyclopropyl)amino]furo[2,3-d]pyrimidine-5-carboxamide;

N-[(6-chloro-2-fluoro-3-methoxyphenyl)methyl]-6-methyl-4-[(1-methylcyclopropyl)amino]furo[2,3-d]pyrimidine-5-carboxamide;

N-[(4-methoxy-2-methylphenyl)methyl]-6-methyl-4-[(1-methylcyclopropyl)amino]furo[2,3-d]pyrimidine-5-carboxamide;

N-[(4-fluoro-2-methoxyphenyl)methyl]-6-methyl-4-[(1-methylcyclopropyl)amino]furo[2,3-d]pyrimidine-5-carboxamide;

N-[(3-chloro-5-fluorophenyl)methyl]-6-methyl-4-[(1-methylcyclopropyl)amino]furo[2,3-d]pyrimidine-5-carboxamide;

N-[(2-methoxyphenyl)methyl]-N,6-dimethyl-4-[(1-methylcyclopropyl)amino]furo[2,3-d]pyrimidine-5-carboxamide;

N-[(5-cyano-2-fluorophenyl)methyl]-6-methyl-4-[(1-methylcyclopropyl)amino]furo[2,3-d]pyrimidine-5-carboxamide;

N-[(4-chloro-2-fluorophenyl)methyl]-6-methyl-4-[(1-methylcyclopropyl)amino]furo[2,3-d]pyrimidine-5-carboxamide;

N-[2-(3-ethoxy-4-methoxyphenyl)ethyl]-6-methyl-4-[(1-methylcyclopropyl)amino]furo[2,3-d]pyrimidine-5-carboxamide;

N-[2-(3,5-difluorophenyl)ethyl]-6-methyl-4-[(1-methylcyclopropyl)amino]furo[2,3-d]pyrimidine-5-carboxamide;

N-[2-(5-chloro-2-fluorophenyl)ethyl]-6-methyl-4-[(1-methylcyclopropyl)amino]furo[2,3-d]pyrimidine-5-carboxamide;
N-[2-(2,5-dimethoxyphenyl)ethyl]-6-methyl-4-[(1-methylcyclopropyl)amino]furo[2,3-d]pyrimidine-5-carboxamide;
N-[2-(2,3-dimethoxyphenyl)ethyl]-6-methyl-4-[(1-methylcyclopropyl)amino]furo[2,3-d]pyrimidine-5-carboxamide;
N-[2-(3-chloro-4-fluorophenyl)ethyl]-6-methyl-4-[(1-methylcyclopropyl)amino]furo[2,3-d]pyrimidine-5-carboxamide;
N-[2-(3,4-dimethoxyphenyl)ethyl]-6-methyl-4-[(1-methylcyclopropyl)amino]furo[2,3-d]pyrimidine-5-carboxamide;
N-[(2-fluoro-6-methoxyphenyl)methyl]-6-methyl-4-[(1-methylcyclopropyl)amino]furo[2,3-d]pyrimidine-5-carboxamide;
N-[(5-chloro-2 4-difluorophenyl)methyl]-6-methyl-4-[(1-methylcyclopropyl)amino]furo[2,3-d]pyrimidine-5-carboxamide;
N-[(2-fluoro-3-methylphenyl)methyl]-6-methyl-4-[(1-methylcyclopropyl)amino]furo[2,3-d]pyrimidine-5-carboxamide;
N-[(2-chloro-4-methoxyphenyl)methyl]-6-methyl-4-[(1-methylcyclopropyl)amino]furo[2,3-d]pyrimidine-5-carboxamide;
N-[(2-ethoxy-6-fluorophenyl)methyl]-6-methyl-4-[(1-methylcyclopropyl)amino]furo[2,3-d]pyrimidine-5-carboxamide;
N-[(4-fluoro-3-methylphenyl)methyl]-6-methyl-4-[(1-methylcyclopropyl)amino]furo[2,3-d]pyrimidine-5-carboxamide;
N-[(5-fluoro-2-methylphenyl)methyl]-6-methyl-4-[(1-methylcyclopropyl)amino]furo[2,3-d]pyrimidine-5-carboxamide;
N-[(5-chloro-2-fluorophenyl)methyl]-6-methyl-4-[(1-methylcyclopropyl)amino]furo[2,3-d]pyrimidine-5-carboxamide;
N-[(3-fluoro-4-methylphenyl)methyl]-6-methyl-4-[(1-methylcyclopropyl)amino]furo[2,3-d]pyrimidine-5-carboxamide;
6-methyl-4-[(1-methylcyclopropyl)amino]-N-[(3,4,5-trifluorophenyl)methyl]furo[2,3-d]pyrimidine-5-carboxamide;
N-[(3-chloro-2-fluorophenyl)methyl]-6-methyl-4-[(1-methylcyclopropyl)amino]furo[2,3-d]pyrimidine-5-carboxamide;
N-[3-(5-fluoro-1H-1,3-benzodiazol-2-yl)propyl]-6-methyl-4-[(1-methylcyclopropyl)amino]furo[2,3-d]pyrimidine-5-carboxamide;
N-[(5-fluoro-1H-indol-2-yl)methyl]-N,6-dimethyl-4-[(1-methylcyclopropyl)amino]furo[2,3-d]pyrimidine-5-carboxamide;
N-[(5-methoxy-1H-indol-2-yl)methyl]-6-methyl-4-[(1-methylcyclopropyl)amino]furo[2,3-d]pyrimidine-5-carboxamide;
N-{[1-(4-fluorophenyl)-1H-pyrazol-4-yl]methyl}-6-methyl-4-[(1-methylcyclopropyl)amino]furo[2,3-d]pyrimidine-5-carboxamide;
N-{[1-(3-fluorophenyl)-1H-pyrazol-4-yl]methyl}-6-methyl-4-[(1-methylcyclopropyl)amino]furo[2,3-d]pyrimidine-5-carboxamide;
N-(3-hydroxypropyl)-N-[(4-methoxyphenyl)methyl]-6-methyl-4-[(1-methylcyclopropyl)amino]furo[2,3-d]pyrimidine-5-carboxamide;
N-[(4-fluorophenyl)methyl]-N-(3-hydroxypropyl)-6-methyl-4-[(1-methylcyclopropyl)amino]furo[2,3-d]pyrimidine-5-carboxamide;
N-[(6-fluoro-1H-1,3-benzodiazol-2-yl)methyl]-N,6-dimethyl-4-[(1-methylcyclopropyl)amino]furo[2,3-d]pyrimidine-5-carboxamide;
N-(2-hydroxyethyl)-N-[(2-methoxyphenyl)methyl]-6-methyl-4-[(1-methylcyclopropyl)amino]furo[2,3-d]pyrimidine-5-carboxamide;
N-(2-methoxyethyl)-N-[(2-methoxyphenyl)methyl]-6-methyl-4-[(1-methylcyclopropyl)amino]furo[2,3-d]pyrimidine-5-carboxamide;
N-(2-methoxyethyl)-N-[(3-methoxyphenyl)methyl]-6-methyl-4-[(1-methylcyclopropyl)amino]furo[2,3-d]pyrimidine-5-carboxamide;
N-{[3-(4-fluorophenyl)-1H-pyrazol-4-yl]methyl}-6-methyl-4-[(1-methylcyclopropyl)amino]furo[2,3-d]pyrimidine-5-carboxamide;
N-[2-(5-fluoro-1H-1,3-benzodiazol-2-yl)ethyl]-N,6-dimethyl-4-[(1-methylcyclopropyl)amino]furo[2,3-d]pyrimidine-5-carboxamide;
N-[(7-fluoro-2-oxo-1,2-dihydroquinolin-3-yl)methyl]-6-methyl-4-[(1-methylcyclopropyl)amino]furo[2,3-d]pyrimidine-5-carboxamide;
N-{[1-(4-fluorophenyl)pyrrolidin-3-yl]methyl}-6-methyl-4-[(1-methylcyclopropyl)amino]furo[2,3-d]pyrimidine-5-carboxamide;
N-ethyl-N-[(2-methoxyphenyl)methyl]-6-methyl-4-[(1-methylcyclopropyl)amino]furo[2,3-d]pyrimidine-5-carboxamide;
N-{[3-methoxy-4-(propan-2-yloxy)phenyl]methyl}-6-methyl-4-[(1-methylcyclopropyl)amino]furo[2,3-d]pyrimidine-5-carboxamide;
N-{[3-(3-fluorophenyl)-1,2-oxazol-5-yl]methyl}-6-methyl-4-[(1-methylcyclopropyl)amino]furo[2,3-d]pyrimidine-5-carboxamide;
N-[(3-hydroxy-4-methoxyphenyl)methyl]-N,6-dimethyl-4-[(1-methylcyclopropyl)amino]furo[2,3-d]pyrimidine-5-carboxamide;
N-[(4-methoxyphenyl)methyl]-6-methyl-4-[(1-methylcyclopropyl)amino]-N-(prop-2-yn-1-yl)furo[2,3-d]pyrimidine-5-carboxamide;
N-[(4-fluorophenyl)methyl]-6-methyl-4-[(1-methylcyclopropyl)amino]-N-(prop-2-yn-1-yl)furo[2,3-d]pyrimidine-5-carboxamide;
N-[(5-chloro-2-methoxyphenyl)methyl]-N,6-dimethyl-4-[(1-methylcyclopropyl)amino]furo[2,3-d]pyrimidine-5-carboxamide;
N-ethyl-N-[(4-fluorophenyl)methyl]-6-methyl-4-[(1-methylcyclopropyl)amino]furo[2,3-d]pyrimidine-5-carboxamide;
N-[(2-chloro-4,5-difluorophenyl)methyl]-6-methyl-4-[(1-methylcyclopropyl)amino]furo[2,3-d]pyrimidine-5-carboxamide;
N-[(2-fluoro-5-methylphenyl)methyl]-6-methyl-4-[(1-methylcyclopropyl)amino]furo[2,3-d]pyrimidine-5-carboxamide;
N-[(4-chloro-2,6-difluorophenyl)methyl]-6-methyl-4-[(1-methylcyclopropyl)amino]furo[2,3-d]pyrimidine-5-carboxamide;
N-[(2-fluoro-5-nitrophenyl)methyl]-6-methyl-4-[(1-methylcyclopropyl)amino]furo[2,3-d]pyrimidine-5-carboxamide;
N-ethyl-N-[(3-fluorophenyl)methyl]-6-methyl-4-[(1-methylcyclopropyl)amino]furo[2,3-d]pyrimidine-5-carboxamide;

N-[2-(3,4-dimethoxyphenyl)ethyl]-N,6-dimethyl-4-[(1-methylcyclopropyl)amino]furo[2,3-d]pyrimidine-5-carboxamide N-[2-(4-methoxyphenyl)ethyl]-6-methyl-4-[(1-methylcyclopropyl)amino]furo[2,3-d]pyrimidine-5-carboxamide;

6-methyl-4-[(1-methylcyclopropyl)amino]-N-[(2-methylpyrimidin-4-yl)methyl]furo[2,3-d]pyrimidine-5-carboxamide;

N-{[5-(chlorodifluoromethyl)-1,2,4-oxadiazol-3-yl]methyl}-6-methyl-4-[(1-methylcyclopropyl)amino]furo[2,3-d]pyrimidine-5-carboxamide;

6-methyl-N-[(3-methyl-1,2,4-oxadiazol-5-yl)methyl]-4-[(1-methylcyclopropyl)amino]furo[2,3-d]pyrimidine-5-carboxamide;

6-methyl-4-[(1-methylcyclopropyl)amino]-N-{[2-(propan-2-yl)pyrimidin-4-yl]methyl}furo[2,3-d]pyrimidine-5-carboxamide;

6-methyl-N-[(1-methyl-1H-pyrazol-4-yl)methyl]-4-[(1-methylcyclopropyl)amino]furo[2,3-d]pyrimidine-5-carboxamide;

6-methyl-4-[(1-methylcyclopropyl)amino]-N-(pyrimidin-5-ylmethyl)furo[2,3-d]pyrimidine-5-carboxamide;

N-{5H,6H,7H-cyclopenta[d]pyrimidin-2-ylmethyl}-6-methyl-4-[(1-methylcyclopropyl)amino]furo[2,3-d]pyrimidine-5-carboxamide;

6-methyl-N-{[4-methyl-6-(trifluoromethyl)pyrimidin-2-yl]methyl}-4-[(1-methylcyclopropyl)amino]furo[2,3-d]pyrimidine-5-carboxamide;

6-methyl-4-[(1-methylcyclopropyl)amino]-N-(pyrimidin-4-ylmethyl)furo[2,3-d]pyrimidine-5-carboxamide;

6-methyl-4-[(1-methylcyclopropyl)amino]-N-(pyrimidin-2-ylmethyl)furo[2,3-d]pyrimidine-5-carboxamide;

6-methyl-4-[(1-methylcyclopropyl)amino]-N-[(6-methylpyrimidin-4-yl)methyl]furo[2,3-d]pyrimidine-5-carboxamide;

6-methyl-4-[(1-methylcyclopropyl)amino]-N-[(4-methylpyrimidin-5-yl)methyl]furo[2,3-d]pyrimidine-5-carboxamide;

6-methyl-4-[(1-methylcyclopropyl)amino]-N-[(6-oxo-1,6-dihydropyrimidin-4-yl)methyl]furo[2,3-d]pyrimidine-5-carboxamide;

6-methyl-N-[(2-methyl-6-oxo-1,6-dihydropyrimidin-4-yl)methyl]-4-[(1-methylcyclopropyl)amino]furo[2,3-d]pyrimidine-5-carboxamide;

6-methyl-4-[(1-methylcyclopropyl)amino]-N-{[5-(propan-2-yl)-1,3-oxazol-2-yl]methyl}furo[2,3-d]pyrimidine-5-carboxamide;

N-[(6-methoxypyrimidin-4-yl)methyl]-6-methyl-4-[(1-methylcyclopropyl)amino]furo[2,3-d]pyrimidine-5-carboxamide;

N-[(6-methoxy-2-methylpyrimidin-4-yl)methyl]-6-methyl-4-[(1-methylcyclopropyl)amino]furo[2,3-d]pyrimidine-5-carboxamide;

6-methyl-N-[(2-methyl-6-oxo-1,6-dihydropyrimidin-5-yl)methyl]-4-[(1-methylcyclopropyl)amino]furo[2,3-d]pyrimidine-5-carboxamide;

N-{[2-(1H-imidazol-1-yl)pyridin-4-yl]methyl}-6-methyl-4-[(1-methylcyclopropyl)amino]furo[2,3-d]pyrimidine-5-carboxamide;

6-methyl-4-[(1-methylcyclopropyl)amino]-N-{[2-(morpholin-4-yl)pyridin-4-yl]methyl}furo[2,3-d]pyrimidine-5-carboxamide;

N-[(4-methoxy-2-methylpyrimidin-5-yl)methyl]-6-methyl-4-[(1-methylcyclopropyl)amino]furo[2,3-d]pyrimidine-5-carboxamide;

N-[(2-chloropyrimidin-4-yl)methyl]-6-methyl-4-[(1-methylcyclopropyl)amino]furo[2,3-d]pyrimidine-5-carboxamide;

N-[(6-fluoro-5-methoxypyridin-2-yl)methyl]-6-methyl-4-[(1-methylcyclopropyl)amino]furo[2,3-d]pyrimidine-5-carboxamide;

6-methyl-4-[(1-methylcyclopropyl)amino]-N-[(2-methylpyrimidin-5-yl)methyl]furo[2,3-d]pyrimidine-5-carboxamide;

6-methyl-4-[(1-methylcyclopropyl)amino]-N-{[4-(trifluoromethyl)pyrimidin-2-yl]methyl}furo[2,3-d]pyrimidine-5-carboxamide;

N-[(6-methoxypyrimidin-4-yl)methyl]-N,6-dimethyl-4-[(1-methylcyclopropyl)amino]furo[2,3-d]pyrimidine-5-carboxamide;

N-[(6-cyclopropylpyrimidin-4-yl)methyl]-6-methyl-4-[(1-methylcyclopropyl)amino]furo[2,3-d]pyrimidine-5-carboxamide;

N-[(2-cyclopropylpyrimidin-4-yl)methyl]-6-methyl-4-[(1-methylcyclopropyl)amino]furo[2,3-d]pyrimidine-5-carboxamide;

N-[(5-tert-butyl-1,3-oxazol-2-yl)methyl]-6-methyl-4-[(1-methylcyclopropyl)amino]furo[2,3-d]pyrimidine-5-carboxamide;

N,6-dimethyl-4-[(1-methylcyclopropyl)amino]-N-(1,3-oxazol-2-ylmethyl)furo[2,3-d]pyrimidine-5-carboxamide;

N-[2-(2-cyclopropylpyrimidin-5-yl)ethyl]-6-methyl-4-[(1-methylcyclopropyl)amino]furo[2,3-d]pyrimidine-5-carboxamide;

6-methyl-4-[(1-methylcyclopropyl)amino]-N-{[5-(trifluoromethyl)pyrimidin-2-yl]methyl}furo[2,3-d]pyrimidine-5-carboxamide;

6-methyl-4-[(1-methylcyclopropyl)amino]-N-[(6-methylpyridin-2-yl)methyl]furo[2,3-d]pyrimidine-5-carboxamide;

N-[(2-methoxypyrimidin-5-yl)methyl]-6-methyl-4-[(1-methylcyclopropyl)amino]furo[2,3-d]pyrimidine-5-carboxamide;

N,6-dimethyl-N-[(4-methyl-1,3-thiazol-2-yl)methyl]-4-[(1-methylcyclopropyl)amino]furo[2,3-d]pyrimidine-5-carboxamide;

N,6-dimethyl-4-[(1-methylcyclopropyl)amino]-N-(1,3-thiazol-2-ylmethyl)furo[2,3-d]pyrimidine-5-carboxamide;

N,6-dimethyl-N-[(5-methyl-1,3-thiazol-2-yl)methyl]-4-[(1-methylcyclopropyl)amino]furo[2,3-d]pyrimidine-5-carboxamide;

6-methyl-N-[(4-methyl-1,3-thiazol-2-yl)methyl]-4-[(1-methylcyclopropyl)amino]furo[2,3-d]pyrimidine-5-carboxamide;

6-methyl-4-[(1-methylcyclopropyl)amino]-N-{[4-(trifluoromethyl)-1,3-thiazol-2-yl]methyl}furo[2,3-d]pyrimidine-5-carboxamide;

6-methyl-4-[(1-methylcyclopropyl)amino]-N-[(5-methylpyrimidin-2-yl)methyl]furo[2,3-d]pyrimidine-5-carboxamide;

N-{[5-(difluoromethyl)pyrimidin-2-yl]methyl}-6-methyl-4-[(1-methylcyclopropyl)amino]furo[2,3-d]pyrimidine-5-carboxamide;

N-{[4-(difluoromethyl)pyrimidin-2-yl]methyl}-6-methyl-4-[(1-methylcyclopropyl)amino]furo[2,3-d]pyrimidine-5-carboxamide;

N-[(2-cyclopropylpyrimidin-5-yl)methyl]-6-methyl-4-[(1-methylcyclopropyl)amino]furo[2,3-d]pyrimidine-5-carboxamide;

N-[(6-methoxypyridazin-3-yl)methyl]-6-methyl-4-[(1-methylcyclopropyl)amino]furo[2,3-d]pyrimidine-5-carboxamide;

6-methyl-4-[(1-methylcyclopropyl)amino]-N-(1,3-oxazol-2-ylmethyl)furo[2,3-d]pyrimidine-5-carboxamide;

N-[(5-methoxy-1,3-benzoxazol-2-yl)methyl]-6-methyl-4-[(1-methylcyclopropyl)amino]furo[2,3-d]pyrimidine-5-carboxamide;

6-methyl-N-[(1-methyl-1H-imidazol-2-yl)methyl]-4-[(1-methylcyclopropyl)amino]furo[2,3-d]pyrimidine-5-carboxamide;

N-[(5-chloropyrimidin-2-yl)methyl]-6-methyl-4-[(1-methylcyclopropyl)amino]furo[2,3-d]pyrimidine-5-carboxamide;

6-methyl-N-[(5-methyl-1,3,4-oxadiazol-2-yl)methyl]-4-[(1-methylcyclopropyl)amino]furo[2,3-d]pyrimidine-5-carboxamide;

6-methyl-4-[(1-methylcyclopropyl)amino]-N-[(6-methylpyridazin-3-yl)methyl]furo[2,3-d]pyrimidine-5-carboxamide;

N-{imidazo[1,2-a]pyrazin-6-ylmethyl}-6-methyl-4-[(1-methylcyclopropyl)amino]furo[2,3-d]pyrimidine-5-carboxamide;

6-methyl-4-[(1-methylcyclopropyl)amino]-N-{[4-(trifluoromethoxy)phenyl]methyl}furo[2,3-d]pyrimidine-5-carboxamide;

N-{[2-fluoro-4-(trifluoromethoxy)phenyl]methyl}-6-methyl-4-[(1-methylcyclopropyl)amino]furo[2,3-d]pyrimidine-5-carboxamide;

N-[2-(5-fluoro-1H-1,3-benzodiazol-2-yl)ethyl]-6-methyl-4-[(1-methylcyclopropyl)amino]furo[2,3-d]pyrimidine-5-carboxamide;

N-[(6-fluoro-1-methyl-1H-1,3-benzodiazol-2-yl)methyl]-6-methyl-4-[(1-methylcyclopropyl)amino]furo[2,3-d]pyrimidine-5-carboxamide;

N-[(2-ethylpyrimidin-4-yl)methyl]-6-methyl-4-[(1-methylcyclopropyl)amino]furo[2,3-d]pyrimidine-5-carboxamide;

N-[(dimethyl-1,3-oxazol-2-yl)methyl]-6-methyl-4-[(1-methylcyclopropyl)amino]furo[2,3-d]pyrimidine-5-carboxamide;

N-[(5-fluoro-1H-1,3-benzodiazol-2-yl)methyl]-6-methyl-4-[(1-methylcyclopropyl)amino]furo[2,3-d]pyrimidine-5-carboxamide;

N-[2-(5-fluoro-1,3-benzoxazol-2-yl)ethyl]-6-methyl-4-[(1-methylcyclopropyl)amino]furo[2,3-d]pyrimidine-5-carboxamide;

N-[(5-methoxypyrazin-2-yl)methyl]-6-methyl-4-[(1-methylcyclopropyl)amino]furo[2,3-d]pyrimidine-5-carboxamide;

N-[(5-cyclopropylpyrazin-2-yl)methyl]-6-methyl-4-[(1-methylcyclopropyl)amino]furo[2,3-d]pyrimidine-5-carboxamide;

N-[(5-fluoro-1-methyl-1H-1,3-benzodiazol-2-yl)methyl]-6-methyl-4-[(1-methylcyclopropyl)amino]furo[2,3-d]pyrimidine-5-carboxamide;

N-[2-(5-fluoro-1-methyl-1H-1,3-benzodiazol-2-yl)ethyl]-6-methyl-4-[(1-methylcyclopropyl)amino]furo[2,3-d]pyrimidine-5-carboxamide;

6-methyl-4-[(1-methylcyclopropyl)amino]-N-{[6-(morpholin-4-yl)pyridin-2-yl]methyl}furo[2,3-d]pyrimidine-5-carboxamide;

6-methyl-N-[(2-methyl-2H-1,2,3,4-tetrazol-5-yl)methyl]-4-[(1-methylcyclopropyl)amino]furo[2,3-d]pyrimidine-5-carboxamide;

6-methyl-4-[(1-methylcyclopropyl)amino]-N-{[2-(morpholin-4-yl)-1,3-thiazol-4-yl]methyl}furo[2,3-d]pyrimidine-5-carboxamide;

6-methyl-N-[(2-methyl-2H-1,2,3-triazol-4-yl)methyl]-4-[(1-methylcyclopropyl)amino]furo[2,3-d]pyrimidine-5-carboxamide;

6-methyl-N-[(1-methyl-1H-1,2,4-triazol-3-yl)methyl]-4-[(1-methylcyclopropyl)amino]furo[2,3-d]pyrimidine-5-carboxamide;

6-methyl-N-[(2-methyl-1,3-thiazol-5-yl)methyl]-4-[(1-methylcyclopropyl)amino]furo[2,3-d]pyrimidine-5-carboxamide;

6-methyl-N-[(2-methyl-1,3-oxazol-5-yl)methyl]-4-[(1-methylcyclopropyl)amino]furo[2,3-d]pyrimidine-5-carboxamide;

6-methyl-4-[(1-methylcyclopropyl)amino]-N-{[6-(morpholin-4-yl)pyridazin-3-yl]methyl}furo[2,3-d]pyrimidine-5-carboxamide;

6-methyl-N-[(2-methyl-1,3-oxazol-4-yl)methyl]-4-[(1-methylcyclopropyl)amino]furo[2,3-d]pyrimidine-5-carboxamide;

N-[(5-fluoro-1,3-benzoxazol-2-yl)methyl]-6-methyl-4-[(1-methylcyclopropyl)amino]furo[2,3-d]pyrimidine-5-carboxamide;

6-methyl-4-[(1-methylcyclopropyl)amino]-N-[3-(pyrrolidin-1-yl)propyl]furo[2,3-d]pyrimidine-5-carboxamide;

6-methyl-N-[(4-methyl-1,3-oxazol-2-yl)methyl]-4-[(1-methylcyclopropyl)amino]furo[2,3-d]pyrimidine-5-carboxamide;

N-ethyl-N-[(6-methoxypyrimidin-4-yl)methyl]-6-methyl-4-[(1-methylcyclopropyl)amino]furo[2,3-d]pyrimidine-5-carboxamide;

N-[2-(4-fluorophenyl)ethyl]-6-methyl-4-[(1-methylcyclopropyl)amino]furo[2,3-d]pyrimidine-5-carboxamide;

6-methyl-4-[(1-methylcyclopropyl)amino]-N-[2-(morpholin-4-yl)ethyl]furo[2,3-d]pyrimidine-5-carboxamide;

6-methyl-4-[(1-methylcyclopropyl)amino]-N-[2-(1H-pyrrol-1-yl)ethyl]furo[2,3-d]pyrimidine-5-carboxamide;

N-[2-(furan-2-yl)ethyl]-6-methyl-4-[(1-methylcyclopropyl)amino]furo[2,3-d]pyrimidine-5-carboxamide;

N-[2-(1H-imidazol-1-yl)ethyl]-6-methyl-4-[(1-methylcyclopropyl)amino]furo[2,3-d]pyrimidine-5-carboxamide;

6-methyl-4-[(1-methylcyclopropyl)amino]-N-(2-phenylethyl)furo[2,3-d]pyrimidine-5-carboxamide;

N-[2-(3-chlorophenyl)ethyl]-6-methyl-4-[(1-methylcyclopropyl)amino]furo[2,3-d]pyrimidine-5-carboxamide;

N-[2-(4-methoxyphenyl)ethyl]-N,6-dimethyl-4-[(1-methylcyclopropyl)amino]furo[2,3-d]pyrimidine-5-carboxamide;

N-[2-(5-fluoro-1H-indol-3-yl)ethyl]-6-methyl-4-[(1-methylcyclopropyl)amino]furo[2,3-d]pyrimidine-5-carboxamide;

N-[3-(1H-imidazol-1-yl)propyl]-6-methyl-4-[(1-methylcyclopropyl)amino]furo[2,3-d]pyrimidine-5-carboxamide;

6-methyl-4-[(1-methylcyclopropyl)amino]-N-[2-(thiophen-2-yl)ethyl]furo[2,3-d]pyrimidine-5-carboxamide;

6-methyl-4-[(1-methylcyclopropyl)amino]-N-[2-(4-methylphenyl)ethyl]furo[2,3-d]pyrimidine-5-carboxamide;

6-methyl-4-[(1-methylcyclopropyl)amino]-N-[2-(2-methylphenyl)ethyl]furo[2,3-d]pyrimidine-5-carboxamide;
N-(2-cyclohexylethyl)-6-methyl-4-[(1-methylcyclopropyl)amino]furo[2,3-d]pyrimidine-5-carboxamide;
N,6-dimethyl-4-[(1-methylcyclopropyl)amino]-N-(2-phenylethyl)furo[2,3-d]pyrimidine-5-carboxamide;
N,6-dimethyl-4-[(1-methylcyclopropyl)amino]-N-[2-(pyridin-2-yl)ethyl]furo[2,3-d]pyrimidine-5-carboxamide;
6-methyl-4-[(1-methylcyclopropyl)amino]-N-[3-(morpholin-4-yl)propyl]furo[2,3-d]pyrimidine-5-carboxamide;
N-{[1-(ethoxymethyl)cyclopropyl]methyl}-6-methyl-4-[(1-methylcyclopropyl)amino]furo[2,3-d]pyrimidine-5-carboxamide;
N-{[1-(3-fluorophenyl)cyclopentyl]methyl}-6-methyl-4-[(1-methylcyclopropyl)amino]furo[2,3-d]pyrimidine-5-carboxamide;
N-{[1-(2-fluorophenyl)cyclopentyl]methyl}-6-methyl-4-[(1-methylcyclopropyl)amino]furo[2,3-d]pyrimidine-5-carboxamide;
N-ethyl-N-[(3-methoxyphenyl)methyl]-6-methyl-4-[(1-methylcyclopropyl)amino]furo[2,3-d]pyrimidine-5-carboxamide;
N-cyclopropyl-N-[(2-methoxyphenyl)methyl]-6-methyl-4-[(1-methylcyclopropyl)amino]furo[2,3-d]pyrimidine-5-carboxamide;
N-(cyclopropylmethyl)-6-methyl-4-[(1-methylcyclopropyl)amino]furo[2,3-d]pyrimidine-5-carboxamide;
N-[(2,2-difluorocyclopropyl)methyl]-6-methyl-4-[(1-methylcyclopropyl)amino]furo[2,3-d]pyrimidine-5-carboxamide;
N-[1-(5-fluoropyridin-2-yl)ethyl]-6-methyl-4-[(1-methylcyclopropyl)amino]furo[2,3-d]pyrimidine-5-carboxamide;
N-[1-(4-fluorophenyl)ethyl]-6-methyl-4-[(1-methylcyclopropyl)amino]furo[2,3-d]pyrimidine-5-carboxamide;
6-methyl-4-[(1-methylcyclopropyl)amino]-N-[1-(pyridin-2-yl)ethyl]furo[2,3-d]pyrimidine-5-carboxamide;
6-methyl-4-[(1-methylcyclopropyl)amino]-N-[2-(pyridin-2-yl)propan-2-yl]furo[2,3-d]pyrimidine-5-carboxamide;
N,6-dimethyl-4-[(1-methylcyclopropyl)amino]furo[2,3-d]pyrimidine-5-carboxamide;
N,N,6-trimethyl-4-[(1-methylcyclopropyl)amino]furo[2,3-d]pyrimidine-5-carboxamide;
N-(2-methoxyethyl)-6-methyl-4-[(1-methylcyclopropyl)amino]furo[2,3-d]pyrimidine-5-carboxamide;
N-(2-fluoroethyl)-6-methyl-4-[(1-methylcyclopropyl)amino]furo[2,3-d]pyrimidine-5-carboxamide;
N-(2-hydroxyethyl)-6-methyl-4-[(1-methylcyclopropyl)amino]furo[2,3-d]pyrimidine-5-carboxamide;
N-(4-hydroxy-2-methylbutan-2-yl)-6-methyl-4-[(1-methylcyclopropyl)amino]furo[2,3-d]pyrimidine-5-carboxamide;
6-methyl-4-[(1-methylcyclopropyl)amino]-N-(propan-2-yl)furo[2,3-d]pyrimidine-5-carboxamide;
6-methyl-4-[(1-methylcyclopropyl)amino]-N-(2-methylpropyl)furo[2,3-d]pyrimidine-5-carboxamide;
N-tert-butyl-6-methyl-4-[(1-methylcyclopropyl)amino]furo[2,3-d]pyrimidine-5-carboxamide;
6-methyl-4-[(1-methylcyclopropyl)amino]-N-pentylfuro[2,3-d]pyrimidine-5-carboxamide;
6-methyl-N-(3-methylbutyl)-4-[(1-methylcyclopropyl)amino]furo[2,3-d]pyrimidine-5-carboxamide;
6-methyl-4-[(1-methylcyclopropyl)amino]-N-(pentan-3-yl)furo[2,3-d]pyrimidine-5-carboxamide;
6-methyl-N-(3-methylbutan-2-yl)-4-[(1-methylcyclopropyl)amino]furo[2,3-d]pyrimidine-5-carboxamide;
N-(2-ethoxyethyl)-6-methyl-4-[(1-methylcyclopropyl)amino]furo[2,3-d]pyrimidine-5-carboxamide;
6-methyl-4-[(1-methylcyclopropyl)amino]-N-[2-(propan-2-yloxy)ethyl]furo[2,3-d]pyrimidine-5-carboxamide;
6-methyl-4-[(1-methylcyclopropyl)amino]-N-(1-phenylethyl)furo[2,3-d]pyrimidine-5-carboxamide;
6-methyl-4-[(1-methylcyclopropyl)amino]-N-(prop-2-yn-1-yl)furo[2,3-d]pyrimidine-5-carboxamide;
6-methyl-4-[(1-methylcyclopropyl)amino]-N-propylfuro[2,3-d]pyrimidine-5-carboxamide;
N-butyl-6-methyl-4-[(1-methylcyclopropyl)amino]furo[2,3-d]pyrimidine-5-carboxamide;
6-methyl-4-[(1-methylcyclopropyl)amino]-N-(2-phenylpropan-2-yl)furo[2,3-d]pyrimidine-5-carboxamide;
N-[1-(5-fluoropyrimidin-2-yl)ethyl]-6-methyl-4-[(1-methylcyclopropyl)amino]furo[2,3-d]pyrimidine-5-carboxamide;
N-[1-(3-fluoro-4-methoxyphenyl)ethyl]-6-methyl-4-[(1-methylcyclopropyl)amino]furo[2,3-d]pyrimidine-5-carboxamide;
N-[(1S)-1-(2-fluoro-4-methoxyphenyl)ethyl]-6-methyl-4-[(1-methylcyclopropyl)amino]furo[2,3-d]pyrimidine-5-carboxamide;
N-[(1R)-1-(2-fluoro-4-methoxyphenyl)ethyl]-6-methyl-4-[(1-methylcyclopropyl)amino]furo[2,3-d]pyrimidine-5-carboxamide;
6-methyl-4-[(1-methylcyclopropyl)amino]-N-[1-(pyrazin-2-yl)ethyl]furo[2,3-d]pyrimidine-5-carboxamide;
6-methyl-4-[(1-methylcyclopropyl)amino]-N-[1-(pyrimidin-4-yl)ethyl]furo[2,3-d]pyrimidine-5-carboxamide;
6-methyl-N-[1-(5-methyl-1,2-oxazol-3-yl)ethyl]-4-[(1-methylcyclopropyl)amino]furo[2,3-d]pyrimidine-5-carboxamide;
N'-(5-fluoropyrimidin-2-yl)-6-methyl-4-[(1-methylcyclopropyl)amino]furo[2,3-d]pyrimidine-5-carbohydrazide;
N-(1-fluoro-2-methylpropan-2-yl)-6-methyl-4-[(1-methylcyclopropyl)amino]furo[2,3-d]pyrimidine-5-carboxamide;
N-(1-cyclopropylethyl)-6-methyl-4-[(1-methylcyclopropyl)amino]furo[2,3-d]pyrimidine-5-carboxamide;
N-(1-cyclopropylpropyl)-6-methyl-4-[(1-methylcyclopropyl)amino]furo[2,3-d]pyrimidine-5-carboxamide;
6-methyl-4-[(1-methylcyclopropyl)amino]-N-[1-(1-methylcyclopropyl)ethyl]furo[2,3-d]pyrimidine-5-carboxamide;
6-methyl-4-[(1-methylcyclopropyl)amino]-N-[(1-methylcyclopropyl)methyl]furo[2,3-d]pyrimidine-5-carboxamide;
N-[1-(4-methoxyphenyl)propyl]-6-methyl-4-[(1-methylcyclopropyl)amino]furo[2,3-d]pyrimidine-5-carboxamide;
N-[1-(3-methoxyphenyl)ethyl]-N,6-dimethyl-4-[(1-methylcyclopropyl)amino]furo[2,3-d]pyrimidine-5-carboxamide;
N-[(1S)-1-(3-methoxyphenyl)ethyl]-6-methyl-4-[(1-methylcyclopropyl)amino]furo[2,3-d]pyrimidine-5-carboxamide;
N-[(1R)-1-(3-methoxyphenyl)ethyl]-6-methyl-4-[(1-methylcyclopropyl)amino]furo[2,3-d]pyrimidine-5-carboxamide;

N-[(1S)-1-(4-methoxyphenyl)ethyl]-6-methyl-4-[(1-methylcyclopropyl)amino]furo[2,3-d]pyrimidine-5-carboxamide;
N-[(1S)-1-(2-methoxyphenyl)ethyl]-6-methyl-4-[(1-methylcyclopropyl)amino]furo[2,3-d]pyrimidine-5-carboxamide;
N-[(1R)-1-(4-fluorophenyl)ethyl]-6-methyl-4-[(1-methylcyclopropyl)amino]furo[2,3-d]pyrimidine-5-carboxamide;
N-[(1S)-1-(4-fluorophenyl)ethyl]-6-methyl-4-[(1-methylcyclopropyl)amino]furo[2,3-d]pyrimidine-5-carboxamide;
N-[1-(2,5-difluorophenyl)ethyl]-6-methyl-4-[(1-methylcyclopropyl)amino]furo[2,3-d]pyrimidine-5-carboxamide;
N-[1-(3-methoxyphenyl)ethyl]-6-methyl-4-[(1-methylcyclopropyl)amino]furo[2,3-d]pyrimidine-5-carboxamide;
N-[2-hydroxy-3-(4-methoxyphenoxy)propyl]-6-methyl-4-[(1-methylcyclopropyl)amino]furo[2,3-d]pyrimidine-5-carboxamide;
N-[1-(4-methoxy-3-methylphenyl)ethyl]-6-methyl-4-[(1-methylcyclopropyl)amino]furo[2,3-d]pyrimidine-5-carboxamide;
N-[1-(3-fluoro-4-methoxyphenyl)ethyl]-N,6-dimethyl-4-[(1-methylcyclopropyl)amino]furo[2,3-d]pyrimidine-5-carboxamide;
N-[1-(4-fluorophenyl)-2-hydroxyethyl]-6-methyl-4-[(1-methylcyclopropyl)amino]furo[2,3-d]pyrimidine-5-carboxamide;
N-[(1R)-1-(2,4-difluorophenyl)ethyl]-6-methyl-4-[(1-methylcyclopropyl)amino]furo[2,3-d]pyrimidine-5-carboxamide;
N-[(1S)-1-(5-fluoropyrimidin-2-yl)ethyl]-6-methyl-4-[(1-methylcyclopropyl)amino]furo[2,3-d]pyrimidine-5-carboxamide;
6-methyl-N-(2-methylbut-3-yn-2-yl)-4-[(1-methylcyclopropyl)amino]furo[2,3-d]pyrimidine-5-carboxamide;
N-[1-(4-fluorophenyl)propan-2-yl]-6-methyl-4-[(1-methylcyclopropyl)amino]furo[2,3-d]pyrimidine-5-carboxamide;
N-[1-(3,5-difluorophenyl)ethyl]-6-methyl-4-[(1-methylcyclopropyl)amino]furo[2,3-d]pyrimidine-5-carboxamide;
N-[1-(4-fluorophenyl)propyl]-6-methyl-4-[(1-methylcyclopropyl)amino]furo[2,3-d]pyrimidine-5-carboxamide;
N-[1-(3,5-dimethoxyphenyl)ethyl]-6-methyl-4-[(1-methylcyclopropyl)amino]furo[2,3-d]pyrimidine-5-carboxamide;
N-[(1R)-1-(3,4-dimethoxyphenyl)ethyl]-6-methyl-4-[(1-methylcyclopropyl)amino]furo[2,3-d]pyrimidine-5-carboxamide;
N-[2-(2-methoxyphenoxy)ethyl]-6-methyl-4-[(1-methylcyclopropyl)amino]furo[2,3-d]pyrimidine-5-carboxamide;
N-[2-(2-methoxyphenoxy)ethyl]-N,6-dimethyl-4-[(1-methylcyclopropyl)amino]furo[2,3-d]pyrimidine-5-carboxamide;
N-[2-(2-fluorophenoxy)ethyl]-6-methyl-4-[(1-methylcyclopropyl)amino]furo[2,3-d]pyrimidine-5-carboxamide;
N-[(1R)-1-(4-methoxyphenyl)ethyl]-6-methyl-4-[(1-methylcyclopropyl)amino]furo[2,3-d]pyrimidine-5-carboxamide;
N-[1-(2-methoxyphenyl)ethyl]-N,6-dimethyl-4-[(1-methylcyclopropyl)amino]furo[2,3-d]pyrimidine-5-carboxamide;
N-[2-(4-fluorophenoxy)ethyl]-6-methyl-4-[(1-methylcyclopropyl)amino]furo[2,3-d]pyrimidine-5-carboxamide;
N-{2-[(4-methoxyphenyl)sulfanyl]ethyl}-6-methyl-4-[(1-methylcyclopropyl)amino]furo[2,3-d]pyrimidine-5-carboxamide;
N-[1-(4-ethoxy-3-fluorophenyl)ethyl]-6-methyl-4-[(1-methylcyclopropyl)amino]furo[2,3-d]pyrimidine-5-carboxamide;
N-[1-(3,4-dimethoxyphenyl)propyl]-6-methyl-4-[(1-methylcyclopropyl)amino]furo[2,3-d]pyrimidine-5-carboxamide;
N-[1-(4-methoxy-3,5-dimethylphenyl)ethyl]-6-methyl-4-[(1-methylcyclopropyl)amino]furo[2,3-d]pyrimidine-5-carboxamide;
N-[2-hydroxy-3-(3-methoxyphenoxy)propyl]-6-methyl-4-[(1-methylcyclopropyl)amino]furo[2,3-d]pyrimidine-5-carboxamide;
N-ethyl-N-[2-(4-methoxyphenoxy)ethyl]-6-methyl-4-[(1-methylcyclopropyl)amino]furo[2,3-d]pyrimidine-5-carboxamide;
N-[3-(4-methoxyphenoxy)propyl]-N,6-dimethyl-4-[(1-methylcyclopropyl)amino]furo[2,3-d]pyrimidine-5-carboxamide;
N-[1-(2-methoxyphenyl)ethyl]-6-methyl-4-[(1-methylcyclopropyl)amino]furo[2,3-d]pyrimidine-5-carboxamide;
N-[(1R)-1-(5-fluoropyrimidin-2-yl)ethyl]-6-methyl-4-[(1-methylcyclopropyl)amino]furo[2,3-d]pyrimidine-5-carboxamide;
N-[1-(4-fluorophenyl)ethyl]-N,6-dimethyl-4-[(1-methylcyclopropyl)amino]furo[2,3-d]pyrimidine-5-carboxamide;
N-methoxy-N,6-dimethyl-4-[(1-methylcyclopropyl)amino]furo[2,3-d]pyrimidine-5-carboxamide;
6-methyl-4-[(1-methylcyclopropyl)amino]-N-[1-(pyrimidin-5-yl)ethyl]furo[2,3-d]pyrimidine-5-carboxamide;
6-methyl-4-[(1-methylcyclopropyl)amino]-N-[1-(1,3-oxazol-2-yl)ethyl]furo[2,3-d]pyrimidine-5-carboxamide;
6-methyl-4-[(1-methylcyclopropyl)amino]-N-[1-(1,2-oxazol-3-yl)ethyl]furo[2,3-d]pyrimidine-5-carboxamide;
6-methyl-4-[(1-methylcyclopropyl)amino]-N-(3,3,3-trifluoropropyl)furo[2,3-d]pyrimidine-5-carboxamide;
N-(2-{[dimethyl(oxo)-$\lambda^6$-sulfanylidene]amino}ethyl)-6-methyl-4-[(1-methylcyclopropyl)amino]furo[2,3-d]pyrimidine-5-carboxamide;
6-methyl-4-[(1-methylcyclopropyl)amino]furo[2,3-d]pyrimidine-5-carboxamide;
3-fluoro-5-(1-{6-methyl-4-[(1-methylcyclopropyl)amino]furo[2,3-d]pyrimidine-5-carbonyl}-1,2,3,6-tetrahydropyridin-4-yl)pyridine-2-carbonitrile;
5-[4-(5-fluoro-6-methoxypyridin-3-yl)-1,2,3,6-tetrahydropyridine-1-carbonyl]-6-methyl-N-(1-methylcyclopropyl)furo[2,3-d]pyrimidin-4-amine;
5-[4-(5-fluoro-6-methoxypyridin-3-yl)piperidine-1-carbonyl]-6-methyl-N-(1-methylcyclopropyl)furo[2,3-d]pyrimidin-4-amine;
5-[4-(5-fluoropyrimidin-2-yl)-1,2,3,6-tetrahydropyridine-1-carbonyl]-6-methyl-N-(1-methylcyclopropyl)furo[2,3-d]pyrimidin-4-amine;

5-[3-(2-fluoropyridin-4-yl)pyrrolidine-1-carbonyl]-6-methyl-N-(1-methylcyclopropyl)furo[2,3-d]pyrimidin-4-amine;

N-(2-fluoroethyl)-2-(1-{6-methyl-4-[(1-methylcyclopropyl)amino]furo[2,3-d]pyrimidine-5-carbonyl}piperidin-4-yl)pyrimidin-4-amine;

5-[3-(5-fluoropyridin-2-yl)azetidine-1-carbonyl]-6-methyl-N-(1-methylcyclopropyl)furo[2,3-d]pyrimidin-4-amine;

4-(1-{6-methyl-4-[(1-methylcyclopropyl)amino]furo[2,3-d]pyrimidine-5-carbonyl}azetidin-3-yl)benzonitrile;

6-methyl-N-(1-methylcyclopropyl)-5-[3-(1,3-thiazol-2-yl)azetidine-1-carbonyl]furo[2,3-d]pyrimidin-4-amine;

5-{3-[3-fluoro-5-(trifluoromethyl)pyridin-2-yl]azetidine-1-carbonyl}-6-methyl-N-(1-methylcyclopropyl)furo[2,3-d]pyrimidin-4-amine;

5-[3-(4-fluorophenyl)azetidine-1-carbonyl]-6-methyl-N-(1-methylcyclopropyl)furo[2,3-d]pyrimidin-4-amine;

5-[3-(4-fluorophenyl)pyrrolidine-1-carbonyl]-6-methyl-N-(1-methylcyclopropyl)furo[2,3-d]pyrimidin-4-amine;

5-[4-(4-fluorophenyl)piperidine-1-carbonyl]-6-methyl-N-(1-methylcyclopropyl)furo[2,3-d]pyrimidin-4-amine;

5-[4-fluoro-4-(pyridin-2-yl)piperidine-1-carbonyl]-6-methyl-N-(1-methylcyclopropyl)furo[2,3-d]pyrimidin-4-amine;

4-(4-fluorophenyl)-1-{6-methyl-4-[(1-methylcyclopropyl)amino]furo[2,3-d]pyrimidine-5-carbonyl}piperidin-4-ol;

3-(4-fluorophenyl)-1-{6-methyl-4-[(1-methylcyclopropyl)amino]furo[2,3-d]pyrimidine-5-carbonyl}pyrrolidin-3-ol;

6-methyl-N-(1-methylcyclopropyl)-5-[3-(pyridin-2-yl)pyrrolidine-1-carbonyl]furo[2,3-d]pyrimidin-4-amine;

6-methyl-N-(1-methylcyclopropyl)-5-[3-(pyridin-3-yl)pyrrolidine-1-carbonyl]furo[2,3-d]pyrimidin-4-amine;

6-methyl-N-(1-methylcyclopropyl)-5-[3-(pyridin-4-yl)pyrrolidine-1-carbonyl]furo[2,3-d]pyrimidin-4-amine;

5-[3-(4-fluorophenyl)-3-methylpyrrolidine-1-carbonyl]-6-methyl-N-(1-methylcyclopropyl)furo[2,3-d]pyrimidin-4-amine;

3-(4-fluorophenyl)-1-{6-methyl-4-[(1-methylcyclopropyl)amino]furo[2,3-d]pyrimidine-5-carbonyl}azetidin-3-ol;

5-(3-methoxy-3-phenylazetidine-1-carbonyl)-6-methyl-N-(1-methylcyclopropyl)furo[2,3-d]pyrimidin-4-amine;

6-methyl-N-(1-methylcyclopropyl)-5-(morpholine-4-carbonyl)furo[2,3-d]pyrimidin-4-amine;

5-{3-[4-(difluoromethyl)phenyl]pyrrolidine-1-carbonyl}-6-methyl-N-(1-methylcyclopropyl)furo[2,3-d]pyrimidin-4-amine;

5-(3-fluoro-3-phenylpyrrolidine-1-carbonyl)-6-methyl-N-(1-methylcyclopropyl)furo[2,3-d]pyrimidin-4-amine;

5-[3-fluoro-3-(4-fluorophenyl)pyrrolidine-1-carbonyl]-6-methyl-N-(1-methylcyclopropyl)furo[2,3-d]pyrimidin-4-amine;

1-{6-methyl-4-[(1-methylcyclopropyl)amino]furo[2,3-d]pyrimidine-5-carbonyl}pyrrolidin-3-ol;

N,N-dimethyl-1-{6-methyl-4-[(1-methylcyclopropyl)amino]furo[2,3-d]pyrimidine-5-carbonyl}piperidin-4-amine;

5-[2-(furan-2-yl)pyrrolidine-1-carbonyl]-6-methyl-N-(1-methylcyclopropyl)furo[2,3-d]pyrimidin-4-amine;

1-{6-methyl-4-[(1-methylcyclopropyl)amino]furo[2,3-d]pyrimidine-5-carbonyl}-4-phenylpiperidine-4-carbonitrile;

5-[3-(4-fluorophenyl)azepane-1-carbonyl]-6-methyl-N-(1-methylcyclopropyl)furo[2,3-d]pyrimidin-4-amine;

5-[4-(4-fluorophenyl)azepane-1-carbonyl]-6-methyl-N-(1-methylcyclopropyl)furo[2,3-d]pyrimidin-4-amine;

6-methyl-N-(1-methylcyclopropyl)-5-[4-(pyridin-2-yl)piperidine-1-carbonyl]furo[2,3-d]pyrimidin-4-amine;

6-methyl-N-(1-methylcyclopropyl)-5-[4-(pyrimidin-2-yl)piperidine-1-carbonyl]furo[2,3-d]pyrimidin-4-amine;

5-(3-fluoro-3-phenylazetidine-1-carbonyl)-6-methyl-N-(1-methylcyclopropyl)furo[2,3-d]pyrimidin-4-amine;

6-methyl-5-[3-(1-methyl-1H-imidazol-2-yl)pyrrolidine-1-carbonyl]-N-(1-methylcyclopropyl)furo[2,3-d]pyrimidin-4-amine;

6-methyl-5-[3-(1-methyl-1H-pyrazol-4-yl)pyrrolidine-1-carbonyl]-N-(1-methylcyclopropyl)furo[2,3-d]pyrimidin-4-amine;

5-[4-(3-chloro-5-fluoropyridin-2-yl)piperidine-1-carbonyl]-6-methyl-N-(1-methylcyclopropyl)furo[2,3-d]pyrimidin-4-amine;

5-[3-(5-chloropyrimidin-2-yl)pyrrolidine-1-carbonyl]-6-methyl-N-(1-methylcyclopropyl)furo[2,3-d]pyrimidin-4-amine;

5-[3-(5-fluoropyridin-3-yl)pyrrolidine-1-carbonyl]-6-methyl-N-(1-methylcyclopropyl)furo[2,3-d]pyrimidin-4-amine;

5-[4-(5-chloropyrimidin-2-yl)piperidine-1-carbonyl]-6-methyl-N-(1-methylcyclopropyl)furo[2,3-d]pyrimidin-4-amine;

5-[4-(4-methoxypyrimidin-2-yl)piperidine-1-carbonyl]-6-methyl-N-(1-methylcyclopropyl)furo[2,3-d]pyrimidin-4-amine;

4-(1-{6-methyl-4-[(1-methylcyclopropyl)amino]furo[2,3-d]pyrimidine-5-carbonyl}pyrrolidin-3-yl)phenol;

1-{6-methyl-4-[(1-methylcyclopropyl)amino]furo[2,3-d]pyrimidine-5-carbonyl}-3-phenylpyrrolidin-3-ol;

5-[3-(5-chloropyridin-2-yl)pyrrolidine-1-carbonyl]-6-methyl-N-(1-methylcyclopropyl)furo[2,3-d]pyrimidin-4-amine;

5-[4-(2-chloro-5-fluoropyrimidin-4-yl)piperidine-1-carbonyl]-6-methyl-N-(1-methylcyclopropyl)furo[2,3-d]pyrimidin-4-amine;

5-[3-(6-fluoropyridin-2-yl)azetidine-1-carbonyl]-6-methyl-N-(1-methylcyclopropyl)furo[2,3-d]pyrimidin-4-amine;

2-(1-{6-methyl-4-[(1-methylcyclopropyl)amino]furo[2,3-d]pyrimidine-5-carbonyl}piperidin-4-yl)pyrimidin-5-ol;

5-[4-(5-fluoropyrimidin-2-yl)piperidine-1-carbonyl]-6-methyl-N-(1-methylcyclopropyl)furo[2,3-d]pyrimidin-4-amine;

6-methyl-N-(1-methylcyclopropyl)-5-[4-(5-methylpyrimidin-2-yl)piperidine-1-carbonyl]furo[2,3-d]pyrimidin-4-amine;

5-[3-(3-methoxyphenyl)pyrrolidine-1-carbonyl]-6-methyl-N-(1-methylcyclopropyl)furo[2,3-d]pyrimidin-4-amine;

5-[4-(6-methoxypyridazin-3-yl)piperidine-1-carbonyl]-6-methyl-N-(1-methylcyclopropyl)furo[2,3-d]pyrimidin-4-amine;

5-[4-(5-methoxypyrazin-2-yl)piperidine-1-carbonyl]-6-methyl-N-(1-methylcyclopropyl)furo[2,3-d]pyrimidin-4-amine;

5-[4-(5-methoxypyridin-2-yl)piperidine-1-carbonyl]-6-methyl-N-(1-methylcyclopropyl)furo[2,3-d]pyrimidin-4-amine;

5-[3-(6-methoxypyridin-2-yl)pyrrolidine-1-carbonyl]-6-methyl-N-(1-methylcyclopropyl)furo[2,3-d]pyrimidin-4-amine;

5-[4-(4-cyclopropylpyrimidin-2-yl)piperidine-1-carbonyl]-6-methyl-N-(1-methylcyclopropyl)furo[2,3-d]pyrimidin-4-amine;

6-methyl-N-(1-methylcyclopropyl)-5-[4-(4-propylpyrimidin-2-yl)piperidine-1-carbonyl]furo[2,3-d]pyrimidin-4-amine;

5-[4-(5-methoxypyrimidin-2-yl)piperidine-1-carbonyl]-6-methyl-N-(1-methylcyclopropyl)furo[2,3-d]pyrimidin-4-amine;

5-[3-(6-bromopyridin-2-yl)pyrrolidine-1-carbonyl]-6-methyl-N-(1-methylcyclopropyl)furo[2,3-d]pyrimidin-4-amine;

5-[3-(5-bromopyridin-2-yl)pyrrolidine-1-carbonyl]-6-methyl-N-(1-methylcyclopropyl)furo[2,3-d]pyrimidin-4-amine;

4-(1-{6-methyl-4-[(1-methylcyclopropyl)amino]furo[2,3-d]pyrimidine-5-carbonyl}piperidin-4-yl)benzamide;

6-methyl-N-(1-methylcyclopropyl)-5-[4-(6-methylpyridin-3-yl)piperidine-1-carbonyl]furo[2,3-d]pyrimidin-4-amine;

6-methyl-N-(1-methylcyclopropyl)-5-[4-(4-methylphenyl)piperidine-1-carbonyl]furo[2,3-d]pyrimidin-4-amine;

4-(1-{6-methyl-4-[(1-methylcyclopropyl)amino]furo[2,3-d]pyrimidine-5-carbonyl}piperidin-4-yl)benzonitrile;

5-[3-(3-fluorophenyl)pyrrolidine-1-carbonyl]-6-methyl-N-(1-methylcyclopropyl)furo[2,3-d]pyrimidin-4-amine;

6-methyl-N-(1-methylcyclopropyl)-5-[4-(4-methylpyrimidin-2-yl)piperidine-1-carbonyl]furo[2,3-d]pyrimidin-4-amine;

5-[4-(4,5-dimethylpyrimidin-2-yl)piperidine-1-carbonyl]-6-methyl-N-(1-methylcyclopropyl)furo[2,3-d]pyrimidin-4-amine;

6-methyl-N-(1-methylcyclopropyl)-5-[4-(5-methylpyrazin-2-yl)piperidine-1-carbonyl]furo[2,3-d]pyrimidin-4-amine;

5-[4-(2-methoxypyrimidin-5-yl)piperidine-1-carbonyl]-6-methyl-N-(1-methylcyclopropyl)furo[2,3-d]pyrimidin-4-amine;

6-methyl-N-(1-methylcyclopropyl)-5-[3-(3-methylphenyl)pyrrolidine-1-carbonyl]furo[2,3-d]pyrimidin-4-amine;

6-methyl-N-(1-methylcyclopropyl)-5-{3-[3-(trifluoromethyl)phenyl]pyrrolidine-1-carbonyl}furo[2,3-d]pyrimidin-4-amine;

5-[3-(3,5-dimethylphenyl)pyrrolidine-1-carbonyl]-6-methyl-N-(1-methylcyclopropyl)furo[2,3-d]pyrimidin-4-amine;

5-[3-(3-fluorophenoxy)pyrrolidine-1-carbonyl]-6-methyl-N-(1-methylcyclopropyl)furo[2,3-d]pyrimidin-4-amine;

5-[3-(4-fluorophenoxy)pyrrolidine-1-carbonyl]-6-methyl-N-(1-methylcyclopropyl)furo[2,3-d]pyrimidin-4-amine;

5-{3-[(4-fluorophenyl)methyl]pyrrolidine-1-carbonyl}-6-methyl-N-(1-methylcyclopropyl)furo[2,3-d]pyrimidin-4-amine;

5-[4-(6-methoxypyridin-2-yl)piperidine-1-carbonyl]-6-methyl-N-(1-methylcyclopropyl)furo[2,3-d]pyrimidin-4-amine;

5-[4-(5-methoxy-4-methylpyrimidin-2-yl)piperidine-1-carbonyl]-6-methyl-N-(1-methylcyclopropyl)furo[2,3-d]pyrimidin-4-amine;

6-methyl-N-(1-methylcyclopropyl)-5-{4-[5-(trifluoromethyl)pyrimidin-2-yl]piperidine-1-carbonyl}furo[2,3-d]pyrimidin-4-amine;

4-(6-fluoropyridin-2-yl)-1-{6-methyl-4-[(1-methylcyclopropyl)amino]furo[2,3-d]pyrimidine-5-carbonyl}piperidine-4-carbonitrile;

methyl 2-(1-{6-methyl-4-[(1-methylcyclopropyl)amino]furo[2,3-d]pyrimidine-5-carbonyl}azetidin-3-yl)pyrimidine-5-carboxylate;

5-{3-[(2-fluorophenyl)methoxy]azetidine-1-carbonyl}-6-methyl-N-(1-methylcyclopropyl)furo[2,3-d]pyrimidin-4-amine;

5-{3-[(3-fluorophenyl)methoxy]azetidine-1-carbonyl}-6-methyl-N-(1-methylcyclopropyl)furo[2,3-d]pyrimidin-4-amine;

5-[2-(3-fluorophenyl)pyrrolidine-1-carbonyl]-6-methyl-N-(1-methylcyclopropyl)furo[2,3-d]pyrimidin-4-amine;

5-[3-(4-fluorophenoxy)azetidine-1-carbonyl]-6-methyl-N-(1-methylcyclopropyl)furo[2,3-d]pyrimidin-4-amine;

5-[4-(3-methoxyphenyl)piperidine-1-carbonyl]-6-methyl-N-(1-methylcyclopropyl)furo[2,3-d]pyrimidin-4-amine;

5-[4-(4,6-dimethoxypyrimidin-2-yl)piperidine-1-carbonyl]-6-methyl-N-(1-methylcyclopropyl)furo[2,3-d]pyrimidin-4-amine;

5-[3-(3-fluoropyridin-2-yl)pyrrolidine-1-carbonyl]-6-methyl-N-(1-methylcyclopropyl)furo[2,3-d]pyrimidin-4-amine;

5-[4-(6-fluoro-5-methoxypyridin-2-yl)piperidine-1-carbonyl]-6-methyl-N-(1-methylcyclopropyl)furo[2,3-d]pyrimidin-4-amine;

5-fluoro-2-(1-{6-methyl-4-[(1-methylcyclopropyl)amino]furo[2,3-d]pyrimidine-5-carbonyl}piperidin-4-yl)-N-(propan-2-yl)pyrimidin-4-amine;

5-[3-(6-fluoropyridin-2-yl)pyrrolidine-1-carbonyl]-6-methyl-N-(1-methylcyclopropyl)furo[2,3-d]pyrimidin-4-amine;

5-[2-(4-fluorophenyl)piperidine-1-carbonyl]-6-methyl-N-(1-methylcyclopropyl)furo[2,3-d]pyrimidin-4-amine;

5-[2-(3-methoxyphenyl)pyrrolidine-1-carbonyl]-6-methyl-N-(1-methylcyclopropyl)furo[2,3-d]pyrimidin-4-amine;

5-[2-(3-methoxyphenyl)piperidine-1-carbonyl]-6-methyl-N-(1-methylcyclopropyl)furo[2,3-d]pyrimidin-4-amine;

5-[4-(2-fluorophenoxy)piperidine-1-carbonyl]-6-methyl-N-(1-methylcyclopropyl)furo[2,3-d]pyrimidin-4-amine;

5-[4-(4-fluorophenoxy)piperidine-1-carbonyl]-6-methyl-N-(1-methylcyclopropyl)furo[2,3-d]pyrimidin-4-amine;

5-[2-(3-fluorophenyl)azepane-1-carbonyl]-6-methyl-N-(1-methylcyclopropyl)furo[2,3-d]pyrimidin-4-amine;

5-[3-(2-methoxyphenoxy)azetidine-1-carbonyl]-6-methyl-N-(1-methylcyclopropyl)furo[2,3-d]pyrimidin-4-amine;

5-[3-(3-methoxyphenoxy)azetidine-1-carbonyl]-6-methyl-N-(1-methylcyclopropyl)furo[2,3-d]pyrimidin-4-amine;
5-{4-[5-(fluoromethoxy)pyrimidin-2-yl]piperidine-1-carbonyl}-6-methyl-N-(1-methylcyclopropyl)furo[2,3-d]pyrimidin-4-amine;
5-{3-[4-(fluoromethoxy)phenyl]pyrrolidine-1-carbonyl}-6-methyl-N-(1-methylcyclopropyl)furo[2,3-d]pyrimidin-4-amine;
5-[3-(5-fluoropyrimidin-2-yl)-2,5-dihydro-1H-pyrrole-1-carbonyl]-6-methyl-N-(1-methylcyclopropyl)furo[2,3-d]pyrimidin-4-amine;
2-(1-{6-methyl-4-[(1-methylcyclopropyl)amino]furo[2,3-d]pyrimidine-5-carbonyl}-1,2,3,6-tetrahydropyridin-4-yl)pyrimidine-4-carbonitrile;
6-methyl-5-[4-(1-methyl-1H-pyrazol-3-yl)piperidine-1-carbonyl]-N-(1-methylcyclopropyl)furo[2,3-d]pyrimidin-4-amine;
6-methyl-5-[4-(1-methyl-1H-1,2,4-triazol-3-yl)piperidine-1-carbonyl]-N-(1-methylcyclopropyl)furo[2,3-d]pyrimidin-4-amine;
6-methyl-5-[4-(1-methyl-1H-1,2,3-triazol-4-yl)piperidine-1-carbonyl]-N-(1-methylcyclopropyl)furo[2,3-d]pyrimidin-4-amine;
5-[4-(1,5-dimethyl-1H-pyrazol-3-yl)piperidine-1-carbonyl]-6-methyl-N-(1-methylcyclopropyl)furo[2,3-d]pyrimidin-4-amine;
5-[4-(2,4-dimethyl-1H-imidazol-5-yl)piperidine-1-carbonyl]-6-methyl-N-(1-methylcyclopropyl)furo[2,3-d]pyrimidin-4-amine;
6-methyl-N-(1-methylcyclopropyl)-5{-4-[1-(propan-2-yl)-1H-pyrazol-3-yl]piperidine-1-carbonyl}furo[2,3-d]pyrimidin-4-amine;
6-methyl-5-[4-(1-methyl-1H-pyrazol-4-yl)piperidine-1-carbonyl]-N-(1-methylcyclopropyl)furo[2,3-d]pyrimidin-4-amine;
5-[4-(2-fluoro-1,3-thiazol-5-yl)-1,2,3,6-tetrahydropyridine-1-carbonyl]-6-methyl-N-(1-methylcyclopropyl)furo[2,3-d]pyrimidin-4-amine;
5-[4-(5-methoxypyrazin-2-yl)-1,2,3,6-tetrahydropyridine-1-carbonyl]-6-methyl-N-(1-methylcyclopropyl)furo[2,3-d]pyrimidin-4-amine;
5-[4-(5-methoxypyridin-2-yl)-1,2,3,6-tetrahydropyridine-1-carbonyl]-6-methyl-N-(1-methylcyclopropyl)furo[2,3-d]pyrimidin-4-amine;
5-{3-[4-(2-fluoroethoxy)phenyl]pyrrolidine-1-carbonyl}-6-methyl-N-(1-methylcyclopropyl)furo[2,3-d]pyrimidin-4-amine;
5-[3-(6-fluoro-4-methylpyridin-2-yl)pyrrolidine-1-carbonyl]-6-methyl-N-(1-methylcyclopropyl)furo[2,3-d]pyrimidin-4-amine;
5-[3-(5-fluoro-6-methylpyridin-2-yl)pyrrolidine-1-carbonyl]-6-methyl-N-(1-methylcyclopropyl)furo[2,3-d]pyrimidin-4-amine;
5-[3-(5-fluoro-4-methylpyrimidin-2-yl)pyrrolidine-1-carbonyl]-6-methyl-N-(1-methylcyclopropyl)furo[2,3-d]pyrimidin-4-amine;
6-methyl-N-(1-methylcyclopropyl)-5-{3-[6-(trifluoromethyl)pyridin-2-yl]pyrrolidine-1-carbonyl}furo[2,3-d]pyrimidin-4-amine;
6-methyl-N-(1-methylcyclopropyl)-5-{3-[4-(trifluoromethyl)pyridin-2-yl]pyrrolidine-1-carbonyl}furo[2,3-d]pyrimidin-4-amine;
6-methyl-N-(1-methylcyclopropyl)-5-(4-phenylpiperazine-1-carbonyl)furo[2,3-d]pyrimidin-4-amine;
6-methyl-N-(1-methylcyclopropyl)-5-[4-(1,3-thiazol-2-yl)piperazine-1-carbonyl]furo[2,3-d]pyrimidin-4-amine;
6-methyl-N-(1-methylcyclopropyl)-5-[4-(pyridin-2-yl)piperazine-1-carbonyl]furo[2,3-d]pyrimidin-4-amine;
5-[4-(5-fluoropyridin-2-yl)piperazine-1-carbonyl]-6-methyl-N-(1-methylcyclopropyl)furo[2,3-d]pyrimidin-4-amine;
6-methyl-N-(1-methylcyclopropyl)-5-[4-(5-methylpyridin-2-yl)piperazine-1-carbonyl]furo[2,3-d]pyrimidin-4-amine;
4-(4-{6-methyl-4-[(1-methylcyclopropyl)amino]furo[2,3-d]pyrimidine-5-carbonyl}piperazin-1-yl)benzonitrile;
5-[4-(4-fluorophenyl)piperazine-1-carbonyl]-6-methyl-N-(1-methylcyclopropyl)furo[2,3-d]pyrimidin-4-amine;
1-(3,4-difluorophenyl)-4-{6-methyl-4-[(1-methylcyclopropyl)amino]furo[2,3-d]pyrimidine-5-carbonyl}piperazin-2-one;
6-methyl-N-(1-methylcyclopropyl)-5-[2-(pyridin-2-yl)morpholine-4-carbonyl]furo[2,3-d]pyrimidin-4-amine;
6-methyl-N-(1-methylcyclopropyl)-5-[2-(pyridin-4-yl)morpholine-4-carbonyl]furo[2,3-d]pyrimidin-4-amine;
6-methyl-N-(1-methylcyclopropyl)-5-[2-(pyridin-3-yl)morpholine-4-carbonyl]furo[2,3-d]pyrimidin-4-amine;
6-methyl-5-[2-(1-methyl-1H-pyrazol-4-yl)morpholine-4-carbonyl]-N-(1-methylcyclopropyl)furo[2,3-d]pyrimidin-4-amine;
5-[2-(4-fluorophenyl)morpholine-4-carbonyl]-6-methyl-N-(1-methylcyclopropyl)furo[2,3-d]pyrimidin-4-amine;
5-[2-(4-methoxyphenyl)morpholine-4-carbonyl]-6-methyl-N-(1-methylcyclopropyl)furo[2,3-d]pyrimidin-4-amine;
5-[4-(3-fluoropyridin-2-yl)piperazine-1-carbonyl]-6-methyl-N-(1-methylcyclopropyl)furo[2,3-d]pyrimidin-4-amine;
5-[4-(5-fluoropyrimidin-2-yl)piperazine-1-carbonyl]-6-methyl-N-(1-methylcyclopropyl)furo[2,3-d]pyrimidin-4-amine;
5-[4-(6-fluoropyridin-2-yl)piperazine-1-carbonyl]-6-methyl-N-(1-methylcyclopropyl)furo[2,3-d]pyrimidin-4-amine;
5-[4-(2-fluorophenyl)-1,4-diazepane-1-carbonyl]-6-methyl-N-(1-methylcyclopropyl)furo[2,3-d]pyrimidin-4-amine;
6-methyl-N-(1-methylcyclopropyl)-5-(4-phenyl-1,4-diazepane-1-carbonyl)furo[2,3-d]pyrimidin-4-amine;
6-methyl-N-(1-methylcyclopropyl)-5-[4-(pyridin-2-yl)-1,4-diazepane-1-carbonyl]furo[2,3-d]pyrimidin-4-amine;
5-[4-(4-methoxyphenyl)-1,4-diazepane-1-carbonyl]-6-methyl-N-(1-methylcyclopropyl)furo[2,3-d]pyrimidin-4-amine;
5-[4-(2-fluoropyridin-4-yl)piperazine-1-carbonyl]-6-methyl-N-(1-methylcyclopropyl)furo[2,3-d]pyrimidin-4-amine;
5-[4-(6-fluoropyrimidin-4-yl)piperazine-1-carbonyl]-6-methyl-N-(1-methylcyclopropyl)furo[2,3-d]pyrimidin-4-amine;
5-[4-(2-fluoropyrimidin-4-yl)piperazine-1-carbonyl]-6-methyl-N-(1-methylcyclopropyl)furo[2,3-d]pyrimidin-4-amine;
5-[4-(4-methoxyphenyl)piperazine-1-carbonyl]-6-methyl-N-(1-methylcyclopropyl)furo[2,3-d]pyrimidin-4-amine;

6-methyl-5-(4-methyl-1,4-diazepane-1-carbonyl)-N-(1-methylcyclopropyl)furo[2,3-d]pyrimidin-4-amine;

1-(4-{6-methyl-4-[(1-methylcyclopropyl)amino]furo[2,3-d]pyrimidine-5-carbonyl}piperazin-1-yl)ethan-1-one;

1-(4-{6-methyl-4-[(1-methylcyclopropyl)amino]furo[2,3-d]pyrimidine-5-carbonyl}-1,4-diazepan-1-yl)ethan-1-one;

5-(4-tert-butylpiperazine-1-carbonyl)-6-methyl-N-(1-methylcyclopropyl)furo[2,3-d]pyrimidin-4-amine;

5-[4-(2-methoxyethyl)piperazine-1-carbonyl]-6-methyl-N-(1-methylcyclopropyl)furo[2,3-d]pyrimidin-4-amine;

5-[4-(6-fluoropyridin-3-yl)piperazine-1-carbonyl]-6-methyl-N-(1-methylcyclopropyl)furo[2,3-d]pyrimidin-4-amine;

6-methyl-N-(1-methylcyclopropyl)-5-[4-(tetrachloropyridin-2-yl)piperazine-1-carbonyl]furo[2,3-d]pyrimidin-4-amine;

5-[4-(5-methoxypyrimidin-2-yl)piperazine-1-carbonyl]-6-methyl-N-(1-methylcyclopropyl)furo[2,3-d]pyrimidin-4-amine;

5-[4-(5-fluoropyrimidin-2-yl)-2-methylpiperazine-1-carbonyl]-6-methyl-N-(1-methylcyclopropyl)furo[2,3-d]pyrimidin-4-amine;

5-[4-(5-fluoropyrimidin-2-yl)-3-methylpiperazine-1-carbonyl]-6-methyl-N-(1-methylcyclopropyl)furo[2,3-d]pyrimidin-4-amine;

5-[4-(2-fluoro-4-methanesulfonylphenyl)piperazine-1-carbonyl]-6-methyl-N-(1-methylcyclopropyl)furo[2,3-d]pyrimidin-4-amine;

5-[4-(2-chloro-5-fluoropyrimidin-4-yl)piperazine-1-carbonyl]-6-methyl-N-(1-methylcyclopropyl)furo[2,3-d]pyrimidin-4-amine;

6-methyl-N-(1-methylcyclopropyl)-5-[4-(pyrimidin-5-yl)piperazine-1-carbonyl]furo[2,3-d]pyrimidin-4-amine;

5-{4-[(4-fluorophenyl)methyl]piperazine-1-carbonyl}-6-methyl-N-(1-methylcyclopropyl)furo[2,3-d]pyrimidin-4-amine;

5-[4-(4-methoxypyrimidin-2-yl)piperazine-1-carbonyl]-6-methyl-N-(1-methylcyclopropyl)furo[2,3-d]pyrimidin-4-amine;

5-[4-(4-fluoro-2-methanesulfonylphenyl)piperazine-1-carbonyl]-6-methyl-N-(1-methylcyclopropyl)furo[2,3-d]pyrimidin-4-amine;

5-[4-(2-fluoro-4-methanesulfonylphenyl)-2-methylpiperazine-1-carbonyl]-6-methyl-N-(1-methylcyclopropyl)furo[2,3-d]pyrimidin-4-amine;

5-[4-(2-fluoro-4-nitrophenyl)piperazine-1-carbonyl]-6-methyl-N-(1-methylcyclopropyl)furo[2,3-d]pyrimidin-4-amine;

5-[4-(2,4-difluorophenyl)piperazine-1-carbonyl]-6-methyl-N-(1-methylcyclopropyl)furo[2,3-d]pyrimidin-4-amine;

5-[3-(4-fluorophenyl)piperazine-1-carbonyl]-6-methyl-N-(1-methylcyclopropyl)furo[2,3-d]pyrimidin-4-amine;

5{-4-[(3-fluorophenyl)methyl]piperazine-1-carbonyl}-6-methyl-N-(1-methylcyclopropyl)furo[2,3-d]pyrimidin-4-amine;

5-{2-cyclopropyl-5H,6H,7H,8H-pyrido[4,3-d]pyrimidine-6-carbonyl}-6-methyl-N-(1-methylcyclopropyl)furo[2,3-d]pyrimidin-4-amine;

5{-4-methoxy-5H,6H,7H,8H-pyrido[3,4-d]pyrimidine-7-carbonyl}-6-methyl-N-(1-methylcyclopropyl)furo[2,3-d]pyrimidin-4-amine;

5{-4-fluoro-5H,6H,7H,8H-pyrido[3,4-d]pyrimidine-7-carbonyl}-6-methyl-N-(1-methylcyclopropyl)furo[2,3-d]pyrimidin-4-amine;

5{-4-chloro-5H,6H,7H,8H-pyrido[3,4-d]pyrimidine-7-carbonyl}-6-methyl-N-(1-methylcyclopropyl)furo[2,3-d]pyrimidin-4-amine;

5{-4-[(2-fluoroethyl)amino]-5H,6H,7H,8H-pyrido[3,4-d]pyrimidine-7-carbonyl}-6-methyl-N-(1-methylcyclopropyl)furo[2,3-d]pyrimidin-4-amine;

3-(fluoromethyl)-7-{6-methyl-4-[(1-methylcyclopropyl)amino]furo[2,3-d]pyrimidine-5-carbonyl}-3H,4H,5H,6H,7H,8H-pyrido[3,4-d]pyrimidin-4-one;

5-[4-(fluoromethoxy)-5H,6H,7H,8H-pyrido[3,4-d]pyrimidine-7-carbonyl]-6-methyl-N-(1-methylcyclopropyl)furo[2,3-d]pyrimidin-4-amine;

5{-4-[(3R)-3-fluoropyrrolidin-1-yl]-5H,6H,7H,8H-pyrido[3,4-d]pyrimidine-7-carbonyl}-6-methyl-N-(1-methylcyclopropyl)furo[2,3-d]pyrimidin-4-amine;

7-{6-methyl-4-[(1-methylcyclopropyl)amino]furo[2,3-d]pyrimidine-5-carbonyl}-5,6,7,8-tetrahydro-1,7-naphthyridin-4-ol;

5-[4-(2-fluoroethoxy)-5,6,7,8-tetrahydro-1,7-naphthyridine-7-carbonyl]-6-methyl-N-(1-methylcyclopropyl)furo[2,3-d]pyrimidin-4-amine;

7-{6-methyl-4-[(1-methylcyclopropyl)amino]furo[2,3-d]pyrimidine-5-carbonyl}-2-(propan-2-yl)-3H,4H,5H,6H,7H 8H-pyrido[3,4-d]pyrimidin-4-one;

5-{4-ethyl-5H,6H,7H,8H-pyrido[3,4-d]pyrimidine-7-carbonyl}-6-methyl-N-(1-methylcyclopropyl)furo[2,3-d]pyrimidin-4-amine;

7-{6-methyl-4-[(1-methylcyclopropyl)amino]furo[2,3-d]pyrimidine-5-carbonyl}-5H,6H,7H,8H-pyrido[3,4-d]pyrimidine-4-carbonitrile;

5-{4-ethoxy-5H,6H,7H,8H-pyrido[3,4-d]pyrimidine-7-carbonyl}-6-methyl-N-(1-methylcyclopropyl)furo[2,3-d]pyrimidin-4-amine;

5-[4-methoxy-2-(propan-2-yl)-5H,6H,7H,8H-pyrido[3,4-d]pyrimidine-7-carbonyl]-6-methyl-N-(1-methylcyclopropyl)furo[2,3-d]pyrimidin-4-amine;

6-methyl-N-(1-methylcyclopropyl)-5-[2-(trifluoromethyl)-5H,6H,7H-pyrrolo[3,4-d]pyrimidine-6-carbonyl]furo[2,3-d]pyrimidin-4-amine;

5-[2-(4-fluorophenyl)-5H,6H,7H-pyrrolo[3,4-d]pyrimidine-6-carbonyl]-6-methyl-N-(1-methylcyclopropyl)furo[2,3-d]pyrimidin-4-amine;

6-methyl-5-{2-methyl-5H,6H,7H,8H-pyrido[4,3-d]pyrimidine-6-carbonyl}-N-(1-methylcyclopropyl)furo[2,3-d]pyrimidin-4-amine;

5-(5-methoxy-1,2,3,4-tetrahydro-2,6-naphthyridine-2-carbonyl)-6-methyl-N-(1-methylcyclopropyl)furo[2,3-d]pyrimidin-4-amine;

5-{2-tert-butyl-5H,6H,7H,8H-pyrido[4,3-d]pyrimidine-6-carbonyl}-6-methyl-N-(1-methylcyclopropyl)furo[2,3-d]pyrimidin-4-amine;

5-{2-methoxy-5H,6H,7H,8H-pyrido[4,3-d]pyrimidine-6-carbonyl}-6-methyl-N-(1-methylcyclopropyl)furo[2,3-d]pyrimidin-4-amine;

2-{6-methyl-4-[(1-methylcyclopropyl)amino]furo[2,3-d]pyrimidine-5-carbonyl}-1,2,3,4-tetrahydroisoquinoline-6-carbonitrile;

6-methyl-N-(1-methylcyclopropyl)-5-(1,2,3,4-tetrahydroisoquinoline-2-carbonyl)furo[2,3-d]pyrimidin-4-amine;

6-methyl-N-(1-methylcyclopropyl)-5-{5H,6H,7H-pyrrolo[3,4-b]pyridine-6-carbonyl}furo[2,3-d]pyrimidin-4-amine;

6-methyl-5-(7-methyl-1,2,3,4-tetrahydro-2,6-naphthyridine-2-carbonyl)-N-(1-methylcyclopropyl)furo[2,3-d]pyrimidin-4-amine;

6-methyl-5-(2-methyl-5,6,7,8-tetrahydro-1,6-naphthyridine-6-carbonyl)-N-(1-methylcyclopropyl)furo[2,3-d]pyrimidin-4-amine;

5-(5-chloro-1,2,3,4-tetrahydro-2,6-naphthyridine-2-carbonyl)-6-methyl-N-(1-methylcyclopropyl)furo[2,3-d]pyrimidin-4-amine;

5-(2-chloro-5,6,7,8-tetrahydro-1,7-naphthyridine-7-carbonyl)-6-methyl-N-(1-methylcyclopropyl)furo[2,3-d]pyrimidin-4-amine;

5-(2-chloro-5,6,7,8-tetrahydro-1,6-naphthyridine-6-carbonyl)-6-methyl-N-(1-methylcyclopropyl)furo[2,3-d]pyrimidin-4-amine;

5-{3-chloro-5H,6H,7H,8H-pyrido[4,3-c]pyridazine-6-carbonyl}-6-methyl-N-(1-methylcyclopropyl)furo[2,3-d]pyrimidin-4-amine;

5-{2-chloro-5H,6H,7H,8H-pyrido[4,3-d]pyrimidine-6-carbonyl}-6-methyl-N-(1-methylcyclopropyl)furo[2,3-d]pyrimidin-4-amine;

6-methyl-N-(1-methylcyclopropyl)-5-[2-(oxan-4-yl)-5,6,7,8-tetrahydro-1,6-naphthyridine-6-carbonyl]furo[2,3-d]pyrimidin-4-amine;

6-methyl-N-(1-methylcyclopropyl)-5-[2-(propan-2-yl)-5H,6H,7H,8H-pyrido[3,4-d]pyrimidine-7-carbonyl]furo[2,3-d]pyrimidin-4-amine;

5-{2-cyclopropyl-5H,6H,7H,8H-pyrido[3,4-d]pyrimidine-7-carbonyl}-6-methyl-N-(1-methylcyclopropyl)furo[2,3-d]pyrimidin-4-amine;

5-{2-fluoro-5H,6H,7H,8H-pyrido[4,3-d]pyrimidine-6-carbonyl}-6-methyl-N-(1-methylcyclopropyl)furo[2,3-d]pyrimidin-4-amine;

5-{2-fluoro-5H,6H,7H,8H-pyrido[3,4-d]pyrimidine-7-carbonyl}-6-methyl-N-(1-methylcyclopropyl)furo[2,3-d]pyrimidin-4-amine;

2-{6-methyl-4-[(1-methylcyclopropyl)amino]furo[2,3-d]pyrimidine-5-carbonyl}-1,2,3,4-tetrahydroisoquinolin-5-ol;

2-{6-methyl-4-[(1-methylcyclopropyl)amino]furo[2,3-d]pyrimidine-5-carbonyl}-1,2,3,4-tetrahydroisoquinolin-6-ol;

2-{6-methyl-4-[(1-methylcyclopropyl)amino]furo[2,3-d]pyrimidine-5-carbonyl}-1,2,3,4-tetrahydroisoquinolin-8-ol;

2-{6-methyl-4-[(1-methylcyclopropyl)amino]furo[2,3-d]pyrimidine-5-carbonyl}-1,2,3,4-tetrahydroisoquinolin-7-ol;

6-{6-methyl-4-[(1-methylcyclopropyl)amino]furo[2,3-d]pyrimidine-5-carbonyl}-5,6,7,8-tetrahydro-1,6-naphthyridin-3-ol;

6-{6-methyl-4-[(1-methylcyclopropyl)amino]furo[2,3-d]pyrimidine-5-carbonyl}-1,2,5,6,7,8-hexahydro-2,6-naphthyridin-1-one;

1-methyl-2-{6-methyl-4-[(1-methylcyclopropyl)amino]furo[2,3-d]pyrimidine-5-carbonyl}-1,2,3,4-tetrahydroisoquinolin-7-ol;

5-[4-(cyclopropylamino)-5H,6H,7H,8H-pyrido[3,4-d]pyrimidine-7-carbonyl]-6-methyl-N-(1-methylcyclopropyl)furo[2,3-d]pyrimidin-4-amine;

5{-4-[(cyclopropylmethyl)amino]-5H,6H,7H,8H-pyrido[3,4-d]pyrimidine-7-carbonyl}-6-methyl-N-(1-methylcyclopropyl)furo[2,3-d]pyrimidin-4-amine;

2-(4-fluorophenyl)-7-{6-methyl-4-[(1-methylcyclopropyl)amino]furo[2,3-d]pyrimidine-5-carbonyl}-3H,4H,5H,6H,7H,8H-pyrido[3,4-d]pyrimidin-4-one;

2-(methoxymethyl)-7-{6-methyl-4-[(1-methylcyclopropyl)amino]furo[2,3-d]pyrimidine-5-carbonyl}-3H,4H,5H,6H,7H,8H-pyrido[3,4-d]pyrimidin-4-one;

6-methyl-5-{4-methyl-5H,6H,7H,8H-pyrido[3,4-d]pyrimidine-7-carbonyl}-N-(1-methylcyclopropyl)furo[2,3-d]pyrimidin-4-amine;

6-methyl-N-(1-methylcyclopropyl)-5-[4-(propan-2-yloxy)-5H,6H,7H,8H-pyrido[3,4-d]pyrimidine-7-carbonyl]furo[2,3-d]pyrimidin-4-amine;

6-methyl-N-(1-methylcyclopropyl)-5-{5H,6H,7H,8H-pyrido[3,4-d]pyrimidine-7-carbonyl}furo[2,3-d]pyrimidin-4-amine;

7-methoxy-1-methyl-2-{6-methyl-4-[(1-methylcyclopropyl)amino]furo[2,3-d]pyrimidine-5-carbonyl}-1,2,3,4-tetrahydroisoquinolin-6-ol;

5-(7-fluoro-1,2,3,4-tetrahydroisoquinoline-2-carbonyl)-6-methyl-N-(1-methylcyclopropyl)furo[2,3-d]pyrimidin-4-amine;

5-{4-methoxy-5H,6H,7H-pyrrolo[3,4-d]pyrimidine-6-carbonyl}-6-methyl-N-(1-methylcyclopropyl)furo[2,3-d]pyrimidin-4-amine;

6-methyl-N-(1-methylcyclopropyl)-5-[4-(propan-2-yl)-5H,6H,7H,8H-pyrido[3,4-d]pyrimidine-7-carbonyl]furo[2,3-d]pyrimidin-4-amine;

6-methyl-N-(1-methylcyclopropyl)-5-(5,6,7,8-tetrahydro-1,7-naphthyridine-7-carbonyl)furo[2,3-d]pyrimidin-4-amine;

6-methyl-N-(1-methylcyclopropyl)-5-(5,6,7,8-tetrahydro-1,6-naphthyridine-6-carbonyl)furo[2,3-d]pyrimidin-4-amine;

5-(6-methoxy-1,2,3,4-tetrahydro-2,7-naphthyridine-2-carbonyl)-6-methyl-N-(1-methylcyclopropyl)furo[2,3-d]pyrimidin-4-amine;

5-(2-methoxy-5,6,7,8-tetrahydro-1,6-naphthyridine-6-carbonyl)-6-methyl-N-(1-methylcyclopropyl)furo[2,3-d]pyrimidin-4-amine;

6-methyl-N-(1-methylcyclopropyl)-5-(1,2,3,4-tetrahydro-2,7-naphthyridine-2-carbonyl)furo[2,3-d]pyrimidin-4-amine;

5-(6-chloro-1,2,3,4-tetrahydro-2,7-naphthyridine-2-carbonyl)-6-methyl-N-(1-methylcyclopropyl)furo[2,3-d]pyrimidin-4-amine;

5-{4-methoxy-5H,6H,7H,8H-pyrido[4,3-d]pyrimidine-6-carbonyl}-6-methyl-N-(1-methylcyclopropyl)furo[2,3-d]pyrimidin-4-amine;

6-methyl-N-(1-methylcyclopropyl)-5-(1,2,3,4-tetrahydro-2,6-naphthyridine-2-carbonyl)furo[2,3-d]pyrimidin-4-amine;

2-cyclopropyl-6-{6-methyl-4-[(1-methylcyclopropyl)amino]furo[2,3-d]pyrimidine-5-carbonyl}-3H,4H,5H,6H,7H-pyrrolo[3,4-d]pyrimidin-4-one;

6-{6-methyl-4-[(1-methylcyclopropyl)amino]furo[2,3-d]pyrimidine-5-carbonyl}-2-(propan-2-yl)-3H,4H,5H,6H,7H-pyrrolo[3,4-d]pyrimidin-4-one;

5-{2-cyclopropyl-4-methoxy-5H,6H,7H-pyrrolo[3,4-d]pyrimidine-6-carbonyl}-6-methyl-N-(1-methylcyclopropyl)furo[2,3-d]pyrimidin-4-amine;

5-[4-methoxy-2-(propan-2-yl)-5H,6H,7H-pyrrolo[3,4-d]pyrimidine-6-carbonyl]-6-methyl-N-(1-methylcyclopropyl)furo[2,3-d]pyrimidin-4-amine;

5-{2-chloro-5H,6H,7H,8H-pyrido[3,4-d]pyrimidine-7-carbonyl}-6-methyl-N-(1-methylcyclopropyl)furo[2,3-d]pyrimidin-4-amine;

5-{2-methoxy-5H,6H,7H,8H-pyrido[3,4-d]pyrimidine-7-carbonyl}-6-methyl-N-(1-methylcyclopropyl)furo[2,3-d]pyrimidin-4-amine;

5-{4-methoxy-2-methyl-5H,6H,7H-pyrrolo[3,4-d]pyrimidine-6-carbonyl}-6-methyl-N-(1-methylcyclopropyl)furo[2,3-d]pyrimidin-4-amine;

5-{4-methoxy-2-methyl-5H,6H,7H,8H-pyrido[4,3-d]pyrimidine-6-carbonyl}-6-methyl-N-(1-methylcyclopropyl)furo[2,3-d]pyrimidin-4-amine;

5-{3-bromo-5H,6H,7H-pyrrolo[3,4-b]pyridine-6-carbonyl}-6-methyl-N-(1-methylcyclopropyl)furo[2,3-d]pyrimidin-4-amine;

6-methyl-N-(1-methylcyclopropyl)-5-[3-(oxan-4-yl)-5H,6H,7H-pyrrolo[3,4-b]pyridine-6-carbonyl]furo[2,3-d]pyrimidin-4-amine;

6-methyl-N-(1-methylcyclopropyl)-5{-4-[(propan-2-yl)amino]-5H,6H,7H,8H-pyrido[3,4-d]pyrimidine-7-carbonyl}furo[2,3-d]pyrimidin-4-amine;

5-[4-(fluoromethoxy)-5,6,7,8-tetrahydro-1,7-naphthyridine-7-carbonyl]-6-methyl-N-(1-methylcyclopropyl)furo[2,3-d]pyrimidin-4-amine;

5-[5-(fluoromethoxy)-1,2,3,4-tetrahydroisoquinoline-2-carbonyl]-6-methyl-N-(1-methylcyclopropyl)furo[2,3-d]pyrimidin-4-amine;

5-[6-(fluoromethoxy)-1,2,3,4-tetrahydroisoquinoline-2-carbonyl]-6-methyl-N-(1-methylcyclopropyl)furo[2,3-d]pyrimidin-4-amine;

5-[8-(fluoromethoxy)-1,2,3,4-tetrahydroisoquinoline-2-carbonyl]-6-methyl-N-(1-methylcyclopropyl)furo[2,3-d]pyrimidin-4-amine;

5-[7-(fluoromethoxy)-1,2,3,4-tetrahydroisoquinoline-2-carbonyl]-6-methyl-N-(1-methylcyclopropyl)furo[2,3-d]pyrimidin-4-amine;

5-[3-(fluoromethoxy)-5,6,7,8-tetrahydro-1,6-naphthyridine-6-carbonyl]-6-methyl-N-(1-methylcyclopropyl)furo[2,3-d]pyrimidin-4-amine;

5-[5-(fluoromethoxy)-1,2,3,4-tetrahydro-2,6-naphthyridine-2-carbonyl]-6-methyl-N-(1-methylcyclopropyl)furo[2,3-d]pyrimidin-4-amine;

5-[7-(fluoromethoxy)-1-methyl-1,2,3,4-tetrahydroisoquinoline-2-carbonyl]-6-methyl-N-(1-methylcyclopropyl)furo[2,3-d]pyrimidin-4-amine;

5-[4-(fluoromethoxy)-2-(methoxymethyl)-5H,6H,7H,8H-pyrido[3,4-d]pyrimidine-7-carbonyl]-6-methyl-N-(1-methylcyclopropyl)furo[2,3-d]pyrimidin-4-amine;

5{-4-[(3S)-3-fluoropyrrolidin-1-yl]-5H,6H,7H,8H-pyrido[3,4-d]pyrimidine-7-carbonyl}-6-methyl-N-(1-methylcyclopropyl)furo[2,3-d]pyrimidin-4-amine;

6-methyl-N-(1-methylcyclopropyl)-5-[4-(morpholin-4-yl)-5H,6H,7H,8H-pyrido[3,4-d]pyrimidine-7-carbonyl]furo[2,3-d]pyrimidin-4-amine;

5-[4-(3-fluoroazetidin-1-yl)-5H,6H,7H,8H-pyrido[3,4-d]pyrimidine-7-carbonyl]-6-methyl-N-(1-methylcyclopropyl)furo[2,3-d]pyrimidin-4-amine;

5-{2-chloro-4-[(propan-2-yl)amino]-5H,6H,7H,8H-pyrido[3,4-d]pyrimidine-7-carbonyl}-6-methyl-N-(1-methylcyclopropyl)furo[2,3-d]pyrimidin-4-amine;

5{-4-[cyclopropyl(methyl)amino]-5H,6H,7H,8H-pyrido[3,4-d]pyrimidine-7-carbonyl}-6-methyl-N-(1-methylcyclopropyl)furo[2,3-d]pyrimidin-4-amine;

5-[4-(dimethylamino)-5H,6H,7H,8H-pyrido[3,4-d]pyrimidine-7-carbonyl]-6-methyl-N-(1-methylcyclopropyl)furo[2,3-d]pyrimidin-4-amine;

6-methyl-5-[4-(methylamino)-5H,6H,7H,8H-pyrido[3,4-d]pyrimidine-7-carbonyl]-N-(1-methylcyclopropyl)furo[2,3-d]pyrimidin-4-amine;

6-methyl-5{-4-[methyl(oxan-4-yl)amino]-5H,6H,7H,8H-pyrido[3,4-d]pyrimidine-7-carbonyl}-N-(1-methylcyclopropyl)furo[2,3-d]pyrimidin-4-amine;

6-methyl-N-(1-methylcyclopropyl)-5{-4-[(oxan-4-yl)amino]-5H,6H,7H,8H-pyrido[3,4-d]pyrimidine-7-carbonyl}furo[2,3-d]pyrimidin-4-amine;

5-(4-{[1-(methoxymethyl)cyclopropyl]amino}-5H,6H,7H,8H-pyrido[3,4-d]pyrimidine-7-carbonyl)-6-methyl-N-(1-methylcyclopropyl)furo[2,3-d]pyrimidin-4-amine;

6-methyl-N-(1-methylcyclopropyl)-5{-4-[(1-methylcyclopropyl)amino]-5H,6H,7H,8H-pyrido[3,4-d]pyrimidine-7-carbonyl}furo[2,3-d]pyrimidin-4-amine;

6-methyl-N-(1-methylcyclopropyl)-5-[4-(oxan-4-yl)-5H,6H,7H,8H-pyrido[3,4-d]pyrimidine-7-carbonyl]furo[2,3-d]pyrimidin-4-amine;

6-methyl-N-(1-methylcyclopropyl)-5-[4-(prop-1-en-2-yl)-5H,6H,7H,8H-pyrido[3,4-d]pyrimidine-7-carbonyl]furo[2,3-d]pyrimidin-4-amine;

5-{4-cyclopropyl-5H,6H,7H,8H-pyrido[3,4-d]pyrimidine-7-carbonyl}-6-methyl-N-(1-methylcyclopropyl)furo[2,3-d]pyrimidin-4-amine;

6-methyl-N-(1-methylcyclopropyl)-5-{4-propoxy-5H,6H,7H,8H-pyrido[3,4-d]pyrimidine-7-carbonyl}furo[2,3-d]pyrimidin-4-amine;

6-methyl-N-(1-methylcyclopropyl)-5-[4-(2-methylpropoxy)-5H,6H,7H,8H-pyrido[3,4-d]pyrimidine-7-carbonyl]furo[2,3-d]pyrimidin-4-amine;

5-[4-(cyclopropylmethoxy)-5H,6H,7H,8H-pyrido[3,4-d]pyrimidine-7-carbonyl]-6-methyl-N-(1-methylcyclopropyl)furo[2,3-d]pyrimidin-4-amine;

5-[4-(2-methoxyethoxy)-5H,6H,7H,8H-pyrido[3,4-d]pyrimidine-7-carbonyl]-6-methyl-N-(1-methylcyclopropyl)furo[2,3-d]pyrimidin-4-amine;

5-{4-cyclobutoxy-5H,6H,7H,8H-pyrido[3,4-d]pyrimidine-7-carbonyl}-6-methyl-N-(1-methylcyclopropyl)furo[2,3-d]pyrimidin-4-amine;

5-{4-cyclopropoxy-5H,6H,7H,8H-pyrido[3,4-d]pyrimidine-7-carbonyl}-6-methyl-N-(1-methylcyclopropyl)furo[2,3-d]pyrimidin-4-amine;

5-{2-cyclopropyl-4-methoxy-5H,6H,7H,8H-pyrido[3,4-d]pyrimidine-7-carbonyl}-6-methyl-N-(1-methylcyclopropyl)furo[2,3-d]pyrimidin-4-amine;

6-methyl-N-(1-methylcyclopropyl)-5-[4-(propan-2-yl)-1H-pyrazole-1-carbonyl]furo[2,3-d]pyrimidin-4-amine;

6-methyl-N-(1-methylcyclopropyl)-5-(4-phenyl-1H-pyrazole-1-carbonyl)furo[2,3-d]pyrimidin-4-amine;

5-[4-(4-methoxyphenyl)-1H-pyrazole-1-carbonyl]-6-methyl-N-(1-methylcyclopropyl)furo[2,3-d]pyrimidin-4-amine;

5-[4-(4-fluorophenyl)-1H-pyrazole-1-carbonyl]-6-methyl-N-(1-methylcyclopropyl)furo[2,3-d]pyrimidin-4-amine;

6-methyl-5-(4-methyl-1H-pyrazole-1-carbonyl)-N-(1-methylcyclopropyl)furo[2,3-d]pyrimidin-4-amine;

6-methyl-N-(1-methylcyclopropyl)-5-(trimethyl-1H-pyrazole-1-carbonyl)furo[2,3-d]pyrimidin-4-amine;

6-methyl-N-(1-methylcyclopropyl)-5-(1H-pyrazole-1-carbonyl)furo[2,3-d]pyrimidin-4-amine;

5-(3,5-dimethyl-1H-pyrazole-1-carbonyl)-6-methyl-N-(1-methylcyclopropyl)furo[2,3-d]pyrimidin-4-amine;

5-[4-(3-methoxyphenyl)-1H-pyrazole-1-carbonyl]-6-methyl-N-(1-methylcyclopropyl)furo[2,3-d]pyrimidin-4-amine;

5-[3,5-dimethyl-4-(morpholin-4-ylmethyl)-1H-pyrazole-1-carbonyl]-6-methyl-N-(1-methylcyclopropyl)furo[2,3-d]pyrimidin-4-amine;

5-{3-cyclopropyl-1-ethyl-5H,6H,7H,8H-imidazo[1,5-a]pyrazine-7-carbonyl}-6-methyl-N-(1-methylcyclopropyl)furo[2,3-d]pyrimidin-4-amine;

5-[(8aS)-octahydropyrrolo[1,2-a]piperazine-2-carbonyl]-6-methyl-N-(1-methylcyclopropyl)furo[2,3-d]pyrimidin-4-amine;

5-{5H,6H,7H,8H-imidazo[1,2-a]pyrazine-7-carbonyl}-6-methyl-N-(1-methylcyclopropyl)furo[2,3-d]pyrimidin-4-amine;

6-methyl-N-(1-methylcyclopropyl)-5-[2-(trifluoromethyl)-5H,6H,7H,8H-imidazo[1,2-a]pyrazine-7-carbonyl]furo[2,3-d]pyrimidin-4-amine;

5-{3-bromo-5H,6H,7H,8H-imidazo[1,2-a]pyrazine-7-carbonyl}-6-methyl-N-(1-methylcyclopropyl)furo[2,3-d]pyrimidin-4-amine;

6-methyl-5-{2-methyl-4H,5H,6H,7H-pyrazolo[1,5-a]pyrazine-5-carbonyl}-N-(1-methylcyclopropyl)furo[2,3-d]pyrimidin-4-amine;

6-methyl-5-{2-methyl-5H,6H,7H,8H-imidazo[1,2-a]pyrazine-7-carbonyl}-N-(1-methylcyclopropyl)furo[2,3-d]pyrimidin-4-amine;

5-{6-methyl-4-[(1-methylcyclopropyl)amino]furo[2,3-d]pyrimidine-5-carbonyl}-4H,5H,6H,7H-pyrazolo[1,5-a]pyrazine-2-carbonitrile;

6-methyl-N-(1-methylcyclopropyl)-5-[1-(oxan-4-yl)-3-(trifluoromethyl)-5H,6H,7H,8H-imidazo[1,5-a]pyrazine-7-carbonyl]furo[2,3-d]pyrimidin-4-amine;

6-methyl-5-[3-methyl-1-(oxan-4-yl)-5H,6H,7H,8H-imidazo[1,5-a]pyrazine-7-carbonyl]-N-(1-methylcyclopropyl)furo[2,3-d]pyrimidin-4-amine;

5-{5H,6H,7H,8H-imidazo[1,5-a]pyrazine-7-carbonyl}-6-methyl-N-(1-methylcyclopropyl)furo[2,3-d]pyrimidin-4-amine;

5-{3-bromo-4H,5H,6H,7H-pyrazolo[1,5-a]pyrazine-5-carbonyl}-6-methyl-N-(1-methylcyclopropyl)furo[2,3-d]pyrimidin-4-amine;

6-methyl-N-(1-methylcyclopropyl)-5-{4H,5H,6H,7H-pyrazolo[1,5-a]pyrazine-5-carbonyl}furo[2,3-d]pyrimidin-4-amine;

5-{3-cyclopropyl-5H,6H,7H,8H-imidazo[1,5-a]pyrazine-7-carbonyl}-6-methyl-N-(1-methylcyclopropyl)furo[2,3-d]pyrimidin-4-amine;

5-{1-chloro-3-cyclopropyl-5H,6H,7H,8H-imidazo[1,5-a]pyrazine-7-carbonyl}-6-methyl-N-(1-methylcyclopropyl)furo[2,3-d]pyrimidin-4-amine;

5-{3-cyclopropyl-1-iodo-5H,6H,7H,8H-imidazo[1,5-a]pyrazine-7-carbonyl}-6-methyl-N-(1-methylcyclopropyl)furo[2,3-d]pyrimidin-4-amine;

5-{1,3-dimethyl-5H,6H,7H,8H-imidazo[1,5-a]pyrazine-7-carbonyl}-6-methyl-N-(1-methylcyclopropyl)furo[2,3-d]pyrimidin-4-amine;

6-methyl-N-(1-methylcyclopropyl)-5-[(1R,5S,6S)-6-(pyridin-2-yl)-3-azabicyclo[3.1.0]hexane-3-carbonyl]furo[2,3-d]pyrimidin-4-amine;

6-methyl-N-(1-methylcyclopropyl)-5-[(1R,5S,6S)-6-[5-(trifluoromethyl)pyridin-2-yl]-3-azabicyclo[3.1.0]hexane-3-carbonyl]furo[2,3-d]pyrimidin-4-amine;

5-[(3aS,6aS)-hexahydro-2H-furo[3,2-b]pyrrole-4-carbonyl]-6-methyl-N-(1-methylcyclopropyl)furo[2,3-d]pyrimidin-4-amine;

5-[(1R,5S)-3-azabicyclo[3.1.0]hexane-3-carbonyl]-6-methyl-N-(1-methylcyclopropyl)furo[2,3-d]pyrimidin-4-amine;

5-[(3aR,6aS)-octahydrocyclopenta[c]pyrrole-2-carbonyl]-6-methyl-N-(1-methylcyclopropyl)furo[2,3-d]pyrimidin-4-amine;

6-methyl-N-(1-methylcyclopropyl)-5-[(1R,5S,6S)-6-phenyl-3-azabicyclo[3.1.0]hexane-3-carbonyl]furo[2,3-d]pyrimidin-4-amine;

5-[(1R,5S,6S)-6-(2-methoxyphenyl)-3-azabicyclo[3.1.0]hexane-3-carbonyl]-6-methyl-N-(1-methylcyclopropyl)furo[2,3-d]pyrimidin-4-amine;

5-[(4aS,8aR)-decahydroisoquinoline-2-carbonyl]-6-methyl-N-(1-methylcyclopropyl)furo[2,3-d]pyrimidin-4-amine;

6-methyl-N-(1-methylcyclopropyl)-5-{4H,5H,6H,7H-thieno[3,2-c]pyridine-5-carbonyl}furo[2,3-d]pyrimidin-4-amine;

5-{6,6-dimethyl-3-azabicyclo[3.1.0]hexane-3-carbonyl}-6-methyl-N-(1-methylcyclopropyl)furo[2,3-d]pyrimidin-4-amine;

5-[(1R,5S,6S)-6-(4-fluorophenyl)-3-azabicyclo[3.1.0]hexane-3-carbonyl]-6-methyl-N-(1-methylcyclopropyl)furo[2,3-d]pyrimidin-4-amine;

1'-{6-methyl-4-[(1-methylcyclopropyl)amino]furo[2,3-d]pyrimidine-5-carbonyl}-1,2-dihydrospiro[indole-3,3'-piperidine]-2-one;

1-methyl-1'-{6-methyl-4-[(1-methylcyclopropyl)amino]furo[2,3-d]pyrimidine-5-carbonyl}-1,2-dihydrospiro[indole-3,3'-piperidine]-2-one;

1'-{6-methyl-4-[(1-methylcyclopropyl)amino]furo[2,3-d]pyrimidine-5-carbonyl}-2-oxo-1,2-dihydrospiro[indole-3,3'-pyrrolidine]-4'-carbonitrile;

5-({2,3-dihydrospiro[indene-1,2'-morpholine]-4'-yl}carbonyl)-6-methyl-N-(1-methylcyclopropyl)furo[2,3-d]pyrimidin-4-amine;

6-methyl-N-(1-methylcyclopropyl)-5-({3H-spiro[2-benzofuran-1,3'-piperidine]-1'-yl}carbonyl)furo[2,3-d]pyrimidin-4-amine;

6-methyl-N-(1-methylcyclopropyl)-5-({3H-spiro[2-benzofuran-1,3'-pyrrolidine]-1'-yl}carbonyl)furo[2,3-d]pyrimidin-4-amine;

6-fluoro-1'-{6-methyl-4-[(1-methylcyclopropyl)amino]furo[2,3-d]pyrimidine-5-carbonyl}-1,2-dihydrospiro[3,1-benzoxazine-4,4'-piperidine]-2-one;

6-methyl-N-(1-methylcyclopropyl)-5-({spiro[indene-1,4'-piperidine]-1'-yl}carbonyl)furo[2,3-d]pyrimidin-4-amine;

6-methyl-N-(1-methylcyclopropyl)-5-({3H-spiro[2-benzothiophene-1,4'-piperidine]-1'-yl}carbonyl)furo[2,3-d]pyrimidin-4-amine;

1'-{6-methyl-4-[(1-methylcyclopropyl)amino]furo[2,3-d]pyrimidine-5-carbonyl}-1,2-dihydrospiro[indole-3,3'-pyrrolidine]-2-one;

5-{10-azatricyclo[6.3.1.0$^{2,7}$]dodeca-2,4,6-triene-10-carbonyl}-6-methyl-N-(1-methylcyclopropyl)furo[2,3-d]pyrimidin-4-amine;

6-methyl-N-(1-methylcyclopropyl)-5-[(1R,5S)-8-oxa-3-azabicyclo[3.2.1]octane-3-carbonyl]furo[2,3-d]pyrimidin-4-amine;

5-(10-methoxy-3,4,5,6-tetrahydro-2H-1,5-benzoxazocine-5-carbonyl)-6-methyl-N-(1-methylcyclopropyl)furo[2,3-d]pyrimidin-4-amine;

5-{4-methoxy-5H,6H,7H,8H,9H-pyrimido[4,5-d]azepine-7-carbonyl}-6-methyl-N-(1-methylcyclopropyl)furo[2,3-d]pyrimidin-4-amine;

and pharmaceutically acceptable salts thereof.

18. A pharmaceutical composition comprising a compound, or pharmaceutically acceptable salt thereof, of claim 1, and a pharmaceutically acceptable carrier.

19. A method of enhancing memory in a subject in need thereof, comprising administering to the subject an effective amount of a compound of claim 1.

20. The compound of claim 17, selected from the group consisting of:

6-methyl-4-[(1-methylcyclopropyl)amino]-N-(1,3-thiazol-4-ylmethyl)furo[2,3-d]pyrimidine-5-carboxamide;

6-methyl-4-[(1-methylcyclopropyl)amino]-N-(1H-pyrrol-2-ylmethyl)furo[2,3-d]pyrimidine-5-carboxamide;

N-[(2-fluorophenyl)methyl]-6-methyl-4-[(1-methylcyclopropyl)amino]furo[2,3-d]pyrimidine-5-carboxamide;

N-[(5-cyclopropyl-1H-pyrazol-3-yl)methyl]-N,6-dimethyl-4-[(1-methylcyclopropyl)amino]furo[2,3-d]pyrimidine-5-carboxamide;

N-[(6-chloropyridin-3-yl)methyl]-6-methyl-4-[(1-methylcyclopropyl)amino]furo[2,3-d]pyrimidine-5-carboxamide;

and pharmaceutically acceptable salts thereof.

21. The compound of claim 17, selected from the group consisting of:

6-methyl-N-{[5-(1-methyl-1H-pyrazol-4-yl)-1,2-oxazol-3-yl]methyl}-4-[(1-methylcyclopropyl)amino]furo[2,3-d]pyrimidine-5-carboxamide;

6-methyl-N-[(5-methyl-1,3-oxazol-2-yl)methyl]-4-[(1-methylcyclopropyl)amino]furo[2,3-d]pyrimidine-5-carboxamide;

6-methyl-4-[(1-methylcyclopropyl)amino]-N-[(5-methylpyrazin-2-yl)methyl]furo[2,3-d]pyrimidine-5-carboxamide;

6-methyl-N-[(5-methyl-1,3-thiazol-2-yl)methyl]-4-[(1-methylcyclopropyl)amino]furo[2,3-d]pyrimidine-5-carboxamide;

6-methyl-4-[(1-methylcyclopropyl)amino]-N-{[5-(propan-2-yl)-1,3-oxazol-2-yl]methyl}furo[2,3-d]pyrimidine-5-carboxamide;

and pharmaceutically acceptable salts thereof.

22. The compound of claim 17, selected from the group consisting of:

N-[(3-chloro-4-methoxyphenyl)methyl]-6-methyl-4-[(1-methylcyclopropyl)amino]furo[2,3-d]pyrimidine-5-carboxamide;

N-{[1-(4-fluorophenyl)-1H-pyrazol-4-yl]methyl}-6-methyl-4-[(1-methylcyclopropyl)amino]furo[2,3-d]pyrimidine-5-carboxamide;

N-{[1-(3-fluorophenyl)-1H-pyrazol-4-yl]methyl}-6-methyl-4-[(1-methylcyclopropyl)amino]furo[2,3-d]pyrimidine-5-carboxamide;

N-[(6-methoxypyrimidin-4-yl)methyl]-6-methyl-4-[(1-methylcyclopropyl)amino]furo[2,3-d]pyrimidine-5-carboxamide;

N-[(6-methoxy-2-methylpyrimidin-4-yl)methyl]-6-methyl-4-[(1-methylcyclopropyl)amino]furo[2,3-d]pyrimidine-5-carboxamide;

and pharmaceutically acceptable salts thereof.

23. The compound of claim 21, which is 6-methyl-N-[(5-methyl-1,3-oxazol-2-yl)methyl]-4-[(1-methylcyclopropyl)amino]furo[2,3-d]pyrimidine-5-carboxamide, or a pharmaceutically acceptable salt thereof.

24. The compound of claim 22, which is N-[(6-methoxypyrimidin-4-yl)methyl]-6-methyl-4-[(1-methylcyclopropyl)amino]furo[2,3-d]pyrimidine-5-carboxamide, or a pharmaceutically acceptable salt thereof.

\* \* \* \* \*